US009744175B2

(12) United States Patent
Chaturvedi et al.

(10) Patent No.: US 9,744,175 B2
(45) Date of Patent: Aug. 29, 2017

(54) COMPOSITIONS OF COMBINATIONS OF NON-COVALENT DNA BINDING AGENTS AND ANTI-CANCER AND/OR ANTI-INFLAMMATORY AGENTS AND THEIR USE IN DISEASE TREATMENT

(71) Applicants: INDUS PHARMACEUTICALS, INC., Woburn, MA (US); Pravin R. Chaturvedi, Andover, MA (US); Palaniyandi Manivasakam, West Roxbury, MA (US); Steven Grossman, Richmond, VA (US); Sharon Cantor, Weston, MA (US)

(72) Inventors: Pravin R. Chaturvedi, Andover, MA (US); Palaniyandi Manivasakam, West Roxbury, MA (US); Steven Grossman, Richmond, VA (US); Sharon Cantor, Weston, MA (US)

(73) Assignee: INDUS PHARMACEUTICALS, INC., Woburn, MA (US)

(*) Notice: Subject to any disclaimer, the term of this patent is extended or adjusted under 35 U.S.C. 154(b) by 54 days.

(21) Appl. No.: 14/390,847

(22) PCT Filed: Feb. 28, 2013

(86) PCT No.: PCT/US2013/028358
§ 371 (c)(1),
(2) Date: Oct. 6, 2014

(87) PCT Pub. No.: WO2013/151638
PCT Pub. Date: Oct. 10, 2013

(65) Prior Publication Data

US 2015/0056192 A1 Feb. 26, 2015

Related U.S. Application Data

(60) Provisional application No. 61/621,149, filed on Apr. 6, 2012.

(51) Int. Cl.

| | |
|---|---|
| ***A61K 31/5517*** | (2006.01) |
| ***A61K 45/06*** | (2006.01) |
| ***A61K 31/165*** | (2006.01) |
| ***A61K 31/337*** | (2006.01) |
| ***A61K 31/407*** | (2006.01) |
| ***A61K 31/45*** | (2006.01) |
| ***A61K 31/4745*** | (2006.01) |
| ***A61K 31/475*** | (2006.01) |
| ***A61K 31/502*** | (2006.01) |
| ***A61K 31/513*** | (2006.01) |
| ***A61K 31/517*** | (2006.01) |
| ***A61K 31/52*** | (2006.01) |
| ***A61K 31/5377*** | (2006.01) |
| ***A61K 31/555*** | (2006.01) |
| ***A61K 31/704*** | (2006.01) |
| ***A61K 33/24*** | (2006.01) |
| ***A61K 31/713*** | (2006.01) |
| ***A61K 38/00*** | (2006.01) |

(52) U.S. Cl.
CPC ........ *A61K 31/5517* (2013.01); *A61K 31/165* (2013.01); *A61K 31/337* (2013.01); *A61K 31/407* (2013.01); *A61K 31/45* (2013.01); *A61K 31/475* (2013.01); *A61K 31/4745* (2013.01); *A61K 31/502* (2013.01); *A61K 31/513* (2013.01); *A61K 31/517* (2013.01); *A61K 31/52* (2013.01); *A61K 31/5377* (2013.01); *A61K 31/555* (2013.01); *A61K 31/704* (2013.01); *A61K 31/713* (2013.01); *A61K 33/24* (2013.01); *A61K 38/00* (2013.01); *A61K 45/06* (2013.01); *C12N 2310/14* (2013.01)

(58) Field of Classification Search
CPC ............................ A61K 31/5517; A61K 45/06
USPC .......................................................... 514/220
See application file for complete search history.

(56) References Cited

U.S. PATENT DOCUMENTS

| | | | |
|---|---|---|---|
| 4,002,531 | A | 1/1977 | Royer |
| 5,252,714 | A | 10/1993 | Harris et al. |
| 5,672,662 | A | 9/1997 | Harris et al. |
| 5,968,767 | A | 10/1999 | Sheikh et al. |
| 5,990,237 | A | 11/1999 | Bentley et al. |
| 6,362,331 | B1 | 3/2002 | Kamal et al. |
| 6,683,073 | B1 | 1/2004 | Kamal et al. |
| 6,800,622 | B1 | 10/2004 | Kamal et al. |
| 6,884,799 | B2 | 4/2005 | Kamal et al. |
| 7,015,215 | B2 | 3/2006 | Kamal et al. |
| 7,329,638 | B2 | 2/2008 | Yang et al. |

(Continued)

FOREIGN PATENT DOCUMENTS

WO WO 00/07629 A2 2/2000

OTHER PUBLICATIONS

Ashworth, A., A synthetic lethal therapeutic approach: Poly(ADP) Ribose Polymerase Inhibitors for the Treatment of Cancers Deficient in DNA Double-Strand Break Repair, *J. Clinical Oncology* 26:3785-3790, 2008. (Exhibit 16).
Berge, S.M.et al., Pharmaceutical salts, *J. Pharmaceutical Sciences*, 66:1-19, 1977. (Exhibit 17).
Bendardaf R. et al., Mismatch repair status is a predictive factor of tumour response to 5-fluorouracil and irinotecan chemotherapy in patients with advanced colorectal cancer, *Tumour Biol.*, 28(4): 212-220, 2007; Epub 2007. (Exhibit 18).
Carey, L., et al., Triple-negative breast cancer: disease entity or title of convenience. *Nature Reviews* 7: 683-692, 2010. (Exhibit 19).

(Continued)

*Primary Examiner* — Yan Xiao
(74) *Attorney, Agent, or Firm* — Adriano & Associates

(57) ABSTRACT

The invention provides for compositions for treating a cancer or an inflammatory disorder comprising a combination of agents in a pharmaceutically acceptable carrier, wherein said agents comprise: (i) a non-covalent DNA binding agent; and (ii) an anti-cancer or anti-inflammatory agent.

9 Claims, 149 Drawing Sheets

(56) References Cited

U.S. PATENT DOCUMENTS

| | | | | |
|---|---|---|---|---|
| 2007/0292396 | A1* | 12/2007 | Fueyo | A61K 45/06 424/93.6 |
| 2008/0153891 | A1 | 6/2008 | Dorr et al. | |
| 2009/0306094 | A1 | 12/2009 | Lee et al. | |

OTHER PUBLICATIONS

Cheok, C.F., et al., Translating p53 into the clinic. *Nat. Rev. Clin. Oncol.* 8: 25-37, 2011. (Exhibit 20).

Evers, B., et al., Targeting homologous recombination repair defects in cancer. *Trends Pharmacol. Sci.* 31: 372-380, 2010. (Exhibit 21).

Fullerton, S.M., et al., Local rates of recombination are positively correlated with GC content in human genome. *Mol. Biol. Evol.* 18(6): 1139-1142, 2001. (Exhibit 22).

Hawkins, N., et al. CpG island methylation in sporadic colorectal cancers and its relationship to microsatellite instability. *Gastroenterology* 122(5): 1376-1387, 2002. (Exhibit 23).

Helleday, T., et al., DNA repair pathways as targets for cancer therapy. *Nat. Rev. Cancer* 8: 193-204, 2008. (Exhibit 24).

Hewish, M., et al., Mismatch repair deficient colorectal cancer in the era of personalized treatment. *Nat. Rev. Clin. Oncol.* 7: 197-208, 2010. (Exhibit 25).

Jones, P.A. and Baylin, S.B. The fundamental role of epigenetic events in cancer. *Nat. Rev. Genetics* 3: 415-428, 2002. (Exhibit 26).

Kawashima, M. et al., Effect of treatment of rheumatoid arthritis with infliximab on IFN gamma, IL4, T-bet, and GATA-3 expression: link with improvement of systemic inflammation and disease activity, *Ann. Rheum. Dis.*, 64(3): 415-418. 2005, Epub 2004. (Exhibit 27).

ISR of PCT/US2013/028358 (Exhibit 15), Jul. 4, 2013.

Kulagowski, J.J., et al., 3-[[4-(4-Chlorophenyl)piperazin-1-yl]methyl]1*H*-pyrrolo[2,3-b]pyridine: An Antagonist with High Affinity and Selectivity for the Human Dopamine $D_4$ Receptor, *J. Med. Chem.* 39(10): 1941-1942, 1996, (Exhibit 28).

Loeb, L.A., et al., Multiple mutations and cancer. *Proc. Nat. Acad. Sci.* 100(3): 776-781, 2003. (Exhibit 29).

Marcus et al., Immunohistochemistry for hMLH1 and hMSH2: a practical test for DNA mismatch repair-deficient tumors, *Am. J. Surg. Pathol.* 23(10): 1248-1255, 1999. (Exhibit 30).

Masunaga S. et al., Usefulness of hexamethylenetetramine as an adjuvant to radiaton and cisplatin in the treatment of solid tumors: its independency of p53 status. *J. Radiat. Res.*, 51(1),pp. 27-35, especially, p. 28., 2010. (Exhibit 31).

O'Shaughnessy, J. et al., Inipaib plys chemotherapy in metastatic triple-negative breast cancer, *N. Engl. J. Med.*, 364: 205-214, 2011. (Exhibit 32).

Oliver, J.L. and Marin, A. A relationship between GC content and Coding-sequence length. *J. Mol. Evol.* 43: 216-223, 1996. (Exhibit 33).

Reddy, B.S., et al., Synthetic DNA minor groove-binding drugs, *Pharmacol. Ther.*, 84(1): 1-111, 1999. (Exhibit 34).

Rehman, F.L. et al., Synthetic lethal approaches to breast cancer therapy, *Nat. Rev. Clin. Oncol.* 7:718-724, 2010. (Exhibit 35).

Rosa, R. et al., Toll-like Receptor 9 Agonist IMO Cooperates with Cetuximab in K-Ras Mutant Colorectal and Pancreatic Cancers. *Clin. Cancer Res.*, 17: 6531-6541, especially, abstract, p. 6536, 2011. (Exhibit 36).

* cited by examiner

U2OS cells are osteosarcoma cells that are MMR-proficient

Novel IndUS PBDs are very potent in leukemia cells (CEM) with PTEN (homologous recombination) gene deficiency A = NSC 718813 IC50 = 12 nM
B = NSC 723734 IC50 = 16 nM
D= NSC726260 IC50 = 67 nM Genetically-resistant breast cancer cells (MDA-MB-468) with deficiencies in PTEN and epigenetic DNA mismatch repair mutations are very sensitive to novel IndUS PBDs A= NSC718813 – IC50 = 6 nM;
B= NSC723734; - IC50 = 15 nM
D= NSC726260 – IC50 = 317 nM Selected novel IndUS preclinical lead PBD molecules show potent growth inhibition in colorectal cancer cells, with normal or mutated Kras IC50 nM

| PBDs | SW403 | SW480 |
|---|---|---|
| NSC718813 | 200 | 60 |
| NSC723734 | 700 | 80 |
| NSC726260 | 1000 | 700 |

Selected novel IndUS preclinical lead PBD molecules show potent growth inhibition in colorectal cancer cells, with mutated Kras coupled with DNA mismatch repair (MMR) deficiency in HCT116 cells

IC50 nM

| PBDs | SW620 | HCT116 |
|---|---|---|
| NSC 718813 | 200 | **15** |
| NSC 723734 | 225 | **150** |
| NSC 726260 | 1100 | **450** |

PBDs are Synthetic Lethal with Homologous Recombination Repair Deficiencies

BRCA1, XRCC1 and RAD51 RNAi-Knock-down in Colorectal HCT116 cells

723734

IC50 nM
Control = 1000
(Random siRNA)
Rad51 = 100
Brca2 = 50
Xrcc1 = 250

726260

IC50 nM
Control = 200
(Random siRNA)
Rad51 = 18
Brca2 = 15
Xrcc1 = 15

Comparison of Activity of IndUS PBDs in Isogenic U2OS with RNAi knockdowns of MMR, p53, REV functions
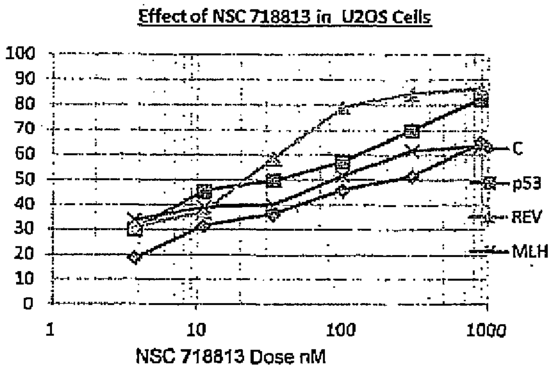
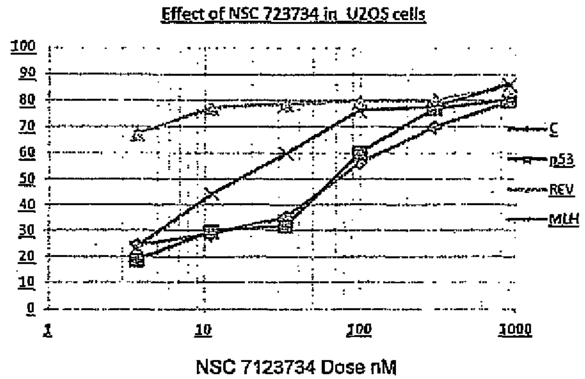
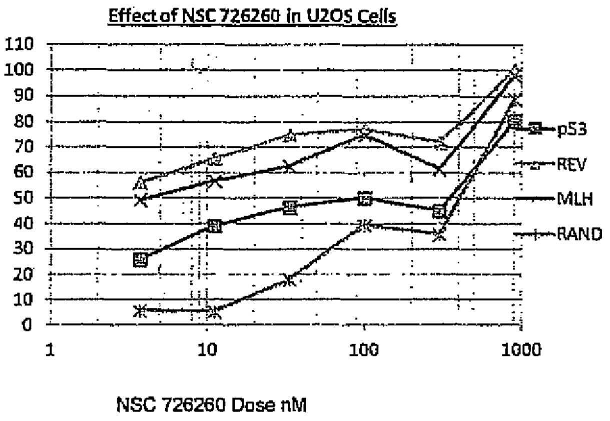
| IC 50 nM | | | |
|---|---|---|---|
| Gene Knock out by siRNA | NSC 718813 | NSC 723734 | NSC 726260 |
| Control (Random siRNA) | 300 | 70 | 400 |
| mlh1 | 100 | 20 | 3 |
| p53 | 30 | 60 | 350 |
| rev | 60 | 1 | 3 |
Figure 9A-C

Comparison of Activity of IndUS PBDs in Isogenic p53-deficient H1299 cells with RNAi knockdown of MMR genes

| IC 50 nM | | |
|---|---|---|
| Gene Knock out by siRNA | NSC 718813 | NSC 723734 |
| Control (Random siRNA) | 600 | 800 |
| MLH1 | 500 | 500 |
| MSH2 | 350 | 350 |

Comparison of Activity of IndUS PBDs in Isogenic MMR-deficient HCT116 cells with RNAi knockdown of p53 and REV3 genes
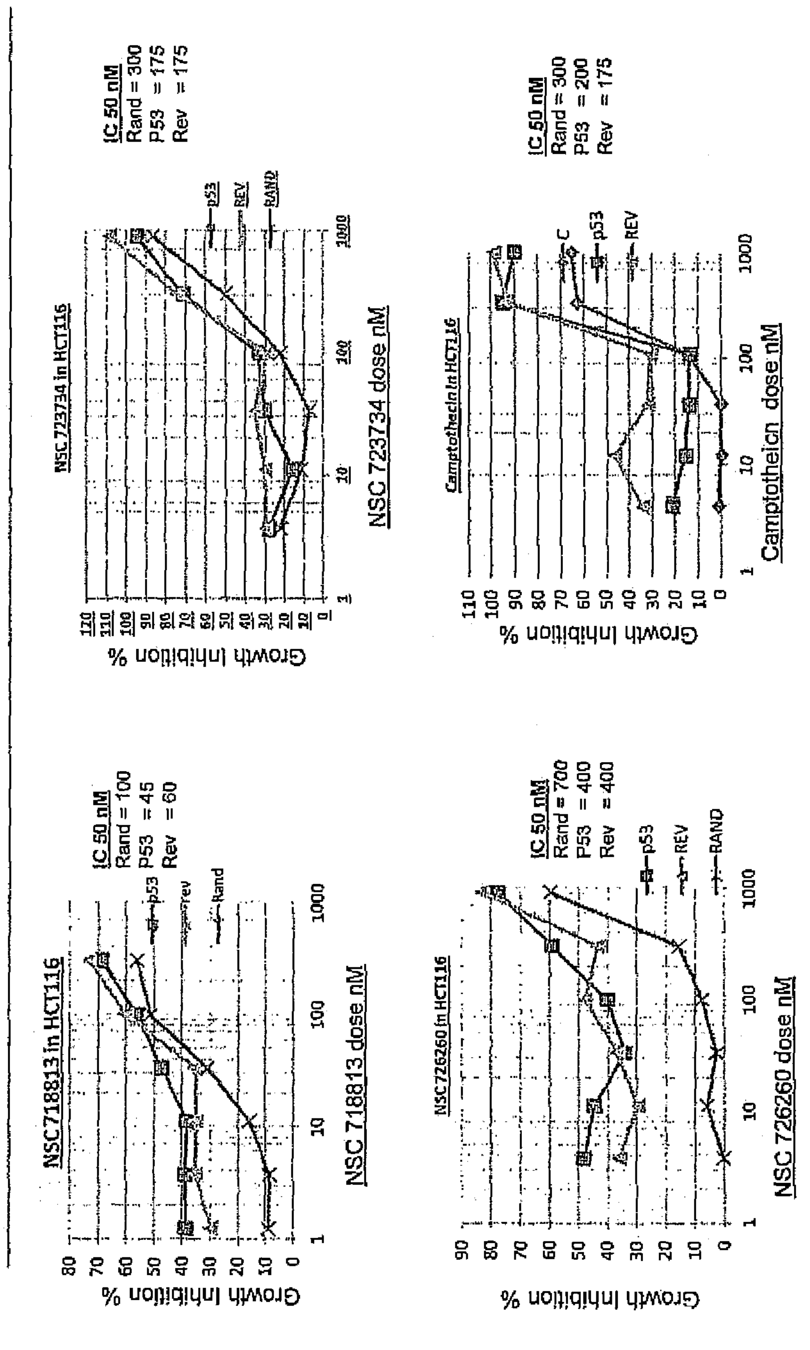
Figure 11A-D

Comparison of Activity of IndUS PBDs in p53, mlh1 and rev deficient U2OS cells (using siRNA)
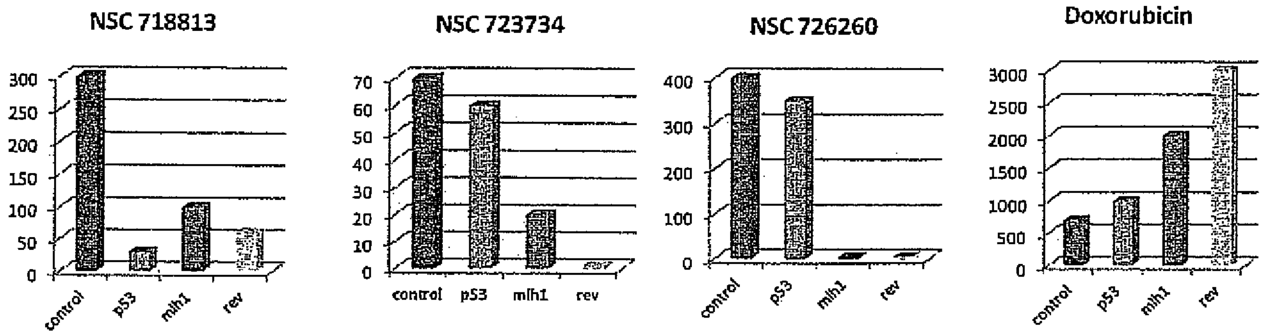
| Fold improvement in IC50 | | |
|---|---|---|
| *p53* | *rev* | *mlh1* |
| **10** | **3** | **5** |
| **1.2** | **3.5** | **>70** |
| **1.1** | **135** | **135** |
| **0.7** | **0.23** | **0.35** |
U2OS Cells
(Wild type for
p53, mlh1 and rev)
Figure 12A-D

MEEPQSDPSVEPPLSQETFSDLWKLLPENNVLSPLPSQAMDDLM
LSPDDIEQWFTEDPGPDEAPRMPEAAPPVAPAPAAPTPAAPAPAPSWPLSSSVPSQKT
YQGSYGFRLGFLHSGTAKSVTCTYSPALNKMFCQLAKTCPVQLWVDSTPPPGTRVRAM
AIYKQSQHMTEVVRRCPHHERCSDSDGLAPPQHLIRVEGNLRVEYLDDRNTFRHSVVV
PYEPPEVGSDCTTIHYNYMCNSSCMGGMNRRPILTIITLEDSSGNLLGRNSFEVRVCA
CPGRDRRTEEENLRKKGEPHHELPPGSTKRALPNNTSSSPQPKKKPLDGEYFTLQIRG
RERFEMFRELNEALELKDAQAGKEPGGSRAHSSHLKSKKGQSTSRHKKLMFKTEGPDS
D

1 gattggggtt ttcccctccc atgtgctcaa gactggcgct aaaagttttg agcttctcaa
61 aagtctagag ccaccgtcca gggagcaggt agctgctggg ctccggggac actttgcgtt
121 cgggctggga gcgtgctttc cacgacggtg acacgcttcc ctggattggc agccagactg
181 ccttccgggt cactgccatg gaggagccgc agtcagatcc tagcgtcgag ccccctctga
241 gtcaggaaac attttcagac ctatggaaac tacttcctga aaacaacgtt ctgtccccct
301 tgccgtccca agcaatggat gatttgatgc tgtccccgga cgatattgaa caatggttca
361 ctgaagaccc aggtccagat gaagctccca gaatgccaga ggctgctccc cccgtggccc
421 ctgcaccagc agctcctaca ccggcggccc ctgcaccagc cccctcctgg cccctgtcat
481 cttctgtccc ttcccagaaa acctaccagg gcagctacgg tttccgtctg ggcttcttgc
541 attctgggac agccaagtct gtgacttgca cgtactcccc tgccctcaac aagatgtttt
601 gccaactggc caagacctgc cctgtgcagc tgtgggttga ttccacaccc ccgcccggca
661 cccgcgtccg cgccatggcc atctacaagc agtcacagca catgacggag gttgtgaggc
721 gctgccccca ccatgagcgc tgctcagata gcgatggtct ggcccctcct cagcatctta
781 tccgagtgga aggaaatttg cgtgtggagt atttggatga cagaaacact tttcgacata
841 gtgtggtggt gccctatgag ccgcctgagg ttggctctga ctgtaccacc atccactaca
901 actacatgtg taacagttcc tgcatgggcg gcatgaaccg gaggcccatc ctcaccatca
961 tcacactgga agactccagt ggtaatctac tgggacggaa cagctttgag gtgcgtgttt 1021 gtgcctgtcc tgggagagac cggcgcacag aggaagagaa tctccgcaag aaaggggagc
1081 ctcaccacga gctgccccca gggagcacta agcgagcact gcccaacaac accagctcct
1141 ctccccagcc aaagaagaaa ccactggatg gagaatattt caccccttcag atccgtgggc
1201 gtgagcgctt cgagatgttc cgagagctga atgaggcctt ggaactcaag gatgcccagg
1261 ctgggaagga gccagggggg agcagggctc actccagcca cctgaagtcc aaaaagggtc
1321 agtctacctc ccgccataaa aaactcatgt tcaagacaga agggcctgac tcagactgac
1381 attctccact tcttgttccc cactgacagc ctcccacccc catctctccc tcccctgcca
1441 ttttgggttt tgggtctttg aacccttgct tgcaataggt gtgcgtcaga agcacccagg
1501 acttccattt gctttgtccc ggggctccac tgaacaagtt ggcctgcact ggtgttttgt
1561 tgtggggagg aggatgggga gtaggacata ccagcttaga ttttaaggtt tttactgtga
1621 gggatgtttg ggagatgtaa gaaatgttct tgcagttaag ggttagttta caatcagcca
1681 cattctaggt aggggcccac ttcaccgtac taaccaggga agctgtccct cactgttgaa
1741 ttttctctaa cttcaaggcc catatctgtg aaatgctggc atttgcacct acctcacaga
1801 gtgcattgtg agggttaatg aaataatgta catctggcct tgaaaccacc ttttattaca
1861 tggggtctag aacttgaccc ccttgagggt gcttgttccc tctccctgtt ggtcggtggg
1921 ttggtagttt ctacagttgg gcagctggtt aggtagaggg agttgtcaag tctctgctgg
1981 cccagccaaa ccctgtctga caacctcttg gtgaacctta gtacctaaaa ggaaatctca
2041 ccccatccca caccctggag gatttcatct cttgtatatg atgatctgga tccaccaaga
2101 cttgttttat gctcagggtc aatttctttt ttcttttttt tttttttttt tctttttctt
2161 tgagactggg tctcgctttg ttgcccaggc tggagtggag tggcgtgatc ttggcttact
2221 gcagcctttg cctcccggc tcgagcagtc ctgcctcagc ctccggagta gctgggacca
2281 caggttcatg ccaccatggc cagccaactt ttgcatgttt tgtagagatg gggtctcaca
2341 gtgttgccca ggctggtctc aaactcctgg gctcaggcga tccacctgtc tcagcctccc
2401 agagtgctgg gattacaatt gtgagccacc acgtccagct ggaagggtca acatctttta
2461 cattctgcaa gcacatctgc attttcaccc cacccttccc ctccttctcc ctttttatat
2521 cccattttta tatcgatctc ttattttaca Figure 13B (continued)

Figure 14A

MLH1

MSFVAGVIRRLDETVVNRIAAGEVIQRPANAIKEMIENCLDAKS
TSIQVIVKEGGLKLIQIQDNGTGIRKEDLDIVCERFTTSKLQSFEDLASISTYGFRGE
ALASISHVAHVTITTKTADGKCAYRASYSDGKLKAPPKPCAGNQGTQITVEDLFYNIA
TRRKALKNPSEEYGKILEVVGRYSVHNAGISFSVKKQGETVADVRTLPNASTVDNIRS
IFGNAVSRELIEIGCEDKTLAFKMNGYISNANYSVKKCIFLLFINHRLVESTSLRKAI
ETVYAAYLPKNTHPFLYLSLEISPQNVDVNVHPTKHEVHFLHEESILERVQQHIESKL
LGSNSSRMYFTQTLLPGLAGPSGEMVKSTTSLTSSSTSGSSDKVYAHQMVRTDSREQK
LDAFLQPLSKPLSSQPQAIVTEDKTDISSGRARQQDEEMLELPAPAEVAAKNQSLEGD
TTKGTSEMSEKRGPTSSNPRKRHREDSDVEMVEDDSRKEMTAACTPRRRIINLTSVLS
LQEEINEQGHEVLREMLHNHSFVGCVNPQWALAQHQTKLYLLNTTKLSEELFYQILIY
DFANFGVLRLSEPAPLFDLAMLALDSPESGWTEEDGPKEGLAEYIVEFLKKKAEMLAD
YFSLEIDEEGNLIGLPLLIDNYVPPLEGLPIFILRLATEVNWDEEKECFESLSKECAM
FYSIRKQYISEESTLSGQQSEVPGSIPNSWKWTVEHIVYKALRSHILPPKHFTEDGNI
LQLANLPDLYKVFERC"

Figure 14B

MLH1

1 gaagagaccc agcaacccac agagttgaga aatttgactg gcattcaagc tgtccaatca
61 atagctgccg ctgaagggtg gggctggatg gcgtaagcta cagctgaagg aagaacgtga
121 gcacgaggca ctgaggtgat tggctgaagg cacttccgtt gagcatctag acgtttcctt
181 ggctcttctg gcgccaaaat gtcgttcgtg gcaggggtta ttcggcggct ggacgagaca
241 gtggtgaacc gcatcgcggc gggggaagtt atccagcggc cagctaatgc tatcaaagag
301 atgattgaga actgtttaga tgcaaaatcc acaagtattc aagtgattgt taaagaggga
361 ggcctgaagt tgattcagat ccaagacaat ggcaccggga tcaggaaaga agatctggat
421 attgtatgtg aaaggttcac tactagtaaa ctgcagtcct ttgaggattt agccagtatt
481 tctacctatg gctttcgagg tgaggctttg gccagcataa gccatgtggc tcatgttact
541 attacaacga aaacagctga tggaaagtgt gcatacagag caagttactc agatggaaaa
601 ctgaaagccc ctcctaaacc atgtgctggc aatcaaggga cccagatcac ggtggaggac 661 ctttttttaca acatagccac gaggagaaaa gctttaaaaa atccaagtga agaatatggg
721 aaaattttgg aagttgttgg caggtattca gtacacaatg caggcattag tttctcagtt
781 aaaaaacaag gagagacagt agctgatgtt aggacactac ccaatgcctc aaccgtggac
841 aatattcgct ccatctttgg aaatgctgtt agtcgagaac tgatagaaat tggatgtgag
901 gataaaaccc tagccttcaa aatgaatggt tacatatcca atgcaaacta ctcagtgaag
961 aagtgcatct tcttactctt catcaaccat cgtctggtag aatcaacttc cttgagaaaa
1021 gccatagaaa cagtgtatgc agcctatttg cccaaaaaca cacacccatt cctgtacctc
1081 agtttagaaa tcagtcccca gaatgtggat gttaatgtgc accccacaaa gcatgaagtt
1141 cacttcctgc acgaggagag catcctggag cgggtgcagc agcacatcga gagcaagctc
1201 ctgggctcca attcctccag gatgtacttc acccagactt tgctaccagg acttgctggc
1261 ccctctgggg agatggttaa atccacaaca agtctgacct cgtcttctac ttctggaagt
1321 agtgataagg tctatgccca ccagatggtt cgtacagatt cccgggaaca gaagcttgat
1381 gcatttctgc agcctctgag caaacccctg tccagtcagc cccaggccat tgtcacagag
1441 gataagacag atatttctag tggcagggct aggcagcaag atgaggagat gcttgaactc
1501 ccagcccctg ctgaagtggc tgccaaaaat cagagcttgg agggggatac aacaaagggg
1561 acttcagaaa tgtcagagaa gagaggacct acttccagca accccagaaa gagacatcgg
1621 gaagattctg atgtggaaat ggtggaagat gattcccgaa aggaaatgac tgcagcttgt
1681 acccccccgga gaaggatcat taacctcact agtgttttga gtctccagga agaaattaat
1741 gagcagggac atgaggttct ccgggagatg ttgcataacc actccttcgt gggctgtgtg
1801 aatcctcagt gggccttggc acagcatcaa accaagttat accttctcaa caccaccaag
1861 cttagtgaag aactgttcta ccagatactc atttatgatt ttgccaattt tggtgttctc
1921 aggttatcgg agccagcacc gctctttgac cttgccatgc ttgccttaga tagtccagag
1981 agtggctgga cagaggaaga tggtcccaaa gaaggacttg ctgaatacat tgttgagttt
2041 ctgaagaaga aggctgagat gcttgcagac tatttctctt tggaaattga tgaggaaggg
2101 aacctgattg gattacccct tctgattgac aactatgtgc cccctttgga gggactgcct
2161 atcttcattc ttcgactagc cactgaggtg aattgggacg aagaaaagga atgttttgaa
2221 agcctcagta aagaatgcgc tatgttctat tccatccgga agcagtacat atctgaggag
2281 tcgaccctct caggccagca gagtgaagtg cctggctcca ttccaaactc ctggaagtgg
2341 actgtggaac acattgtcta taaagccttg cgctcacaca ttctgcctcc taaacatttc Figure 14B (continued)

```
2401 acagaagatg gaaatatcct gcagcttgct aacctgcctg atctatacaa agtctttgag
2461 aggtgttaaa tatggttatt tatgcactgt gggatgtgtt cttctttctc tgtattccga
2521 tacaaagtgt tgtatcaaag tgtgatatac aaagtgtacc aacataagtg ttggtagcac
2581 ttaagactta tacttgcctt ctgatagtat tcctttatac acagtggatt gattataaat
2641 aaatagatgt gtcttaacat aa
```

MSH2

MAVQPKETLQLESAAEVGFVRFFQGMPEKPTTTVRLFDRGDFYT
AHGEDALLAAREVFKTQGVIKYMGPAGAKNLQSVVLSKMNFESFVKDLLLVRQYRVEV
YKNRAGNKASKENDWYLAYKASPGNLSQFEDILFGNNDMSASIGVVGVKMSAVDGQRQ
VGVGYVDSIQRKLGLCEFPDNDQFSNLEALLIQIGPKECVLPGGETAGDMGKLRQIIQ
RGGILITERKKADFSTKDIYQDLNRLLKGKKGEQMNSAVLPEMENQVAVSSLSAVIKF
LELLSDDSNFGQFELTTFDFSQYMKLDIAAVRALNLFQGSVEDTTGSQSLAALLNKCK
TPQGQRLVNQWIKQPLMDKNRIEERLNLVEAFVEDAELRQTLQEDLLRRFPDLNRLAK
KFQRQAANLQDCYRLYQGINQLPNVIQALEKHEGKHQKLLLAVFVTPLTDLRSDFSKF
QEMIETTLDMDQVENHEFLVKPSFDPNLSELREIMNDLEKKMQSTLISAARDLGLDPG
KQIKLDSSAQFGYYFRVTCKEEKVLRNNKNFSTVDIQKNGVKFTNSKLTSLNEEYTKN
KTEYEEAQDAIVKEIVNISSGYVEPMQTLNDVLAQLDAVVSFAHVSNGAPVPYVRPAI
LEKGQGRIILKASRHACVEVQDEIAFIPNDVYFEKDKQMFHIITGPNMGGKSTYIRQT
GVIVLMAQIGCFVPCESAEVSIVDCILARVGAGDSQLKGVSTFMAEMLETASILRSAT
KDSLIIIDELGRGTSTYDGFGLAWAISEYIATKIGAFCMFATHFHELTALANQIPTVN
NLHVTALTTEETLTMLYQVKKGVCDQSFGIHVAELANFPKHVIECAKQKALELEEFQY
IGESQGYDIMEPAAKKCYLEREQGEKIIQEFLSKVKQMPFTEMSEENITIKLKQLKAE
VIAKNNSFVNEIISRIKVTT

Figure 15B

MSH2

1 ggcgggaaac agcttagtgg gtgtggggtc gcgcattttc ttcaaccagg aggtgaggag
61 gtttcgacat ggcggtgcag ccgaaggaga cgctgcagtt ggagagcgcg gccgaggtcg
121 gcttcgtgcg cttctttcag ggcatgccgg agaagccgac caccacagtg cgccttttcg
181 accggggcga cttctatacg gcgcacggcg aggacgcgct gctggccgcc cgggaggtgt
241 tcaagaccca gggggtgatc aagtacatgg ggccggcagg agcaaagaat ctgcagagtg
301 ttgtgcttag taaaatgaat tttgaatctt ttgtaaaaga tcttcttctg gttcgtcagt

```
 361 atagagttga agtttataag aatagagctg gaaataaggc atccaaggag aatgattggt
 421 atttggcata taaggcttct cctggcaatc tctctcagtt tgaagacatt ctctttggta
 481 acaatgatat gtcagcttcc attggtgttg tgggtgttaa aatgtccgca gttgatggcc
 541 agagacaggt tggagttggg tatgtggatt ccatacagag gaaactagga ctgtgtgaat
 601 tccctgataa tgatcagttc tccaatcttg aggctctcct catccagatt ggaccaaagg
 661 aatgtgtttt acccggagga gagactgctg gagacatggg gaaactgaga cagataattc
 721 aaagaggagg aattctgatc acagaaagaa aaaaagctga cttttccaca aaagacattt
 781 atcaggacct caaccggttg ttgaaaggca aaaagggaga gcagatgaat agtgctgtat
 841 tgccagaaat ggagaatcag gttgcagttt catcactgtc tgcggtaatc aagtttttag
 901 aactcttatc agatgattcc aactttggac agtttgaact gactactttt gacttcagcc
 961 agtatatgaa attggatatt gcagcagtca gagcccttaa ccttttttcag ggttctgttg
1021 aagataccac tggctctcag tctctggctg ccttgctgaa taagtgtaaa acccctcaag
1081 gacaaagact tgttaaccag tggattaagc agcctctcat ggataagaac agaatagagg
1141 agagattgaa tttagtggaa gcttttgtag aagatgcaga attgaggcag actttacaag
1201 aagatttact tcgtcgattc ccagatctta accgacttgc caagaagttt caaagacaag
1261 cagcaaactt acaagattgt taccgactct atcagggtat aaatcaacta cctaatgtta
1321 tacaggctct ggaaaaacat gaaggaaaac accagaaatt attgttggca gtttttgtga
1381 ctcctcttac tgatcttcgt tctgacttct ccaagtttca ggaaatgata gaaacaactt
1441 tagatatgga tcaggtggaa aaccatgaat tccttgtaaa accttcattt gatcctaatc
1501 tcagtgaatt aagagaaata atgaatgact tggaaaagaa gatgcagtca acattaataa
1561 gtgcagccag agatcttggc ttggaccctg gcaaacagat taaactggat tccagtgcac
1621 agtttggata ttactttcgt gtaacctgta aggaagaaaa agtccttcgt aacaataaaa
1681 actttagtac tgtagatatc cagaagaatg gtgttaaatt taccaacagc aaattgactt
1741 ctttaaatga agagtatacc aaaaataaaa cagaatatga agaagcccag gatgccattg
1801 ttaaagaaat tgtcaatatt tcttcaggct atgtagaacc aatgcagaca ctcaatgatg
1861 tgttagctca gctagatgct gttgtcagct ttgctcacgt gtcaaatgga gcacctgttc
1921 catatgtacg accagccatt ttggagaaag gacaaggaag aattatatta aaagcatcca
1981 ggcatgcttg tgttgaagtt caagatgaaa ttgcatttat tcctaatgac gtatactttg
2041 aaaaagataa acagatgttc cacatcatta ctggccccaa tatgggaggt aaatcaacat
```

Figure 15B (continued)

2101 atattcgaca aactggggtg atagtactca tggcccaaat tgggtgtttt gtgccatgtg
2161 agtcagcaga agtgtccatt gtggactgca tcttagcccg agtaggggct ggtgacagtc
2221 aattgaaagg agtctccacg ttcatggctg aaatgttgga aactgcttct atcctcaggt
2281 ctgcaaccaa agattcatta ataatcatag atgaattggg aagaggaact tctacctacg
2341 atggatttgg gttagcatgg gctatatcag aatacattgc aacaaagatt ggtgcttttt
2401 gcatgtttgc aacccatttt catgaactta ctgccttggc caatcagata ccaactgtta
2461 ataatctaca tgtcacagca ctcaccactg aagagacctt aactatgctt tatcaggtga
2521 agaaaggtgt ctgtgatcaa agttttggga ttcatgttgc agagcttgct aatttcccta
2581 agcatgtaat agagtgtgct aaacagaaag ccctggaact tgaggagttt cagtatattg
2641 gagaatcgca aggatatgat atcatggaac cagcagcaaa gaagtgctat ctggaaagag
2701 agcaaggtga aaaaattatt caggagttcc tgtccaaggt gaaacaaatg ccctttactg
2761 aaatgtcaga agaaaacatc acaataaagt taaaacagct aaaagctgaa gtaatagcaa
2821 agaataatag ctttgtaaat gaaatcattt cacgaataaa agttactacg tgaaaaatcc
2881 cagtaatgga atgaaggtaa tattgataag ctattgtctg taatagtttt atattgtttt
2941 atattaaccc tttttccata gtgttaactg tcagtgccca tgggctatca acttaataag
3001 atatttagta atattttact ttgaggacat tttcaaagat ttttattttg aaaaatgaga
3061 gctgtaactg aggactgttt gcaattgaca taggcaataa taagtgatgt gctgaatttt
3121 ataaataaaa tcatgtagtt tgtgg Figure 15B (continued)

Figure 16A

BRCA1

MDLSALRVEEVQNVINAMQKILECPICLELIKEPVSTKCDHIFC
KFCMLKLLNQKKGPSQCPLCKNDITKRSLQESTRFSQLVEELLKIICAFQLDTGLEYA
NSYNFAKKENNSPEHLKDEVSIIQSMGYRNRAKRLLQSEPENPSLQETSLSVQLSNLG
TVRTLRTKQRIQPQKTSVYIELGSDSSEDTVNKATYCSVGDQELLQITPQGTRDEISL
DSAKKAACEFSETDVTNTEHHQPSNNDLNTTEKRAAERHPEKYQGSSVSNLHVEPCGT
NTHASSLQHENSSLLLTKDRMNVEKAEFCNKSKQPGLARSQHNRWAGSKETCNDRRTP
STEKKVDLNADPLCERKEWNKQKLPCSENPRDTEDVPWITLNSSIQKVNEWFSRSDEL
LGSDDSHDGESESNAKVADVLDVLNEVDEYSGSSEKIDLLASDPHEALICKSERVHSK
SVESNIEDKIFGKTYRKKASLPNLSHVTENLIIGAFVTEPQIIQERPLTNKLKRKRRP
TSGLHPEDFIKKADLAVQKTPEMINQGTNQTEQNGQVMNITNSGHENKTKGDSIQNEK
NPNPIESLEKESAFKTKAEPISSSISNMELELNIHNSKAPKKNRLRRKSSTRHIHALE
LVVSRNLSPPNCTELQIDSCSSSEEIKKKKYNQMPVRHSRNLQLMEGKEPATGAKKSN
KPNEQTSKRHDSDTFPELKLTNAPGSFTKCSNTSELKEFVNPSLPREEKEEKLETVKV
SNNAEDPKDLMLSGERVLQTERSVESSSISLVPGTDYGTQESISLLEVSTLGKAKTEP
NKCVSQCAAFENPKGLIHGCSKDNRNDTEGFKYPLGHEVNHSRETSIEMEESELDAQY
LQNTFKVSKRQSFAPFSNPGNAEEECATFSAHSGSLKKQSPKVTFECEQKEENQGKNE
SNIKPVQTVNITAGFPVVGQKDKPVDNAKCSIKGGSRFCLSSQFRGNETGLITPNKHG
LLQNPYRIPPLFPIKSFVKTKCKKNLLEENFEEHSMSPEREMGNENIPSTVSTISRNN
IRENVFKEASSSNINEVGSSTNEVGSSINEIGSSDENIQAELGRNRGPKLNAMLRLGV
LQPEVYKQSLPGSNCKHPEIKKQEYEEVVQTVNTDFSPYLISDNLEQPMGSSHASQVC
SETPDDLLDDGEIKEDTSFAENDIKESSAVFSKSVQKGELSRSPSPFTHTHLAQGYRR
GAKKLESSEENLSSEDEELPCFQHLLFGKVNNIPSQSTRHSTVATECLSKNTEENLLS
LKNSLNDCSNQVILAKASQEHHLSEETKCSASLFSSQCSELEDLTANTNTQDPFLIGS
SKQMRHQSESQGVGLSDKELVSDDEERGTGLEENNQEEQSMDSNLGEAASGCESETSV
SEDCSGLSSQSDILTTQQRDTMQHNLIKLQQEMAELEAVLEQHGSQPSNSYPSIISDS
SALEDLRNPEQSTSEKAVLTSQKSSEYPISQNPEGLSADKFEVSADSSTSKNKEPGVE
RSSPSKCPSLDDRWYMHSCSGSLQNRNYPSQEELIKVVDVEEQQLEESGPHDLTETSY

Figure 16A (continued)

LPRQDLEGTPYLESGISLFSDDPESDPSEDRAPESARVGNIPSSTSALKVPQLKVAES

AQSPAAAHTTDTAGYNAMEESVSREKPELTASTERVNKRMSMVVSGLTPEEFMLVYKF

ARKHHITLTNLITEETTHVVMKTDAEFVCERTLKYFLGIAGGKWVVSYFWVTQSIKER

KMLNEHDFEVRGDVVNGRNHQGPKRARESQDRKIFRGLEICCYGPFTNMPTDQLEWMV

QLCGASVVKELSSFTLGTGVHPIVVVQPDAWTEDNGFHAIGQMCEAPVVTREWVLDSV

ALYQCQELDTYLIPQIPHSHY

Figure 16B

BRCA1

```
   1 gtaccttgat ttcgtattct gagaggctgc tgcttagcgg tagcccttg gtttccgtgg
  61 caacggaaaa gcgcgggaat tacagataaa ttaaaactgc gactgcgcgg cgtgagctcg
 121 ctgagacttc ctggacgggg gacaggctgt ggggtttctc agataactgg gcccctgcgc
 181 tcaggaggcc ttcaccctct gctctgggta aagttcattg gaacagaaag aaatggattt
 241 atctgctctt cgcgttgaag aagtacaaaa tgtcattaat gctatgcaga aaatcttaga
 301 gtgtcccatc tgtctggagt tgatcaagga acctgtctcc acaaagtgtg accacatatt
 361 ttgcaaattt tgcatgctga aacttctcaa ccagaagaaa gggccttcac agtgtccttt
 421 atgtaagaat gatataacca aaaggagcct acaagaaagt acgagattta gtcaacttgt
 481 tgaagagcta ttgaaaatca tttgtgcttt tcagcttgac acaggtttgg agtatgcaaa
 541 cagctataat tttgcaaaaa aggaaaataa ctctcctgaa catctaaaag atgaagtttc
 601 tatcatccaa agtatgggct acagaaaccg tgccaaaaga cttctacaga gtgaacccga
 661 aaatccttcc ttgcaggaaa ccagtctcag tgtccaactc tctaaccttg gaactgtgag
 721 aactctgagg acaaagcagc ggatacaacc tcaaaagacg tctgtctaca ttgaattggg
 781 atctgattct tctgaagata ccgttaataa ggcaacttat tgcagtgtgg gagatcaaga
 841 attgttacaa atcacccctc aaggaaccag ggatgaaatc agtttggatt ctgcaaaaaa
 901 ggctgcttgt gaattttctg agacggatgt aacaaatact gaacatcatc aacccagtaa
 961 taatgatttg aacaccactg agaagcgtgc agctgagagg catccagaaa agtatcaggg
1021 tagttctgtt tcaaacttgc atgtggagcc atgtggcaca aatactcatg ccagctcatt
1081 acagcatgag aacagcagtt tattactcac taaagacaga atgaatgtag aaaaggctga
1141 attctgtaat aaaagcaaac agcctggctt agcaaggagc caacataaca gatgggctgg
```

1201 aagtaaggaa acatgtaatg ataggcggac tcccagcaca gaaaaaaagg tagatctgaa
1261 tgctgatccc ctgtgtgaga gaaaagaatg gaataagcag aaactgccat gctcagagaa
1321 tcctagagat actgaagatg ttccttggat aacactaaat agcagcattc agaaagttaa
1381 tgagtggttt tccagaagtg atgaactgtt aggttctgat gactcacatg atggggagtc
1441 tgaatcaaat gccaaagtag ctgatgtatt ggacgttcta aatgaggtag atgaatattc
1501 tggttcttca gagaaaatag acttactggc cagtgatcct catgaggctt taatatgtaa
1561 aagtgaaaga gttcactcca aatcagtaga gagtaatatt gaagacaaaa tatttgggaa
1621 aacctatcgg aagaaggcaa gcctccccaa cttaagccat gtaactgaaa atctaattat
1681 aggagcattt gttactgagc cacagataat acaagagcgt cccctcacaa ataaattaaa
1741 gcgtaaaagg agacctacat caggccttca tcctgaggat tttatcaaga aagcagattt
1801 ggcagttcaa aagactcctg aaatgataaa tcagggaact aaccaaacgg agcagaatgg
1861 tcaagtgatg aatattacta atagtggtca tgagaataaa acaaaaggtg attctattca
1921 gaatgagaaa aatcctaacc caatagaatc actcgaaaaa gaatctgctt tcaaaacgaa
1981 agctgaacct ataagcagca gtataagcaa tatggaactc gaattaaata tccacaattc
2041 aaaagcacct aaaaagaata ggctgaggag gaagtcttct accaggcata ttcatgcgct
2101 tgaactagta gtcagtagaa atctaagccc acctaattgt actgaattgc aaattgatag
2161 ttgttctagc agtgaagaga taaagaaaaa aaagtacaac caaatgccag tcaggcacag
2221 cagaaaccta caactcatgg aaggtaaaga acctgcaact ggagccaaga agagtaacaa
2281 gccaaatgaa cagacaagta aaagacatga cagcgatact ttcccagagc tgaagttaac
2341 aaatgcacct ggttctttta ctaagtgttc aaataccagt gaacttaaag aatttgtcaa
2401 tcctagcctt ccaagagaag aaaaagaaga gaaactagaa acagttaaag tgtctaataa
2461 tgctgaagac cccaaagatc tcatgttaag tggagaaagg gttttgcaaa ctgaaagatc
2521 tgtagagagt agcagtattt cattggtacc tggtactgat tatggcactc aggaaagtat
2581 ctcgttactg gaagttagca ctctagggaa ggcaaaaaca gaaccaaata aatgtgtgag
2641 tcagtgtgca gcatttgaaa accccaaggg actaattcat ggttgttcca aagataatag
2701 aaatgacaca gaaggcttta agtatccatt gggacatgaa gttaaccaca gtcgggaaac
2761 aagcatagaa atggaagaaa gtgaacttga tgctcagtat ttgcagaata cattcaaggt
2821 ttcaaagcgc cagtcatttg ctccgttttc aaatccagga aatgcagaag aggaatgtgc
2881 aacattctct gcccactctg ggtccttaaa gaaacaaagt ccaaaagtca cttttgaatg Figure 16B (continued)

2941 tgaacaaaag gaagaaaatc aaggaaagaa tgagtctaat atcaagcctg tacagacagt
3001 taatatcact gcaggctttc ctgtggttgg tcagaaagat aagccagttg ataatgccaa
3061 atgtagtatc aaaggaggct ctaggttttg tctatcatct cagttcagag gcaacgaaac
3121 tggactcatt actccaaata aacatggact tttacaaaac ccatatcgta taccaccact
3181 ttttcccatc aagtcatttg ttaaaactaa atgtaagaaa aatctgctag aggaaaactt
3241 tgaggaacat tcaatgtcac ctgaaagaga aatgggaaat gagaacattc caagtacagt
3301 gagcacaatt agccgtaata acattagaga aaatgttttt aaagaagcca gctcaagcaa
3361 tattaatgaa gtaggttcca gtactaatga agtgggctcc agtattaatg aaataggttc
3421 cagtgatgaa aacattcaag cagaactagg tagaaacaga gggccaaaat tgaatgctat
3481 gcttagatta ggggttttgc aacctgaggt ctataaacaa agtcttcctg gaagtaattg
3541 taagcatcct gaaataaaaa agcaagaata tgaagaagta gttcagactg ttaatacaga
3601 tttctctcca tatctgattt cagataactt agaacagcct atgggaagta gtcatgcatc
3661 tcaggtttgt tctgagacac ctgatgacct gttagatgat ggtgaaataa aggaagatac
3721 tagttttgct gaaaatgaca ttaaggaaag ttctgctgtt tttagcaaaa gcgtccagaa
3781 aggagagctt agcaggagtc ctagcccttt cacccataca catttggctc agggttaccg
3841 aagaggggcc aagaaattag agtcctcaga agagaactta tctagtgagg atgaagagct
3901 tccctgcttc caacacttgt tatttggtaa agtaaacaat ataccttctc agtctactag
3961 gcatagcacc gttgctaccg agtgtctgtc taagaacaca gaggagaatt tattatcatt
4021 gaagaatagc ttaaatgact gcagtaacca ggtaatattg gcaaaggcat ctcaggaaca
4081 tcaccttagt gaggaaacaa aatgttctgc tagcttgttt tcttcacagt gcagtgaatt
4141 ggaagacttg actgcaaata caaacaccca ggatcctttc ttgattggtt cttccaaaca
4201 aatgaggcat cagtctgaaa gccagggagt tggtctgagt gacaaggaat tggtttcaga
4261 tgatgaagaa agaggaacgg gcttggaaga aaataatcaa gaagagcaaa gcatggattc
4321 aaacttaggt gaagcagcat ctgggtgtga gagtgaaaca agcgtctctg aagactgctc
4381 agggctatcc tctcagagtg acattttaac cactcagcag agggatacca tgcaacataa
4441 cctgataaag ctccagcagg aaatggctga actagaagct gtgttagaac agcatgggag
4501 ccagccttct aacagctacc cttccatcat aagtgactct tctgcccttg aggacctgcg
4561 aaatccagaa caaagcacat cagaaaaagc agtattaact tcacagaaaa gtagtgaata
4621 ccctataagc cagaatccag aaggcctttc tgctgacaag tttgaggtgt ctgcagatag Figure 16B (continued)

4681 ttctaccagt aaaaataaag aaccaggagt ggaaaggtca tccccttcta aatgcccatc
4741 attagatgat aggtggtaca tgcacagttg ctctgggagt cttcagaata gaaactaccc
4801 atctcaagag gagctcatta aggttgttga tgtggaggag caacagctgg aagagtctgg
4861 gccacacgat ttgacggaaa catcttactt gccaaggcaa gatctagagg gaacccctta
4921 cctggaatct ggaatcagcc tcttctctga tgaccctgaa tctgatcctt ctgaagacag
4981 agccccagag tcagctcgtg ttggcaacat accatcttca acctctgcat tgaaagttcc
5041 ccaattgaaa gttgcagaat ctgcccagag tccagctgct gctcatacta ctgatactgc
5101 tgggtataat gcaatggaag aaagtgtgag cagggagaag ccagaattga cagcttcaac
5161 agaaagggtc aacaaaagaa tgtccatggt ggtgtctggc ctgaccccag aagaatttat
5221 gctcgtgtac aagtttgcca gaaaacacca catcacttta actaatctaa ttactgaaga
5281 gactactcat gttgttatga aaacagatgc tgagtttgtg tgtgaacgga cactgaaata
5341 ttttctagga attgcgggag gaaaatgggt agttagctat ttctgggtga cccagtctat
5401 taaagaaaga aaaatgctga atgagcatga ttttgaagtc agaggagatg tggtcaatgg
5461 aagaaaccac caaggtccaa agcgagcaag agaatcccag gacagaaaga tcttcagggg
5521 gctagaaatc tgttgctatg ggcccttcac caacatgccc acagatcaac tggaatggat
5581 ggtacagctg tgtggtgctt ctgtggtgaa ggagctttca tcattcaccc ttggcacagg
5641 tgtccaccca attgtggttg tgcagccaga tgcctggaca gaggacaatg gcttccatgc
5701 aattgggcag atgtgtgagg cacctgtggt gacccgagag tgggtgttgg acagtgtagc
5761 actctaccag tgccaggagc tggacaccta cctgataccc cagatccccc acagccacta
5821 ctgactgcag ccagccacag gtacagagcc acaggacccc aagaatgagc ttacaaagtg
5881 gcctttccag gccctgggag ctcctctcac tcttcagtcc ttctactgtc ctggctacta
5941 aatattttat gtacatcagc ctgaaaagga cttctggcta tgcaagggtc ccttaaagat
6001 tttctgcttg aagtctccct tggaaatctg ccatgagcac aaaattatgg taatttttca
6061 cctgagaaga ttttaaaacc atttaaacgc caccaattga gcaagatgct gattcattat
6121 ttatcagccc tattctttct attcaggctg ttgttggctt agggctggaa gcacagagtg
6181 gcttggcctc aagagaatag ctggtttccc taagtttact tctctaaaac cctgtgttca
6241 caaaggcaga gagtcagacc cttcaatgga aggagagtgc ttgggatcga ttatgtgact
6301 taaagtcaga atagtccttg ggcagttctc aaatgttgga gtggaacatt ggggaggaaa
6361 ttctgaggca ggtattagaa atgaaaagga aacttgaaac ctgggcatgg tggctcacgc Figure 16B (continued)

6421 ctgtaatccc agcactttgg gaggccaagg tgggcagatc actggaggtc aggagttcga
6481 aaccagcctg gccaacatgg tgaaacccca tctctactaa aaatacagaa attagccggt
6541 catggtggtg gacacctgta atcccagcta ctcaggtggc taaggcagga gaatcacttc
6601 agcccgggag gtggaggttg cagtgagcca agatcatacc acggcactcc agcctgggtg
6661 acagtgagac tgtggctcaa aaaaaaaaaa aaaaaaagga aaatgaaact agaagagatt
6721 tctaaaagtc tgagatatat ttgctagatt tctaaagaat gtgttctaaa acagcagaag
6781 attttcaaga accggtttcc aaagacagtc ttctaattcc tcattagtaa taagtaaaat
6841 gtttattgtt gtagctctgg tatataatcc attcctctta aaatataaga cctctggcat
6901 gaatatttca tatctataaa atgacagatc ccaccaggaa ggaagctgtt gctttctttg
6961 aggtgatttt tttcctttgc tccctgttgc tgaaaccata cagcttcata aataattttg
7021 cttgctgaag gaagaaaaag tgtttttcat aaacccatta tccaggactg tttatagctg
7081 ttggaaggac taggtcttcc ctagcccccc cagtgtgcaa gggcagtgaa gacttgattg
7141 tacaaaatac gttttgtaaa tgttgtgctg ttaacactgc aaataaactt ggtagcaaac
7201 acttccaaaa aaaaaaaaaa aaaa Figure 16B (continued)

Figure 17A

REV3L

MFSVRIVTADYYMASPLQGLDTCQSPLTQAPVKKVPVVRVFGAT
PAGQKTCLHLHGIFPYLYVPYDGYGQQPESYLSQMAFSIDRALNVALGNPSSTAQHVF
KVSLVSGMPFYGYHEKERHFMKIYLYNPTMVKRICELLQSGAIMNKFYQPHEAHIPYL
LQLFIDYNLYGMNLINLAAVKFRKARRKSNTLHATGSCKNHLSGNSLADTLFRWEQDE
IPSSLILEGVEPQSTCELEVDAVAADILNRLDIEAQIGGNPGLQAIWEDEKQRRRNRN
ETSQMSQPESQDHRFVPATESEKKFQKRLQEILKQNDFSVTLSGSVDYSDGSQEFSAE
LTLHSEVLSPEMLQCTPANMVEVHKDKESSKGHTRHKVEEALINEEAILNLMENSQTF
QPLTQRLSESPVFMDSSPDEALVHLLAGLESDGYRGERNRMPSPCRSFGNNKYPQNSD
DEENEPQIEKEEMELSLVMSQRWDSNIEEHCAKKRSLCRNTHRSSTEDDDSSSGEEME
WSDNSLLLASLSIPQLDGTADENSDNPLNNENSRTHSSVIATSKLSVKPSIFHKDAAT
LEPSSSAKITFQCKHTSALSSHVLNKEDLIEDLSQTNKNTEKGLDNSVTSFTNESTYS
MKYPGSLSSTVHSENSHKENSKKEILPVSSCESSIFDYEEDIPSVTRQVPSRKYTNIR
KIEKDSPFIHMHRHPNENTLGKNSFNFSDLNHSKNKVSSEGNEKGNSTALSSLFPSSF
TENCELLSCSGENRTMVHSLNSTADESGLNKLKIRYEEFQEHKTEKPSLSQQAAHYMF
FPSVVLSNCLTRPQKLSPVTYKLQPGNKPSRLKLNKRKLAGHQETSTKSSETGSTKDN
FIQNNPCNSNPEKDNALASDLTKTTRGAFENKTPTDGFIDCHFGDGTLETEQSFGLYG
NKYTLRAKRKVNYETEDSESSFVTHNSKISLPHPMEIGESLDGTLKSRKRRKMSKKLP
PVIIKYIIINRFRGRKNMLVKLGKIDSKEKQVILTEEKMELYKKLAPLKDFWPKVPDS
PATKYPIYPLTPKKSHRRKSKHKSAKKKTGKQQRTNNENIKRTLSFRKKRSHAILSPP
SPSYNAETEDCDLNYSDVMSKLGFLSERSTSPINSSPPRCWSPTDPRAEEIMAAAEKE
AMLFKGPNVYKKTVNSRIGKTSRARAQIKKSKAKLANPSIVTKKRNKRNQTNKLVDDG
KKKPRAKQKTNEKGTSRKHTTLKDEKIKSQSGAEVKFVLKHQNVSEFASSSGGSQLLF
KQKDMPLMGSAVDHPLSASLPTGINAQQKLSGCFSSFLESKKSVDLQTFPSSRDDLHP
SVVCNSIGPGVSKINVQRPHNQSAMFTLKESTLIQKNIFDLSNHLSQVAQNTQISSGM
SSKIEDNANNIQRNYLSSIGKLSEYRNSLESKLDQAYTPNFLHCKDSQQQIVCIAEQS
KHSETCSPGNTASEESQMPNNCFVTSLRSPIKQIAWEQKQRGFILDMSNFKPERVKPR
SLSEAISQTKALSQCKNRNVSTPSAFGEGQSGLAVLKELLQKRQQKAQNANTTQDPLS

NKHQPNKNISGSLEHNKANKRTRSVTSPRKPRTPRSTKQKEKIPKLLKVDSLNLQNSS

QLDNSVSDDSPIFFSDPGFESCYSLEDSLSPEHNYNFDINTIGQTGFCSFYSGSQFVP

ADQNLPQKFLSDAVQDLFPGQAIEKNEFLSHDNQKCDEDKHHTTDSASWIRSGTLSPE

IFEKSTIDSNENRRHNQWKNSFHPLTTRSNSIMDSFCVQQAEDCLSEKSRLNRSSVSK

EVFLSLPQPNNSDWIQGHTRKEMGQSLDSANTSFTAILSSPDGELVDVACEDLELYVS

RNNDMLTPTPDSSPRSTSSPSQSKNGSFTPRTANILKPLMSPPSREEIMATLLDHDLS

ETIYQEPFCSNPSDVPEKPREIGGRLLMVETRLANDLAEFEGDFSLEGLRLWKTAFSA

MTQNPRPGSPLRSGQGVVNKGSSNSPKMVEDKKIVIMPCKCAPSRQLVQVWLQAKEEY

ERSKKLPKTKPTGVVKSAENFSSSVNPDDKPVVPPKMDVSPCILPTTAHTKEDVDNSQ

IALQAPTTGCSQTASESQMLPPVASASDPEKDEDDDDNYYISYSSPDSPVIPPWQQPI

SPDSKALNGDDRPSSPVEELPSLAFENFLKPIKDGIQKSPCSEPQEPLVISPINTRAR

TGKCESLCFHSTPIIQRKLLERLPEAPGLSPLSTEPKTQKLSNKKGSNTDTLRRVLLT

QAKNQFAAVNTPQKETSQIDGPSLNNTYGFKVSIQNLQEAKALHEIQNLTLISVELHA

RTRRDLEPDPEFDPICALFYCISSDTPLPDTEKTELTGVIVIDKDKTVFSQDIRYQTP

LLIRSGITGLEVTYAADEKALFHEIANIIKRYDPDILLGYEIQMHSWGYLLQRAAALS

IDLCRMISRVPDDKIENRFAAERDEYGSYTMSEINIVGRITLNLWRIMRNEVALTNYT

FENVSFHVLHQRFPLFTFRVLSDWFDNKTDLYRWKMVDHYVSRVRGNLQMLEQLDLIG

KTSEMARLFGIQFLHVLTRGSQYRVESMMLRIAKPMNYIPVTPSVQQRSQMRAPQCVP

LIMEPESRFYSNSVLVLDFQSLYPSIVIAYNYCFSTCLGHVENLGKYDEFKFGCTSLR

VPPDLLYQVRHDITVSPNGVAFVKPSVRKGVLPRMLEEILKTRFMVKQSMKAYKQDRA

LSRMLDARQLGLKLIANVTFGYTSANFSGRMPCIEVGDSIVHKARETLERAIKLVNDT

KKWGARVVYGDTDSMFVLLKGATKEQSFKIGQEIAEAVTATNPKPVKLKFEKVYLPCV

LQTKKRYVGYMYETLDQKDPVFDAKGIETVRRDSCPAVSKILERSLKLLFETRDISLI

KQYVQRQCMKLLEGKASIQDFIFAKEYRGSFSYKPGACVPALELTRKMLTYDRRSEPQ

VGERVPYVIIYGTPGVPLIQLVRRPVEVLQDPTLRLNATYYITKQILPPLARIFSLIG

IDVFSWYHELPRIHKATSSSRSEPEGRKGTISQYFTTLHCPVCDDLTQHGICSKCRSQ

PQHVAVILNQEIRELERQQEQLVKICKNCTGCFDRHIPCVSLNCPVLFKLSRVNRELS

KAPYLRQLLDQF

REV3L

```
   1 catcatcatg gcaacaagag ctgcagcctg ggaccgagga gcccgtgtga ttcccggcgg
  61 tggcggcagt ggcggcagca ccagcaccga cgaaagctcg agggcttctc tcctgcggcc
 121 ccttgccggg tgctcctgag gaggcggcgg cagcagcgcc tacaccgccc cgcccgccgc
 181 tcctcgaggt gcctctgtgt gaggggaggg ggccgtgccg agaaggggag ggggcgccgc
 241 cgccgctgcg gagggagccg ccgccgctgc tgctgccgct gccgggtcgc cagtgaaggg
 301 aggcagtggc ggcggcggcg aacatgtttt cagtaaggat agtgactgca gactactaca
 361 tggccagccc gctgcagggg ctggatacct gccaatcccc cctcacccag gcccctgtca
 421 agaaggtgcc ggtggtgcga gtcttcggag cgaccccggc aggtcagaag acatgtcttc
 481 atctacatgg catctttcct tacctctatg tgccatacga tggttatgga cagcagccag
 541 aaagctatct ttctcagatg gcattcagta tcgacagagc acttaatgtg gctttaggca
 601 atccatcttc cactgctcag catgtgttca aagtgtcatt agtatcagga atgccttttt
 661 atggttatca tgagaaggaa agacacttta tgaagatcta tctttacaat cctacaatgg
 721 tgaaaaggat atgtgaactt ttgcaaagcg gagccataat gaataaattt taccagcctc
 781 atgaagcgca tattccctac ctcctacagc tcttcattga ctacaatctt tatggcatga
 841 atttaataaa tctggctgct gtcaagttcc gaaaagcaag aaggaaaagt aatacattgc
 901 atgcaactgg atcctgcaag aatcatttat caggaaattc tcttgctgat actttatttc
 961 ggtgggaaca agatgaaata ccaagctctt taatattgga aggtgttgaa ccacagagta
1021 catgtgaatt agaagtggat gctgtagctg ctgatatctt aaatcgtctg gacattgaag
1081 ctcaaattgg tggaaaccct ggtctacagg ccatatggga agatgaaaag caacggcgaa
1141 gaaacagaaa tgaaacttct caaatgagcc aacctgagtc acaagatcac aggtttgtgc
1201 cagcaacaga aagtgaaaaa aaatttcaga agagacttca ggaaattctc aaacagaatg
1261 atttctctgt aacattatca ggatctgtgg actacagcga tggatcccag gagttctctg
1321 ctgagttaac attgcactct gaggttctgt ctcctgaaat gcttcagtgt acaccagcca
1381 atatggtaga agttcacaaa gacaaagagt caagcaaagg tcacactaga cacaaagtgg
1441 aagaagctct tattaatgaa gaagcaattt tgaaccttat ggaaaatagt cagacttttc
1501 agcctttgac ccaaagactg agtgagtcac ctgttttcat ggacagtagt cctgatgagg
1561 ctctggtaca tcttcttgct ggtttggaaa gtgatggata tcggggggaa agaaatagga
```

1621 tgccatcacc atgtcgctcc tttggaaata ataaatatcc acaaaatagt gatgatgaag
1681 aaaatgaacc acagattgaa aaagaggaaa tggagcttag tttggtgatg tcccagagat
1741 gggacagcaa tattgaagaa cattgtgcca aaaagagatc actgtgcaga aatacccaca
1801 gaagttcaac tgaagatgat gactcatctt caggagaaga aatggaatgg agtgataaca
1861 gtttgcttct agccagtctt tctatacctc agttagatgg aactgcagat gaaaatagtg
1921 acaatccatt gaacaatgaa aattctagaa cccactcttc tgtaattgca acaagcaagc
1981 tttcagttaa accctccatc tttcacaaag atgctgctac attagaaccc tcatcttctg
2041 ctaagattac ctttcagtgt aaacacacaa gtgccctttc ttcccatgtt ttgaacaagg
2101 aagatttaat tgaagacctt tcacagacaa acaaaaatac agaaaaaggt ctagataact
2161 cagtcacttc ttttacaaac gaaagcactt attctatgaa ataccctgga tctttaagca
2221 gtactgttca ttcagaaaat tctcataaag agaatagtaa gaaagagatc ctcccagtat
2281 cttcctgtga aagtagtatt tttgattatg aagaagatat tccatctgtt acaagacaag
2341 taccaagtag aaaatataca aacattagaa aaatcgaaaa ggattcccct tttatacata
2401 tgcaccgtca ccctaacgag aatacattgg gcaaaaattc tttcaacttt tctgacttaa
2461 atcattcaaa aaataaagta tcctctgaag gaaatgaaaa aggaaacagc acagctctga
2521 gtagtttatt cccttcatca tttactgaaa attgtgaatt actgtcatgc tcaggggaga
2581 atagaactat ggtgcattct cttaatagca ctgctgatga aagtggacta aataaactta
2641 aaattaggta tgaagaattt caagaacata aaacagaaaa gccaagcctc agccagcaag
2701 cagcacacta tatgtttttt cccagtgttg ttctttctaa ctgtcttact agaccacaga
2761 aactatctcc tgtcacatat aaattacaac ctggcaataa accatcccgg ttaaaattga
2821 ataaaaggaa acttgcaggt catcaggaga cttctaccaa aagtagtgag actggatcca
2881 caaaagataa ttttatacaa aataatcctt gtaatagtaa tcctgagaag gataatgcat
2941 tggctagtga tttaactaaa accactcgtg gagcttttga aaataaaaca cccacagatg
3001 gttttataga ctgtcacttt ggagatggaa cgttagaaac tgagcagtcc tttggactat
3061 atggaaataa atacacactt agagccaaac gcaaggtaaa ttatgagact gaagacagtg
3121 agtcaagttt tgtaactcac aactcaaaaa ttagtctacc tcatcccatg gaaattggtg
3181 aaagtttaga tggaactctc aaatcccgaa aacgaagaaa aatgtctaaa aagctgcccc
3241 ctgtcatcat aaagtatatt attattaata gatttagagg gagaaaaaat atgcttgtga
3301 agctaggaaa aatagactct aaagaaaaac aagtaatatt aacagaagaa aaaatggaac Figure 17B (continued)

3361 tatataaaaa gcttgcacct ttgaaggact tttggccaaa agttccccgac tcccctgcaa
3421 ccaaatatcc catttatcca ctaacaccaa agaaaagtca cagaagaaag tcaaaacata
3481 aatctgctaa gaaaaaaact ggtaaacaac aaaggacaaa taatgaaaat attaaaagaa
3541 ctttgtcttt caggaaaaaa cggtcacatg ctattctttc tcctccctca ccatcttaca
3601 atgctgaaac cgaagattgt gacctgaatt atagtgatgt tatgtctaaa ctaggttttc
3661 tttctgagag aagcacaagt cccataaatt cttctccacc tcgctgctgg tctcccacag
3721 atccaagagc tgaagaaatc atggctgctg cagaaaaaga ggcaatgctt tttaagggtc
3781 ctaatgtata taagaagact gttaattctc gtataggaaa aactagtcgc gcaagagcac
3841 agattaagaa atcaaaagca aagcttgcta atccctctat agttactaag aaaaggaaca
3901 aacgaaatca gacaaataaa ctagtagatg atggaaaaaa gaaaccaaga gcaaaacaaa
3961 aaacaaatga gaaaggtaca tcgagaaagc atacaacact taaggatgaa aaaataaaat
4021 ctcagtctgg tgctgaggtt aagtttgtac tgaaacacca gaatgtgtct gaatttgcaa
4081 gtagttctgg aggctctcaa ctacttttta aacagaaaga tatgccacta atgggctctg
4141 ctgtagatca tcccctttct gcttccctac ccactggaat taatgcacaa cagaagttat
4201 ctggctgctt ttcttctttc ttagaaagca agaagtctgt agatttgcag acattcccca
4261 gttcacgaga tgatttgcat ccatcagttg tttgtaattc tataggacct ggagtctcaa
4321 aaattaatgt tcaaaggcct cataatcaaa gtgctatgtt tactctaaag gaatcaacgt
4381 taattcaaaa aaatatattt gacctttcca atcatttatc tcaggtagca cagaatacac
4441 agatatcttc tggtatgtcc tcaaagatag aagataatgc aaataatata caaagaaact
4501 atttgtcatc aatcggaaag ttaagtgaat atcgcaattc cctagaatca aagctggacc
4561 aagcatatac ccctaatttt ttgcattgca aagacagtca gcagcagatt gtgtgcatag
4621 cggaacagtc aaagcacagt gaaacttgtt ctccgggaaa tacagcttca gaggaaagcc
4681 aaatgcctaa taattgcttt gtaacttcct tgagaagtcc aatcaaacaa atagcatggg
4741 agcaaaagca aaggggcttt attttagata tgtcaaattt taaacctgaa agagtaaaac
4801 cgaggtcgtt atcagaagca atttcacaaa ccaaagcact ttctcagtgt aaaaatcgaa
4861 atgtgtcaac accttcagca tttggtgaag gacagtctgg actggcagtt ctaaaagaat
4921 tgttacaaaa aagacagcag aaagcacaaa atgcaaatac tacacaagac ccattatcca
4981 ataaacatca accaaataaa aatatttctg gttcccttga gcataacaaa gcaaataaac
5041 ggacacgatc ggtaacgtcc ccaagaaaac ctcgaactcc cagaagtaca aaacaaaaag Figure 17B (continued)

5101 aaaaaatccc caaacttctc aaagtagact ctttaaattt acaaaactct agccagttgg
5161 ataactctgt atcagatgat agtcccatct ttttttcaga tccaggcttt gaaagttgtt
5221 actcacttga agatagttta tctcctgaac ataattataa ttttgatatt aacacaatag
5281 gtcagactgg attttgtagc ttttattctg gaagtcagtt tgtcccagct gatcagaatt
5341 tgcctcagaa gttcctaagt gatgctgttc aggatctttt tccaggacaa gctatagaaa
5401 aaaatgagtt tttaagtcat gacaaccaga aatgtgatga agacaagcat cataccacag
5461 actcagcctc atggattaga tctggtactt taagtcctga aatttttgag aagtcaacca
5521 tagatagcaa tgagaatcgt cgccacaacc agtggaaaaa tagctttcat cctctaacaa
5581 ctcggtctaa ctcaataatg gattctttct gtgttcagca ggcagaagac tgtctaagtg
5641 aaaaatctag attgaatagg agttcagtaa gcaaagaagt gtttcttagc ctcccacagc
5701 caaacaattc agactggatt caaggtcaca ccagaaaaga aatgggacag tctcttgact
5761 cagccaatac ctcttttact gcaatactct cctcccctga tggtgaactt gtagacgtgg
5821 cctgtgaaga tttagaactg tatgtttcaa gaaacaatga tatgttgaca ccaactcctg
5881 atagttcacc aagatctact agctctcctt cacaatctaa aaatggcagc ttcacccctc
5941 gaactgctaa cattctgaaa ccacttatgt ccccccccaag tagggaagaa attatggcaa
6001 ctttgttgga tcatgacctg tctgagacta tttaccagga accattttgc agtaatcctt
6061 ctgatgtacc agaaaagccc agggagattg gtggacggct cctcatggta gaaactcgac
6121 ttgcaaatga tctggctgag tttgagggag acttttcctt ggaaggactt cgtctttgga
6181 aaacagcatt ctcagcaatg actcagaatc caaggccagg gtcacccctt cgcagtggcc
6241 aaggagttgt caataaaggg tcaagtaata gccctaagat ggttgaagat aaaaaaattg
6301 tgattatgcc ttgcaaatgt gccccaagtc gacaactggt tcaagtgtgg cttcaagcca
6361 aagaagaata cgaacgttcc aagaaactgc ctaaaaccaa gccaactgga gttgtaaaat
6421 ctgctgagaa ctttagctct tcagttaacc cagatgacaa acctgtagtg cctccaaaaa
6481 tggatgtaag tccatgtata ctccccacta cagcacatac caaggaggat gttgataatt
6541 ctcagattgc tttacaagca ccaaccacgg gatgtagtca aactgcaagt gaaagtcaga
6601 tgctgccacc agttgcctct gcaagtgatc ccgaaaaaga tgaagatgat gatgataact
6661 attacattag ttatagctcc cctgattctc cagtaattcc cccttggcaa caaccaatat
6721 ccccagattc caaagcatta aatggagatg atagaccctc atcaccagta gaggagctgc
6781 cttcattggc ttttgagaac ttcttaaagc caataaaaga tggtatacaa aaaagcccct Figure 17B (continued)

6841 gcagtgagcc tcaagagcct ctagtgatat ctccaattaa tactagggca agaactggga
6901 aatgtgaatc actttgcttt catagtacac caatcataca gagaaaactt ctggaaaggc
6961 ttcctgaagc acctggcctt agcccattat caacagaacc aaaaacacag aagttgagta
7021 ataagaaagg aagtaatact gacactctta gaagagtact gttaacacaa gcaaagaatc
7081 aatttgcagc agtaaatacc ccacagaaag aaacttctca gattgatgga ccatctttaa
7141 acaatactta cggtttcaaa gtcagcatac aaaacttaca ggaggcaaaa gctttacatg
7201 agatacaaaa tcttacccta atcagtgtgg agttgcatgc tcgaactaga cgagacttag
7261 aaccggatcc tgaatttgac ccaatctgtg ctctgttcta ctgcatctca tctgacactc
7321 cactgccaga tacagaaaaa acagaactca caggtgtaat agtgattgat aaagacaaga
7381 cagttttcag tcaagatatc agatatcaga ctccattact tattagatct ggaattacag
7441 gactcgaagt cacctatgct gctgatgaga aggcactttt tcatgaaatt gcaaatataa
7501 taaagaggta tgatcctgat attctgctag gatatgagat tcagatgcat tcctggggtt
7561 acctcttaca aagggctgcc gctttaagta ttgacttatg tcggatgatc tctcgggtgc
7621 cagatgacaa aattgagaac agatttgcag ctgaaagaga tgagtatgga tcatatacaa
7681 tgagtgagat aaatattgtt ggccgaatta cactaaatct ttggagaatc atgagaaatg
7741 aggtggctct aactaactac acctttgaaa atgtgagctt tcatgttctt catcagcgtt
7801 ttcccctctt tacctttcga gtcttgtcag actggtttga taacaagaca gatctataca
7861 gatggaaaat ggttgatcat tatgttagcc gtgtccgtgg aaatctccaa atgttagaac
7921 agctggacct gattgggaaa accagtgaga tggctagact tttggcattt cagtttttac
7981 atgtactgac aaggggttca cagtaccgtg tggaatcaat gatgttgcgt attgctaaac
8041 caatgaacta tattcctgtg acacctagtg ttcagcaaag atcccagatg agagccccac
8101 agtgtgttcc tctaattatg gagcctgaat cccgcttcta tagcaactct gttctcgttt
8161 tggatttcca atcactttat ccttctattg tgattgcata taactactgc ttttccacct
8221 gccttggcca tgtggagaac ttgggaaagt atgatgagtt caaatttggc tgtacctctc
8281 tgagagtacc tccagattta ctttaccaag ttaggcatga tatcacagtg tcccccaatg
8341 gagtagcttt tgtcaagcct tcagtaagaa aaggtgtact accaagaatg cttgaagaaa
8401 ttttgaagac tagatttatg gtgaagcagt caatgaaggc ttacaagcaa gacagagccc
8461 tgtcacgaat gcttgatgcg cgtcagttgg gacttaagct gatagcaaat gtcacatttg
8521 gctatacatc tgctaatttt tctgggagaa tgccatgcat tgaggttggc gatagtattg Figure 17B (continued)

8581 ttcacaaagc cagagagacc ttggaacgag ctattaaact ggtgaatgat accaagaaat
8641 ggggggctag ggttgtatat ggcgatactg acagtatgtt tgtgctactg aaaggagcca
8701 ctaaggagca gtcttttaag attggtcagg aaattgccga agctgtaact gctaccaatc
8761 ctaaaccagt gaaattgaag tttgaaaagg tatatttgcc ctgtgtttta caaacaaaaa
8821 agaggtatgt gggttacatg tatgaaacac tggatcagaa ggacccagta tttgatgcaa
8881 aaggaataga aacagtcaga agagattcct gccctgctgt ttctaagata cttgagcgtt
8941 ctctaaagct gctatttgaa acgagagata taagtctaat taaacagtat gttcagcgac
9001 aatgtatgaa gcttctggaa ggaaaggcca gcatacaaga ctttatcttt gccaaggaat
9061 acagaggaag tttttcttat aaaccaggag cttgtgtgcc agcccttgaa cttacaagga
9121 aaatgctgac ttatgaccgg cgctctgagc ctcaggttgg ggagcgagtg ccatacgtca
9181 tcatttatgg gacccccgga gtaccactta tccagcttgt aaggcgccca gtggaagtcc
9241 tgcaggaccc aactctgaga ctgaatgcta cttactatat taccaagcaa atccttccac
9301 ccttggcaag aatcttctca cttattggta ttgatgtctt cagctggtat catgaattac
9361 caaggatcca taaagctacc agctcctcgc gaagtgaacc tgaagggcgg aaaggcacta
9421 tttcacaata ttttactacc ttacactgtc ctgtgtgtga tgacctaact cagcatggca
9481 tctgtagtaa atgtcggagc caacctcagc atgttgcagt catcctcaac caagaaatcc
9541 gggagttgga acgtcaacag gagcaacttg taaagatatg caagaactgt acaggttgct
9601 ttgatcgaca catcccatgt gtttctctga actgcccagt acttttcaaa ctctcccgag
9661 taaatagaga attgtccaag gcaccatatc tccggcagtt attagaccag ttttaaattg
9721 tcaatatcac agtattacag gtgctatttt tttcagtgct taccactaaa ctgttgtgca
9781 tggtgctttt taactttcat cgagtcaagg atgttcactg tctgttatct gaagactatg
9841 aagacttcta tgctaaccga attaaaatgt acttgttgat ctctgaatag ctcacttctt
9901 acaatgtaca aattcctcat tctgtcacct tttaaacatt gttttataat gcaggtgttg
9961 gatttgctcc agtatgtgta ccatcttgta aattcatttg agtagatcat gtttacttcc
10021 cagtggaagg agcactgaaa acctcttaaa gaaaaagcat ttgtgtgttt tccttgaact
10081 gtctgtatca agacgtgtta cttcgagata tccattcact ttataatttt gactgcaaaa
10141 tattttgtaa atacactttt ttacttttca aacgagcaaa ataatgtgca atgattttta
10201 tacaaatgat tttcaagttg tttggtatat ttcctctagg ttttgcttga ctcaaagtag
10261 atcgttattt tgatcaaact gtgcaaacag tagtaccacg tgtagcattt tgaaacatta Figure 17B (continued)

10321 tttttttttta aaaaatgctg tcttgcttta gctattaatg gggcattgtg aggaactgtg
10381 caaagacatt tttgttacaa acctgtgggc ctgttgcaat actttaaaaa taaaaaattt
10441 tattccattt gcttgttttg tatagacatt tctattgctt ctaaatatac ttaaaatatt
10501 ttctttcctt atgtactgta cagttaatct tatttgccat catcttgaac acaaaatgtg
10561 tatttagaat atttgtataa ctgtgtaaaa taaaaaagga attatgtggt cagtgcattg
10621 tttttttaaac tggaaatcat tttgttttaa aagttaataa tggaaaccat attaaaattg
10681 aataaaatat aaaataatat aaaaaaaaaa aaaaaaaaa Figure 17B (continued)

Figure 18A

PARP1

MAESSDKLYRVEYAKSGRASCKKCSESIPKDSLRMAIMVQSPMF
DGKVPHWYHFSCFWKVGHSIRHPDVEVDGFSELRWDDQQKVKKTAEAGGVTGKGQDGI
GSKAEKTLGDFAAEYAKSNRSTCKGCMEKIEKGQVRLSKKMVDPEKPQLGMIDRWYHP
GCFVKNREELGFRPEYSASQLKGFSLLATEDKEALKKQLPGVKSEGKRKGDEVDGVDE
VAKKKSKKEKDKDSKLEKALKAQNDLIWNIKDELKKVCSTNDLKELLIFNKQQVPSGE
SAILDRVADGMVFGALLPCEECSGQLVFKSDAYYCTGDVTAWTKCMVKTQTPNRKEWV
TPKEFREISYLKKLKVKKQDRIFPPETSASVAATPPPSTASAPAAVNSSASADKPLSN
MKILTLGKLSRNKDEVKAMIEKLGGKLTGTANKASLCISTKKEVEKMNKKMEEVKEAN
IRVVSEDFLQDVSASTKSLQELFLAHILSPWGAEVKAEPVEVVAPRGKSGAALSKKSK
GQVKEEGINKSEKRMKLTLKGGAAVDPDSGLEHSAHVLEKGGKVFSATLGLVDIVKGT
NSYYKLQLLEDDKENRYWIFRSWGRVGTVIGSNKLEQMPSKEDAIEHFMKLYEEKTGN
AWHSKNFTKYPKKFYPLEIDYGQDEEAVKKLTVNPGTKSKLPKPVQDLIKMIFDVESM
KKAMVEYEIDLQKMPLGKLSKRQIQAAYSILSEVQQAVSQGSSDSQILDLSNRFYTLI
PHDFGMKKPPLLNNADSVQAKVEMLDNLLDIEVAYSLLRGGSDDSSKDPIDVNYEKLK
TDIKVVDRDSEEAEIIRKYVKNTHATTHNAYDLEVIDIFKIEREGECQRYKPFKQLHN
RRLLWHGSRTTNFAGILSQGLRIAPPEAPVTGYMFGKGIYFADMVSKSANYCHTSQGD
PIGLILLGEVALGNMYELKHASHISKLPKGKHSVKGLGKTTPDPSANISLDGVDVPLG
TGISSGVNDTSLLYNEYIVYDIAQVNLKYLLKLKFNFKTSLW

Figure 18B

PARP1

1 aggcatcagc aatctatcag ggaacggcgg tggccggtgc ggcgtgttcg gtggcggctc
61 tggccgctca ggcgcctgcg gctgggtgag cgcacgcgag gcggcgaggc ggcagcgtgt
121 ttctaggtcg tggcgtcggg cttccggagc tttggcggca gctaggggag gatggcggag
181 tcttcggata agctctatcg agtcgagtac gccaagagcg ggcgcgcctc ttgcaagaaa
241 tgcagcgaga gcatccccaa ggactcgctc cggatggcca tcatggtgca gtcgcccatg 301 tttgatggaa aagtcccaca ctggtaccac ttctcctgct tctggaaggt gggccactcc
361 atccggcacc ctgacgttga ggtggatggg ttctctgagc ttcggtggga tgaccagcag
421 aaagtcaaga agacagcgga agctggagga gtgacaggca aaggccagga tggaattggt
481 agcaaggcag agaagactct gggtgacttt gcagcagagt atgccaagtc caacagaagt
541 acgtgcaagg ggtgtatgga gaagatagaa aagggccagg tgcgcctgtc caagaagatg
601 gtggacccgg agaagccaca gctaggcatg attgaccgct ggtaccatcc aggctgcttt
661 gtcaagaaca gggaggagct gggtttccgg cccgagtaca gtgcgagtca gctcaagggc
721 ttcagcctcc ttgctacaga ggataaagaa gccctgaaga agcagctccc aggagtcaag
781 agtgaaggaa agagaaaagg cgatgaggtg gatggagtgg atgaagtggc gaagaagaaa
841 tctaaaaaag aaaaagacaa ggatagtaag cttgaaaaag ccctaaaggc tcagaacgac
901 ctgatctgga acatcaagga cgagctaaag aaagtgtgtt caactaatga cctgaaggag
961 ctactcatct tcaacaagca gcaagtgcct tctggggagt cggcgatctt ggaccgagta
1021 gctgatggca tggtgttcgg tgccctcctt ccctgcgagg aatgctcggg tcagctggtc
1081 ttcaagagcg atgcctatta ctgcactggg gacgtcactg cctggaccaa gtgtatggtc
1141 aagacacaga cacccaaccg gaaggagtgg gtaaccccaa aggaattccg agaaatctct
1201 tacctcaaga aattgaaggt taaaaaacag gaccgtatat tcccccccaga aaccagcgcc
1261 tccgtggcgg ccacgcctcc gccctccaca gcctcggctc ctgctgctgt gaactcctct
1321 gcttcagcag ataagccatt atccaacatg aagatcctga ctctcgggaa gctgtcccgg
1381 aacaaggatg aagtgaaggc catgattgag aaactcgggg ggaagttgac ggggacggcc
1441 aacaaggctt ccctgtgcat cagcaccaaa aaggaggtgg aaaagatgaa taagaagatg
1501 gaggaagtaa aggaagccaa catccgagtt gtgtctgagg acttcctcca ggacgtctcc
1561 gcctccacca agagccttca ggagttgttc ttagcgcaca tcttgtcccc ttgggggggca
1621 gaggtgaagg cagagcctgt tgaagttgtg gccccaagag ggaagtcagg ggctgcgctc
1681 tccaaaaaaa gcaagggcca ggtcaaggag gaaggtatca acaaatctga aaagagaatg
1741 aaattaactc ttaaaggagg agcagctgtg gatcctgatt ctggactgga acactctgcg
1801 catgtcctgg agaaaggtgg gaaggtcttc agtgccaccc ttggcctggt ggacatcgtt
1861 aaaggaacca actcctacta caagctgcag cttctggagg acgacaagga aaacaggtat
1921 tggatattca ggtcctgggg ccgtgtgggt acggtgatcg gtagcaacaa actggaacag
1981 atgccgtcca aggaggatgc cattgagcac ttcatgaaat tatatgaaga aaaaaccggg Figure 18B (continued)

2041 aacgcttggc actccaaaaa tttcacgaag tatcccaaaa agttctaccc cctggagatt
2101 gactatggcc aggatgaaga ggcagtgaag aagctgacag taaatcctgg caccaagtcc
2161 aagctcccca agccagttca ggacctcatc aagatgatct ttgatgtgga aagtatgaag
2221 aaagccatgg tggagtatga gatcgacctt cagaagatgc ccttggggaa gctgagcaaa
2281 aggcagatcc aggccgcata ctccatcctc agtgaggtcc agcaggcggt gtctcagggc
2341 agcagcgact ctcagatcct ggatctctca aatcgctttt acaccctgat cccccacgac
2401 tttgggatga agaagcctcc gctcctgaac aatgcagaca gtgtgcaggc caaggtggaa
2461 atgcttgaca acctgctgga catcgaggtg gcctacagtc tgctcagggg agggtctgat
2521 gatagcagca aggatcccat cgatgtcaac tatgagaagc tcaaaactga cattaaggtg
2581 gttgacagag attctgaaga agccgagatc atcaggaagt atgttaagaa cactcatgca
2641 accacacaca atgcgtatga cttggaagtc atcgatatct ttaagataga gcgtgaaggc
2701 gaatgccagc gttacaagcc ctttaagcag cttcataacc gaagattgct gtggcacggg
2761 tccaggacca ccaactttgc tgggatcctg tcccagggtc ttcggatagc ccccgcctgaa
2821 gcgccccgtga caggctacat gtttggtaaa gggatctatt tcgctgacat ggtctccaag
2881 agtgccaact actgccatac gtctcaggga gacccaatag gcttaatcct gttgggagaa
2941 gttgcccttg gaaacatgta tgaactgaag cacgcttcac atatcagcaa gttacccaag
3001 ggcaagcaca gtgtcaaagg tttgggcaaa actacccctg atccttcagc taacattagt
3061 ctggatggtg tagacgttcc tcttgggacc gggatttcat ctggtgtgaa tgacacctct
3121 ctactatata acgagtacat tgtctatgat attgctcagg taaatctgaa gtatctgctg
3181 aaactgaaat tcaattttaa gacctccctg tggtaattgg gagaggtagc cgagtcacac
3241 ccggtggctc tggtatgaat tcacccgaag cgcttctgca ccaactcacc tggccgctaa
3301 gttgctgatg ggtagtacct gtactaaacc acctcagaaa ggattttaca gaaacgtgtt
3361 aaaggttttc tctaacttct caagtccctt gttttgtgtt gtgtctgtgg ggaggggttg
3421 ttttggggtt gtttttgttt tttcttgcca ggtagataaa actgacatag agaaaaggct
3481 ggagagagat tctgttgcat agactagtcc tatggaaaaa accaagcttc gttagaatgt
3541 ctgccttact ggtttcccca gggaaggaaa aatacacttc cacccttttt tctaagtgtt
3601 cgtctttagt tttgattttg gaaagatgtt aagcatttat ttttagttaa aaataaaaac
3661 taatttcata ctatttagat tttctttttt atcttgcact tattgtcccc tttttagttt
3721 tttttgtttg cctcttgtgg tgaggggtgt gggaagacca aaggaaggaa cgctaacaat Figure 18B (continued)

3781 ttctcatact tagaaacaaa aagagctttc cttctccagg aatactgaac atgggagctc
3841 ttgaaatatg tagtattaaa agttgcattt gaaattcttg actttcttat gggcactttt
3901 gtcttccaaa ttaaaactct accacaaata tacttaccca agggctaata gtaatactcg
3961 attaaaaatg cagatgcctt ctctaaaaaa aaaaaaaaaa a Figure 18B (continued)

RAD51

MAMQMQLEANADTSVEEESFGPQPISRLEQCGINANDVKKLEEA
GFHTVEAVAYAPKKELINIKGISEAKADKILAEAAKLVPMGFTTATEFHQRRSEIIQI
TTGSKELDKLLQGGIETGSITEMFGEFRTGKTQICHTLAVTCQLPIDRGGGEGKAMYI
DTEGTFRPERLLAVAERYGLSGSDVLDNVAYARAFNTDHQTQLLYQASAMMVESRYAL
LIVDSATALYRTDYSGRGELSARQMHLARFLRMLLRLADEFGVAVVITNQVVAQVDGA
AMFAADPKKPIGGNIIAHASTTRLYLRKGRGETRICKIYDSPCLPEAEAMFAINADGV
GDAKD

Figure 19B

RAD51

```
  1 gttacgtcga cgcgggcgtg accctgggcg agagggtttg gcgggaattc tgaaagccgc
 61 tggcggaccg cgcgcagcgg ccagagaccg agccctaagg agagtgcggc gcttcccgag
121 gcgtgcagct gggaactgca actcatctgg gttgtgcgca gaaggctggg gcaagcgagt
181 agagaagtgg agcgtaagcc aggggcgttg ggggccgtgc gggtcgggcg cgtgccacgc
241 ccgcggggtg aagtcggagc gcggggcctg ctggagagag gagcgctgcg gaccgagtaa
301 tggcaatgca gatgcagctt gaagcaaatg cagatacttc agtggaagaa gaaagctttg
361 gcccacaacc catttcacgg ttagagcagt gtggcataaa tgccaacgat gtgaagaaat
421 tggaagaagc tggattccat actgtggagg ctgttgccta tgcgccaaag aaggagctaa
481 taaatattaa gggaattagt gaagccaaag ctgataaaat tctggctgag gcagctaaat
541 tagttccaat gggtttcacc actgcaactg aattccacca aaggcggtca gagatcatac
601 agattactac tggctccaaa gagcttgaca aactacttca aggtggaatt gagactggat
661 ctatcacaga aatgtttgga gaattccgaa ctgggaagac ccagatctgt catacgctag
721 ctgtcacctg ccagcttccc attgaccggg gtggaggtga aggaaaggcc atgtacattg
781 acactgaggg tacctttagg ccagaacggc tgctggcagt ggctgagagg tatggtctct
841 ctggcagtga tgtcctggat aatgtagcat atgctcgagc gttcaacaca gaccaccaga
901 cccagctcct ttatcaagca tcagccatga tggtagaatc taggtatgca ctgcttattg
961 tagacagtgc caccgccctt tacagaacag actactcggg tcgaggtgag ctttcagcca
```

1021 ggcagatgca cttggccagg tttctgcgga tgcttctgcg actcgctgat gagtttggtg
1081 tagcagtggt aatcactaat caggtggtag ctcaagtgga tggagcagcg atgtttgctg
1141 ctgatcccaa aaaacctatt ggaggaaata tcatcgccca tgcatcaaca accagattgt
1201 atctgaggaa aggaagaggg gaaaccagaa tctgcaaaat ctacgactct ccctgtcttc
1261 ctgaagctga agctatgttc gccattaatg cagatggagt gggagatgcc aaagactgaa
1321 tcattgggtt tttcctctgt taaaaacctt aagtgctgca gcctaatgag agtgcactgc
1381 tccctggggt tctctacagg cctcttcctg ttgtgactgc caggataaag cttccgggaa
1441 aacagctatt atatcagctt ttctgatggt ataaacagga gacaggtcag tagtcacaaa
1501 ctgatctaaa atgtttattc cttctgtagt gtattaatct ctgtgtgttt tctttggttt
1561 tggaggaggg gtatgaagta tctttgacat ggtgccttag gaatgacttg ggtttaacaa
1621 gctgtctact ggacaatctt atgtttccaa gagaactaaa gctggagaga cctgacccct
1681 ctctcacttc taaattaatg gtaaaataaa atgcctcagc tatgtagcaa agggaatggg
1741 tctgcacaga ttcttttttt ctgtcagtaa aactctcaag caggttttta agttgtctgt
1801 ctgaatgatc ttgtgtaagg ttttggttat ggagtcttgt gccaaaccta ctaggccatt
1861 agcccttcac catctacctg cttggtcttt cattgctaag actaactcaa gataatccta
1921 gagtcttaaa gcatttcagg ccagtgtggt gtcttgcgcc tgtactccca gcactttggg
1981 aggccgaggc aggtggatcg cttgagccca ggagttttaa gtccagcttg gccaaggtgg
2041 tgaaatccca tctctacaaa aaatgcagaa cttaatctgg acacactgtt acacgtgcct
2101 gtagtcccag ctactcgata gcctgaggtg ggagaatcac ttaagcctgg aaggtggaag
2161 ttgcagtgag tcgagattgc actgctgcat tccagccagg gtgacagagt gagaccatgt
2221 ttcaaacaag aaacatttca gagggtaagt aaacagattt gattgtgagg cttctaataa
2281 agtagttatt agtagtgaa Figure 19B (continued)

Figure 20A

MRE11A

MSTADALDDENTFKILVATDIHLGFMEKDAVRGNDTFVTLDEIL
RLAQENEVDFILLGGDLFHENKPSRKTLHTCLELLRKYCMGDRPVQFEILSDQSVNFG
FSKFPWVNYQDGNLNISIPVFSIHGNHDDPTGADALCALDILSCAGFVNHFGRSMSVE
KIDISPVLLQKGSTKIALYGLGSIPDERLYRMFVNKKVTMLRPKEDENSWFNLFVIHQ
NRSKHGSTNFIPEQFLDDFIDLVIWGHEHECKIAPTKNEQQLFYISQPGSSVVTSLSP
GEAVKKHVGLLRIKGRKMNMHKIPLHTVRQFFMEDIVLANHPDIFNPDNPKVTQAIQS
FCLEKIEEMLENAERERLGNSHQPEKPLVRLRVDYSGGFEPFSVLRFSQKFVDRVANP
KDIIHFFRHREQKEKTGEEINFGKLITKPSEGTTLRVEDLVKQYFQTAEKNVQLSLLT
ERGMGEAVQEFVDKEEKDAIEELVKYQLEKTQRFLKERHIDALEDKIDEEVRRFRETR
QKNTNEEDDEVREAMTRARALRSQSEESASAFSADDLMSIDLAEQMANDSDDSISAAT
NKGRGRGRGRRGGRGQNSASRGGSQRGRADTGLETSTRSRNSKTAVSASRNMSIIDAF
KSTRQQPSRNVTTKNYSEVIEVDESDVEEDIFPTTSKTDQRWSSTSSSKIMSQSQVSK
GVDFESSEDDDDDPFMNTSSLRRNRR

Figure 20B

MRE11A 1 acgttatcca tgaagtgtcg cgagagaaac ggacgccgtt ctctcccgcg gaattcaggt
61 ttacggccct gcgggttctc agagaatttc tagaatttgg aatcgagtgc attttctgac
121 atttgagtac agtacccagg ggttcttgga gaagaacctg gtcccagagg agcttgactg
181 accataaaaa tgagtactgc agatgcactt gatgatgaaa acacatttaa aatattagtt
241 gcaacagata ttcatcttgg atttatggag aaagatgcag tcagaggaaa tgatacgttt
301 gtaacactcg atgaaatttt aagacttgcc caggaaaatg aagtggattt tattttgtta
361 ggtggtgatc tttttcatga aaataagccc tcaaggaaaa cattacatac ctgcctcgag
421 ttattaagaa aatattgtat gggtgatcgg cctgtccagt ttgaaattct cagtgatcag
481 tcagtcaact ttggttttag taagtttcca tgggtgaact atcaagatgg caacctcaac
541 atttcaattc cagtgtttag tattcatggc aatcatgacg atcccacagg ggcagatgca
601 ctttgtgcct tggacatttt aagttgtgct ggatttgtaa atcactttgg acgttcaatg 661 tctgtggaga agatagacat tagtccggtt ttgcttcaaa aaggaagcac aaagattgcg
721 ctatatggtt taggatccat tccagatgaa aggctctatc gaatgtttgt caataaaaaa
781 gtaacaatgt tgagaccaaa ggaagatgag aactcttggt ttaacttatt tgtgattcat
841 cagaacagga gtaaacatgg aagtactaac ttcattccag aacaattttt ggatgacttc
901 attgatcttg ttatctgggg ccatgaacat gagtgtaaaa tagctccaac caaaaatgaa
961 caacagctgt tttatatctc acaacctgga agctcagtgg ttacttctct ttccccagga
1021 gaagctgtaa agaaacatgt tggtttgctg cgtattaaag ggaggaagat gaatatgcat
1081 aaaattcctc ttcacacagt gcggcagttt ttcatggagg atattgttct agctaatcat
1141 ccagacattt ttaacccaga taatcctaaa gtaacccaag ccatacaaag cttctgtttg
1201 gagaagattg aagaaatgct tgaaaatgct gaacgggaac gtctgggtaa ttctcaccag
1261 ccagagaagc ctcttgtacg actgcgagtg gactatagtg gaggttttga acctttcagt
1321 gttcttcgct ttagccagaa atttgtggat cgggtagcta atccaaaaga cattatccat
1381 tttttcaggc atagagaaca aaaggaaaaa acaggagaag agatcaactt tgggaaactt
1441 atcacaaagc cttcagaagg aacaacttta agggtagaag atcttgtaaa acagtacttt
1501 caaaccgcag agaagaatgt gcagctctca ctgctaacag aaagagggat gggtgaagca
1561 gtacaagaat ttgtggacaa ggaggagaaa gatgccattg aggaattagt gaaataccag
1621 ttggaaaaaa cacagcgatt tcttaaagaa cgtcatattg atgccctcga agacaaaatc
1681 gatgaggagg tacgtcgttt cagagaaacc agacaaaaaa atactaatga agaagatgat
1741 gaagtccgtg aggctatgac cagggccaga gcactcagat ctcagtcaga ggagtctgct
1801 tctgccttta gtgctgatga ccttatgagt atagatttag cagaacagat ggctaatgac
1861 tctgatgata gcatctcagc agcaaccaac aaaggaagag gccgaggaag aggtcgaaga
1921 ggtggaagag ggcagaattc agcatcgaga ggagggtctc aaagaggaag agcagacact
1981 ggtctggaga cttctacccg tagcaggaac tcaaagactg ctgtgtcagc atctagaaat
2041 atgtctatta tagatgcctt taaatctaca agacagcagc cttcccgaaa tgtcactact
2101 aagaattatt cagaggtgat tgaggtagat gaatcagatg tggaagaaga cattttttcct
2161 accacttcaa agacagatca aaggtggtcc agcacatcat ccagcaaaat catgtcccag
2221 agtcaagtat cgaaaggggt tgattttgaa tcaagtgagg atgatgatga tgatcctttt
2281 atgaacacta gttctttaag aagaaataga agataatata tttaatggca ctgagaaaca
2341 tgcaagatac aggaaaaatg aaaatgttac aagctaagag tttacagttt aagattttaa Figure 20B (continued)

2401 gtattgtttc ctgagcataa ctccataagt aagaaatttc tagttcacag acatacaata
2461 gcattgattc accttgtttt tttaacctgg ttgttgtagt aagagctttg tttcaatatc
2521 actcttgagt aaagattaaa ataaagctac cattttacat ttctatttca taatgaaaaa
2581 ctatgtcagt attttaatat ggttacattt agccaaagtt gagggaaaga gcttataaaa
2641 tttaacttct tcataatttt agtaatttcc tagaggttct gggttttctg aaagtaaaac
2701 aatttatgcg aacctatgtc taaattcact gtttgttact atgtatgttt ttttccaatg
2761 cttcttataa gactaaatga ttagaagtac ctaatagttt gaacagatat gtttttattt
2821 aaaagagtag aataaccttt cagaattact gagtttttta ttccagttgt agcaaagatt
2881 tcaaaagatt gtgttcccat taagtggtag taatttcctt tattattctg tatccttaat
2941 ggtgttctct ctctctctct ctctctctct ctctccctct cccccccgtt ccccactctt
3001 cctttctcct ttgctttttc ttctctttca tacatatatg cgtgcctagt tctaggagga
3061 aacgggttaa aaattgtttt aaactacatc ttgaaaatat tgaagaattt gttttaggta
3121 gagtggtcag ttgaacctta cagtaaagta tagaaatata tttaatgtgg aatgtcaatg
3181 ccaggatttc tcattaacaa tattttatct caactttggt tcctgtgata catttctgaa
3241 tgggcaattc cagaaatctt agtagcccat gttaagcttc tatttttttac ttgttttcgg
3301 ggagaaataa gaattagaca tcttcagatt taagttaaat aatcccattc tttataatcc
3361 tctgtaaaaa gatccctgag attattcctt cttctagttt tatgcgacag ctttacttta
3421 aaattcaagt tatacatctt gggagtacaa tggcccgaca tttcttcata ggtagaaaca
3481 aatacttgac tcagtgatac tcatgaccat tagaatagtc atacctggaa tgtgtcaaat
3541 tataagagac agacacttgg ttagtggctg cctcatatag cacttttgaa gaggcctaag
3601 tcaaaacttg caatataaca ttctattgac tttcttaaaa atattttttc tgtacctaac
3661 ttgagcataa gggttatttg agcaagtaac attaactcag tggaaggcat tgtcctgtga
3721 aatattctta ggcagatctg cccacatctt tattgaactt gaaatctaat atttctagta
3781 tttgaacaaa gcagaaggtt aagtcaggga agagcagtgc tgtccatgat gtaatggaag
3841 ctaccagggg aggcagtgtc tggatgatgc tgtgctacct acccctgcac aagccatgct
3901 ggctcagtct gagctgtggg ccacatcagc tagtggctct tctcatgcat cagttaggtg
3961 ggtctgggtg agagttatag tgagggaatg gtcactaaag tatcctgaca agttcctagg
4021 aaaaaaggaa taaagttttt ttccttaaaa aaaaaaaaat tgctcttggc tgtgaaaaga
4081 ggtactaaat gcgattcagt tcaccgctaa ggaaagtgat gacatagcag ttacagaggg Figure 20B (continued)

4141 tgataaatct ctccagctaa ttcaggtcat tttgtgaata ctatgtatca agccctgaaa
4201 atatggtaaa taaaacgtga cagggaaacc ttttttgat tgaatattgt tacatagtta
4261 aatgtgctat atatccttaa tattttatat tgatcctgca aaatctgttg gttttagggg
4321 agttttgttt tttgtttcta acaattttca gacctgttgg tataggaatg tagaagtctt
4381 tcagatgatt tgaaagcagc tgcatttgct cttggaggct ttgggagagc aggaatgaaa
4441 acattcagag gaagacatct gtagggaatt cttctgttac ttaccaaaga ataagtgtct
4501 ttctggtgtt ttatttccta tcataaaaat acaacagtgc atttacaagg ttaaagattc
4561 ctcgaagttc taggaaattc ttgaaaatat aagtggtgct tagaaaattc aagcatttag
4621 gaatgtgacc tttaattcag gtatgtaaaa gactttttc ccaaactttt aaaagtagga
4681 aatacaataa atacagaaaa gtcatatggt tgaataaata attataaatt gagcactgat
4741 ggaatccctc tacaggtcaa gaaatagcgc agtgtcctgg atgcccatta tattgttttc
4801 tcctttctgg gtaacaagcc ctaacttctg taatttaaaa gctcctactt ttgccacaag
4861 gtggtgcttc tgccattaga cgcagttagg aggatgcaac tgcaaatcta aaattacgaa
4921 gttagtgtag ttgcaataaa cttagaacat atgcattaat actaaaccta tgcagtaata
4981 ccataattag ccttctaatc atgtaatttg ctttacttag gtatttcatt tggttcagcc
5041 tgttatggaa tttaccagct tgataaattt gcctataaag ttttataaag aaaaggaata
5101 ttttgttttc ataaagagga aaatccattc ttagaaaaaa a Figure 20B (continued)

Figure 21A

ATM

MSLVLNDLLICCRQLEHDRATERKKEVEKFKRLIRDPETIKHLD

RHSDSKQGKYLNWDAVFRFLQKYIQKETECLRIAKPNVSASTQASRQKKMQEISSLVK

YFIKCANRRAPRLKCQELLNYIMDTVKDSSNGAIYGADCSNILLKDILSVRKYWCEIS

QQQWLELFSVYFRLYLKPSQDVHRVLVARIIHAVTKGCCSQTDGLNSKFLDFFSKAIQ

CARQEKSSSGLNHILAALTIFLKTLAVNFRIRVCELGDEILPTLLYIWTQHRLNDSLK

EVIIELFQLQIYIHHPKGAKTQEKGAYESTKWRSILYNLYDLLVNEISHIGSRGKYSS

GFRNIAVKENLIELMADICHQVFNEDTRSLEISQSYTTTQRESSDYSVPCKRKKIELG

WEVIKDHLQKSQNDFDLVPWLQIATQLISKYPASLPNCELSPLLMILSQLLPQQRHGE

RTPYVLRCLTEVALCQDKRSNLESSQKSDLLKLWNKIWCITFRGISSEQIQAENFGLL

GAIIQGSLVEVDREFWKLFTGSACRPSCPAVCCLTLALTTSIVPGTVKMGIEQNMCEV

NRSFSLKESIMKWLLFYQLEGDLENSTEVPPILHSNFPHLVLEKILVSLTMKNCKAAM

NFFQSVPECEHHQKDKEELSFSEVEELFLQTTFDKMDFLTIVRECGIEKHQSSIGFSV

HQNLKESLDRCLLGLSEQLLNNYSSEITNSETLVRCSRLLVGVLGCYCYMGVIAEEEA

YKSELFQKAKSLMQCAGESITLFKNKTNEEFRIGSLRNMMQLCTRCLSNCTKKSPNKI

ASGFFLRLLTSKLMNDIADICKSLASFIKKPFDRGEVESMEDDTNGNLMEVEDQSSMN

LFNDYPDSSVSDANEPGESQSTIGAINPLAEEYLSKQDLLFLDMLKFLCLCVTTAQTN

TVSFRAADIRRKLLMLIDSSTLEPTKSLHLHMYLMLLKELPGEEYPLPMEDVLELLKP

LSNVCSLYRRDQDVCKTILNHVLHVVKNLGQSNMDSENTRDAQGQFLTVIGAFWHLTK

ERKYIFSVRMALVNCLKTLLEADPYSKWAILNVMGKDFPVNEVFTQFLADNHHQVRML

AAESINRLFQDTKGDSSRLLKALPLKLQQTAFENAYLKAQEGMREMSHSAENPETLDE

IYNRKSVLLTLIAVVLSCSPICEKQALFALCKSVKENGLEPHLVKKVLEKVSETFGYR

RLEDFMASHLDYLVLEWLNLQDTEYNLSSFPFILLNYTNIEDFYRSCYKVLIPHLVIR

SHFDEVKSIANQIQEDWKSLLTDCFPKILVNILPYFAYEGTRDSGMAQQRETATKVYD

MLKSENLLGKQIDHLFISNLPEIVVELLMTLHEPANSSASQSTDLCDFSGDLDPAPNP

PHFPSHVIKATFAYISNCHKTKLKSILEILSKSPDSYQKILLAICEQAAETNNVYKKH

RILKIYHLFVSLLLKDIKSGLGGAWAFVLRDVIYTLIHYINQRPSCIMDVSLRSFSLC

CDLLSQVCQTAVTYCKDALENHLHVIVGTLIPLVYEQVEVQKQVLDLLKYLVIDNKDN

Figure 21A (continued)

ENLYITIKLLDPFPDHVVFKDLRITQQKIKYSRGPFSLLEEINHFLSVSVYDALPLTR
LEGLKDLRRQLELHKDQMVDIMRASQDNPQDGIMVKLVVNLLQLSKMAINHTGEKEVL
EAVGSCLGEVGPIDFSTIAIQHSKDASYTKALKLFEDKELQWTFIMLTYLNNTLVEDC
VKVRSAAVTCLKNILATKTGHSFWEIYKMTTDPMLAYLQPFRTSRKKFLEVPRFDKEN
PFEGLDDINLWIPLSENHDIWIKTLTCAFLDSGGTKCEILQLLKPMCEVKTDFCQTVL
PYLIHDILLQDTNESWRNLLSTHVQGFFTSCLRHFSQTSRSTTPANLDSESEHFFRCC
LDKKSQRTMLAVVDYMRRQKRPSSGTIFNDAFWLDLNYLEVAKVAQSCAAHFTALLYA
EIYADKKSMDDQEKRSLAFEEGSQSTTISSLSEKSKEETGISLQDLLLEIYRSIGEPD
SLYGCGGGKMLQPITRLRTYEHEAMWGKALVTYDLETAIPSSTRQAGIIQALQNLGLC
HILSVYLKGLDYENKDWCPELEELHYQAAWRNMQWDHCTSVSKEVEGTSYHESLYNAL
QSLRDREFSTFYESLKYARVKEVEEMCKRSLESVYSLYPTLSRLQAIGELESIGELFS
RSVTHRQLSEVYIKWQKHSQLLKDSDFSFQEPIMALRTVILEILMEKEMDNSQRECIK
DILTKHLVELSILARTFKNTQLPERAIFQIKQYNSVSCGVSEWQLEEAQVFWAKKEQS
LALSILKQMIKKLDASCAANNPSLKLTYTECLRVCGNWLAETCLENPAVIMQTYLEKA
VEVAGNYDGESSDELRNGKMKAFLSLARFSDTQYQRIENYMKSSEFENKQALLKRAKE
EVGLLREHKIQTNRYTVKVQRELELDELALRALKEDRKRFLCKAVENYINCLLSGEEH
DMWVFRLCSLWLENSGVSEVNGMMKRDGMKIPTYKFLPLMYQLAARMGTKMMGGLGFH
EVLNNLISRISMDHPHHTLFIILALANANRDEFLTKPEVARRSRITKNVPKQSSQLDE
DRTEAANRIICTIRSRRPQMVRSVEALCDAYIILANLDATQWKTQRKGINIPADQPIT
KLKNLEDVVVPTMEIKVDHTGEYGNLVTIQSFKAEFRLAGGVNLPKIIDCVGSDGKER
RQLVKGRDDLRQDAVMQQVFQMCNTLLQRNTETRKRKLTICTYKVVPLSQRSGVLEWC
TGTVPIGEFLVNNEDGAHKRYRPNDFSAFQCQKKMMEVQKKSFEEKYEVFMDVCQNFQ
PVFRYFCMEKFLDPAIWFEKRLAYTRSVATSSIVGYILGLGDRHVQNILINEQSAELV
HIDLGVAFEQGKILPTPETVPFRLTRDIVDGMGITGVEGVFRRCCEKTMEVMRNSQET
LLTIVEVLLYDPLFDWTMNPLKALYLQQRPEDETELHPTLNADDQECKRNLSDIDQSF
NKVAERVLMRLQEKLKGVEEGTVLSVGGQVNLLIQQAIDPKNLSRLFPGWKAWV

Figure 21B

ATM 1 ccggagcccg agccgaaggg cgagccgcaa acgctaagtc gctggccatt ggtggacatg
61 gcgcaggcgc gtttgctccg acgggccgaa tgttttgggg cagtgttttg agcgcggaga
121 ccgcgtgata ctggatgcgc atgggcatac cgtgctctgc ggctgcttgg cgttgcttct
181 tcctccagaa gtgggcgctg ggcagtcacg cagggtttga accggaagcg ggagtaggta
241 gctgcgtggc taacggagaa aagaagccgt ggccgcggga ggaggcgaga ggagtcggga
301 tctgcgctgc agccaccgcc gcggttgata ctactttgac cttccgagtg cagtgacagt
361 gatgtgtgtt ctgaaattgt gaaccatgag tctagtactt aatgatctgc ttatctgctg
421 ccgtcaacta gaacatgata gagctacaga acgaaagaaa gaagttgaga aatttaagcg
481 cctgattcga gatcctgaaa caattaaaca tctagatcgg cattcagatt ccaaacaagg
541 aaaatatttg aattgggatg ctgtttttag atttttacag aaatatattc agaaagaaac
601 agaatgtctg agaatagcaa aaccaaatgt atcagcctca acacaagcct ccaggcagaa
661 aaagatgcag gaaatcagta gtttggtcaa atacttcatc aaatgtgcaa acagaagagc
721 acctaggcta aaatgtcaag aactcttaaa ttatatcatg gatacagtga aagattcatc
781 taatggtgct atttacggag ctgattgtag caacatacta ctcaaagaca ttctttctgt
841 gagaaaatac tggtgtgaaa tatctcagca acagtggtta gaattgttct ctgtgtactt
901 caggctctat ctgaaacctt cacaagatgt tcatagagtt ttagtggcta gaataattca
961 tgctgttacc aaaggatgct gttctcagac tgacggatta aattccaaat ttttggactt
1021 tttttccaag gctattcagt gtgcgagaca agaaaagagc tcttcaggtc taaatcatat
1081 cttagcagct cttactatct tcctcaagac tttggctgtc aactttcgaa ttcgagtgtg
1141 tgaattagga gatgaaattc ttcccacttt gctttatatt tggactcaac ataggcttaa
1201 tgattcttta aaagaagtca ttattgaatt atttcaactg caaatttata tccatcatcc
1261 gaaaggagcc aaaacccaag aaaaaggtgc ttatgaatca acaaaatgga gaagtatttt
1321 atacaactta tatgatctgc tagtgaatga gataagtcat ataggaagta gaggaaagta
1381 ttcttcagga tttcgtaata ttgccgtcaa agaaaatttg attgaattga tggcagatat
1441 ctgtcaccag gtttttaatg aagataccag atccttggag atttctcaat cttacactac
1501 tacacaaaga gaatctagtg attacagtgt cccttgcaaa aggaagaaaa tagaactagg
1561 ctgggaagta ataaaagatc accttcagaa gtcacagaat gattttgatc ttgtgccttg
1621 gctacagatt gcaacccaat taatatcaaa gtatcctgca agtttaccta actgtgagct
1681 gtctccatta ctgatgatac tatctcagct tctaccccaa cagcgacatg gggaacgtac Figure 21B (continued)

1741 accatatgtg ttacgatgcc ttacggaagt tgcattgtgt caagacaaga ggtcaaacct
1801 agaaagctca caaaagtcag atttattaaa actctggaat aaaatttggt gtattacctt
1861 tcgtggtata agttctgagc aaatacaagc tgaaaacttt ggcttacttg gagccataat
1921 tcagggtagt ttagttgagg ttgacagaga attctggaag ttatttactg ggtcagcctg
1981 cagaccttca tgtcctgcag tatgctgttt gactttggca ctgaccacca gtatagttcc
2041 aggaacggta aaaatgggaa tagagcaaaa tatgtgtgaa gtaaatagaa gcttttcttt
2101 aaaggaatca ataatgaaat ggctcttatt ctatcagtta gagggtgact tagaaaatag
2161 cacagaagtg cctccaattc ttcacagtaa ttttcctcat cttgtactgg agaaaattct
2221 tgtgagtctc actatgaaaa actgtaaagc tgcaatgaat tttttccaaa gcgtgccaga
2281 atgtgaacac caccaaaaag ataaagaaga actttcattc tcagaagtag aagaactatt
2341 tcttcagaca acttttgaca agatggactt tttaaccatt gtgagagaat gtggtataga
2401 aaagcaccag tccagtattg gcttctctgt ccaccagaat ctcaaggaat cactggatcg
2461 ctgtcttctg ggattatcag aacagcttct gaataattac tcatctgaga ttacaaattc
2521 agaaactctt gtccggtgtt cacgtctttt ggtgggtgtc cttggctgct actgttacat
2581 gggtgtaata gctgaagagg aagcatataa gtcagaatta ttccagaaag ccaagtctct
2641 aatgcaatgt gcaggagaaa gtatcactct gtttaaaaat aagacaaatg aggaattcag
2701 aattggttcc ttgagaaata tgatgcagct atgtacacgt tgcttgagca actgtaccaa
2761 gaagagtcca aataagattg catctggctt tttcctgcga ttgttaacat caaagctaat
2821 gaatgacatt gcagatattt gtaaaagttt agcatccttc atcaaaaagc catttgaccg
2881 tggagaagta gaatcaatgg aagatgatac taatggaaat ctaatggagg tggaggatca
2941 gtcatccatg aatctattta acgattaccc tgatagtagt gttagtgatg caaacgaacc
3001 tggagagagc caaagtacca taggtgccat taatccttta gctgaagaat atctgtcaaa
3061 gcaagatcta cttttcttag acatgctcaa gttcttgtgt ttgtgtgtaa ctactgctca
3121 gaccaatact gtgtccttta gggcagctga tattcggagg aaattgttaa tgttaattga
3181 ttctagcacg ctagaaccta ccaaatccct ccacctgcat atgtatctaa tgcttttaaa
3241 ggagcttcct ggagaagagt acccccttgcc aatggaagat gttcttgaac ttctgaaacc
3301 actatccaat gtgtgttctt tgtatcgtcg tgaccaagat gtttgtaaaa ctattttaaa
3361 ccatgtcctt catgtagtga aaaacctagg tcaaagcaat atggactctg agaacacaag
3421 ggatgctcaa ggacagtttc ttacagtaat tggagcattt tggcatctaa caaaggagag Figure 21B (continued)

3481 gaaatatata ttctctgtaa gaatggccct agtaaattgc cttaaaactt tgcttgaggc
3541 tgatccttat tcaaaatggg ccattcttaa tgtaatggga aaagactttc ctgtaaatga
3601 agtatttaca caatttcttg ctgacaatca tcaccaagtt cgcatgttgg ctgcagagtc
3661 aatcaataga ttgttccagg acacgaaggg agattcttcc aggttactga aagcacttcc
3721 tttgaagctt cagcaaacag cttttgaaaa tgcatacttg aaagctcagg aaggaatgag
3781 agaaatgtcc catagtgctg agaaccctga aactttggat gaaatttata atagaaaatc
3841 tgttttactg acgttgatag ctgtggtttt atcctgtagc cctatctgcg aaaaacaggc
3901 tttgtttgcc ctgtgtaaat ctgtgaaaga gaatggatta gaacctcacc ttgtgaaaaa
3961 ggttttagag aaagtttctg aaacttttgg atatagacgt ttagaagact ttatggcatc
4021 tcatttagat tatctggttt tggaatggct aaatcttcaa gatactgaat acaacttatc
4081 ttcttttcct tttattttat taaactacac aaatattgag gatttctata gatcttgtta
4141 taaggttttg attccacatc tggtgattag aagtcatttt gatgaggtga agtccattgc
4201 taatcagatt caagaggact ggaaaagtct tctaacagac tgctttccaa agattcttgt
4261 aaatattctt ccttattttg cctatgaggg taccagagac agtgggatgg cacagcaaag
4321 agagactgct accaaggtct atgatatgct taaaagtgaa aacttattgg gaaaacagat
4381 tgatcactta ttcattagta atttaccaga gattgtggtg gagttattga tgacgttaca
4441 tgagccagca aattctagtg ccagtcagag cactgacctc tgtgactttt caggggattt
4501 ggatcctgct cctaatccac ctcattttcc atcgcatgtg attaaagcaa catttgccta
4561 tatcagcaat tgtcataaaa ccaagttaaa aagcatttta gaaattcttt ccaaaagccc
4621 tgattcctat cagaaaattc ttcttgccat atgtgagcaa gcagctgaaa caaataatgt
4681 ttataagaag cacagaattc ttaaaatata tcacctgttt gttagtttat tactgaaaga
4741 tataaaaagt ggcttaggag gagcttgggc ctttgttctt cgagacgtta tttatacttt
4801 gattcactat atcaaccaaa ggccttcttg tatcatggat gtgtcattac gtagcttctc
4861 cctttgttgt gacttattaa gtcaggtttg ccagacagcc gtgacttact gtaaggatgc
4921 tctagaaaac catcttcatg ttattgttgg tacacttata ccccttgtgt atgagcaggt
4981 ggaggttcag aaacaggtat tggacttgtt gaaatactta gtgatagata acaaggataa
5041 tgaaaacctc tatatcacga ttaagctttt agatcctttt cctgaccatg ttgtttttaa
5101 ggatttgcgt attactcagc aaaaaaatcaa atacagtaga ggaccctttt cactcttgga
5161 ggaaattaac cattttctct cagtaagtgt ttatgatgca cttccattga caagacttga Figure 21B (continued)

5221 aggactaaag gatcttcgaa gacaactgga actacataaa gatcagatgg tggacattat
5281 gagagcttct caggataatc cgcaagatgg gattatggtg aaactagttg tcaatttgtt
5341 gcagttatcc aagatggcaa taaaccacac tggtgaaaaa gaagttctag aggctgttgg
5401 aagctgcttg ggagaagtgg gtcctataga tttctctacc atagctatac aacatagtaa
5461 agatgcatct tataccaagg cccttaagtt atttgaagat aaagaacttc agtggacctt
5521 cataatgctg acctacctga ataacacact ggtagaagat tgtgtcaaag ttcgatcagc
5581 agctgttacc tgtttgaaaa acattttagc cacaaagact ggacatagtt tctgggagat
5641 ttataagatg acaacagatc caatgctggc ctatctacag ccttttagaa catcaagaaa
5701 aaagtttttta gaagtaccca gatttgacaa agaaaaccct tttgaaggcc tggatgatat
5761 aaatctgtgg attcctctaa gtgaaaatca tgacatttgg ataaagacac tgacttgtgc
5821 ttttttggac agtggaggca caaaatgtga aattcttcaa ttattaaagc caatgtgtga
5881 agtgaaaact gacttttgtc agactgtact tccatacttg attcatgata ttttactcca
5941 agatacaaat gaatcatgga gaaatctgct ttctacacat gttcagggat ttttcaccag
6001 ctgtcttcga cacttctcgc aaacgagccg atccacaacc cctgcaaact tggattcaga
6061 gtcagagcac tttttccgat gctgtttgga taaaaaatca caaagaacaa tgcttgctgt
6121 tgtggactac atgagaagac aaaagagacc ttcttcagga acaattttta atgatgcttt
6181 ctggctggat ttaaattatc tagaagttgc caaggtagct cagtcttgtg ctgctcactt
6241 tacagcttta ctctatgcag aaatctatgc agataagaaa agtatggatg atcaagagaa
6301 aagaagtctt gcatttgaag aaggaagcca gagtacaact atttctagct tgagtgaaaa
6361 aagtaaagaa gaaactggaa taagtttaca ggatcttctc ttagaaatct acagaagtat
6421 aggggagcca gatagtttgt atggctgtgg tggagggaag atgttacaac ccattactag
6481 actacgaaca tatgaacacg aagcaatgtg gggcaaagcc ctagtaacat atgacctcga
6541 aacagcaatc ccctcatcaa cacgccaggc aggaatcatt caggccttgc agaatttggg
6601 actctgccat attctttccg tctatttaaa aggattggat tatgaaaata aagactggtg
6661 tcctgaacta gaagaacttc attaccaagc agcatggagg aatatgcagt gggaccattg
6721 cacttccgtc agcaaagaag tagaaggaac cagttaccat gaatcattgt acaatgctct
6781 acaatctcta agagacagag aattctctac attttatgaa agtctcaaat atgccagagt
6841 aaaagaagtg gaagagatgt gtaagcgcag ccttgagtct gtgtattcgc tctatcccac
6901 acttagcagg ttgcaggcca ttggagagct ggaaagcatt ggggagcttt tctcaagatc Figure 21B (continued)

6961 agtcacacat agacaactct ctgaagtata tattaagtgg cagaaacact cccagcttct
7021 caaggacagt gattttagtt ttcaggagcc tatcatggct ctacgcacag tcattttgga
7081 gatcctgatg gaaaaggaaa tggacaactc acaaagagaa tgtattaagg acattctcac
7141 caaacacctt gtagaactct ctatactggc cagaactttc aagaacactc agctccctga
7201 aagggcaata tttcaaatta aacagtacaa ttcagttagc tgtggagtct ctgagtggca
7261 gctggaagaa gcacaagtat tctgggcaaa aaaggagcag agtcttgccc tgagtattct
7321 caagcaaatg atcaagaagt tggatgccag ctgtgcagcg aacaatccca gcctaaaact
7381 tacatacaca gaatgtctga gggtttgtgg caactggtta gcagaaacgt gcttagaaaa
7441 tcctgcggtc atcatgcaga cctatctaga aaaggcagta gaagttgctg gaaattatga
7501 tggagaaagt agtgatgagc taagaaatgg aaaaatgaag gcatttctct cattagcccg
7561 gttttcagat actcaatacc aaagaattga aaactacatg aaatcatcgg aatttgaaaa
7621 caagcaagct ctcctgaaaa gagccaaaga ggaagtaggt ctccttaggg aacataaaat
7681 tcagacaaac agatacacag taaaggttca gcgagagctg gagttggatg aattagccct
7741 gcgtgcactg aaagaggatc gtaaacgctt cttatgtaaa gcagttgaaa attatatcaa
7801 ctgcttatta agtggagaag aacatgatat gtgggtattc cgactttgtt ccctctggct
7861 tgaaaattct ggagtttctg aagtcaatgg catgatgaag agagacggaa tgaagattcc
7921 aacatataaa tttttgcctc ttatgtacca attggctgct agaatgggga ccaagatgat
7981 gggaggccta ggatttcatg aagtcctcaa taatctaatc tctagaattt caatggatca
8041 cccccatcac actttgttta ttatactggc cttagcaaat gcaaacagag atgaatttct
8101 gactaaacca gaggtagcca gaagaagcag aataactaaa aatgtgccta aacaaagctc
8161 tcagcttgat gaggatcgaa cagaggctgc aaatagaata atatgtacta tcagaagtag
8221 gagacctcag atggtcagaa gtgttgaggc actttgtgat gcttatatta tattagcaaa
8281 cttagatgcc actcagtgga agactcagag aaaaggcata aatattccag cagaccagcc
8341 aattactaaa cttaagaatt tagaagatgt tgttgtccct actatggaaa ttaaggtgga
8401 ccacacagga gaatatggaa atctggtgac tatacagtca tttaaagcag aatttcgctt
8461 agcaggaggt gtaaatttac caaaaataat agattgtgta ggttccgatg gcaaggagag
8521 gagacagctt gttaagggcc gtgatgacct gagacaagat gctgtcatgc aacaggtctt
8581 ccagatgtgt aatacattac tgcagagaaa cacggaaact aggaagagga aattaactat
8641 ctgtacttat aaggtggttc cctctctca gcgaagtggt gttcttgaat ggtgcacagg Figure 21B (continued)

8701 aactgtcccc attggtgaat ttcttgttaa caatgaagat ggtgctcata aaagatacag 8761 gccaaatgat ttcagtgcct ttcagtgcca aaagaaaatg atggaggtgc aaaaaaagtc 8821 ttttgaagag aaatatgaag tcttcatgga tgtttgccaa aattttcaac cagttttccg 8881 ttacttctgc atggaaaaat tcttggatcc agctatttgg tttgagaagc gattggctta 8941 tacgcgcagt gtagctactt cttctattgt tggttacata cttggacttg gtgatagaca 9001 tgtacagaat atcttgataa atgagcagtc agcagaactt gtacatatag atctaggtgt 9061 tgcttttgaa cagggcaaaa tccttcctac tcctgagaca gttcctttta gactcaccag 9121 agatattgtg gatggcatgg gcattacggg tgttgaaggt gtcttcagaa gatgctgtga 9181 gaaaaccatg gaagtgatga gaaactctca ggaaactctg ttaaccattg tagaggtcct 9241 tctatatgat ccactctttg actggaccat gaatcctttg aaagctttgt atttacagca 9301 gaggccggaa gatgaaactg agcttcaccc tactctgaat gcagatgacc aagaatgcaa 9361 acgaaatctc agtgatattg accagagttt caacaaagta gctgaacgtg tcttaatgag 9421 actacaagag aaactgaaag gagtggaaga aggcactgtg ctcagtgttg gtggacaagt 9481 gaatttgctc atacagcagg ccatagaccc caaaaatctc agccgacttt tcccaggatg 9541 gaaagcttgg gtgtgatctt cagtatatga attacccttt cattcagcct ttagaaatta 9601 tattttagcc tttattttta acctgccaac atactttaag tagggattaa tatttaagtg 9661 aactattgtg ggttttttg aatgttggtt ttaatacttg atttaatcac cactcaaaaa 9721 tgttttgatg gtcttaagga acatctctgc tttcactctt tagaaataat ggtcattcgg 9781 gctgggcgca gcggctcacg cctgtaatcc cagcactttg ggaggccgag gtgagcggat 9841 cacaaggtca ggagttcgag accagcctgg ccaagagacc agcctggcca gtatggtgaa 9901 accctgtctc tactaaaaat acaaaaatta gccgagcatg gtggcgggca cctgtaatcc 9961 cagctactcg agaggctgag gcaggagaat ctcttgaacc tgggaggtga aggttgctgt 10021 gggccaaaat catgccattg cactccagcc tgggtgacaa gagcgaaact ccatctcaaa 10081 aaaaaaaaaa aaaaaacaga aacgtatttg gatttttcct agtaagatca ctcagtgtta 10141 ctaaataatg aagttgttat ggagaacaaa tttcaaagac acagttagtg tagttactat 10201 ttttttaagt gtgtattaaa acttctcatt ctattctctt tatcttttaa gcccttctgt 10261 actgtccatg tatgttatct ttctgtgata acttcataga ttgccttcta gttcatgaat 10321 tctcttgtca gatgtatata atctctttta ccctatccat tgggcttctt ctttcagaaa 10381 ttgtttttca tttctaatta tgcatcattt ttcagatctc tgtttcttga tgtcattttt Figure 21B (continued)

10441 aatgtttttt taatgttttt tatgtcacta attattttaa atgtctgtac ttgatagaca
10501 ctgtaatagt tctattaaat ttagttcctg ctgtttatat ctgttgattt ttgtatttga
10561 taggctgttc atccagtttt gtctttttga aaagtgagtt tattttcagc aaggctttat
10621 ctatgggaat cttgagtgtc tgtttatgtc atattcccag ggctgttgct gcacacaagc
10681 ccattcttat tttaatttct tggctttagg gtttccatac ctgaagtgta gcataaatac
10741 tgataggaga tttcccaggc caaggcaaac acacttcctc ctcatctcct tgtgctagtg
10801 ggcagaatat ttgattgatg cctttttcac tgagagtata agcttccatg tgtcccacct
10861 ttatggcagg ggtggaagga ggtacattta attcccactg cctgcctttg gcaagccctg
10921 ggttctttgc tccccatata gatgtctaag ctaaaagccg tgggttaatg agactggcaa
10981 attgttccag gacagctaca gcatcagctc acatattcac ctctctggtt tttcattccc
11041 ctcatttttt tctgagacag agtcttgctc tgtcacccag gctggagtgc agtggcatga
11101 tctcagctca ctgaaacctc tgcctcctgg gttcaagcaa ttctcctgcc tcagcctccc
11161 gagtagctgg gactacaggc gtgtgccaac acgcccggct aatttttgt atttttatta
11221 gagacggagt ttcaccgtgt tagccaggat ggtctcgatc gcttgacctc gtgatccacc
11281 ctcctcggcc tcccaaagtg ctgggattac aggtgtgagc caccgcgccc ggcctcattc
11341 ccctcatttt tgaccgtaag gatttcccct ttcttgtaag ttctgctatg tatttaaaag
11401 aatgttttct acattttatc cagcatttct ctgtgttctg ttggaaggga agggcttagg
11461 tatctagttt gatacatagg tagaagtgga acatttctct gtccccccagc tgtcatcata
11521 taagataaac atcagataaa aagccacctg aaagtaaaac tactgactcg tgtattagtg
11581 agtataatct cttctccatc cttaggaaaa tgttcatccc agctgcggag attaacaaat
11641 gggtgattga gctttctcct cgtatttgga ccttgaaggt tatataaatt tttttcttat
11701 gaagagttgg catttctttt tattgccaat ggcaggcact cattcatatt tgatctcctc
11761 accttcccct cccctaaaac caatctccag aactttttgg actataaatt tcttggtttg
11821 acttctggag aactgttcag aatattactt tgcatttcaa attacaaact taccttggtg
11881 tatctttttc ttacaagctg cctaaatgaa tatttggtat atattggtag ttttattact
11941 atagtaaatc aaggaaatgc agtaaactta aaatgtcttt aagaaagccc tgaaatcttc
12001 atgggtgaaa ttagaaatta tcaactagat aatagtatag ataaatgaat ttgtagctaa
12061 ttcttgctag ttgttgcatc cagagagctt tgaataacat cattaatcta ctctttagcc
12121 ttgcatggta tgctatgagg ctcctgttct gttcaagtat tctaatcaat ggctttgaaa Figure 21B (continued)

12181 agtttatcaa atttacatac agatcacaag cctaggagaa ataactaatt cacagatgac 12241 agaattaaga ttataaaaga tttttttttt gtaattttag tagagacagg gttgccattg 12301 tattccagcc ttggcgacag agcaagactc tgcctcaaaa aaaaaaaaaa aaaggttttg 12361 gcaagctgga actctttctg caaatgacta agatagaaaa ctgccaagga caaatgagga 12421 gtagttagat tttgaaaata ttaatcatag aatagttgtt gtatgctaag tcactgaccc 12481 atattatgta cagcatttct gatctttact ttgcaagatt agtgatacta tcccaataca 12541 ctgctggaga aatcagaatt tggagaaata agttgtccaa ggcaagaaga tagtaaatta 12601 taagtacaag tgtaatatgg acagtatcta acttgaaaag atttcaggcg aaaagaatct 12661 ggggtttgcc agtcagttgc tcaaaaggtc aatgaaaacc aaatagtgaa gctatcagag 12721 aagctaataa attatagact gcttgaacag ttgtgtccag attaagggag ataatagctt 12781 tcccacccta ctttgtgcag gtcatacctc cccaaagtgt ttacctaatc agtaggttca 12841 caaactcttg gtcattatag tatatgccta aaatgtatgc acttaggaat gctaaaaatt 12901 taaatatggt ctaaagcaaa taaaagcaaa gaggaaaaac tttggacagc gtaaagacta 12961 gaatagtctt ttaaaaagaa agccagtata ttggtttgaa atatagagat gtgtcccaat 13021 ttcaagtatt ttaattgcac cttaatgaaa ttatctattt tctatagatt ttagtactat 13081 tgaatgtatt actttactgt tacctgaatt tattataaag tgtttttgaa taaataattc 13141 taaaagc Figure 21B (continued)

Figure 22A

ATR

MGEHGLELASMIPALRELGSATPEEYNTVVQKPRQILCQFIDRI
LTDVNVVAVELVKKTDSQPTSVMLLDFIQHIMKSSPLMFVNVSGSHEAKGSCIEFSNW
IITRLLRIAATPSCHLLHKKICEVICSLLFLFKSKSPAIFGVLTKELLQLFEDLVYLH
RRNVMGHAVEWPVVMSRFLSQLDEHMGYLQSAPLQLMSMQNLEFIEVTLLMVLTRIIA
IVFFRRQELLLWQIGCVLLEYGSPKIKSLAISFLTELFQLGGLPAQPASTFFSSFLEL
LKHLVEMDTDQLKLYEEPLSKLIKTLFPFEAEAYRNIEPVYLNMLLEKLCVMFEDGVL
MRLKSDLLKAALCHLLQYFLKFVPAGYESALQVRKVYVRNICKALLDVLGIEVDAEYL
LGPLYAALKMESMEIIEEIQCQTQQENLSSNSDGISPKRRRLSSSLNPSKRAPKQTEE
IKHVDMNQKSILWSALKQKAESLQISLEYSGLKNPVIEMLEGIAVVLQLTALCTVHCS
HQNMNCRTFKDCQHKSKKKPSVVITWMSLDFYTKVLKSCRSLLESVQKLDLEATIDKV
VKIYDALIYMQVNSSFEDHILEDLCGMLSLPWIYSHSDDGCLKLTTFAANLLTLSCRI
SDSYSPQAQSRCVFLLTLFPRRIFLEWRTAVYNWALQSSHEVIRASCVSGFFILLQQQ
NSCNRVPKILIDKVKDDSDIVKKEFASILGQLVCTLHGMFYLTSSLTEPFSEHGHVDL
FCRNLKATSQHECSSSQLKASVCKPFLFLLKKKIPSPVKLAFIDNLHHLCKHLDFRED
ETDVKAVLGTLLNLMEDPDKDVRVAFSGNIKHILESLDSEDGFIKELFVLRMKEAYTH
AQISRNNELKDTLILTTGDIGRAAKGDLVPFALLHLLHCLLSKSASVSGAAYTEIRAL
VAAKSVKLQSFFSQYKKPICQFLVESLHSSQMTALPNTPCQNADVRKQDVAHQREMAL
NTLSEIANVFDFPDLNRFLTRTLQVLLPDLAAKASPAASALIRTLGKQLNVNRREILI
NNFKYIFSHLVCSCSKDELERALHYLKNETEIELGSLLRQDFQGLHNELLLRIGEHYQ
QVFNGLSILASFASSDDPYQGPRDIISPELMADYLQPKLLGILAFFNMQLLSSSVGIE
DKKMALNSLMSLMKLMGPKHVSSVRVKMMTTLRTGLRFKDDFPELCCRAWDCFVRCLD
HACLGSLLSHVIVALLPLIHIQPKETAAIFHYLIIENRDAVQDFLHEIYFLPDHPELK
KIKAVLQEYRKETSESTDLQTTLQLSMKAIQHENVDVRIHALTSLKETLYKNQEKLIK
YATDSETVEPIISQLVTVLLKGCQDANSQARLLCGECLGELGAIDPGRLDFSTTETQG
KDFTFVTGVEDSSFAYGLLMELTRAYLAYADNSRAQDSAAYAIQELLSIYDCREMETN
GPGHQLWRRFPEHVREILEPHLNTRYKSSQKSTDWSGVKKPIYLSKLGSNFAEWSASW
AGYLITKVRHDLASKIFTCCSIMMKHDFKVTIYLLPHILVYVLLGCNQEDQQEVYAEI

Figure 22A (continued)

MAVLKHDDQHTINTQDIASDLCQLSTQTVFSMLDHLTQWARHKFQALKAEKCPHSKSN
RNKVDSMVSTVDYEDYQSVTRFLDLIPQDTLAVASFRSKAYTRAVMHFESFITEKKQN
IQEHLGFLQKLYAAMHEPDGVAGVSAIRKAEPSLKEQILEHESLGLLRDATACYDRAI
QLEPDQIIHYHGVVKSMLGLGQLSTVITQVNGVHANRSEWTDELNTYRVEAAWKLSQW
DLVENYLAADGKSTTWSVRLGQLLLSAKKRDITAFYDSLKLVRAEQIVPLSAASFERG
SYQRGYEYIVRLHMLCELEHSIKPLFQHSPGDSSQEDSLNWVARLEMTQNSYRAKEPI
LALRRALLSLNKRPDYNEMVGECWLQSARVARKAGHHQTAYNALLNAGESRLAELYVE
RAKWLWSKGDVHQALIVLQKGVELCFPENETPPEGKNMLIHGRAMLLVGRFMEETANF
ESNAIMKKYKDVTACLPEWEDGHFYLAKYYDKLMPMVTDNKMEKQGDLIRYIVLHFGR
SLQYGNQFIYQSMPRMLTLWLDYGTKAYEWEKAGRSDRVQMRNDLGKINKVITEHTNY
LAPYQFLTAFSQLISRICHSHDEVFVVLMEIIAKVFLAYPQQAMWMMTAVSKSSYPMR
VNRCKEILNKAIHMKKSLEKFVGDATRLTDKLLELCNKPVDGSSSTLSMSTHFKMLKK
LVEEATFSEILIPLQSVMIPTLPSILGTHANHASHEPFPGHWAYIAGFDDMVEILASL
QKPKKISLKGSDGKFYIMMCKPKDDLRKDCRLMEFNSLINKCLRKDAESRRRELHIRT
YAVIPLNDECGIIEWVNNTAGLRPILTKLYKEKGVYMTGKELRQCMLPKSAALSEKLK
VFREFLLPRHPPIFHEWFLRTFPDPTSWYSSRSAYCRSTAVMSMVGYILGLGDRHGEN
ILFDSLTGECVHVDFNCLFNKGETFEVPEIVPFRLTHNMVNGMGPMGTEGLFRRACEV
TMRLMRDQREPLMSVLKTFLHDPLVEWSKPVKGHSKAPLNETGEVVNEKAKTHVLDIE
QRLQGVIKTRNRVTGLPLSIEGHVHYLIQEATDENLLCQMYLGWTPYM

Figure 22B

ATR

```
  1 ttccgggagg agttttggcc tccacacggc tccgtcgggc gccgcgctct tccggcagcg
 61 gtagctttgg agacgccggg aacccgcgtt ggcgtggttg actagtgcct cgcagcctca
121 gcatggggga acatggcctg gagctggctt ccatgatccc cgccctgcgg gagctgggca
181 gtgccacacc agaggaatat aatacagttg tacagaagcc aagacaaatt ctgtgtcaat
241 tcattgaccg gatacttaca gatgtaaatg ttgttgctgt agaacttgta agaaaactg
301 actctcagcc aacctccgtg atgttgcttg atttcatcca gcatatcatg aaatcctccc
361 cacttatgtt tgtaaatgtg agtggaagcc atgaggccaa aggcagttgt attgaattca
```

421 gtaattggat cataacgaga cttctgcgga ttgcagcaac tccctcctgt catttgttac
481 acaagaaaat ctgtgaagtc atctgttcat tattatttct ttttaaaagc aagagtcctg
541 ctatttttgg ggtactcaca aaagaattat tacaactttt tgaagacttg gtttacctcc
601 atagaagaaa tgtgatgggt catgctgtgg aatggccagt ggtcatgagc cgatttttaa
661 gtcaattaga tgaacacatg ggatatttac aatcagctcc tttgcagttg atgagtatgc
721 aaaatttaga atttattgaa gtcactttat taatggttct tactcgtatt attgcaattg
781 tgttttttag aaggcaagaa ctcttacttt ggcagatagg ttgtgttctg ctagagtatg
841 gtagtccaaa aattaaatcc ctagcaatta gctttttaac agaacttttt cagcttggag
901 gactaccagc acaaccagct agcacttttt tcagctcatt tttggaatta ttaaaacacc
961 ttgtagaaat ggatactgac caattgaaac tctatgaaga gccattatca aagctgataa
1021 agacactatt tccctttgaa gcagaagctt atagaaatat tgaacctgtc tatttaaata
1081 tgctgctgga aaaactctgt gtcatgtttg aagacggtgt gctcatgcgg cttaagtctg
1141 atttgctaaa agcagctttg tgccatttac tgcagtattt ccttaaattt gtgccagctg
1201 ggtatgaatc tgctttacaa gtcaggaagg tctatgtgag aaatatttgt aaagctcttt
1261 tggatgtgct tggaattgag gtagatgcag agtacttgtt gggcccactt tatgcagctt
1321 tgaaaatgga aagtatggaa atcattgagg agattcaatg ccaaactcaa caggaaaacc
1381 tcagcagtaa tagtgatgga atatcaccca aaaggcgtcg tctcagctcg tctctaaacc
1441 cttctaaaag agcaccaaaa cagactgagg aaattaaaca tgtggacatg aaccaaaaga
1501 gcatattatg gagtgcactg aaacagaaag ctgaatccct tcagatttcc cttgaataca
1561 gtggcctaaa gaatcctgtt attgagatgt tagaaggaat tgctgttgtc ttacaactga
1621 ctgctctgtg tactgttcat tgttctcatc aaaacatgaa ctgccgtact ttcaaggact
1681 gtcaacataa atccaagaag aaaccttctg tagtgataac ttggatgtca ttggattttt
1741 acacaaaagt gcttaagagc tgtagaagtt tgttagaatc tgttcagaaa ctggacctgg
1801 aggcaaccat tgataaggtg gtgaaaattt atgatgcttt gatttatatg caagtaaaca
1861 gttcatttga agatcatatc ctggaagatt tatgtggtat gctctcactt ccatggattt
1921 attcccattc tgatgatggc tgtttaaagt tgaccacatt tgccgctaat cttctaacat
1981 taagctgtag gatttcagat agctattcac cacaggcaca atcacgatgt gtgtttcttc
2041 tgactctgtt tccaagaaga atattccttg agtggagaac agcagtttac aactgggccc
2101 tgcagagctc ccatgaagta atccgggcta gttgtgttag tggatttttt atcttattgc Figure 22B (continued)

2161 agcagcagaa ttcttgtaac agagttccca agattcttat agataaagtc aaagatgatt
2221 ctgacattgt caagaaagaa tttgcttcta tacttggtca acttgtctgt actcttcacg
2281 gcatgtttta tctgacaagt tctttaacag aacctttctc tgaacacgga catgtggacc
2341 tcttctgtag gaacttgaaa gccacttctc aacatgaatg ttcatcttct caactaaaag
2401 cttctgtctg caagccattc cttttcctac tgaaaaaaaa aatacctagt ccagtaaaac
2461 ttgctttcat agataatcta catcatcttt gtaagcatct tgattttaga gaagatgaaa
2521 cagatgtaaa agcagttctt ggaactttat taaatttaat ggaagatcca gacaaagatg
2581 ttagagtggc ttttagtgga aatatcaagc acatattgga atccttggac tctgaagatg
2641 gatttataaa ggagcttttt gtcttaagaa tgaaggaagc atatacacat gcccaaatat
2701 caagaaataa tgagctgaag gataccttga ttcttacaac aggggatatt ggaagggccg
2761 caaaaggaga tttggtacca tttgcactct tacacttatt gcattgtttg ttatccaagt
2821 cagcatctgt ctctggagca gcatacacag aaattagagc tctggttgca gctaaaagtg
2881 ttaaactgca aagttttttc agccagtata agaaacccat ctgtcagttt ttggtagaat
2941 cccttcactc tagtcagatg acagcacttc cgaatactcc atgccagaat gctgacgtgc
3001 gaaaacaaga tgtggctcac cagagagaaa tggctttaaa tacgttgtct gaaattgcca
3061 acgttttcga ctttcctgat cttaatcgtt ttcttactag gacattacaa gttctactac
3121 ctgatcttgc tgccaaagca agccctgcag cttctgctct cattcgaact ttaggaaaac
3181 aattaaatgt caatcgtaga gagattttaa taaacaactt caaatatatt ttttctcatt
3241 tggtctgttc ttgttccaaa gatgaattag aacgtgccct tcattatctg aagaatgaaa
3301 cagaaattga actggggagc ctgttgagac aagatttcca aggattgcat aatgaattat
3361 tgctgcgtat tggagaacac tatcaacagg tttttaatgg tttgtcaata cttgcctcat
3421 ttgcatccag tgatgatcca tatcagggcc cgagagatat catatcacct gaactgatgg
3481 ctgattattt acaacccaaa ttgttgggca ttttggcttt ttttaacatg cagttactga
3541 gctctagtgt tggcattgaa gataagaaaa tggccttgaa cagtttgatg tctttgatga
3601 agttaatggg acccaaacat gtcagttctg tgagggtgaa gatgatgacc acactgagaa
3661 ctggccttcg attcaaggat gattttcctg aattgtgttg cagagcttgg gactgctttg
3721 ttcgctgcct ggatcatgct tgtctgggct cccttctcag tcatgtaata gtagctttgt
3781 tacctcttat acacatccag cctaaagaaa ctgcagctat cttccactac ctcataattg
3841 aaaacaggga tgctgtgcaa gattttcttc atgaaatata tttttacct gatcatccag Figure 22B (continued)

3901 aattaaaaaa gataaaagcc gttctccagg aatacagaaa ggagacctct gagagcactg
3961 atcttcagac aactcttcag ctctctatga aggccattca acatgaaaat gtcgatgttc
4021 gtattcatgc tcttacaagc ttgaaggaaa ccttgtataa aaatcaggaa aaactgataa
4081 agtatgcaac agacagtgaa acagtagaac ctattatctc acagttggtg acagtgcttt
4141 tgaaaggttg ccaagatgca aactctcaag ctcggttgct ctgtggggaa tgtttagggg
4201 aattgggggc gatagatcca ggtcgattag atttctcaac aactgaaact caaggaaaag
4261 attttacatt tgtgactgga gtagaagatt caagctttgc ctatggatta ttgatggagc
4321 taacaagagc ttaccttgcg tatgctgata atagccgagc tcaagattca gctgcctatg
4381 ccattcagga gttgctttct atttatgact gtagagagat ggagaccaac ggcccaggtc
4441 accaattgtg gaggagattt cctgagcatg ttcgggaaat actagaacct catctaaata
4501 ccagatacaa gagttctcag aagtcaaccg attggtctgg agtaaagaag ccaatttact
4561 taagtaaatt gggtagtaac tttgcagaat ggtcagcatc ttgggcaggt tatcttatta
4621 caaaggttcg acatgatctt gccagtaaaa ttttcacctg ctgtagcatt atgatgaagc
4681 atgatttcaa agtgaccatc tatcttcttc cacatattct ggtgtatgtc ttactgggtt
4741 gtaatcaaga agatcagcag gaggtttatg cagaaattat ggcagttcta aagcatgacg
4801 atcagcatac cataaatacc caagacattg catctgatct gtgtcaactc agtacacaga
4861 ctgtgttctc catgcttgac catctcacac agtgggcaag gcacaaattt caggcactga
4921 aagctgagaa atgtccacac agcaaatcaa acagaaataa ggtagactca atggtatcta
4981 ctgtggatta tgaagactat cagagtgtaa cccgttttct agacctcata ccccaggata
5041 ctctggcagt agcttccttt cgctccaaag catacacacg agctgtaatg cactttgaat
5101 catttattac agaaaagaag caaaatattc aggaacatct tggatttttta cagaaattgt
5161 atgctgctat gcatgaacct gatggagtgg ccggagtcag tgcaattaga aaggcagaac
5221 catctctaaa agaacagatc cttgaacatg aaagccttgg cttgctgagg gatgccactg
5281 cttgttatga cagggctatt cagctagaac cagaccagat cattcattat catggtgtag
5341 taaagtccat gttaggtctt ggtcagctgt ctactgttat cactcaggtg aatggagtgc
5401 atgctaacag gtccgagtgg acagatgaat taaacacgta cagagtggaa gcagcttgga
5461 aattgtcaca gtgggatttg gtggaaaact atttggcagc agatggaaaa tctacaacat
5521 ggagtgtcag actgggacag ctattattat cagccaaaaa aagagatatc acagcttttt
5581 atgactcact gaaactagtg agagcagaac aaattgtacc tctttcagct gcaagctttg Figure 22B (continued)

5641 aaagaggctc ctaccaacga ggatatgaat atattgtgag attgcacatg ttatgtgagt
5701 tggagcatag catcaaacca cttttccagc attctccagg tgacagttct caagaagatt
5761 ctctaaactg ggtagctcga ctagaaatga cccagaattc ctacagagcc aaggagccta
5821 tcctggctct ccggagggct ttactaagcc tcaacaaaag accagattac aatgaaatgg
5881 ttggagaatg ctggctgcag agtgccaggg tagctagaaa ggctggtcac caccagacag
5941 cctacaatgc tctccttaat gcaggggaat cacgactcgc tgaactgtac gtggaaaggg
6001 caaagtggct ctggtccaag ggtgatgttc accaggcact aattgttctt caaaaaggtg
6061 ttgaattatg ttttcctgaa aatgaaaccc cacctgaggg taagaacatg ttaatccatg
6121 gtcgagctat gctactagtg ggccgattta tggaagaaac agctaacttt gaaagcaatg
6181 caattatgaa aaaatataag gatgtgaccg cgtgcctgcc agaatgggag gatgggcatt
6241 tttaccttgc caagtactat gacaaattga tgcccatggt cacagacaac aaaatggaaa
6301 agcaaggtga tctcatccgg tatatagttc ttcattttgg cagatctcta caatatggaa
6361 atcagttcat atatcagtca atgccacgaa tgttaactct atggcttgat tatggtacaa
6421 aggcatatga atgggaaaaa gctggccgct ccgatcgtgt acaaatgagg aatgatttgg
6481 gtaaaataaa caaggttatc acagagcata caaactattt agctccatat caatttttga
6541 ctgctttttc acaattgatc tctcgaattt gtcattctca cgatgaagtt tttgttgtct
6601 tgatggaaat aatagccaaa gtatttctag cctatcctca acaagcaatg tggatgatga
6661 cagctgtgtc aaagtcatct tatcccatgc gtgtgaacag atgcaaggaa atcctcaata
6721 aagctattca tatgaaaaaa tccttagaga agtttgttgg agatgcaact cgcctaacag
6781 ataagcttct agaattgtgc aataaaccgg ttgatggaag tagttccaca ttaagcatga
6841 gcactcattt taaaatgctt aaaaagctgg tagaagaagc aacatttagt gaaatcctca
6901 ttcctctaca atcagtcatg atacctacac ttccatcaat tctgggtacc catgctaacc
6961 atgctagcca tgaaccattt cctggacatt gggcctatat tgcagggttt gatgatatgg
7021 tggaaattct tgcttctctt cagaaaccaa agaagatttc tttaaaaggc tcagatggaa
7081 agttctacat catgatgtgt aagccaaaag atgacctgag aaaggattgt agactaatgg
7141 aattcaattc cttgattaat aagtgcttaa gaaaagatgc agagtctcgt agaagagaac
7201 ttcatattcg aacatatgca gttattccac taaatgatga atgtgggatt attgaatggg
261 tgaacaacac tgctggtttg agacctattc tgaccaaact atataaagaa aagggagtgt
7321 atatgacagg aaaagaactt cgccagtgta tgctaccaaa gtcagcagct ttatctgaaa Figure 22B (continued)

7381 aactcaaagt attccgagaa tttctcctgc ccaggcatcc tcctattttt catgagtggt
7441 ttctgagaac attccctgat cctacatcat ggtacagtag tagatcagct tactgccgtt
7501 ccactgcagt aatgtcaatg gttggttata ttctggggct tggagaccgt catggtgaaa
7561 atattctctt tgattctttg actggtgaat gcgtacatgt agatttcaat tgtcttttca
7621 ataagggaga aacctttgaa gttccagaaa ttgtgccatt tcgcctgact cataatatgg
7681 ttaatggaat gggtcctatg ggaacagagg gtctttttcg aagagcatgt gaagttacaa
7741 tgaggctgat gcgtgatcag cgagagcctt taatgagtgt cttaaagact tttctacatg
7801 atcctcttgt ggaatggagt aaaccagtga aagggcattc caaagcgcca ctgaatgaaa
7861 ctggagaagt tgtcaatgaa aaggccaaga cccatgttct tgacattgag cagcgactac
7921 aaggtgtaat caagactcga aatagagtga caggactgcc gttatctatt gaaggacatg
7981 tgcattacct tatacaggaa gctactgatg aaaacttact atgccagatg tatcttggtt
8041 ggactccata tatgtgaaat gaaattatgt aaaagaatat gttaataatc taaaagtaat
8101 gcatttggta tgaatctgtg gttgtatctg ttcaattcta aagtacaaca taaatttacg
8161 ttctcagcaa ctgttatttc tctctgatca ttaattatat gtaaaataat atacattcag
8221 ttattaagaa ataaactgct ttcttaatac aaaaaaaa Figure 22B (continued)

Figure 23A

PTEN

MTAIIKEIVSRNKRRYQEDGFDLDLTYIYPNIIAMGFPAERLEG

VYRNNIDDVVRFLDSKHKNHYKIYNLCAERHYDTAKFNCRVAQYPFEDHNPPQLELIK

PFCEDLDQWLSEDDNHVAAIHCKAGKGRTGVMICAYLLHRGKFLKAQEALDFYGEVRT

RDKKGVTIPSQRRYVYYYSYLLKNHLDYRPVALLFHKMMFETIPMFSGGTCNPQFVVC

QLKVKIYSSNSGPTRREDKFMYFEFPQPLPVCGDIKVEFFHKQNKMLKKDKMFHFWVN

TFFIPGPEETSEKVENGSLCDQEIDSICSIERADNDKEYLVLTLTKNDLDKANKDKAN

RYFSPNFKVKLYFTKTVEEPSNPEASSSTSVTPDVSDNEPDHYRYSDTTDSDPENEPF

DEDQHTQITKV

Figure 23B

PTEN 1 cctcccctcg cccggcgcgg tcccgtccgc ctctcgctcg cctcccgcct cccctcggtc 61 ttccgaggcg cccgggctcc cggcgcggcg gcggaggggg cgggcaggcc ggcgggcggt 121 gatgtggcgg gactctttat gcgctgcggc aggatacgcg ctcggcgctg ggacgcgact 181 gcgctcagtt ctctcctctc ggaagctgca gccatgatgg aagtttgaga gttgagccgc 241 tgtgaggcga ggccgggctc aggcgaggga gatgagagac ggcggcggcc gcggcccgga 301 gcccctctca gcgcctgtga gcagccgcgg gggcagcgcc ctcggggagc cggccggcct 361 gcggcggcgg cagcggcggc gtttctcgcc tcctcttcgt cttttctaac cgtgcagcct 421 cttcctcggc ttctcctgaa agggaaggtg gaagccgtgg gctcgggcgg gagccggctg 481 aggcgcggcg gcggcggcgg cacctcccgc tcctggagcg gggggagaa gcggcggcgg 541 cggcggccgc ggcggctgca gctccaggga gggggtctga gtcgcctgtc accatttcca 601 gggctgggaa cgcccggagag ttggtctctc cccttctact gcctccaaca cggcggcggc 661 ggcggcggca catccaggga cccgggccgg ttttaaacct cccgtccgcc gccgccgcac 721 cccccgtggc ccgggctccg gaggccgccg gcggaggcag ccgttcggag gattattcgt 781 cttctcccca ttccgctgcc gccgctgcca ggcctctggc tgctgaggag aagcaggccc 841 agtcgctgca accatccagc agccgccgca gcagccatta cccggctgcg gtccagagcc 901 aagcggcggc agagcgaggg gcatcagcta ccgccaagtc cagagccatt tccatcctgc 961 agaagaagcc ccgccaccag cagcttctgc catctctctc ctcctttttc ttcagccaca
1021 ggctcccaga catgacagcc atcatcaaag agatcgttag cagaaacaaa aggagatatc
1081 aagaggatgg attcgactta gacttgacct atatttatcc aaacattatt gctatgggat
1141 ttcctgcaga aagacttgaa ggcgtataca ggaacaatat tgatgatgta gtaaggtttt
1201 tggattcaaa gcataaaaac cattacaaga tatacaatct ttgtgctgaa agacattatg
1261 acaccgccaa atttaattgc agagttgcac aatatccttt tgaagaccat aacccaccac
1321 agctagaact tatcaaaccc ttttgtgaag atcttgacca atggctaagt gaagatgaca
1381 atcatgttgc agcaattcac tgtaaagctg gaaagggacg aactggtgta atgatatgtg
1441 catatttatt acatcggggc aaatttttaa aggcacaaga ggccctagat ttctatgggg
1501 aagtaaggac cagagacaaa aagggagtaa ctattcccag tcagaggcgc tatgtgtatt
1561 attatagcta cctgttaaag aatcatctgg attatagacc agtggcactg ttgtttcaca
1621 agatgatgtt tgaaactatt ccaatgttca gtggcggaac ttgcaatcct cagtttgtgg
1681 tctgccagct aaaggtgaag atatattcct ccaattcagg acccacacga cgggaagaca
1741 agttcatgta ctttgagttc cctcagccgt tacctgtgtg tggtgatatc aaagtagagt
1801 tcttccacaa acagaacaag atgctaaaaa aggacaaaat gtttcacttt tgggtaaata
1861 cattcttcat accaggacca gaggaaacct cagaaaaagt agaaaatgga agtctatgtg
1921 atcaagaaat cgatagcatt tgcagtatag agcgtgcaga taatgacaag gaatatctag
1981 tacttacttt aacaaaaaat gatcttgaca aagcaaataa agacaaagcc aaccgatact
2041 tttctccaaa ttttaaggtg aagctgtact tcacaaaaac agtagaggag ccgtcaaatc
2101 cagaggctag cagttcaact tctgtaacac cagatgttag tgacaatgaa cctgatcatt
2161 atagatattc tgacaccact gactctgatc cagagaatga acctttttgat gaagatcagc
2221 atacacaaat tacaaaagtc tgaatttttt tttatcaaga gggataaaac accatgaaaa
2281 taaacttgaa taaactgaaa atggaccttt tttttttaa tggcaatagg acattgtgtc
2341 agattaccag ttataggaac aattctcttt tcctgaccaa tcttgtttta ccctatacat
2401 ccacagggtt ttgacacttg ttgtccagtt gaaaaaaggt tgtgtagctg tgtcatgtat
2461 ataccttttt gtgtcaaaag gacatttaaa attcaattag gattaataaa gatggcactt
2521 tcccgtttta ttccagtttt ataaaaagtg gagacagact gatgtgtata cgtaggaatt
2581 ttttcctttt gtgttctgtc accaactgaa gtggctaaag agctttgtga tatactggtt
2641 cacatcctac ccctttgcac ttgtggcaac agataagttt gcagttggct aagagaggtt Figure 23B (continued)

2701 tccgaagggt tttgctacat tctaatgcat gtattcgggt taggggaatg gagggaatgc
2761 tcagaaagga aataatttta tgctggactc tggaccatat accatctcca gctatttaca
2821 cacacctttc tttagcatgc tacagttatt aatctggaca ttcgaggaat tggccgctgt
2881 cactgcttgt tgtttgcgca ttttttttta aagcatattg gtgctagaaa aggcagctaa
2941 aggaagtgaa tctgtattgg ggtacaggaa tgaaccttct gcaacatctt aagatccaca
3001 aatgaaggga tataaaaata atgtcatagg taagaaacac agcaacaatg acttaaccat
3061 ataaatgtgg aggctatcaa caaagaatgg gcttgaaaca ttataaaaat tgacaatgat
3121 ttattaaata tgttttctca attgtaacga cttctccatc tcctgtgtaa tcaaggccag
3181 tgctaaaatt cagatgctgt tagtacctac atcagtcaac aacttacact tattttacta
3241 gttttcaatc ataatacctg ctgtggatgc ttcatgtgct gcctgcaagc ttcttttttc
3301 tcattaaata taaaatattt tgtaatgctg cacagaaatt ttcaatttga gattctacag
3361 taagcgtttt ttttctttga agatttatga tgcacttatt caatagctgt cagccgttcc
3421 acccttttga ccttacacat tctattacaa tgaattttgc agttttgcac atttttttaaa
3481 tgtcattaac tgttagggaa ttttacttga atactgaata catataatgt ttatattaaa
3541 aaggacattt gtgttaaaaa ggaaattaga gttgcagtaa actttcaatg ctgcacacaa
3601 aaaaaagaca tttgattttt cagtagaaat tgtcctacat gtgctttatt gatttgctat
3661 tgaaagaata gggttttttt tttttttttt tttttttttt ttaaatgtgc agtgttgaat
3721 catttcttca tagtgctccc ccgagttggg actagggctt caatttcact tcttaaaaaa
3781 aatcatcata tatttgatat gcccagactg catacgattt taagcggagt acaactacta
3841 ttgtaaagct aatgtgaaga tattattaaa aaggtttttt tttccagaaa tttggtgtct
3901 tcaaattata ccttcacctt gacatttgaa tatccagcca ttttgtttct taatggtata
3961 aaattccatt ttcaataact tattggtgct gaaattgttc actagctgtg gtctgaccta
4021 gttaatttac aaatacagat tgaataggac ctactagagc agcatttata gagtttgatg
4081 gcaaatagat taggcagaac ttcatctaaa atattcttag taaataatgt tgacacgttt
4141 tccatacctt gtcagtttca ttcaacaatt tttaaatttt taacaaagct cttaggattt
4201 acacatttat atttaaacat tgatatatag agtattgatt gattgctcat aagttaaatt
4261 ggtaaagtta gagacaacta ttctaacacc tcaccattga aatttatatg ccaccttgtc
4321 tttcataaaa gctgaaaatt gttacctaaa atgaaaatca acttcatgtt ttgaagatag
4381 ttataaatat tgttctttgt tacaatttcg ggcaccgcat attaaaacgt aactttattg Figure 23B (continued)

4441 ttccaatatg taacatggag ggccaggtca taaataatga cattataatg ggcttttgca
4501 ctgttattat ttttcctttg gaatgtgaag gtctgaatga gggttttgat tttgaatgtt
4561 tcaatgtttt tgagaagcct tgcttacatt ttatggtgta gtcattggaa atggaaaaat
4621 ggcattatat atattatata tataaatata tattatacat actctcctta ctttatttca
4681 gttaccatcc ccatagaatt tgacaagaat tgctatgact gaaaggtttt cgagtcctaa
4741 ttaaaacttt atttatggca gtattcataa ttagcctgaa atgcattctg taggtaatct
4801 ctgagtttct ggaatatttt cttagacttt ttggatgtgc agcagcttac atgtctgaag
4861 ttacttgaag gcatcacttt taagaaagct tacagttggg ccctgtacca tcccaagtcc
4921 tttgtagctc ctcttgaaca tgtttgccat acttttaaaa gggtagttga ataaatagca
4981 tcaccattct ttgctgtggc acaggttata aacttaagtg gagtttaccg gcagcatcaa
5041 atgtttcagc tttaaaaaat aaaagtaggg tacaagttta atgtttagtt ctagaaattt
5101 tgtgcaatat gttcataacg atggctgtgg ttgccacaaa gtgcctcgtt tacctttaaa
5161 tactgttaat gtgtcatgca tgcagatgga aggggtggaa ctgtgcacta aagtgggggc
5221 tttaactgta gtatttggca gagttgcctt ctacctgcca gttcaaaagt tcaacctgtt
5281 ttcatataga atatatatac taaaaaattt cagtctgtta aacagcctta ctctgattca
5341 gcctcttcag atactcttgt gctgtgcagc agtggctctg tgtgtaaatg ctatgcactg
5401 aggatacaca aaaataccaa tatgatgtgt acaggataat gcctcatccc aatcagatgt
5461 ccatttgtta ttgtgtttgt taacaaccct ttatctctta gtgttataaa ctccacttaa
5521 aactgattaa agtctcattc ttgtcaaaaa aaaaaaaaaa aaaaaaaaaa aa Figure 23B (continued)

Figure 24A

ERCC1

MDPGKDKEGVPQPSGPPARKKFVIPLDEDEVPPGVAKPLFRSTQ

SLPTVDTSAQAAPQTYAEYAISQPLEGAGATCPTGSEPLAGETPNQALKPGAKSNSII

VSPRQRGNPVLKFVRNVPWEFGDVIPDYVLGQSTCALFLSLRYHNLHPDYIHGRLQSL

GKNFALRVLLVQVDVKDPQQALKELAKMCILADCTLILAWSPEEAGRYLETYKAYEQK

PADLLMEKLEQDFVSRVTECLTTVKSVNKTDSQTLLTTFGSLEQLIAASREDLALCPG

LGPQKARRLFDVLHEPFLKVP

Figure 24B

ERCC1

1 ccggaagtgc tgcgagccct gggccacgct ggccgtgctg gcagtgggcc gcctcgatcc 61 ctctgcagtc tttcccttga ggctccaaga ccagcaggtg aggcctcgcg gcgctgaaac 121 cgtgaggccc ggaccacagg ctccagatgg accctgggaa ggacaaagag gggggtgcccc 181 agccctcagg gccgccagca aggaagaaat ttgtgatacc cctcgacgag gatgaggtcc 241 ctcctggagt ggccaagccc ttattccgat ctacacagag ccttccccact gtggacacct 301 cggcccaggc ggcccctcag acctacgccg aatatgccat ctcacagcct ctggaagggg 361 ctggggccac gtgccccaca gggtcagagc ccctggcagg agagacgccc aaccaggccc 421 tgaaacccgg ggcaaaatcc aacagcatca ttgtgagccc tcggcagagg ggcaatcccg 481 tactgaagtt cgtgcgcaat gtgccctggg aatttggcga cgtaattccc gactatgtgc 541 tgggccagag cacctgtgcc ctgttcctca gcctccgcta ccacaacctg cacccagact 601 acatccatgg gcggctgcag agcctgggga agaacttcgc cttgcgggtc ctgcttgtcc 661 aggtggatgt gaaagatccc cagcaggccc tcaaggagct ggctaagatg tgtatcctgg 721 ccgactgcac attgatcctc gcctggagcc ccgaggaagc tgggcggtac ctggagacct 781 acaaggccta tgagcagaaa ccagcggacc tcctgatgga gaagctagag caggacttcg 841 tctcccgggt gactgaatgt ctgaccaccg tgaagtcagt caacaaaacg gacagtcaga 901 ccctcctgac cacatttgga tctctggaac agctcatcgc cgcatcaaga gaagatctgg 961 ccttatgccc aggcctgggc cctcagaaag cccggaggct gtttgatgtc ctgcacgagc 1021 ccttcttgaa agtaccctga tgaccccagc tgccaaggaa acccccagtg taataataaa 1081 tcgtcctccc aggccaggct cctgctggct gcgctggtgc agtctctggg gagggattct 1141 gggggtgtca ccttctggtg gcccaggtgg gcaccttcag ctttctttag ttcctcagtt 1201 tcccgggggc agactacaca ggctgctgct gctgctgctt ccgcttcttg tcccggcctg 1261 tgggagcctc ctccccagac tctgaattca gtggcggccc tggcatctcc tcttggggca 1321 ctgtctctgg catccggctt tcctgactct gcttcttcct cttcttggtg gatcccggag 1381 ttgccctggc ttcaggctgt ccctcccctg gcagttcagg ctctagtggc tgaattggct 1441 cagtcactgt gtgacctctc tctttcttct tcttcttctt cttggtggat gtgggagctg 1501 cctgaggctc aaggtcatcc ggcagctcag gccccaccac ctctgtctct ggctccactg 1561 tggcatcttg ctgtttttct ttcttcgtct tctttttggg agctgccaga gctgcctggg 1621 cctgaggctt cgctccttct ggctgttgag gcgccatggt ccccccctggg gactccagag 1681 gcttcatctc cggctccact ggctccatcg cctccgtccc tggctccatc attgccatct 1741 gtccctttc tttttcctc ttcttcgtag ggggcagagg gatggcttcc tccagtggct 1801 ccaccttcac ctgtggctga gactcaactg tcaccccctc ctctggctcc atcccttccg 1861 tcccctttg cctctttctc tttttggtcg gggacaggac tgtgtcttct agaggctcag 1921 tgttaatctg ttcctgcttc actgtcttgt cttctggctc gaaggtttct ttccctttgg 1981 gcttcttcct cttcttggtg gtggacggga acagcactcc cagaggctcc agtgtctcca 2041 ctgtgggctc tgtccccaca ggccctgctg cctctggttc tttcagctgc tgattttttt 2101 tcttcttctt cttccgcaca tccatttctg gcgaccccaa agccatgtcc acctccaggg 2161 ccccgtgccc attcactgcc tcctgagtga ctggggcctc tgtcacctgc atctcctttt 2221 tcttcttccc tgaggtgagc aggttggggg ccaaggctga cctaggccct gtgactggtg 2281 ggttgccccc aaaggcacag aaccgaggcc tcaggccagg agggatctgt ggtgggggac 2341 ttgctgggat gggctgcaga gggctccctg acagggattg ctggggaccc tcaaggatcc 2401 ttagggtgcc ctggggggct gaggcacagg tgagtccacc tcctgcctcc gttgaggggg 2461 ccagcagggt cgcttctcca gcttggggac agctgctgag gactcgatag cggtgccgct 2521 tgcctgccaa tttgcccttg acgatctggg agccagagag aggcacatgc cgcccattga 2581 agctacagag agaaacaggg agggcagagg cttaagtgga acaggagagg gaaggttttt 2641 tgattttttt tttgtttttt tttgagagag tcttgctctg ttgcctaggc tggagtgcag 2701 tggcatgatc tcggctcact gcaatgtcca cctcctgggt tcaagcgatt ctcctgcctc 2761 agcctctcaa gtagctggga ttacaggcac ctgccaccac gcccagccaa tttttgtatt Figure 24B (continued)

2821 tttagtagag acaatttcac tatgttggcc aggctggtct tgaactcctg acctcaagtg
2881 atctgctcgc ctcggcctcc caaaggatgg gattacaggc accagccact gcgcctggct
2941 ggcctctggt ttttaataaa acatgactag agtgactcca tcttaaagtg agtagctagg
3001 cacttacaag gttcatgctt atggcctgaa aataaccaca tcccaggctg accaccaatt
3061 ataattacag aatatttatg gccatacaga acatgttcca ccaagcctgc agaatgtcca
3121 aatgtcctaa gaatgcagcc cccattactt aaatataaca taaatgagca agcttaggtt
3181 gcaggattaa tggtcgtgga taacaccaat agcccctacc tttagtgagc ttatctgcac
3241 actccaagtt taactatagt tccttatagt ttcttataag tagaaatact aacaaagggc
3301 tgtgggtttc tccccctgct ttctgaggac actctactct gtaaaggagt agtttccaat
3361 aaacttgttt ctttcactgt gcaaaaaaaa aaaaaaaaaa Figure 24B (continued)

Figure 25A

BRCA2

MPIGSKERPTFFEIFKTRCNKADLGPISLNWFEELSSEAPPYNS
EPAEESEHKNNNYEPNLFKTPQRKPSYNQLASTPIIFKEQGLTLPLYQSPVKELDKFK
LDLGRNVPNSRHKSLRTVKTKMDQADDVSCPLLNSCLSESPVVLQCTHVTPQRDKSVV
CGSLFHTPKFVKGRQTPKHISESLGAEVDPDMSWSSSLATPPTLSSTVLIVRNEEASE
TVFPHDTTANVKSYFSNHDESLKKNDRFIASVTDSENTNQREAASHGFGKTSGNSFKV
NSCKDHIGKSMPNVLEDEVYETVVDTSEEDSFSLCFSKCRTKNLQKVRTSKTRKKIFH
EANADECEKSKNQVKEKYSFVSEVEPNDTDPLDSNVANQKPFESGSDKISKEVVPSLA
CEWSQLTLSGLNGAQMEKIPLLHISSCDQNISEKDLLDTENKRKKDFLTSENSLPRIS
SLPKSEKPLNEETVVNKRDEEQHLESHTDCILAVKQAISGTSPVASSFQGIKKSIFRI
RESPKETFNASFSGHMTDPNFKKETEASESGLEIHTVCSQKEDSLCPNLIDNGSWPAT
TTQNSVALKNAGLISTLKKKTNKFIYAIHDETSYKGKKIPKDQKSELINCSAQFEANA
FEAPLTFANADSGLLHSSVKRSCSQNDSEEPTLSLTSSFGTILRKCSRNETCSNNTVI
SQDLDYKEAKCNKEKLQLFITPEADSLSCLQEGQCENDPKSKKVSDIKEEVLAAACHP
VQHSKVEYSDTDFQSQKSLLYDHENASTLILTPTSKDVLSNLVMISRGKESYKMSDKL
KGNNYESDVELTKNIPMEKNQDVCALNENYKNVELLPPEKYMRVASPSRKVQFNQNTN
LRVIQKNQEETTSISKITVNPDSEELFSDNENNFVFQVANERNNLALGNTKELHETDL
TCVNEPIFKNSTMVLYGDTGDKQATQVSIKKDLVYVLAEENKNSVKQHIKMTLGQDLK
SDISLNIDKIPEKNNDYMNKWAGLLGPISNHSFGGSFRTASNKEIKLSEHNIKKSKMF
FKDIEEQYPTSLACVEIVNTLALDNQKKLSKPQSINTVSAHLQSSVVVSDCKNSHITP
QMLFSKQDFNSNHNLTPSQKAEITELSTILEESGSQFEFTQFRKPSYILQKSTFEVPE
NQMTILKTTSEECRDADLHVIMNAPSIGQVDSSKQFEGTVEIKRKFAGLLKNDCNKSA
SGYLTDENEVGFRGFYSAHGTKLNVSTEALQKAVKLFSDIENISEETSAEVHPISLSS
SKCHDSVVSMFKIENHNDKTVSEKNNKCQLILQNNIEMTTGTFVEEITENYKRNTENE
DNKYTAASRNSHNLEFDGSDSSKNDTVCIHKDETDLLFTDQHNICLKLSGQFMKEGNT
QIKEDLSDLTFLEVAKAQEACHGNTSNKEQLTATKTEQNIKDFETSDTFFQTASGKNI
SVAKESFNKIVNFFDQKPEELHNFSLNSELHSDIRKNKMDILSYEETDIVKHKILKES
VPVGTGNQLVTFQGQPERDEKIKEPTLLGFHTASGKKVKIAKESLDKVKNLFDEKEQG

TSEITSFSHQWAKTLKYREACKDLELACETIEITAAPKCKEMQNSLNNDKNLVSIETV
VPPKLLSDNLCRQTENLKTSKSIFLKVKVHENVEKETAKSPATCYTNQSPYSVIENSA
LAFYTSCSRKTSVSQTSLLEAKKWLREGIFDGQPERINTADYVGNYLYENNSNSTIAE
NDKNHLSEKQDTYLSNSSMSNSYSYHSDEVYNDSGYLSKNKLDSGIEPVLKNVEDQKN
TSFSKVISNVKDANAYPQTVNEDICVEELVTSSSPCKNKNAAIKLSISNSNNFEVGPP
AFRIASGKIVCVSHETIKKVKDIFTDSFSKVIKENNENKSKICQTKIMAGCYEALDDS
EDILHNSLDNDECSTHSHKVFADIQSEEILQHNQNMSGLEKVSKISPCDVSLETSDIC
KCSIGKLHKSVSSANTCGIFSTASGKSVQVSDASLQNARQVFSEIEDSTKQVFSKVLF
KSNEHSDQLTREENTAIRTPEHLISQKGFSYNVVNSSAFSGFSTASGKQVSILESSLH
KVKGVLEEFDLIRTEHSLHYSPTSRQNVSKILPRVDKRNPEHCVNSEMEKTCSKEFKL
SNNLNVEGGSSENNHSIKVSPYLSQFQQDKQQLVLGTKVSLVENIHVLGKEQASPKNV
KMEIGKTETFSDVPVKTNIEVCSTYSKDSENYFETEAVEIAKAFMEDDELTDSKLPSH
ATHSLFTCPENEEMVLSNSRIGKRRGEPLILVGEPSIKRNLLNEFDRIIENQEKSLKA
SKSTPDGTIKDRRLFMHHVSLEPITCVPFRTTKERQEIQNPNFTAPGQEFLSKSHLYE
HLTLEKSSSNLAVSGHPFYQVSATRNEKMRHLITTGRPTKVFVPPFKTKSHFHRVEQC
VRNINLEENRQKQNIDGHGSDDSKNKINDNEIHQFNKNNSNQAAAVTFTKCEEEPLDL
ITSLQNARDIQDMRIKKKQRQRVFPQPGSLYLAKTSTLPRISLKAAVGGQVPSACSHK
QLYTYGVSKHCIKINSKNAESFQFHTEDYFGKESLWTGKGIQLADGGWLIPSNDGKAG
KEEFYRALCDTPGVDPKLISRIWVYNHYRWIIWKLAAMECAFPKEFANRCLSPERVLL
QLKYRYDTEIDRSRRSAIKKIMERDDTAAKTLVLCVSDIISLSANISETSSNKTSSAD
TQKVAIIELTDGWYAVKAQLDPPLLAVLKNGRLTVGQKIILHGAELVGSPDACTPLEA
PESLMLKISANSTRPARWYTKLGFFPDPRPFPLPLSSLFSDGGNVGCVDVIIQRAYPI
QWMEKTSSGLYIFRNEREEEKEAAKYVEAQQKRLEALFTKIQEEFEEHEENTTKPYLP
SRALTRQQVRALQDGAELYEAVKNAADPAYLEGYFSEEQLRALNNHRQMLNDKKQAQI
QLEIRKAMESAEQKEQGLSRDVTTVWKLRIVSYSKKEKDSVILSIWRPSSDLYSLLTE
GKRYRIYHLATSKSKSKSERANIQLAATKKTQYQQLPVSDEILFQIYQPREPLHFSKF
LDPDFQPSCSEVDLIGFVVSVVKKTGLAPFVYLSDECYNLLAIKFWIDLNEDIIKPHM
LIAASNLQWRPESKSGLLTLFAGDFSVFSASPKEGHFQETFNKMKNTVENIDILCNEA
ENKLMHILHANDPKWSTPTKDCTSGPYTAQIIPGTGNKLLMSSPNCEIYYQSPLSLCM

AKRKSVSTPVSAQMTSKSCKGEKEIDDQKNCKKRRALDFLSRLPLPPPVSPICTFVSP

AAQKAFQPPRSCGTKYETPIKKKELNSPQMTPFKKFNEISLLESNSIADEELALINTQ

ALLSGSTGEKQFISVSESTRTAPTSSEDYLRLKRRCTTSLIKEQESSQASTEECEKNK

QDTITTKKYI

Figure 25B

BRCA2

1 gtggcgcgag cttctgaaac taggcggcag aggcggagcc gctgtggcac tgctgcgcct 61 ctgctgcgcc tcgggtgtct tttgcggcgg tgggtcgccg ccgggagaag cgtgagggga 121 cagatttgtg accggcgcgg tttttgtcag cttactccgg ccaaaaaaga actgcacctc 181 tggagcggac ttatttacca agcattggag gaatatcgta ggtaaaaatg cctattggat 241 ccaaagagag gccaacattt tttgaaattt ttaagacacg ctgcaacaaa gcagatttag 301 gaccaataag tcttaattgg tttgaagaac tttcttcaga agctccaccc tataattctg 361 aacctgcaga agaatctgaa cataaaaaca acaattacga accaaaccta tttaaaactc 421 cacaaaggaa accatcttat aatcagctgg cttcaactcc aataatattc aaagagcaag 481 ggctgactct gccgctgtac caatctcctg taaaagaatt agataaattc aaattagact 541 taggaaggaa tgttcccaat agtagacata aaagtcttcg cacagtgaaa actaaaatgg 601 atcaagcaga tgatgtttcc tgtccacttc taaattcttg tcttagtgaa agtcctgttg 661 ttctacaatg tacacatgta acaccacaaa gagataagtc agtggtatgt gggagtttgt 721 ttcatacacc aaagtttgtg aagggtcgtc agacaccaaa acatatttct gaaagtctag 781 gagctgaggt ggatcctgat atgtcttggt caagttcttt agctacacca cccaccctta 841 gttctactgt gctcatagtc agaaatgaag aagcatctga aactgtattt cctcatgata 901 ctactgctaa tgtgaaaagc tatttttcca atcatgatga aagtctgaag aaaaatgata 961 gatttatcgc ttctgtgaca gacagtgaaa acacaaatca aagagaagct gcaagtcatg 1021 gatttggaaa aacatcaggg aattcattta aagtaaatag ctgcaaagac cacattggaa 1081 agtcaatgcc aaatgtccta gaagatgaag tatatgaaac agttgtagat acctctgaag 1141 aagatagttt ttcattatgt tttttctaaat gtagaacaaa aaatctacaa aaagtaagaa 1201 ctagcaagac taggaaaaaa attttccatg aagcaaacgc tgatgaatgt gaaaaatcta 1261 aaaaccaagt gaaagaaaaa tactcatttg tatctgaagt ggaaccaaat gatactgatc 1321 cattagattc aaatgtagca aatcagaagc cctttgagag tggaagtgac aaaatctcca
1381 aggaagttgt accgtctttg gcctgtgaat ggtctcaact aacccttca ggtctaaatg
1441 gagcccagat ggagaaaata cccctattgc atatttcttc atgtgaccaa aatatttcag
1501 aaaaagacct attagacaca gagaacaaaa gaaagaaaga ttttcttact tcagagaatt
1561 ctttgccacg tatttctagc ctaccaaaat cagagaagcc attaaatgag gaaacagtgg
1621 taaataagag agatgaagag cagcatcttg aatctcatac agactgcatt cttgcagtaa
1681 agcaggcaat atctggaact tctccagtgg cttcttcatt tcagggtatc aaaaagtcta
1741 tattcagaat aagagaatca cctaaagaga ctttcaatgc aagtttttca ggtcatatga
1801 ctgatccaaa ctttaaaaaa gaaactgaag cctctgaaag tggactggaa atacatactg
1861 tttgctcaca gaaggaggac tccttatgtc caaatttaat tgataatgga agctggccag
1921 ccaccaccac acagaattct gtagctttga agaatgcagg tttaatatcc actttgaaaa
1981 agaaaacaaa taagtttatt tatgctatac atgatgaaac atcttataaa ggaaaaaaaa
2041 taccgaaaga ccaaaaatca gaactaatta actgttcagc ccagtttgaa gcaaatgctt
2101 ttgaagcacc acttacattt gcaaatgctg attcaggttt attgcattct tctgtgaaaa
2161 gaagctgttc acagaatgat tctgaagaac caactttgtc cttaactagc tcttttggga
2221 caattctgag gaaatgttct agaaatgaaa catgttctaa taatacagta atctctcagg
2281 atcttgatta taaagaagca aaatgtaata aggaaaaact acagttattt attaccccag
2341 aagctgattc tctgtcatgc ctgcaggaag gacagtgtga aaatgatcca aaaagcaaaa
2401 aagtttcaga tataaaagaa gaggtcttgg ctgcagcatg tcacccagta caacattcaa
2461 aagtggaata cagtgatact gactttcaat cccagaaaag tcttttatat gatcatgaaa
2521 atgccagcac tcttatttta actcctactt ccaaggatgt tctgtcaaac ctagtcatga
2581 tttctagagg caaagaatca tacaaaatgt cagacaagct caaaggtaac aattatgaat
2641 ctgatgttga attaaccaaa aatattccca tggaaaagaa tcaagatgta tgtgctttaa
2701 atgaaaatta taaaaacgtt gagctgttgc cacctgaaaa atacatgaga gtagcatcac
2761 cttcaagaaa ggtacaattc aaccaaaaca caaatctaag agtaatccaa aaaaatcaag
2821 aagaaactac ttcaatttca aaaataactg tcaatccaga ctctgaagaa cttttctcag
2881 acaatgagaa taattttgtc ttccaagtag ctaatgaaag gaataatctt gctttaggaa
2941 atactaagga acttcatgaa acagacttga cttgtgtaaa cgaacccatt ttcaagaact
3001 ctaccatggt tttatatgga gacacaggtg ataaacaagc aacccaagtg tcaattaaaa Figure 25B (continued)

3061 aagatttggt ttatgttctt gcagaggaga acaaaaatag tgtaaagcag catataaaaa
3121 tgactctagg tcaagattta aaatcggaca tctccttgaa tatagataaa ataccagaaa
3181 aaaataatga ttacatgaac aaatgggcag gactcttagg tccaatttca aatcacagtt
3241 ttggaggtag cttcagaaca gcttcaaata aggaaatcaa gctctctgaa cataacatta
3301 agaagagcaa aatgttcttc aaagatattg aagaacaata tcctactagt ttagcttgtg
3361 ttgaaattgt aaataccttg gcattagata atcaaaagaa actgagcaag cctcagtcaa
3421 ttaatactgt atctgcacat ttacagagta gtgtagttgt ttctgattgt aaaaatagtc
3481 atataacccc tcagatgtta ttttccaagc aggattttaa ttcaaaccat aatttaacac
3541 ctagccaaaa ggcagaaatt acagaacttt ctactatatt agaagaatca ggaagtcagt
3601 ttgaatttac tcagtttaga aaaccaagct acatattgca gaagagtaca tttgaagtgc
3661 ctgaaaacca gatgactatc ttaaagacca cttctgagga atgcagagat gctgatcttc
3721 atgtcataat gaatgcccca tcgattggtc aggtagacag cagcaagcaa tttgaaggta
3781 cagttgaaat taaacggaag tttgctggcc tgttgaaaaa tgactgtaac aaaagtgctt
3841 ctggttattt aacagatgaa aatgaagtgg ggtttagggg cttttattct gctcatggca
3901 caaaactgaa tgtttctact gaagctctgc aaaaagctgt gaaactgttt agtgatattg
3961 agaatattag tgaggaaact tctgcagagg tacatccaat aagtttatct tcaagtaaat
4021 gtcatgattc tgttgtttca atgtttaaga tagaaaatca taatgataaa actgtaagtg
4081 aaaaaaataa taaatgccaa ctgatattac aaaataatat tgaaatgact actggcactt
4141 ttgttgaaga aattactgaa aattacaaga gaaatactga aaatgaagat aacaaatata
4201 ctgctgccag tagaaattct cataacttag aatttgatgg cagtgattca agtaaaaatg
4261 atactgtttg tattcataaa gatgaaacgg acttgctatt tactgatcag cacaacatat
4321 gtcttaaatt atctggccag tttatgaagg agggaaacac tcagattaaa gaagatttgt
4381 cagatttaac tttttggaa gttgcgaaag ctcaagaagc atgtcatggt aatacttcaa
4441 ataaagaaca gttaactgct actaaaacgg agcaaaatat aaaagatttt gagacttctg
4501 atacattttt tcagactgca agtgggaaaa atattagtgt cgccaaagag tcatttaata
4561 aaattgtaaa tttctttgat cagaaaccag aagaattgca taacttttcc ttaaattctg
4621 aattacattc tgacataaga aagaacaaaa tggacattct aagttatgag gaaacagaca
4681 tagttaaaca caaaatactg aaagaaagtg tcccagttgg tactggaaat caactagtga
4741 ccttccaggg acaacccgaa cgtgatgaaa agatcaaaga acctactcta ttgggttttc Figure 25B (continued)

4801 atacagctag cgggaaaaaa gttaaaattg caaaggaatc tttggacaaa gtgaaaaacc
4861 tttttgatga aaaagagcaa ggtactagtg aaatcaccag ttttagccat caatgggcaa
4921 agaccctaaa gtacagagag gcctgtaaag accttgaatt agcatgtgag accattgaga
4981 tcacagctgc cccaaagtgt aaagaaatgc agaattctct caataatgat aaaaaccttg
5041 tttctattga gactgtggtg ccacctaagc tcttaagtga taatttatgt agacaaactg
5101 aaaatctcaa aacatcaaaa agtatctttt tgaaagttaa agtacatgaa aatgtagaaa
5161 aagaaacagc aaaaagtcct gcaacttgtt acacaaatca gtccccttat tcagtcattg
5221 aaaattcagc cttagctttt tacacaagtt gtagtagaaa aacttctgtg agtcagactt
5281 cattacttga agcaaaaaaa tggcttagag aaggaatatt tgatggtcaa ccagaaagaa
5341 taaatactgc agattatgta ggaaattatt tgtatgaaaa taattcaaac agtactatag
5401 ctgaaaatga caaaaatcat ctctccgaaa aacaagatac ttatttaagt aacagtagca
5461 tgtctaacag ctattcctac cattctgatg aggtatataa tgattcagga tatctctcaa
5521 aaaataaact tgattctggt attgagccag tattgaagaa tgttgaagat caaaaaaaca
5581 ctagtttttc caaagtaata tccaatgtaa aagatgcaaa tgcataccca caaactgtaa
5641 atgaagatat ttgcgttgag gaacttgtga ctagctcttc accctgcaaa aataaaaatg
5701 cagccattaa attgtccata tctaatagta ataattttga ggtagggcca cctgcattta
5761 ggatagccag tggtaaaatc gtttgtgttt cacatgaaac aattaaaaaa gtgaaagaca
5821 tatttacaga cagtttcagt aaagtaatta aggaaaacaa cgagaataaa tcaaaaattt
5881 gccaaacgaa aattatggca ggttgttacg aggcattgga tgattcagag gatattcttc
5941 ataactctct agataatgat gaatgtagca cgcattcaca taaggttttt gctgacattc
6001 agagtgaaga aattttacaa cataaccaaa atatgtctgg attggagaaa gtttctaaaa
6061 tatcaccttg tgatgttagt ttggaaactt cagatatatg taaatgtagt atagggaagc
6121 ttcataagtc agtctcatct gcaaatactt gtgggatttt tagcacagca agtggaaaat
6181 ctgtccaggt atcagatgct tcattacaaa acgcaagaca agtgttttct gaaatagaag
6241 atagtaccaa gcaagtcttt tccaaagtat tgtttaaaag taacgaacat tcagaccagc
6301 tcacaagaga agaaaatact gctatacgta ctccagaaca tttaatatcc caaaaaggct
6361 tttcatataa tgtggtaaat tcatctgctt tctctggatt tagtacagca agtggaaagc
6421 aagtttccat tttagaaagt tccttacaca aagttaaggg agtgttagag gaatttgatt
6481 taatcagaac tgagcatagt cttcactatt cacctacgtc tagacaaaat gtatcaaaaa Figure 25B (continued)

6541 tacttcctcg tgttgataag agaaacccag agcactgtgt aaactcagaa atggaaaaaa
6601 cctgcagtaa agaatttaaa ttatcaaata acttaaatgt tgaaggtggt tcttcagaaa
6661 ataatcactc tattaaagtt tctccatatc tctctcaatt tcaacaagac aaacaacagt
6721 tggtattagg aaccaaagtg tcacttgttg agaacattca tgttttggga aaagaacagg
6781 cttcacctaa aaacgtaaaa atggaaattg gtaaaactga aacttttctt gatgttcctg
6841 tgaaaacaaa tatagaagtt tgttctactt actccaaaga ttcagaaaac tactttgaaa
6901 cagaagcagt agaaattgct aaagctttta tggaagatga tgaactgaca gattctaaac
6961 tgccaagtca tgccacacat tctcttttta catgtcccga aaatgaggaa atggttttgt
7021 caaattcaag aattggaaaa agaagaggag agccccttat cttagtggga gaaccctcaa
7081 tcaaaagaaa cttattaaat gaatttgaca ggataataga aaatcaagaa aaatccttaa
7141 aggcttcaaa aagcactcca gatggcacaa taaaagatcg aagattgttt atgcatcatg
7201 tttctttaga gccgattacc tgtgtaccct ttcgcacaac taaggaacgt caagagatac
7261 agaatccaaa ttttaccgca cctggtcaag aatttctgtc taaatctcat ttgtatgaac
7321 atctgacttt ggaaaaatct tcaagcaatt tagcagtttc aggacatcca ttttatcaag
7381 tttctgctac aagaaatgaa aaaatgagac acttgattac tacaggcaga ccaaccaaag
7441 tctttgttcc accttttaaa actaaatcac attttcacag agttgaacag tgtgttagga
7501 atattaactt ggaggaaaac agacaaaagc aaaacattga tggacatggc tctgatgata
7561 gtaaaaataa gattaatgac aatgagattc atcagtttaa caaaaacaac tccaatcaag
7621 cagcagctgt aactttcaca aagtgtgaag aagaaccttt agatttaatt acaagtcttc
7681 agaatgccag agatatacag gatatgcgaa ttaagaagaa acaaaggcaa cgcgtctttc
7741 cacagccagg cagtctgtat cttgcaaaaa catccactct gcctcgaatc tctctgaaag
7801 cagcagtagg aggccaagtt ccctctgcgt gttctcataa acagctgtat acgtatggcg
7861 tttctaaaca ttgcataaaa attaacagca aaaatgcaga gtcttttcag tttcacactg
7921 aagattattt tggtaaggaa agtttatgga ctggaaaagg aatacagttg gctgatggtg
7981 gatggctcat accctccaat gatggaaagg ctggaaaaga agaattttat agggctctgt
8041 gtgacactcc aggtgtggat ccaaagctta tttctagaat ttgggtttat aatcactata
8101 gatggatcat atggaaactg gcagctatgg aatgtgcctt tcctaaggaa tttgctaata
8161 gatgcctaag cccagaaagg gtgcttcttc aactaaaata cagatatgat acggaaattg
8221 atagaagcag aagatcggct ataaaaaaga taatggaaag ggatgacaca gctgcaaaaa Figure 25B (continued)

8281 cacttgttct ctgtgtttct gacataattt cattgagcgc aaatatatct gaaacttcta
8341 gcaataaaac tagtagtgca gatacccaaa aagtggccat tattgaactt acagatgggt
8401 ggtatgctgt taaggcccag ttagatcctc ccctcttagc tgtcttaaag aatggcagac
8461 tgacagttgg tcagaagatt attcttcatg gagcagaact ggtgggctct cctgatgcct
8521 gtacacctct tgaagcccca gaatctctta tgttaaagat ttctgctaac agtactcggc
8581 ctgctcgctg gtataccaaa cttggattct ttcctgaccc tagacctttt cctctgccct
8641 tatcatcgct tttcagtgat ggaggaaatg ttggttgtgt tgatgtaatt attcaaagag
8701 catacccctat acagtggatg gagaagacat catctggatt atacatattt cgcaatgaaa
8761 gagaggaaga aaaggaagca gcaaaatatg tggaggccca acaaaagaga ctagaagcct
8821 tattcactaa aattcaggag gaatttgaag aacatgaaga aaacacaaca aaaccatatt
8881 taccatcacg tgcactaaca agacagcaag ttcgtgcttt gcaagatggt gcagagcttt
8941 atgaagcagt gaagaatgca gcagacccag cttaccttga gggttatttc agtgaagagc
9001 agttaagagc cttgaataat cacaggcaaa tgttgaatga taagaaacaa gctcagatcc
9061 agttggaaat taggaaggcc atggaatctg ctgaacaaaa ggaacaaggt ttatcaaggg
9121 atgtcacaac cgtgtggaag ttgcgtattg taagctattc aaaaaaagaa aaagattcag
9181 ttatactgag tatttggcgt ccatcatcag atttatattc tctgttaaca gaaggaaaga
9241 gatacagaat ttatcatctt gcaacttcaa aatctaaaag taaatctgaa agagctaaca
9301 tacagttagc agcgacaaaa aaaactcagt atcaacaact accggtttca gatgaaattt
9361 tatttcagat ttaccagcca cgggagcccc ttcacttcag caaattttta gatccagact
9421 ttcagccatc ttgttctgag gtggacctaa taggatttgt cgtttctgtt gtgaaaaaaa
9481 caggacttgc ccctttcgtc tatttgtcag acgaatgtta caatttactg gcaataaagt
9541 tttggataga ccttaatgag gacattatta agcctcatat gttaattgct gcaagcaacc
9601 tccagtggcg accagaatcc aaatcaggcc ttcttacttt atttgctgga gatttttctg
9661 tgttttctgc tagtccaaaa gagggccact ttcaagagac attcaacaaa atgaaaaata
9721 ctgttgagaa tattgacata ctttgcaatg aagcagaaaa caagcttatg catatactgc
9781 atgcaaatga tcccaagtgg tccaccccaa ctaaagactg tacttcaggg ccgtacactg
9841 ctcaaatcat tcctggtaca ggaaacaagc ttctgatgtc ttctcctaat tgtgagatat
9901 attatcaaag tcctttatca ctttgtatgg ccaaaaggaa gtctgtttcc acacctgtct
9961 cagcccagat gacttcaaag tcttgtaaag gggagaaaga gattgatgac caaaagaact Figure 25B (continued)

10021 gcaaaaagag aagagccttg gatttcttga gtagactgcc tttacctcca cctgttagtc 10081 ccatttgtac atttgtttct ccggctgcac agaaggcatt tcagccacca aggagttgtg 10141 gcaccaaata cgaaacaccc ataaagaaaa aagaactgaa ttctcctcag atgactccat 10201 ttaaaaaatt caatgaaatt tctcttttgg aaagtaattc aatagctgac gaagaacttg 10261 cattgataaa tacccaagct cttttgtctg gttcaacagg agaaaaacaa tttatatctg 10321 tcagtgaatc cactaggact gctcccacca gttcagaaga ttatctcaga ctgaaacgac 10381 gttgtactac atctctgatc aaagaacagg agagttccca ggccagtacg gaagaatgtg 10441 agaaaaataa gcaggacaca attacaacta aaaaatatat ctaagcattt gcaaaggcga 10501 caataaatta ttgacgctta acctttccag tttataagac tggaatataa tttcaaacca 10561 cacattagta cttatgttgc acaatgagaa aagaaattag tttcaaattt acctcagcgt 10621 ttgtgtatcg ggcaaaaatc gttttgcccg attccgtatt ggtatacttt tgcttcagtt 10681 gcatatctta aaactaaatg taatttatta actaatcaag aaaaacatct ttggctgagc 10741 tcggtggctc atgcctgtaa tcccaacact ttgagaagct gaggtgggag gagtgcttga 10801 ggccaggagt tcaagaccag cctgggcaac atagggagac ccccatcttt acaaagaaaa 10861 aaaaaagggg aaaagaaaat cttttaaatc tttggatttg atcactacaa gtattatttt 10921 acaagtgaaa taaacatacc attttctttt agattgtgtc attaaatgga atgaggtctc 10981 ttagtacagt tattttgatg cagataattc cttttagttt agctactatt ttaggggatt 11041 ttttttagag gtaactcact atgaaatagt tctccttaat gcaaatatgt tggttctgct 11101 atagttccat cctgttcaaa agtcaggatg aatatgaaga gtggtgtttc cttttgagca 11161 attcttcatc cttaagtcag catgattata agaaaaatag aaccctcagt gtaactctaa 11221 ttcctttttta ctattccagt gtgatctctg aaattaaatt acttcaacta aaaattcaaa 11281 tactttaaat cagaagattt catagttaat ttattttttt tttcaacaaa atggtcatcc 11341 aaactcaaac ttgagaaaat atcttgcttt caaattggca ctgatt Figure 25B (continued)

Figure 26A

XRCC1

MPEIRLRHVVSCSSQDSTHCAENLLKADTYRKWRAAKAGEKTIS
VVLQLEKEEQIHSVDIGNDGSAFVEVLVGSSAGGAGEQDYEVLLVTSSFMSPSESRSG
SNPNRVRMFGPDKLVRAAAEKRWDRVKIVCSQPYSKDSPFGLSFVRFHSPPDKDEAEA
PSQKVTVTKLGQFRVKEEDESANSLRPGALFFSRINKTSPVTASDPAGPSYAAATLQA
SSAASSASPVSRAIGSTSKPQESPKGKRKLDLNQEEKKTPSKPPAQLSPSVPKRPKLP
APTRTPATAPVPARAQGAVTGKPRGEGTEPRRPRAGPEELGKILQGVVVVLSGFQNPF
RSELRDKALELGAKYRPDWTRDSTHLICAFANTPKYSQVLGLGGRIVRKEWVLDCHRM
RRRLPSQRYLMAGPGSSSEEDEASHSGGSGDEAPKLPQKQPQTKTKPTQAAGPSSPQK
PPTPEETKAASPVLQEDIDIEGVQSEGQDNGAEDSGDTEDELRRVAEQKEHRLPPGQE
ENGEDPYAGSTDENTDSEEHQEPPDLPVPELPDFFQGKHFFLYGEFPGDERRKLIRYV
TAFNGELEDYMSDRVQFVITAQEWDPSFEEALMDNPSLAFVRPRWIYSCNEKQKLLPH
QLYGVVPQA

Figure 26B

XRCC1

1 ctcgcgcgct tgcgcacttt agccagcgca gggcgcaccc cgccccctcc cactctccct
61 gcccctcgga ccccatactc tacctcatcc ttctggccag gcgaagccca cgacgttgac
121 atgccggaga tccgcctccg ccatgtcgtg tcctgcagca gccaggactc gactcactgt
181 gcagaaaatc ttctcaaggc agacacttac cgaaaatggc gggcagccaa ggcaggcgag
241 aagaccatct ctgtggtcct acagttggag aaggaggagc agatacacag tgtggacatt
301 gggaatgatg gctcagcttt cgtggaggtg ctggtgggca gttcagctgg aggcgctggg
361 gagcaagact atgaggtcct tctggtcacc tcatctttca tgtccccttc cgagagccgc
421 agtggctcaa accccaaccg cgttcgcatg tttgggcctg acaagctggt ccgggcagcc
481 gccgagaagc gctgggaccg ggtcaaaatt gtttgcagcc agccctacag caaggactcc
541 ccctttggct tgagttttgt acggtttcat agcccccag acaaagatga ggcagaggcc
601 ccgtcccaga aggtgacagt gaccaagctt ggccagttcc gtgtgaagga ggaggatgag
661 agcgccaact ctctgaggcc gggggctctc ttcttcagcc ggatcaacaa gacatcccca 721 gtcacagcca gcgacccagc aggacctagc tatgcagctg ctaccctcca ggcttctagt
781 gctgcctcct cagcctctcc agtctccagg gccataggca gcacctccaa gccccaggag
841 tctcccaaag ggaagaggaa gttggatttg aaccaagaag aaaagaagac ccccagcaaa
901 ccaccagccc agctgtcgcc atctgttccc aagagaccta aattgccagc tccaactcgt
961 accccagcca cagccccagt ccctgccccga gcacaggggg cagtgacagg caaaccccga
1021 ggagaaggca ccgagcccag acgaccccga gctggcccag aggagctggg gaagatcctt
1081 cagggtgtgg tagtggtgct gagtggcttc cagaacccct tccgctccga gctgcgagat
1141 aaggccctag agcttggggc caagtatcgg ccagactgga cccgggacag cacgcacctc
1201 atctgtgcct ttgccaacac cccccaagtac agccaggtcc taggcctggg aggccgcatc
1261 gtgcgtaagg agtgggtgct ggactgtcac cgcatgcgtc ggcggctgcc ctcccagagg
1321 tacctcatgg cagggccagg ttccagcagt gaggaggatg aggcctctca cagcggtggc
1381 agcggagatg aagcccccaa gcttcctcag aagcaacccc agaccaaaac caagcccact
1441 caggcagctg gacccagctc accccagaag cccccaaccc ctgaagagac caaagcagcc
1501 tcaccagtgc tccaggaaga tatagacatt gagggggtac agtcagaagg acaggacaat
1561 ggggcggaag attctgggga cacagaggat gagctgagga gggtggcaga gcagaaggaa
1621 cacagactgc cccctggcca ggaggagaat ggggaagacc cgtatgcagg ctccacggat
1681 gagaacacgg acagtgagga acaccaggag cctcctgatc tgccagtccc tgagctccca
1741 gatttcttcc agggcaagca cttctttctt tacggggagt tccctgggga cgagcggcgg
1801 aaactcatcc gatacgtcac agccttcaat ggggagctcg aggactatat gagtgaccgg
1861 gttcagtttg tgatcacagc acaggaatgg gatcccagct ttgaggaggc cctgatggac
1921 aacccctccc tggcattcgt tcgtccccga tggatctaca gttgcaatga gaagcagaag
1981 ttacttcctc accagctcta tggggtggtg ccgcaagcct gaagtatgtg ctatacacac
2041 acacacacac acacacacac acacacacac acgatgcatt taataaagat gagttggttc
2101 tc Figure 26B (continued)

Figure 27A

KRAS

MTEYKLVVVGAGGVGKSALTIQLIQNHFVDEYDPTIEDSYRKQV
VIDGETCLLDILDTAGQEEYSAMRDQYMRTGEGFLCVFAINNTKSFEDIHHYREQIKR
VKDSEDVPMVLVGNKCDLPSRTVDTKQAQDLARSYGIPFIETSAKTRQRVEDAFYTLV
REIRQYRLKKISKEEKTPGCVKIKKCIIM

Figure 27B

KRAS 1 ggccgcggcg gcggaggcag cagcggcggc ggcagtggcg gcggcgaagg tggcggcggc
61 tcggccagta ctcccggccc ccgccatttc ggactgggag cgagcgcggc gcaggcactg
121 aaggcggcgg cggggccaga ggctcagcgg ctcccaggtg cgggagagag gcctgctgaa
181 aatgactgaa tataaacttg tggtagttgg agctggtggc gtaggcaaga gtgccttgac
241 gatacagcta attcagaatc attttgtgga cgaatatgat ccaacaatag aggattccta
301 caggaagcaa gtagtaattg atggagaaac ctgtctcttg gatattctcg acacagcagg
361 tcaagaggag tacagtgcaa tgagggacca gtacatgagg actggggagg gctttctttg
421 tgtatttgcc ataaataata ctaaatcatt tgaagatatt caccattata gagaacaaat
481 taaaagagtt aaggactctg aagatgtacc tatggtccta gtaggaaata aatgtgattt
541 gccttctaga acagtagaca caaaacaggc tcaggactta gcaagaagtt atggaattcc
601 ttttattgaa acatcagcaa agacaagaca gagagtggag gatgcttttt atacattggt
661 gagggagatc cgacaataca gattgaaaaa aatcagcaaa gaagaaaaga ctcctggctg
721 tgtgaaaatt aaaaaatgca ttataatgta atctgggtgt tgatgatgcc ttctatacat
781 tagttcgaga aattcgaaaa cataaagaaa agatgagcaa agatggtaaa aagaagaaaa
841 agaagtcaaa gacaaagtgt gtaattatgt aaatacaatt tgtacttttt tcttaaggca
901 tactagtaca agtggtaatt tttgtacatt acactaaatt attagcattt gttttagcat
961 tacctaattt ttttcctgct ccatgcagac tgttagcttt taccttaaat gcttatttta
1021 aaatgacagt ggaagttttt ttttcctcta agtgccagta ttcccagagt tttggttttt
1081 gaactagcaa tgcctgtgaa aaagaaactg aatacctaag atttctgtct tggggttttt
1141 ggtgcatgca gttgattact tcttattttt cttaccaatt gtgaatgttg gtgtgaaaca 1201 aattaatgaa gcttttgaat catccctatt ctgtgtttta tctagtcaca taaatggatt
1261 aattactaat ttcagttgag accttctaat tggtttttac tgaaacattg agggaacaca
1321 aatttatggg cttcctgatg atgattcttc taggcatcat gtcctatagt ttgtcatccc
1381 tgatgaatgt aaagttacac tgttcacaaa ggttttgtct cctttccact gctattagtc
1441 atggtcactc tccccaaaat attatatttt ttctataaaa agaaaaaaat ggaaaaaaat
1501 tacaaggcaa tggaaactat tataaggcca tttccttttc acattagata aattactata
1561 aagactccta atagcttttc ctgttaaggc agacccagta tgaaatgggg attattatag
1621 caaccatttt ggggctatat ttacatgcta ctaaattttt ataataattg aaaagatttt
1681 aacaagtata aaaaattctc ataggaatta aatgtagtct ccctgtgtca gactgctctt
1741 tcatagtata actttaaatc ttttcttcaa cttgagtctt tgaagatagt tttaattctg
1801 cttgtgacat taaaagatta tttgggccag ttatagctta ttaggtgttg aagagaccaa
1861 ggttgcaagg ccaggccctg tgtgaacctt tgagctttca tagagagttt cacagcatgg
1921 actgtgtccc cacggtcatc cagtgttgtc atgcattggt tagtcaaaat ggggagggac
1981 tagggcagtt tggatagctc aacaagatac aatctcactc tgtggtggtc ctgctgacaa
2041 atcaagagca ttgcttttgt ttcttaagaa aacaaactct tttttaaaaa ttacttttaa
2101 atattaactc aaaagttgag attttggggt ggtggtgtgc caagacatta attttttttt
2161 taaacaatga agtgaaaaag ttttacaatc tctaggtttg gctagttctc ttaacactgg
2221 ttaaattaac attgcataaa cacttttcaa gtctgatcca tatttaataa tgctttaaaa
2281 taaaaataaa aacaatcctt ttgataaatt taaaatgtta cttattttaa aataaatgaa
2341 gtgagatggc atggtgaggt gaaagtatca ctggactagg aagaaggtga cttaggttct
2401 agataggtgt cttttaggac tctgattttg aggacatcac ttactatcca tttcttcatg
2461 ttaaaagaag tcatctcaaa ctcttagttt ttttttttta caactatgta atttatattc
2521 catttacata aggatacact tatttgtcaa gctcagcaca atctgtaaat ttttaaccta
2581 tgttacacca tcttcagtgc cagtcttggg caaaattgtg caagaggtga agtttatatt
2641 tgaatatcca ttctcgtttt aggactcttc ttccatatta gtgtcatctt gcctccctac
2701 cttccacatg ccccatgact tgatgcagtt ttaatacttg taattcccct aaccataaga
2761 tttactgctg ctgtggatat ctccatgaag ttttcccact gagtcacatc agaaatgccc
2821 tacatcttat ttcctcaggg ctcaagagaa tctgacagat accataaagg gatttgacct
2881 aatcactaat tttcaggtgg tggctgatgc tttgaacatc tctttgctgc ccaatccatt Figure 27B (continued)

2941 agcgacagta ggatttttca aacctggtat gaatagacag aaccctatcc agtggaagga
3001 gaatttaata aagatagtgc tgaaagaatt ccttaggtaa tctataacta ggactactcc
3061 tggtaacagt aatacattcc attgttttag taaccagaaa tcttcatgca atgaaaaata
3121 ctttaattca tgaagcttac tttttttttt tggtgtcaga gtctcgctct tgtcacccag
3181 gctggaatgc agtggcgcca tctcagctca ctgcaacctc catctcccag gttcaagcga
3241 ttctcgtgcc tcggcctcct gagtagctgg gattacaggc gtgtgccact acactcaact
3301 aatttttgta tttttaggag agacggggtt tcaccctgtt ggccaggctg gtctcgaact
3361 cctgacctca agtgattcac ccaccttggc ctcataaacc tgttttgcag aactcattta
3421 ttcagcaaat atttattgag tgcctaccag atgccagtca ccgcacaagg cactgggtat
3481 atggtatccc caaacaagag acataatccc ggtccttagg tagtgctagt gtggtctgta
3541 atatcttact aaggcctttg gtatacgacc cagagataac acgatgcgta ttttagtttt
3601 gcaaagaagg ggtttggtct ctgtgccagc tctataattg ttttgctacg attccactga
3661 aactcttcga tcaagctact ttatgtaaat cacttcattg ttttaaagga ataaacttga
3721 ttatattgtt tttttatttg gcataactgt gattctttta ggacaattac tgtacacatt
3781 aaggtgtatg tcagatattc atattgaccc aaatgtgtaa tattccagtt ttctctgcat
3841 aagtaattaa aatatactta aaaattaata gttttatctg ggtacaaata aacaggtgcc
3901 tgaactagtt cacagacaag gaaacttcta tgtaaaaatc actatgattt ctgaattgct
3961 atgtgaaact acagatcttt ggaacactgt ttaggtaggg tgttaagact tacacagtac
4021 ctcgtttcta cacagagaaa gaaatggcca tacttcagga actgcagtgc ttatgagggg
4081 atatttaggc ctcttgaatt tttgatgtag atgggcattt ttttaaggta gtggttaatt
4141 acctttatgt gaactttgaa tggtttaaca aaagatttgt ttttgtagag attttaaagg
4201 gggagaattc tagaaataaa tgttacctaa ttattacagc cttaaagaca aaaatccttg
4261 ttgaagtttt tttaaaaaaa gctaaattac atagacttag gcattaacat gtttgtggaa
4321 gaatatagca gacgtatatt gtatcatttg agtgaatgtt cccaagtagg cattctaggc
4381 tctatttaac tgagtcacac tgcataggaa tttagaacct aacttttata ggttatcaaa
4441 actgttgtca ccattgcaca atttgtcct aatatataca tagaaacttt gtggggcatg
4501 ttaagttaca gtttgcacaa gttcatctca tttgtattcc attgattttt tttttcttct
4561 aaacattttt tcttcaaaca gtatataact ttttttaggg gatttttttt tagacagcaa
4621 aaactatctg aagatttcca tttgtcaaaa agtaatgatt tcttgataat tgtgtagtaa Figure 27B (continued)

4681 tgtttttttag aacccagcag ttaccttaaa gctgaattta tatttagtaa cttctgtgtt
4741 aatactggat agcatgaatt ctgcattgag aaactgaata gctgtcataa aatgaaactt
4801 tctttctaaa gaaagatact cacatgagtt cttgaagaat agtcataact agattaagat
4861 ctgtgtttta gtttaatagt ttgaagtgcc tgtttgggat aatgataggt aatttagatg
4921 aatttagggg aaaaaaaagt tatctgcaga tatgttgagg gcccatctct ccccccacac
4981 ccccacagag ctaactgggt tacagtgttt tatccgaaag tttccaattc cactgtcttg
5041 tgttttcatg ttgaaaatac ttttgcattt ttcctttgag tgccaatttc ttactagtac
5101 tatttcttaa tgtaacatgt ttacctggaa tgtattttaa ctatttttgt atagtgtaaa
5161 ctgaaacatg cacattttgt acattgtgct ttcttttgtg ggacatatgc agtgtgatcc
5221 agttgttttc catcatttgg ttgcgctgac ctaggaatgt tggtcatatc aaacattaaa
5281 aatgaccact cttttaattg aaattaactt ttaaatgttt ataggagtat gtgctgtgaa
5341 gtgatctaaa atttgtaata tttttgtcat gaactgtact actcctaatt attgtaatgt
5401 aataaaaata gttacagtga caaaaaaaaa aaaaaa Figure 27B (continued)

Figure 28A

BRAF

MAALSGGGGGGAEPGQALFNGDMEPEAGAGAGAAASSAADPAIP
EEVWNIKQMIKLTQEHIEALLDKFGGEHNPPSIYLEAYEEYTSKLDALQQREQQLLES
LGNGTDFSVSSSASMDTVTSSSSSSLSVLPSSLSVFQNPTDVARSNPKSPQKPIVRVF
LPNKQRTVVPARCGVTVRDSLKKALMMRGLIPECCAVYRIQDGEKKPIGWDTDISWLT
GEELHVEVLENVPLTTHNFVRKTFFTLAFCDFCRKLLFQGFRCQTCGYKFHQRCSTEV
PLMCVNYDQLDLLFVSKFFEHHPIPQEEASLAETALTSGSSPSAPASDSIGPQILTSP
SPSKSIPIPQPFRPADEDHRNQFGQRDRSSSAPNVHINTIEPVNIDDLIRDQGFRGDG
GSTTGLSATPPASLPGSLTNVKALQKSPGPQRERKSSSSSEDRNRMKTLGRRDSSDDW
EIPDGQITVGQRIGSGSFGTVYKGKWHGDVAVKMLNVTAPTPQQLQAFKNEVGVLRKT
RHVNILLFMGYSTKPQLAIVTQWCEGSSLYHHLHIIETKFEMIKLIDIARQTAQGMDY
LHAKSIIHRDLKSNNIFLHEDLTVKIGDFGLATVKSRWSGSHQFEQLSGSILWMAPEV
IRMQDKNPYSFQSDVYAFGIVLYELMTGQLPYSNINNRDQIIFMVGRGYLSPDLSKVR
SNCPKAMKRLMAECLKKKRDERPLFPQILASIELLARSLPKIHRSASEPSLNRAGFQT
EDFSLYACASPKTPIQAGGYGAFPVH

Figure 28B

BRAF 1 cgcctccctt ccccctcccc gcccgacagc ggccgctcgg gccccggctc tcggttataa
61 gatggcggcg ctgagcggtg gcggtggtgg cggcgcggag ccgggccagg ctctgttcaa
121 cggggacatg gagcccgagg ccggcgccgg cgccggcgcc gcggcctctt cggctgcgga
181 ccctgccatt ccggaggagg tgtggaatat caaacaaatg attaagttga cacaggaaca
241 tatagaggcc ctattggaca aatttggtgg ggagcataat ccaccatcaa tatatctgga
301 ggcctatgaa gaatacacca gcaagctaga tgcactccaa caaagagaac aacagttatt
361 ggaatctctg gggaacggaa ctgatttttc tgtttctagc tctgcatcaa tggataccgt
421 tacatcttct tcctcttcta gcctttcagt gctaccttca tctctttcag tttttcaaaa
481 tcccacagat gtggcacgga gcaaccccaa gtcaccacaa aaacctatcg ttagagtctt
541 cctgcccaac aaacagagga cagtggtacc tgcaaggtgt ggagttacag tccgagacag

```
601 tctaaagaaa gcactgatga tgagaggtct aatcccagag tgctgtgctg tttacagaat
661 tcaggatgga gagaagaaac caattggttg ggacactgat atttcctggc ttactggaga
721 agaattgcat gtggaagtgt tggagaatgt tccacttaca acacacaact ttgtacgaaa
781 aacgtttttc accttagcat tttgtgactt ttgtcgaaag ctgcttttcc agggtttccg
841 ctgtcaaaca tgtggttata aatttcacca gcgttgtagt acagaagttc cactgatgtg
901 tgttaattat gaccaacttg atttgctgtt tgtctccaag ttctttgaac accacccaat
961 accacaggaa gaggcgtcct tagcagagac tgccctaaca tctggatcat ccccttccgc
1021 acccgcctcg gactctattg ggccccaaat tctcaccagt ccgtctcctt caaaatccat
1081 tccaattcca cagcccttcc gaccagcaga tgaagatcat cgaaatcaat ttgggcaacg
1141 agaccgatcc tcatcagctc ccaatgtgca tataaacaca atagaacctg tcaatattga
1201 tgacttgatt agagaccaag gatttcgtgg tgatggagga tcaaccacag gtttgtctgc
1261 taccccccct gcctcattac ctggctcact aactaacgtg aaagccttac agaaatctcc
1321 aggacctcag cgagaaagga agtcatcttc atcctcagaa gacaggaatc gaatgaaaac
1381 acttggtaga cgggactcga gtgatgattg ggagattcct gatgggcaga ttacagtggg
1441 acaaagaatt ggatctggat catttggaac agtctacaag ggaaagtggc atggtgatgt
1501 ggcagtgaaa atgttgaatg tgacagcacc tacacctcag cagttacaag ccttcaaaaa
1561 tgaagtagga gtactcagga aaacacgaca tgtgaatatc ctactcttca tgggctattc
1621 cacaaagcca caactggcta ttgttaccca gtggtgtgag ggctccagct tgtatcacca
1681 tctccatatc attgagacca aatttgagat gatcaaactt atagatattg cacgacagac
1741 tgcacagggc atggattact tacacgccaa gtcaatcatc cacagagacc tcaagagtaa
1801 taatatattt cttcatgaag acctcacagt aaaaataggt gattttggtc tagctacagt
1861 gaaatctcga tggagtgggt cccatcagtt tgaacagttg tctggatcca ttttgtggat
1921 ggcaccagaa gtcatcagaa tgcaagataa aaatccatac agctttcagt cagatgtata
1981 tgcatttgga attgttctgt atgaattgat gactggacag ttaccttatt caaacatcaa
2041 caacagggac cagataattt ttatggtggg acgaggatac ctgtctccag atctcagtaa
2101 ggtacggagt aactgtccaa aagccatgaa gagattaatg gcagagtgcc tcaaaaagaa
2161 aagagatgag agaccactct ttccccaaat tctcgcctct attgagctgc tggcccgctc
2221 attgccaaaa attcaccgca gtgcatcaga accctccttg aatcgggctg gtttccaaac
2281 agaggatttt agtctatatg cttgtgcttc tccaaaaaca cccatccagg caggggata
```

Figure 28B (continued)

2341 tggtgcgttt cctgtccact gaaacaaatg agtgagagag ttcaggagag tagcaacaaa
2401 aggaaaataa atgaacatat gtttgcttat atgttaaatt gaataaaata ctctcttttt
2461 ttttaaggtg aaccaaagaa cacttgtgtg gttaaagact agatataatt tttccccaaa
2521 ctaaaattta tacttaacat tggattttta acatccaagg gttaaaatac atagacattg
2581 ctaaaaattg gcagagcctc ttctagaggc tttactttct gttccgggtt tgtatcattc
2641 acttggttat tttaagtagt aaacttcagt ttctcatgca acttttgttg ccagctatca
2701 catgtccact agggactcca gaagaagacc ctacctatgc ctgtgtttgc aggtgagaag
2761 ttggcagtcg gttagcctgg gttagataag gcaaactgaa cagatctaat ttaggaagtc
2821 agtagaattt aataattcta ttattattct taataatttt tctataacta tttcttttta
2881 taacaatttg gaaaatgtgg atgtctttta tttccttgaa gcaataaact aagtttcttt
2941 ttataaaaa Figure 28B (continued)

Figure 29A

RAD50

MSRIEKMSILGVRSFGIEDKDKQIITFFSPLTILVGPNGAGKTT
IIECLKYICTGDFPPGTKGNTFVHDPKVAQETDVRAQIRLQFRDVNGELIAVQRSMVC
TQKSKKTEFKTLEGVITRTKHGEKVSLSSKCAEIDREMISSLGVSKAVLNNVIFCHQE
DSNWPLSEGKALKQKFDEIFSATRYIKALETLRQVRQTQGQKVKEYQMELKYLKQYKE
KACEIRDQITSKEAQLTSSKEIVKSYENELDPLKNRLKEIEHNLSKIMKLDNEIKALD
SRKKQMEKDNSELEEKMEKVFQGTDEQLNDLYHNHQRTVREKERKLVDCHRELEKLNK
ESRLLNQEKSELLVEQGRLQLQADRHQEHIRARDSLIQSLATQLELDGFERGPFSERQ
IKNFHKLVRERQEGEAKTANQLMNDFAEKETLKQKQIDEIRDKKTGLGRIIELKSEIL
SKKQNELKNVKYELQQLEGSSDRILELDQELIKAERELSKAEKNSNVETLKMEVISLQ
NEKADLDRTLRKLDQEMEQLNHHTTTRTQMEMLTKDKADKDEQIRKIKSRHSDELTSL
LGYFPNKKQLEDWLHSKSKEINQTRDRLAKLNKELASSEQNKNHINNELKRKEEQLSS
YEDKLFDVCGSQDFESDLDRLKEEIEKSSKQRAMLAGATAVYSQFITQLTDENQSCCP
VCQRVFQTEAELQEVISDLQSKLRLAPDKLKSTESELKKKEKRRDEMLGLVPMRQSII
DLKEKEIPELRNKLQNVNRDIQRLKNDIEEQETLLGTIMPEEESAKVCLTDVTIMERF
QMELKDVERKIAQQAAKLQGIDLDRTVQQVNQEKQEKQHKLDTVSSKIELNRKLIQDQ
QEQIQHLKSTTNELKSEKLQISTNLQRRQQLEEQTVELSTEVQSLYREIKDAKEQVSP
LETTLEKFQQEKEELINKKNTSNKIAQDKLNDIKEKVKNIHGYMKDIENYIQDGKDDY
KKQKETELNKVIAQLSECEKHKEKINEDMRLMRQDIDTQKIQERWLQDNLTLRKRNEE
LKEVEEERKQHLKEMGQMQVLQMKSEHQKLEENIDNIKRNHNLALGRQKGYEEEIIHF
KKELREPQFRDAEEKYREMMIVMRTTELVNKDLDIYYKTLDQAIMKFHSMKMEEINKI
IRDLWRSTYRGQDIEYIEIRSDADENVSASDKRRNYNYRVVMLKGDTALDMRGRCSAG
QKVLASLIIRLALAETFCLNCGIIALDEPTTNLDRENIESLAHALVEIIKSRSQQRNF
QLLVITHDEDFVELLGRSEYVEKFYRIKKNIDQCSEIVKCSVSSLGFNVH

Figure 29B

RAD50

1 tttcccggcg tgccccagga gagcggcgtg gacgcgtgcg ggcctagagg cccacgtgat 61 ccgcagggcg gccgaggcag gaagctgtga gtgcgcggtt gcggggtcgc attgtggcta
121 cggctttgcg tccccggcgg gcagccccag gctggtcccc gcctccgctc tccccaccgg
181 cggggaaagc agctggtgtg ggaggaaagg ctccatcccc cgccccctct ctcccgctgt
241 tggctggcag gatcttttgg cagtcctgtg gcctcgctcc ccgcccggat cctcctgacc
301 ctgagattcg cgggtctcac gtcccgtgca cgccttgctt cggcctcagt taagcctttg
361 tggactccag gtccctggtg agattagaaa cgtttgcaaa catgtcccgg atcgaaaaga
421 tgagcattct gggcgtgcgg agttttggaa tagaggacaa agataagcaa attatcactt
481 tcttcagccc ccttacaatt ttggttggac ccaatggggc gggaaagacg accatcattg
541 aatgtctaaa atatatttgt actggagatt tccctcctgg aaccaaagga aatacatttg
601 tacacgatcc caaggttgct caagaaacag atgtgagagc ccagattcgt ctgcaatttc
661 gtgatgtcaa tggagaactt atagctgtgc aaagatctat ggtgtgtact cagaaaagca
721 aaaagacaga atttaaaact ctggaaggag tcattactag aacaaagcat ggtgaaaagg
781 tcagtctgag ctctaagtgt gcagaaattg accgagaaat gatcagttct cttggggttt
841 ccaaggctgt gctaaataat gtcattttct gtcatcaaga agattctaat tggcctttaa
901 gtgaaggaaa ggctttgaag caaaagtttg atgagatttt ttcagcaaca agatacatta
961 aagccttaga aacacttcgg caggtacgtc agacacaagg tcagaaagta aaagaatatc
1021 aaatggaact aaaatatctg aagcaatata aggaaaaagc ttgtgagatt cgtgatcaga
1081 ttacaagtaa ggaagcccag ttaacatctt caaaggaaat tgtcaaatcc tatgagaatg
1141 aacttgatcc attgaagaat cgtctaaaag aaattgaaca taatctctct aaaataatga
1201 aacttgacaa tgaaattaaa gccttggata gccgaaagaa gcaaatggag aaagataata
1261 gtgaactgga agagaaaatg gaaaaggttt ttcaagggac tgatgagcaa ctaaatgact
1321 tatatcacaa tcaccagaga acagtaaggg agaaagaaag gaaattggta gactgtcatc
1381 gtgaactgga aaaactaaat aaagaatcta ggcttctcaa tcaggaaaaa tcagaactgc
1441 ttgttgaaca gggtcgtcta cagctgcaag cagatcgcca tcaagaacat atccgagcta
1501 gagattcatt aattcagtct ttggcaacac agctagaatt ggatggcttt gagcgtggac
1561 cattcagtga aagacagatt aaaaattttc acaaacttgt gagagagaga caagaagggg
1621 aagcaaaaac tgccaaccaa ctgatgaatg actttgcaga aaaagagact ctgaaacaaa
1681 aacagataga tgagataaga gataagaaaa ctggactggg aagaataatt gagttaaaat
1741 cagaaatcct aagtaagaag cagaatgagc tgaaaaatgt gaagtatgaa ttacagcagt Figure 29B (continued)

1801 tggaaggatc ttcagacagg attcttgaac tggaccagga gctcataaaa gctgaacgtg
1861 agttaagcaa ggctgagaaa aacagcaatg tagaaacctt aaaaatggaa gtaataagtc
1921 tccaaaatga aaaagcagac ttagacagga ccctgcgtaa acttgaccag gagatggagc
1981 agttaaacca tcatacaaca acacgtaccc aaatggagat gctgaccaaa gacaaagctg
2041 acaaagatga acaaatcaga aaaataaaat ctaggcacag tgatgaatta acctcactgt
2101 tgggatattt tcccaacaaa aaacagcttg aagactggct acatagtaaa tcaaaagaaa
2161 ttaatcagac cagggacaga cttgccaaat tgaacaagga actagcttca tctgagcaga
2221 ataaaaatca tataaataat gaactaaaaa gaaaggaaga gcagttgtcc agttacgaag
2281 acaagctgtt tgatgtttgt ggtagccagg attttgaaag tgatttagac aggcttaaag
2341 aggaaattga aaaatcatca aaacagcgag ccatgctggc tggagccaca gcagtttact
2401 cccagttcat tactcagcta acagacgaaa accagtcatg ttgccccgtt tgtcagagag
2461 tttttcagac agaggctgag ttacaagaag tcatcagtga tttgcagtct aaactgcgac
2521 ttgctccaga taaactcaag tcaacagaat cagagctaaa aaaaaaggaa aagcggcgtg
2581 atgaaatgct gggacttgtg cccatgaggc aaagcataat tgatttgaag gagaaggaaa
2641 taccagaatt aagaaacaaa ctgcagaatg tcaatagaga catacagcgc ctaaagaacg
2701 acatagaaga acaagaaaca ctcttgggta caataatgcc tgaagaagaa agtgccaaag
2761 tatgcctgac agatgttaca attatggaga ggttccagat ggaacttaaa gatgttgaaa
2821 gaaaaattgc acaacaagca gctaagctac aaggaataga cttagatcga actgtccaac
2881 aagtcaacca ggagaaacaa gagaaacagc acaagttaga cacagtttct agtaagattg
2941 aattgaatcg taagcttata caggaccagc aggaacagat tcaacatcta aaaagtacaa
3001 caaatgagct aaaatctgag aaacttcaga tatccactaa tttgcaacgt cgtcagcaac
3061 tggaggagca gactgtggaa ttatccactg aagttcagtc tttgtacaga gagataaagg
3121 atgctaaaga gcaggtaagc cctttggaaa caacattgga aaagttccag caagaaaaag
3181 aagaattaat caacaaaaaa aatacaagca acaaaatagc acaggataaa ctgaatgata
3241 ttaaagagaa ggttaaaaat attcatggct atatgaaaga cattgagaat tatattcaag
3301 atgggaaaga cgactataag aagcaaaaag aaactgaact taataaagta atagctcaac
3361 taagtgaatg cgagaaacac aaagaaaaga taaatgaaga tatgagactc atgagacaag
3421 atattgatac acagaagata caagaaaggt ggctacaaga taaccttact ttaagaaaaa
3481 gaaatgagga actaaaagaa gttgaagaag aaagaaaaca acatttgaag gaaatgggtc Figure 29B (continued)

3541 aaatgcaggt tttgcaaatg aaaagtgaac atcagaagtt ggaagagaac atagacaata
3601 taaaaagaaa tcataatttg gcattagggc gacagaaagg ttatgaagaa gaaattattc
3661 attttaagaa agaacttcga gaaccacaat ttcgggatgc tgaggaaaag tatagagaaa
3721 tgatgattgt tatgaggaca acagaacttg tgaacaagga tctggatatt tattataaga
3781 ctcttgacca agcaataatg aaatttcaca gtatgaaaat ggaagaaatc aataaaatta
3841 tacgtgacct gtggcgaagt acctatcgtg gacaagatat tgaatacata gaaatacggt
3901 ctgatgccga tgaaaatgta tcagcttctg ataaaaggcg gaattataac taccgagtgg
3961 tgatgctgaa gggagacaca gccttggata tgcgaggacg atgcagtgct ggacaaaagg
4021 tattagcctc actcatcatt cgcctggccc tggctgaaac gttctgcctc aactgtggca
4081 tcattgcctt ggatgagcca acaacaaatc ttgaccgaga aaacattgaa tctcttgcac
4141 atgctctggt tgagataata aaaagtcgct cacagcagcg taacttccag cttctggtaa
4201 tcactcatga tgaagatttt gtggagcttt taggacgttc tgaatatgtg gagaaattct
4261 acaggattaa aaagaacatc gatcagtgct cagagattgt gaaatgcagt gttagctccc
4321 tgggattcaa tgttcattaa aaatatccaa gatttaaatg ccatagaaat gtaggtcctc
4381 agaaagtgta taataagaaa cttatttctc atatcaactt agtcaataag aaaatatatt
4441 ctttcaaagg aacattgtgt ctaggatttt ggatgttgag aggttctaaa atcatgaaac
4501 ttgtttcact gaaaattgga cagattgcct gtttctgatt tgctgctctt catcccattc
4561 caggcagcct ctgtcaggcc ttcagggttc agcagtacag ccgagactcg actctgtgcc
4621 tccctcccca gtgcaaatgc atgcttcttc tcaaagcact gttgagaagg agataattac
4681 tgccttgaaa atttatggtt ttggtatttt tttaaatcat agttaaatgt tacctctgaa
4741 tttacttcct tgcatgtggt ttgaaaaact gagtattaat atctgaggat gaccagaaat
4801 ggtgagatgt atgtttggct ctgcttttaa ctttataaat ccagtgacct ctctctctgg
4861 gacttggttt ccccaactaa aatttgaagt agttgaatgg ggtctcaaag tttgacagga
4921 accttaagta atcatctaag tcagtaccca ccaccttctt ctcctacata tcccttccag
4981 atggtcatcc agactcagag ctctctctac agagaggaaa ttctccactg tgcacaccca
5041 cctttggaaa gctctgacca cttgaggcct gatctgccca tcgtgaagaa gcctgtaaca
5101 ctcctctgcg tctatcctgt gtagcatact ggcttcacca tcaatcctga ttcctctcta
5161 agtgggcatt gccatgtgga aggcaagcca ggctcactca cagagtcaag gcctgctccc
5221 tgtagggtcc aaccagacct ggaagaacag gcctctccat ttgctcttca gatgccactt Figure 29B (continued)

5281 ctaagaaaag cctaatcaca gtttttcctg gaattgccag ctgacatctt gaatccttcc
5341 attccacaca gaatgcaacc aagtcacacg cttttgaatt atgctttgta gagttttgtc
5401 attcagagtc agccaggacc ataccgggtc ttgattcagt cacatggcat ggttttgtgc
5461 catctgtagc tataatgagc atgtttgcct agacagcttt tctcaactgg gtccagaaga
5521 gaattaagcc ctaaggtcct aaggcatcta tctgtgctag gttaaatggt tggcccccaa
5581 agatagacag gtcctgattt ctagaacccg tgactgttac tttatacagc aaaggaaact
5641 ttgcagatgt gattaaagct aaggacctta agacagagta tcctgggggt ggtggtgggg
5701 tggggggggg tcctaaatgt aatcacgagt aagattaaga gcaaatcaat tctagtcata
5761 tattaaacat ccacaataac caagatattt ttatcccaag aatgcaagat ttcagaaaat
5821 gaaaaatctg ttgataaatc catcactata ataaaaccga aggtgaaaaa aattctgaaa
5881 aaattctagc agctatattt gataaaattc aacatctcct agctttagca aactcacagt
5941 tttgcaaata atattttctt aatgttatct gttgctaaat caaaattaaa cagtcatctt
6001 aactgcaaaa taaaacattt ctcagtaaat attaaagcca gttaccttct atcaacatgt
6061 taatgaaagt gctagttgtt gcagcaaaga ataacaaagg caatacacga tcaatatagg
6121 cagtgaaaca aaagtatcat ttgcaagtta aaacagactt cccaatttta aatctggttt
6181 ccccctgaat atgtggcatc cttggcagca cttctgagag tggctgcttt cattccaaga
6241 agcccatggg tttggaggtg ggataggtgc ctttctggct tctcattgct gcttctagat
6301 cagtctccaa atatccccct tccccacatt ggaatgaata gccatcacag catggatgga
6361 ggttagaatg agccagactg cctgggctca aatcctagca caccactcac tagctgggga
6421 ccttgagcaa gttatttgtc ctgttttctg tttccttata tgtaaaagtg ggtaaaatgg
6481 tacatatttt gtagggttgt tatgaagatt gaatgacatt atttacaaac tgcttagaac
6541 tgcttgccac ctactaaata ctgtgtaagt gttcaagaaa aagctgtctt catttca Figure 29B (continued)

Figure 30A

RAD51

MSGTEEAILGGRDSHPAAGGGSVLCFGQCQYTAEEYQAIQKALR

QRLGPEYISSRMAGGGQKVCYIEGHRVINLANEMFGYNGWAHSITQQNVDFVDLNNGK

FYVGVCAFVRVQLKDGSYHEDVGYGVSEGLKSKALSLEKARKEAVTDGLKRALRSFGN

ALGNCILDKDYLRSLNKLPRQLPLEVDLTKAKRQDLEPSVEEARYNSCRPNMALGHPQ

LQQVTSPSRPSHAVIPADQDCSSRSLSSSAVESEATHQRKLRQKQLQQQFRERMEKQQ

VRVSTPSAEKSEAAPPAPPVTHSTPVTVSEPLLEKDFLAGVTQELIKTLEDNSEKWAV

TPDAGDGVVKPSSRADPAQTSDTLALNNQMVTQNRTPHSVCHQKPQAKSGSWDLQTYS

ADQRTTGNWESHRKSQDMKKRKYDPS

Figure 30B

RAD51

1 cccattctcc tctgcgcggc ctccatctaa gatctcttcc ccttgtccat agcctagatc 61 gagctccctg tgtgcaccgc gcgctgcccg aggcgcaggt caaccagaat caagatgtct 121 gggactgagg aagcaattct tggaggacgt gacagccatc ctgctgctgg cggcggctca 181 gtgttatgct ttggacagtg ccagtacaca gcagaagagt accaggccat ccagaaggcc 241 ctgaggcaga ggctgggccc agaatacata agtagccgca tggctggcgg aggccagaag 301 gtgtgctaca ttgagggtca tcgggtaatt aatctggcca atgagatgtt tggttacaat 361 ggctgggcac actccatcac gcagcagaat gtggattttg ttgacctcaa caatggcaag 421 ttctacgtgg gagtctgtgc atttgtgagg gtccagctga aggatggttc atatcatgaa 481 gatgttggtt atggtgttag tgagggcctc aagtccaagg ctttatcttt ggagaaggca 541 aggaaggagg cggtgacaga cgggctgaag cgagccctca ggagttttgg gaatgcactt 601 ggaaactgta ttctggacaa agactacctg agatcactaa ataagcttcc acgccagttg 661 cctcttgaag tggatttaac taaagcgaag agacaagatc ttgaaccgtc tgtggaggag 721 gcaagataca acagctgccg accgaacatg gccctgggac acccacagct gcagcaggtg 781 acctcccctt ccagacccag ccatgctgtg ataccggcgg accaggactg cagctcccga 841 agcctgagct catccgccgt ggagagcgag gccacgcacc agcggaagct ccggcagaag 901 cagctgcagc agcagttccg ggagcggatg gagaagcagc aggttcgagt ctccacgccg 961 tcagctgaga agagtgaggc agcgcctccg gcccctcctg tgacgcacag cactcctgta
1021 actgtctcag aaccactcct ggagaaagac ttccttgcag gagtgactca agaattaatc
1081 aagactcttg aagacaactc tgaaaagtgg gctgtgactc ccgatgcagg ggatggtgtg
1141 gtcaagccct cgtctagagc agacccagcc cagacctctg acacattagc cttgaacaac
1201 cagatggtga cccagaacag gactccacac agcgtttgcc accagaaacc acaagcaaaa
1261 tctggatctt gggacctcca aacttatagc gctgaccaac gcacaacagg aaactgggaa
1321 tctcatagga agagccagga catgaagaaa aggaaatatg atccatctta actgaggctc
1381 aggccacata attggactct gtcacaaagg gactttggaa aactactttt tggtcatgaa
1441 attgttcatc gctgctggag aatgaacgtc attgcgattt atcttgcttc attctgaacc
1501 ttatcaagag gatctgactg agagcccact gcagttagag ctgagcactt ttgaaaagct
1561 tgtccatcac tctagtaggg agaggctctg gacagatgaa taccttttct tcggcttgtg
1621 aggcttccca ctatttatta ctgaactatt atgttaatga agatggacat tttaggaatc
1681 accaatggct ccttgccctc aagcaatata ggccagactt ggtcctaagc acctgcctca
1741 gcaattgtct acattcagtt gttttgcata acgtctgcct tctttccttt acggtccatg
1801 cctttaatgt tgcccacatt aagcactgtg gatcacgaca ggaaaaaggt tggagcagtg
1861 cttttcacta ctttgtatca atccaggcta caatcttcat ttaatataaa taatttatgg
1921 atttatgaca ttacaatcct gcattgtttc aagactgaca tttttttccta aggaaggaaa
1981 taatcatcta agaccacgaa aaaaggctgt tttttgtttt tttttttttt tttttttttg
2041 agacggggtc tggctgtgtt gccctgactg gagttcagtg gtgcaaacac agctctctcc
2101 acaacctctt gggcccaagt gatactccca cctctgcctt acaaaataca gggattactg
2161 gtgtgagcca ctgtgtctgg ccagaaaagg catttttgag aaagcaaatc gtatacctta
2221 ttaacaaaat agaatatata tatattgctt atctgaaatg cttgaaacca gaattgtttt
2281 gcatttttttg aatatttgta tacacataat gagaccttgg ggatgggacc caagtctgaa
2341 cgtggaattc acctgtgttt cgtgtatatg cctcatacac ataattttgt gcatgaaaca
2401 gagtttttgt ataagaagat acactgcagc tgaagagggc tgggtttttt tttctcttag
2461 ggtcgctgca taaactgttg tatgcctggt gctttgcgac ttgtcacacg aggtcacgtg
2521 tggaattttc cacttctggc atcacgtcag tgctcagaaa ttttctgatc tcagagcatt
2581 tcaattaggg atgctcaaac gcaactgttt ctacttcccc atttcaggtg tgagatgtaa
2641 cccaccttga ccataaattg gcttttcata gtg Figure 30B (continued)

172 TAG
A
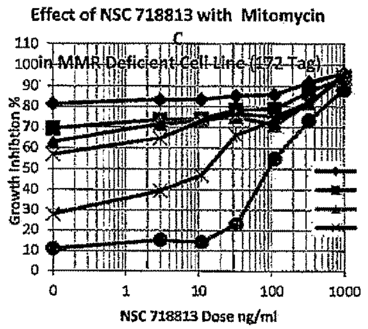
B
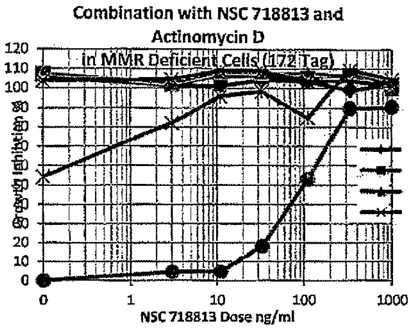
Figure 47

SW403

PBD-C
NSC 723732

Representative NSC 723732 (C) effects in tumor cells in the NCI-60 in vitro evaluation

PBDs show more potent growth inhibition in K-ras mutant colorectal cancer cells that are DNA mismatch repair (MMR) deficient
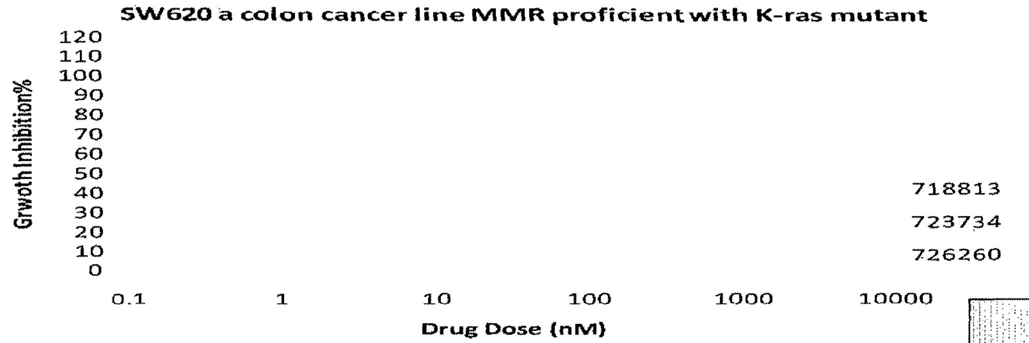
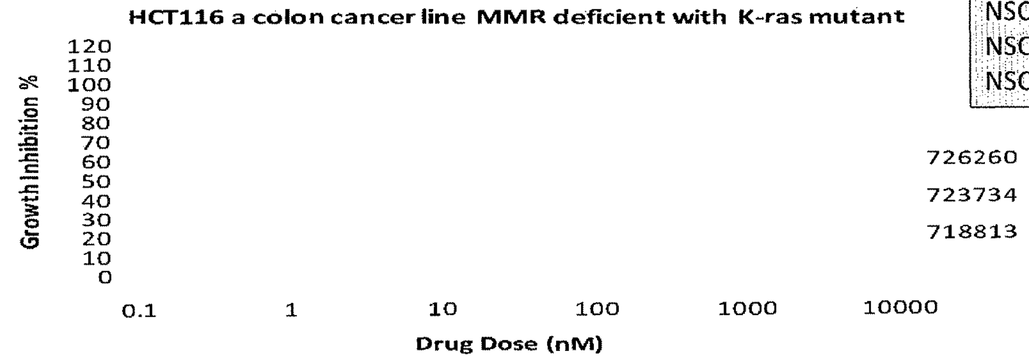
| | IC50 nM | |
|---|---|---|
| PBDs | SW620 | HCT116 |
| NSC 718813 | 200 | 15 |
| NSC 723734 | 225 | 150 |
| NSC 726260 | 1100 | 450 |
Colorectal cancer cells with multiple mutations appeared to be more sensitive to PBDs
Figure 68

Breast cancer cells (MDA-MB-468) with loss of function in PTEN and mlh1 hypermethylation (deficient DNA mismatch repair) are more susceptible to novel IndUS PBDs

Novel IndUS PBDs are very potent in leukemia cells (CEM) that have loss of function in DNA MMR and PTEN compared to that in MSH2 deficient Jurkat lymphoma cells

Comparison of Activity of IndUS PBDs in Isogenic U2OS with RNAi knockdowns of MMR, p53 and REV3 functions
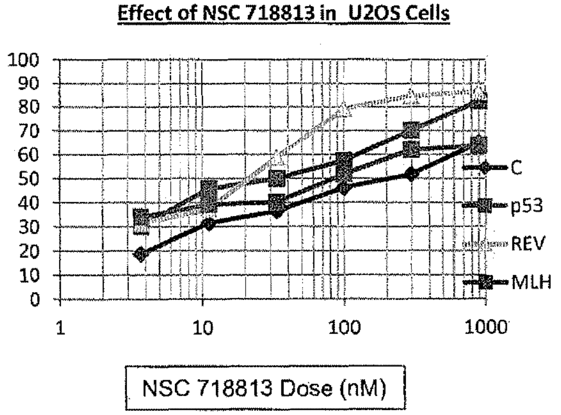
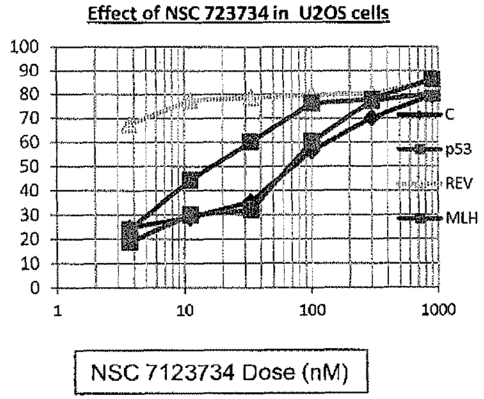
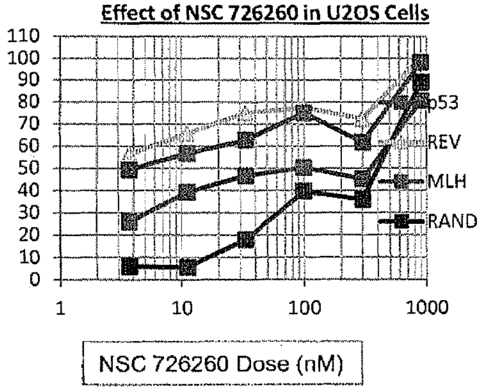
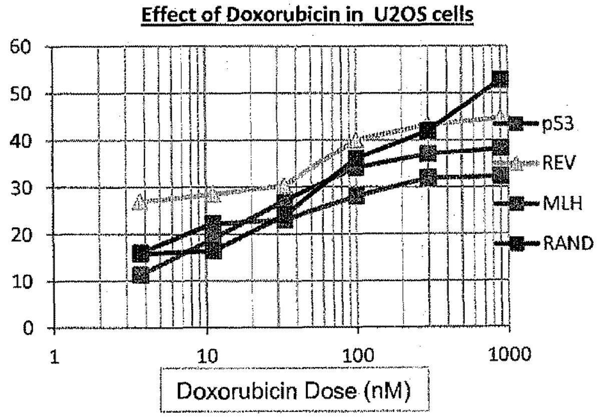
| Gene Knocked out | 718813 (IC50 nM) | 723734 (IC50 nM) | 726260 (IC50 nM) | Doxorubicin (IC30nM) |
|---|---|---|---|---|
| Control (random siRNA) | 300 | 70 | 400 | 50 |
| mlh1 | 100 | 20 | 5 | 200 |
| p53 | 30 | 60 | 350 | 50 |
| rev3 | 60 | 1 | 3 | 32 |
Figure 73

IndUS PBDs Show Synthetic Lethality as Monotherapy in U2OS Cells using RNAi Knockdown of DNA mismatch repair (MMR), apoptosis (p53) and Homologous Recombination/Translesional synthesis (REV3) Genes

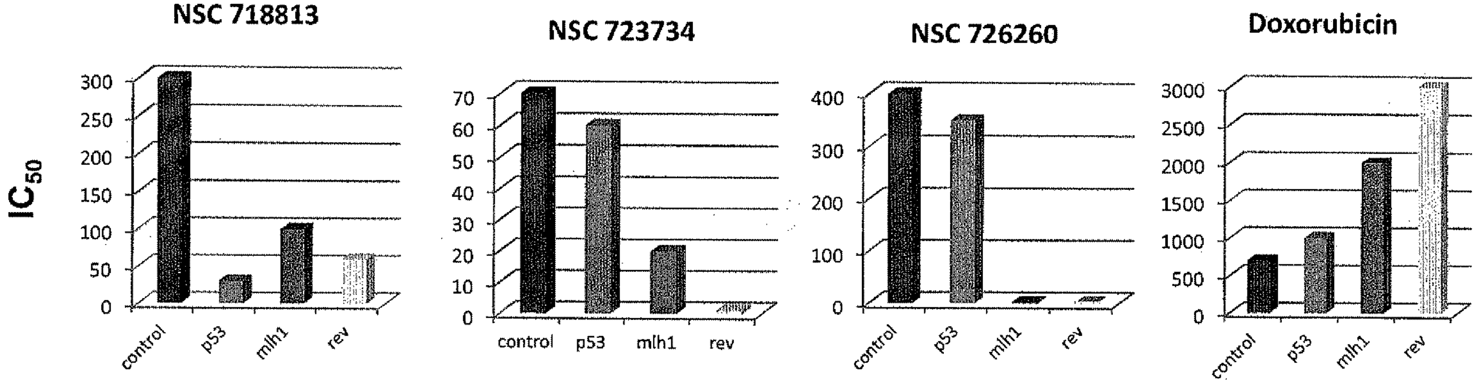

Improved potency for PBDs with knockdown of p53, mlh1 and/or rev3 genes by RNAi

| Drug | Fold (improvement or reduction) in IC50 values in U2OS Cells with RNAi knockdown of genes | | |
|---|---|---|---|
| *Gene knocked down* | *p53* | *rev* | *mlh1* |
| NSC 718813 | 10 | 3 | 5 |
| NSC 723734 | 1.2 | 3.5 | >70 |
| NSC 726260 | 1.1 | 135 | 135 |
| Doxorubicin* | 0.7* | 0.23* | 0.35* |

U2OS (Osteosarcoma Cells) are "wild type" for p53, mlh1 and rev3
*Estimated $IC_{50}$ values for doxorubicin calculated from $IC_{30}$ siRNA calculations

Figure 74

Novel PBDs show "Synthetic Lethality" in Tumor Cells that have Loss of DNA Mismatch Repair (MMR) and/or Apoptosis (p53)

Tumor cells with loss of DNA mismatch repair (MMR) or p53 are resistant to available anticancer agents*

| Class of Anticancer Agent | Estimated IC50 in Mismatch Repair (MMR) Proficient Cells | Estimated IC50 in MMR-deficient cells (Fold shift) | Estimated IC50 in p53-deficient cells (Fold-shift) |
|---|---|---|---|
| Topoisomerase II inhibitor | >1 μM | >4 μM (>4X ) | >1.5 μM (>1.5X) |
| Platinum (DNA) crosslinkers | > 4 μM | >20 μM (>5X) | > 20 μM (>5X) |
| Topoisomerase I inhibitor | 0.4 μM | 0.6 μM (>1.3X) | 0.3 μM (0.75X) |
| Protein synthesis inhibitor | 0.4 μM | 0.6 μM (>1.5X) | 0.15 μM (<2.5X) |
| Antimitotic agent | 0.2 μM | 0.8 μM (>4X) | >2 μM (>10X) |
| RNA Synthesis inhibitor | 0.015 μM | 0.2 μM (>13X) | 0.01 μM (<0.7X) |
| DNA alkylator | > 2 μM | >2 μM (~1) | 0.4 μM (<5X) |
| HDAC inhibitor | 0.35 μM | 0.7 μM (>2X) | 1.2 μM (>3X) |
| **Novel IndUS anticancer compound** | **0.2 μM** | **0.08 μM (<2.5X)** | **0.1 μM (<2X)** |

*Estimated effects for non-PBDs obtained from non-isogenic evaluation in DNA MMR proficient or deficient cell lines and/or RNAi experiments

Figure 75

In Rats, Lead IndUS PBD Compounds have Excellent PK with Long Half-life
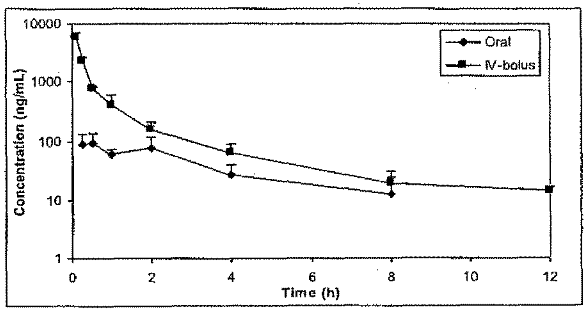
NSC 718813: IV $C_{max}$: 5.7 μg/mL; IV $T_{1/2}$: 2.2 hrs
PO $C_{max}$: 0.11 μg/mL; PO $T_{1/2}$: 1.8 hrs
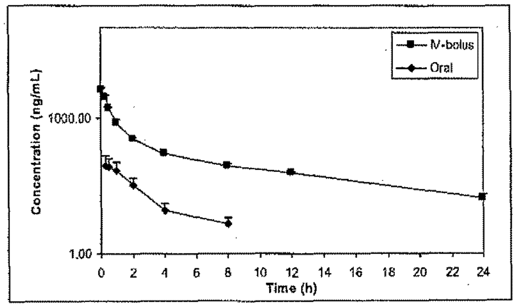
NSC 723734: IV $C_{max}$: 4.05 μg/mL; IV $T_{1/2}$: 6.3 hrs
PO $C_{max}$: 0.09 μg/mL; PO $T_{1/2}$: 2.3 hrs
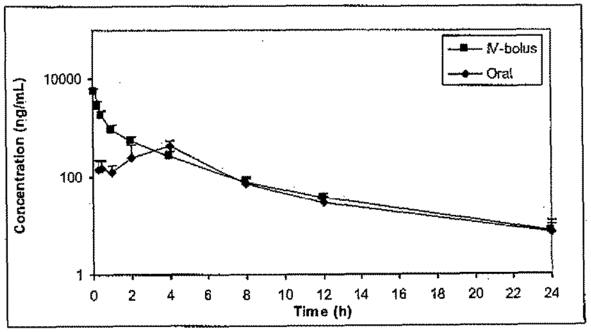
NSC 726260: IV $C_{max}$: 5.06 μg/mL; IV $T_{1/2}$: 4.8 hrs
PO $C_{max}$: 0.44 μg/mL; PO $T_{1/2}$: 4.6 hrs
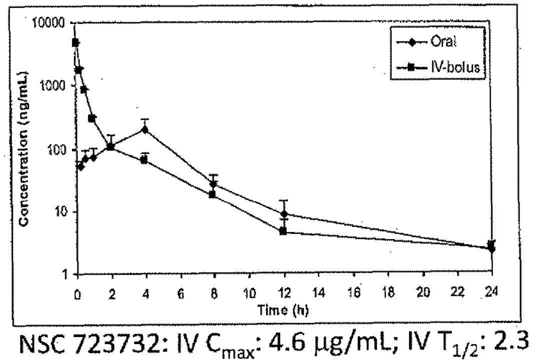
NSC 723732: IV $C_{max}$: 4.6 μg/mL; IV $T_{1/2}$: 2.3 hrs
PO $C_{max}$: 0.195 μg/mL; PO $T_{1/2}$: 2.0 hrs
Figure 76

NSC726260 shows limited pharmacological activity in SW620 colon tumor xenograft model following combined IV and IP administration Quantitative analysis of *in vivo* SW620 colon tumor xenograft data shows that NSC723734 is synergistic with cisplatin at combination doses achieving >50% efficacy

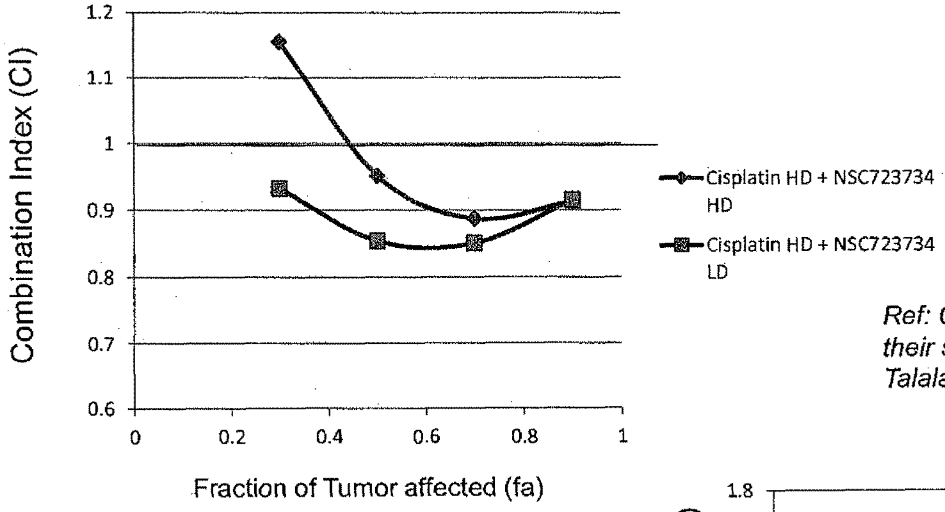

*Ref: Chou, T-C. Drug combination studies and their synergy quantification using the Chou-Talalay method. Cancer Res 70: 440-446, 2010*

*CI Value Interpretation*
*<0.1 – very strong synergism*
*0.1-0.3 – strong synergism*
*0.3-0.7 – synergism*
*0.9 – 1.1 – additive*
*1.1 – 1.45 – slight antagonism*
*1.45 – 3.3 – antagonism*
*>3.3 – strong antagonism*

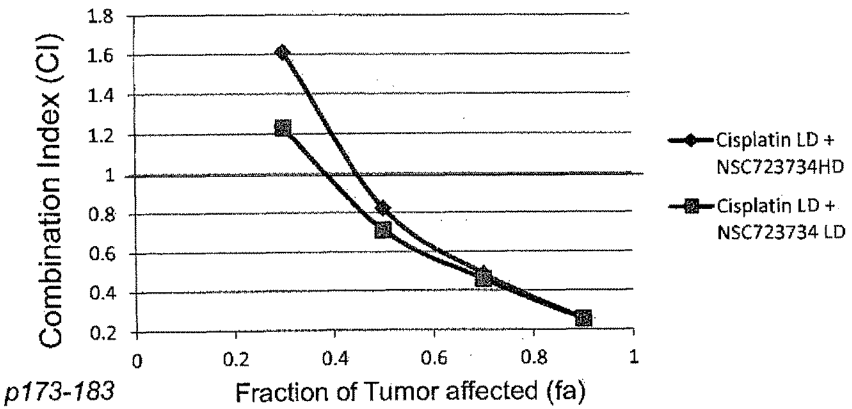

*From: Reynolds & Maurer. Methods in Mol Med vol. 110, p173-183*

Figure 83

Quantitative analysis of *in vivo* effects of NSC723734 and cisplatin results in significant dose-reduction index (DRI) supporting the mutual synergism in SW620 colon tumor xenograft mouse model

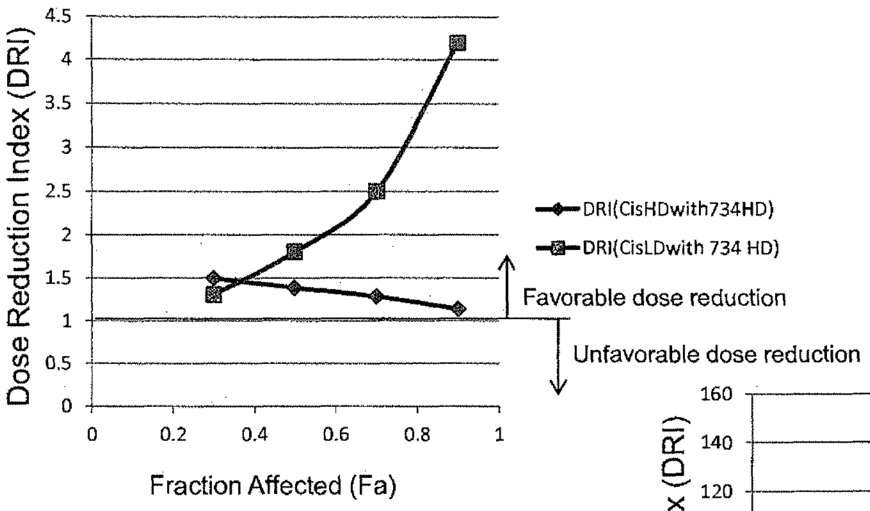

*Synergy and dose-reduction opportunities for using NSC723734 with other anticancer agents consistent with in vitro cellular pharmacological data from other tumor cell lines*

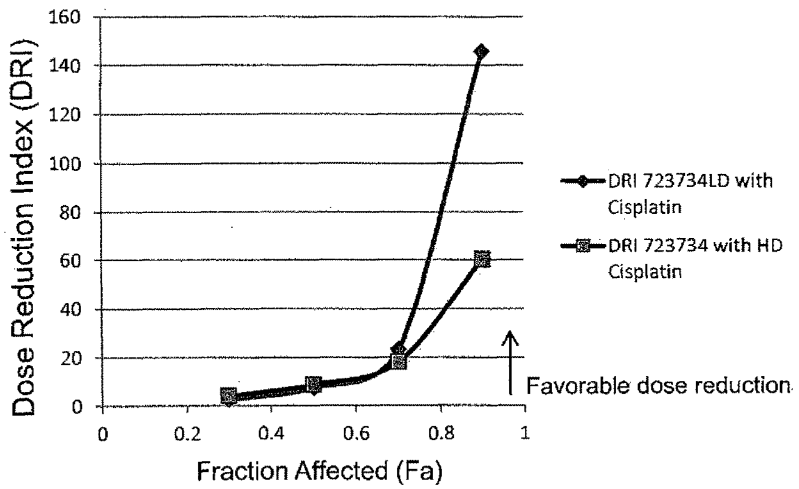

*Ref: Chou, T-C. Drug combination studies and their synergy quantification using the Chou-Talalay method. Cancer Res 70: 440-446, 2010*

Figure 84

Novel IndUS Anticancer PBDs are Significantly Different Compared to previously Described DNA Minor Groove Binders

| Biological Properties | Previous Generation Minor Groove Binders | Novel IndUS Anticancer PBD Compounds |
|---|---|---|

Figure 85

SEQUENCE LISTING

```
<160> NUMBER OF SEQ ID NOS: 36

<210> SEQ ID NO 1
<211> LENGTH: 393
<212> TYPE: PRT
<213> ORGANISM: Artificial Sequence
<220> FEATURE:
<223> OTHER INFORMATION: TP53 sequence

<400> SEQUENCE: 1

Met Glu Glu Pro Gln Ser Asp Pro Ser Val Glu Pro Pro Leu Ser Gln
```

-continued

```
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```

<210> SEQ ID NO 2
<211> LENGTH: 2550
<212> TYPE: DNA
<213> ORGANISM: Artificial Sequence
<220> FEATURE:
<223> OTHER INFORMATION: TP53 sequence

<400> SEQUENCE: 2

```
gattggggtt ttcccctccc atgtgctcaa gactggcgct aaaagttttg agcttctcaa     60

aagtctagag ccaccgtcca gggagcaggt agctgctggg ctccggggac actttgcgtt    120

cgggctggga gcgtgctttc cacgacggtg acacgcttcc ctggattggc agccagactg    180

ccttccgggt cactgccatg gaggagccgc agtcagatcc tagcgtcgag ccccctctga    240

gtcaggaaac attttcagac ctatggaaac tacttcctga aaacaacgtt ctgtccccct    300

tgccgtccca agcaatggat gatttgatgc tgtccccgga cgatattgaa caatggttca    360

ctgaagaccc aggtccagat gaagctccca gaatgccaga ggctgctccc cccgtggccc    420

ctgcaccagc agctcctaca ccggcggccc ctgcaccagc cccctcctgg cccctgtcat    480

cttctgtccc ttcccagaaa acctaccagg gcagctacgg tttccgtctg ggcttcttgc    540

attctgggac agccaagtct gtgacttgca cgtactcccc tgccctcaac aagatgtttt    600

gccaactggc caagacctgc cctgtgcagc tgtgggttga ttccacaccc ccgcccggca    660

cccgcgtccg cgccatggcc atctacaagc agtcacagca catgacggag gttgtgaggc    720

gctgccccca ccatgagcgc tgctcagata gcgatggtct ggcccctcct cagcatctta    780

tccgagtgga aggaaatttg cgtgtggagt atttggatga cagaaacact tttcgacata    840

gtgtggtggt gccctatgag ccgcctgagg ttggctctga ctgtaccacc atccactaca    900

actacatgtg taacagttcc tgcatgggcg gcatgaaccg gaggcccatc ctcaccatca    960

tcacactgga agactccagt ggtaatctac tgggacggaa cagctttgag gtgcgtgttt   1020

gtgcctgtcc tgggagagac cggcgcacag aggaagagaa tctccgcaag aaaggggagc   1080

ctcaccacga gctgccccca gggagcacta agcgagcact gcccaacaac accagctcct   1140

ctccccagcc aaagaagaaa ccactggatg gagaatattt cacccttcag atccgtgggc   1200

gtgagcgctt cgagatgttc cgagagctga atgaggcctt ggaactcaag gatgcccagg   1260

ctgggaagga gccagggggg agcagggctc actccagcca cctgaagtcc aaaaagggtc   1320

agtctacctc ccgccataaa aaactcatgt tcaagacaga agggcctgac tcagactgac   1380

attctccact tcttgttccc cactgacagc ctcccacccc catctctccc tcccctgcca   1440

ttttgggttt tgggtctttg aacccttgct tgcaataggt gtgcgtcaga agcacccagg   1500

acttccattt gctttgtccc ggggctccac tgaacaagtt ggcctgcact ggtgttttgt   1560

tgtggggagg aggatgggga gtaggacata ccagcttaga ttttaaggtt tttactgtga   1620

gggatgtttg ggagatgtaa gaaatgttct tgcagttaag ggttagttta caatcagcca   1680

cattctaggt aggggcccac ttcaccgtac taaccaggga agctgtccct cactgttgaa   1740

ttttctctaa cttcaaggcc catatctgtg aaatgctggc atttgcacct acctcacaga   1800

gtgcattgtg agggttaatg aaataatgta catctggcct tgaaaccacc ttttattaca   1860

tggggtctag aacttgaccc ccttgagggt gcttgttccc tctccctgtt ggtcggtggg   1920

ttggtagttt ctacagttgg gcagctggtt aggtagaggg agttgtcaag tctctgctgg   1980

cccagccaaa ccctgtctga caacctcttg gtgaacctta gtacctaaaa ggaaatctca   2040

ccccatccca caccctggag gatttcatct cttgtatatg atgatctgga tccaccaaga   2100

cttgttttat gctcagggtc aatttctttt ttcttttttt tttttttttt tctttttctt   2160

tgagactggg tctcgctttg ttgcccaggc tggagtggag tggcgtgatc ttggcttact   2220
```

```
gcagcctttg cctccccggc tcgagcagtc ctgcctcagc ctccggagta gctgggacca   2280

caggttcatg ccaccatggc cagccaactt ttgcatgttt tgtagagatg gggtctcaca   2340

gtgttgccca ggctggtctc aaactcctgg gctcaggcga tccacctgtc tcagcctccc   2400

agagtgctgg gattacaatt gtgagccacc acgtccagct ggaagggtca acatctttta   2460

cattctgcaa gcacatctgc attttcaccc caccettccc ctccttctcc ctttttatat   2520

cccattttta tatcgatctc ttattttaca                                    2550


<210> SEQ ID NO 3
<211> LENGTH: 756
<212> TYPE: PRT
<213> ORGANISM: Artificial Sequence
<220> FEATURE:
<223> OTHER INFORMATION: MLH1 sequence

<400> SEQUENCE: 3

Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
            180                 185                 190

Ser Val Lys Lys Gln Gly Glu Thr Val Ala Asp Val Arg Thr Leu Pro
        195                 200                 205

Asn Ala Ser Thr Val Asp Asn Ile Arg Ser Ile Phe Gly Asn Ala Val
    210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
            260                 265                 270

Arg Lys Ala Ile Glu Thr Val Tyr Ala Ala Tyr Leu Pro Lys Asn Thr
        275                 280                 285

His Pro Phe Leu Tyr Leu Ser Leu Glu Ile Ser Pro Gln Asn Val Asp
    290                 295                 300
```

-continued

```
Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
            340                 345                 350

Ala Gly Pro Ser Gly Glu Met Val Lys Ser Thr Thr Ser Leu Thr Ser
        355                 360                 365

Ser Ser Thr Ser Gly Ser Ser Asp Lys Val Tyr Ala His Gln Met Val
    370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
        435                 440                 445

Gly Asp Thr Thr Lys Gly Thr Ser Glu Met Ser Glu Lys Arg Gly Pro
    450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
                485                 490                 495

Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
        515                 520                 525

Ser Phe Val Gly Cys Val Asn Pro Gln Trp Ala Leu Ala Gln His Gln
    530                 535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
        595                 600                 605

Glu Tyr Ile Val Glu Phe Leu Lys Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
```

725 730 735

Asp Gly Asn Ile Leu Gln Leu Ala Asn Leu Pro Asp Leu Tyr Lys Val
740 745 750

Phe Glu Arg Cys
755

<210> SEQ ID NO 4
<211> LENGTH: 2662
<212> TYPE: DNA
<213> ORGANISM: Artificial Sequence
<220> FEATURE:
<223> OTHER INFORMATION: MLH1 sequence

<400> SEQUENCE: 4
gaagagaccc agcaacccac agagttgaga aatttgactg gcattcaagc tgtccaatca 60
atagctgccg ctgaagggtg gggctggatg gcgtaagcta cagctgaagg aagaacgtga 120
gcacgaggca ctgaggtgat tggctgaagg cacttccgtt gagcatctag acgtttcctt 180
ggctcttctg gcgccaaaat gtcgttcgtg gcaggggtta ttcggcggct ggacgagaca 240
gtggtgaacc gcatcgcggc gggggaagtt atccagcggc cagctaatgc tatcaaagag 300
atgattgaga actgtttaga tgcaaaatcc acaagtattc aagtgattgt taaagaggga 360
ggcctgaagt tgattcagat ccaagacaat ggcaccggga tcaggaaaga agatctggat 420
attgtatgtg aaaggttcac tactagtaaa ctgcagtcct ttgaggattt agccagtatt 480
tctacctatg gctttcgagg tgaggctttg gccagcataa gccatgtggc tcatgttact 540
attacaacga aaacagctga tggaaagtgt gcatacagag caagttactc agatggaaaa 600
ctgaaagccc ctcctaaacc atgtgctggc aatcaaggga cccagatcac ggtggaggac 660 ctttttaca acatagccac gaggagaaaa gctttaaaaa atccaagtga agaatatggg 720
aaaattttgg aagttgttgg caggtattca gtacacaatg caggcattag tttctcagtt 780
aaaaaacaag gagagacagt agctgatgtt aggacactac ccaatgcctc aaccgtggac 840
aatattcgct ccatctttgg aaatgctgtt agtcgagaac tgatagaaat tggatgtgag 900
gataaaaccc tagccttcaa aatgaatggt tacatatcca atgcaaacta ctcagtgaag 960
aagtgcatct tcttactctt catcaaccat cgtctggtag aatcaacttc cttgagaaaa 1020
gccatagaaa cagtgtatgc agcctatttg cccaaaaaca cacacccatt cctgtacctc 1080
agtttagaaa tcagtcccca gaatgtggat gttaatgtgc accccacaaa gcatgaagtt 1140
cacttcctgc acgaggagag catcctggag cgggtgcagc agcacatcga gagcaagctc 1200
ctgggctcca attcctccag gatgtacttc acccagactt tgctaccagg acttgctggc 1260
ccctctgggg agatggttaa atccacaaca agtctgacct cgtcttctac ttctggaagt 1320
agtgataagg tctatgccca ccagatggtt cgtacagatt cccgggaaca gaagcttgat 1380
gcatttctgc agcctctgag caaacccctg tccagtcagc cccaggccat tgtcacagag 1440
gataagacag atatttctag tggcagggct aggcagcaag atgaggagat gcttgaactc 1500
ccagcccctg ctgaagtggc tgccaaaaat cagagcttgg agggggatac aacaaagggg 1560
acttcagaaa tgtcagagaa gagaggacct acttccagca accccagaaa gagacatcgg 1620
gaagattctg atgtggaaat ggtggaagat gattcccgaa aggaaatgac tgcagcttgt 1680
accccccgga gaaggatcat taacctcact agtgttttga gtctccagga agaaattaat 1740
gagcagggac atgaggttct ccgggagatg ttgcataacc actccttcgt gggctgtgtg 1800
aatcctcagt gggccttggc acagcatcaa accaagttat accttctcaa caccaccaag 1860

```
cttagtgaag aactgttcta ccagatactc atttatgatt ttgccaattt tggtgttctc   1920

aggttatcgg agccagcacc gctctttgac cttgccatgc ttgccttaga tagtccagag   1980

agtggctgga cagaggaaga tggtcccaaa gaaggacttg ctgaatacat tgttgagttt   2040

ctgaagaaga aggctgagat gcttgcagac tatttctctt tggaaattga tgaggaaggg   2100

aacctgattg gattacccct tctgattgac aactatgtgc ccccttttgga gggactgcct   2160

atcttcattc ttcgactagc cactgaggtg aattgggacg aagaaaagga atgttttgaa   2220

agcctcagta aagaatgcgc tatgttctat tccatccgga agcagtacat atctgaggag   2280

tcgaccctct caggccagca gagtgaagtg cctggctcca ttccaaactc ctggaagtgg   2340

actgtggaac acattgtcta taaagccttg cgctcacaca ttctgcctcc taaacatttc   2400

acagaagatg gaaatatcct gcagcttgct aacctgcctg atctatacaa agtctttgag   2460

aggtgttaaa tatggttatt tatgcactgt gggatgtgtt cttctttctc tgtattccga   2520

tacaaagtgt tgtatcaaag tgtgatatac aaagtgtacc aacataagtg ttggtagcac   2580

ttaagactta tacttgcctt ctgatagtat tcctttatac acagtggatt gattataaat   2640

aaatagatgt gtcttaacat aa                                             2662
```

```
<210> SEQ ID NO 5
<211> LENGTH: 934
<212> TYPE: PRT
<213> ORGANISM: Artificial Sequence
<220> FEATURE:
<223> OTHER INFORMATION: MSH2 sequence

<400> SEQUENCE: 5

Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175

Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Gly Ile Leu Ile
```

-continued

```
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
        275                 280                 285

Phe Glu Leu Thr Thr Phe Asp Phe Ser Gln Tyr Met Lys Leu Asp Ile
    290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
        355                 360                 365

Asp Ala Glu Leu Arg Gln Thr Leu Gln Glu Asp Leu Leu Arg Arg Phe
    370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
            420                 425                 430

Leu Ala Val Phe Val Thr Pro Leu Thr Asp Leu Arg Ser Asp Phe Ser
        435                 440                 445

Lys Phe Gln Glu Met Ile Glu Thr Thr Leu Asp Met Asp Gln Val Glu
    450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
            500                 505                 510

Leu Asp Ser Ser Ala Gln Phe Gly Tyr Tyr Phe Arg Val Thr Cys Lys
        515                 520                 525

Glu Glu Lys Val Leu Arg Asn Asn Lys Asn Phe Ser Thr Val Asp Ile
    530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Glu Ala Gln Asp Ala
                565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
        595                 600                 605

Ala His Val Ser Asn Gly Ala Pro Val Pro Tyr Val Arg Pro Ala Ile
    610                 615                 620

Leu Glu Lys Gly Gln Gly Arg Ile Ile Leu Lys Ala Ser Arg His Ala
625                 630                 635                 640
```

```
Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
            660                 665                 670

Gly Gly Lys Ser Thr Tyr Ile Arg Gln Thr Gly Val Ile Val Leu Met
        675                 680                 685

Ala Gln Ile Gly Cys Phe Val Pro Cys Glu Ser Ala Glu Val Ser Ile
    690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
            740                 745                 750

Gly Thr Ser Thr Tyr Asp Gly Phe Gly Leu Ala Trp Ala Ile Ser Glu
        755                 760                 765

Tyr Ile Ala Thr Lys Ile Gly Ala Phe Cys Met Phe Ala Thr His Phe
    770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
        835                 840                 845

Leu Glu Leu Glu Glu Phe Gln Tyr Ile Gly Glu Ser Gln Gly Tyr Asp
    850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
            900                 905                 910

Ala Glu Val Ile Ala Lys Asn Asn Ser Phe Val Asn Glu Ile Ile Ser
        915                 920                 925

Arg Ile Lys Val Thr Thr
    930
```

<210> SEQ ID NO 6
<211> LENGTH: 3145
<212> TYPE: DNA
<213> ORGANISM: Artificial Sequence
<220> FEATURE:
<223> OTHER INFORMATION: MSH2 nucleotide sequence

<400> SEQUENCE: 6

```
ggcgggaaac agcttagtgg gtgtggggtc gcgcattttc ttcaaccagg aggtgaggag      60

gtttcgacat ggcggtgcag ccgaaggaga cgctgcagtt ggagagcgcg gccgaggtcg     120

gcttcgtgcg cttctttcag ggcatgccgg agaagccgac caccacagtg cgcctttttcg    180

accggggcga cttctatacg gcgcacggcg aggacgcgct gctggccgcc cgggaggtgt     240

tcaagaccca gggggtgatc aagtacatgg ggccggcagg agcaaagaat ctgcagagtg     300

ttgtgcttag taaaatgaat tttgaatctt ttgtaaaaga tcttcttctg gttcgtcagt     360
```

-continued

```
atagagttga agtttataag aatagagctg gaaataaggc atccaaggag aatgattggt    420
atttggcata taaggcttct cctggcaatc tctctcagtt tgaagacatt ctctttggta    480
acaatgatat gtcagcttcc attggtgttg tgggtgttaa aatgtccgca gttgatggcc    540
agagacaggt tggagttggg tatgtggatt ccatacagag gaaactagga ctgtgtgaat    600
tccctgataa tgatcagttc tccaatcttg aggctctcct catccagatt ggaccaaagg    660
aatgtgtttt acccggagga gagactgctg gagacatggg gaaactgaga cagataattc    720
aaagaggagg aattctgatc acagaaagaa aaaaagctga cttttccaca aaagacattt    780
atcaggacct caaccggttg ttgaaaggca aaaagggaga gcagatgaat agtgctgtat    840
tgccagaaat ggagaatcag gttgcagttt catcactgtc tgcggtaatc aagtttttag    900
aactcttatc agatgattcc aactttggac agtttgaact gactactttt gacttcagcc    960
agtatatgaa attggatatt gcagcagtca gagcccttaa ccttttttcag ggttctgttg   1020
aagataccac tggctctcag tctctggctg ccttgctgaa taagtgtaaa acccctcaag   1080
gacaaagact tgttaaccag tggattaagc agcctctcat ggataagaac agaatagagg   1140
agagattgaa tttagtggaa gcttttgtag aagatgcaga attgaggcag actttacaag   1200
aagatttact tcgtcgattc ccagatctta accgacttgc caagaagttt caaagacaag   1260
cagcaaactt acaagattgt taccgactct atcagggtat aaatcaacta cctaatgtta   1320
tacaggctct ggaaaaacat gaaggaaaac accagaaatt attgttggca gtttttgtga   1380
ctcctcttac tgatcttcgt tctgacttct ccaagtttca ggaaatgata gaaacaactt   1440
tagatatgga tcaggtggaa aaccatgaat tccttgtaaa accttcattt gatcctaatc   1500
tcagtgaatt aagagaaata atgaatgact tggaaaagaa gatgcagtca acattaataa   1560
gtgcagccag agatcttggc ttggaccctg gcaaacagat taaactggat tccagtgcac   1620
agtttggata ttactttcgt gtaacctgta aggaagaaaa agtccttcgt aacaataaaa   1680
actttagtac tgtagatatc cagaagaatg gtgttaaatt taccaacagc aaattgactt   1740
ctttaaatga agagtatacc aaaaataaaa cagaatatga agaagcccag gatgccattg   1800
ttaaagaaat tgtcaatatt tcttcaggct atgtagaacc aatgcagaca ctcaatgatg   1860
tgttagctca gctagatgct gttgtcagct ttgctcacgt gtcaaatgga gcacctgttc   1920
catatgtacg accagccatt ttggagaaag gacaaggaag aattatatta aaagcatcca   1980
ggcatgcttg tgttgaagtt caagatgaaa ttgcatttat tcctaatgac gtatactttg   2040
aaaaagataa acagatgttc cacatcatta ctggccccaa tatgggaggt aaatcaacat   2100
atattcgaca aactggggtg atagtactca tggcccaaat tgggtgtttt gtgccatgtg   2160
agtcagcaga agtgtccatt gtggactgca tcttagcccg agtaggggct ggtgacagtc   2220
aattgaaagg agtctccacg ttcatggctg aaatgttgga aactgcttct atcctcaggt   2280
ctgcaaccaa agattcatta ataatcatag atgaattggg aagaggaact tctacctacg   2340
atggatttgg gttagcatgg gctatatcag aatacattgc aacaaagatt ggtgcttttt   2400
gcatgtttgc aacccatttt catgaactta ctgccttggc caatcagata ccaactgtta   2460
ataatctaca tgtcacagca ctcaccactg aagagacctt aactatgctt tatcaggtga   2520
agaaaggtgt ctgtgatcaa agttttggga ttcatgttgc agagcttgct aatttcccta   2580
agcatgtaat agagtgtgct aaacagaaag ccctggaact tgaggagttt cagtatattg   2640
gagaatcgca aggatatgat atcatggaac cagcagcaaa gaagtgctat ctggaaagag   2700
```

-continued

```
agcaaggtga aaaaattatt caggagttcc tgtccaaggt gaaacaaatg ccctttactg   2760

aaatgtcaga agaaaacatc acaataaagt taaaacagct aaaagctgaa gtaatagcaa   2820

agaataatag ctttgtaaat gaaatcattt cacgaataaa agttactacg tgaaaaatcc   2880

cagtaatgga atgaaggtaa tattgataag ctattgtctg taatagtttt atattgtttt   2940

atattaaccc tttttccata gtgttaactg tcagtgccca tgggctatca acttaataag   3000

atatttagta atattttact ttgaggacat tttcaaagat tttatttttg aaaaatgaga   3060

gctgtaactg aggactgttt gcaattgaca taggcaataa taagtgatgt gctgaatttt   3120

ataaataaaa tcatgtagtt tgtgg                                          3145


<210> SEQ ID NO 7
<211> LENGTH: 1863
<212> TYPE: PRT
<213> ORGANISM: Artificial Sequence
<220> FEATURE:
<223> OTHER INFORMATION: BRCA1 sequence

<400> SEQUENCE: 7

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285
```

-continued

```
Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
            420                 425                 430

Ala Ser Asp Pro His Glu Ala Leu Ile Cys Lys Ser Glu Arg Val His
        435                 440                 445

Ser Lys Ser Val Glu Ser Asn Ile Glu Asp Lys Ile Phe Gly Lys Thr
    450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Arg Pro Thr Ser Gly Leu
            500                 505                 510

His Pro Glu Asp Phe Ile Lys Lys Ala Asp Leu Ala Val Gln Lys Thr
        515                 520                 525

Pro Glu Met Ile Asn Gln Gly Thr Asn Gln Thr Glu Gln Asn Gly Gln
    530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
            580                 585                 590

Asn Met Glu Leu Glu Leu Asn Ile His Asn Ser Lys Ala Pro Lys Lys
        595                 600                 605

Asn Arg Leu Arg Arg Lys Ser Ser Thr Arg His Ile His Ala Leu Glu
    610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
            660                 665                 670

Glu Pro Ala Thr Gly Ala Lys Lys Ser Asn Lys Pro Asn Glu Gln Thr
        675                 680                 685

Ser Lys Arg His Asp Ser Asp Thr Phe Pro Glu Leu Lys Leu Thr Asn
    690                 695                 700
```

-continued

```
Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
            740                 745                 750

Ser Gly Glu Arg Val Leu Gln Thr Glu Arg Ser Val Glu Ser Ser Ser
        755                 760                 765

Ile Ser Leu Val Pro Gly Thr Asp Tyr Gly Thr Gln Glu Ser Ile Ser
    770                 775                 780

Leu Leu Glu Val Ser Thr Leu Gly Lys Ala Lys Thr Glu Pro Asn Lys
785                 790                 795                 800

Cys Val Ser Gln Cys Ala Ala Phe Glu Asn Pro Lys Gly Leu Ile His
                805                 810                 815

Gly Cys Ser Lys Asp Asn Arg Asn Asp Thr Glu Gly Phe Lys Tyr Pro
            820                 825                 830

Leu Gly His Glu Val Asn His Ser Arg Glu Thr Ser Ile Glu Met Glu
        835                 840                 845

Glu Ser Glu Leu Asp Ala Gln Tyr Leu Gln Asn Thr Phe Lys Val Ser
    850                 855                 860

Lys Arg Gln Ser Phe Ala Pro Phe Ser Asn Pro Gly Asn Ala Glu Glu
865                 870                 875                 880

Glu Cys Ala Thr Phe Ser Ala His Ser Gly Ser Leu Lys Lys Gln Ser
                885                 890                 895

Pro Lys Val Thr Phe Glu Cys Glu Gln Lys Glu Glu Asn Gln Gly Lys
            900                 905                 910

Asn Glu Ser Asn Ile Lys Pro Val Gln Thr Val Asn Ile Thr Ala Gly
        915                 920                 925

Phe Pro Val Val Gly Gln Lys Asp Lys Pro Val Asp Asn Ala Lys Cys
    930                 935                 940

Ser Ile Lys Gly Gly Ser Arg Phe Cys Leu Ser Ser Gln Phe Arg Gly
945                 950                 955                 960

Asn Glu Thr Gly Leu Ile Thr Pro Asn Lys His Gly Leu Leu Gln Asn
                965                 970                 975

Pro Tyr Arg Ile Pro Pro Leu Phe Pro Ile Lys Ser Phe Val Lys Thr
            980                 985                 990

Lys Cys Lys Lys Asn Leu Leu Glu  Glu Asn Phe Glu Glu  His Ser Met
        995                 1000                1005

Ser Pro  Glu Arg Glu Met Gly  Asn Glu Asn Ile Pro  Ser Thr Val
    1010                1015                1020

Ser Thr  Ile Ser Arg Asn Asn  Ile Arg Glu Asn Val  Phe Lys Glu
    1025                1030                1035

Ala Ser  Ser Ser Asn Ile Asn  Glu Val Gly Ser Ser  Thr Asn Glu
    1040                1045                1050

Val Gly  Ser Ser Ile Asn Glu  Ile Gly Ser Ser Asp  Glu Asn Ile
    1055                1060                1065

Gln Ala  Glu Leu Gly Arg Asn  Arg Gly Pro Lys Leu  Asn Ala Met
    1070                1075                1080

Leu Arg  Leu Gly Val Leu Gln  Pro Glu Val Tyr Lys  Gln Ser Leu
    1085                1090                1095

Pro Gly  Ser Asn Cys Lys His  Pro Glu Ile Lys Lys  Gln Glu Tyr
    1100                1105                1110

Glu Glu  Val Val Gln Thr Val  Asn Thr Asp Phe Ser  Pro Tyr Leu
```

```
    1115                1120                1125

Ile Ser  Asp Asn Leu Glu Gln  Pro Met Gly Ser Ser  His Ala Ser
    1130                1135                1140

Gln Val  Cys Ser Glu Thr Pro  Asp Asp Leu Leu Asp  Asp Gly Glu
    1145                1150                1155

Ile Lys  Glu Asp Thr Ser Phe  Ala Glu Asn Asp Ile  Lys Glu Ser
    1160                1165                1170

Ser Ala  Val Phe Ser Lys Ser  Val Gln Lys Gly Glu  Leu Ser Arg
    1175                1180                1185

Ser Pro  Ser Pro Phe Thr His  Thr His Leu Ala Gln  Gly Tyr Arg
    1190                1195                1200

Arg Gly  Ala Lys Lys Leu Glu  Ser Ser Glu Glu Asn  Leu Ser Ser
    1205                1210                1215

Glu Asp  Glu Glu Leu Pro Cys  Phe Gln His Leu Leu  Phe Gly Lys
    1220                1225                1230

Val Asn  Asn Ile Pro Ser Gln  Ser Thr Arg His Ser  Thr Val Ala
    1235                1240                1245

Thr Glu  Cys Leu Ser Lys Asn  Thr Glu Glu Asn Leu  Leu Ser Leu
    1250                1255                1260

Lys Asn  Ser Leu Asn Asp Cys  Ser Asn Gln Val Ile  Leu Ala Lys
    1265                1270                1275

Ala Ser  Gln Glu His His Leu  Ser Glu Glu Thr Lys  Cys Ser Ala
    1280                1285                1290

Ser Leu  Phe Ser Ser Gln Cys  Ser Glu Leu Glu Asp  Leu Thr Ala
    1295                1300                1305

Asn Thr  Asn Thr Gln Asp Pro  Phe Leu Ile Gly Ser  Ser Lys Gln
    1310                1315                1320

Met Arg  His Gln Ser Glu Ser  Gln Gly Val Gly Leu  Ser Asp Lys
    1325                1330                1335

Glu Leu  Val Ser Asp Asp Glu  Glu Arg Gly Thr Gly  Leu Glu Glu
    1340                1345                1350

Asn Asn  Gln Glu Glu Gln Ser  Met Asp Ser Asn Leu  Gly Glu Ala
    1355                1360                1365

Ala Ser  Gly Cys Glu Ser Glu  Thr Ser Val Ser Glu  Asp Cys Ser
    1370                1375                1380

Gly Leu  Ser Ser Gln Ser Asp  Ile Leu Thr Thr Gln  Gln Arg Asp
    1385                1390                1395

Thr Met  Gln His Asn Leu Ile  Lys Leu Gln Gln Glu  Met Ala Glu
    1400                1405                1410

Leu Glu  Ala Val Leu Glu Gln  His Gly Ser Gln Pro  Ser Asn Ser
    1415                1420                1425

Tyr Pro  Ser Ile Ile Ser Asp  Ser Ser Ala Leu Glu  Asp Leu Arg
    1430                1435                1440

Asn Pro  Glu Gln Ser Thr Ser  Glu Lys Ala Val Leu  Thr Ser Gln
    1445                1450                1455

Lys Ser  Ser Glu Tyr Pro Ile  Ser Gln Asn Pro Glu  Gly Leu Ser
    1460                1465                1470

Ala Asp  Lys Phe Glu Val Ser  Ala Asp Ser Ser Thr  Ser Lys Asn
    1475                1480                1485

Lys Glu  Pro Gly Val Glu Arg  Ser Ser Pro Ser Lys  Cys Pro Ser
    1490                1495                1500

Leu Asp  Asp Arg Trp Tyr Met  His Ser Cys Ser Gly  Ser Leu Gln
    1505                1510                1515
```

```
Asn Arg  Asn Tyr Pro Ser Gln  Glu Glu Leu Ile Lys  Val Val Asp
    1520                 1525                 1530

Val Glu  Glu Gln Gln Leu Glu  Glu Ser Gly Pro His  Asp Leu Thr
    1535                 1540                 1545

Glu Thr  Ser Tyr Leu Pro Arg  Gln Asp Leu Glu Gly  Thr Pro Tyr
    1550                 1555                 1560

Leu Glu  Ser Gly Ile Ser Leu  Phe Ser Asp Asp Pro  Glu Ser Asp
    1565                 1570                 1575

Pro Ser  Glu Asp Arg Ala Pro  Glu Ser Ala Arg Val  Gly Asn Ile
    1580                 1585                 1590

Pro Ser  Ser Thr Ser Ala Leu  Lys Val Pro Gln Leu  Lys Val Ala
    1595                 1600                 1605

Glu Ser  Ala Gln Ser Pro Ala  Ala Ala His Thr Thr  Asp Thr Ala
    1610                 1615                 1620

Gly Tyr  Asn Ala Met Glu Glu  Ser Val Ser Arg Glu  Lys Pro Glu
    1625                 1630                 1635

Leu Thr  Ala Ser Thr Glu Arg  Val Asn Lys Arg Met  Ser Met Val
    1640                 1645                 1650

Val Ser  Gly Leu Thr Pro Glu  Glu Phe Met Leu Val  Tyr Lys Phe
    1655                 1660                 1665

Ala Arg  Lys His His Ile Thr  Leu Thr Asn Leu Ile  Thr Glu Glu
    1670                 1675                 1680

Thr Thr  His Val Val Met Lys  Thr Asp Ala Glu Phe  Val Cys Glu
    1685                 1690                 1695

Arg Thr  Leu Lys Tyr Phe Leu  Gly Ile Ala Gly Gly  Lys Trp Val
    1700                 1705                 1710

Val Ser  Tyr Phe Trp Val Thr  Gln Ser Ile Lys Glu  Arg Lys Met
    1715                 1720                 1725

Leu Asn  Glu His Asp Phe Glu  Val Arg Gly Asp Val  Val Asn Gly
    1730                 1735                 1740

Arg Asn  His Gln Gly Pro Lys  Arg Ala Arg Glu Ser  Gln Asp Arg
    1745                 1750                 1755

Lys Ile  Phe Arg Gly Leu Glu  Ile Cys Cys Tyr Gly  Pro Phe Thr
    1760                 1765                 1770

Asn Met  Pro Thr Asp Gln Leu  Glu Trp Met Val Gln  Leu Cys Gly
    1775                 1780                 1785

Ala Ser  Val Val Lys Glu Leu  Ser Ser Phe Thr Leu  Gly Thr Gly
    1790                 1795                 1800

Val His  Pro Ile Val Val Val  Gln Pro Asp Ala Trp  Thr Glu Asp
    1805                 1810                 1815

Asn Gly  Phe His Ala Ile Gly  Gln Met Cys Glu Ala  Pro Val Val
    1820                 1825                 1830

Thr Arg  Glu Trp Val Leu Asp  Ser Val Ala Leu Tyr  Gln Cys Gln
    1835                 1840                 1845

Glu Leu  Asp Thr Tyr Leu Ile  Pro Gln Ile Pro His  Ser His Tyr
    1850                 1855                 1860
```

<210> SEQ ID NO 8
<211> LENGTH: 7224
<212> TYPE: DNA
<213> ORGANISM: Artificial Sequence
<220> FEATURE:
<223> OTHER INFORMATION: BRCA1 sequence

<400> SEQUENCE: 8

-continued

```
gtaccttgat ttcgtattct gagaggctgc tgcttagcgg tagccccttg gtttccgtgg     60
caacggaaaa gcgcgggaat tacagataaa ttaaaactgc gactgcgcgg cgtgagctcg    120
ctgagacttc ctggacgggg gacaggctgt ggggtttctc agataactgg gcccctgcgc    180
tcaggaggcc ttcaccctct gctctgggta aagttcattg gaacagaaag aaatggattt    240
atctgctctt cgcgttgaag aagtacaaaa tgtcattaat gctatgcaga aaatcttaga    300
gtgtcccatc tgtctggagt tgatcaagga acctgtctcc acaaagtgtg accacatatt    360
ttgcaaattt tgcatgctga aacttctcaa ccagaagaaa gggccttcac agtgtccttt    420
atgtaagaat gatataacca aaaggagcct acaagaaagt acgagattta gtcaacttgt    480
tgaagagcta ttgaaaatca tttgtgcttt tcagcttgac acaggtttgg agtatgcaaa    540
cagctataat tttgcaaaaa aggaaaataa ctctcctgaa catctaaaag atgaagtttc    600
tatcatccaa agtatgggct acagaaaccg tgccaaaaga cttctacaga gtgaacccga    660
aaatccttcc ttgcaggaaa ccagtctcag tgtccaactc tctaaccttg gaactgtgag    720
aactctgagg acaaagcagc ggatacaacc tcaaaagacg tctgtctaca ttgaattggg    780
atctgattct tctgaagata ccgttaataa ggcaacttat tgcagtgtgg gagatcaaga    840
attgttacaa atcacccctc aaggaaccag ggatgaaatc agtttggatt ctgcaaaaaa    900
ggctgcttgt gaattttctg agacggatgt aacaaatact gaacatcatc aacccagtaa    960
taatgatttg aacaccactg agaagcgtgc agctgagagg catccagaaa agtatcaggg   1020
tagttctgtt tcaaacttgc atgtggagcc atgtggcaca aatactcatg ccagctcatt   1080
acagcatgag aacagcagtt tattactcac taaagacaga atgaatgtag aaaaggctga   1140
attctgtaat aaaagcaaac agcctggctt agcaaggagc caacataaca gatgggctgg   1200
aagtaaggaa acatgtaatg ataggcggac tcccagcaca gaaaaaaagg tagatctgaa   1260
tgctgatccc ctgtgtgaga gaaaagaatg gaataagcag aaactgccat gctcagagaa   1320
tcctagagat actgaagatg ttccttggat aacactaaat agcagcattc agaaagttaa   1380
tgagtggttt tccagaagtg atgaactgtt aggttctgat gactcacatg atggggagtc   1440
tgaatcaaat gccaaagtag ctgatgtatt ggacgttcta aatgaggtag atgaatattc   1500
tggttcttca gagaaaatag acttactggc cagtgatcct catgaggctt taatatgtaa   1560
aagtgaaaga gttcactcca aatcagtaga gagtaatatt gaagacaaaa tatttgggaa   1620
aacctatcgg aagaaggcaa gcctccccaa cttaagccat gtaactgaaa atctaattat   1680
aggagcattt gttactgagc cacagataat acaagagcgt cccctcacaa ataaattaaa   1740
gcgtaaaagg agacctacat caggccttca tcctgaggat tttatcaaga aagcagattt   1800
ggcagttcaa aagactcctg aaatgataaa tcagggaact aaccaaacgg agcagaatgg   1860
tcaagtgatg aatattacta atagtggtca tgagaataaa acaaaaggtg attctattca   1920
gaatgagaaa aatcctaacc caatagaatc actcgaaaaa gaatctgctt tcaaaacgaa   1980
agctgaacct ataagcagca gtataagcaa tatggaactc gaattaaata tccacaattc   2040
aaaagcacct aaaaagaata ggctgaggag gaagtcttct accaggcata ttcatgcgct   2100
tgaactagta gtcagtagaa atctaagccc acctaattgt actgaattgc aaattgatag   2160
ttgttctagc agtgaagaga taaagaaaaa aaagtacaac caaatgccag tcaggcacag   2220
cagaaaccta caactcatgg aaggtaaaga acctgcaact ggagccaaga agagtaacaa   2280
gccaaatgaa cagacaagta aaagacatga cagcgatact ttcccagagc tgaagttaac   2340
```

-continued

```
aaatgcacct ggttctttta ctaagtgttc aaataccagt gaacttaaag aatttgtcaa   2400
tcctagcctt ccaagagaag aaaaagaaga gaaactagaa acagttaaag tgtctaataa   2460
tgctgaagac cccaaagatc tcatgttaag tggagaaagg gttttgcaaa ctgaaagatc   2520
tgtagagagt agcagtattt cattggtacc tggtactgat tatggcactc aggaaagtat   2580
ctcgttactg gaagttagca ctctagggaa ggcaaaaaca gaaccaaata aatgtgtgag   2640
tcagtgtgca gcatttgaaa accccaaggg actaattcat ggttgttcca aagataatag   2700
aaatgacaca gaaggcttta agtatccatt gggacatgaa gttaaccaca gtcgggaaac   2760
aagcatagaa atggaagaaa gtgaacttga tgctcagtat ttgcagaata cattcaaggt   2820
ttcaaagcgc cagtcatttg ctccgttttc aaatccagga aatgcagaag aggaatgtgc   2880
aacattctct gcccactctg ggtccttaaa gaaacaaagt ccaaaagtca cttttgaatg   2940
tgaacaaaag gaagaaaatc aaggaaagaa tgagtctaat atcaagcctg tacagacagt   3000
taatatcact gcaggctttc ctgtggttgg tcagaaagat aagccagttg ataatgccaa   3060
atgtagtatc aaaggaggct ctaggttttg tctatcatct cagttcagag gcaacgaaac   3120
tggactcatt actccaaata aacatggact tttacaaaac ccatatcgta taccaccact   3180
ttttcccatc aagtcatttg ttaaaactaa atgtaagaaa aatctgctag aggaaaactt   3240
tgaggaacat tcaatgtcac ctgaaagaga aatgggaaat gagaacattc caagtacagt   3300
gagcacaatt agccgtaata acattagaga aaatgttttt aaagaagcca gctcaagcaa   3360
tattaatgaa gtaggttcca gtactaatga agtgggctcc agtattaatg aaataggttc   3420
cagtgatgaa aacattcaag cagaactagg tagaaacaga gggccaaaat tgaatgctat   3480
gcttagatta ggggttttgc aacctgaggt ctataaacaa agtcttcctg gaagtaattg   3540
taagcatcct gaaataaaaa agcaagaata tgaagaagta gttcagactg ttaatacaga   3600
tttctctcca tatctgattt cagataactt agaacagcct atgggaagta gtcatgcatc   3660
tcaggtttgt tctgagacac ctgatgacct gttagatgat ggtgaaataa aggaagatac   3720
tagttttgct gaaaatgaca ttaaggaaag ttctgctgtt tttagcaaaa gcgtccagaa   3780
aggagagctt agcaggagtc ctagcccttt cacccataca catttggctc agggttaccg   3840
aagaggggcc aagaaattag agtcctcaga agagaactta tctagtgagg atgaagagct   3900
tccctgcttc caacacttgt tatttggtaa agtaaacaat ataccttctc agtctactag   3960
gcatagcacc gttgctaccg agtgtctgtc taagaacaca gaggagaatt tattatcatt   4020
gaagaatagc ttaaatgact gcagtaacca ggtaatattg gcaaaggcat ctcaggaaca   4080
tcaccttagt gaggaaacaa aatgttctgc tagcttgttt tcttcacagt gcagtgaatt   4140
ggaagacttg actgcaaata caaacaccca ggatcctttc ttgattggtt cttccaaaca   4200
aatgaggcat cagtctgaaa gccagggagt tggtctgagt gacaaggaat tggtttcaga   4260
tgatgaagaa agaggaacgg gcttggaaga aaataatcaa gaagagcaaa gcatggattc   4320
aaacttaggt gaagcagcat ctgggtgtga gagtgaaaca agcgtctctg aagactgctc   4380
agggctatcc tctcagagtg acattttaac cactcagcag agggatacca tgcaacataa   4440
cctgataaag ctccagcagg aaatggctga actagaagct gtgttagaac agcatgggag   4500
ccagccttct aacagctacc cttccatcat aagtgactct tctgcccttg aggacctgcg   4560
aaatccagaa caaagcacat cagaaaaagc agtattaact tcacagaaaa gtagtgaata   4620
ccctataagc cagaatccag aaggcctttc tgctgacaag tttgaggtgt ctgcagatag   4680
ttctaccagt aaaaataaag aaccaggagt ggaaaggtca tccccttcta aatgcccatc   4740
```

```
attagatgat aggtggtaca tgcacagttg ctctgggagt cttcagaata gaaactaccc   4800
atctcaagag gagctcatta aggttgttga tgtggaggag caacagctgg aagagtctgg   4860
gccacacgat ttgacggaaa catcttactt gccaaggcaa gatctagagg gaaccccttta  4920
cctggaatct ggaatcagcc tcttctctga tgaccctgaa tctgatcctt ctgaagacag   4980
agccccagag tcagctcgtg ttggcaacat accatcttca acctctgcat tgaaagttcc   5040
ccaattgaaa gttgcagaat ctgcccagag tccagctgct gctcatacta ctgatactgc   5100
tgggtataat gcaatggaag aaagtgtgag cagggagaag ccagaattga cagcttcaac   5160
agaaagggtc aacaaaagaa tgtccatggt ggtgtctggc ctgaccccag aagaatttat   5220
gctcgtgtac aagtttgcca gaaaacacca catcacttta actaatctaa ttactgaaga   5280
gactactcat gttgttatga aaacagatgc tgagtttgtg tgtgaacgga cactgaaata   5340
ttttctagga attgcgggag gaaaatgggt agttagctat ttctgggtga cccagtctat   5400
taaagaaaga aaaatgctga atgagcatga ttttgaagtc agaggagatg tggtcaatgg   5460
aagaaaccac caaggtccaa agcgagcaag agaatcccag gacagaaaga tcttcagggg   5520
gctagaaatc tgttgctatg ggcccttcac caacatgccc acagatcaac tggaatggat   5580
ggtacagctg tgtggtgctt ctgtggtgaa ggagctttca tcattcaccc ttggcacagg   5640
tgtccaccca attgtggttg tgcagccaga tgcctggaca gaggacaatg gcttccatgc   5700
aattgggcag atgtgtgagg cacctgtggt gacccgagag tgggtgttgg acagtgtagc   5760
actctaccag tgccaggagc tggacaccta cctgataccc cagatccccc acagccacta   5820
ctgactgcag ccagccacag gtacagagcc acaggacccc aagaatgagc ttacaaagtg   5880
gcctttccag gccctgggag ctcctctcac tcttcagtcc ttctactgtc ctggctacta   5940
aatattttat gtacatcagc ctgaaaagga cttctggcta tgcaagggtc ccttaaagat   6000
tttctgcttg aagtctccct tggaaatctg ccatgagcac aaaattatgg taatttttca   6060
cctgagaaga ttttaaaacc atttaaacgc caccaattga gcaagatgct gattcattat   6120
ttatcagccc tattctttct attcaggctg ttgttggctt agggctggaa gcacagagtg   6180
gcttggcctc aagagaatag ctggtttccc taagtttact tctctaaaac cctgtgttca   6240
caaaggcaga gagtcagacc cttcaatgga aggagagtgc ttgggatcga ttatgtgact   6300
taaagtcaga atagtccttg ggcagttctc aaatgttgga gtggaacatt ggggaggaaa   6360
ttctgaggca ggtattagaa atgaaaagga aacttgaaac ctgggcatgg tggctcacgc   6420
ctgtaatccc agcactttgg gaggccaagg tgggcagatc actggaggtc aggagttcga   6480
aaccagcctg gccaacatgg tgaaacccca tctctactaa aaatacagaa attagccggt   6540
catggtggtg gacacctgta atcccagcta ctcaggtggc taaggcagga gaatcacttc   6600
agcccgggag gtggaggttg cagtgagcca agatcatacc acggcactcc agcctgggtg   6660
acagtgagac tgtggctcaa aaaaaaaaaa aaaaaaagga aaatgaaact agaagagatt   6720
tctaaaagtc tgagatatat ttgctagatt tctaaagaat gtgttctaaa acagcagaag   6780
attttcaaga accggtttcc aaagacagtc ttctaattcc tcattagtaa taagtaaaat   6840
gtttattgtt gtagctctgg tatataatcc attcctctta aaatataaga cctctggcat   6900
gaatatttca tatctataaa atgacagatc ccaccaggaa ggaagctgtt gctttctttg   6960
aggtgatttt tttcctttgc tccctgttgc tgaaaccata cagcttcata aataattttg   7020
cttgctgaag gaagaaaaag tgtttttcat aaacccatta tccaggactg tttatagctg   7080
```

```
ttggaaggac taggtcttcc ctagcccccc cagtgtgcaa gggcagtgaa gacttgattg   7140

tacaaaatac gttttgtaaa tgttgtgctg ttaacactgc aaataaactt ggtagcaaac   7200

acttccaaaa aaaaaaaaaa aaaa                                          7224


<210> SEQ ID NO 9
<211> LENGTH: 3130
<212> TYPE: PRT
<213> ORGANISM: Artificial Sequence
<220> FEATURE:
<223> OTHER INFORMATION: REV3L sequence

<400> SEQUENCE: 9

Met Phe Ser Val Arg Ile Val Thr Ala Asp Tyr Tyr Met Ala Ser Pro
1               5                   10                  15

Leu Gln Gly Leu Asp Thr Cys Gln Ser Pro Leu Thr Gln Ala Pro Val
            20                  25                  30

Lys Lys Val Pro Val Val Arg Val Phe Gly Ala Thr Pro Ala Gly Gln
        35                  40                  45

Lys Thr Cys Leu His Leu His Gly Ile Phe Pro Tyr Leu Tyr Val Pro
    50                  55                  60

Tyr Asp Gly Tyr Gly Gln Gln Pro Glu Ser Tyr Leu Ser Gln Met Ala
65                  70                  75                  80

Phe Ser Ile Asp Arg Ala Leu Asn Val Ala Leu Gly Asn Pro Ser Ser
                85                  90                  95

Thr Ala Gln His Val Phe Lys Val Ser Leu Val Ser Gly Met Pro Phe
            100                 105                 110

Tyr Gly Tyr His Glu Lys Glu Arg His Phe Met Lys Ile Tyr Leu Tyr
        115                 120                 125

Asn Pro Thr Met Val Lys Arg Ile Cys Glu Leu Leu Gln Ser Gly Ala
    130                 135                 140

Ile Met Asn Lys Phe Tyr Gln Pro His Glu Ala His Ile Pro Tyr Leu
145                 150                 155                 160

Leu Gln Leu Phe Ile Asp Tyr Asn Leu Tyr Gly Met Asn Leu Ile Asn
                165                 170                 175

Leu Ala Ala Val Lys Phe Arg Lys Ala Arg Arg Lys Ser Asn Thr Leu
            180                 185                 190

His Ala Thr Gly Ser Cys Lys Asn His Leu Ser Gly Asn Ser Leu Ala
        195                 200                 205

Asp Thr Leu Phe Arg Trp Glu Gln Asp Glu Ile Pro Ser Ser Leu Ile
    210                 215                 220

Leu Glu Gly Val Glu Pro Gln Ser Thr Cys Glu Leu Glu Val Asp Ala
225                 230                 235                 240

Val Ala Ala Asp Ile Leu Asn Arg Leu Asp Ile Glu Ala Gln Ile Gly
                245                 250                 255

Gly Asn Pro Gly Leu Gln Ala Ile Trp Glu Asp Glu Lys Gln Arg Arg
            260                 265                 270

Arg Asn Arg Asn Glu Thr Ser Gln Met Ser Gln Pro Glu Ser Gln Asp
        275                 280                 285

His Arg Phe Val Pro Ala Thr Glu Ser Glu Lys Lys Phe Gln Lys Arg
    290                 295                 300

Leu Gln Glu Ile Leu Lys Gln Asn Asp Phe Ser Val Thr Leu Ser Gly
305                 310                 315                 320

Ser Val Asp Tyr Ser Asp Gly Ser Gln Glu Phe Ser Ala Glu Leu Thr
                325                 330                 335
```

-continued

```
Leu His Ser Glu Val Leu Ser Pro Glu Met Leu Gln Cys Thr Pro Ala
            340                 345                 350

Asn Met Val Glu Val His Lys Asp Lys Glu Ser Ser Lys Gly His Thr
        355                 360                 365

Arg His Lys Val Glu Glu Ala Leu Ile Asn Glu Glu Ala Ile Leu Asn
    370                 375                 380

Leu Met Glu Asn Ser Gln Thr Phe Gln Pro Leu Thr Gln Arg Leu Ser
385                 390                 395                 400

Glu Ser Pro Val Phe Met Asp Ser Ser Pro Asp Glu Ala Leu Val His
                405                 410                 415

Leu Leu Ala Gly Leu Glu Ser Asp Gly Tyr Arg Gly Glu Arg Asn Arg
            420                 425                 430

Met Pro Ser Pro Cys Arg Ser Phe Gly Asn Asn Lys Tyr Pro Gln Asn
        435                 440                 445

Ser Asp Asp Glu Glu Asn Glu Pro Gln Ile Glu Lys Glu Glu Met Glu
    450                 455                 460

Leu Ser Leu Val Met Ser Gln Arg Trp Asp Ser Asn Ile Glu Glu His
465                 470                 475                 480

Cys Ala Lys Lys Arg Ser Leu Cys Arg Asn Thr His Arg Ser Ser Thr
                485                 490                 495

Glu Asp Asp Asp Ser Ser Ser Gly Glu Glu Met Glu Trp Ser Asp Asn
            500                 505                 510

Ser Leu Leu Leu Ala Ser Leu Ser Ile Pro Gln Leu Asp Gly Thr Ala
        515                 520                 525

Asp Glu Asn Ser Asp Asn Pro Leu Asn Asn Glu Asn Ser Arg Thr His
    530                 535                 540

Ser Ser Val Ile Ala Thr Ser Lys Leu Ser Val Lys Pro Ser Ile Phe
545                 550                 555                 560

His Lys Asp Ala Ala Thr Leu Glu Pro Ser Ser Ser Ala Lys Ile Thr
                565                 570                 575

Phe Gln Cys Lys His Thr Ser Ala Leu Ser Ser His Val Leu Asn Lys
            580                 585                 590

Glu Asp Leu Ile Glu Asp Leu Ser Gln Thr Asn Lys Asn Thr Glu Lys
        595                 600                 605

Gly Leu Asp Asn Ser Val Thr Ser Phe Thr Asn Glu Ser Thr Tyr Ser
    610                 615                 620

Met Lys Tyr Pro Gly Ser Leu Ser Ser Thr Val His Ser Glu Asn Ser
625                 630                 635                 640

His Lys Glu Asn Ser Lys Lys Glu Ile Leu Pro Val Ser Ser Cys Glu
                645                 650                 655

Ser Ser Ile Phe Asp Tyr Glu Glu Asp Ile Pro Ser Val Thr Arg Gln
            660                 665                 670

Val Pro Ser Arg Lys Tyr Thr Asn Ile Arg Lys Ile Glu Lys Asp Ser
        675                 680                 685

Pro Phe Ile His Met His Arg His Pro Asn Glu Asn Thr Leu Gly Lys
    690                 695                 700

Asn Ser Phe Asn Phe Ser Asp Leu Asn His Ser Lys Asn Lys Val Ser
705                 710                 715                 720

Ser Glu Gly Asn Glu Lys Gly Asn Ser Thr Ala Leu Ser Ser Leu Phe
                725                 730                 735

Pro Ser Ser Phe Thr Glu Asn Cys Glu Leu Leu Ser Cys Ser Gly Glu
            740                 745                 750

Asn Arg Thr Met Val His Ser Leu Asn Ser Thr Ala Asp Glu Ser Gly
```

```
        755                 760                 765

Leu Asn Lys Leu Lys Ile Arg Tyr Glu Glu Phe Gln Glu His Lys Thr
    770                 775                 780

Glu Lys Pro Ser Leu Ser Gln Gln Ala Ala His Tyr Met Phe Phe Pro
785                 790                 795                 800

Ser Val Val Leu Ser Asn Cys Leu Thr Arg Pro Gln Lys Leu Ser Pro
                805                 810                 815

Val Thr Tyr Lys Leu Gln Pro Gly Asn Lys Pro Ser Arg Leu Lys Leu
            820                 825                 830

Asn Lys Arg Lys Leu Ala Gly His Gln Glu Thr Ser Thr Lys Ser Ser
        835                 840                 845

Glu Thr Gly Ser Thr Lys Asp Asn Phe Ile Gln Asn Asn Pro Cys Asn
    850                 855                 860

Ser Asn Pro Glu Lys Asp Asn Ala Leu Ala Ser Asp Leu Thr Lys Thr
865                 870                 875                 880

Thr Arg Gly Ala Phe Glu Asn Lys Thr Pro Thr Asp Gly Phe Ile Asp
                885                 890                 895

Cys His Phe Gly Asp Gly Thr Leu Glu Thr Glu Gln Ser Phe Gly Leu
            900                 905                 910

Tyr Gly Asn Lys Tyr Thr Leu Arg Ala Lys Arg Lys Val Asn Tyr Glu
        915                 920                 925

Thr Glu Asp Ser Glu Ser Ser Phe Val Thr His Asn Ser Lys Ile Ser
    930                 935                 940

Leu Pro His Pro Met Glu Ile Gly Glu Ser Leu Asp Gly Thr Leu Lys
945                 950                 955                 960

Ser Arg Lys Arg Arg Lys Met Ser Lys Lys Leu Pro Pro Val Ile Ile
                965                 970                 975

Lys Tyr Ile Ile Ile Asn Arg Phe Arg Gly Arg Lys Asn Met Leu Val
            980                 985                 990

Lys Leu Gly Lys Ile Asp Ser Lys  Glu Lys Gln Val Ile  Leu Thr Glu
        995                 1000                1005

Glu Lys  Met Glu Leu Tyr Lys  Lys Leu Ala Pro Leu  Lys Asp Phe
    1010                 1015                 1020

Trp Pro  Lys Val Pro Asp Ser  Pro Ala Thr Lys Tyr  Pro Ile Tyr
    1025                 1030                 1035

Pro Leu  Thr Pro Lys Lys Ser  His Arg Arg Lys Ser  Lys His Lys
    1040                 1045                 1050

Ser Ala  Lys Lys Lys Thr Gly  Lys Gln Gln Arg Thr  Asn Asn Glu
    1055                 1060                 1065

Asn Ile  Lys Arg Thr Leu Ser  Phe Arg Lys Lys Arg  Ser His Ala
    1070                 1075                 1080

Ile Leu  Ser Pro Pro Ser Pro  Ser Tyr Asn Ala Glu  Thr Glu Asp
    1085                 1090                 1095

Cys Asp  Leu Asn Tyr Ser Asp  Val Met Ser Lys Leu  Gly Phe Leu
    1100                 1105                 1110

Ser Glu  Arg Ser Thr Ser Pro  Ile Asn Ser Ser Pro  Pro Arg Cys
    1115                 1120                 1125

Trp Ser  Pro Thr Asp Pro Arg  Ala Glu Glu Ile Met  Ala Ala Ala
    1130                 1135                 1140

Glu Lys  Glu Ala Met Leu Phe  Lys Gly Pro Asn Val  Tyr Lys Lys
    1145                 1150                 1155

Thr Val  Asn Ser Arg Ile Gly  Lys Thr Ser Arg Ala  Arg Ala Gln
    1160                 1165                 1170
```

-continued

```
Ile Lys  Lys Ser Lys Ala Lys  Leu Ala Asn Pro Ser  Ile Val Thr
    1175                 1180                 1185

Lys Lys  Arg Asn Lys Arg Asn  Gln Thr Asn Lys Leu  Val Asp Asp
    1190                 1195                 1200

Gly Lys  Lys Lys Pro Arg Ala  Lys Gln Lys Thr Asn  Glu Lys Gly
    1205                 1210                 1215

Thr Ser  Arg Lys His Thr Thr  Leu Lys Asp Glu Lys  Ile Lys Ser
    1220                 1225                 1230

Gln Ser  Gly Ala Glu Val Lys  Phe Val Leu Lys His  Gln Asn Val
    1235                 1240                 1245

Ser Glu  Phe Ala Ser Ser Ser  Gly Gly Ser Gln Leu  Leu Phe Lys
    1250                 1255                 1260

Gln Lys  Asp Met Pro Leu Met  Gly Ser Ala Val Asp  His Pro Leu
    1265                 1270                 1275

Ser Ala  Ser Leu Pro Thr Gly  Ile Asn Ala Gln Gln  Lys Leu Ser
    1280                 1285                 1290

Gly Cys  Phe Ser Ser Phe Leu  Glu Ser Lys Lys Ser  Val Asp Leu
    1295                 1300                 1305

Gln Thr  Phe Pro Ser Ser Arg  Asp Asp Leu His Pro  Ser Val Val
    1310                 1315                 1320

Cys Asn  Ser Ile Gly Pro Gly  Val Ser Lys Ile Asn  Val Gln Arg
    1325                 1330                 1335

Pro His  Asn Gln Ser Ala Met  Phe Thr Leu Lys Glu  Ser Thr Leu
    1340                 1345                 1350

Ile Gln  Lys Asn Ile Phe Asp  Leu Ser Asn His Leu  Ser Gln Val
    1355                 1360                 1365

Ala Gln  Asn Thr Gln Ile Ser  Ser Gly Met Ser Ser  Lys Ile Glu
    1370                 1375                 1380

Asp Asn  Ala Asn Asn Ile Gln  Arg Asn Tyr Leu Ser  Ser Ile Gly
    1385                 1390                 1395

Lys Leu  Ser Glu Tyr Arg Asn  Ser Leu Glu Ser Lys  Leu Asp Gln
    1400                 1405                 1410

Ala Tyr  Thr Pro Asn Phe Leu  His Cys Lys Asp Ser  Gln Gln Gln
    1415                 1420                 1425

Ile Val  Cys Ile Ala Glu Gln  Ser Lys His Ser Glu  Thr Cys Ser
    1430                 1435                 1440

Pro Gly  Asn Thr Ala Ser Glu  Glu Ser Gln Met Pro  Asn Asn Cys
    1445                 1450                 1455

Phe Val  Thr Ser Leu Arg Ser  Pro Ile Lys Gln Ile  Ala Trp Glu
    1460                 1465                 1470

Gln Lys  Gln Arg Gly Phe Ile  Leu Asp Met Ser Asn  Phe Lys Pro
    1475                 1480                 1485

Glu Arg  Val Lys Pro Arg Ser  Leu Ser Glu Ala Ile  Ser Gln Thr
    1490                 1495                 1500

Lys Ala  Leu Ser Gln Cys Lys  Asn Arg Asn Val Ser  Thr Pro Ser
    1505                 1510                 1515

Ala Phe  Gly Glu Gly Gln Ser  Gly Leu Ala Val Leu  Lys Glu Leu
    1520                 1525                 1530

Leu Gln  Lys Arg Gln Gln Lys  Ala Gln Asn Ala Asn  Thr Thr Gln
    1535                 1540                 1545

Asp Pro  Leu Ser Asn Lys His  Gln Pro Asn Lys Asn  Ile Ser Gly
    1550                 1555                 1560
```

```
Ser Leu  Glu His Asn Lys Ala  Asn Lys Arg Thr Arg  Ser Val Thr
    1565                 1570                 1575

Ser Pro  Arg Lys Pro Arg Thr  Pro Arg Ser Thr Lys  Gln Lys Glu
    1580                 1585                 1590

Lys Ile  Pro Lys Leu Leu Lys  Val Asp Ser Leu Asn  Leu Gln Asn
    1595                 1600                 1605

Ser Ser  Gln Leu Asp Asn Ser  Val Ser Asp Asp Ser  Pro Ile Phe
    1610                 1615                 1620

Phe Ser  Asp Pro Gly Phe Glu  Ser Cys Tyr Ser Leu  Glu Asp Ser
    1625                 1630                 1635

Leu Ser  Pro Glu His Asn Tyr  Asn Phe Asp Ile Asn  Thr Ile Gly
    1640                 1645                 1650

Gln Thr  Gly Phe Cys Ser Phe  Tyr Ser Gly Ser Gln  Phe Val Pro
    1655                 1660                 1665

Ala Asp  Gln Asn Leu Pro Gln  Lys Phe Leu Ser Asp  Ala Val Gln
    1670                 1675                 1680

Asp Leu  Phe Pro Gly Gln Ala  Ile Glu Lys Asn Glu  Phe Leu Ser
    1685                 1690                 1695

His Asp  Asn Gln Lys Cys Asp  Glu Asp Lys His His  Thr Thr Asp
    1700                 1705                 1710

Ser Ala  Ser Trp Ile Arg Ser  Gly Thr Leu Ser Pro  Glu Ile Phe
    1715                 1720                 1725

Glu Lys  Ser Thr Ile Asp Ser  Asn Glu Asn Arg Arg  His Asn Gln
    1730                 1735                 1740

Trp Lys  Asn Ser Phe His Pro  Leu Thr Thr Arg Ser  Asn Ser Ile
    1745                 1750                 1755

Met Asp  Ser Phe Cys Val Gln  Gln Ala Glu Asp Cys  Leu Ser Glu
    1760                 1765                 1770

Lys Ser  Arg Leu Asn Arg Ser  Ser Val Ser Lys Glu  Val Phe Leu
    1775                 1780                 1785

Ser Leu  Pro Gln Pro Asn Asn  Ser Asp Trp Ile Gln  Gly His Thr
    1790                 1795                 1800

Arg Lys  Glu Met Gly Gln Ser  Leu Asp Ser Ala Asn  Thr Ser Phe
    1805                 1810                 1815

Thr Ala  Ile Leu Ser Ser Pro  Asp Gly Glu Leu Val  Asp Val Ala
    1820                 1825                 1830

Cys Glu  Asp Leu Glu Leu Tyr  Val Ser Arg Asn Asn  Asp Met Leu
    1835                 1840                 1845

Thr Pro  Thr Pro Asp Ser Ser  Pro Arg Ser Thr Ser  Ser Pro Ser
    1850                 1855                 1860

Gln Ser  Lys Asn Gly Ser Phe  Thr Pro Arg Thr Ala  Asn Ile Leu
    1865                 1870                 1875

Lys Pro  Leu Met Ser Pro Pro  Ser Arg Glu Glu Ile  Met Ala Thr
    1880                 1885                 1890

Leu Leu  Asp His Asp Leu Ser  Glu Thr Ile Tyr Gln  Glu Pro Phe
    1895                 1900                 1905

Cys Ser  Asn Pro Ser Asp Val  Pro Glu Lys Pro Arg  Glu Ile Gly
    1910                 1915                 1920

Gly Arg  Leu Leu Met Val Glu  Thr Arg Leu Ala Asn  Asp Leu Ala
    1925                 1930                 1935

Glu Phe  Glu Gly Asp Phe Ser  Leu Glu Gly Leu Arg  Leu Trp Lys
    1940                 1945                 1950

Thr Ala  Phe Ser Ala Met Thr  Gln Asn Pro Arg Pro  Gly Ser Pro
```

```
    1955                1960                1965

Leu Arg  Ser Gly Gln Gly Val  Val Asn Lys Gly Ser  Ser Asn Ser
    1970                1975                1980

Pro Lys  Met Val Glu Asp Lys  Lys Ile Val Ile Met  Pro Cys Lys
    1985                1990                1995

Cys Ala  Pro Ser Arg Gln Leu  Val Gln Val Trp Leu  Gln Ala Lys
    2000                2005                2010

Glu Glu  Tyr Glu Arg Ser Lys  Lys Leu Pro Lys Thr  Lys Pro Thr
    2015                2020                2025

Gly Val  Val Lys Ser Ala Glu  Asn Phe Ser Ser Ser  Val Asn Pro
    2030                2035                2040

Asp Asp  Lys Pro Val Val Pro  Pro Lys Met Asp Val  Ser Pro Cys
    2045                2050                2055

Ile Leu  Pro Thr Thr Ala His  Thr Lys Glu Asp Val  Asp Asn Ser
    2060                2065                2070

Gln Ile  Ala Leu Gln Ala Pro  Thr Thr Gly Cys Ser  Gln Thr Ala
    2075                2080                2085

Ser Glu  Ser Gln Met Leu Pro  Pro Val Ala Ser Ala  Ser Asp Pro
    2090                2095                2100

Glu Lys  Asp Glu Asp Asp Asp  Asp Asn Tyr Tyr Ile  Ser Tyr Ser
    2105                2110                2115

Ser Pro  Asp Ser Pro Val Ile  Pro Pro Trp Gln Gln  Pro Ile Ser
    2120                2125                2130

Pro Asp  Ser Lys Ala Leu Asn  Gly Asp Asp Arg Pro  Ser Ser Pro
    2135                2140                2145

Val Glu  Glu Leu Pro Ser Leu  Ala Phe Glu Asn Phe  Leu Lys Pro
    2150                2155                2160

Ile Lys  Asp Gly Ile Gln Lys  Ser Pro Cys Ser Glu  Pro Gln Glu
    2165                2170                2175

Pro Leu  Val Ile Ser Pro Ile  Asn Thr Arg Ala Arg  Thr Gly Lys
    2180                2185                2190

Cys Glu  Ser Leu Cys Phe His  Ser Thr Pro Ile Ile  Gln Arg Lys
    2195                2200                2205

Leu Leu  Glu Arg Leu Pro Glu  Ala Pro Gly Leu Ser  Pro Leu Ser
    2210                2215                2220

Thr Glu  Pro Lys Thr Gln Lys  Leu Ser Asn Lys Lys  Gly Ser Asn
    2225                2230                2235

Thr Asp  Thr Leu Arg Arg Val  Leu Leu Thr Gln Ala  Lys Asn Gln
    2240                2245                2250

Phe Ala  Ala Val Asn Thr Pro  Gln Lys Glu Thr Ser  Gln Ile Asp
    2255                2260                2265

Gly Pro  Ser Leu Asn Asn Thr  Tyr Gly Phe Lys Val  Ser Ile Gln
    2270                2275                2280

Asn Leu  Gln Glu Ala Lys Ala  Leu His Glu Ile Gln  Asn Leu Thr
    2285                2290                2295

Leu Ile  Ser Val Glu Leu His  Ala Arg Thr Arg Arg  Asp Leu Glu
    2300                2305                2310

Pro Asp  Pro Glu Phe Asp Pro  Ile Cys Ala Leu Phe  Tyr Cys Ile
    2315                2320                2325

Ser Ser  Asp Thr Pro Leu Pro  Asp Thr Glu Lys Thr  Glu Leu Thr
    2330                2335                2340

Gly Val  Ile Val Ile Asp Lys  Asp Lys Thr Val Phe  Ser Gln Asp
    2345                2350                2355
```

Ile Arg Tyr Gln Thr Pro Leu Leu Ile Arg Ser Gly Ile Thr Gly
2360 2365 2370

Leu Glu Val Thr Tyr Ala Ala Asp Glu Lys Ala Leu Phe His Glu
2375 2380 2385

Ile Ala Asn Ile Ile Lys Arg Tyr Asp Pro Asp Ile Leu Leu Gly
2390 2395 2400

Tyr Glu Ile Gln Met His Ser Trp Gly Tyr Leu Leu Gln Arg Ala
2405 2410 2415

Ala Ala Leu Ser Ile Asp Leu Cys Arg Met Ile Ser Arg Val Pro
2420 2425 2430

Asp Asp Lys Ile Glu Asn Arg Phe Ala Ala Glu Arg Asp Glu Tyr
2435 2440 2445

Gly Ser Tyr Thr Met Ser Glu Ile Asn Ile Val Gly Arg Ile Thr
2450 2455 2460

Leu Asn Leu Trp Arg Ile Met Arg Asn Glu Val Ala Leu Thr Asn
2465 2470 2475

Tyr Thr Phe Glu Asn Val Ser Phe His Val Leu His Gln Arg Phe
2480 2485 2490

Pro Leu Phe Thr Phe Arg Val Leu Ser Asp Trp Phe Asp Asn Lys
2495 2500 2505

Thr Asp Leu Tyr Arg Trp Lys Met Val Asp His Tyr Val Ser Arg
2510 2515 2520

Val Arg Gly Asn Leu Gln Met Leu Glu Gln Leu Asp Leu Ile Gly
2525 2530 2535

Lys Thr Ser Glu Met Ala Arg Leu Phe Gly Ile Gln Phe Leu His
2540 2545 2550

Val Leu Thr Arg Gly Ser Gln Tyr Arg Val Glu Ser Met Met Leu
2555 2560 2565

Arg Ile Ala Lys Pro Met Asn Tyr Ile Pro Val Thr Pro Ser Val
2570 2575 2580

Gln Gln Arg Ser Gln Met Arg Ala Pro Gln Cys Val Pro Leu Ile
2585 2590 2595

Met Glu Pro Glu Ser Arg Phe Tyr Ser Asn Ser Val Leu Val Leu
2600 2605 2610

Asp Phe Gln Ser Leu Tyr Pro Ser Ile Val Ile Ala Tyr Asn Tyr
2615 2620 2625

Cys Phe Ser Thr Cys Leu Gly His Val Glu Asn Leu Gly Lys Tyr
2630 2635 2640

Asp Glu Phe Lys Phe Gly Cys Thr Ser Leu Arg Val Pro Pro Asp
2645 2650 2655

Leu Leu Tyr Gln Val Arg His Asp Ile Thr Val Ser Pro Asn Gly
2660 2665 2670

Val Ala Phe Val Lys Pro Ser Val Arg Lys Gly Val Leu Pro Arg
2675 2680 2685

Met Leu Glu Glu Ile Leu Lys Thr Arg Phe Met Val Lys Gln Ser
2690 2695 2700

Met Lys Ala Tyr Lys Gln Asp Arg Ala Leu Ser Arg Met Leu Asp
2705 2710 2715

Ala Arg Gln Leu Gly Leu Lys Leu Ile Ala Asn Val Thr Phe Gly
2720 2725 2730

Tyr Thr Ser Ala Asn Phe Ser Gly Arg Met Pro Cys Ile Glu Val
2735 2740 2745

-continued

```
Gly Asp  Ser Ile Val His Lys  Ala Arg Glu Thr Leu  Glu Arg Ala
    2750                 2755                 2760

Ile Lys  Leu Val Asn Asp Thr  Lys Lys Trp Gly Ala  Arg Val Val
    2765                 2770                 2775

Tyr Gly  Asp Thr Asp Ser Met  Phe Val Leu Leu Lys  Gly Ala Thr
    2780                 2785                 2790

Lys Glu  Gln Ser Phe Lys Ile  Gly Gln Glu Ile Ala  Glu Ala Val
    2795                 2800                 2805

Thr Ala  Thr Asn Pro Lys Pro  Val Lys Leu Lys Phe  Glu Lys Val
    2810                 2815                 2820

Tyr Leu  Pro Cys Val Leu Gln  Thr Lys Lys Arg Tyr  Val Gly Tyr
    2825                 2830                 2835

Met Tyr  Glu Thr Leu Asp Gln  Lys Asp Pro Val Phe  Asp Ala Lys
    2840                 2845                 2850

Gly Ile  Glu Thr Val Arg Arg  Asp Ser Cys Pro Ala  Val Ser Lys
    2855                 2860                 2865

Ile Leu  Glu Arg Ser Leu Lys  Leu Leu Phe Glu Thr  Arg Asp Ile
    2870                 2875                 2880

Ser Leu  Ile Lys Gln Tyr Val  Gln Arg Gln Cys Met  Lys Leu Leu
    2885                 2890                 2895

Glu Gly  Lys Ala Ser Ile Gln  Asp Phe Ile Phe Ala  Lys Glu Tyr
    2900                 2905                 2910

Arg Gly  Ser Phe Ser Tyr Lys  Pro Gly Ala Cys Val  Pro Ala Leu
    2915                 2920                 2925

Glu Leu  Thr Arg Lys Met Leu  Thr Tyr Asp Arg Arg  Ser Glu Pro
    2930                 2935                 2940

Gln Val  Gly Glu Arg Val Pro  Tyr Val Ile Ile Tyr  Gly Thr Pro
    2945                 2950                 2955

Gly Val  Pro Leu Ile Gln Leu  Val Arg Arg Pro Val  Glu Val Leu
    2960                 2965                 2970

Gln Asp  Pro Thr Leu Arg Leu  Asn Ala Thr Tyr Tyr  Ile Thr Lys
    2975                 2980                 2985

Gln Ile  Leu Pro Pro Leu Ala  Arg Ile Phe Ser Leu  Ile Gly Ile
    2990                 2995                 3000

Asp Val  Phe Ser Trp Tyr His  Glu Leu Pro Arg Ile  His Lys Ala
    3005                 3010                 3015

Thr Ser  Ser Ser Arg Ser Glu  Pro Glu Gly Arg Lys  Gly Thr Ile
    3020                 3025                 3030

Ser Gln  Tyr Phe Thr Thr Leu  His Cys Pro Val Cys  Asp Asp Leu
    3035                 3040                 3045

Thr Gln  His Gly Ile Cys Ser  Lys Cys Arg Ser Gln  Pro Gln His
    3050                 3055                 3060

Val Ala  Val Ile Leu Asn Gln  Glu Ile Arg Glu Leu  Glu Arg Gln
    3065                 3070                 3075

Gln Glu  Gln Leu Val Lys Ile  Cys Lys Asn Cys Thr  Gly Cys Phe
    3080                 3085                 3090

Asp Arg  His Ile Pro Cys Val  Ser Leu Asn Cys Pro  Val Leu Phe
    3095                 3100                 3105

Lys Leu  Ser Arg Val Asn Arg  Glu Leu Ser Lys Ala  Pro Tyr Leu
    3110                 3115                 3120

Arg Gln  Leu Leu Asp Gln Phe
    3125                 3130
```

<210> SEQ ID NO 10
<211> LENGTH: 10719
<212> TYPE: DNA
<213> ORGANISM: Artificial Sequence
<220> FEATURE:
<223> OTHER INFORMATION: REV3L sequence

<400> SEQUENCE: 10
catcatcatg gcaacaagag ctgcagcctg ggaccgagga gcccgtgtga ttcccggcgg 60
tggcggcagt ggcggcagca ccagcaccga cgaaagctcg agggcttctc tcctgcggcc 120
ccttgccggg tgctcctgag gaggcggcgg cagcagcgcc tacaccgccc cgcccgccgc 180
tcctcgaggt gcctctgtgt gaggggaggg ggccgtgccg agaaggggag ggggcgccgc 240
cgccgctgcg gagggagccg ccgccgctgc tgctgccgct gccgggtcgc cagtgaaggg 300
aggcagtggc ggcggcggcg aacatgtttt cagtaaggat agtgactgca gactactaca 360
tggccagccc gctgcagggg ctggatacct gccaatcccc cctcacccag gcccctgtca 420
agaaggtgcc ggtggtgcga gtcttcggag cgaccccggc aggtcagaag acatgtcttc 480
atctacatgg catctttcct tacctctatg tgccatacga tggttatgga cagcagccag 540
aaagctatct ttctcagatg gcattcagta tcgacagagc acttaatgtg gctttaggca 600
atccatcttc cactgctcag catgtgttca aagtgtcatt agtatcagga atgccttttt 660
atggttatca tgagaaggaa agacacttta tgaagatcta tctttacaat cctacaatgg 720
tgaaaaggat atgtgaactt ttgcaaagcg gagccataat gaataaattt taccagcctc 780
atgaagcgca tattccctac ctcctacagc tcttcattga ctacaatctt tatggcatga 840
atttaataaa tctggctgct gtcaagttcc gaaaagcaag aaggaaaagt aatacattgc 900
atgcaactgg atcctgcaag aatcatttat caggaaattc tcttgctgat actttatttc 960
ggtgggaaca agatgaaata ccaagctctt taatattgga aggtgttgaa ccacagagta 1020
catgtgaatt agaagtggat gctgtagctg ctgatatctt aaatcgtctg gacattgaag 1080
ctcaaattgg tggaaaccct ggtctacagg ccatatggga agatgaaaag caacggcgaa 1140
gaaacagaaa tgaaacttct caaatgagcc aacctgagtc acaagatcac aggtttgtgc 1200
cagcaacaga aagtgaaaaa aaatttcaga agagacttca ggaaattctc aaacagaatg 1260
atttctctgt aacattatca ggatctgtgg actacagcga tggatcccag gagttctctg 1320
ctgagttaac attgcactct gaggttctgt ctcctgaaat gcttcagtgt acaccagcca 1380
atatggtaga agttcacaaa gacaaagagt caagcaaagg tcacactaga cacaaagtgg 1440
aagaagctct tattaatgaa gaagcaattt tgaaccttat ggaaaatagt cagacttttc 1500
agcctttgac ccaaagactg agtgagtcac ctgttttcat ggacagtagt cctgatgagg 1560
ctctggtaca tcttcttgct ggtttggaaa gtgatggata tcggggggaa agaaatagga 1620
tgccatcacc atgtcgctcc tttggaaata ataaatatcc acaaaatagt gatgatgaag 1680
aaaatgaacc acagattgaa aaagaggaaa tggagcttag tttggtgatg tcccagagat 1740
gggacagcaa tattgaagaa cattgtgcca aaaagagatc actgtgcaga aatacccaca 1800
gaagttcaac tgaagatgat gactcatctt caggagaaga aatggaatgg agtgataaca 1860
gtttgcttct agccagtctt tctatacctc agttagatgg aactgcagat gaaaatagtg 1920
acaatccatt gaacaatgaa aattctagaa cccactcttc tgtaattgca acaagcaagc 1980
tttcagttaa accctccatc tttcacaaag atgctgctac attagaaccc tcatcttctg 2040
ctaagattac ctttcagtgt aaacacacaa gtgccctttc ttcccatgtt ttgaacaagg 2100

-continued

```
aagatttaat tgaagacctt tcacagacaa acaaaaatac agaaaaaggt ctagataact   2160
cagtcacttc ttttacaaac gaaagcactt attctatgaa ataccctgga tctttaagca   2220
gtactgttca ttcagaaaat tctcataaag agaatagtaa gaaagagatc ctcccagtat   2280
cttcctgtga aagtagtatt tttgattatg aagaagatat tccatctgtt acaagacaag   2340
taccaagtag aaaatataca aacattagaa aaatcgaaaa ggattcccct tttatacata   2400
tgcaccgtca ccctaacgag aatacattgg gcaaaaattc tttcaacttt tctgacttaa   2460
atcattcaaa aaataaagta tcctctgaag gaaatgaaaa aggaaacagc acagctctga   2520
gtagtttatt cccttcatca tttactgaaa attgtgaatt actgtcatgc tcaggggaga   2580
atagaactat ggtgcattct cttaatagca ctgctgatga aagtggacta aataaactta   2640
aaattaggta tgaagaattt caagaacata aaacagaaaa gccaagcctc agccagcaag   2700
cagcacacta tatgtttttt cccagtgttg ttctttctaa ctgtcttact agaccacaga   2760
aactatctcc tgtcacatat aaattacaac ctggcaataa accatcccgg ttaaaattga   2820
ataaaaggaa acttgcaggt catcaggaga cttctaccaa aagtagtgag actggatcca   2880
caaaagataa ttttatacaa aataatcctt gtaatagtaa tcctgagaag gataatgcat   2940
tggctagtga tttaactaaa accactcgtg gagcttttga aaataaaaca cccacagatg   3000
gttttataga ctgtcacttt ggagatggaa cgttagaaac tgagcagtcc tttggactat   3060
atggaaataa atacacactt agagccaaac gcaaggtaaa ttatgagact gaagacagtg   3120
agtcaagttt tgtaactcac aactcaaaaa ttagtctacc tcatcccatg gaaattggtg   3180
aaagtttaga tggaactctc aaatcccgaa aacgaagaaa aatgtctaaa aagctgcccc   3240
ctgtcatcat aaagtatatt attattaata gatttagagg gagaaaaaat atgcttgtga   3300
agctaggaaa aatagactct aaagaaaaac aagtaatatt aacagaagaa aaaatggaac   3360
tatataaaaa gcttgcacct ttgaaggact tttggccaaa agttcccgac tcccctgcaa   3420
ccaaatatcc catttatcca ctaacaccaa agaaaagtca cagaagaaag tcaaaacata   3480
aatctgctaa gaaaaaaact ggtaaacaac aaaggacaaa taatgaaaat attaaaagaa   3540
ctttgtcttt caggaaaaaa cggtcacatg ctattctttc tcctccctca ccatcttaca   3600
atgctgaaac cgaagattgt gacctgaatt atagtgatgt tatgtctaaa ctaggttttc   3660
tttctgagag aagcacaagt cccataaatt cttctccacc tcgctgctgg tctcccacag   3720
atccaagagc tgaagaaatc atggctgctg cagaaaaaga ggcaatgctt tttaagggtc   3780
ctaatgtata taagaagact gttaattctc gtataggaaa aactagtcgc gcaagagcac   3840
agattaagaa atcaaaagca aagcttgcta atccctctat agttactaag aaaaggaaca   3900
aacgaaatca gacaaataaa ctagtagatg atggaaaaaa gaaaccaaga gcaaaacaaa   3960
aaacaaatga gaaaggtaca tcgagaaagc atacaacact taaggatgaa aaaataaaat   4020
ctcagtctgg tgctgaggtt aagtttgtac tgaaacacca gaatgtgtct gaatttgcaa   4080
gtagttctgg aggctctcaa ctacttttta aacagaaaga tatgccacta atgggctctg   4140
ctgtagatca tccccttct gcttccctac ccactggaat taatgcacaa cagaagttat   4200
ctggctgctt ttcttctttc ttagaaagca agaagtctgt agatttgcag acattcccca   4260
gttcacgaga tgatttgcat ccatcagttg tttgtaattc tataggacct ggagtctcaa   4320
aaattaatgt tcaaaggcct cataatcaaa gtgctatgtt tactctaaag gaatcaacgt   4380
taattcaaaa aaatatattt gacctttcca atcatttatc tcaggtagca cagaatacac   4440
agatatcttc tggtatgtcc tcaaagatag aagataatgc aaataatata caaagaaact   4500
```

-continued

```
atttgtcatc aatcggaaag ttaagtgaat atcgcaattc cctagaatca aagctggacc   4560
aagcatatac ccctaatttt ttgcattgca aagacagtca gcagcagatt gtgtgcatag   4620
cggaacagtc aaagcacagt gaaacttgtt ctccgggaaa tacagcttca gaggaaagcc   4680
aaatgcctaa taattgcttt gtaacttcct tgagaagtcc aatcaaacaa atagcatggg   4740
agcaaaagca aaggggcttt attttagata tgtcaaattt taaacctgaa agagtaaaac   4800
cgaggtcgtt atcagaagca atttcacaaa ccaaagcact ttctcagtgt aaaaatcgaa   4860
atgtgtcaac accttcagca tttggtgaag gacagtctgg actggcagtt ctaaaagaat   4920
tgttacaaaa aagacagcag aaagcacaaa atgcaaatac tacacaagac ccattatcca   4980
ataaacatca accaaataaa aatatttctg gttcccttga gcataacaaa gcaaataaac   5040
ggacacgatc ggtaacgtcc ccaagaaaac ctcgaactcc cagaagtaca aaacaaaaag   5100
aaaaaatccc caaacttctc aaagtagact ctttaaattt acaaaactct agccagttgg   5160
ataactctgt atcagatgat agtcccatct ttttttcaga tccaggcttt gaaagttgtt   5220
actcacttga agatagttta tctcctgaac ataattataa ttttgatatt aacacaatag   5280
gtcagactgg attttgtagc ttttattctg gaagtcagtt tgtcccagct gatcagaatt   5340
tgcctcagaa gttcctaagt gatgctgttc aggatctttt tccaggacaa gctatagaaa   5400
aaaatgagtt tttaagtcat gacaaccaga aatgtgatga agacaagcat cataccacag   5460
actcagcctc atggattaga tctggtactt taagtcctga aatttttgag aagtcaacca   5520
tagatagcaa tgagaatcgt cgccacaacc agtggaaaaa tagctttcat cctctaacaa   5580
ctcggtctaa ctcaataatg gattctttct gtgttcagca ggcagaagac tgtctaagtg   5640
aaaaatctag attgaatagg agttcagtaa gcaaagaagt gtttcttagc ctcccacagc   5700
caaacaattc agactggatt caaggtcaca ccagaaaaga aatgggacag tctcttgact   5760
cagccaatac ctcttttact gcaatactct cctcccctga tggtgaactt gtagacgtgg   5820
cctgtgaaga tttagaactg tatgtttcaa gaaacaatga tatgttgaca ccaactcctg   5880
atagttcacc aagatctact agctctcctt cacaatctaa aaatggcagc ttcacccctc   5940
gaactgctaa cattctgaaa ccacttatgt ccccccccaag tagggaagaa attatggcaa   6000
ctttgttgga tcatgacctg tctgagacta tttaccagga accattttgc agtaatcctt   6060
ctgatgtacc agaaaagccc agggagattg gtggacggct cctcatggta gaaactcgac   6120
ttgcaaatga tctggctgag tttgagggag acttttcctt ggaaggactt cgtctttgga   6180
aaacagcatt ctcagcaatg actcagaatc caaggccagg gtcacccctt cgcagtggcc   6240
aaggagttgt caataaaggg tcaagtaata gccctaagat ggttgaagat aaaaaaattg   6300
tgattatgcc ttgcaaatgt gccccaagtc gacaactggt tcaagtgtgg cttcaagcca   6360
aagaagaata cgaacgttcc aagaaactgc ctaaaaccaa gccaactgga gttgtaaaat   6420
ctgctgagaa ctttagctct tcagttaacc cagatgacaa acctgtagtg cctccaaaaa   6480
tggatgtaag tccatgtata ctccccacta cagcacatac caaggaggat gttgataatt   6540
ctcagattgc tttacaagca ccaaccacgg gatgtagtca aactgcaagt gaaagtcaga   6600
tgctgccacc agttgcctct gcaagtgatc ccgaaaaaga tgaagatgat gatgataact   6660
attacattag ttatagctcc cctgattctc cagtaattcc cccttggcaa caaccaatat   6720
ccccagattc caaagcatta aatggagatg atagaccctc atcaccagta gaggagctgc   6780
cttcattggc ttttgagaac ttcttaaagc caataaaaga tggtatacaa aaaagcccct   6840
```

-continued

```
gcagtgagcc tcaagagcct ctagtgatat ctccaattaa tactagggca agaactggga   6900
aatgtgaatc actttgcttt catagtacac caatcataca gagaaaactt ctggaaaggc   6960
ttcctgaagc acctggcctt agcccattat caacagaacc aaaaacacag aagttgagta   7020
ataagaaagg aagtaatact gacactctta gaagagtact gttaacacaa gcaaagaatc   7080
aatttgcagc agtaaatacc ccacagaaag aaacttctca gattgatgga ccatctttaa   7140
acaatactta cggtttcaaa gtcagcatac aaaacttaca ggaggcaaaa gctttacatg   7200
agatacaaaa tcttacccta atcagtgtgg agttgcatgc tcgaactaga cgagacttag   7260
aaccggatcc tgaatttgac ccaatctgtg ctctgttcta ctgcatctca tctgacactc   7320
cactgccaga tacagaaaaa acagaactca caggtgtaat agtgattgat aaagacaaga   7380
cagttttcag tcaagatatc agatatcaga ctccattact tattagatct ggaattacag   7440
gactcgaagt cacctatgct gctgatgaga aggcactttt tcatgaaatt gcaaatataa   7500
taaagaggta tgatcctgat attctgctag gatatgagat tcagatgcat tcctggggtt   7560
acctcttaca aagggctgcc gctttaagta ttgacttatg tcggatgatc tctcgggtgc   7620
cagatgacaa aattgagaac agatttgcag ctgaaagaga tgagtatgga tcatatacaa   7680
tgagtgagat aaatattgtt ggccgaatta cactaaatct ttggagaatc atgagaaatg   7740
aggtggctct aactaactac acctttgaaa atgtgagctt tcatgttctt catcagcgtt   7800
ttcccctctt tacctttcga gtcttgtcag actggtttga taacaagaca gatctataca   7860
gatggaaaat ggttgatcat tatgttagcc gtgtccgtgg aaatctccaa atgttagaac   7920
agctggacct gattgggaaa accagtgaga tggctagact tttggcatt cagtttttac    7980
atgtactgac aaggggttca cagtaccgtg tggaatcaat gatgttgcgt attgctaaac   8040
caatgaacta tattcctgtg acacctagtg ttcagcaaag atcccagatg agagccccac   8100
agtgtgttcc tctaattatg gagcctgaat cccgcttcta tagcaactct gttctcgttt   8160
tggatttcca atcactttat ccttctattg tgattgcata taactactgc ttttccacct   8220
gccttggcca tgtggagaac ttgggaaagt atgatgagtt caaatttggc tgtacctctc   8280
tgagagtacc tccagattta ctttaccaag ttaggcatga tatcacagtg tcccccaatg   8340
gagtagcttt tgtcaagcct tcagtaagaa aaggtgtact accaagaatg cttgaagaaa   8400
ttttgaagac tagatttatg gtgaagcagt caatgaaggc ttacaagcaa gacagagccc   8460
tgtcacgaat gcttgatgcg cgtcagttgg gacttaagct gatagcaaat gtcacatttg   8520
gctatacatc tgctaatttt tctgggagaa tgccatgcat tgaggttggc gatagtattg   8580
ttcacaaagc cagagagacc ttggaacgag ctattaaact ggtgaatgat accaagaaat   8640
ggggggctag ggttgtatat ggcgatactg acagtatgtt tgtgctactg aaaggagcca   8700
ctaaggagca gtcttttaag attggtcagg aaattgccga agctgtaact gctaccaatc   8760
ctaaaccagt gaaattgaag tttgaaaagg tatatttgcc ctgtgtttta caaacaaaaa   8820
agaggtatgt gggttacatg tatgaaacac tggatcagaa ggacccagta tttgatgcaa   8880
aaggaataga aacagtcaga agagattcct gccctgctgt ttctaagata cttgagcgtt   8940
ctctaaagct gctatttgaa acgagagata taagtctaat taaacagtat gttcagcgac   9000
aatgtatgaa gcttctggaa ggaaaggcca gcatacaaga ctttatcttt gccaaggaat   9060
acagaggaag tttttcttat aaaccaggag cttgtgtgcc agcccttgaa cttacaagga   9120
aaatgctgac ttatgaccgg cgctctgagc ctcaggttgg ggagcgagtg ccatacgtca   9180
tcatttatgg gacccccgga gtaccactta tccagcttgt aaggcgccca gtggaagtcc   9240
```

-continued

```
tgcaggaccc aactctgaga ctgaatgcta cttactatat taccaagcaa atccttccac   9300

ccttggcaag aatcttctca cttattggta ttgatgtctt cagctggtat catgaattac   9360

caaggatcca taaagctacc agctcctcgc gaagtgaacc tgaagggcgg aaaggcacta   9420

tttcacaata ttttactacc ttacactgtc ctgtgtgtga tgacctaact cagcatggca   9480

tctgtagtaa atgtcggagc caacctcagc atgttgcagt catcctcaac caagaaatcc   9540

gggagttgga acgtcaacag gagcaacttg taaagatatg caagaactgt acaggttgct   9600

ttgatcgaca catcccatgt gtttctctga actgcccagt acttttcaaa ctctcccgag   9660

taaatagaga attgtccaag gcaccatatc tccggcagtt attagaccag ttttaaattg   9720

tcaatatcac agtattacag gtgctatttt tttcagtgct taccactaaa ctgttgtgca   9780

tggtgctttt taactttcat cgagtcaagg atgttcactg tctgttatct gaagactatg   9840

aagacttcta tgctaaccga attaaaatgt acttgttgat ctctgaatag ctcacttctt   9900

acaatgtaca aattcctcat tctgtcacct tttaaacatt gttttataat gcaggtgttg   9960

gatttgctcc agtatgtgta ccatcttgta aattcatttg agtagatcat gtttacttcc  10020

cagtggaagg agcactgaaa acctcttaaa gaaaaagcat ttgtgtgttt tccttgaact  10080

gtctgtatca agacgtgtta cttcgagata tccattcact ttataatttt gactgcaaaa  10140

tattttgtaa atacactttt ttacttttca aacgagcaaa ataatgtgca atgattttta  10200

tacaaatgat tttcaagttg tttggtatat ttcctctagg ttttgcttga ctcaaagtag  10260

atcgttattt tgatcaaact gtgcaaacag tagtaccacg tgtagcattt tgaaacatta  10320

ttttttttta aaaaatgctg tcttgcttta gctattaatg gggcattgtg aggaactgtg  10380

caaagacatt tttgttacaa acctgtgggc ctgttgcaat actttaaaaa taaaaaattt  10440

tattccattt gcttgttttg tatagacatt tctattgctt ctaaatatac ttaaaatatt  10500

ttctttcctt atgtactgta cagttaatct tatttgccat catcttgaac acaaaatgtg  10560

tatttagaat atttgtataa ctgtgtaaaa taaaaaagga attatgtggt cagtgcattg  10620

tttttaaac tggaaatcat tttgttttaa aagttaataa tggaaaccat attaaaattg  10680

aataaaatat aaaataatat aaaaaaaaaa aaaaaaaaa                         10719
```

```
<210> SEQ ID NO 11
<211> LENGTH: 1014
<212> TYPE: PRT
<213> ORGANISM: Artificial Sequence
<220> FEATURE:
<223> OTHER INFORMATION: PARP1 sequence

<400> SEQUENCE: 11

Met Ala Glu Ser Ser Asp Lys Leu Tyr Arg Val Glu Tyr Ala Lys Ser
1               5                   10                  15

Gly Arg Ala Ser Cys Lys Lys Cys Ser Glu Ser Ile Pro Lys Asp Ser
            20                  25                  30

Leu Arg Met Ala Ile Met Val Gln Ser Pro Met Phe Asp Gly Lys Val
        35                  40                  45

Pro His Trp Tyr His Phe Ser Cys Phe Trp Lys Val Gly His Ser Ile
    50                  55                  60

Arg His Pro Asp Val Glu Val Asp Gly Phe Ser Glu Leu Arg Trp Asp
65                  70                  75                  80

Asp Gln Gln Lys Val Lys Lys Thr Ala Glu Ala Gly Gly Val Thr Gly
                85                  90                  95
```

-continued

```
Lys Gly Gln Asp Gly Ile Gly Ser Lys Ala Glu Lys Thr Leu Gly Asp
            100                 105                 110

Phe Ala Ala Glu Tyr Ala Lys Ser Asn Arg Ser Thr Cys Lys Gly Cys
        115                 120                 125

Met Glu Lys Ile Glu Lys Gly Gln Val Arg Leu Ser Lys Lys Met Val
    130                 135                 140

Asp Pro Glu Lys Pro Gln Leu Gly Met Ile Asp Arg Trp Tyr His Pro
145                 150                 155                 160

Gly Cys Phe Val Lys Asn Arg Glu Glu Leu Gly Phe Arg Pro Glu Tyr
                165                 170                 175

Ser Ala Ser Gln Leu Lys Gly Phe Ser Leu Leu Ala Thr Glu Asp Lys
            180                 185                 190

Glu Ala Leu Lys Lys Gln Leu Pro Gly Val Lys Ser Glu Gly Lys Arg
        195                 200                 205

Lys Gly Asp Glu Val Asp Gly Val Asp Glu Val Ala Lys Lys Lys Ser
    210                 215                 220

Lys Lys Glu Lys Asp Lys Asp Ser Lys Leu Glu Lys Ala Leu Lys Ala
225                 230                 235                 240

Gln Asn Asp Leu Ile Trp Asn Ile Lys Asp Glu Leu Lys Lys Val Cys
                245                 250                 255

Ser Thr Asn Asp Leu Lys Glu Leu Leu Ile Phe Asn Lys Gln Gln Val
            260                 265                 270

Pro Ser Gly Glu Ser Ala Ile Leu Asp Arg Val Ala Asp Gly Met Val
        275                 280                 285

Phe Gly Ala Leu Leu Pro Cys Glu Glu Cys Ser Gly Gln Leu Val Phe
    290                 295                 300

Lys Ser Asp Ala Tyr Tyr Cys Thr Gly Asp Val Thr Ala Trp Thr Lys
305                 310                 315                 320

Cys Met Val Lys Thr Gln Thr Pro Asn Arg Lys Glu Trp Val Thr Pro
                325                 330                 335

Lys Glu Phe Arg Glu Ile Ser Tyr Leu Lys Lys Leu Lys Val Lys Lys
            340                 345                 350

Gln Asp Arg Ile Phe Pro Pro Glu Thr Ser Ala Ser Val Ala Ala Thr
        355                 360                 365

Pro Pro Pro Ser Thr Ala Ser Ala Pro Ala Ala Val Asn Ser Ser Ala
    370                 375                 380

Ser Ala Asp Lys Pro Leu Ser Asn Met Lys Ile Leu Thr Leu Gly Lys
385                 390                 395                 400

Leu Ser Arg Asn Lys Asp Glu Val Lys Ala Met Ile Glu Lys Leu Gly
                405                 410                 415

Gly Lys Leu Thr Gly Thr Ala Asn Lys Ala Ser Leu Cys Ile Ser Thr
            420                 425                 430

Lys Lys Glu Val Glu Lys Met Asn Lys Lys Met Glu Glu Val Lys Glu
        435                 440                 445

Ala Asn Ile Arg Val Val Ser Glu Asp Phe Leu Gln Asp Val Ser Ala
    450                 455                 460

Ser Thr Lys Ser Leu Gln Glu Leu Phe Leu Ala His Ile Leu Ser Pro
465                 470                 475                 480

Trp Gly Ala Glu Val Lys Ala Glu Pro Val Glu Val Val Ala Pro Arg
                485                 490                 495

Gly Lys Ser Gly Ala Ala Leu Ser Lys Lys Ser Lys Gly Gln Val Lys
            500                 505                 510

Glu Glu Gly Ile Asn Lys Ser Glu Lys Arg Met Lys Leu Thr Leu Lys
```

```
        515                 520                 525

Gly Gly Ala Ala Val Asp Pro Asp Ser Gly Leu Glu His Ser Ala His
    530                 535                 540

Val Leu Glu Lys Gly Gly Lys Val Phe Ser Ala Thr Leu Gly Leu Val
545                 550                 555                 560

Asp Ile Val Lys Gly Thr Asn Ser Tyr Tyr Lys Leu Gln Leu Leu Glu
                565                 570                 575

Asp Asp Lys Glu Asn Arg Tyr Trp Ile Phe Arg Ser Trp Gly Arg Val
            580                 585                 590

Gly Thr Val Ile Gly Ser Asn Lys Leu Glu Gln Met Pro Ser Lys Glu
        595                 600                 605

Asp Ala Ile Glu His Phe Met Lys Leu Tyr Glu Glu Lys Thr Gly Asn
    610                 615                 620

Ala Trp His Ser Lys Asn Phe Thr Lys Tyr Pro Lys Lys Phe Tyr Pro
625                 630                 635                 640

Leu Glu Ile Asp Tyr Gly Gln Asp Glu Glu Ala Val Lys Lys Leu Thr
                645                 650                 655

Val Asn Pro Gly Thr Lys Ser Lys Leu Pro Lys Pro Val Gln Asp Leu
            660                 665                 670

Ile Lys Met Ile Phe Asp Val Glu Ser Met Lys Lys Ala Met Val Glu
        675                 680                 685

Tyr Glu Ile Asp Leu Gln Lys Met Pro Leu Gly Lys Leu Ser Lys Arg
    690                 695                 700

Gln Ile Gln Ala Ala Tyr Ser Ile Leu Ser Glu Val Gln Gln Ala Val
705                 710                 715                 720

Ser Gln Gly Ser Ser Asp Ser Gln Ile Leu Asp Leu Ser Asn Arg Phe
                725                 730                 735

Tyr Thr Leu Ile Pro His Asp Phe Gly Met Lys Lys Pro Pro Leu Leu
            740                 745                 750

Asn Asn Ala Asp Ser Val Gln Ala Lys Val Glu Met Leu Asp Asn Leu
        755                 760                 765

Leu Asp Ile Glu Val Ala Tyr Ser Leu Leu Arg Gly Gly Ser Asp Asp
    770                 775                 780

Ser Ser Lys Asp Pro Ile Asp Val Asn Tyr Glu Lys Leu Lys Thr Asp
785                 790                 795                 800

Ile Lys Val Val Asp Arg Asp Ser Glu Glu Ala Glu Ile Ile Arg Lys
                805                 810                 815

Tyr Val Lys Asn Thr His Ala Thr Thr His Asn Ala Tyr Asp Leu Glu
            820                 825                 830

Val Ile Asp Ile Phe Lys Ile Glu Arg Glu Gly Glu Cys Gln Arg Tyr
        835                 840                 845

Lys Pro Phe Lys Gln Leu His Asn Arg Arg Leu Leu Trp His Gly Ser
    850                 855                 860

Arg Thr Thr Asn Phe Ala Gly Ile Leu Ser Gln Gly Leu Arg Ile Ala
865                 870                 875                 880

Pro Pro Glu Ala Pro Val Thr Gly Tyr Met Phe Gly Lys Gly Ile Tyr
                885                 890                 895

Phe Ala Asp Met Val Ser Lys Ser Ala Asn Tyr Cys His Thr Ser Gln
            900                 905                 910

Gly Asp Pro Ile Gly Leu Ile Leu Leu Gly Glu Val Ala Leu Gly Asn
        915                 920                 925

Met Tyr Glu Leu Lys His Ala Ser His Ile Ser Lys Leu Pro Lys Gly
    930                 935                 940
```

Lys His Ser Val Lys Gly Leu Gly Lys Thr Thr Pro Asp Pro Ser Ala
945 950 955 960

Asn Ile Ser Leu Asp Gly Val Asp Val Pro Leu Gly Thr Gly Ile Ser
965 970 975

Ser Gly Val Asn Asp Thr Ser Leu Leu Tyr Asn Glu Tyr Ile Val Tyr
980 985 990

Asp Ile Ala Gln Val Asn Leu Lys Tyr Leu Leu Lys Leu Lys Phe Asn
995 1000 1005

Phe Lys Thr Ser Leu Trp
1010

<210> SEQ ID NO 12
<211> LENGTH: 4001
<212> TYPE: DNA
<213> ORGANISM: Artificial Sequence
<220> FEATURE:
<223> OTHER INFORMATION: PARP1 sequence

<400> SEQUENCE: 12
aggcatcagc aatctatcag ggaacggcgg tggccggtgc ggcgtgttcg gtggcggctc 60
tggccgctca ggcgcctgcg gctgggtgag cgcacgcgag gcggcgaggc ggcagcgtgt 120
ttctaggtcg tggcgtcggg cttccggagc tttggcggca gctaggggag gatggcggag 180
tcttcggata agctctatcg agtcgagtac gccaagagcg ggcgcgcctc ttgcaagaaa 240
tgcagcgaga gcatccccaa ggactcgctc cggatggcca tcatggtgca gtcgcccatg 300
tttgatggaa aagtcccaca ctggtaccac ttctcctgct tctggaaggt gggccactcc 360
atccggcacc ctgacgttga ggtggatggg ttctctgagc ttcggtggga tgaccagcag 420
aaagtcaaga agacagcgga agctggagga gtgacaggca aaggccagga tggaattggt 480
agcaaggcag agaagactct gggtgacttt gcagcagagt atgccaagtc caacagaagt 540
acgtgcaagg ggtgtatgga gaagatagaa aagggccagg tgcgcctgtc caagaagatg 600
gtggacccgg agaagccaca gctaggcatg attgaccgct ggtaccatcc aggctgcttt 660
gtcaagaaca gggaggagct gggtttccgg cccgagtaca gtgcgagtca gctcaagggc 720
ttcagcctcc ttgctacaga ggataaagaa gccctgaaga agcagctccc aggagtcaag 780
agtgaaggaa agagaaaagg cgatgaggtg gatggagtgg atgaagtggc gaagaagaaa 840
tctaaaaaag aaaaagacaa ggatagtaag cttgaaaaag ccctaaaggc tcagaacgac 900
ctgatctgga acatcaagga cgagctaaag aaagtgtgtt caactaatga cctgaaggag 960
ctactcatct tcaacaagca gcaagtgcct tctggggagt cggcgatctt ggaccgagta 1020
gctgatggca tggtgttcgg tgccctcctt ccctgcgagg aatgctcggg tcagctggtc 1080
ttcaagagcg atgcctatta ctgcactggg gacgtcactg cctggaccaa gtgtatggtc 1140
aagacacaga cacccaaccg gaaggagtgg gtaaccccaa aggaattccg agaaatctct 1200
tacctcaaga aattgaaggt taaaaaacag gaccgtatat tcccccccaga aaccagcgcc 1260 tccgtggcgg ccacgcctcc gccctccaca gcctcggctc ctgctgctgt gaactcctct 1320
gcttcagcag ataagccatt atccaacatg aagatcctga ctctcgggaa gctgtcccgg 1380
aacaaggatg aagtgaaggc catgattgag aaactcgggg ggaagttgac ggggacggcc 1440
aacaaggctt ccctgtgcat cagcaccaaa aaggaggtgg aaaagatgaa taagaagatg 1500
gaggaagtaa aggaagccaa catccgagtt gtgtctgagg acttcctcca ggacgtctcc 1560
gcctccacca agagccttca ggagttgttc ttagcgcaca tcttgtcccc ttgggggca 1620

-continued

```
gaggtgaagg cagagcctgt tgaagttgtg gccccaagag ggaagtcagg ggctgcgctc   1680
tccaaaaaaa gcaagggcca ggtcaaggag gaaggtatca acaaatctga aaagagaatg   1740
aaattaactc ttaaaggagg agcagctgtg gatcctgatt ctggactgga acactctgcg   1800
catgtcctgg agaaaggtgg gaaggtcttc agtgccaccc ttggcctggt ggacatcgtt   1860
aaaggaacca actcctacta caagctgcag cttctggagg acgacaagga aaacaggtat   1920
tggatattca ggtcctgggg ccgtgtgggt acggtgatcg gtagcaacaa actggaacag   1980
atgccgtcca aggaggatgc cattgagcac ttcatgaaat tatatgaaga aaaaaccggg   2040
aacgcttggc actccaaaaa tttcacgaag tatcccaaaa agttctaccc cctggagatt   2100
gactatggcc aggatgaaga ggcagtgaag aagctgacag taaatcctgg caccaagtcc   2160
aagctcccca agccagttca ggacctcatc aagatgatct ttgatgtgga aagtatgaag   2220
aaagccatgg tggagtatga gatcgacctt cagaagatgc ccttggggaa gctgagcaaa   2280
aggcagatcc aggccgcata ctccatcctc agtgaggtcc agcaggcggt gtctcagggc   2340
agcagcgact ctcagatcct ggatctctca aatcgctttt acaccctgat cccccacgac   2400
tttgggatga agaagcctcc gctcctgaac aatgcagaca gtgtgcaggc caaggtggaa   2460
atgcttgaca acctgctgga catcgaggtg gcctacagtc tgctcagggg agggtctgat   2520
gatagcagca aggatcccat cgatgtcaac tatgagaagc tcaaaactga cattaaggtg   2580
gttgacagag attctgaaga agccgagatc atcaggaagt atgttaagaa cactcatgca   2640
accacacaca atgcgtatga cttggaagtc atcgatatct ttaagataga gcgtgaaggc   2700
gaatgccagc gttacaagcc ctttaagcag cttcataacc gaagattgct gtggcacggg   2760
tccaggacca ccaactttgc tgggatcctg tcccagggtc ttcggatagc cccgcctgaa   2820
gcgcccgtga caggctacat gtttggtaaa gggatctatt tcgctgacat ggtctccaag   2880
agtgccaact actgccatac gtctcaggga gacccaatag gcttaatcct gttgggagaa   2940
gttgcccttg gaaacatgta tgaactgaag cacgcttcac atatcagcaa gttacccaag   3000
ggcaagcaca gtgtcaaagg tttgggcaaa actacccctg atccttcagc taacattagt   3060
ctggatggtg tagacgttcc tcttgggacc gggatttcat ctggtgtgaa tgacacctct   3120
ctactatata acgagtacat tgtctatgat attgctcagg taaatctgaa gtatctgctg   3180
aaactgaaat tcaattttaa gacctccctg tggtaattgg gagaggtagc cgagtcacac   3240
ccggtggctc tggtatgaat tcacccgaag cgcttctgca ccaactcacc tggccgctaa   3300
gttgctgatg ggtagtacct gtactaaacc acctcagaaa ggattttaca gaaacgtgtt   3360
aaaggttttc tctaacttct caagtccctt gttttgtgtt gtgtctgtgg ggaggggttg   3420
ttttggggtt gtttttgttt tttcttgcca ggtagataaa actgacatag agaaaaggct   3480
ggagagagat tctgttgcat agactagtcc tatggaaaaa accaagcttc gttagaatgt   3540
ctgccttact ggtttcccca gggaaggaaa aatacacttc caccctttttt tctaagtgtt   3600
cgtctttagt tttgattttg gaaagatgtt aagcatttat ttttagttaa aaataaaaac   3660
taatttcata ctatttagat tttctttttt atcttgcact tattgtcccc tttttagttt   3720
tttttgtttg cctcttgtgg tgaggggtgt gggaagacca aaggaaggaa cgctaacaat   3780
ttctcatact tagaaacaaa aagagctttc cttctccagg aatactgaac atgggagctc   3840
ttgaaatatg tagtattaaa agttgcattt gaaattcttg actttcttat gggcactttt   3900
gtcttccaaa ttaaaactct accacaaata tacttaccca agggctaata gtaatactcg   3960
```

```
attaaaaatg cagatgcctt ctctaaaaaa aaaaaaaaaa a                    4001


<210> SEQ ID NO 13
<211> LENGTH: 339
<212> TYPE: PRT
<213> ORGANISM: Artificial Sequence
<220> FEATURE:
<223> OTHER INFORMATION: RAD51 sequence

<400> SEQUENCE: 13

Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
            20                  25                  30

Ile Asn Ala Asn Asp Val Lys Lys Leu Glu Glu Ala Gly Phe His Thr
        35                  40                  45

Val Glu Ala Val Ala Tyr Ala Pro Lys Lys Glu Leu Ile Asn Ile Lys
    50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
            100                 105                 110

Leu Gln Gly Gly Ile Glu Thr Gly Ser Ile Thr Glu Met Phe Gly Glu
        115                 120                 125

Phe Arg Thr Gly Lys Thr Gln Ile Cys His Thr Leu Ala Val Thr Cys
    130                 135                 140

Gln Leu Pro Ile Asp Arg Gly Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Ala Phe Asn Thr Asp His Gln Thr Gln Leu Leu Tyr Gln Ala Ser
        195                 200                 205

Ala Met Met Val Glu Ser Arg Tyr Ala Leu Leu Ile Val Asp Ser Ala
    210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Leu Arg Leu Ala
                245                 250                 255

Asp Glu Phe Gly Val Ala Val Val Ile Thr Asn Gln Val Val Ala Gln
            260                 265                 270

Val Asp Gly Ala Ala Met Phe Ala Ala Asp Pro Lys Lys Pro Ile Gly
        275                 280                 285

Gly Asn Ile Ile Ala His Ala Ser Thr Thr Arg Leu Tyr Leu Arg Lys
    290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp


<210> SEQ ID NO 14
```

<211> LENGTH: 2299
<212> TYPE: DNA
<213> ORGANISM: Artificial Sequence
<220> FEATURE:
<223> OTHER INFORMATION: RAD51 sequence

<400> SEQUENCE: 14

| | | | | | |
|---|---|---|---|---|---|
| gttacgtcga | cgcgggcgtg | accctgggcg | agagggtttg | gcgggaattc | tgaaagccgc | 60 |
| tggcggaccg | cgcgcagcgg | ccagagaccg | agccctaagg | agagtgcggc | gcttcccgag | 120 |
| gcgtgcagct | gggaactgca | actcatctgg | gttgtgcgca | gaaggctggg | gcaagcgagt | 180 |
| agagaagtgg | agcgtaagcc | aggggcgttg | ggggccgtgc | gggtcgggcg | cgtgccacgc | 240 |
| ccgcggggtg | aagtcggagc | gcggggcctg | ctggagagag | gagcgctgcg | gaccgagtaa | 300 |
| tggcaatgca | gatgcagctt | gaagcaaatg | cagatacttc | agtggaagaa | gaaagctttg | 360 |
| gcccacaacc | catttcacgg | ttagagcagt | gtggcataaa | tgccaacgat | gtgaagaaat | 420 |
| tggaagaagc | tggattccat | actgtggagg | ctgttgccta | tgcgccaaag | aaggagctaa | 480 |
| taaatattaa | gggaattagt | gaagccaaag | ctgataaaat | tctggctgag | gcagctaaat | 540 |
| tagttccaat | gggtttcacc | actgcaactg | aattccacca | aaggcggtca | gagatcatac | 600 |
| agattactac | tggctccaaa | gagcttgaca | aactacttca | aggtggaatt | gagactggat | 660 |
| ctatcacaga | aatgtttgga | gaattccgaa | ctgggaagac | ccagatctgt | catacgctag | 720 |
| ctgtcacctg | ccagcttccc | attgaccggg | gtggaggtga | aggaaaggcc | atgtacattg | 780 |
| acactgaggg | tacctttagg | ccagaacggc | tgctggcagt | ggctgagagg | tatggtctct | 840 |
| ctggcagtga | tgtcctggat | aatgtagcat | atgctcgagc | gttcaacaca | gaccaccaga | 900 |
| cccagctcct | ttatcaagca | tcagccatga | tggtagaatc | taggtatgca | ctgcttattg | 960 |
| tagacagtgc | caccgccctt | tacagaacag | actactcggg | tcgaggtgag | ctttcagcca | 1020 |
| ggcagatgca | cttggccagg | tttctgcgga | tgcttctgcg | actcgctgat | gagtttggtg | 1080 |
| tagcagtggt | aatcactaat | caggtggtag | ctcaagtgga | tggagcagcg | atgtttgctg | 1140 |
| ctgatcccaa | aaaacctatt | ggaggaaata | tcatcgccca | tgcatcaaca | accagattgt | 1200 |
| atctgaggaa | aggaagaggg | gaaaccagaa | tctgcaaaat | ctacgactct | ccctgtcttc | 1260 |
| ctgaagctga | agctatgttc | gccattaatg | cagatggagt | gggagatgcc | aaagactgaa | 1320 |
| tcattgggtt | tttcctctgt | taaaaacctt | aagtgctgca | gcctaatgag | agtgcactgc | 1380 |
| tccctggggt | tctctacagg | cctcttcctg | ttgtgactgc | caggataaag | cttccgggaa | 1440 |
| aacagctatt | atatcagctt | ttctgatggt | ataaacagga | gacaggtcag | tagtcacaaa | 1500 |
| ctgatctaaa | atgtttattc | cttctgtagt | gtattaatct | ctgtgtgttt | tctttggttt | 1560 |
| tggaggaggg | gtatgaagta | tctttgacat | ggtgccttag | gaatgacttg | ggtttaacaa | 1620 |
| gctgtctact | ggacaatctt | atgtttccaa | gagaactaaa | gctggagaga | cctgacccct | 1680 |
| ctctcacttc | taaattaatg | gtaaaataaa | atgcctcagc | tatgtagcaa | agggaatggg | 1740 |
| tctgcacaga | ttcttttttt | ctgtcagtaa | aactctcaag | caggttttta | agttgtctgt | 1800 |
| ctgaatgatc | ttgtgtaagg | ttttggttat | ggagtcttgt | gccaaaccta | ctaggccatt | 1860 |
| agcccttcac | catctacctg | cttggtcttt | cattgctaag | actaactcaa | gataatccta | 1920 |
| gagtcttaaa | gcatttcagg | ccagtgtggt | gtcttgcgcc | tgtactccca | gcactttggg | 1980 |
| aggccgaggc | aggtggatcg | cttgagccca | ggagttttaa | gtccagcttg | gccaaggtgg | 2040 |
| tgaaatccca | tctctacaaa | aaatgcagaa | cttaatctgg | acacactgtt | acacgtgcct | 2100 |
| gtagtcccag | ctactcgata | gcctgaggtg | ggagaatcac | ttaagcctgg | aaggtggaag | 2160 |

```
ttgcagtgag tcgagattgc actgctgcat tccagccagg gtgacagagt gagaccatgt   2220

ttcaaacaag aaacatttca gagggtaagt aaacagattt gattgtgagg cttctaataa   2280

agtagttatt agtagtgaa                                                2299


<210> SEQ ID NO 15
<211> LENGTH: 708
<212> TYPE: PRT
<213> ORGANISM: Artificial Sequence
<220> FEATURE:
<223> OTHER INFORMATION: MRE11A sequence

<400> SEQUENCE: 15

Met Ser Thr Ala Asp Ala Leu Asp Asp Glu Asn Thr Phe Lys Ile Leu
1               5                   10                  15

Val Ala Thr Asp Ile His Leu Gly Phe Met Glu Lys Asp Ala Val Arg
            20                  25                  30

Gly Asn Asp Thr Phe Val Thr Leu Asp Glu Ile Leu Arg Leu Ala Gln
        35                  40                  45

Glu Asn Glu Val Asp Phe Ile Leu Leu Gly Gly Asp Leu Phe His Glu
    50                  55                  60

Asn Lys Pro Ser Arg Lys Thr Leu His Thr Cys Leu Glu Leu Leu Arg
65                  70                  75                  80

Lys Tyr Cys Met Gly Asp Arg Pro Val Gln Phe Glu Ile Leu Ser Asp
                85                  90                  95

Gln Ser Val Asn Phe Gly Phe Ser Lys Phe Pro Trp Val Asn Tyr Gln
            100                 105                 110

Asp Gly Asn Leu Asn Ile Ser Ile Pro Val Phe Ser Ile His Gly Asn
        115                 120                 125

His Asp Asp Pro Thr Gly Ala Asp Ala Leu Cys Ala Leu Asp Ile Leu
    130                 135                 140

Ser Cys Ala Gly Phe Val Asn His Phe Gly Arg Ser Met Ser Val Glu
145                 150                 155                 160

Lys Ile Asp Ile Ser Pro Val Leu Leu Gln Lys Gly Ser Thr Lys Ile
                165                 170                 175

Ala Leu Tyr Gly Leu Gly Ser Ile Pro Asp Glu Arg Leu Tyr Arg Met
            180                 185                 190

Phe Val Asn Lys Lys Val Thr Met Leu Arg Pro Lys Glu Asp Glu Asn
        195                 200                 205

Ser Trp Phe Asn Leu Phe Val Ile His Gln Asn Arg Ser Lys His Gly
    210                 215                 220

Ser Thr Asn Phe Ile Pro Glu Gln Phe Leu Asp Asp Phe Ile Asp Leu
225                 230                 235                 240

Val Ile Trp Gly His Glu His Glu Cys Lys Ile Ala Pro Thr Lys Asn
                245                 250                 255

Glu Gln Gln Leu Phe Tyr Ile Ser Gln Pro Gly Ser Ser Val Val Thr
            260                 265                 270

Ser Leu Ser Pro Gly Glu Ala Val Lys Lys His Val Gly Leu Leu Arg
        275                 280                 285

Ile Lys Gly Arg Lys Met Asn Met His Lys Ile Pro Leu His Thr Val
    290                 295                 300

Arg Gln Phe Phe Met Glu Asp Ile Val Leu Ala Asn His Pro Asp Ile
305                 310                 315                 320

Phe Asn Pro Asp Asn Pro Lys Val Thr Gln Ala Ile Gln Ser Phe Cys
                325                 330                 335
```

```
Leu Glu Lys Ile Glu Glu Met Leu Glu Asn Ala Glu Arg Glu Arg Leu
            340                 345                 350

Gly Asn Ser His Gln Pro Glu Lys Pro Leu Val Arg Leu Arg Val Asp
        355                 360                 365

Tyr Ser Gly Gly Phe Glu Pro Phe Ser Val Leu Arg Phe Ser Gln Lys
    370                 375                 380

Phe Val Asp Arg Val Ala Asn Pro Lys Asp Ile Ile His Phe Phe Arg
385                 390                 395                 400

His Arg Glu Gln Lys Glu Lys Thr Gly Glu Glu Ile Asn Phe Gly Lys
                405                 410                 415

Leu Ile Thr Lys Pro Ser Glu Gly Thr Thr Leu Arg Val Glu Asp Leu
            420                 425                 430

Val Lys Gln Tyr Phe Gln Thr Ala Glu Lys Asn Val Gln Leu Ser Leu
        435                 440                 445

Leu Thr Glu Arg Gly Met Gly Glu Ala Val Gln Glu Phe Val Asp Lys
    450                 455                 460

Glu Glu Lys Asp Ala Ile Glu Glu Leu Val Lys Tyr Gln Leu Glu Lys
465                 470                 475                 480

Thr Gln Arg Phe Leu Lys Glu Arg His Ile Asp Ala Leu Glu Asp Lys
                485                 490                 495

Ile Asp Glu Glu Val Arg Arg Phe Arg Glu Thr Arg Gln Lys Asn Thr
            500                 505                 510

Asn Glu Glu Asp Asp Glu Val Arg Glu Ala Met Thr Arg Ala Arg Ala
        515                 520                 525

Leu Arg Ser Gln Ser Glu Glu Ser Ala Ser Ala Phe Ser Ala Asp Asp
    530                 535                 540

Leu Met Ser Ile Asp Leu Ala Glu Gln Met Ala Asn Asp Ser Asp Asp
545                 550                 555                 560

Ser Ile Ser Ala Ala Thr Asn Lys Gly Arg Gly Arg Gly Arg Gly Arg
                565                 570                 575

Arg Gly Gly Arg Gly Gln Asn Ser Ala Ser Arg Gly Gly Ser Gln Arg
            580                 585                 590

Gly Arg Ala Asp Thr Gly Leu Glu Thr Ser Thr Arg Ser Arg Asn Ser
        595                 600                 605

Lys Thr Ala Val Ser Ala Ser Arg Asn Met Ser Ile Ile Asp Ala Phe
    610                 615                 620

Lys Ser Thr Arg Gln Gln Pro Ser Arg Asn Val Thr Thr Lys Asn Tyr
625                 630                 635                 640

Ser Glu Val Ile Glu Val Asp Glu Ser Asp Val Glu Glu Asp Ile Phe
                645                 650                 655

Pro Thr Thr Ser Lys Thr Asp Gln Arg Trp Ser Ser Thr Ser Ser Ser
            660                 665                 670

Lys Ile Met Ser Gln Ser Gln Val Ser Lys Gly Val Asp Phe Glu Ser
        675                 680                 685

Ser Glu Asp Asp Asp Asp Asp Pro Phe Met Asn Thr Ser Ser Leu Arg
    690                 695                 700

Arg Asn Arg Arg
705


<210> SEQ ID NO 16
<211> LENGTH: 5141
<212> TYPE: DNA
<213> ORGANISM: Artificial Sequence
<220> FEATURE:
```

<223> OTHER INFORMATION: MRE11A sequence

<400> SEQUENCE: 16

```
acgttatcca tgaagtgtcg cgagagaaac ggacgccgtt ctctcccgcg gaattcaggt     60
ttacggccct gcgggttctc agagaatttc tagaatttgg aatcgagtgc attttctgac    120
atttgagtac agtacccagg ggttcttgga gaagaacctg gtcccagagg agcttgactg    180
accataaaaa tgagtactgc agatgcactt gatgatgaaa acacatttaa aatattagtt    240
gcaacagata ttcatcttgg atttatggag aaagatgcag tcagaggaaa tgatacgttt    300
gtaacactcg atgaaatttt aagacttgcc caggaaaatg aagtggattt tattttgtta    360
ggtggtgatc tttttcatga aaataagccc tcaaggaaaa cattacatac ctgcctcgag    420
ttattaagaa aatattgtat gggtgatcgg cctgtccagt ttgaaattct cagtgatcag    480
tcagtcaact ttggttttag taagtttcca tgggtgaact atcaagatgg caacctcaac    540
atttcaattc cagtgtttag tattcatggc aatcatgacg atcccacagg ggcagatgca    600
ctttgtgcct tggacatttt aagttgtgct ggatttgtaa atcactttgg acgttcaatg    660
tctgtggaga agatagacat tagtccggtt ttgcttcaaa aaggaagcac aaagattgcg    720
ctatatggtt taggatccat tccagatgaa aggctctatc gaatgtttgt caataaaaaa    780
gtaacaatgt tgagaccaaa ggaagatgag aactcttggt ttaacttatt tgtgattcat    840
cagaacagga gtaaacatgg aagtactaac ttcattccag aacaattttt ggatgacttc    900
attgatcttg ttatctgggg ccatgaacat gagtgtaaaa tagctccaac caaaaatgaa    960
caacagctgt tttatatctc acaacctgga agctcagtgg ttacttctct ttccccagga   1020
gaagctgtaa agaaacatgt tggtttgctg cgtattaaag ggaggaagat gaatatgcat   1080
aaaattcctc ttcacacagt gcggcagttt ttcatggagg atattgttct agctaatcat   1140
ccagacattt ttaacccaga taatcctaaa gtaacccaag ccatacaaag cttctgtttg   1200
gagaagattg aagaaatgct tgaaaatgct gaacgggaac gtctgggtaa ttctcaccag   1260
ccagagaagc ctcttgtacg actgcgagtg gactatagtg gaggttttga acctttcagt   1320
gttcttcgct ttagccagaa atttgtggat cgggtagcta atccaaaaga cattatccat   1380
tttttcaggc atagagaaca aaaggaaaaa acaggagaag agatcaactt tgggaaactt   1440
atcacaaagc cttcagaagg aacaacttta agggtagaag atcttgtaaa acagtacttt   1500
caaaccgcag agaagaatgt gcagctctca ctgctaacag aaagagggat gggtgaagca   1560
gtacaagaat ttgtggacaa ggaggagaaa gatgccattg aggaattagt gaaataccag   1620
ttggaaaaaa cacagcgatt tcttaaagaa cgtcatattg atgccctcga agacaaaatc   1680
gatgaggagg tacgtcgttt cagagaaacc agacaaaaaa atactaatga agaagatgat   1740
gaagtccgtg aggctatgac cagggccaga gcactcagat ctcagtcaga ggagtctgct   1800
tctgccttta gtgctgatga ccttatgagt atagatttag cagaacagat ggctaatgac   1860
tctgatgata gcatctcagc agcaaccaac aaaggaagag gccgaggaag aggtcgaaga   1920
ggtggaagag ggcagaattc agcatcgaga ggagggtctc aaagaggaag agcagacact   1980
ggtctggaga cttctacccg tagcaggaac tcaaagactg ctgtgtcagc atctagaaat   2040
atgtctatta tagatgcctt taaatctaca agacagcagc cttcccgaaa tgtcactact   2100
aagaattatt cagaggtgat tgaggtagat gaatcagatg tggaagaaga catttttcct   2160
accacttcaa agacagatca aaggtggtcc agcacatcat ccagcaaaat catgtcccag   2220
agtcaagtat cgaaaggggt tgattttgaa tcaagtgagg atgatgatga tgatcctttt   2280
```

```
atgaacacta gttctttaag aagaaataga agataatata tttaatggca ctgagaaaca   2340
tgcaagatac aggaaaaatg aaaatgttac aagctaagag tttacagttt aagattttaa   2400
gtattgtttc ctgagcataa ctccataagt aagaaatttc tagttcacag acatacaata   2460
gcattgattc accttgtttt tttaacctgg ttgttgtagt aagagctttg tttcaatatc   2520
actcttgagt aaagattaaa ataaagctac cattttacat ttctatttca taatgaaaaa   2580
ctatgtcagt attttaatat ggttacattt agccaaagtt gagggaaaga gcttataaaa   2640
tttaacttct tcataatttt agtaatttcc tagaggttct gggttttctg aaagtaaaac   2700
aatttatgcg aacctatgtc taaattcact gtttgttact atgtatgttt ttttccaatg   2760
cttcttataa gactaaatga ttagaagtac ctaatagttt gaacagatat gtttttattt   2820
aaaagagtag aataaccttt cagaattact gagtttttta ttccagttgt agcaaagatt   2880
tcaaaagatt gtgttcccat taagtggtag taatttcctt tattattctg tatccttaat   2940
ggtgttctct ctctctctct ctctctctct ctctccctct cccccccgtt ccccactctt   3000
cctttctcct ttgcttttc ttctctttca tacatatatg cgtgcctagt tctaggagga   3060
aacgggttaa aaattgtttt aaactacatc ttgaaaatat tgaagaattt gttttaggta   3120
gagtggtcag ttgaacctta cagtaaagta tagaaatata tttaatgtgg aatgtcaatg   3180
ccaggatttc tcattaacaa tattttatct caactttggt tcctgtgata catttctgaa   3240
tgggcaattc cagaaatctt agtagcccat gttaagcttc tattttttac ttgttttcgg   3300
ggagaaataa gaattagaca tcttcagatt taagttaaat aatcccattc tttataatcc   3360
tctgtaaaaa gatccctgag attattcctt cttctagttt tatgcgacag ctttacttta   3420
aaattcaagt tatacatctt gggagtacaa tggcccgaca tttcttcata ggtagaaaca   3480
aatacttgac tcagtgatac tcatgaccat tagaatagtc atacctggaa tgtgtcaaat   3540
tataagagac agacacttgg ttagtggctg cctcatatag cacttttgaa gaggcctaag   3600
tcaaaacttg caatataaca ttctattgac tttcttaaaa atattttttc tgtacctaac   3660
ttgagcataa gggttatttg agcaagtaac attaactcag tggaaggcat tgtcctgtga   3720
aatattctta ggcagatctg cccacatctt tattgaactt gaaatctaat atttctagta   3780
tttgaacaaa gcagaaggtt aagtcaggga agagcagtgc tgtccatgat gtaatggaag   3840
ctaccagggg aggcagtgtc tggatgatgc tgtgctacct acccctgcac aagccatgct   3900
ggctcagtct gagctgtggg ccacatcagc tagtggctct tctcatgcat cagttaggtg   3960
ggtctgggtg agagttatag tgagggaatg gtcactaaag tatcctgaca agttcctagg   4020
aaaaaaggaa taaagttttt ttccttaaaa aaaaaaaaat tgctcttggc tgtgaaaaga   4080
ggtactaaat gcgattcagt tcaccgctaa ggaaagtgat gacatagcag ttacagaggg   4140
tgataaatct ctccagctaa ttcaggtcat tttgtgaata ctatgtatca agccctgaaa   4200
atatggtaaa taaaacgtga cagggaaacc ttttttttgat tgaatattgt tacatagtta   4260
aatgtgctat atatccttaa tattttatat tgatcctgca aaatctgttg gttttagggg   4320
agttttgttt tttgtttcta acaattttca gacctgttgg tataggaatg tagaagtctt   4380
tcagatgatt tgaaagcagc tgcatttgct cttggaggct ttgggagagc aggaatgaaa   4440
acattcagag gaagacatct gtagggaatt cttctgttac ttaccaaaga ataagtgtct   4500
ttctggtgtt ttatttccta tcataaaaat acaacagtgc atttacaagg ttaaagattc   4560
ctcgaagttc taggaaattc ttgaaaatat aagtggtgct tagaaaattc aagcatttag   4620
```

```
gaatgtgacc tttaattcag gtatgtaaaa gacttttttc ccaaactttt aaaagtagga   4680

aatacaataa atacagaaaa gtcatatggt tgaataaata attataaatt gagcactgat   4740

ggaatccctc tacaggtcaa gaaatagcgc agtgtcctgg atgcccatta tattgttttc   4800

tcctttctgg gtaacaagcc ctaacttctg taatttaaaa gctcctactt ttgccacaag   4860

gtggtgcttc tgccattaga cgcagttagg aggatgcaac tgcaaatcta aaattacgaa   4920

gttagtgtag ttgcaataaa cttagaacat atgcattaat actaaaccta tgcagtaata   4980

ccataattag ccttctaatc atgtaatttg ctttacttag gtatttcatt tggttcagcc   5040

tgttatggaa tttaccagct tgataaattt gcctataaag ttttataaag aaaaggaata   5100

ttttgttttc ataaagagga aaatccattc ttagaaaaaa a                       5141


<210> SEQ ID NO 17
<211> LENGTH: 3056
<212> TYPE: PRT
<213> ORGANISM: Artificial Sequence
<220> FEATURE:
<223> OTHER INFORMATION: ATM sequence

<400> SEQUENCE: 17

Met Ser Leu Val Leu Asn Asp Leu Leu Ile Cys Cys Arg Gln Leu Glu
1               5                   10                  15

His Asp Arg Ala Thr Glu Arg Lys Lys Glu Val Glu Lys Phe Lys Arg
            20                  25                  30

Leu Ile Arg Asp Pro Glu Thr Ile Lys His Leu Asp Arg His Ser Asp
        35                  40                  45

Ser Lys Gln Gly Lys Tyr Leu Asn Trp Asp Ala Val Phe Arg Phe Leu
    50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255

Glu Ile Leu Pro Thr Leu Leu Tyr Ile Trp Thr Gln His Arg Leu Asn
            260                 265                 270
```

```
Asp Ser Leu Lys Glu Val Ile Ile Glu Leu Phe Gln Leu Gln Ile Tyr
        275                 280                 285

Ile His His Pro Lys Gly Ala Lys Thr Gln Glu Lys Gly Ala Tyr Glu
    290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
            340                 345                 350

Cys His Gln Val Phe Asn Glu Asp Thr Arg Ser Leu Glu Ile Ser Gln
        355                 360                 365

Ser Tyr Thr Thr Thr Gln Arg Glu Ser Ser Asp Tyr Ser Val Pro Cys
    370                 375                 380

Lys Arg Lys Lys Ile Glu Leu Gly Trp Glu Val Ile Lys Asp His Leu
385                 390                 395                 400

Gln Lys Ser Gln Asn Asp Phe Asp Leu Val Pro Trp Leu Gln Ile Ala
                405                 410                 415

Thr Gln Leu Ile Ser Lys Tyr Pro Ala Ser Leu Pro Asn Cys Glu Leu
            420                 425                 430

Ser Pro Leu Leu Met Ile Leu Ser Gln Leu Leu Pro Gln Gln Arg His
        435                 440                 445

Gly Glu Arg Thr Pro Tyr Val Leu Arg Cys Leu Thr Glu Val Ala Leu
    450                 455                 460

Cys Gln Asp Lys Arg Ser Asn Leu Glu Ser Ser Gln Lys Ser Asp Leu
465                 470                 475                 480

Leu Lys Leu Trp Asn Lys Ile Trp Cys Ile Thr Phe Arg Gly Ile Ser
                485                 490                 495

Ser Glu Gln Ile Gln Ala Glu Asn Phe Gly Leu Leu Gly Ala Ile Ile
            500                 505                 510

Gln Gly Ser Leu Val Glu Val Asp Arg Glu Phe Trp Lys Leu Phe Thr
        515                 520                 525

Gly Ser Ala Cys Arg Pro Ser Cys Pro Ala Val Cys Cys Leu Thr Leu
    530                 535                 540

Ala Leu Thr Thr Ser Ile Val Pro Gly Thr Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
            580                 585                 590

Thr Glu Val Pro Pro Ile Leu His Ser Asn Phe Pro His Leu Val Leu
        595                 600                 605

Glu Lys Ile Leu Val Ser Leu Thr Met Lys Asn Cys Lys Ala Ala Met
    610                 615                 620

Asn Phe Phe Gln Ser Val Pro Glu Cys Glu His His Gln Lys Asp Lys
625                 630                 635                 640

Glu Glu Leu Ser Phe Ser Glu Val Glu Glu Leu Phe Leu Gln Thr Thr
                645                 650                 655

Phe Asp Lys Met Asp Phe Leu Thr Ile Val Arg Glu Cys Gly Ile Glu
            660                 665                 670

Lys His Gln Ser Ser Ile Gly Phe Ser Val His Gln Asn Leu Lys Glu
        675                 680                 685

Ser Leu Asp Arg Cys Leu Leu Gly Leu Ser Glu Gln Leu Leu Asn Asn
```

```
    690                 695                 700

Tyr Ser Ser Glu Ile Thr Asn Ser Glu Thr Leu Val Arg Cys Ser Arg
705                 710                 715                 720

Leu Leu Val Gly Val Leu Gly Cys Tyr Cys Tyr Met Gly Val Ile Ala
                725                 730                 735

Glu Glu Glu Ala Tyr Lys Ser Glu Leu Phe Gln Lys Ala Lys Ser Leu
            740                 745                 750

Met Gln Cys Ala Gly Glu Ser Ile Thr Leu Phe Lys Asn Lys Thr Asn
        755                 760                 765

Glu Glu Phe Arg Ile Gly Ser Leu Arg Asn Met Met Gln Leu Cys Thr
    770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
                805                 810                 815

Asp Ile Cys Lys Ser Leu Ala Ser Phe Ile Lys Lys Pro Phe Asp Arg
            820                 825                 830

Gly Glu Val Glu Ser Met Glu Asp Asp Thr Asn Gly Asn Leu Met Glu
        835                 840                 845

Val Glu Asp Gln Ser Ser Met Asn Leu Phe Asn Asp Tyr Pro Asp Ser
    850                 855                 860

Ser Val Ser Asp Ala Asn Glu Pro Gly Glu Ser Gln Ser Thr Ile Gly
865                 870                 875                 880

Ala Ile Asn Pro Leu Ala Glu Glu Tyr Leu Ser Lys Gln Asp Leu Leu
                885                 890                 895

Phe Leu Asp Met Leu Lys Phe Leu Cys Leu Cys Val Thr Thr Ala Gln
            900                 905                 910

Thr Asn Thr Val Ser Phe Arg Ala Ala Asp Ile Arg Arg Lys Leu Leu
        915                 920                 925

Met Leu Ile Asp Ser Ser Thr Leu Glu Pro Thr Lys Ser Leu His Leu
    930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
            980                 985                 990

His Val Leu His Val Val Lys Asn  Leu Gly Gln Ser Asn  Met Asp Ser
        995                 1000                1005

Glu Asn  Thr Arg Asp Ala Gln  Gly Gln Phe Leu Thr  Val Ile Gly
    1010                1015                1020

Ala Phe  Trp His Leu Thr Lys  Glu Arg Lys Tyr Ile  Phe Ser Val
    1025                1030                1035

Arg Met  Ala Leu Val Asn Cys  Leu Lys Thr Leu Leu  Glu Ala Asp
    1040                1045                1050

Pro Tyr  Ser Lys Trp Ala Ile  Leu Asn Val Met Gly  Lys Asp Phe
    1055                1060                1065

Pro Val  Asn Glu Val Phe Thr  Gln Phe Leu Ala Asp  Asn His His
    1070                1075                1080

Gln Val  Arg Met Leu Ala Ala  Glu Ser Ile Asn Arg  Leu Phe Gln
    1085                1090                1095

Asp Thr  Lys Gly Asp Ser Ser  Arg Leu Leu Lys Ala  Leu Pro Leu
    1100                1105                1110
```

```
Lys Leu  Gln Gln Thr Ala Phe  Glu Asn Ala Tyr Leu  Lys Ala Gln
    1115                 1120                 1125

Glu Gly  Met Arg Glu Met Ser  His Ser Ala Glu Asn  Pro Glu Thr
    1130                 1135                 1140

Leu Asp  Glu Ile Tyr Asn Arg  Lys Ser Val Leu Leu  Thr Leu Ile
    1145                 1150                 1155

Ala Val  Val Leu Ser Cys Ser  Pro Ile Cys Glu Lys  Gln Ala Leu
    1160                 1165                 1170

Phe Ala  Leu Cys Lys Ser Val  Lys Glu Asn Gly Leu  Glu Pro His
    1175                 1180                 1185

Leu Val  Lys Lys Val Leu Glu  Lys Val Ser Glu Thr  Phe Gly Tyr
    1190                 1195                 1200

Arg Arg  Leu Glu Asp Phe Met  Ala Ser His Leu Asp  Tyr Leu Val
    1205                 1210                 1215

Leu Glu  Trp Leu Asn Leu Gln  Asp Thr Glu Tyr Asn  Leu Ser Ser
    1220                 1225                 1230

Phe Pro  Phe Ile Leu Leu Asn  Tyr Thr Asn Ile Glu  Asp Phe Tyr
    1235                 1240                 1245

Arg Ser  Cys Tyr Lys Val Leu  Ile Pro His Leu Val  Ile Arg Ser
    1250                 1255                 1260

His Phe  Asp Glu Val Lys Ser  Ile Ala Asn Gln Ile  Gln Glu Asp
    1265                 1270                 1275

Trp Lys  Ser Leu Leu Thr Asp  Cys Phe Pro Lys Ile  Leu Val Asn
    1280                 1285                 1290

Ile Leu  Pro Tyr Phe Ala Tyr  Glu Gly Thr Arg Asp  Ser Gly Met
    1295                 1300                 1305

Ala Gln  Gln Arg Glu Thr Ala  Thr Lys Val Tyr Asp  Met Leu Lys
    1310                 1315                 1320

Ser Glu  Asn Leu Leu Gly Lys  Gln Ile Asp His Leu  Phe Ile Ser
    1325                 1330                 1335

Asn Leu  Pro Glu Ile Val Val  Glu Leu Leu Met Thr  Leu His Glu
    1340                 1345                 1350

Pro Ala  Asn Ser Ser Ala Ser  Gln Ser Thr Asp Leu  Cys Asp Phe
    1355                 1360                 1365

Ser Gly  Asp Leu Asp Pro Ala  Pro Asn Pro Pro His  Phe Pro Ser
    1370                 1375                 1380

His Val  Ile Lys Ala Thr Phe  Ala Tyr Ile Ser Asn  Cys His Lys
    1385                 1390                 1395

Thr Lys  Leu Lys Ser Ile Leu  Glu Ile Leu Ser Lys  Ser Pro Asp
    1400                 1405                 1410

Ser Tyr  Gln Lys Ile Leu Leu  Ala Ile Cys Glu Gln  Ala Ala Glu
    1415                 1420                 1425

Thr Asn  Asn Val Tyr Lys Lys  His Arg Ile Leu Lys  Ile Tyr His
    1430                 1435                 1440

Leu Phe  Val Ser Leu Leu Leu  Lys Asp Ile Lys Ser  Gly Leu Gly
    1445                 1450                 1455

Gly Ala  Trp Ala Phe Val Leu  Arg Asp Val Ile Tyr  Thr Leu Ile
    1460                 1465                 1470

His Tyr  Ile Asn Gln Arg Pro  Ser Cys Ile Met Asp  Val Ser Leu
    1475                 1480                 1485

Arg Ser  Phe Ser Leu Cys Cys  Asp Leu Leu Ser Gln  Val Cys Gln
    1490                 1495                 1500
```

```
Thr Ala  Val Thr Tyr Cys Lys  Asp Ala Leu Glu Asn  His Leu His
    1505                 1510                 1515

Val Ile  Val Gly Thr Leu Ile  Pro Leu Val Tyr Glu  Gln Val Glu
    1520                 1525                 1530

Val Gln  Lys Gln Val Leu Asp  Leu Leu Lys Tyr Leu  Val Ile Asp
    1535                 1540                 1545

Asn Lys  Asp Asn Glu Asn Leu  Tyr Ile Thr Ile Lys  Leu Leu Asp
    1550                 1555                 1560

Pro Phe  Pro Asp His Val Val  Phe Lys Asp Leu Arg  Ile Thr Gln
    1565                 1570                 1575

Gln Lys  Ile Lys Tyr Ser Arg  Gly Pro Phe Ser Leu  Leu Glu Glu
    1580                 1585                 1590

Ile Asn  His Phe Leu Ser Val  Ser Val Tyr Asp Ala  Leu Pro Leu
    1595                 1600                 1605

Thr Arg  Leu Glu Gly Leu Lys  Asp Leu Arg Arg Gln  Leu Glu Leu
    1610                 1615                 1620

His Lys  Asp Gln Met Val Asp  Ile Met Arg Ala Ser  Gln Asp Asn
    1625                 1630                 1635

Pro Gln  Asp Gly Ile Met Val  Lys Leu Val Val Asn  Leu Leu Gln
    1640                 1645                 1650

Leu Ser  Lys Met Ala Ile Asn  His Thr Gly Glu Lys  Glu Val Leu
    1655                 1660                 1665

Glu Ala  Val Gly Ser Cys Leu  Gly Glu Val Gly Pro  Ile Asp Phe
    1670                 1675                 1680

Ser Thr  Ile Ala Ile Gln His  Ser Lys Asp Ala Ser  Tyr Thr Lys
    1685                 1690                 1695

Ala Leu  Lys Leu Phe Glu Asp  Lys Glu Leu Gln Trp  Thr Phe Ile
    1700                 1705                 1710

Met Leu  Thr Tyr Leu Asn Asn  Thr Leu Val Glu Asp  Cys Val Lys
    1715                 1720                 1725

Val Arg  Ser Ala Ala Val Thr  Cys Leu Lys Asn Ile  Leu Ala Thr
    1730                 1735                 1740

Lys Thr  Gly His Ser Phe Trp  Glu Ile Tyr Lys Met  Thr Thr Asp
    1745                 1750                 1755

Pro Met  Leu Ala Tyr Leu Gln  Pro Phe Arg Thr Ser  Arg Lys Lys
    1760                 1765                 1770

Phe Leu  Glu Val Pro Arg Phe  Asp Lys Glu Asn Pro  Phe Glu Gly
    1775                 1780                 1785

Leu Asp  Asp Ile Asn Leu Trp  Ile Pro Leu Ser Glu  Asn His Asp
    1790                 1795                 1800

Ile Trp  Ile Lys Thr Leu Thr  Cys Ala Phe Leu Asp  Ser Gly Gly
    1805                 1810                 1815

Thr Lys  Cys Glu Ile Leu Gln  Leu Leu Lys Pro Met  Cys Glu Val
    1820                 1825                 1830

Lys Thr  Asp Phe Cys Gln Thr  Val Leu Pro Tyr Leu  Ile His Asp
    1835                 1840                 1845

Ile Leu  Leu Gln Asp Thr Asn  Glu Ser Trp Arg Asn  Leu Leu Ser
    1850                 1855                 1860

Thr His  Val Gln Gly Phe Phe  Thr Ser Cys Leu Arg  His Phe Ser
    1865                 1870                 1875

Gln Thr  Ser Arg Ser Thr Thr  Pro Ala Asn Leu Asp  Ser Glu Ser
    1880                 1885                 1890

Glu His  Phe Phe Arg Cys Cys  Leu Asp Lys Lys Ser  Gln Arg Thr
```

```
    1895                1900                1905

Met Leu Ala Val Val Asp Tyr Met Arg Arg Gln Lys Arg Pro Ser
    1910                1915                1920

Ser Gly Thr Ile Phe Asn Asp Ala Phe Trp Leu Asp Leu Asn Tyr
    1925                1930                1935

Leu Glu Val Ala Lys Val Ala Gln Ser Cys Ala Ala His Phe Thr
    1940                1945                1950

Ala Leu Leu Tyr Ala Glu Ile Tyr Ala Asp Lys Lys Ser Met Asp
    1955                1960                1965

Asp Gln Glu Lys Arg Ser Leu Ala Phe Glu Glu Gly Ser Gln Ser
    1970                1975                1980

Thr Thr Ile Ser Ser Leu Ser Glu Lys Ser Lys Glu Glu Thr Gly
    1985                1990                1995

Ile Ser Leu Gln Asp Leu Leu Leu Glu Ile Tyr Arg Ser Ile Gly
    2000                2005                2010

Glu Pro Asp Ser Leu Tyr Gly Cys Gly Gly Gly Lys Met Leu Gln
    2015                2020                2025

Pro Ile Thr Arg Leu Arg Thr Tyr Glu His Glu Ala Met Trp Gly
    2030                2035                2040

Lys Ala Leu Val Thr Tyr Asp Leu Glu Thr Ala Ile Pro Ser Ser
    2045                2050                2055

Thr Arg Gln Ala Gly Ile Ile Gln Ala Leu Gln Asn Leu Gly Leu
    2060                2065                2070

Cys His Ile Leu Ser Val Tyr Leu Lys Gly Leu Asp Tyr Glu Asn
    2075                2080                2085

Lys Asp Trp Cys Pro Glu Leu Glu Glu Leu His Tyr Gln Ala Ala
    2090                2095                2100

Trp Arg Asn Met Gln Trp Asp His Cys Thr Ser Val Ser Lys Glu
    2105                2110                2115

Val Glu Gly Thr Ser Tyr His Glu Ser Leu Tyr Asn Ala Leu Gln
    2120                2125                2130

Ser Leu Arg Asp Arg Glu Phe Ser Thr Phe Tyr Glu Ser Leu Lys
    2135                2140                2145

Tyr Ala Arg Val Lys Glu Val Glu Glu Met Cys Lys Arg Ser Leu
    2150                2155                2160

Glu Ser Val Tyr Ser Leu Tyr Pro Thr Leu Ser Arg Leu Gln Ala
    2165                2170                2175

Ile Gly Glu Leu Glu Ser Ile Gly Glu Leu Phe Ser Arg Ser Val
    2180                2185                2190

Thr His Arg Gln Leu Ser Glu Val Tyr Ile Lys Trp Gln Lys His
    2195                2200                2205

Ser Gln Leu Leu Lys Asp Ser Asp Phe Ser Phe Gln Glu Pro Ile
    2210                2215                2220

Met Ala Leu Arg Thr Val Ile Leu Glu Ile Leu Met Glu Lys Glu
    2225                2230                2235

Met Asp Asn Ser Gln Arg Glu Cys Ile Lys Asp Ile Leu Thr Lys
    2240                2245                2250

His Leu Val Glu Leu Ser Ile Leu Ala Arg Thr Phe Lys Asn Thr
    2255                2260                2265

Gln Leu Pro Glu Arg Ala Ile Phe Gln Ile Lys Gln Tyr Asn Ser
    2270                2275                2280

Val Ser Cys Gly Val Ser Glu Trp Gln Leu Glu Glu Ala Gln Val
    2285                2290                2295
```

```
Phe Trp Ala Lys Lys Glu Gln Ser Leu Ala Leu Ser Ile Leu Lys
    2300                2305                2310

Gln Met Ile Lys Lys Leu Asp Ala Ser Cys Ala Ala Asn Asn Pro
    2315                2320                2325

Ser Leu Lys Leu Thr Tyr Thr Glu Cys Leu Arg Val Cys Gly Asn
    2330                2335                2340

Trp Leu Ala Glu Thr Cys Leu Glu Asn Pro Ala Val Ile Met Gln
    2345                2350                2355

Thr Tyr Leu Glu Lys Ala Val Glu Val Ala Gly Asn Tyr Asp Gly
    2360                2365                2370

Glu Ser Ser Asp Glu Leu Arg Asn Gly Lys Met Lys Ala Phe Leu
    2375                2380                2385

Ser Leu Ala Arg Phe Ser Asp Thr Gln Tyr Gln Arg Ile Glu Asn
    2390                2395                2400

Tyr Met Lys Ser Ser Glu Phe Glu Asn Lys Gln Ala Leu Leu Lys
    2405                2410                2415

Arg Ala Lys Glu Glu Val Gly Leu Leu Arg Glu His Lys Ile Gln
    2420                2425                2430

Thr Asn Arg Tyr Thr Val Lys Val Gln Arg Glu Leu Glu Leu Asp
    2435                2440                2445

Glu Leu Ala Leu Arg Ala Leu Lys Glu Asp Arg Lys Arg Phe Leu
    2450                2455                2460

Cys Lys Ala Val Glu Asn Tyr Ile Asn Cys Leu Leu Ser Gly Glu
    2465                2470                2475

Glu His Asp Met Trp Val Phe Arg Leu Cys Ser Leu Trp Leu Glu
    2480                2485                2490

Asn Ser Gly Val Ser Glu Val Asn Gly Met Met Lys Arg Asp Gly
    2495                2500                2505

Met Lys Ile Pro Thr Tyr Lys Phe Leu Pro Leu Met Tyr Gln Leu
    2510                2515                2520

Ala Ala Arg Met Gly Thr Lys Met Met Gly Gly Leu Gly Phe His
    2525                2530                2535

Glu Val Leu Asn Asn Leu Ile Ser Arg Ile Ser Met Asp His Pro
    2540                2545                2550

His His Thr Leu Phe Ile Ile Leu Ala Leu Ala Asn Ala Asn Arg
    2555                2560                2565

Asp Glu Phe Leu Thr Lys Pro Glu Val Ala Arg Arg Ser Arg Ile
    2570                2575                2580

Thr Lys Asn Val Pro Lys Gln Ser Ser Gln Leu Asp Glu Asp Arg
    2585                2590                2595

Thr Glu Ala Ala Asn Arg Ile Ile Cys Thr Ile Arg Ser Arg Arg
    2600                2605                2610

Pro Gln Met Val Arg Ser Val Glu Ala Leu Cys Asp Ala Tyr Ile
    2615                2620                2625

Ile Leu Ala Asn Leu Asp Ala Thr Gln Trp Lys Thr Gln Arg Lys
    2630                2635                2640

Gly Ile Asn Ile Pro Ala Asp Gln Pro Ile Thr Lys Leu Lys Asn
    2645                2650                2655

Leu Glu Asp Val Val Val Pro Thr Met Glu Ile Lys Val Asp His
    2660                2665                2670

Thr Gly Glu Tyr Gly Asn Leu Val Thr Ile Gln Ser Phe Lys Ala
    2675                2680                2685
```

```
Glu Phe  Arg Leu Ala Gly Gly  Val Asn Leu Pro Lys  Ile Ile Asp
    2690                 2695                 2700

Cys Val  Gly Ser Asp Gly Lys  Glu Arg Arg Gln Leu  Val Lys Gly
    2705                 2710                 2715

Arg Asp  Asp Leu Arg Gln Asp  Ala Val Met Gln Gln  Val Phe Gln
    2720                 2725                 2730

Met Cys  Asn Thr Leu Leu Gln  Arg Asn Thr Glu Thr  Arg Lys Arg
    2735                 2740                 2745

Lys Leu  Thr Ile Cys Thr Tyr  Lys Val Val Pro Leu  Ser Gln Arg
    2750                 2755                 2760

Ser Gly  Val Leu Glu Trp Cys  Thr Gly Thr Val Pro  Ile Gly Glu
    2765                 2770                 2775

Phe Leu  Val Asn Asn Glu Asp  Gly Ala His Lys Arg  Tyr Arg Pro
    2780                 2785                 2790

Asn Asp  Phe Ser Ala Phe Gln  Cys Gln Lys Lys Met  Met Glu Val
    2795                 2800                 2805

Gln Lys  Lys Ser Phe Glu Glu  Lys Tyr Glu Val Phe  Met Asp Val
    2810                 2815                 2820

Cys Gln  Asn Phe Gln Pro Val  Phe Arg Tyr Phe Cys  Met Glu Lys
    2825                 2830                 2835

Phe Leu  Asp Pro Ala Ile Trp  Phe Glu Lys Arg Leu  Ala Tyr Thr
    2840                 2845                 2850

Arg Ser  Val Ala Thr Ser Ser  Ile Val Gly Tyr Ile  Leu Gly Leu
    2855                 2860                 2865

Gly Asp  Arg His Val Gln Asn  Ile Leu Ile Asn Glu  Gln Ser Ala
    2870                 2875                 2880

Glu Leu  Val His Ile Asp Leu  Gly Val Ala Phe Glu  Gln Gly Lys
    2885                 2890                 2895

Ile Leu  Pro Thr Pro Glu Thr  Val Pro Phe Arg Leu  Thr Arg Asp
    2900                 2905                 2910

Ile Val  Asp Gly Met Gly Ile  Thr Gly Val Glu Gly  Val Phe Arg
    2915                 2920                 2925

Arg Cys  Cys Glu Lys Thr Met  Glu Val Met Arg Asn  Ser Gln Glu
    2930                 2935                 2940

Thr Leu  Leu Thr Ile Val Glu  Val Leu Leu Tyr Asp  Pro Leu Phe
    2945                 2950                 2955

Asp Trp  Thr Met Asn Pro Leu  Lys Ala Leu Tyr Leu  Gln Gln Arg
    2960                 2965                 2970

Pro Glu  Asp Glu Thr Glu Leu  His Pro Thr Leu Asn  Ala Asp Asp
    2975                 2980                 2985

Gln Glu  Cys Lys Arg Asn Leu  Ser Asp Ile Asp Gln  Ser Phe Asn
    2990                 2995                 3000

Lys Val  Ala Glu Arg Val Leu  Met Arg Leu Gln Glu  Lys Leu Lys
    3005                 3010                 3015

Gly Val  Glu Glu Gly Thr Val  Leu Ser Val Gly Gly  Gln Val Asn
    3020                 3025                 3030

Leu Leu  Ile Gln Gln Ala Ile  Asp Pro Lys Asn Leu  Ser Arg Leu
    3035                 3040                 3045

Phe Pro  Gly Trp Lys Ala Trp  Val
    3050                 3055
```

<210> SEQ ID NO 18
<211> LENGTH: 13147
<212> TYPE: DNA

-continued

<213> ORGANISM: Artificial Sequence
<220> FEATURE:
<223> OTHER INFORMATION: ATM sequence

<400> SEQUENCE: 18
ccggagcccg agccgaaggg cgagccgcaa acgctaagtc gctggccatt ggtggacatg 60
gcgcaggcgc gtttgctccg acgggccgaa tgttttgggg cagtgttttg agcgcggaga 120
ccgcgtgata ctggatgcgc atgggcatac cgtgctctgc ggctgcttgg cgttgcttct 180
tcctccagaa gtgggcgctg ggcagtcacg cagggtttga accggaagcg ggagtaggta 240
gctgcgtggc taacggagaa aagaagccgt ggccgcggga ggaggcgaga ggagtcggga 300
tctgcgctgc agccaccgcc gcggttgata ctactttgac cttccgagtg cagtgacagt 360
gatgtgtgtt ctgaaattgt gaaccatgag tctagtactt aatgatctgc ttatctgctg 420
ccgtcaacta gaacatgata gagctacaga acgaaagaaa gaagttgaga aatttaagcg 480
cctgattcga gatcctgaaa caattaaaca tctagatcgg cattcagatt ccaaacaagg 540
aaaatatttg aattgggatg ctgtttttag atttttacag aaatatattc agaaagaaac 600
agaatgtctg agaatagcaa aaccaaatgt atcagcctca acacaagcct ccaggcagaa 660
aaagatgcag gaaatcagta gtttggtcaa atacttcatc aaatgtgcaa acagaagagc 720
acctaggcta aaatgtcaag aactcttaaa ttatatcatg gatacagtga aagattcatc 780
taatggtgct atttacggag ctgattgtag caacatacta ctcaaagaca ttctttctgt 840
gagaaaatac tggtgtgaaa tatctcagca acagtggtta gaattgttct ctgtgtactt 900
caggctctat ctgaaacctt cacaagatgt tcatagagtt ttagtggcta gaataattca 960
tgctgttacc aaaggatgct gttctcagac tgacggatta aattccaaat tttggacttt 1020
tttttccaag gctattcagt gtgcgagaca agaaaagagc tcttcaggtc taaatcatat 1080
cttagcagct cttactatct tcctcaagac tttggctgtc aactttcgaa ttcgagtgtg 1140
tgaattagga gatgaaattc ttcccacttt gctttatatt tggactcaac ataggcttaa 1200
tgattcttta aaagaagtca ttattgaatt atttcaactg caaatttata tccatcatcc 1260
gaaaggagcc aaaacccaag aaaaaggtgc ttatgaatca acaaaatgga gaagtatttt 1320
atacaactta tatgatctgc tagtgaatga gataagtcat ataggaagta gaggaaagta 1380
ttcttcagga tttcgtaata ttgccgtcaa agaaaatttg attgaattga tggcagatat 1440
ctgtcaccag gtttttaatg aagataccag atccttggag atttctcaat cttacactac 1500
tacacaaaga gaatctagtg attacagtgt cccttgcaaa aggaagaaaa tagaactagg 1560
ctgggaagta ataaaagatc accttcagaa gtcacagaat gattttgatc ttgtgccttg 1620
gctacagatt gcaacccaat taatatcaaa gtatcctgca agtttaccta actgtgagct 1680
gtctccatta ctgatgatac tatctcagct tctaccccaa cagcgacatg gggaacgtac 1740
accatatgtg ttacgatgcc ttacggaagt tgcattgtgt caagacaaga ggtcaaacct 1800
agaaagctca caaaagtcag atttattaaa actctggaat aaaatttggt gtattacctt 1860
tcgtggtata agttctgagc aaatacaagc tgaaaacttt ggcttacttg gagccataat 1920
tcagggtagt ttagttgagg ttgacagaga attctggaag ttatttactg ggtcagcctg 1980
cagaccttca tgtcctgcag tatgctgttt gactttggca ctgaccacca gtatagttcc 2040
aggaacggta aaaatgggaa tagagcaaaa tatgtgtgaa gtaaatagaa gcttttcttt 2100
aaaggaatca ataatgaaat ggctcttatt ctatcagtta gagggtgact tagaaaatag 2160
cacagaagtg cctccaattc ttcacagtaa ttttcctcat cttgtactgg agaaaattct 2220

-continued

```
tgtgagtctc actatgaaaa actgtaaagc tgcaatgaat tttttccaaa gcgtgccaga   2280
atgtgaacac caccaaaaag ataaagaaga actttcattc tcagaagtag aagaactatt   2340
tcttcagaca acttttgaca agatggactt tttaaccatt gtgagagaat gtggtataga   2400
aaagcaccag tccagtattg gcttctctgt ccaccagaat ctcaaggaat cactggatcg   2460
ctgtcttctg ggattatcag aacagcttct gaataattac tcatctgaga ttacaaattc   2520
agaaactctt gtccggtgtt cacgtctttt ggtgggtgtc cttggctgct actgttacat   2580
gggtgtaata gctgaagagg aagcatataa gtcagaatta ttccagaaag ccaagtctct   2640
aatgcaatgt gcaggagaaa gtatcactct gtttaaaaat aagacaaatg aggaattcag   2700
aattggttcc ttgagaaata tgatgcagct atgtacacgt tgcttgagca actgtaccaa   2760
gaagagtcca aataagattg catctggctt tttcctgcga ttgttaacat caaagctaat   2820
gaatgacatt gcagatattt gtaaaagttt agcatccttc atcaaaaagc catttgaccg   2880
tggagaagta gaatcaatgg aagatgatac taatggaaat ctaatggagg tggaggatca   2940
gtcatccatg aatctattta acgattaccc tgatagtagt gttagtgatg caaacgaacc   3000
tggagagagc caaagtacca taggtgccat taatccttta gctgaagaat atctgtcaaa   3060
gcaagatcta cttttcttag acatgctcaa gttcttgtgt ttgtgtgtaa ctactgctca   3120
gaccaatact gtgtccttta gggcagctga tattcggagg aaattgttaa tgttaattga   3180
ttctagcacg ctagaaccta ccaaatccct ccacctgcat atgtatctaa tgcttttaaa   3240
ggagcttcct ggagaagagt accccttgcc aatggaagat gttcttgaac ttctgaaacc   3300
actatccaat gtgtgttctt tgtatcgtcg tgaccaagat gtttgtaaaa ctattttaaa   3360
ccatgtcctt catgtagtga aaaacctagg tcaaagcaat atggactctg agaacacaag   3420
ggatgctcaa ggacagtttc ttacagtaat tggagcattt tggcatctaa caaaggagag   3480
gaaatatata ttctctgtaa gaatggccct agtaaattgc cttaaaactt tgcttgaggc   3540
tgatccttat tcaaaatggg ccattcttaa tgtaatggga aaagactttc ctgtaaatga   3600
agtatttaca caatttcttg ctgacaatca tcaccaagtt cgcatgttgg ctgcagagtc   3660
aatcaataga ttgttccagg acacgaaggg agattcttcc aggttactga aagcacttcc   3720
tttgaagctt cagcaaacag cttttgaaaa tgcatacttg aaagctcagg aaggaatgag   3780
agaaatgtcc catagtgctg agaaccctga aactttggat gaaatttata atagaaaatc   3840
tgttttactg acgttgatag ctgtggtttt atcctgtagc cctatctgcg aaaaacaggc   3900
tttgtttgcc ctgtgtaaat ctgtgaaaga gaatggatta gaacctcacc ttgtgaaaaa   3960
ggttttagag aaagtttctg aaacttttgg atatagacgt ttagaagact ttatggcatc   4020
tcatttagat tatctggttt tggaatggct aaatcttcaa gatactgaat acaacttatc   4080
ttcttttcct tttattttat taaactacac aaatattgag gatttctata gatcttgtta   4140
taaggttttg attccacatc tggtgattag aagtcatttt gatgaggtga agtccattgc   4200
taatcagatt caagaggact ggaaaagtct tctaacagac tgctttccaa agattcttgt   4260
aaatattctt ccttattttg cctatgaggg taccagagac agtgggatgg cacagcaaag   4320
agagactgct accaaggtct atgatatgct taaaagtgaa aacttattgg gaaaacagat   4380
tgatcactta ttcattagta atttaccaga gattgtggtg gagttattga tgacgttaca   4440
tgagccagca aattctagtg ccagtcagag cactgacctc tgtgactttt caggggattt   4500
ggatcctgct cctaatccac ctcattttcc atcgcatgtg attaaagcaa catttgccta   4560
```

-continued

```
tatcagcaat tgtcataaaa ccaagttaaa aagcatttta gaaattcttt ccaaaagccc   4620
tgattcctat cagaaaattc ttcttgccat atgtgagcaa gcagctgaaa caaataatgt   4680
ttataagaag cacagaattc ttaaaatata tcacctgttt gttagtttat tactgaaaga   4740
tataaaaagt ggcttaggag gagcttgggc ctttgttctt cgagacgtta tttatacttt   4800
gattcactat atcaaccaaa ggccttcttg tatcatggat gtgtcattac gtagcttctc   4860
cctttgttgt gacttattaa gtcaggtttg ccagacagcc gtgacttact gtaaggatgc   4920
tctagaaaac catcttcatg ttattgttgg tacacttata ccccttgtgt atgagcaggt   4980
ggaggttcag aaacaggtat tggacttgtt gaaatactta gtgatagata acaaggataa   5040
tgaaaacctc tatatcacga ttaagctttt agatcctttt cctgaccatg ttgtttttaa   5100
ggatttgcgt attactcagc aaaaaatcaa atacagtaga ggaccctttt cactcttgga   5160
ggaaattaac cattttctct cagtaagtgt ttatgatgca cttccattga caagacttga   5220
aggactaaag gatcttcgaa gacaactgga actacataaa gatcagatgg tggacattat   5280
gagagcttct caggataatc cgcaagatgg gattatggtg aaactagttg tcaatttgtt   5340
gcagttatcc aagatggcaa taaaccacac tggtgaaaaa gaagttctag aggctgttgg   5400
aagctgcttg ggagaagtgg gtcctataga tttctctacc atagctatac aacatagtaa   5460
agatgcatct tataccaagg cccttaagtt atttgaagat aaagaacttc agtggacctt   5520
cataatgctg acctacctga ataacacact ggtagaagat tgtgtcaaag ttcgatcagc   5580
agctgttacc tgtttgaaaa acattttagc cacaaagact ggacatagtt tctgggagat   5640
ttataagatg acaacagatc caatgctggc ctatctacag ccttttagaa catcaagaaa   5700
aaagttttta gaagtaccca gatttgacaa agaaaaccct tttgaaggcc tggatgatat   5760
aaatctgtgg attcctctaa gtgaaaatca tgacatttgg ataaagacac tgacttgtgc   5820
tttttggac agtggaggca caaaatgtga aattcttcaa ttattaaagc caatgtgtga   5880
agtgaaaact gacttttgtc agactgtact tccatacttg attcatgata ttttactcca   5940
agatacaaat gaatcatgga gaaatctgct ttctacacat gttcagggat tttcaccag    6000
ctgtcttcga cacttctcgc aaacgagccg atccacaacc cctgcaaact tggattcaga   6060
gtcagagcac tttttccgat gctgtttgga taaaaaatca caaagaacaa tgcttgctgt   6120
tgtggactac atgagaagac aaaagagacc ttcttcagga acaattttta atgatgcttt   6180
ctggctggat ttaaattatc tagaagttgc caaggtagct cagtcttgtg ctgctcactt   6240
tacagcttta ctctatgcag aaatctatgc agataagaaa agtatggatg atcaagagaa   6300
aagaagtctt gcatttgaag aaggaagcca gagtacaact atttctagct tgagtgaaaa   6360
aagtaaagaa gaaactggaa taagtttaca ggatcttctc ttagaaatct acagaagtat   6420
aggggagcca gatagtttgt atggctgtgg tggagggaag atgttacaac ccattactag   6480
actacgaaca tatgaacacg aagcaatgtg gggcaaagcc ctagtaacat atgacctcga   6540
aacagcaatc ccctcatcaa cacgccaggc aggaatcatt caggccttgc agaatttggg   6600
actctgccat attctttccg tctatttaaa aggattggat tatgaaaata aagactggtg   6660
tcctgaacta gaagaacttc attaccaagc agcatggagg aatatgcagt gggaccattg   6720
cacttccgtc agcaaagaag tagaaggaac cagttaccat gaatcattgt acaatgctct   6780
acaatctcta agagacagag aattctctac attttatgaa agtctcaaat atgccagagt   6840
aaaagaagtg gaagagatgt gtaagcgcag ccttgagtct gtgtattcgc tctatcccac   6900
acttagcagg ttgcaggcca ttggagagct ggaaagcatt ggggagcttt tctcaagatc   6960
```

```
agtcacacat agacaactct ctgaagtata tattaagtgg cagaaacact cccagcttct   7020
caaggacagt gattttagtt ttcaggagcc tatcatggct ctacgcacag tcattttgga   7080
gatcctgatg gaaaaggaaa tggacaactc acaaagagaa tgtattaagg acattctcac   7140
caaacacctt gtagaactct ctatactggc cagaactttc aagaacactc agctccctga   7200
aagggcaata tttcaaatta aacagtacaa ttcagttagc tgtggagtct ctgagtggca   7260
gctggaagaa gcacaagtat tctgggcaaa aaaggagcag agtcttgccc tgagtattct   7320
caagcaaatg atcaagaagt tggatgccag ctgtgcagcg aacaatccca gcctaaaact   7380
tacatacaca gaatgtctga gggtttgtgg caactggtta gcagaaacgt gcttagaaaa   7440
tcctgcggtc atcatgcaga cctatctaga aaaggcagta gaagttgctg gaaattatga   7500
tggagaaagt agtgatgagc taagaaatgg aaaaatgaag gcatttctct cattagcccg   7560
gttttcagat actcaatacc aaagaattga aaactacatg aaatcatcgg aatttgaaaa   7620
caagcaagct ctcctgaaaa gagccaaaga ggaagtaggt ctccttaggg aacataaaat   7680
tcagacaaac agatacacag taaaggttca gcgagagctg gagttggatg aattagccct   7740
gcgtgcactg aaagaggatc gtaaacgctt cttatgtaaa gcagttgaaa attatatcaa   7800
ctgcttatta agtggagaag aacatgatat gtgggtattc cgactttgtt ccctctggct   7860
tgaaaattct ggagtttctg aagtcaatgg catgatgaag agagacggaa tgaagattcc   7920
aacatataaa tttttgcctc ttatgtacca attggctgct agaatgggga ccaagatgat   7980
gggaggccta ggatttcatg aagtcctcaa taatctaatc tctagaattt caatggatca   8040
cccccatcac actttgttta ttatactggc cttagcaaat gcaaacagag atgaatttct   8100
gactaaacca gaggtagcca gaagaagcag aataactaaa aatgtgccta aacaaagctc   8160
tcagcttgat gaggatcgaa cagaggctgc aaatagaata atatgtacta tcagaagtag   8220
gagacctcag atggtcagaa gtgttgaggc actttgtgat gcttatatta tattagcaaa   8280
cttagatgcc actcagtgga agactcagag aaaaggcata aatattccag cagaccagcc   8340
aattactaaa cttaagaatt tagaagatgt tgttgtccct actatggaaa ttaaggtgga   8400
ccacacagga gaatatggaa atctggtgac tatacagtca tttaaagcag aatttcgctt   8460
agcaggaggt gtaaatttac caaaaataat agattgtgta ggttccgatg gcaaggagag   8520
gagacagctt gttaagggcc gtgatgacct gagacaagat gctgtcatgc aacaggtctt   8580
ccagatgtgt aatacattac tgcagagaaa cacggaaact aggaagagga aattaactat   8640
ctgtacttat aaggtggttc ccctctctca gcgaagtggt gttcttgaat ggtgcacagg   8700
aactgtcccc attggtgaat ttcttgttaa caatgaagat ggtgctcata aaagatacag   8760
gccaaatgat ttcagtgcct ttcagtgcca aaagaaaatg atggaggtgc aaaaaaagtc   8820
ttttgaagag aaatatgaag tcttcatgga tgtttgccaa aattttcaac cagttttccg   8880
ttacttctgc atggaaaaat tcttggatcc agctatttgg tttgagaagc gattggctta   8940
tacgcgcagt gtagctactt cttctattgt tggttacata cttggacttg gtgatagaca   9000
tgtacagaat atcttgataa atgagcagtc agcagaactt gtacatatag atctaggtgt   9060
tgcttttgaa cagggcaaaa tccttcctac tcctgagaca gttcctttta gactcaccag   9120
agatattgtg gatggcatgg gcattacggg tgttgaaggt gtcttcagaa gatgctgtga   9180
gaaaaccatg gaagtgatga gaaactctca ggaaactctg ttaaccattg tagaggtcct   9240
tctatatgat ccactctttg actggaccat gaatcctttg aaagctttgt atttacagca   9300
```

-continued

```
gaggccggaa gatgaaactg agcttcaccc tactctgaat gcagatgacc aagaatgcaa   9360
acgaaatctc agtgatattg accagagttt caacaaagta gctgaacgtg tcttaatgag   9420
actacaagag aaactgaaag gagtggaaga aggcactgtg ctcagtgttg gtggacaagt   9480
gaatttgctc atacagcagg ccatagaccc caaaaatctc agccgacttt tcccaggatg   9540
gaaagcttgg gtgtgatctt cagtatatga attacccttt cattcagcct ttagaaatta   9600
tattttagcc tttattttta acctgccaac atactttaag tagggattaa tatttaagtg   9660
aactattgtg ggtttttttg aatgttggtt ttaatacttg atttaatcac cactcaaaaa   9720
tgttttgatg gtcttaagga acatctctgc tttcactctt tagaaataat ggtcattcgg   9780
gctgggcgca gcggctcacg cctgtaatcc cagcactttg ggaggccgag gtgagcggat   9840
cacaaggtca ggagttcgag accagcctgg ccaagagacc agcctggcca gtatggtgaa   9900
accctgtctc tactaaaaat acaaaaatta gccgagcatg gtggcgggca cctgtaatcc   9960
cagctactcg agaggctgag gcaggagaat ctcttgaacc tgggaggtga aggttgctgt  10020
gggccaaaat catgccattg cactccagcc tgggtgacaa gagcgaaact ccatctcaaa  10080
aaaaaaaaaa aaaaaacaga aacgtatttg gatttttcct agtaagatca ctcagtgtta  10140
ctaaataatg aagttgttat ggagaacaaa tttcaaagac acagttagtg tagttactat  10200
tttttaagt gtgtattaaa acttctcatt ctattctctt tatcttttaa gcccttctgt  10260
actgtccatg tatgttatct ttctgtgata acttcataga ttgccttcta gttcatgaat  10320
tctcttgtca gatgtatata atctctttta ccctatccat tgggcttctt ctttcagaaa  10380
ttgtttttca tttctaatta tgcatcattt ttcagatctc tgtttcttga tgtcattttt  10440
aatgtttttt taatgttttt tatgtcacta attattttaa atgtctgtac ttgatagaca  10500
ctgtaatagt tctattaaat ttagttcctg ctgtttatat ctgttgattt ttgtatttga  10560
taggctgttc atccagtttt gtctttttga aaagtgagtt tattttcagc aaggctttat  10620
ctatgggaat cttgagtgtc tgtttatgtc atattcccag ggctgttgct gcacacaagc  10680
ccattcttat tttaatttct tggctttagg gtttccatac ctgaagtgta gcataaatac  10740
tgataggaga tttcccaggc caaggcaaac acacttcctc ctcatctcct tgtgctagtg  10800
ggcagaatat ttgattgatg ccttttcac tgagagtata agcttccatg tgtcccacct  10860
ttatggcagg ggtggaagga ggtacattta attcccactg cctgcctttg gcaagccctg  10920
ggttctttgc tccccatata gatgtctaag ctaaaagccg tgggttaatg agactggcaa  10980
attgttccag gacagctaca gcatcagctc acatattcac ctctctggtt tttcattccc  11040
ctcatttttt tctgagacag agtcttgctc tgtcacccag gctggagtgc agtggcatga  11100
tctcagctca ctgaaacctc tgcctcctgg gttcaagcaa ttctcctgcc tcagcctccc  11160
gagtagctgg gactacaggc gtgtgccaac acgcccggct aattttttgt atttttatta  11220
gagacggagt ttcaccgtgt tagccaggat ggtctcgatc gcttgacctc gtgatccacc  11280
ctcctcggcc tcccaaagtg ctgggattac aggtgtgagc caccgcgccc ggcctcattc  11340
ccctcatttt tgaccgtaag gatttcccct ttcttgtaag ttctgctatg tatttaaaag  11400
aatgttttct acattttatc cagcatttct ctgtgttctg ttggaaggga agggcttagg  11460
tatctagttt gatacatagg tagaagtgga acatttctct gtcccccagc tgtcatcata  11520
taagataaac atcagataaa aagccacctg aaagtaaaac tactgactcg tgtattagtg  11580
agtataatct cttctccatc cttaggaaaa tgttcatccc agctgcggag attaacaaat  11640
gggtgattga gctttctcct cgtatttgga ccttgaaggt tatataaatt tttttcttat  11700
```

gaagagttgg catttctttt tattgccaat ggcaggcact cattcatatt tgatctcctc 11760
accttcccct cccctaaaac caatctccag aactttttgg actataaatt tcttggtttg 11820
acttctggag aactgttcag aatattactt tgcatttcaa attacaaact taccttggtg 11880
tatctttttc ttacaagctg cctaaatgaa tatttggtat atattggtag ttttattact 11940
atagtaaatc aaggaaatgc agtaaactta aaatgtcttt aagaaagccc tgaaatcttc 12000
atgggtgaaa ttagaaatta tcaactagat aatagtatag ataaatgaat ttgtagctaa 12060
ttcttgctag ttgttgcatc cagagagctt tgaataacat cattaatcta ctctttagcc 12120
ttgcatggta tgctatgagg ctcctgttct gttcaagtat tctaatcaat ggctttgaaa 12180
agtttatcaa atttacatac agatcacaag cctaggagaa ataactaatt cacagatgac 12240
agaattaaga ttataaaaga ttttttttt gtaattttag tagagacagg gttgccattg 12300
tattccagcc ttggcgacag agcaagactc tgcctcaaaa aaaaaaaaaa aaaggttttg 12360
gcaagctgga actctttctg caaatgacta agatagaaaa ctgccaagga caaatgagga 12420
gtagttagat tttgaaaata ttaatcatag aatagttgtt gtatgctaag tcactgaccc 12480
atattatgta cagcatttct gatctttact ttgcaagatt agtgatacta tcccaataca 12540
ctgctggaga aatcagaatt tggagaaata agttgtccaa ggcaagaaga tagtaaatta 12600
taagtacaag tgtaatatgg acagtatcta acttgaaaag atttcaggcg aaaagaatct 12660
ggggtttgcc agtcagttgc tcaaaaggtc aatgaaaacc aaatagtgaa gctatcagag 12720
aagctaataa attatagact gcttgaacag ttgtgtccag attaagggag ataatagctt 12780
tcccacccta ctttgtgcag gtcatacctc cccaaagtgt ttacctaatc agtaggttca 12840
caaactcttg gtcattatag tatatgccta aaatgtatgc acttaggaat gctaaaaatt 12900
taaatatggt ctaaagcaaa taaaagcaaa gaggaaaaac tttggacagc gtaaagacta 12960
gaatagtctt ttaaaaagaa agccagtata ttggtttgaa atatagagat gtgtcccaat 13020
ttcaagtatt ttaattgcac cttaatgaaa ttatctattt tctatagatt ttagtactat 13080
tgaatgtatt actttactgt tacctgaatt tattataaag tgtttttgaa taaataattc 13140
taaaagc 13147

<210> SEQ ID NO 19
<211> LENGTH: 2644
<212> TYPE: PRT
<213> ORGANISM: Artificial Sequence
<220> FEATURE:
<223> OTHER INFORMATION: ATR sequence

<400> SEQUENCE: 19

Met Gly Glu His Gly Leu Glu Leu Ala Ser Met Ile Pro Ala Leu Arg
1 5 10 15

Glu Leu Gly Ser Ala Thr Pro Glu Glu Tyr Asn Thr Val Val Gln Lys
20 25 30

Pro Arg Gln Ile Leu Cys Gln Phe Ile Asp Arg Ile Leu Thr Asp Val
35 40 45

Asn Val Val Ala Val Glu Leu Val Lys Lys Thr Asp Ser Gln Pro Thr
50 55 60

Ser Val Met Leu Leu Asp Phe Ile Gln His Ile Met Lys Ser Ser Pro
65 70 75 80

Leu Met Phe Val Asn Val Ser Gly Ser His Glu Ala Lys Gly Ser Cys
85 90 95

-continued

```
Ile Glu Phe Ser Asn Trp Ile Ile Thr Arg Leu Leu Arg Ile Ala Ala
            100                 105                 110

Thr Pro Ser Cys His Leu Leu His Lys Lys Ile Cys Glu Val Ile Cys
        115                 120                 125

Ser Leu Leu Phe Leu Phe Lys Ser Lys Ser Pro Ala Ile Phe Gly Val
    130                 135                 140

Leu Thr Lys Glu Leu Leu Gln Leu Phe Glu Asp Leu Val Tyr Leu His
145                 150                 155                 160

Arg Arg Asn Val Met Gly His Ala Val Glu Trp Pro Val Val Met Ser
                165                 170                 175

Arg Phe Leu Ser Gln Leu Asp Glu His Met Gly Tyr Leu Gln Ser Ala
            180                 185                 190

Pro Leu Gln Leu Met Ser Met Gln Asn Leu Glu Phe Ile Glu Val Thr
        195                 200                 205

Leu Leu Met Val Leu Thr Arg Ile Ile Ala Ile Val Phe Phe Arg Arg
    210                 215                 220

Gln Glu Leu Leu Leu Trp Gln Ile Gly Cys Val Leu Leu Glu Tyr Gly
225                 230                 235                 240

Ser Pro Lys Ile Lys Ser Leu Ala Ile Ser Phe Leu Thr Glu Leu Phe
                245                 250                 255

Gln Leu Gly Gly Leu Pro Ala Gln Pro Ala Ser Thr Phe Phe Ser Ser
            260                 265                 270

Phe Leu Glu Leu Leu Lys His Leu Val Glu Met Asp Thr Asp Gln Leu
        275                 280                 285

Lys Leu Tyr Glu Glu Pro Leu Ser Lys Leu Ile Lys Thr Leu Phe Pro
    290                 295                 300

Phe Glu Ala Glu Ala Tyr Arg Asn Ile Glu Pro Val Tyr Leu Asn Met
305                 310                 315                 320

Leu Leu Glu Lys Leu Cys Val Met Phe Glu Asp Gly Val Leu Met Arg
                325                 330                 335

Leu Lys Ser Asp Leu Leu Lys Ala Ala Leu Cys His Leu Leu Gln Tyr
            340                 345                 350

Phe Leu Lys Phe Val Pro Ala Gly Tyr Glu Ser Ala Leu Gln Val Arg
        355                 360                 365

Lys Val Tyr Val Arg Asn Ile Cys Lys Ala Leu Leu Asp Val Leu Gly
    370                 375                 380

Ile Glu Val Asp Ala Glu Tyr Leu Leu Gly Pro Leu Tyr Ala Ala Leu
385                 390                 395                 400

Lys Met Glu Ser Met Glu Ile Ile Glu Glu Ile Gln Cys Gln Thr Gln
                405                 410                 415

Gln Glu Asn Leu Ser Ser Asn Ser Asp Gly Ile Ser Pro Lys Arg Arg
            420                 425                 430

Arg Leu Ser Ser Ser Leu Asn Pro Ser Lys Arg Ala Pro Lys Gln Thr
        435                 440                 445

Glu Glu Ile Lys His Val Asp Met Asn Gln Lys Ser Ile Leu Trp Ser
    450                 455                 460

Ala Leu Lys Gln Lys Ala Glu Ser Leu Gln Ile Ser Leu Glu Tyr Ser
465                 470                 475                 480

Gly Leu Lys Asn Pro Val Ile Glu Met Leu Glu Gly Ile Ala Val Val
                485                 490                 495

Leu Gln Leu Thr Ala Leu Cys Thr Val His Cys Ser His Gln Asn Met
            500                 505                 510

Asn Cys Arg Thr Phe Lys Asp Cys Gln His Lys Ser Lys Lys Lys Pro
```

```
        515                 520                 525

Ser Val Val Ile Thr Trp Met Ser Leu Asp Phe Tyr Thr Lys Val Leu
    530                 535                 540

Lys Ser Cys Arg Ser Leu Leu Glu Ser Val Gln Lys Leu Asp Leu Glu
545                 550                 555                 560

Ala Thr Ile Asp Lys Val Val Lys Ile Tyr Asp Ala Leu Ile Tyr Met
                565                 570                 575

Gln Val Asn Ser Ser Phe Glu Asp His Ile Leu Glu Asp Leu Cys Gly
            580                 585                 590

Met Leu Ser Leu Pro Trp Ile Tyr Ser His Ser Asp Asp Gly Cys Leu
        595                 600                 605

Lys Leu Thr Thr Phe Ala Ala Asn Leu Leu Thr Leu Ser Cys Arg Ile
    610                 615                 620

Ser Asp Ser Tyr Ser Pro Gln Ala Gln Ser Arg Cys Val Phe Leu Leu
625                 630                 635                 640

Thr Leu Phe Pro Arg Arg Ile Phe Leu Glu Trp Arg Thr Ala Val Tyr
                645                 650                 655

Asn Trp Ala Leu Gln Ser Ser His Glu Val Ile Arg Ala Ser Cys Val
            660                 665                 670

Ser Gly Phe Phe Ile Leu Leu Gln Gln Gln Asn Ser Cys Asn Arg Val
        675                 680                 685

Pro Lys Ile Leu Ile Asp Lys Val Lys Asp Asp Ser Asp Ile Val Lys
    690                 695                 700

Lys Glu Phe Ala Ser Ile Leu Gly Gln Leu Val Cys Thr Leu His Gly
705                 710                 715                 720

Met Phe Tyr Leu Thr Ser Ser Leu Thr Glu Pro Phe Ser Glu His Gly
                725                 730                 735

His Val Asp Leu Phe Cys Arg Asn Leu Lys Ala Thr Ser Gln His Glu
            740                 745                 750

Cys Ser Ser Ser Gln Leu Lys Ala Ser Val Cys Lys Pro Phe Leu Phe
        755                 760                 765

Leu Leu Lys Lys Lys Ile Pro Ser Pro Val Lys Leu Ala Phe Ile Asp
    770                 775                 780

Asn Leu His His Leu Cys Lys His Leu Asp Phe Arg Glu Asp Glu Thr
785                 790                 795                 800

Asp Val Lys Ala Val Leu Gly Thr Leu Leu Asn Leu Met Glu Asp Pro
                805                 810                 815

Asp Lys Asp Val Arg Val Ala Phe Ser Gly Asn Ile Lys His Ile Leu
            820                 825                 830

Glu Ser Leu Asp Ser Glu Asp Gly Phe Ile Lys Glu Leu Phe Val Leu
        835                 840                 845

Arg Met Lys Glu Ala Tyr Thr His Ala Gln Ile Ser Arg Asn Asn Glu
    850                 855                 860

Leu Lys Asp Thr Leu Ile Leu Thr Thr Gly Asp Ile Gly Arg Ala Ala
865                 870                 875                 880

Lys Gly Asp Leu Val Pro Phe Ala Leu Leu His Leu Leu His Cys Leu
                885                 890                 895

Leu Ser Lys Ser Ala Ser Val Ser Gly Ala Ala Tyr Thr Glu Ile Arg
            900                 905                 910

Ala Leu Val Ala Ala Lys Ser Val Lys Leu Gln Ser Phe Phe Ser Gln
        915                 920                 925

Tyr Lys Lys Pro Ile Cys Gln Phe Leu Val Glu Ser Leu His Ser Ser
    930                 935                 940
```

-continued

```
Gln Met Thr Ala Leu Pro Asn Thr Pro Cys Gln Asn Ala Asp Val Arg
945                 950                 955                 960

Lys Gln Asp Val Ala His Gln Arg Glu Met Ala Leu Asn Thr Leu Ser
                965                 970                 975

Glu Ile Ala Asn Val Phe Asp Phe Pro Asp Leu Asn Arg Phe Leu Thr
            980                 985                 990

Arg Thr Leu Gln Val Leu Leu Pro  Asp Leu Ala Ala Lys  Ala Ser Pro
        995                 1000                 1005

Ala Ala  Ser Ala Leu Ile Arg  Thr Leu Gly Lys Gln  Leu Asn Val
    1010                 1015                 1020

Asn Arg  Arg Glu Ile Leu Ile  Asn Asn Phe Lys Tyr  Ile Phe Ser
    1025                 1030                 1035

His Leu  Val Cys Ser Cys Ser  Lys Asp Glu Leu Glu  Arg Ala Leu
    1040                 1045                 1050

His Tyr  Leu Lys Asn Glu Thr  Glu Ile Glu Leu Gly  Ser Leu Leu
    1055                 1060                 1065

Arg Gln  Asp Phe Gln Gly Leu  His Asn Glu Leu Leu  Leu Arg Ile
    1070                 1075                 1080

Gly Glu  His Tyr Gln Gln Val  Phe Asn Gly Leu Ser  Ile Leu Ala
    1085                 1090                 1095

Ser Phe  Ala Ser Ser Asp Asp  Pro Tyr Gln Gly Pro  Arg Asp Ile
    1100                 1105                 1110

Ile Ser  Pro Glu Leu Met Ala  Asp Tyr Leu Gln Pro  Lys Leu Leu
    1115                 1120                 1125

Gly Ile  Leu Ala Phe Phe Asn  Met Gln Leu Leu Ser  Ser Ser Val
    1130                 1135                 1140

Gly Ile  Glu Asp Lys Lys Met  Ala Leu Asn Ser Leu  Met Ser Leu
    1145                 1150                 1155

Met Lys  Leu Met Gly Pro Lys  His Val Ser Ser Val  Arg Val Lys
    1160                 1165                 1170

Met Met  Thr Thr Leu Arg Thr  Gly Leu Arg Phe Lys  Asp Asp Phe
    1175                 1180                 1185

Pro Glu  Leu Cys Cys Arg Ala  Trp Asp Cys Phe Val  Arg Cys Leu
    1190                 1195                 1200

Asp His  Ala Cys Leu Gly Ser  Leu Leu Ser His Val  Ile Val Ala
    1205                 1210                 1215

Leu Leu  Pro Leu Ile His Ile  Gln Pro Lys Glu Thr  Ala Ala Ile
    1220                 1225                 1230

Phe His  Tyr Leu Ile Ile Glu  Asn Arg Asp Ala Val  Gln Asp Phe
    1235                 1240                 1245

Leu His  Glu Ile Tyr Phe Leu  Pro Asp His Pro Glu  Leu Lys Lys
    1250                 1255                 1260

Ile Lys  Ala Val Leu Gln Glu  Tyr Arg Lys Glu Thr  Ser Glu Ser
    1265                 1270                 1275

Thr Asp  Leu Gln Thr Thr Leu  Gln Leu Ser Met Lys  Ala Ile Gln
    1280                 1285                 1290

His Glu  Asn Val Asp Val Arg  Ile His Ala Leu Thr  Ser Leu Lys
    1295                 1300                 1305

Glu Thr  Leu Tyr Lys Asn Gln  Glu Lys Leu Ile Lys  Tyr Ala Thr
    1310                 1315                 1320

Asp Ser  Glu Thr Val Glu Pro  Ile Ile Ser Gln Leu  Val Thr Val
    1325                 1330                 1335
```

```
Leu Leu Lys Gly Cys Gln Asp Ala Asn Ser Gln Ala Arg Leu Leu
    1340                1345                1350

Cys Gly Glu Cys Leu Gly Glu Leu Gly Ala Ile Asp Pro Gly Arg
    1355                1360                1365

Leu Asp Phe Ser Thr Thr Glu Thr Gln Gly Lys Asp Phe Thr Phe
    1370                1375                1380

Val Thr Gly Val Glu Asp Ser Ser Phe Ala Tyr Gly Leu Leu Met
    1385                1390                1395

Glu Leu Thr Arg Ala Tyr Leu Ala Tyr Ala Asp Asn Ser Arg Ala
    1400                1405                1410

Gln Asp Ser Ala Ala Tyr Ala Ile Gln Glu Leu Leu Ser Ile Tyr
    1415                1420                1425

Asp Cys Arg Glu Met Glu Thr Asn Gly Pro Gly His Gln Leu Trp
    1430                1435                1440

Arg Arg Phe Pro Glu His Val Arg Glu Ile Leu Glu Pro His Leu
    1445                1450                1455

Asn Thr Arg Tyr Lys Ser Ser Gln Lys Ser Thr Asp Trp Ser Gly
    1460                1465                1470

Val Lys Lys Pro Ile Tyr Leu Ser Lys Leu Gly Ser Asn Phe Ala
    1475                1480                1485

Glu Trp Ser Ala Ser Trp Ala Gly Tyr Leu Ile Thr Lys Val Arg
    1490                1495                1500

His Asp Leu Ala Ser Lys Ile Phe Thr Cys Cys Ser Ile Met Met
    1505                1510                1515

Lys His Asp Phe Lys Val Thr Ile Tyr Leu Leu Pro His Ile Leu
    1520                1525                1530

Val Tyr Val Leu Leu Gly Cys Asn Gln Glu Asp Gln Gln Glu Val
    1535                1540                1545

Tyr Ala Glu Ile Met Ala Val Leu Lys His Asp Asp Gln His Thr
    1550                1555                1560

Ile Asn Thr Gln Asp Ile Ala Ser Asp Leu Cys Gln Leu Ser Thr
    1565                1570                1575

Gln Thr Val Phe Ser Met Leu Asp His Leu Thr Gln Trp Ala Arg
    1580                1585                1590

His Lys Phe Gln Ala Leu Lys Ala Glu Lys Cys Pro His Ser Lys
    1595                1600                1605

Ser Asn Arg Asn Lys Val Asp Ser Met Val Ser Thr Val Asp Tyr
    1610                1615                1620

Glu Asp Tyr Gln Ser Val Thr Arg Phe Leu Asp Leu Ile Pro Gln
    1625                1630                1635

Asp Thr Leu Ala Val Ala Ser Phe Arg Ser Lys Ala Tyr Thr Arg
    1640                1645                1650

Ala Val Met His Phe Glu Ser Phe Ile Thr Glu Lys Lys Gln Asn
    1655                1660                1665

Ile Gln Glu His Leu Gly Phe Leu Gln Lys Leu Tyr Ala Ala Met
    1670                1675                1680

His Glu Pro Asp Gly Val Ala Gly Val Ser Ala Ile Arg Lys Ala
    1685                1690                1695

Glu Pro Ser Leu Lys Glu Gln Ile Leu Glu His Glu Ser Leu Gly
    1700                1705                1710

Leu Leu Arg Asp Ala Thr Ala Cys Tyr Asp Arg Ala Ile Gln Leu
    1715                1720                1725

Glu Pro Asp Gln Ile Ile His Tyr His Gly Val Val Lys Ser Met
```

```
    1730                1735                1740

Leu Gly  Leu Gly Gln Leu Ser  Thr Val Ile Thr Gln  Val Asn Gly
    1745                1750                1755

Val His  Ala Asn Arg Ser Glu  Trp Thr Asp Glu Leu  Asn Thr Tyr
    1760                1765                1770

Arg Val  Glu Ala Ala Trp Lys  Leu Ser Gln Trp Asp  Leu Val Glu
    1775                1780                1785

Asn Tyr  Leu Ala Ala Asp Gly  Lys Ser Thr Thr Trp  Ser Val Arg
    1790                1795                1800

Leu Gly  Gln Leu Leu Leu Ser  Ala Lys Lys Arg Asp  Ile Thr Ala
    1805                1810                1815

Phe Tyr  Asp Ser Leu Lys Leu  Val Arg Ala Glu Gln  Ile Val Pro
    1820                1825                1830

Leu Ser  Ala Ala Ser Phe Glu  Arg Gly Ser Tyr Gln  Arg Gly Tyr
    1835                1840                1845

Glu Tyr  Ile Val Arg Leu His  Met Leu Cys Glu Leu  Glu His Ser
    1850                1855                1860

Ile Lys  Pro Leu Phe Gln His  Ser Pro Gly Asp Ser  Ser Gln Glu
    1865                1870                1875

Asp Ser  Leu Asn Trp Val Ala  Arg Leu Glu Met Thr  Gln Asn Ser
    1880                1885                1890

Tyr Arg  Ala Lys Glu Pro Ile  Leu Ala Leu Arg Arg  Ala Leu Leu
    1895                1900                1905

Ser Leu  Asn Lys Arg Pro Asp  Tyr Asn Glu Met Val  Gly Glu Cys
    1910                1915                1920

Trp Leu  Gln Ser Ala Arg Val  Ala Arg Lys Ala Gly  His His Gln
    1925                1930                1935

Thr Ala  Tyr Asn Ala Leu Leu  Asn Ala Gly Glu Ser  Arg Leu Ala
    1940                1945                1950

Glu Leu  Tyr Val Glu Arg Ala  Lys Trp Leu Trp Ser  Lys Gly Asp
    1955                1960                1965

Val His  Gln Ala Leu Ile Val  Leu Gln Lys Gly Val  Glu Leu Cys
    1970                1975                1980

Phe Pro  Glu Asn Glu Thr Pro  Pro Glu Gly Lys Asn  Met Leu Ile
    1985                1990                1995

His Gly  Arg Ala Met Leu Leu  Val Gly Arg Phe Met  Glu Glu Thr
    2000                2005                2010

Ala Asn  Phe Glu Ser Asn Ala  Ile Met Lys Lys Tyr  Lys Asp Val
    2015                2020                2025

Thr Ala  Cys Leu Pro Glu Trp  Glu Asp Gly His Phe  Tyr Leu Ala
    2030                2035                2040

Lys Tyr  Tyr Asp Lys Leu Met  Pro Met Val Thr Asp  Asn Lys Met
    2045                2050                2055

Glu Lys  Gln Gly Asp Leu Ile  Arg Tyr Ile Val Leu  His Phe Gly
    2060                2065                2070

Arg Ser  Leu Gln Tyr Gly Asn  Gln Phe Ile Tyr Gln  Ser Met Pro
    2075                2080                2085

Arg Met  Leu Thr Leu Trp Leu  Asp Tyr Gly Thr Lys  Ala Tyr Glu
    2090                2095                2100

Trp Glu  Lys Ala Gly Arg Ser  Asp Arg Val Gln Met  Arg Asn Asp
    2105                2110                2115

Leu Gly  Lys Ile Asn Lys Val  Ile Thr Glu His Thr  Asn Tyr Leu
    2120                2125                2130
```

```
Ala Pro  Tyr Gln Phe Leu Thr  Ala Phe Ser Gln Leu  Ile Ser Arg
    2135                 2140                 2145

Ile Cys  His Ser His Asp Glu  Val Phe Val Val Leu  Met Glu Ile
    2150                 2155                 2160

Ile Ala  Lys Val Phe Leu Ala  Tyr Pro Gln Gln Ala  Met Trp Met
    2165                 2170                 2175

Met Thr  Ala Val Ser Lys Ser  Ser Tyr Pro Met Arg  Val Asn Arg
    2180                 2185                 2190

Cys Lys  Glu Ile Leu Asn Lys  Ala Ile His Met Lys  Lys Ser Leu
    2195                 2200                 2205

Glu Lys  Phe Val Gly Asp Ala  Thr Arg Leu Thr Asp  Lys Leu Leu
    2210                 2215                 2220

Glu Leu  Cys Asn Lys Pro Val  Asp Gly Ser Ser Ser  Thr Leu Ser
    2225                 2230                 2235

Met Ser  Thr His Phe Lys Met  Leu Lys Lys Leu Val  Glu Glu Ala
    2240                 2245                 2250

Thr Phe  Ser Glu Ile Leu Ile  Pro Leu Gln Ser Val  Met Ile Pro
    2255                 2260                 2265

Thr Leu  Pro Ser Ile Leu Gly  Thr His Ala Asn His  Ala Ser His
    2270                 2275                 2280

Glu Pro  Phe Pro Gly His Trp  Ala Tyr Ile Ala Gly  Phe Asp Asp
    2285                 2290                 2295

Met Val  Glu Ile Leu Ala Ser  Leu Gln Lys Pro Lys  Lys Ile Ser
    2300                 2305                 2310

Leu Lys  Gly Ser Asp Gly Lys  Phe Tyr Ile Met Met  Cys Lys Pro
    2315                 2320                 2325

Lys Asp  Asp Leu Arg Lys Asp  Cys Arg Leu Met Glu  Phe Asn Ser
    2330                 2335                 2340

Leu Ile  Asn Lys Cys Leu Arg  Lys Asp Ala Glu Ser  Arg Arg Arg
    2345                 2350                 2355

Glu Leu  His Ile Arg Thr Tyr  Ala Val Ile Pro Leu  Asn Asp Glu
    2360                 2365                 2370

Cys Gly  Ile Ile Glu Trp Val  Asn Asn Thr Ala Gly  Leu Arg Pro
    2375                 2380                 2385

Ile Leu  Thr Lys Leu Tyr Lys  Glu Lys Gly Val Tyr  Met Thr Gly
    2390                 2395                 2400

Lys Glu  Leu Arg Gln Cys Met  Leu Pro Lys Ser Ala  Ala Leu Ser
    2405                 2410                 2415

Glu Lys  Leu Lys Val Phe Arg  Glu Phe Leu Leu Pro  Arg His Pro
    2420                 2425                 2430

Pro Ile  Phe His Glu Trp Phe  Leu Arg Thr Phe Pro  Asp Pro Thr
    2435                 2440                 2445

Ser Trp  Tyr Ser Ser Arg Ser  Ala Tyr Cys Arg Ser  Thr Ala Val
    2450                 2455                 2460

Met Ser  Met Val Gly Tyr Ile  Leu Gly Leu Gly Asp  Arg His Gly
    2465                 2470                 2475

Glu Asn  Ile Leu Phe Asp Ser  Leu Thr Gly Glu Cys  Val His Val
    2480                 2485                 2490

Asp Phe  Asn Cys Leu Phe Asn  Lys Gly Glu Thr Phe  Glu Val Pro
    2495                 2500                 2505

Glu Ile  Val Pro Phe Arg Leu  Thr His Asn Met Val  Asn Gly Met
    2510                 2515                 2520
```

```
Gly Pro  Met Gly Thr Glu Gly  Leu Phe Arg Arg Ala  Cys Glu Val
    2525                 2530                 2535

Thr Met  Arg Leu Met Arg Asp  Gln Arg Glu Pro Leu  Met Ser Val
    2540                 2545                 2550

Leu Lys  Thr Phe Leu His Asp  Pro Leu Val Glu Trp  Ser Lys Pro
    2555                 2560                 2565

Val Lys  Gly His Ser Lys Ala  Pro Leu Asn Glu Thr  Gly Glu Val
    2570                 2575                 2580

Val Asn  Glu Lys Ala Lys Thr  His Val Leu Asp Ile  Glu Gln Arg
    2585                 2590                 2595

Leu Gln  Gly Val Ile Lys Thr  Arg Asn Arg Val Thr  Gly Leu Pro
    2600                 2605                 2610

Leu Ser  Ile Glu Gly His Val  His Tyr Leu Ile Gln  Glu Ala Thr
    2615                 2620                 2625

Asp Glu  Asn Leu Leu Cys Gln  Met Tyr Leu Gly Trp  Thr Pro Tyr
    2630                 2635                 2640

Met


<210> SEQ ID NO 20
<211> LENGTH: 8258
<212> TYPE: DNA
<213> ORGANISM: Artificial Sequence
<220> FEATURE:
<223> OTHER INFORMATION: ATR sequence

<400> SEQUENCE: 20

ttccgggagg agttttggcc tccacacggc tccgtcgggc gccgcgctct tccggcagcg     60

gtagctttgg agacgccggg aacccgcgtt ggcgtggttg actagtgcct cgcagcctca    120

gcatgggggga acatggcctg gagctggctt ccatgatccc cgccctgcgg gagctgggca    180

gtgccacacc agaggaatat aatacagttg tacagaagcc aagacaaatt ctgtgtcaat    240

tcattgaccg gatacttaca gatgtaaatg ttgttgctgt agaacttgta aagaaaactg    300

actctcagcc aacctccgtg atgttgcttg atttcatcca gcatatcatg aaatcctccc    360

cacttatgtt tgtaaatgtg agtggaagcc atgaggccaa aggcagttgt attgaattca    420

gtaattggat cataacgaga cttctgcgga ttgcagcaac tccctcctgt catttgttac    480

acaagaaaat ctgtgaagtc atctgttcat tattatttct ttttaaaagc aagagtcctg    540

ctatttttgg ggtactcaca aaagaattat tacaactttt tgaagacttg gtttacctcc    600

atagaagaaa tgtgatgggt catgctgtgg aatggccagt ggtcatgagc cgatttttaa    660

gtcaattaga tgaacacatg ggatatttac aatcagctcc tttgcagttg atgagtatgc    720

aaaatttaga atttattgaa gtcactttat taatggttct tactcgtatt attgcaattg    780

tgttttttag aaggcaagaa ctcttacttt ggcagatagg ttgtgttctg ctagagtatg    840

gtagtccaaa aattaaatcc ctagcaatta gctttttaac agaacttttt cagcttggag    900

gactaccagc acaaccagct agcacttttt tcagctcatt tttggaatta ttaaaacacc    960

ttgtagaaat ggatactgac caattgaaac tctatgaaga gccattatca aagctgataa   1020

agacactatt tccctttgaa gcagaagctt atagaaatat tgaacctgtc tatttaaata   1080

tgctgctgga aaaactctgt gtcatgtttg aagacggtgt gctcatgcgg cttaagtctg   1140

atttgctaaa agcagctttg tgccatttac tgcagtattt ccttaaattt gtgccagctg   1200

ggtatgaatc tgctttacaa gtcaggaagg tctatgtgag aaatatttgt aaagctcttt   1260

tggatgtgct tggaattgag gtagatgcag agtacttgtt gggcccactt tatgcagctt   1320
```

```
tgaaaatgga aagtatggaa atcattgagg agattcaatg ccaaactcaa caggaaaacc   1380
tcagcagtaa tagtgatgga atatcaccca aaaggcgtcg tctcagctcg tctctaaacc   1440
cttctaaaag agcaccaaaa cagactgagg aaattaaaca tgtggacatg aaccaaaaga   1500
gcatattatg gagtgcactg aaacagaaag ctgaatccct tcagatttcc cttgaataca   1560
gtggcctaaa gaatcctgtt attgagatgt tagaaggaat tgctgttgtc ttacaactga   1620
ctgctctgtg tactgttcat tgttctcatc aaaacatgaa ctgccgtact ttcaaggact   1680
gtcaacataa atccaagaag aaaccttctg tagtgataac ttggatgtca ttggattttt   1740
acacaaaagt gcttaagagc tgtagaagtt tgttagaatc tgttcagaaa ctggacctgg   1800
aggcaaccat tgataaggtg gtgaaaattt atgatgcttt gatttatatg caagtaaaca   1860
gttcatttga agatcatatc ctggaagatt tatgtggtat gctctcactt ccatggattt   1920
attcccattc tgatgatggc tgtttaaagt tgaccacatt tgccgctaat cttctaacat   1980
taagctgtag gatttcagat agctattcac cacaggcaca atcacgatgt gtgtttcttc   2040
tgactctgtt tccaagaaga atattccttg agtggagaac agcagtttac aactgggccc   2100
tgcagagctc ccatgaagta atccgggcta gttgtgttag tggatttttt atcttattgc   2160
agcagcagaa ttcttgtaac agagttccca agattcttat agataaagtc aaagatgatt   2220
ctgacattgt caagaaagaa tttgcttcta tacttggtca acttgtctgt actcttcacg   2280
gcatgtttta tctgacaagt tctttaacag aacctttctc tgaacacgga catgtggacc   2340
tcttctgtag gaacttgaaa gccacttctc aacatgaatg ttcatcttct caactaaaag   2400
cttctgtctg caagccattc cttttcctac tgaaaaaaaa aatacctagt ccagtaaaac   2460
ttgctttcat agataatcta catcatcttt gtaagcatct tgattttaga gaagatgaaa   2520
cagatgtaaa agcagttctt ggaactttat taaatttaat ggaagatcca gacaaagatg   2580
ttagagtggc ttttagtgga aatatcaagc acatattgga atccttggac tctgaagatg   2640
gatttataaa ggagcttttt gtcttaagaa tgaaggaagc atatacacat gcccaaatat   2700
caagaaataa tgagctgaag gataccttga ttcttacaac aggggatatt ggaagggccg   2760
caaaaggaga tttggtacca tttgcactct tacacttatt gcattgtttg ttatccaagt   2820
cagcatctgt ctctggagca gcatacacag aaattagagc tctggttgca gctaaaagtg   2880
ttaaactgca aagtttttc agccagtata agaaacccat ctgtcagttt ttggtagaat   2940
cccttcactc tagtcagatg acagcacttc cgaatactcc atgccagaat gctgacgtgc   3000
gaaaacaaga tgtggctcac cagagagaaa tggctttaaa tacgttgtct gaaattgcca   3060
acgttttcga ctttcctgat cttaatcgtt ttcttactag gacattacaa gttctactac   3120
ctgatcttgc tgccaaagca agccctgcag cttctgctct cattcgaact ttaggaaaac   3180
aattaaatgt caatcgtaga gagattttaa taaacaactt caaatatatt ttttctcatt   3240
tggtctgttc ttgttccaaa gatgaattag aacgtgccct tcattatctg aagaatgaaa   3300
cagaaattga actggggagc ctgttgagac aagatttcca aggattgcat aatgaattat   3360
tgctgcgtat tggagaacac tatcaacagg tttttaatgg tttgtcaata cttgcctcat   3420
ttgcatccag tgatgatcca tatcagggcc cgagagatat catatcacct gaactgatgg   3480
ctgattattt acaacccaaa ttgttgggca ttttggcttt ttttaacatg cagttactga   3540
gctctagtgt tggcattgaa gataagaaaa tggccttgaa cagtttgatg tctttgatga   3600
agttaatggg acccaaacat gtcagttctg tgagggtgaa gatgatgacc acactgagaa   3660
```

-continued

```
ctggccttcg attcaaggat gattttcctg aattgtgttg cagagcttgg gactgctttg   3720
ttcgctgcct ggatcatgct tgtctgggct cccttctcag tcatgtaata gtagctttgt   3780
tacctcttat acacatccag cctaaagaaa ctgcagctat cttccactac ctcataattg   3840
aaaacaggga tgctgtgcaa gattttcttc atgaaatata ttttttacct gatcatccag   3900
aattaaaaaa gataaaagcc gttctccagg aatacagaaa ggagacctct gagagcactg   3960
atcttcagac aactcttcag ctctctatga aggccattca acatgaaaat gtcgatgttc   4020
gtattcatgc tcttacaagc ttgaaggaaa ccttgtataa aaatcaggaa aaactgataa   4080
agtatgcaac agacagtgaa acagtagaac ctattatctc acagttggtg acagtgcttt   4140
tgaaaggttg ccaagatgca aactctcaag ctcggttgct ctgtggggaa tgtttagggg   4200
aattgggggc gatagatcca ggtcgattag atttctcaac aactgaaact caaggaaaag   4260
attttacatt tgtgactgga gtagaagatt caagctttgc ctatggatta ttgatggagc   4320
taacaagagc ttaccttgcg tatgctgata atagccgagc tcaagattca gctgcctatg   4380
ccattcagga gttgctttct atttatgact gtagagagat ggagaccaac ggcccaggtc   4440
accaattgtg gaggagattt cctgagcatg ttcgggaaat actagaacct catctaaata   4500
ccagatacaa gagttctcag aagtcaaccg attggtctgg agtaaagaag ccaatttact   4560
taagtaaatt gggtagtaac tttgcagaat ggtcagcatc ttgggcaggt tatcttatta   4620
caaaggttcg acatgatctt gccagtaaaa ttttcacctg ctgtagcatt atgatgaagc   4680
atgatttcaa agtgaccatc tatcttcttc cacatattct ggtgtatgtc ttactgggtt   4740
gtaatcaaga agatcagcag gaggtttatg cagaaattat ggcagttcta aagcatgacg   4800
atcagcatac cataaatacc caagacattg catctgatct gtgtcaactc agtacacaga   4860
ctgtgttctc catgcttgac catctcacac agtgggcaag gcacaaattt caggcactga   4920
aagctgagaa atgtccacac agcaaatcaa acagaaataa ggtagactca atggtatcta   4980
ctgtggatta tgaagactat cagagtgtaa cccgttttct agacctcata ccccaggata   5040
ctctggcagt agcttccttt cgctccaaag catacacacg agctgtaatg cactttgaat   5100
catttattac agaaaagaag caaaatattc aggaacatct tggattttta cagaaattgt   5160
atgctgctat gcatgaacct gatggagtgg ccggagtcag tgcaattaga aaggcagaac   5220
catctctaaa agaacagatc cttgaacatg aaagccttgg cttgctgagg gatgccactg   5280
cttgttatga cagggctatt cagctagaac cagaccagat cattcattat catggtgtag   5340
taaagtccat gttaggtctt ggtcagctgt ctactgttat cactcaggtg aatggagtgc   5400
atgctaacag gtccgagtgg acagatgaat taaacacgta cagagtggaa gcagcttgga   5460
aattgtcaca gtgggatttg gtggaaaact atttggcagc agatggaaaa tctacaacat   5520
ggagtgtcag actgggacag ctattattat cagccaaaaa aagagatatc acagcttttt   5580
atgactcact gaaactagtg agagcagaac aaattgtacc tctttcagct gcaagctttg   5640
aaagaggctc ctaccaacga ggatatgaat atattgtgag attgcacatg ttatgtgagt   5700
tggagcatag catcaaacca cttttccagc attctccagg tgacagttct caagaagatt   5760
ctctaaactg ggtagctcga ctagaaatga cccagaattc ctacagagcc aaggagccta   5820
tcctggctct ccggagggct ttactaagcc tcaacaaaag accagattac aatgaaatgg   5880
ttggagaatg ctggctgcag agtgccaggg tagctagaaa ggctggtcac caccagacag   5940
cctacaatgc tctccttaat gcaggggaat cacgactcgc tgaactgtac gtggaaaggg   6000
caaagtggct ctggtccaag ggtgatgttc accaggcact aattgttctt caaaaaggtg   6060
```

ttgaattatg ttttcctgaa aatgaaaccc cacctgaggg taagaacatg ttaatccatg 6120
gtcgagctat gctactagtg ggccgattta tggaagaaac agctaacttt gaaagcaatg 6180
caattatgaa aaaatataag gatgtgaccg cgtgcctgcc agaatgggag gatgggcatt 6240
tttaccttgc caagtactat gacaaattga tgcccatggt cacagacaac aaaatggaaa 6300
agcaaggtga tctcatccgg tatatagttc ttcattttgg cagatctcta caatatggaa 6360
atcagttcat atatcagtca atgccacgaa tgttaactct atggcttgat tatggtacaa 6420
aggcatatga atgggaaaaa gctggccgct ccgatcgtgt acaaatgagg aatgatttgg 6480
gtaaaataaa caaggttatc acagagcata caaactattt agctccatat caatttttga 6540
ctgctttttc acaattgatc tctcgaattt gtcattctca cgatgaagtt tttgttgtct 6600
tgatggaaat aatagccaaa gtatttctag cctatcctca acaagcaatg tggatgatga 6660
cagctgtgtc aaagtcatct tatcccatgc gtgtgaacag atgcaaggaa atcctcaata 6720
aagctattca tatgaaaaaa tccttagaga agtttgttgg agatgcaact cgcctaacag 6780
ataagcttct agaattgtgc aataaaccgg ttgatggaag tagttccaca ttaagcatga 6840
gcactcattt taaaatgctt aaaaagctgg tagaagaagc aacatttagt gaaatcctca 6900
ttcctctaca atcagtcatg atacctacac ttccatcaat tctgggtacc catgctaacc 6960
atgctagcca tgaaccattt cctggacatt gggcctatat tgcagggttt gatgatatgg 7020
tggaaattct tgcttctctt cagaaaccaa agaagatttc tttaaaaggc tcagatggaa 7080
agttctacat catgatgtgt aagccaaaag atgacctgag aaaggattgt agactaatgg 7140
aattcaattc cttgattaat aagtgcttaa gaaaagatgc agagtctcgt agaagagaac 7200
ttcatattcg aacatatgca gttattccac taaatgatga atgtgggatt attgaatggg 7260
tgaacaacac tgctggtttg agacctattc tgaccaaact atataaagaa aagggagtgt 7320
atatgacagg aaaagaactt cgccagtgta tgctaccaaa gtcagcagct ttatctgaaa 7380
aactcaaagt attccgagaa tttctcctgc ccaggcatcc tcctattttt catgagtggt 7440
ttctgagaac attccctgat cctacatcat ggtacagtag tagatcagct tactgccgtt 7500
ccactgcagt aatgtcaatg gttggttata ttctggggct tggagaccgt catggtgaaa 7560
atattctctt tgattctttg actggtgaat gcgtacatgt agatttcaat tgtcttttca 7620
ataagggaga aacctttgaa gttccagaaa ttgtgccatt tcgcctgact cataatatgg 7680
ttaatggaat gggtcctatg ggaacagagg gtctttttcg aagagcatgt gaagttacaa 7740
tgaggctgat gcgtgatcag cgagagcctt taatgagtgt cttaaagact tttctacatg 7800
atcctcttgt ggaatggagt aaaccagtga aagggcattc caaagcgcca ctgaatgaaa 7860
ctggagaagt tgtcaatgaa aaggccaaga cccatgttct tgacattgag cagcgactac 7920
aaggtgtaat caagactcga aatagagtga caggactgcc gttatctatt gaaggacatg 7980
tgcattacct tatacaggaa gctactgatg aaaacttact atgccagatg tatcttggtt 8040
ggactccata tatgtgaaat gaaattatgt aaaagaatat gttaataatc taaaagtaat 8100
gcatttggta tgaatctgtg gttgtatctg ttcaattcta aagtacaaca taaatttacg 8160
ttctcagcaa ctgttatttc tctctgatca ttaattatat gtaaaataat atacattcag 8220
ttattaagaa ataaactgct ttcttaatac aaaaaaaa 8258

<210> SEQ ID NO 21
<211> LENGTH: 403
<212> TYPE: PRT

<213> ORGANISM: Artificial Sequence
<220> FEATURE:
<223> OTHER INFORMATION: PTEN sequence

<400> SEQUENCE: 21

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
```

-continued 385 390 395 400

Thr Lys Val

<210> SEQ ID NO 22
<211> LENGTH: 5572
<212> TYPE: DNA
<213> ORGANISM: Artificial Sequence
<220> FEATURE:
<223> OTHER INFORMATION: PTEN sequence

<400> SEQUENCE: 22
cctcccctcg cccggcgcgg tcccgtccgc ctctcgctcg cctcccgcct cccctcggtc 60
ttccgaggcg cccgggctcc cggcgcggcg gcggaggggg cgggcaggcc ggcgggcggt 120
gatgtggcgg gactctttat gcgctgcggc aggatacgcg ctcggcgctg ggacgcgact 180
gcgctcagtt ctctcctctc ggaagctgca gccatgatgg aagtttgaga gttgagccgc 240
tgtgaggcga ggccgggctc aggcgaggga gatgagagac ggcggcggcc gcggcccgga 300
gcccctctca gcgcctgtga gcagccgcgg gggcagcgcc ctcggggagc cggccggcct 360
gcggcggcgg cagcggcggc gtttctcgcc tcctcttcgt cttttctaac cgtgcagcct 420
cttcctcggc ttctcctgaa agggaaggtg gaagccgtgg gctcgggcgg gagccggctg 480
aggcgcggcg gcggcggcgg cacctcccgc tcctggagcg gggggagaa gcggcggcgg 540 cggcggccgc ggcggctgca gctccaggga gggggtctga gtcgcctgtc accatttcca 600
gggctgggaa cgccggagag ttggtctctc cccttctact gcctccaaca cggcggcggc 660
ggcggcggca catccaggga cccgggccgg ttttaaacct cccgtccgcc gccgccgcac 720
cccccgtggc ccgggctccg gaggccgccg gcggaggcag ccgttcggag gattattcgt 780
cttctcccca ttccgctgcc gccgctgcca ggcctctggc tgctgaggag aagcaggccc 840
agtcgctgca accatccagc agccgccgca gcagccatta cccggctgcg gtccagagcc 900
aagcggcggc agagcgaggg gcatcagcta ccgccaagtc cagagccatt tccatcctgc 960
agaagaagcc ccgccaccag cagcttctgc catctctctc ctcctttttc ttcagccaca 1020
ggctcccaga catgacagcc atcatcaaag agatcgttag cagaaacaaa aggagatatc 1080
aagaggatgg attcgactta gacttgacct atatttatcc aaacattatt gctatgggat 1140
ttcctgcaga aagacttgaa ggcgtataca ggaacaatat tgatgatgta gtaaggtttt 1200
tggattcaaa gcataaaaac cattacaaga tatacaatct ttgtgctgaa agacattatg 1260
acaccgccaa atttaattgc agagttgcac aatatccttt tgaagaccat aacccaccac 1320
agctagaact tatcaaaccc ttttgtgaag atcttgacca atggctaagt gaagatgaca 1380
atcatgttgc agcaattcac tgtaaagctg gaaagggacg aactggtgta atgatatgtg 1440
catatttatt acatcggggc aaatttttaa aggcacaaga ggccctagat ttctatgggg 1500
aagtaaggac cagagacaaa aagggagtaa ctattcccag tcagaggcgc tatgtgtatt 1560
attatagcta cctgttaaag aatcatctgg attatagacc agtggcactg ttgtttcaca 1620
agatgatgtt tgaaactatt ccaatgttca gtggcggaac ttgcaatcct cagtttgtgg 1680
tctgccagct aaaggtgaag atatattcct ccaattcagg acccacacga cgggaagaca 1740
agttcatgta ctttgagttc cctcagccgt tacctgtgtg tggtgatatc aaagtagagt 1800
tcttccacaa acagaacaag atgctaaaaa aggacaaaat gtttcacttt tgggtaaata 1860
cattcttcat accaggacca gaggaaacct cagaaaaagt agaaaatgga agtctatgtg 1920
atcaagaaat cgatagcatt tgcagtatag agcgtgcaga taatgacaag gaatatctag 1980

-continued

```
tacttacttt aacaaaaaat gatcttgaca aagcaaataa agacaaagcc aaccgatact   2040
tttctccaaa ttttaaggtg aagctgtact tcacaaaaac agtagaggag ccgtcaaatc   2100
cagaggctag cagttcaact tctgtaacac cagatgttag tgacaatgaa cctgatcatt   2160
atagatattc tgacaccact gactctgatc cagagaatga accttttgat gaagatcagc   2220
atacacaaat tacaaaagtc tgaatttttt tttatcaaga gggataaaac accatgaaaa   2280
taaacttgaa taaactgaaa atggaccttt tttttttaa tggcaatagg acattgtgtc   2340
agattaccag ttataggaac aattctcttt tcctgaccaa tcttgtttta ccctatacat   2400
ccacagggtt ttgacacttg ttgtccagtt gaaaaaaggt tgtgtagctg tgtcatgtat   2460
ataccttttt gtgtcaaaag gacatttaaa attcaattag gattaataaa gatggcactt   2520
tcccgtttta ttccagtttt ataaaaagtg gagacagact gatgtgtata cgtaggaatt   2580
ttttcctttt gtgttctgtc accaactgaa gtggctaaag agctttgtga tatactggtt   2640
cacatcctac ccctttgcac ttgtggcaac agataagttt gcagttggct aagagaggtt   2700
tccgaagggt tttgctacat tctaatgcat gtattcgggt taggggaatg gagggaatgc   2760
tcagaaagga aataatttta tgctggactc tggaccatat accatctcca gctatttaca   2820
cacacctttc tttagcatgc tacagttatt aatctggaca ttcgaggaat tggccgctgt   2880
cactgcttgt tgtttgcgca ttttttttta aagcatattg gtgctagaaa aggcagctaa   2940
aggaagtgaa tctgtattgg ggtacaggaa tgaaccttct gcaacatctt aagatccaca   3000
aatgaaggga tataaaaata atgtcatagg taagaaacac agcaacaatg acttaaccat   3060
ataaatgtgg aggctatcaa caaagaatgg gcttgaaaca ttataaaaat tgacaatgat   3120
ttattaaata tgttttctca attgtaacga cttctccatc tcctgtgtaa tcaaggccag   3180
tgctaaaatt cagatgctgt tagtacctac atcagtcaac aacttacact tattttacta   3240
gttttcaatc ataatacctg ctgtggatgc ttcatgtgct gcctgcaagc ttcttttttc   3300
tcattaaata taaaatattt tgtaatgctg cacagaaatt ttcaatttga gattctacag   3360
taagcgtttt ttttctttga agatttatga tgcacttatt caatagctgt cagccgttcc   3420
acccttttga ccttacacat tctattacaa tgaattttgc agttttgcac atttttttaaa   3480
tgtcattaac tgttagggaa ttttacttga atactgaata catataatgt ttatattaaa   3540
aaggacattt gtgttaaaaa ggaaattaga gttgcagtaa actttcaatg ctgcacacaa   3600
aaaaaagaca tttgattttt cagtagaaat tgtcctacat gtgctttatt gatttgctat   3660
tgaaagaata gggttttttt tttttttttt tttttttttt ttaaatgtgc agtgttgaat   3720
catttcttca tagtgctccc ccgagttggg actagggctt caatttcact tcttaaaaaa   3780
aatcatcata tatttgatat gcccagactg catacgattt taagcggagt acaactacta   3840
ttgtaaagct aatgtgaaga tattattaaa aaggtttttt tttccagaaa tttggtgtct   3900
tcaaattata ccttcacctt gacatttgaa tatccagcca ttttgtttct taatggtata   3960
aaattccatt ttcaataact tattggtgct gaaattgttc actagctgtg gtctgaccta   4020
gttaatttac aaatacagat tgaataggac ctactagagc agcatttata gagtttgatg   4080
gcaaatagat taggcagaac ttcatctaaa atattcttag taaataatgt tgacacgttt   4140
tccatacctt gtcagtttca ttcaacaatt tttaaatttt taacaaagct cttaggattt   4200
acacatttat atttaaacat tgatatatag agtattgatt gattgctcat aagttaaatt   4260
ggtaaagtta gagacaacta ttctaacacc tcaccattga aatttatatg ccaccttgtc   4320
```

```
tttcataaaa gctgaaaatt gttacctaaa atgaaaatca acttcatgtt ttgaagatag   4380
ttataaatat tgttctttgt tacaatttcg ggcaccgcat attaaaacgt aactttattg   4440
ttccaatatg taacatggag ggccaggtca taaataatga cattataatg ggcttttgca   4500
ctgttattat ttttcctttg gaatgtgaag gtctgaatga gggttttgat tttgaatgtt   4560
tcaatgtttt tgagaagcct tgcttacatt ttatggtgta gtcattggaa atggaaaaat   4620
ggcattatat atattatata tataaatata tattatacat actctcctta ctttatttca   4680
gttaccatcc ccatagaatt tgacaagaat tgctatgact gaaaggtttt cgagtcctaa   4740
ttaaaacttt atttatggca gtattcataa ttagcctgaa atgcattctg taggtaatct   4800
ctgagtttct ggaatatttt cttagacttt ttggatgtgc agcagcttac atgtctgaag   4860
ttacttgaag gcatcacttt taagaaagct tacagttggg ccctgtacca tcccaagtcc   4920
tttgtagctc ctcttgaaca tgtttgccat acttttaaaa gggtagttga ataaatagca   4980
tcaccattct ttgctgtggc acaggttata aacttaagtg gagtttaccg gcagcatcaa   5040
atgtttcagc tttaaaaaat aaaagtaggg tacaagttta atgtttagtt ctagaaattt   5100
tgtgcaatat gttcataacg atggctgtgg ttgccacaaa gtgcctcgtt tacctttaaa   5160
tactgttaat gtgtcatgca tgcagatgga aggggtggaa ctgtgcacta aagtgggggc   5220
tttaactgta gtatttggca gagttgcctt ctacctgcca gttcaaaagt tcaacctgtt   5280
ttcatataga atatatatac taaaaaattt cagtctgtta aacagcctta ctctgattca   5340
gcctcttcag atactcttgt gctgtgcagc agtggctctg tgtgtaaatg ctatgcactg   5400
aggatacaca aaaataccaa tatgatgtgt acaggataat gcctcatccc aatcagatgt   5460
ccatttgtta ttgtgtttgt taacaaccct ttatctctta gtgttataaa ctccacttaa   5520
aactgattaa agtctcattc ttgtcaaaaa aaaaaaaaaa aaaaaaaaaa aa           5572
```

<210> SEQ ID NO 23
<211> LENGTH: 297
<212> TYPE: PRT
<213> ORGANISM: Artificial Sequence
<220> FEATURE:
<223> OTHER INFORMATION: ERCC1 sequence

<400> SEQUENCE: 23

```
Met Asp Pro Gly Lys Asp Lys Glu Gly Val Pro Gln Pro Ser Gly Pro
1               5                   10                  15

Pro Ala Arg Lys Lys Phe Val Ile Pro Leu Asp Glu Asp Glu Val Pro
            20                  25                  30

Pro Gly Val Ala Lys Pro Leu Phe Arg Ser Thr Gln Ser Leu Pro Thr
        35                  40                  45

Val Asp Thr Ser Ala Gln Ala Ala Pro Gln Thr Tyr Ala Glu Tyr Ala
    50                  55                  60

Ile Ser Gln Pro Leu Glu Gly Ala Gly Ala Thr Cys Pro Thr Gly Ser
65                  70                  75                  80

Glu Pro Leu Ala Gly Glu Thr Pro Asn Gln Ala Leu Lys Pro Gly Ala
                85                  90                  95

Lys Ser Asn Ser Ile Ile Val Ser Pro Arg Gln Arg Gly Asn Pro Val
            100                 105                 110

Leu Lys Phe Val Arg Asn Val Pro Trp Glu Phe Gly Asp Val Ile Pro
        115                 120                 125

Asp Tyr Val Leu Gly Gln Ser Thr Cys Ala Leu Phe Leu Ser Leu Arg
    130                 135                 140
```

-continued

```
Tyr His Asn Leu His Pro Asp Tyr Ile His Gly Arg Leu Gln Ser Leu
145                 150                 155                 160

Gly Lys Asn Phe Ala Leu Arg Val Leu Leu Val Gln Val Asp Val Lys
                165                 170                 175

Asp Pro Gln Gln Ala Leu Lys Glu Leu Ala Lys Met Cys Ile Leu Ala
            180                 185                 190

Asp Cys Thr Leu Ile Leu Ala Trp Ser Pro Glu Glu Ala Gly Arg Tyr
        195                 200                 205

Leu Glu Thr Tyr Lys Ala Tyr Glu Gln Lys Pro Ala Asp Leu Leu Met
    210                 215                 220

Glu Lys Leu Glu Gln Asp Phe Val Ser Arg Val Thr Glu Cys Leu Thr
225                 230                 235                 240

Thr Val Lys Ser Val Asn Lys Thr Asp Ser Gln Thr Leu Leu Thr Thr
                245                 250                 255

Phe Gly Ser Leu Glu Gln Leu Ile Ala Ala Ser Arg Glu Asp Leu Ala
            260                 265                 270

Leu Cys Pro Gly Leu Gly Pro Gln Lys Ala Arg Arg Leu Phe Asp Val
        275                 280                 285

Leu His Glu Pro Phe Leu Lys Val Pro
    290                 295
```

<210> SEQ ID NO 24
<211> LENGTH: 3400
<212> TYPE: DNA
<213> ORGANISM: Artificial Sequence
<220> FEATURE:
<223> OTHER INFORMATION: ERCC1 sequence

<400> SEQUENCE: 24

```
ccggaagtgc tgcgagccct gggccacgct ggccgtgctg gcagtgggcc gcctcgatcc     60

ctctgcagtc tttcccttga ggctccaaga ccagcaggtg aggcctcgcg gcgctgaaac    120

cgtgaggccc ggaccacagg ctccagatgg accctgggaa ggacaaagag gggtgcccc    180

agccctcagg gccgccagca aggaagaaat ttgtgatacc cctcgacgag gatgaggtcc    240

ctcctggagt ggccaagccc ttattccgat ctacacagag ccttcccact gtggacacct    300

cggcccaggc ggcccctcag acctacgccg aatatgccat ctcacagcct ctggaagggg    360

ctggggccac gtgccccaca gggtcagagc ccctggcagg agagacgccc aaccaggccc    420

tgaaacccgg ggcaaaatcc aacagcatca ttgtgagccc tcggcagagg ggcaatcccg    480

tactgaagtt cgtgcgcaat gtgccctggg aatttggcga cgtaattccc gactatgtgc    540

tgggccagag cacctgtgcc ctgttcctca gcctccgcta ccacaacctg cacccagact    600

acatccatgg gcggctgcag agcctgggga agaacttcgc cttgcgggtc ctgcttgtcc    660

aggtggatgt gaaagatccc cagcaggccc tcaaggagct ggctaagatg tgtatcctgg    720

ccgactgcac attgatcctc gcctggagcc ccgaggaagc tgggcggtac ctggagacct    780

acaaggccta tgagcagaaa ccagcggacc tcctgatgga gaagctagag caggacttcg    840

tctcccgggt gactgaatgt ctgaccaccg tgaagtcagt caacaaaacg gacagtcaga    900

ccctcctgac cacatttgga tctctggaac agctcatcgc cgcatcaaga gaagatctgg    960

ccttatgccc aggcctgggc cctcagaaag cccggaggct gtttgatgtc ctgcacgagc   1020

ccttcttgaa agtaccctga tgaccccagc tgccaaggaa acccccagtg taataataaa   1080

tcgtcctccc aggccaggct cctgctggct gcgctggtgc agtctctggg gagggattct   1140

gggggtgtca ccttctggtg gcccaggtgg gcaccttcag ctttctttag ttcctcagtt   1200
```

```
tcccgggggc agactacaca ggctgctgct gctgctgctt ccgcttcttg tcccggcctg   1260
tgggagcctc ctccccagac tctgaattca gtggcggccc tggcatctcc tcttggggca   1320
ctgtctctgg catccggctt tcctgactct gcttcttcct cttcttggtg gatcccggag   1380
ttgccctggc ttcaggctgt ccctcccctg gcagttcagg ctctagtggc tgaattggct   1440
cagtcactgt gtgacctctc tctttcttct tcttcttctt cttggtggat gtgggagctg   1500
cctgaggctc aaggtcatcc ggcagctcag gccccaccac ctctgtctct ggctccactg   1560
tggcatcttg ctgtttttct ttcttcgtct tctttttggg agctgccaga gctgcctggg   1620
cctgaggctt cgctccttct ggctgttgag gcgccatggt ccccccctggg gactccagag   1680
gcttcatctc cggctccact ggctccatcg cctccgtccc tggctccatc attgccatct   1740
gtccctttc tttttcctc ttcttcgtag ggggcagagg gatggcttcc tccagtggct   1800
ccaccttcac ctgtggctga gactcaactg tcacccccctc ctctggctcc atcccttccg   1860
tccccttttg cctctttctc tttttggtcg gggacaggac tgtgtcttct agaggctcag   1920
tgttaatctg ttcctgcttc actgtcttgt cttctggctc gaaggtttct ttccctttgg   1980
gcttcttcct cttcttggtg gtggacggga acagcactcc cagaggctcc agtgtctcca   2040
ctgtgggctc tgtccccaca ggccctgctg cctctggttc tttcagctgc tgattttttt   2100
tcttcttctt cttccgcaca tccatttctg gcgaccccaa agccatgtcc acctccaggg   2160
ccccgtgccc attcactgcc tcctgagtga ctggggcctc tgtcacctgc atctcctttt   2220
tcttcttccc tgaggtgagc aggttggggg ccaaggctga cctaggccct gtgactggtg   2280
ggttgccccc aaaggcacag aaccgaggcc tcaggccagg agggatctgt ggtgggggac   2340
ttgctgggat gggctgcaga gggctccctg acagggattg ctggggaccc tcaaggatcc   2400
ttagggtgcc ctggggggct gaggcacagg tgagtccacc tcctgcctcc gttgaggggg   2460
ccagcagggt cgcttctcca gcttggggac agctgctgag gactcgatag cggtgccgct   2520
tgcctgccaa tttgcccttg acgatctggg agccagagag aggcacatgc cgcccattga   2580
agctacagag agaaacaggg agggcagagg cttaagtgga acaggagagg gaaggttttt   2640
tgattttttt tttgtttttt tttgagagag tcttgctctg ttgcctaggc tggagtgcag   2700
tggcatgatc tcggctcact gcaatgtcca cctcctgggt tcaagcgatt ctcctgcctc   2760
agcctctcaa gtagctggga ttacaggcac ctgccaccac gcccagccaa tttttgtatt   2820
tttagtagag acaatttcac tatgttggcc aggctggtct tgaactcctg acctcaagtg   2880
atctgctcgc ctcggcctcc caaaggatgg gattacaggc accagccact gcgcctggct   2940
ggcctctggt ttttaataaa acatgactag agtgactcca tcttaaagtg agtagctagg   3000
cacttacaag gttcatgctt atggcctgaa aataaccaca tcccaggctg accaccaatt   3060
ataattacag aatatttatg gccatacaga acatgttcca ccaagcctgc agaatgtcca   3120
aatgtcctaa gaatgcagcc cccattactt aaatataaca taaatgagca agcttaggtt   3180
gcaggattaa tggtcgtgga taacaccaat agcccctacc tttagtgagc ttatctgcac   3240
actccaagtt taactatagt tccttatagt ttcttataag tagaaatact aacaaagggc   3300
tgtgggtttc tccccctgct ttctgaggac actctactct gtaaaggagt agtttccaat   3360
aaacttgttt ctttcactgt gcaaaaaaaa aaaaaaaaaa                         3400
```

<210> SEQ ID NO 25
<211> LENGTH: 3418
<212> TYPE: PRT

```
<213> ORGANISM: Artificial Sequence
<220> FEATURE:
<223> OTHER INFORMATION: BRCA2 sequence

<400> SEQUENCE: 25

Met Pro Ile Gly Ser Lys Glu Arg Pro Thr Phe Phe Glu Ile Phe Lys
1               5                   10                  15

Thr Arg Cys Asn Lys Ala Asp Leu Gly Pro Ile Ser Leu Asn Trp Phe
            20                  25                  30

Glu Glu Leu Ser Ser Glu Ala Pro Pro Tyr Asn Ser Glu Pro Ala Glu
        35                  40                  45

Glu Ser Glu His Lys Asn Asn Asn Tyr Glu Pro Asn Leu Phe Lys Thr
    50                  55                  60

Pro Gln Arg Lys Pro Ser Tyr Asn Gln Leu Ala Ser Thr Pro Ile Ile
65                  70                  75                  80

Phe Lys Glu Gln Gly Leu Thr Leu Pro Leu Tyr Gln Ser Pro Val Lys
                85                  90                  95

Glu Leu Asp Lys Phe Lys Leu Asp Leu Gly Arg Asn Val Pro Asn Ser
            100                 105                 110

Arg His Lys Ser Leu Arg Thr Val Lys Thr Lys Met Asp Gln Ala Asp
        115                 120                 125

Asp Val Ser Cys Pro Leu Leu Asn Ser Cys Leu Ser Glu Ser Pro Val
    130                 135                 140

Val Leu Gln Cys Thr His Val Thr Pro Gln Arg Asp Lys Ser Val Val
145                 150                 155                 160

Cys Gly Ser Leu Phe His Thr Pro Lys Phe Val Lys Gly Arg Gln Thr
                165                 170                 175

Pro Lys His Ile Ser Glu Ser Leu Gly Ala Glu Val Asp Pro Asp Met
            180                 185                 190

Ser Trp Ser Ser Ser Leu Ala Thr Pro Pro Thr Leu Ser Ser Thr Val
        195                 200                 205

Leu Ile Val Arg Asn Glu Glu Ala Ser Glu Thr Val Phe Pro His Asp
    210                 215                 220

Thr Thr Ala Asn Val Lys Ser Tyr Phe Ser Asn His Asp Glu Ser Leu
225                 230                 235                 240

Lys Lys Asn Asp Arg Phe Ile Ala Ser Val Thr Asp Ser Glu Asn Thr
                245                 250                 255

Asn Gln Arg Glu Ala Ala Ser His Gly Phe Gly Lys Thr Ser Gly Asn
            260                 265                 270

Ser Phe Lys Val Asn Ser Cys Lys Asp His Ile Gly Lys Ser Met Pro
        275                 280                 285

Asn Val Leu Glu Asp Glu Val Tyr Glu Thr Val Val Asp Thr Ser Glu
    290                 295                 300

Glu Asp Ser Phe Ser Leu Cys Phe Ser Lys Cys Arg Thr Lys Asn Leu
305                 310                 315                 320

Gln Lys Val Arg Thr Ser Lys Thr Arg Lys Lys Ile Phe His Glu Ala
                325                 330                 335

Asn Ala Asp Glu Cys Glu Lys Ser Lys Asn Gln Val Lys Glu Lys Tyr
            340                 345                 350

Ser Phe Val Ser Glu Val Glu Pro Asn Asp Thr Asp Pro Leu Asp Ser
        355                 360                 365

Asn Val Ala Asn Gln Lys Pro Phe Glu Ser Gly Ser Asp Lys Ile Ser
    370                 375                 380

Lys Glu Val Val Pro Ser Leu Ala Cys Glu Trp Ser Gln Leu Thr Leu
```

-continued

```
385                 390                 395                 400

Ser Gly Leu Asn Gly Ala Gln Met Glu Lys Ile Pro Leu Leu His Ile
                405                 410                 415

Ser Ser Cys Asp Gln Asn Ile Ser Glu Lys Asp Leu Leu Asp Thr Glu
            420                 425                 430

Asn Lys Arg Lys Lys Asp Phe Leu Thr Ser Glu Asn Ser Leu Pro Arg
        435                 440                 445

Ile Ser Ser Leu Pro Lys Ser Glu Lys Pro Leu Asn Glu Glu Thr Val
    450                 455                 460

Val Asn Lys Arg Asp Glu Glu Gln His Leu Glu Ser His Thr Asp Cys
465                 470                 475                 480

Ile Leu Ala Val Lys Gln Ala Ile Ser Gly Thr Ser Pro Val Ala Ser
                485                 490                 495

Ser Phe Gln Gly Ile Lys Lys Ser Ile Phe Arg Ile Arg Glu Ser Pro
            500                 505                 510

Lys Glu Thr Phe Asn Ala Ser Phe Ser Gly His Met Thr Asp Pro Asn
        515                 520                 525

Phe Lys Lys Glu Thr Glu Ala Ser Glu Ser Gly Leu Glu Ile His Thr
    530                 535                 540

Val Cys Ser Gln Lys Glu Asp Ser Leu Cys Pro Asn Leu Ile Asp Asn
545                 550                 555                 560

Gly Ser Trp Pro Ala Thr Thr Thr Gln Asn Ser Val Ala Leu Lys Asn
                565                 570                 575

Ala Gly Leu Ile Ser Thr Leu Lys Lys Lys Thr Asn Lys Phe Ile Tyr
            580                 585                 590

Ala Ile His Asp Glu Thr Ser Tyr Lys Gly Lys Lys Ile Pro Lys Asp
        595                 600                 605

Gln Lys Ser Glu Leu Ile Asn Cys Ser Ala Gln Phe Glu Ala Asn Ala
    610                 615                 620

Phe Glu Ala Pro Leu Thr Phe Ala Asn Ala Asp Ser Gly Leu Leu His
625                 630                 635                 640

Ser Ser Val Lys Arg Ser Cys Ser Gln Asn Asp Ser Glu Glu Pro Thr
                645                 650                 655

Leu Ser Leu Thr Ser Ser Phe Gly Thr Ile Leu Arg Lys Cys Ser Arg
            660                 665                 670

Asn Glu Thr Cys Ser Asn Asn Thr Val Ile Ser Gln Asp Leu Asp Tyr
        675                 680                 685

Lys Glu Ala Lys Cys Asn Lys Glu Lys Leu Gln Leu Phe Ile Thr Pro
    690                 695                 700

Glu Ala Asp Ser Leu Ser Cys Leu Gln Glu Gly Gln Cys Glu Asn Asp
705                 710                 715                 720

Pro Lys Ser Lys Lys Val Ser Asp Ile Lys Glu Glu Val Leu Ala Ala
                725                 730                 735

Ala Cys His Pro Val Gln His Ser Lys Val Glu Tyr Ser Asp Thr Asp
            740                 745                 750

Phe Gln Ser Gln Lys Ser Leu Leu Tyr Asp His Glu Asn Ala Ser Thr
        755                 760                 765

Leu Ile Leu Thr Pro Thr Ser Lys Asp Val Leu Ser Asn Leu Val Met
    770                 775                 780

Ile Ser Arg Gly Lys Glu Ser Tyr Lys Met Ser Asp Lys Leu Lys Gly
785                 790                 795                 800

Asn Asn Tyr Glu Ser Asp Val Glu Leu Thr Lys Asn Ile Pro Met Glu
                805                 810                 815
```

```
Lys Asn Gln Asp Val Cys Ala Leu Asn Glu Asn Tyr Lys Asn Val Glu
            820                 825                 830

Leu Leu Pro Pro Glu Lys Tyr Met Arg Val Ala Ser Pro Ser Arg Lys
        835                 840                 845

Val Gln Phe Asn Gln Asn Thr Asn Leu Arg Val Ile Gln Lys Asn Gln
    850                 855                 860

Glu Glu Thr Thr Ser Ile Ser Lys Ile Thr Val Asn Pro Asp Ser Glu
865                 870                 875                 880

Glu Leu Phe Ser Asp Asn Glu Asn Asn Phe Val Phe Gln Val Ala Asn
                885                 890                 895

Glu Arg Asn Asn Leu Ala Leu Gly Asn Thr Lys Glu Leu His Glu Thr
            900                 905                 910

Asp Leu Thr Cys Val Asn Glu Pro Ile Phe Lys Asn Ser Thr Met Val
        915                 920                 925

Leu Tyr Gly Asp Thr Gly Asp Lys Gln Ala Thr Gln Val Ser Ile Lys
    930                 935                 940

Lys Asp Leu Val Tyr Val Leu Ala Glu Glu Asn Lys Asn Ser Val Lys
945                 950                 955                 960

Gln His Ile Lys Met Thr Leu Gly Gln Asp Leu Lys Ser Asp Ile Ser
                965                 970                 975

Leu Asn Ile Asp Lys Ile Pro Glu Lys Asn Asn Asp Tyr Met Asn Lys
            980                 985                 990

Trp Ala Gly Leu Leu Gly Pro Ile  Ser Asn His Ser Phe  Gly Gly Ser
        995                 1000                1005

Phe Arg  Thr Ala Ser Asn Lys  Glu Ile Lys Leu Ser  Glu His Asn
    1010                 1015                 1020

Ile Lys  Lys Ser Lys Met Phe  Phe Lys Asp Ile Glu  Glu Gln Tyr
    1025                 1030                 1035

Pro Thr  Ser Leu Ala Cys Val  Glu Ile Val Asn Thr  Leu Ala Leu
    1040                 1045                 1050

Asp Asn  Gln Lys Lys Leu Ser  Lys Pro Gln Ser Ile  Asn Thr Val
    1055                 1060                 1065

Ser Ala  His Leu Gln Ser Ser  Val Val Val Ser Asp  Cys Lys Asn
    1070                 1075                 1080

Ser His  Ile Thr Pro Gln Met  Leu Phe Ser Lys Gln  Asp Phe Asn
    1085                 1090                 1095

Ser Asn  His Asn Leu Thr Pro  Ser Gln Lys Ala Glu  Ile Thr Glu
    1100                 1105                 1110

Leu Ser  Thr Ile Leu Glu Glu  Ser Gly Ser Gln Phe  Glu Phe Thr
    1115                 1120                 1125

Gln Phe  Arg Lys Pro Ser Tyr  Ile Leu Gln Lys Ser  Thr Phe Glu
    1130                 1135                 1140

Val Pro  Glu Asn Gln Met Thr  Ile Leu Lys Thr Thr  Ser Glu Glu
    1145                 1150                 1155

Cys Arg  Asp Ala Asp Leu His  Val Ile Met Asn Ala  Pro Ser Ile
    1160                 1165                 1170

Gly Gln  Val Asp Ser Ser Lys  Gln Phe Glu Gly Thr  Val Glu Ile
    1175                 1180                 1185

Lys Arg  Lys Phe Ala Gly Leu  Leu Lys Asn Asp Cys  Asn Lys Ser
    1190                 1195                 1200

Ala Ser  Gly Tyr Leu Thr Asp  Glu Asn Glu Val Gly  Phe Arg Gly
    1205                 1210                 1215
```

```
Phe Tyr  Ser Ala His Gly Thr  Lys Leu Asn Val Ser  Thr Glu Ala
    1220                 1225                 1230

Leu Gln  Lys Ala Val Lys Leu  Phe Ser Asp Ile Glu  Asn Ile Ser
    1235                 1240                 1245

Glu Glu  Thr Ser Ala Glu Val  His Pro Ile Ser Leu  Ser Ser Ser
    1250                 1255                 1260

Lys Cys  His Asp Ser Val Val  Ser Met Phe Lys Ile  Glu Asn His
    1265                 1270                 1275

Asn Asp  Lys Thr Val Ser Glu  Lys Asn Asn Lys Cys  Gln Leu Ile
    1280                 1285                 1290

Leu Gln  Asn Asn Ile Glu Met  Thr Thr Gly Thr Phe  Val Glu Glu
    1295                 1300                 1305

Ile Thr  Glu Asn Tyr Lys Arg  Asn Thr Glu Asn Glu  Asp Asn Lys
    1310                 1315                 1320

Tyr Thr  Ala Ala Ser Arg Asn  Ser His Asn Leu Glu  Phe Asp Gly
    1325                 1330                 1335

Ser Asp  Ser Ser Lys Asn Asp  Thr Val Cys Ile His  Lys Asp Glu
    1340                 1345                 1350

Thr Asp  Leu Leu Phe Thr Asp  Gln His Asn Ile Cys  Leu Lys Leu
    1355                 1360                 1365

Ser Gly  Gln Phe Met Lys Glu  Gly Asn Thr Gln Ile  Lys Glu Asp
    1370                 1375                 1380

Leu Ser  Asp Leu Thr Phe Leu  Glu Val Ala Lys Ala  Gln Glu Ala
    1385                 1390                 1395

Cys His  Gly Asn Thr Ser Asn  Lys Glu Gln Leu Thr  Ala Thr Lys
    1400                 1405                 1410

Thr Glu  Gln Asn Ile Lys Asp  Phe Glu Thr Ser Asp  Thr Phe Phe
    1415                 1420                 1425

Gln Thr  Ala Ser Gly Lys Asn  Ile Ser Val Ala Lys  Glu Ser Phe
    1430                 1435                 1440

Asn Lys  Ile Val Asn Phe Phe  Asp Gln Lys Pro Glu  Glu Leu His
    1445                 1450                 1455

Asn Phe  Ser Leu Asn Ser Glu  Leu His Ser Asp Ile  Arg Lys Asn
    1460                 1465                 1470

Lys Met  Asp Ile Leu Ser Tyr  Glu Glu Thr Asp Ile  Val Lys His
    1475                 1480                 1485

Lys Ile  Leu Lys Glu Ser Val  Pro Val Gly Thr Gly  Asn Gln Leu
    1490                 1495                 1500

Val Thr  Phe Gln Gly Gln Pro  Glu Arg Asp Glu Lys  Ile Lys Glu
    1505                 1510                 1515

Pro Thr  Leu Leu Gly Phe His  Thr Ala Ser Gly Lys  Lys Val Lys
    1520                 1525                 1530

Ile Ala  Lys Glu Ser Leu Asp  Lys Val Lys Asn Leu  Phe Asp Glu
    1535                 1540                 1545

Lys Glu  Gln Gly Thr Ser Glu  Ile Thr Ser Phe Ser  His Gln Trp
    1550                 1555                 1560

Ala Lys  Thr Leu Lys Tyr Arg  Glu Ala Cys Lys Asp  Leu Glu Leu
    1565                 1570                 1575

Ala Cys  Glu Thr Ile Glu Ile  Thr Ala Ala Pro Lys  Cys Lys Glu
    1580                 1585                 1590

Met Gln  Asn Ser Leu Asn Asn  Asp Lys Asn Leu Val  Ser Ile Glu
    1595                 1600                 1605

Thr Val  Val Pro Pro Lys Leu  Leu Ser Asp Asn Leu  Cys Arg Gln
```

```
    1610                1615                1620

Thr Glu Asn Leu Lys Thr Ser Lys Ser Ile Phe Leu Lys Val Lys
    1625                1630                1635

Val His Glu Asn Val Glu Lys Glu Thr Ala Lys Ser Pro Ala Thr
    1640                1645                1650

Cys Tyr Thr Asn Gln Ser Pro Tyr Ser Val Ile Glu Asn Ser Ala
    1655                1660                1665

Leu Ala Phe Tyr Thr Ser Cys Ser Arg Lys Thr Ser Val Ser Gln
    1670                1675                1680

Thr Ser Leu Leu Glu Ala Lys Lys Trp Leu Arg Glu Gly Ile Phe
    1685                1690                1695

Asp Gly Gln Pro Glu Arg Ile Asn Thr Ala Asp Tyr Val Gly Asn
    1700                1705                1710

Tyr Leu Tyr Glu Asn Asn Ser Asn Ser Thr Ile Ala Glu Asn Asp
    1715                1720                1725

Lys Asn His Leu Ser Glu Lys Gln Asp Thr Tyr Leu Ser Asn Ser
    1730                1735                1740

Ser Met Ser Asn Ser Tyr Ser Tyr His Ser Asp Glu Val Tyr Asn
    1745                1750                1755

Asp Ser Gly Tyr Leu Ser Lys Asn Lys Leu Asp Ser Gly Ile Glu
    1760                1765                1770

Pro Val Leu Lys Asn Val Glu Asp Gln Lys Asn Thr Ser Phe Ser
    1775                1780                1785

Lys Val Ile Ser Asn Val Lys Asp Ala Asn Ala Tyr Pro Gln Thr
    1790                1795                1800

Val Asn Glu Asp Ile Cys Val Glu Glu Leu Val Thr Ser Ser Ser
    1805                1810                1815

Pro Cys Lys Asn Lys Asn Ala Ala Ile Lys Leu Ser Ile Ser Asn
    1820                1825                1830

Ser Asn Asn Phe Glu Val Gly Pro Pro Ala Phe Arg Ile Ala Ser
    1835                1840                1845

Gly Lys Ile Val Cys Val Ser His Glu Thr Ile Lys Lys Val Lys
    1850                1855                1860

Asp Ile Phe Thr Asp Ser Phe Ser Lys Val Ile Lys Glu Asn Asn
    1865                1870                1875

Glu Asn Lys Ser Lys Ile Cys Gln Thr Lys Ile Met Ala Gly Cys
    1880                1885                1890

Tyr Glu Ala Leu Asp Asp Ser Glu Asp Ile Leu His Asn Ser Leu
    1895                1900                1905

Asp Asn Asp Glu Cys Ser Thr His Ser His Lys Val Phe Ala Asp
    1910                1915                1920

Ile Gln Ser Glu Glu Ile Leu Gln His Asn Gln Asn Met Ser Gly
    1925                1930                1935

Leu Glu Lys Val Ser Lys Ile Ser Pro Cys Asp Val Ser Leu Glu
    1940                1945                1950

Thr Ser Asp Ile Cys Lys Cys Ser Ile Gly Lys Leu His Lys Ser
    1955                1960                1965

Val Ser Ser Ala Asn Thr Cys Gly Ile Phe Ser Thr Ala Ser Gly
    1970                1975                1980

Lys Ser Val Gln Val Ser Asp Ala Ser Leu Gln Asn Ala Arg Gln
    1985                1990                1995

Val Phe Ser Glu Ile Glu Asp Ser Thr Lys Gln Val Phe Ser Lys
    2000                2005                2010
```

Val Leu Phe Lys Ser Asn Glu His Ser Asp Gln Leu Thr Arg Glu
2015 2020 2025

Glu Asn Thr Ala Ile Arg Thr Pro Glu His Leu Ile Ser Gln Lys
2030 2035 2040

Gly Phe Ser Tyr Asn Val Val Asn Ser Ser Ala Phe Ser Gly Phe
2045 2050 2055

Ser Thr Ala Ser Gly Lys Gln Val Ser Ile Leu Glu Ser Ser Leu
2060 2065 2070

His Lys Val Lys Gly Val Leu Glu Glu Phe Asp Leu Ile Arg Thr
2075 2080 2085

Glu His Ser Leu His Tyr Ser Pro Thr Ser Arg Gln Asn Val Ser
2090 2095 2100

Lys Ile Leu Pro Arg Val Asp Lys Arg Asn Pro Glu His Cys Val
2105 2110 2115

Asn Ser Glu Met Glu Lys Thr Cys Ser Lys Glu Phe Lys Leu Ser
2120 2125 2130

Asn Asn Leu Asn Val Glu Gly Gly Ser Ser Glu Asn Asn His Ser
2135 2140 2145

Ile Lys Val Ser Pro Tyr Leu Ser Gln Phe Gln Gln Asp Lys Gln
2150 2155 2160

Gln Leu Val Leu Gly Thr Lys Val Ser Leu Val Glu Asn Ile His
2165 2170 2175

Val Leu Gly Lys Glu Gln Ala Ser Pro Lys Asn Val Lys Met Glu
2180 2185 2190

Ile Gly Lys Thr Glu Thr Phe Ser Asp Val Pro Val Lys Thr Asn
2195 2200 2205

Ile Glu Val Cys Ser Thr Tyr Ser Lys Asp Ser Glu Asn Tyr Phe
2210 2215 2220

Glu Thr Glu Ala Val Glu Ile Ala Lys Ala Phe Met Glu Asp Asp
2225 2230 2235

Glu Leu Thr Asp Ser Lys Leu Pro Ser His Ala Thr His Ser Leu
2240 2245 2250

Phe Thr Cys Pro Glu Asn Glu Glu Met Val Leu Ser Asn Ser Arg
2255 2260 2265

Ile Gly Lys Arg Arg Gly Glu Pro Leu Ile Leu Val Gly Glu Pro
2270 2275 2280

Ser Ile Lys Arg Asn Leu Leu Asn Glu Phe Asp Arg Ile Ile Glu
2285 2290 2295

Asn Gln Glu Lys Ser Leu Lys Ala Ser Lys Ser Thr Pro Asp Gly
2300 2305 2310

Thr Ile Lys Asp Arg Arg Leu Phe Met His His Val Ser Leu Glu
2315 2320 2325

Pro Ile Thr Cys Val Pro Phe Arg Thr Thr Lys Glu Arg Gln Glu
2330 2335 2340

Ile Gln Asn Pro Asn Phe Thr Ala Pro Gly Gln Glu Phe Leu Ser
2345 2350 2355

Lys Ser His Leu Tyr Glu His Leu Thr Leu Glu Lys Ser Ser Ser
2360 2365 2370

Asn Leu Ala Val Ser Gly His Pro Phe Tyr Gln Val Ser Ala Thr
2375 2380 2385

Arg Asn Glu Lys Met Arg His Leu Ile Thr Thr Gly Arg Pro Thr
2390 2395 2400

Lys Val Phe Val Pro Pro Phe Lys Thr Lys Ser His Phe His Arg
2405 2410 2415

Val Glu Gln Cys Val Arg Asn Ile Asn Leu Glu Glu Asn Arg Gln
2420 2425 2430

Lys Gln Asn Ile Asp Gly His Gly Ser Asp Asp Ser Lys Asn Lys
2435 2440 2445

Ile Asn Asp Asn Glu Ile His Gln Phe Asn Lys Asn Asn Ser Asn
2450 2455 2460

Gln Ala Ala Ala Val Thr Phe Thr Lys Cys Glu Glu Glu Pro Leu
2465 2470 2475

Asp Leu Ile Thr Ser Leu Gln Asn Ala Arg Asp Ile Gln Asp Met
2480 2485 2490

Arg Ile Lys Lys Lys Gln Arg Gln Arg Val Phe Pro Gln Pro Gly
2495 2500 2505

Ser Leu Tyr Leu Ala Lys Thr Ser Thr Leu Pro Arg Ile Ser Leu
2510 2515 2520

Lys Ala Ala Val Gly Gly Gln Val Pro Ser Ala Cys Ser His Lys
2525 2530 2535

Gln Leu Tyr Thr Tyr Gly Val Ser Lys His Cys Ile Lys Ile Asn
2540 2545 2550

Ser Lys Asn Ala Glu Ser Phe Gln Phe His Thr Glu Asp Tyr Phe
2555 2560 2565

Gly Lys Glu Ser Leu Trp Thr Gly Lys Gly Ile Gln Leu Ala Asp
2570 2575 2580

Gly Gly Trp Leu Ile Pro Ser Asn Asp Gly Lys Ala Gly Lys Glu
2585 2590 2595

Glu Phe Tyr Arg Ala Leu Cys Asp Thr Pro Gly Val Asp Pro Lys
2600 2605 2610

Leu Ile Ser Arg Ile Trp Val Tyr Asn His Tyr Arg Trp Ile Ile
2615 2620 2625

Trp Lys Leu Ala Ala Met Glu Cys Ala Phe Pro Lys Glu Phe Ala
2630 2635 2640

Asn Arg Cys Leu Ser Pro Glu Arg Val Leu Leu Gln Leu Lys Tyr
2645 2650 2655

Arg Tyr Asp Thr Glu Ile Asp Arg Ser Arg Arg Ser Ala Ile Lys
2660 2665 2670

Lys Ile Met Glu Arg Asp Asp Thr Ala Ala Lys Thr Leu Val Leu
2675 2680 2685

Cys Val Ser Asp Ile Ile Ser Leu Ser Ala Asn Ile Ser Glu Thr
2690 2695 2700

Ser Ser Asn Lys Thr Ser Ser Ala Asp Thr Gln Lys Val Ala Ile
2705 2710 2715

Ile Glu Leu Thr Asp Gly Trp Tyr Ala Val Lys Ala Gln Leu Asp
2720 2725 2730

Pro Pro Leu Leu Ala Val Leu Lys Asn Gly Arg Leu Thr Val Gly
2735 2740 2745

Gln Lys Ile Ile Leu His Gly Ala Glu Leu Val Gly Ser Pro Asp
2750 2755 2760

Ala Cys Thr Pro Leu Glu Ala Pro Glu Ser Leu Met Leu Lys Ile
2765 2770 2775

Ser Ala Asn Ser Thr Arg Pro Ala Arg Trp Tyr Thr Lys Leu Gly
2780 2785 2790

Phe Phe Pro Asp Pro Arg Pro Phe Pro Leu Pro Leu Ser Ser Leu

```
    2795                2800                2805

Phe Ser  Asp Gly Gly Asn Val  Gly Cys Val Asp Val  Ile Ile Gln
    2810                2815                2820

Arg Ala  Tyr Pro Ile Gln Trp  Met Glu Lys Thr Ser  Ser Gly Leu
    2825                2830                2835

Tyr Ile  Phe Arg Asn Glu Arg  Glu Glu Glu Lys Glu  Ala Ala Lys
    2840                2845                2850

Tyr Val  Glu Ala Gln Gln Lys  Arg Leu Glu Ala Leu  Phe Thr Lys
    2855                2860                2865

Ile Gln  Glu Glu Phe Glu Glu  His Glu Glu Asn Thr  Thr Lys Pro
    2870                2875                2880

Tyr Leu  Pro Ser Arg Ala Leu  Thr Arg Gln Gln Val  Arg Ala Leu
    2885                2890                2895

Gln Asp  Gly Ala Glu Leu Tyr  Glu Ala Val Lys Asn  Ala Ala Asp
    2900                2905                2910

Pro Ala  Tyr Leu Glu Gly Tyr  Phe Ser Glu Glu Gln  Leu Arg Ala
    2915                2920                2925

Leu Asn  Asn His Arg Gln Met  Leu Asn Asp Lys Lys  Gln Ala Gln
    2930                2935                2940

Ile Gln  Leu Glu Ile Arg Lys  Ala Met Glu Ser Ala  Glu Gln Lys
    2945                2950                2955

Glu Gln  Gly Leu Ser Arg Asp  Val Thr Thr Val Trp  Lys Leu Arg
    2960                2965                2970

Ile Val  Ser Tyr Ser Lys Lys  Glu Lys Asp Ser Val  Ile Leu Ser
    2975                2980                2985

Ile Trp  Arg Pro Ser Ser Asp  Leu Tyr Ser Leu Leu  Thr Glu Gly
    2990                2995                3000

Lys Arg  Tyr Arg Ile Tyr His  Leu Ala Thr Ser Lys  Ser Lys Ser
    3005                3010                3015

Lys Ser  Glu Arg Ala Asn Ile  Gln Leu Ala Ala Thr  Lys Lys Thr
    3020                3025                3030

Gln Tyr  Gln Gln Leu Pro Val  Ser Asp Glu Ile Leu  Phe Gln Ile
    3035                3040                3045

Tyr Gln  Pro Arg Glu Pro Leu  His Phe Ser Lys Phe  Leu Asp Pro
    3050                3055                3060

Asp Phe  Gln Pro Ser Cys Ser  Glu Val Asp Leu Ile  Gly Phe Val
    3065                3070                3075

Val Ser  Val Val Lys Lys Thr  Gly Leu Ala Pro Phe  Val Tyr Leu
    3080                3085                3090

Ser Asp  Glu Cys Tyr Asn Leu  Leu Ala Ile Lys Phe  Trp Ile Asp
    3095                3100                3105

Leu Asn  Glu Asp Ile Ile Lys  Pro His Met Leu Ile  Ala Ala Ser
    3110                3115                3120

Asn Leu  Gln Trp Arg Pro Glu  Ser Lys Ser Gly Leu  Leu Thr Leu
    3125                3130                3135

Phe Ala  Gly Asp Phe Ser Val  Phe Ser Ala Ser Pro  Lys Glu Gly
    3140                3145                3150

His Phe  Gln Glu Thr Phe Asn  Lys Met Lys Asn Thr  Val Glu Asn
    3155                3160                3165

Ile Asp  Ile Leu Cys Asn Glu  Ala Glu Asn Lys Leu  Met His Ile
    3170                3175                3180

Leu His  Ala Asn Asp Pro Lys  Trp Ser Thr Pro Thr  Lys Asp Cys
    3185                3190                3195
```

```
Thr Ser  Gly Pro Tyr Thr Ala  Gln Ile Ile Pro Gly  Thr Gly Asn
    3200                 3205                 3210

Lys Leu  Leu Met Ser Ser Pro  Asn Cys Glu Ile Tyr  Tyr Gln Ser
    3215                 3220                 3225

Pro Leu  Ser Leu Cys Met Ala  Lys Arg Lys Ser Val  Ser Thr Pro
    3230                 3235                 3240

Val Ser  Ala Gln Met Thr Ser  Lys Ser Cys Lys Gly  Glu Lys Glu
    3245                 3250                 3255

Ile Asp  Asp Gln Lys Asn Cys  Lys Lys Arg Arg Ala  Leu Asp Phe
    3260                 3265                 3270

Leu Ser  Arg Leu Pro Leu Pro  Pro Pro Val Ser Pro  Ile Cys Thr
    3275                 3280                 3285

Phe Val  Ser Pro Ala Ala Gln  Lys Ala Phe Gln Pro  Pro Arg Ser
    3290                 3295                 3300

Cys Gly  Thr Lys Tyr Glu Thr  Pro Ile Lys Lys Lys  Glu Leu Asn
    3305                 3310                 3315

Ser Pro  Gln Met Thr Pro Phe  Lys Lys Phe Asn Glu  Ile Ser Leu
    3320                 3325                 3330

Leu Glu  Ser Asn Ser Ile Ala  Asp Glu Glu Leu Ala  Leu Ile Asn
    3335                 3340                 3345

Thr Gln  Ala Leu Leu Ser Gly  Ser Thr Gly Glu Lys  Gln Phe Ile
    3350                 3355                 3360

Ser Val  Ser Glu Ser Thr Arg  Thr Ala Pro Thr Ser  Ser Glu Asp
    3365                 3370                 3375

Tyr Leu  Arg Leu Lys Arg Arg  Cys Thr Thr Ser Leu  Ile Lys Glu
    3380                 3385                 3390

Gln Glu  Ser Ser Gln Ala Ser  Thr Glu Glu Cys Glu  Lys Asn Lys
    3395                 3400                 3405

Gln Asp  Thr Ile Thr Thr Lys  Lys Tyr Ile
    3410                 3415
```

<210> SEQ ID NO 26
<211> LENGTH: 11386
<212> TYPE: DNA
<213> ORGANISM: Artificial Sequence
<220> FEATURE:
<223> OTHER INFORMATION: BRCA2 sequence

<400> SEQUENCE: 26

```
gtggcgcgag cttctgaaac taggcggcag aggcggagcc gctgtggcac tgctgcgcct     60

ctgctgcgcc tcgggtgtct tttgcggcgg tgggtcgccg ccgggagaag cgtgagggga    120

cagatttgtg accggcgcgg tttttgtcag cttactccgg ccaaaaaaga actgcacctc    180

tggagcggac ttatttacca agcattggag gaatatcgta ggtaaaaatg cctattggat    240

ccaaagagag gccaacattt tttgaaattt ttaagacacg ctgcaacaaa gcagatttag    300

gaccaataag tcttaattgg tttgaagaac tttcttcaga agctccaccc tataattctg    360

aacctgcaga agaatctgaa cataaaaaca acaattacga accaaaccta tttaaaactc    420

cacaaaggaa accatcttat aatcagctgg cttcaactcc aataatattc aaagagcaag    480

ggctgactct gccgctgtac caatctcctg taaaagaatt agataaattc aaattagact    540

taggaaggaa tgttcccaat agtagacata aaagtcttcg cacagtgaaa actaaaatgg    600

atcaagcaga tgatgtttcc tgtccacttc taaattcttg tcttagtgaa agtcctgttg    660

ttctacaatg tacacatgta acaccacaaa gagataagtc agtggtatgt gggagtttgt    720
```

```
ttcatacacc aaagtttgtg aagggtcgtc agacaccaaa acatatttct gaaagtctag    780
gagctgaggt ggatcctgat atgtcttggt caagttcttt agctacacca cccaccctta    840
gttctactgt gctcatagtc agaaatgaag aagcatctga aactgtattt cctcatgata    900
ctactgctaa tgtgaaaagc tatttttcca atcatgatga aagtctgaag aaaaatgata    960
gatttatcgc ttctgtgaca gacagtgaaa acacaaatca aagagaagct gcaagtcatg   1020
gatttggaaa aacatcaggg aattcattta aagtaaatag ctgcaaagac cacattggaa   1080
agtcaatgcc aaatgtccta gaagatgaag tatatgaaac agttgtagat acctctgaag   1140
aagatagttt ttcattatgt ttttctaaat gtagaacaaa aaatctacaa aaagtaagaa   1200
ctagcaagac taggaaaaaa attttccatg aagcaaacgc tgatgaatgt gaaaaatcta   1260
aaaaccaagt gaaagaaaaa tactcatttg tatctgaagt ggaaccaaat gatactgatc   1320
cattagattc aaatgtagca aatcagaagc cctttgagag tggaagtgac aaaatctcca   1380
aggaagttgt accgtctttg gcctgtgaat ggtctcaact aaccctttca ggtctaaatg   1440
gagcccagat ggagaaaata cccctattgc atatttcttc atgtgaccaa aatatttcag   1500
aaaaagacct attagacaca gagaacaaaa gaaagaaaga ttttcttact tcagagaatt   1560
ctttgccacg tatttctagc ctaccaaaat cagagaagcc attaaatgag gaaacagtgg   1620
taaataagag agatgaagag cagcatcttg aatctcatac agactgcatt cttgcagtaa   1680
agcaggcaat atctggaact tctccagtgg cttcttcatt tcagggtatc aaaaagtcta   1740
tattcagaat aagagaatca cctaaagaga ctttcaatgc aagtttttca ggtcatatga   1800
ctgatccaaa ctttaaaaaa gaaactgaag cctctgaaag tggactggaa atacatactg   1860
tttgctcaca gaaggaggac tccttatgtc caaatttaat tgataatgga agctggccag   1920
ccaccaccac acagaattct gtagctttga agaatgcagg tttaatatcc actttgaaaa   1980
agaaaacaaa taagtttatt tatgctatac atgatgaaac atcttataaa ggaaaaaaaa   2040
taccgaaaga ccaaaaatca gaactaatta actgttcagc ccagtttgaa gcaaatgctt   2100
ttgaagcacc acttacattt gcaaatgctg attcaggttt attgcattct tctgtgaaaa   2160
gaagctgttc acagaatgat tctgaagaac caactttgtc cttaactagc tcttttggga   2220
caattctgag gaaatgttct agaaatgaaa catgttctaa taatacagta atctctcagg   2280
atcttgatta taaagaagca aaatgtaata aggaaaaact acagttattt attaccccag   2340
aagctgattc tctgtcatgc ctgcaggaag gacagtgtga aaatgatcca aaaagcaaaa   2400
aagtttcaga tataaaagaa gaggtcttgg ctgcagcatg tcacccagta caacattcaa   2460
aagtggaata cagtgatact gactttcaat cccagaaaag tcttttatat gatcatgaaa   2520
atgccagcac tcttatttta actcctactt ccaaggatgt tctgtcaaac ctagtcatga   2580
tttctagagg caaagaatca tacaaaatgt cagacaagct caaaggtaac aattatgaat   2640
ctgatgttga attaaccaaa aatattccca tggaaaagaa tcaagatgta tgtgctttaa   2700
atgaaaatta taaaaacgtt gagctgttgc cacctgaaaa atacatgaga gtagcatcac   2760
cttcaagaaa ggtacaattc aaccaaaaca caaatctaag agtaatccaa aaaaatcaag   2820
aagaaactac ttcaatttca aaaataactg tcaatccaga ctctgaagaa cttttctcag   2880
acaatgagaa taattttgtc ttccaagtag ctaatgaaag gaataatctt gctttaggaa   2940
atactaagga acttcatgaa acagacttga cttgtgtaaa cgaacccatt ttcaagaact   3000
ctaccatggt tttatatgga gacacaggtg ataaacaagc aacccaagtg tcaattaaaa   3060
```

```
aagatttggt ttatgttctt gcagaggaga acaaaaatag tgtaaagcag catataaaaa   3120
tgactctagg tcaagattta aaatcggaca tctccttgaa tatagataaa ataccagaaa   3180
aaaataatga ttacatgaac aaatgggcag gactcttagg tccaatttca aatcacagtt   3240
ttggaggtag cttcagaaca gcttcaaata aggaaatcaa gctctctgaa cataacatta   3300
agaagagcaa aatgttcttc aaagatattg aagaacaata tcctactagt ttagcttgtg   3360
ttgaaattgt aaataccttg gcattagata atcaaaagaa actgagcaag cctcagtcaa   3420
ttaatactgt atctgcacat ttacagagta gtgtagttgt ttctgattgt aaaaatagtc   3480
atataacccc tcagatgtta ttttccaagc aggattttaa ttcaaaccat aatttaacac   3540
ctagccaaaa ggcagaaatt acagaacttt ctactatatt agaagaatca ggaagtcagt   3600
ttgaatttac tcagtttaga aaaccaagct acatattgca gaagagtaca tttgaagtgc   3660
ctgaaaacca gatgactatc ttaaagacca cttctgagga atgcagagat gctgatcttc   3720
atgtcataat gaatgcccca tcgattggtc aggtagacag cagcaagcaa tttgaaggta   3780
cagttgaaat taaacggaag tttgctggcc tgttgaaaaa tgactgtaac aaaagtgctt   3840
ctggttattt aacagatgaa aatgaagtgg ggtttagggg cttttattct gctcatggca   3900
caaaactgaa tgtttctact gaagctctgc aaaaagctgt gaaactgttt agtgatattg   3960
agaatattag tgaggaaact tctgcagagg tacatccaat aagtttatct tcaagtaaat   4020
gtcatgattc tgttgtttca atgtttaaga tagaaaatca taatgataaa actgtaagtg   4080
aaaaaaataa taaatgccaa ctgatattac aaaataatat tgaaatgact actggcactt   4140
ttgttgaaga aattactgaa aattacaaga gaaatactga aaatgaagat aacaaatata   4200
ctgctgccag tagaaattct cataacttag aatttgatgg cagtgattca agtaaaaatg   4260
atactgtttg tattcataaa gatgaaacgg acttgctatt tactgatcag cacaacatat   4320
gtcttaaatt atctggccag tttatgaagg agggaaacac tcagattaaa gaagatttgt   4380
cagatttaac tttttggaa gttgcgaaag ctcaagaagc atgtcatggt aatacttcaa   4440
ataaagaaca gttaactgct actaaaacgg agcaaaatat aaaagatttt gagacttctg   4500
atacattttt tcagactgca agtgggaaaa atattagtgt cgccaaagag tcatttaata   4560
aaattgtaaa tttctttgat cagaaaccag aagaattgca taacttttcc ttaaattctg   4620
aattacattc tgacataaga aagaacaaaa tggacattct aagttatgag gaaacagaca   4680
tagttaaaca caaaatactg aaagaaagtg tcccagttgg tactggaaat caactagtga   4740
ccttccaggg acaacccgaa cgtgatgaaa agatcaaaga acctactcta ttgggttttc   4800
atacagctag cgggaaaaaa gttaaaattg caaaggaatc tttggacaaa gtgaaaaacc   4860
tttttgatga aaaagagcaa ggtactagtg aaatcaccag ttttagccat caatgggcaa   4920
agaccctaaa gtacagagag gcctgtaaag accttgaatt agcatgtgag accattgaga   4980
tcacagctgc cccaaagtgt aaagaaatgc agaattctct caataatgat aaaaaccttg   5040
tttctattga gactgtggtg ccacctaagc tcttaagtga taatttatgt agacaaactg   5100
aaaatctcaa aacatcaaaa agtatctttt tgaaagttaa agtacatgaa aatgtagaaa   5160
aagaaacagc aaaaagtcct gcaacttgtt acacaaatca gtccccttat tcagtcattg   5220
aaaattcagc cttagctttt tacacaagtt gtagtagaaa aacttctgtg agtcagactt   5280
cattacttga agcaaaaaaa tggcttagag aaggaatatt tgatggtcaa ccagaaagaa   5340
taaatactgc agattatgta ggaaattatt tgtatgaaaa taattcaaac agtactatag   5400
ctgaaaatga caaaaatcat ctctccgaaa aacaagatac ttatttaagt aacagtagca   5460
```

tgtctaacag ctattcctac cattctgatg aggtatataa tgattcagga tatctctcaa 5520
aaaataaact tgattctggt attgagccag tattgaagaa tgttgaagat caaaaaaaca 5580
ctagtttttc caaagtaata tccaatgtaa aagatgcaaa tgcataccca caaactgtaa 5640
atgaagatat ttgcgttgag gaacttgtga ctagctcttc accctgcaaa aataaaaatg 5700
cagccattaa attgtccata tctaatagta ataattttga ggtagggcca cctgcattta 5760
ggatagccag tggtaaaatc gtttgtgttt cacatgaaac aattaaaaaa gtgaaagaca 5820
tatttacaga cagtttcagt aaagtaatta aggaaaacaa cgagaataaa tcaaaaattt 5880
gccaaacgaa aattatggca ggttgttacg aggcattgga tgattcagag gatattcttc 5940
ataactctct agataatgat gaatgtagca cgcattcaca taaggttttt gctgacattc 6000
agagtgaaga aattttacaa cataaccaaa atatgtctgg attggagaaa gtttctaaaa 6060
tatcaccttg tgatgttagt ttggaaactt cagatatatg taaatgtagt atagggaagc 6120
ttcataagtc agtctcatct gcaaatactt gtgggatttt tagcacagca agtggaaaat 6180
ctgtccaggt atcagatgct tcattacaaa acgcaagaca agtgttttct gaaatagaag 6240
atagtaccaa gcaagtcttt tccaaagtat tgtttaaaag taacgaacat tcagaccagc 6300
tcacaagaga agaaaatact gctatacgta ctccagaaca tttaatatcc caaaaaggct 6360
tttcatataa tgtggtaaat tcatctgctt tctctggatt tagtacagca agtggaaagc 6420
aagtttccat tttagaaagt tccttacaca aagttaaggg agtgttagag gaatttgatt 6480
taatcagaac tgagcatagt cttcactatt cacctacgtc tagacaaaat gtatcaaaaa 6540
tacttcctcg tgttgataag agaaacccag agcactgtgt aaactcagaa atggaaaaaa 6600
cctgcagtaa agaatttaaa ttatcaaata acttaaatgt tgaaggtggt tcttcagaaa 6660
ataatcactc tattaaagtt tctccatatc tctctcaatt tcaacaagac aaacaacagt 6720
tggtattagg aaccaaagtg tcacttgttg agaacattca tgttttggga aaagaacagg 6780
cttcacctaa aaacgtaaaa atggaaattg gtaaaactga aactttttct gatgttcctg 6840
tgaaaacaaa tatagaagtt tgttctactt actccaaaga ttcagaaaac tactttgaaa 6900
cagaagcagt agaaattgct aaagctttta tggaagatga tgaactgaca gattctaaac 6960
tgccaagtca tgccacacat tctcttttta catgtcccga aaatgaggaa atggttttgt 7020
caaattcaag aattggaaaa agaagaggag agccccttat cttagtggga gaaccctcaa 7080
tcaaaagaaa cttattaaat gaatttgaca ggataataga aaatcaagaa aaatccttaa 7140
aggcttcaaa aagcactcca gatggcacaa taaaagatcg aagattgttt atgcatcatg 7200
tttctttaga gccgattacc tgtgtaccct ttcgcacaac taaggaacgt caagagatac 7260
agaatccaaa ttttaccgca cctggtcaag aatttctgtc taaatctcat ttgtatgaac 7320
atctgacttt ggaaaaatct tcaagcaatt tagcagtttc aggacatcca ttttatcaag 7380
tttctgctac aagaaatgaa aaaatgagac acttgattac tacaggcaga ccaaccaaag 7440
tctttgttcc acctttaaa actaaatcac attttcacag agttgaacag tgtgttagga 7500
atattaactt ggaggaaaac agacaaaagc aaaacattga tggacatggc tctgatgata 7560
gtaaaaataa gattaatgac aatgagattc atcagtttaa caaaaacaac tccaatcaag 7620
cagcagctgt aactttcaca aagtgtgaag aagaaccttt agatttaatt acaagtcttc 7680
agaatgccag agatatacag gatatgcgaa ttaagaagaa acaaaggcaa cgcgtctttc 7740
cacagccagg cagtctgtat cttgcaaaaa catccactct gcctcgaatc tctctgaaag 7800
cagcagtagg aggccaagtt ccctctgcgt gttctcataa acagctgtat acgtatggcg 7860
tttctaaaca ttgcataaaa attaacagca aaaatgcaga gtcttttcag tttcacactg 7920
aagattattt tggtaaggaa agtttatgga ctggaaaagg aatacagttg gctgatggtg 7980
gatggctcat accctccaat gatggaaagg ctggaaaaga agaattttat agggctctgt 8040
gtgacactcc aggtgtggat ccaaagctta tttctagaat ttgggtttat aatcactata 8100
gatggatcat atggaaactg gcagctatgg aatgtgcctt tcctaaggaa tttgctaata 8160
gatgcctaag cccagaaagg gtgcttcttc aactaaaata cagatatgat acggaaattg 8220
atagaagcag aagatcggct ataaaaaaga taatggaaag ggatgacaca gctgcaaaaa 8280
cacttgttct ctgtgtttct gacataattt cattgagcgc aaatatatct gaaacttcta 8340
gcaataaaac tagtagtgca gatacccaaa aagtggccat tattgaactt acagatgggt 8400
ggtatgctgt taaggcccag ttagatcctc ccctcttagc tgtcttaaag aatggcagac 8460
tgacagttgg tcagaagatt attcttcatg gagcagaact ggtgggctct cctgatgcct 8520
gtacacctct tgaagcccca gaatctctta tgttaaagat ttctgctaac agtactcggc 8580
ctgctcgctg gtataccaaa cttggattct ttcctgaccc tagacctttt cctctgccct 8640
tatcatcgct tttcagtgat ggaggaaatg ttggttgtgt tgatgtaatt attcaaagag 8700 catacccctat acagtggatg gagaagacat catctggatt atacatattt cgcaatgaaa 8760
gagaggaaga aaaggaagca gcaaaatatg tggaggccca acaaaagaga ctagaagcct 8820
tattcactaa aattcaggag gaatttgaag aacatgaaga aaacacaaca aaaccatatt 8880
taccatcacg tgcactaaca agacagcaag ttcgtgcttt gcaagatggt gcagagcttt 8940
atgaagcagt gaagaatgca gcagacccag cttaccttga gggttatttc agtgaagagc 9000
agttaagagc cttgaataat cacaggcaaa tgttgaatga taagaaacaa gctcagatcc 9060
agttggaaat taggaaggcc atggaatctg ctgaacaaaa ggaacaaggt ttatcaaggg 9120
atgtcacaac cgtgtggaag ttgcgtattg taagctattc aaaaaaagaa aaagattcag 9180
ttatactgag tatttggcgt ccatcatcag atttatattc tctgttaaca gaaggaaaga 9240
gatacagaat ttatcatctt gcaacttcaa aatctaaaag taaatctgaa agagctaaca 9300
tacagttagc agcgacaaaa aaaactcagt atcaacaact accggtttca gatgaaattt 9360
tatttcagat ttaccagcca cgggagcccc ttcacttcag caaattttta gatccagact 9420
ttcagccatc ttgttctgag gtggacctaa taggatttgt cgtttctgtt gtgaaaaaaa 9480
caggacttgc ccctttcgtc tatttgtcag acgaatgtta caatttactg gcaataaagt 9540
tttggataga ccttaatgag gacattatta agcctcatat gttaattgct gcaagcaacc 9600
tccagtggcg accagaatcc aaatcaggcc ttcttacttt atttgctgga gatttttctg 9660
tgttttctgc tagtccaaaa gagggccact ttcaagagac attcaacaaa atgaaaaata 9720
ctgttgagaa tattgacata ctttgcaatg aagcagaaaa caagcttatg catatactgc 9780
atgcaaatga tcccaagtgg tccaccccaa ctaaagactg tacttcaggg ccgtacactg 9840
ctcaaatcat tcctggtaca ggaaacaagc ttctgatgtc ttctcctaat tgtgagatat 9900
attatcaaag tcctttatca ctttgtatgg ccaaaaggaa gtctgtttcc acacctgtct 9960
cagcccagat gacttcaaag tcttgtaaag gggagaaaga gattgatgac caaaagaact 10020
gcaaaaagag aagagccttg gatttcttga gtagactgcc tttacctcca cctgttagtc 10080
ccatttgtac atttgtttct ccggctgcac agaaggcatt tcagccacca aggagttgtg 10140
gcaccaaata cgaaacaccc ataaagaaaa aagaactgaa ttctcctcag atgactccat 10200

```
ttaaaaaatt caatgaaatt tctcttttgg aaagtaattc aatagctgac gaagaacttg  10260

cattgataaa tacccaagct cttttgtctg gttcaacagg agaaaaacaa tttatatctg  10320

tcagtgaatc cactaggact gctcccacca gttcagaaga ttatctcaga ctgaaacgac  10380

gttgtactac atctctgatc aaagaacagg agagttccca ggccagtacg gaagaatgtg  10440

agaaaaataa gcaggacaca attacaacta aaaaatatat ctaagcattt gcaaaggcga  10500

caataaatta ttgacgctta acctttccag tttataagac tggaatataa tttcaaacca  10560

cacattagta cttatgttgc acaatgagaa aagaaattag tttcaaattt acctcagcgt  10620

ttgtgtatcg ggcaaaaatc gttttgcccg attccgtatt ggtatacttt tgcttcagtt  10680

gcatatctta aaactaaatg taatttatta actaatcaag aaaaacatct ttggctgagc  10740

tcggtggctc atgcctgtaa tcccaacact ttgagaagct gaggtgggag gagtgcttga  10800

ggccaggagt tcaagaccag cctgggcaac atagggagac cccatcttt acaaagaaaa  10860

aaaaaagggg aaaagaaaat cttttaaatc tttggatttg atcactacaa gtattatttt  10920

acaagtgaaa taaacatacc attttctttt agattgtgtc attaaatgga atgaggtctc  10980

ttagtacagt tattttgatg cagataattc cttttagttt agctactatt ttaggggatt  11040

tttttagag gtaactcact atgaaatagt tctccttaat gcaaatatgt tggttctgct  11100

atagttccat cctgttcaaa agtcaggatg aatatgaaga gtggtgtttc cttttgagca  11160

attcttcatc cttaagtcag catgattata agaaaaatag aaccctcagt gtaactctaa  11220

ttccttttta ctattccagt gtgatctctg aaattaaatt acttcaacta aaaattcaaa  11280

tactttaaat cagaagattt catagttaat ttattttttt tttcaacaaa atggtcatcc  11340

aaactcaaac ttgagaaaat atcttgcttt caaattggca ctgatt                11386
```

<210> SEQ ID NO 27
<211> LENGTH: 633
<212> TYPE: PRT
<213> ORGANISM: Artificial Sequence
<220> FEATURE:
<223> OTHER INFORMATION: XRCC1 sequence

<400> SEQUENCE: 27

```
Met Pro Glu Ile Arg Leu Arg His Val Val Ser Cys Ser Ser Gln Asp
1               5                   10                  15

Ser Thr His Cys Ala Glu Asn Leu Leu Lys Ala Asp Thr Tyr Arg Lys
            20                  25                  30

Trp Arg Ala Ala Lys Ala Gly Glu Lys Thr Ile Ser Val Val Leu Gln
        35                  40                  45

Leu Glu Lys Glu Glu Gln Ile His Ser Val Asp Ile Gly Asn Asp Gly
    50                  55                  60

Ser Ala Phe Val Glu Val Leu Val Gly Ser Ser Ala Gly Gly Ala Gly
65                  70                  75                  80

Glu Gln Asp Tyr Glu Val Leu Leu Val Thr Ser Ser Phe Met Ser Pro
                85                  90                  95

Ser Glu Ser Arg Ser Gly Ser Asn Pro Asn Arg Val Arg Met Phe Gly
            100                 105                 110

Pro Asp Lys Leu Val Arg Ala Ala Ala Glu Lys Arg Trp Asp Arg Val
        115                 120                 125

Lys Ile Val Cys Ser Gln Pro Tyr Ser Lys Asp Ser Pro Phe Gly Leu
    130                 135                 140

Ser Phe Val Arg Phe His Ser Pro Pro Asp Lys Asp Glu Ala Glu Ala
```

-continued

```
145                 150                 155                 160

Pro Ser Gln Lys Val Thr Val Thr Lys Leu Gly Gln Phe Arg Val Lys
                165                 170                 175

Glu Glu Asp Glu Ser Ala Asn Ser Leu Arg Pro Gly Ala Leu Phe Phe
            180                 185                 190

Ser Arg Ile Asn Lys Thr Ser Pro Val Thr Ala Ser Asp Pro Ala Gly
        195                 200                 205

Pro Ser Tyr Ala Ala Ala Thr Leu Gln Ala Ser Ser Ala Ala Ser Ser
    210                 215                 220

Ala Ser Pro Val Ser Arg Ala Ile Gly Ser Thr Ser Lys Pro Gln Glu
225                 230                 235                 240

Ser Pro Lys Gly Lys Arg Lys Leu Asp Leu Asn Gln Glu Glu Lys Lys
                245                 250                 255

Thr Pro Ser Lys Pro Pro Ala Gln Leu Ser Pro Ser Val Pro Lys Arg
            260                 265                 270

Pro Lys Leu Pro Ala Pro Thr Arg Thr Pro Ala Thr Ala Pro Val Pro
        275                 280                 285

Ala Arg Ala Gln Gly Ala Val Thr Gly Lys Pro Arg Gly Glu Gly Thr
    290                 295                 300

Glu Pro Arg Arg Pro Arg Ala Gly Pro Glu Glu Leu Gly Lys Ile Leu
305                 310                 315                 320

Gln Gly Val Val Val Val Leu Ser Gly Phe Gln Asn Pro Phe Arg Ser
                325                 330                 335

Glu Leu Arg Asp Lys Ala Leu Glu Leu Gly Ala Lys Tyr Arg Pro Asp
            340                 345                 350

Trp Thr Arg Asp Ser Thr His Leu Ile Cys Ala Phe Ala Asn Thr Pro
        355                 360                 365

Lys Tyr Ser Gln Val Leu Gly Leu Gly Gly Arg Ile Val Arg Lys Glu
    370                 375                 380

Trp Val Leu Asp Cys His Arg Met Arg Arg Arg Leu Pro Ser Gln Arg
385                 390                 395                 400

Tyr Leu Met Ala Gly Pro Gly Ser Ser Ser Glu Glu Asp Glu Ala Ser
                405                 410                 415

His Ser Gly Gly Ser Gly Asp Glu Ala Pro Lys Leu Pro Gln Lys Gln
            420                 425                 430

Pro Gln Thr Lys Thr Lys Pro Thr Gln Ala Ala Gly Pro Ser Ser Pro
        435                 440                 445

Gln Lys Pro Pro Thr Pro Glu Glu Thr Lys Ala Ala Ser Pro Val Leu
    450                 455                 460

Gln Glu Asp Ile Asp Ile Glu Gly Val Gln Ser Glu Gly Gln Asp Asn
465                 470                 475                 480

Gly Ala Glu Asp Ser Gly Asp Thr Glu Asp Glu Leu Arg Arg Val Ala
                485                 490                 495

Glu Gln Lys Glu His Arg Leu Pro Pro Gly Gln Glu Glu Asn Gly Glu
            500                 505                 510

Asp Pro Tyr Ala Gly Ser Thr Asp Glu Asn Thr Asp Ser Glu Glu His
        515                 520                 525

Gln Glu Pro Pro Asp Leu Pro Val Pro Glu Leu Pro Asp Phe Phe Gln
    530                 535                 540

Gly Lys His Phe Phe Leu Tyr Gly Glu Phe Pro Gly Asp Glu Arg Arg
545                 550                 555                 560

Lys Leu Ile Arg Tyr Val Thr Ala Phe Asn Gly Glu Leu Glu Asp Tyr
                565                 570                 575
```

```
Met Ser Asp Arg Val Gln Phe Val Ile Thr Ala Gln Glu Trp Asp Pro
            580                 585                 590

Ser Phe Glu Glu Ala Leu Met Asp Asn Pro Ser Leu Ala Phe Val Arg
        595                 600                 605

Pro Arg Trp Ile Tyr Ser Cys Asn Glu Lys Gln Lys Leu Leu Pro His
    610                 615                 620

Gln Leu Tyr Gly Val Val Pro Gln Ala
625                 630


<210> SEQ ID NO 28
<211> LENGTH: 2102
<212> TYPE: DNA
<213> ORGANISM: Artificial Sequence
<220> FEATURE:
<223> OTHER INFORMATION: XRCC1 sequence

<400> SEQUENCE: 28

ctcgcgcgct tgcgcacttt agccagcgca gggcgcaccc cgccccctcc cactctccct      60

gcccctcgga ccccatactc tacctcatcc ttctggccag gcgaagccca cgacgttgac     120

atgccggaga tccgcctccg ccatgtcgtg tcctgcagca gccaggactc gactcactgt     180

gcagaaaatc ttctcaaggc agacacttac cgaaaatggc gggcagccaa ggcaggcgag     240

aagaccatct ctgtggtcct acagttggag aaggaggagc agatacacag tgtggacatt     300

gggaatgatg gctcagcttt cgtggaggtg ctggtgggca gttcagctgg aggcgctggg     360

gagcaagact atgaggtcct tctggtcacc tcatctttca tgtccccttc cgagagccgc     420

agtggctcaa accccaaccg cgttcgcatg tttgggcctg acaagctggt ccgggcagcc     480

gccgagaagc gctgggaccg ggtcaaaatt gtttgcagcc agccctacag caaggactcc     540

ccctttggct tgagttttgt acggtttcat agcccccccag acaaagatga ggcagaggcc     600

ccgtcccaga aggtgacagt gaccaagctt ggccagttcc gtgtgaagga ggaggatgag     660

agcgccaact ctctgaggcc gggggctctc ttcttcagcc ggatcaacaa gacatcccca     720

gtcacagcca gcgacccagc aggacctagc tatgcagctg ctaccctcca ggcttctagt     780

gctgcctcct cagcctctcc agtctccagg gccataggca gcacctccaa gccccaggag     840

tctcccaaag ggaagaggaa gttggatttg aaccaagaag aaaagaagac ccccagcaaa     900

ccaccagccc agctgtcgcc atctgttccc aagagaccta aattgccagc tccaactcgt     960

accccagcca cagccccagt ccctgcccga gcacaggggg cagtgacagg caaaccccga    1020

ggagaaggca ccgagcccag acgaccccga gctggcccag aggagctggg gaagatcctt    1080

cagggtgtgg tagtggtgct gagtggcttc cagaacccct tccgctccga gctgcgagat    1140

aaggccctag agcttggggc caagtatcgg ccagactgga cccgggacag cacgcacctc    1200

atctgtgcct ttgccaacac ccccaagtac agccaggtcc taggcctggg aggccgcatc    1260

gtgcgtaagg agtgggtgct ggactgtcac cgcatgcgtc ggcggctgcc ctcccagagg    1320

tacctcatgg cagggccagg ttccagcagt gaggaggatg aggcctctca cagcggtggc    1380

agcggagatg aagcccccaa gcttcctcag aagcaacccc agaccaaaac caagcccact    1440

caggcagctg gacccagctc accccagaag cccccaaccc ctgaagagac caaagcagcc    1500

tcaccagtgc tccaggaaga tatagacatt gagggggtac agtcagaagg acaggacaat    1560

ggggcggaag attctgggga cacagaggat gagctgagga gggtggcaga gcagaaggaa    1620

cacagactgc cccctggcca ggaggagaat ggggaagacc cgtatgcagg ctccacggat    1680
```

-continued

```
gagaacacgg acagtgagga acaccaggag cctcctgatc tgccagtccc tgagctccca   1740

gatttcttcc agggcaagca cttctttctt tacggggagt tccctgggga cgagcggcgg   1800

aaactcatcc gatacgtcac agccttcaat ggggagctcg aggactatat gagtgaccgg   1860

gttcagtttg tgatcacagc acaggaatgg gatcccagct ttgaggaggc cctgatggac   1920

aacccctccc tggcattcgt tcgtccccga tggatctaca gttgcaatga gaagcagaag   1980

ttacttcctc accagctcta tggggtggtg ccgcaagcct gaagtatgtg ctatacacac   2040

acacacacac acacacacac acacacacac acgatgcatt taataaagat gagttggttc   2100

tc                                                                  2102


<210> SEQ ID NO 29
<211> LENGTH: 189
<212> TYPE: PRT
<213> ORGANISM: Artificial Sequence
<220> FEATURE:
<223> OTHER INFORMATION: KRAS sequence

<400> SEQUENCE: 29

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185


<210> SEQ ID NO 30
<211> LENGTH: 5436
<212> TYPE: DNA
<213> ORGANISM: Artificial Sequence
<220> FEATURE:
<223> OTHER INFORMATION: KRAS sequence

<400> SEQUENCE: 30

ggccgcggcg gcggaggcag cagcggcggc ggcagtggcg gcggcgaagg tggcggcggc     60

tcggccagta ctcccggccc ccgccatttc ggactgggag cgagcgcggc gcaggcactg    120

aaggcggcgg cggggccaga ggctcagcgg ctcccaggtg cgggagagag gcctgctgaa    180

aatgactgaa tataaacttg tggtagttgg agctggtggc gtaggcaaga gtgccttgac    240
```

```
gatacagcta attcagaatc attttgtgga cgaatatgat ccaacaatag aggattccta    300
caggaagcaa gtagtaattg atggagaaac ctgtctcttg gatattctcg acacagcagg    360
tcaagaggag tacagtgcaa tgagggacca gtacatgagg actggggagg gctttctttg    420
tgtatttgcc ataaataata ctaaatcatt tgaagatatt caccattata gagaacaaat    480
taaaagagtt aaggactctg aagatgtacc tatggtccta gtaggaaata aatgtgattt    540
gccttctaga acagtagaca caaaacaggc tcaggactta gcaagaagtt atggaattcc    600
ttttattgaa acatcagcaa agacaagaca gagagtggag gatgcttttt atacattggt    660
gagggagatc cgacaataca gattgaaaaa aatcagcaaa gaagaaaaga ctcctggctg    720
tgtgaaaatt aaaaaatgca ttataatgta atctgggtgt tgatgatgcc ttctatacat    780
tagttcgaga aattcgaaaa cataaagaaa agatgagcaa agatggtaaa aagaagaaaa    840
agaagtcaaa gacaaagtgt gtaattatgt aaatacaatt tgtacttttt tcttaaggca    900
tactagtaca agtggtaatt tttgtacatt acactaaatt attagcattt gttttagcat    960
tacctaattt ttttcctgct ccatgcagac tgttagcttt taccttaaat gcttatttta   1020
aaatgacagt ggaagttttt ttttcctcta agtgccagta ttcccagagt tttggttttt   1080
gaactagcaa tgcctgtgaa aaagaaactg aatacctaag atttctgtct tggggttttt   1140
ggtgcatgca gttgattact tcttattttt cttaccaatt gtgaatgttg gtgtgaaaca   1200
aattaatgaa gcttttgaat catccctatt ctgtgtttta tctagtcaca taaatggatt   1260
aattactaat ttcagttgag accttctaat tggtttttac tgaaacattg agggaacaca   1320
aatttatggg cttcctgatg atgattcttc taggcatcat gtcctatagt ttgtcatccc   1380
tgatgaatgt aaagttacac tgttcacaaa ggttttgtct cctttccact gctattagtc   1440
atggtcactc tccccaaaat attatatttt ttctataaaa agaaaaaaat ggaaaaaaat   1500
tacaaggcaa tggaaactat tataaggcca tttccttttc acattagata aattactata   1560
aagactccta atagcttttc ctgttaaggc agacccagta tgaaatgggg attattatag   1620
caaccatttt ggggctatat ttacatgcta ctaaattttt ataataattg aaaagatttt   1680
aacaagtata aaaaattctc ataggaatta aatgtagtct ccctgtgtca gactgctctt   1740
tcatagtata actttaaatc ttttcttcaa cttgagtctt tgaagatagt tttaattctg   1800
cttgtgacat taaaagatta tttgggccag ttatagctta ttaggtgttg aagagaccaa   1860
ggttgcaagg ccaggccctg tgtgaacctt tgagctttca tagagagttt cacagcatgg   1920
actgtgtccc cacggtcatc cagtgttgtc atgcattggt tagtcaaaat ggggagggac   1980
tagggcagtt tggatagctc aacaagatac aatctcactc tgtggtggtc ctgctgacaa   2040
atcaagagca ttgcttttgt ttcttaagaa aacaaactct tttttaaaaa ttacttttaa   2100
atattaactc aaaagttgag attttggggt ggtggtgtgc caagacatta attttttttt   2160
taaacaatga agtgaaaaag ttttacaatc tctaggtttg gctagttctc ttaacactgg   2220
ttaaattaac attgcataaa cacttttcaa gtctgatcca tatttaataa tgctttaaaa   2280
taaaaataaa aacaatcctt ttgataaatt taaaatgtta cttattttaa aataaatgaa   2340
gtgagatggc atggtgaggt gaaagtatca ctggactagg aagaaggtga cttaggttct   2400
agataggtgt cttttaggac tctgattttg aggacatcac ttactatcca tttcttcatg   2460
ttaaaagaag tcatctcaaa ctcttagttt ttttttttta caactatgta atttatattc   2520
catttacata aggatacact tatttgtcaa gctcagcaca atctgtaaat ttttaaccta   2580
```

-continued

```
tgttacacca tcttcagtgc cagtcttggg caaaattgtg caagaggtga agtttatatt   2640
tgaatatcca ttctcgtttt aggactcttc ttccatatta gtgtcatctt gcctccctac   2700
cttccacatg ccccatgact tgatgcagtt ttaatacttg taattcccct aaccataaga   2760
tttactgctg ctgtggatat ctccatgaag ttttcccact gagtcacatc agaaatgccc   2820
tacatcttat ttcctcaggg ctcaagagaa tctgacagat accataaagg gatttgacct   2880
aatcactaat tttcaggtgg tggctgatgc tttgaacatc tctttgctgc ccaatccatt   2940
agcgacagta ggatttttca aacctggtat gaatagacag aaccctatcc agtggaagga   3000
gaatttaata aagatagtgc tgaaagaatt ccttaggtaa tctataacta ggactactcc   3060
tggtaacagt aatacattcc attgttttag taaccagaaa tcttcatgca atgaaaaata   3120
ctttaattca tgaagcttac tttttttttt tggtgtcaga gtctcgctct tgtcacccag   3180
gctggaatgc agtggcgcca tctcagctca ctgcaacctc catctcccag gttcaagcga   3240
ttctcgtgcc tcggcctcct gagtagctgg gattacaggc gtgtgccact acactcaact   3300
aatttttgta tttttaggag agacggggtt tcaccctgtt ggccaggctg gtctcgaact   3360
cctgacctca agtgattcac ccaccttggc ctcataaacc tgttttgcag aactcattta   3420
ttcagcaaat atttattgag tgcctaccag atgccagtca ccgcacaagg cactgggtat   3480
atggtatccc caaacaagag acataatccc ggtccttagg tagtgctagt gtggtctgta   3540
atatcttact aaggcctttg gtatacgacc cagagataac acgatgcgta ttttagtttt   3600
gcaaagaagg ggtttggtct ctgtgccagc tctataattg ttttgctacg attccactga   3660
aactcttcga tcaagctact ttatgtaaat cacttcattg ttttaaagga ataaacttga   3720
ttatattgtt tttttatttg gcataactgt gattctttta ggacaattac tgtacacatt   3780
aaggtgtatg tcagatattc atattgaccc aaatgtgtaa tattccagtt ttctctgcat   3840
aagtaattaa aatatactta aaaattaata gttttatctg ggtacaaata aacaggtgcc   3900
tgaactagtt cacagacaag gaaacttcta tgtaaaaatc actatgattt ctgaattgct   3960
atgtgaaact acagatcttt ggaacactgt ttaggtaggg tgttaagact tacacagtac   4020
ctcgtttcta cacagagaaa gaaatggcca tacttcagga actgcagtgc ttatgagggg   4080
atatttaggc ctcttgaatt tttgatgtag atgggcattt ttttaaggta gtggttaatt   4140
acctttatgt gaactttgaa tggtttaaca aaagatttgt ttttgtagag attttaaagg   4200
gggagaattc tagaaataaa tgttacctaa ttattacagc cttaaagaca aaaatccttg   4260
ttgaagtttt tttaaaaaaa gctaaattac atagacttag gcattaacat gtttgtggaa   4320
gaatatagca gacgtatatt gtatcatttg agtgaatgtt cccaagtagg cattctaggc   4380
tctatttaac tgagtcacac tgcataggaa tttagaacct aacttttata ggttatcaaa   4440
actgttgtca ccattgcaca attttgtcct aatatataca tagaaacttt gtggggcatg   4500
ttaagttaca gtttgcacaa gttcatctca tttgtattcc attgattttt tttttcttct   4560
aaacattttt tcttcaaaca gtatataact ttttttaggg gattttttttt tagacagcaa   4620
aaactatctg aagatttcca tttgtcaaaa agtaatgatt tcttgataat tgtgtagtaa   4680
tgttttttag aacccagcag ttaccttaaa gctgaattta tatttagtaa cttctgtgtt   4740
aatactggat agcatgaatt ctgcattgag aaactgaata gctgtcataa aatgaaactt   4800
tctttctaaa gaaagatact cacatgagtt cttgaagaat agtcataact agattaagat   4860
ctgtgtttta gtttaatagt ttgaagtgcc tgtttgggat aatgataggt aatttagatg   4920
aatttagggg aaaaaaaagt tatctgcaga tatgttgagg gcccatctct ccccccacac   4980
```

```
ccccacagag ctaactgggt tacagtgttt tatccgaaag tttccaattc cactgtcttg   5040

tgttttcatg ttgaaaatac ttttgcattt ttcctttgag tgccaatttc ttactagtac   5100

tatttcttaa tgtaacatgt ttacctggaa tgtattttaa ctatttttgt atagtgtaaa   5160

ctgaaacatg cacattttgt acattgtgct ttcttttgtg ggacatatgc agtgtgatcc   5220

agttgttttc catcatttgg ttgcgctgac ctaggaatgt tggtcatatc aaacattaaa   5280

aatgaccact cttttaattg aaattaactt ttaaatgttt ataggagtat gtgctgtgaa   5340

gtgatctaaa atttgtaata tttttgtcat gaactgtact actcctaatt attgtaatgt   5400

aataaaaata gttacagtga caaaaaaaaa aaaaaa                             5436


<210> SEQ ID NO 31
<211> LENGTH: 766
<212> TYPE: PRT
<213> ORGANISM: Artificial Sequence
<220> FEATURE:
<223> OTHER INFORMATION: BRAF sequence

<400> SEQUENCE: 31

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
    50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
    130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
    210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
```

-continued

```
        275                 280                 285

Leu Phe Val Ser Lys Phe Phe Glu His His Pro Ile Pro Gln Glu Glu
    290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg
    370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Lys Arg Asp Glu Arg
    690                 695                 700
```

```
Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765


<210> SEQ ID NO 32
<211> LENGTH: 2949
<212> TYPE: DNA
<213> ORGANISM: Artificial Sequence
<220> FEATURE:
<223> OTHER INFORMATION: BRAF sequence

<400> SEQUENCE: 32

cgcctccctt cccccctccc gcccgacagc ggccgctcgg gccccggctc tcggttataa     60

gatggcggcg ctgagcggtg gcggtggtgg cggcgcggag ccgggccagg ctctgttcaa    120

cggggacatg gagcccgagg ccggcgccgg cgccggcgcc gcggcctctt cggctgcgga    180

ccctgccatt ccggaggagg tgtggaatat caaacaaatg attaagttga cacaggaaca    240

tatagaggcc ctattggaca aatttggtgg ggagcataat ccaccatcaa tatatctgga    300

ggcctatgaa gaatacacca gcaagctaga tgcactccaa caaagagaac aacagttatt    360

ggaatctctg gggaacggaa ctgatttttc tgtttctagc tctgcatcaa tggataccgt    420

tacatcttct tcctcttcta gcctttcagt gctaccttca tctctttcag tttttcaaaa    480

tcccacagat gtggcacgga gcaaccccaa gtcaccacaa aaacctatcg ttagagtctt    540

cctgcccaac aaacagagga cagtggtacc tgcaaggtgt ggagttacag tccgagacag    600

tctaaagaaa gcactgatga tgagaggtct aatcccagag tgctgtgctg tttacagaat    660

tcaggatgga gagaagaaac caattggttg ggacactgat atttcctggc ttactggaga    720

agaattgcat gtggaagtgt tggagaatgt tccacttaca acacacaact ttgtacgaaa    780

aacgtttttc accttagcat tttgtgactt ttgtcgaaag ctgcttttcc agggtttccg    840

ctgtcaaaca tgtggttata aatttcacca gcgttgtagt acagaagttc cactgatgtg    900

tgttaattat gaccaacttg atttgctgtt tgtctccaag ttctttgaac accacccaat    960

accacaggaa gaggcgtcct tagcagagac tgccctaaca tctggatcat ccccttccgc   1020

acccgcctcg gactctattg ggccccaaat tctcaccagt ccgtctcctt caaaatccat   1080

tccaattcca cagcccttcc gaccagcaga tgaagatcat cgaaatcaat ttgggcaacg   1140

agaccgatcc tcatcagctc ccaatgtgca tataaacaca atagaacctg tcaatattga   1200

tgacttgatt agagaccaag gatttcgtgg tgatggagga tcaaccacag gtttgtctgc   1260

taccccccct gcctcattac ctggctcact aactaacgtg aaagccttac agaaatctcc   1320

aggacctcag cgagaaagga agtcatcttc atcctcagaa gacaggaatc gaatgaaaac   1380

acttggtaga cgggactcga gtgatgattg ggagattcct gatgggcaga ttacagtggg   1440

acaaagaatt ggatctggat catttggaac agtctacaag ggaaagtggc atggtgatgt   1500

ggcagtgaaa atgttgaatg tgacagcacc tacacctcag cagttacaag ccttcaaaaa   1560

tgaagtagga gtactcagga aaacacgaca tgtgaatatc ctactcttca tgggctattc   1620

cacaaagcca caactggcta ttgttaccca gtggtgtgag ggctccagct tgtatcacca   1680
```

tctccatatc attgagacca aatttgagat gatcaaactt atagatattg cacgacagac 1740
tgcacagggc atggattact tacacgccaa gtcaatcatc cacagagacc tcaagagtaa 1800
taatatattt cttcatgaag acctcacagt aaaaataggt gattttggtc tagctacagt 1860
gaaatctcga tggagtgggt cccatcagtt tgaacagttg tctggatcca ttttgtggat 1920
ggcaccagaa gtcatcagaa tgcaagataa aaatccatac agctttcagt cagatgtata 1980
tgcatttgga attgttctgt atgaattgat gactggacag ttaccttatt caaacatcaa 2040
caacagggac cagataattt ttatggtggg acgaggatac ctgtctccag atctcagtaa 2100
ggtacggagt aactgtccaa aagccatgaa gagattaatg gcagagtgcc tcaaaaagaa 2160
aagagatgag agaccactct ttccccaaat tctcgcctct attgagctgc tggcccgctc 2220
attgccaaaa attcaccgca gtgcatcaga accctccttg aatcgggctg gtttccaaac 2280
agaggatttt agtctatatg cttgtgcttc tccaaaaaca cccatccagg caggggggata 2340 tggtgcgttt cctgtccact gaaacaaatg agtgagagag ttcaggagag tagcaacaaa 2400
aggaaaataa atgaacatat gtttgcttat atgttaaatt gaataaaata ctctcttttt 2460
ttttaaggtg aaccaaagaa cacttgtgtg gttaaagact agatataatt tttccccaaa 2520
ctaaaattta tacttaacat tggattttta acatccaagg gttaaaatac atagacattg 2580
ctaaaaattg gcagagcctc ttctagaggc tttactttct gttccgggtt tgtatcattc 2640
acttggttat tttaagtagt aaacttcagt ttctcatgca acttttgttg ccagctatca 2700
catgtccact agggactcca gaagaagacc ctacctatgc ctgtgtttgc aggtgagaag 2760
ttggcagtcg gttagcctgg gttagataag gcaaactgaa cagatctaat ttaggaagtc 2820
agtagaattt aataattcta ttattattct taataatttt tctataacta tttcttttta 2880
taacaatttg gaaaatgtgg atgtctttta tttccttgaa gcaataaact aagtttcttt 2940
ttataaaaa 2949

<210> SEQ ID NO 33
<211> LENGTH: 1312
<212> TYPE: PRT
<213> ORGANISM: Artificial Sequence
<220> FEATURE:
<223> OTHER INFORMATION: RAD50 sequence

<400> SEQUENCE: 33

Met Ser Arg Ile Glu Lys Met Ser Ile Leu Gly Val Arg Ser Phe Gly
1 5 10 15

Ile Glu Asp Lys Asp Lys Gln Ile Ile Thr Phe Phe Ser Pro Leu Thr
20 25 30

Ile Leu Val Gly Pro Asn Gly Ala Gly Lys Thr Thr Ile Ile Glu Cys
35 40 45

Leu Lys Tyr Ile Cys Thr Gly Asp Phe Pro Pro Gly Thr Lys Gly Asn
50 55 60

Thr Phe Val His Asp Pro Lys Val Ala Gln Glu Thr Asp Val Arg Ala
65 70 75 80

Gln Ile Arg Leu Gln Phe Arg Asp Val Asn Gly Glu Leu Ile Ala Val
85 90 95

Gln Arg Ser Met Val Cys Thr Gln Lys Ser Lys Lys Thr Glu Phe Lys
100 105 110

Thr Leu Glu Gly Val Ile Thr Arg Thr Lys His Gly Glu Lys Val Ser
115 120 125

Leu Ser Ser Lys Cys Ala Glu Ile Asp Arg Glu Met Ile Ser Ser Leu

```
    130                 135                 140

Gly Val Ser Lys Ala Val Leu Asn Asn Val Ile Phe Cys His Gln Glu
145                 150                 155                 160

Asp Ser Asn Trp Pro Leu Ser Glu Gly Lys Ala Leu Lys Gln Lys Phe
                165                 170                 175

Asp Glu Ile Phe Ser Ala Thr Arg Tyr Ile Lys Ala Leu Glu Thr Leu
            180                 185                 190

Arg Gln Val Arg Gln Thr Gln Gly Gln Lys Val Lys Glu Tyr Gln Met
        195                 200                 205

Glu Leu Lys Tyr Leu Lys Gln Tyr Lys Glu Lys Ala Cys Glu Ile Arg
    210                 215                 220

Asp Gln Ile Thr Ser Lys Glu Ala Gln Leu Thr Ser Ser Lys Glu Ile
225                 230                 235                 240

Val Lys Ser Tyr Glu Asn Glu Leu Asp Pro Leu Lys Asn Arg Leu Lys
                245                 250                 255

Glu Ile Glu His Asn Leu Ser Lys Ile Met Lys Leu Asp Asn Glu Ile
            260                 265                 270

Lys Ala Leu Asp Ser Arg Lys Lys Gln Met Glu Lys Asp Asn Ser Glu
        275                 280                 285

Leu Glu Glu Lys Met Glu Lys Val Phe Gln Gly Thr Asp Glu Gln Leu
    290                 295                 300

Asn Asp Leu Tyr His Asn His Gln Arg Thr Val Arg Glu Lys Glu Arg
305                 310                 315                 320

Lys Leu Val Asp Cys His Arg Glu Leu Glu Lys Leu Asn Lys Glu Ser
                325                 330                 335

Arg Leu Leu Asn Gln Glu Lys Ser Glu Leu Leu Val Glu Gln Gly Arg
            340                 345                 350

Leu Gln Leu Gln Ala Asp Arg His Gln Glu His Ile Arg Ala Arg Asp
        355                 360                 365

Ser Leu Ile Gln Ser Leu Ala Thr Gln Leu Glu Leu Asp Gly Phe Glu
    370                 375                 380

Arg Gly Pro Phe Ser Glu Arg Gln Ile Lys Asn Phe His Lys Leu Val
385                 390                 395                 400

Arg Glu Arg Gln Glu Gly Glu Ala Lys Thr Ala Asn Gln Leu Met Asn
                405                 410                 415

Asp Phe Ala Glu Lys Glu Thr Leu Lys Gln Lys Gln Ile Asp Glu Ile
            420                 425                 430

Arg Asp Lys Lys Thr Gly Leu Gly Arg Ile Ile Glu Leu Lys Ser Glu
        435                 440                 445

Ile Leu Ser Lys Lys Gln Asn Glu Leu Lys Asn Val Lys Tyr Glu Leu
    450                 455                 460

Gln Gln Leu Glu Gly Ser Ser Asp Arg Ile Leu Glu Leu Asp Gln Glu
465                 470                 475                 480

Leu Ile Lys Ala Glu Arg Glu Leu Ser Lys Ala Glu Lys Asn Ser Asn
                485                 490                 495

Val Glu Thr Leu Lys Met Glu Val Ile Ser Leu Gln Asn Glu Lys Ala
            500                 505                 510

Asp Leu Asp Arg Thr Leu Arg Lys Leu Asp Gln Glu Met Glu Gln Leu
        515                 520                 525

Asn His His Thr Thr Thr Arg Thr Gln Met Glu Met Leu Thr Lys Asp
    530                 535                 540

Lys Ala Asp Lys Asp Glu Gln Ile Arg Lys Ile Lys Ser Arg His Ser
545                 550                 555                 560
```

```
Asp Glu Leu Thr Ser Leu Leu Gly Tyr Phe Pro Asn Lys Lys Gln Leu
                565                 570                 575

Glu Asp Trp Leu His Ser Lys Ser Lys Glu Ile Asn Gln Thr Arg Asp
            580                 585                 590

Arg Leu Ala Lys Leu Asn Lys Glu Leu Ala Ser Ser Glu Gln Asn Lys
        595                 600                 605

Asn His Ile Asn Asn Glu Leu Lys Arg Lys Glu Glu Gln Leu Ser Ser
    610                 615                 620

Tyr Glu Asp Lys Leu Phe Asp Val Cys Gly Ser Gln Asp Phe Glu Ser
625                 630                 635                 640

Asp Leu Asp Arg Leu Lys Glu Glu Ile Glu Lys Ser Ser Lys Gln Arg
                645                 650                 655

Ala Met Leu Ala Gly Ala Thr Ala Val Tyr Ser Gln Phe Ile Thr Gln
            660                 665                 670

Leu Thr Asp Glu Asn Gln Ser Cys Cys Pro Val Cys Gln Arg Val Phe
        675                 680                 685

Gln Thr Glu Ala Glu Leu Gln Glu Val Ile Ser Asp Leu Gln Ser Lys
    690                 695                 700

Leu Arg Leu Ala Pro Asp Lys Leu Lys Ser Thr Glu Ser Glu Leu Lys
705                 710                 715                 720

Lys Lys Glu Lys Arg Arg Asp Glu Met Leu Gly Leu Val Pro Met Arg
                725                 730                 735

Gln Ser Ile Ile Asp Leu Lys Glu Lys Glu Ile Pro Glu Leu Arg Asn
            740                 745                 750

Lys Leu Gln Asn Val Asn Arg Asp Ile Gln Arg Leu Lys Asn Asp Ile
        755                 760                 765

Glu Glu Gln Glu Thr Leu Leu Gly Thr Ile Met Pro Glu Glu Glu Ser
    770                 775                 780

Ala Lys Val Cys Leu Thr Asp Val Thr Ile Met Glu Arg Phe Gln Met
785                 790                 795                 800

Glu Leu Lys Asp Val Glu Arg Lys Ile Ala Gln Gln Ala Ala Lys Leu
                805                 810                 815

Gln Gly Ile Asp Leu Asp Arg Thr Val Gln Gln Val Asn Gln Glu Lys
            820                 825                 830

Gln Glu Lys Gln His Lys Leu Asp Thr Val Ser Ser Lys Ile Glu Leu
        835                 840                 845

Asn Arg Lys Leu Ile Gln Asp Gln Gln Glu Gln Ile Gln His Leu Lys
    850                 855                 860

Ser Thr Thr Asn Glu Leu Lys Ser Glu Lys Leu Gln Ile Ser Thr Asn
865                 870                 875                 880

Leu Gln Arg Arg Gln Gln Leu Glu Glu Gln Thr Val Glu Leu Ser Thr
                885                 890                 895

Glu Val Gln Ser Leu Tyr Arg Glu Ile Lys Asp Ala Lys Glu Gln Val
            900                 905                 910

Ser Pro Leu Glu Thr Thr Leu Glu Lys Phe Gln Gln Glu Lys Glu Glu
        915                 920                 925

Leu Ile Asn Lys Lys Asn Thr Ser Asn Lys Ile Ala Gln Asp Lys Leu
    930                 935                 940

Asn Asp Ile Lys Glu Lys Val Lys Asn Ile His Gly Tyr Met Lys Asp
945                 950                 955                 960

Ile Glu Asn Tyr Ile Gln Asp Gly Lys Asp Asp Tyr Lys Lys Gln Lys
                965                 970                 975
```

```
Glu Thr Glu Leu Asn Lys Val Ile Ala Gln Leu Ser Glu Cys Glu Lys
            980                 985                 990

His Lys Glu Lys Ile Asn Glu Asp  Met Arg Leu Met Arg  Gln Asp Ile
        995                 1000                1005

Asp Thr  Gln Lys Ile Gln Glu  Arg Trp Leu Gln Asp  Asn Leu Thr
    1010                 1015                 1020

Leu Arg  Lys Arg Asn Glu Glu  Leu Lys Glu Val Glu  Glu Glu Arg
    1025                 1030                 1035

Lys Gln  His Leu Lys Glu Met  Gly Gln Met Gln Val  Leu Gln Met
    1040                 1045                 1050

Lys Ser  Glu His Gln Lys Leu  Glu Glu Asn Ile Asp  Asn Ile Lys
    1055                 1060                 1065

Arg Asn  His Asn Leu Ala Leu  Gly Arg Gln Lys Gly  Tyr Glu Glu
    1070                 1075                 1080

Glu Ile  Ile His Phe Lys Lys  Glu Leu Arg Glu Pro  Gln Phe Arg
    1085                 1090                 1095

Asp Ala  Glu Glu Lys Tyr Arg  Glu Met Met Ile Val  Met Arg Thr
    1100                 1105                 1110

Thr Glu  Leu Val Asn Lys Asp  Leu Asp Ile Tyr Tyr  Lys Thr Leu
    1115                 1120                 1125

Asp Gln  Ala Ile Met Lys Phe  His Ser Met Lys Met  Glu Glu Ile
    1130                 1135                 1140

Asn Lys  Ile Ile Arg Asp Leu  Trp Arg Ser Thr Tyr  Arg Gly Gln
    1145                 1150                 1155

Asp Ile  Glu Tyr Ile Glu Ile  Arg Ser Asp Ala Asp  Glu Asn Val
    1160                 1165                 1170

Ser Ala  Ser Asp Lys Arg Arg  Asn Tyr Asn Tyr Arg  Val Val Met
    1175                 1180                 1185

Leu Lys  Gly Asp Thr Ala Leu  Asp Met Arg Gly Arg  Cys Ser Ala
    1190                 1195                 1200

Gly Gln  Lys Val Leu Ala Ser  Leu Ile Ile Arg Leu  Ala Leu Ala
    1205                 1210                 1215

Glu Thr  Phe Cys Leu Asn Cys  Gly Ile Ile Ala Leu  Asp Glu Pro
    1220                 1225                 1230

Thr Thr  Asn Leu Asp Arg Glu  Asn Ile Glu Ser Leu  Ala His Ala
    1235                 1240                 1245

Leu Val  Glu Ile Ile Lys Ser  Arg Ser Gln Gln Arg  Asn Phe Gln
    1250                 1255                 1260

Leu Leu  Val Ile Thr His Asp  Glu Asp Phe Val Glu  Leu Leu Gly
    1265                 1270                 1275

Arg Ser  Glu Tyr Val Glu Lys  Phe Tyr Arg Ile Lys  Lys Asn Ile
    1280                 1285                 1290

Asp Gln  Cys Ser Glu Ile Val  Lys Cys Ser Val Ser  Ser Leu Gly
    1295                 1300                 1305

Phe Asn  Val His
    1310
```

<210> SEQ ID NO 34
<211> LENGTH: 6597
<212> TYPE: DNA
<213> ORGANISM: Artificial Sequence
<220> FEATURE:
<223> OTHER INFORMATION: RAD50 sequence

<400> SEQUENCE: 34

-continued

```
tttcccggcg tgccccagga gagcggcgtg gacgcgtgcg ggcctagagg cccacgtgat      60
ccgcagggcg gccgaggcag gaagctgtga gtgcgcggtt gcggggtcgc attgtggcta     120
cggctttgcg tccccggcgg gcagccccag gctggtcccc gcctccgctc tccccaccgg     180
cggggaaagc agctggtgtg ggaggaaagg ctccatcccc cgccccctct ctcccgctgt     240
tggctggcag gatcttttgg cagtcctgtg gcctcgctcc ccgcccggat cctcctgacc     300
ctgagattcg cgggtctcac gtcccgtgca cgccttgctt cggcctcagt taagcctttg     360
tggactccag gtccctggtg agattagaaa cgtttgcaaa catgtcccgg atcgaaaaga     420
tgagcattct gggcgtgcgg agttttggaa tagaggacaa agataagcaa attatcactt     480
tcttcagccc ccttacaatt ttggttggac ccaatggggc gggaaagacg accatcattg     540
aatgtctaaa atatatttgt actggagatt tccctcctgg aaccaaagga aatacatttg     600
tacacgatcc caaggttgct caagaaacag atgtgagagc ccagattcgt ctgcaatttc     660
gtgatgtcaa tggagaactt atagctgtgc aaagatctat ggtgtgtact cagaaaagca     720
aaaagacaga atttaaaact ctggaaggag tcattactag aacaaagcat ggtgaaaagg     780
tcagtctgag ctctaagtgt gcagaaattg accgagaaat gatcagttct cttggggttt     840
ccaaggctgt gctaaataat gtcattttct gtcatcaaga agattctaat tggccttttaa    900
gtgaaggaaa ggctttgaag caaaagtttg atgagatttt ttcagcaaca agatacatta     960
aagccttaga aacacttcgg caggtacgtc agacacaagg tcagaaagta aaagaatatc    1020
aaatggaact aaaatatctg aagcaatata aggaaaaagc ttgtgagatt cgtgatcaga    1080
ttacaagtaa ggaagcccag ttaacatctt caaaggaaat tgtcaaatcc tatgagaatg    1140
aacttgatcc attgaagaat cgtctaaaag aaattgaaca taatctctct aaaataatga    1200
aacttgacaa tgaaattaaa gccttggata gccgaaagaa gcaaatggag aaagataata    1260
gtgaactgga agagaaaatg gaaaaggttt ttcaagggac tgatgagcaa ctaaatgact    1320
tatatcacaa tcaccagaga acagtaaggg agaaagaaag gaaattggta gactgtcatc    1380
gtgaactgga aaaactaaat aaagaatcta ggcttctcaa tcaggaaaaa tcagaactgc    1440
ttgttgaaca gggtcgtcta cagctgcaag cagatcgcca tcaagaacat atccgagcta    1500
gagattcatt aattcagtct ttggcaacac agctagaatt ggatggcttt gagcgtggac    1560
cattcagtga aagacagatt aaaaattttc acaaacttgt gagagagaga caagaagggg    1620
aagcaaaaac tgccaaccaa ctgatgaatg actttgcaga aaaagagact ctgaaacaaa    1680
aacagataga tgagataaga gataagaaaa ctggactggg aagaataatt gagttaaaat    1740
cagaaatcct aagtaagaag cagaatgagc tgaaaaatgt gaagtatgaa ttacagcagt    1800
tggaaggatc ttcagacagg attcttgaac tggaccagga gctcataaaa gctgaacgtg    1860
agttaagcaa ggctgagaaa aacagcaatg tagaaacctt aaaaatggaa gtaataagtc    1920
tccaaaatga aaaagcagac ttagacagga ccctgcgtaa acttgaccag gagatggagc    1980
agttaaacca tcatacaaca acacgtaccc aaatggagat gctgaccaaa gacaaagctg    2040
acaaagatga acaaatcaga aaaataaaat ctaggcacag tgatgaatta acctcactgt    2100
tgggatattt tcccaacaaa aaacagcttg aagactggct acatagtaaa tcaaaagaaa    2160
ttaatcagac cagggacaga cttgccaaat tgaacaagga actagcttca tctgagcaga    2220
ataaaaatca tataaataat gaactaaaaa gaaaggaaga gcagttgtcc agttacgaag    2280
acaagctgtt tgatgtttgt ggtagccagg attttgaaag tgatttagac aggcttaaag    2340
aggaaattga aaaatcatca aaacagcgag ccatgctggc tggagccaca gcagtttact    2400
```

```
cccagttcat tactcagcta acagacgaaa accagtcatg ttgccccgtt tgtcagagag   2460
tttttcagac agaggctgag ttacaagaag tcatcagtga tttgcagtct aaactgcgac   2520
ttgctccaga taaactcaag tcaacagaat cagagctaaa aaaaaaggaa aagcggcgtg   2580
atgaaatgct gggacttgtg cccatgaggc aaagcataat tgatttgaag gagaaggaaa   2640
taccagaatt aagaaacaaa ctgcagaatg tcaatagaga catacagcgc ctaaagaacg   2700
acatagaaga acaagaaaca ctcttgggta caataatgcc tgaagaagaa agtgccaaag   2760
tatgcctgac agatgttaca attatggaga ggttccagat ggaacttaaa gatgttgaaa   2820
gaaaaattgc acaacaagca gctaagctac aaggaataga cttagatcga actgtccaac   2880
aagtcaacca ggagaaacaa gagaaacagc acaagttaga cacagtttct agtaagattg   2940
aattgaatcg taagcttata caggaccagc aggaacagat tcaacatcta aaaagtacaa   3000
caaatgagct aaaatctgag aaacttcaga tatccactaa tttgcaacgt cgtcagcaac   3060
tggaggagca gactgtggaa ttatccactg aagttcagtc tttgtacaga gagataaagg   3120
atgctaaaga gcaggtaagc cctttggaaa caacattgga aaagttccag caagaaaaag   3180
aagaattaat caacaaaaaa aatacaagca acaaaatagc acaggataaa ctgaatgata   3240
ttaaagagaa ggttaaaaat attcatggct atatgaaaga cattgagaat tatattcaag   3300
atgggaaaga cgactataag aagcaaaaag aaactgaact taataaagta atagctcaac   3360
taagtgaatg cgagaaacac aaagaaaaga taaatgaaga tatgagactc atgagacaag   3420
atattgatac acagaagata caagaaaggt ggctacaaga taaccttact ttaagaaaaa   3480
gaaatgagga actaaaagaa gttgaagaag aaagaaaaca acatttgaag gaaatgggtc   3540
aaatgcaggt tttgcaaatg aaaagtgaac atcagaagtt ggaagagaac atagacaata   3600
taaaaagaaa tcataatttg gcattagggc gacagaaagg ttatgaagaa gaaattattc   3660
attttaagaa agaacttcga gaaccacaat ttcgggatgc tgaggaaaag tatagagaaa   3720
tgatgattgt tatgaggaca acagaacttg tgaacaagga tctggatatt tattataaga   3780
ctcttgacca agcaataatg aaatttcaca gtatgaaaat ggaagaaatc aataaaatta   3840
tacgtgacct gtggcgaagt acctatcgtg gacaagatat tgaatacata gaaatacggt   3900
ctgatgccga tgaaaatgta tcagcttctg ataaaaggcg gaattataac taccgagtgg   3960
tgatgctgaa gggagacaca gccttggata tgcgaggacg atgcagtgct ggacaaaagg   4020
tattagcctc actcatcatt cgcctggccc tggctgaaac gttctgcctc aactgtggca   4080
tcattgcctt ggatgagcca acaacaaatc ttgaccgaga aaacattgaa tctcttgcac   4140
atgctctggt tgagataata aaaagtcgct cacagcagcg taacttccag cttctggtaa   4200
tcactcatga tgaagatttt gtggagcttt taggacgttc tgaatatgtg gagaaattct   4260
acaggattaa aaagaacatc gatcagtgct cagagattgt gaaatgcagt gttagctccc   4320
tgggattcaa tgttcattaa aaatatccaa gatttaaatg ccatagaaat gtaggtcctc   4380
agaaagtgta taataagaaa cttatttctc atatcaactt agtcaataag aaaatatatt   4440
ctttcaaagg aacattgtgt ctaggatttt ggatgttgag aggttctaaa atcatgaaac   4500
ttgtttcact gaaaattgga cagattgcct gtttctgatt tgctgctctt catcccattc   4560
caggcagcct ctgtcaggcc ttcagggttc agcagtacag ccgagactcg actctgtgcc   4620
tccctcccca gtgcaaatgc atgcttcttc tcaaagcact gttgagaagg agataattac   4680
tgccttgaaa atttatggtt ttggtatttt tttaaatcat agttaaatgt tacctctgaa   4740
```

-continued

```
tttacttcct tgcatgtggt ttgaaaaact gagtattaat atctgaggat gaccagaaat   4800

ggtgagatgt atgtttggct ctgcttttaa ctttataaat ccagtgacct ctctctctgg   4860

gacttggttt ccccaactaa aatttgaagt agttgaatgg ggtctcaaag tttgacagga   4920

accttaagta atcatctaag tcagtaccca ccaccttctt ctcctacata tcccttccag   4980

atggtcatcc agactcagag ctctctctac agagaggaaa ttctccactg tgcacaccca   5040

cctttggaaa gctctgacca cttgaggcct gatctgccca tcgtgaagaa gcctgtaaca   5100

ctcctctgcg tctatcctgt gtagcatact ggcttcacca tcaatcctga ttcctctcta   5160

agtgggcatt gccatgtgga aggcaagcca ggctcactca cagagtcaag gcctgctccc   5220

tgtagggtcc aaccagacct ggaagaacag gcctctccat ttgctcttca gatgccactt   5280

ctaagaaaag cctaatcaca gtttttcctg gaattgccag ctgacatctt gaatccttcc   5340

attccacaca gaatgcaacc aagtcacacg cttttgaatt atgctttgta gagttttgtc   5400

attcagagtc agccaggacc ataccgggtc ttgattcagt cacatggcat ggttttgtgc   5460

catctgtagc tataatgagc atgtttgcct agacagcttt tctcaactgg gtccagaaga   5520

gaattaagcc ctaaggtcct aaggcatcta tctgtgctag gttaaatggt tggcccccaa   5580

agatagacag gtcctgattt ctagaacccg tgactgttac tttatacagc aaaggaaact   5640

ttgcagatgt gattaaagct aaggacctta agacagagta tcctgggggt ggtggtgggg   5700

tggggggggg tcctaaatgt aatcacgagt aagattaaga gcaaatcaat tctagtcata   5760

tattaaacat ccacaataac caagatattt ttatcccaag aatgcaagat ttcagaaaat   5820

gaaaaatctg ttgataaatc catcactata ataaaaccga aggtgaaaaa aattctgaaa   5880

aaattctagc agctatattt gataaaattc aacatctcct agctttagca aactcacagt   5940

tttgcaaata atattttctt aatgttatct gttgctaaat caaaattaaa cagtcatctt   6000

aactgcaaaa taaaacattt ctcagtaaat attaaagcca gttaccttct atcaacatgt   6060

taatgaaagt gctagttgtt gcagcaaaga ataacaaagg caatacacga tcaatatagg   6120

cagtgaaaca aaagtatcat ttgcaagtta aaacagactt cccaatttta aatctggttt   6180

ccccctgaat atgtggcatc cttggcagca cttctgagag tggctgcttt cattccaaga   6240

agcccatggg tttggaggtg ggataggtgc ctttctggct tctcattgct gcttctagat   6300

cagtctccaa atatccccct tccccacatt ggaatgaata gccatcacag catggatgga   6360

ggttagaatg agccagactg cctgggctca aatcctagca caccactcac tagctgggga   6420

ccttgagcaa gttatttgtc ctgttttctg tttccttata tgtaaaagtg ggtaaaatgg   6480

tacatatttt gtagggttgt tatgaagatt gaatgacatt atttacaaac tgcttagaac   6540

tgcttgccac ctactaaata ctgtgtaagt gttcaagaaa aagctgtctt catttca      6597
```

<210> SEQ ID NO 35
<211> LENGTH: 418
<212> TYPE: PRT
<213> ORGANISM: Artificial Sequence
<220> FEATURE:
<223> OTHER INFORMATION: RAD51 sequence

<400> SEQUENCE: 35

```
Met Ser Gly Thr Glu Glu Ala Ile Leu Gly Gly Arg Asp Ser His Pro
1               5                   10                  15

Ala Ala Gly Gly Gly Ser Val Leu Cys Phe Gly Gln Cys Gln Tyr Thr
            20                  25                  30

Ala Glu Glu Tyr Gln Ala Ile Gln Lys Ala Leu Arg Gln Arg Leu Gly
```

```
        35                  40                  45

Pro Glu Tyr Ile Ser Ser Arg Met Ala Gly Gly Gly Gln Lys Val Cys
    50                  55                  60

Tyr Ile Glu Gly His Arg Val Ile Asn Leu Ala Asn Glu Met Phe Gly
65                  70                  75                  80

Tyr Asn Gly Trp Ala His Ser Ile Thr Gln Gln Asn Val Asp Phe Val
                85                  90                  95

Asp Leu Asn Asn Gly Lys Phe Tyr Val Gly Val Cys Ala Phe Val Arg
            100                 105                 110

Val Gln Leu Lys Asp Gly Ser Tyr His Glu Asp Val Gly Tyr Gly Val
        115                 120                 125

Ser Glu Gly Leu Lys Ser Lys Ala Leu Ser Leu Glu Lys Ala Arg Lys
    130                 135                 140

Glu Ala Val Thr Asp Gly Leu Lys Arg Ala Leu Arg Ser Phe Gly Asn
145                 150                 155                 160

Ala Leu Gly Asn Cys Ile Leu Asp Lys Asp Tyr Leu Arg Ser Leu Asn
                165                 170                 175

Lys Leu Pro Arg Gln Leu Pro Leu Glu Val Asp Leu Thr Lys Ala Lys
            180                 185                 190

Arg Gln Asp Leu Glu Pro Ser Val Glu Glu Ala Arg Tyr Asn Ser Cys
        195                 200                 205

Arg Pro Asn Met Ala Leu Gly His Pro Gln Leu Gln Gln Val Thr Ser
    210                 215                 220

Pro Ser Arg Pro Ser His Ala Val Ile Pro Ala Asp Gln Asp Cys Ser
225                 230                 235                 240

Ser Arg Ser Leu Ser Ser Ser Ala Val Glu Ser Glu Ala Thr His Gln
                245                 250                 255

Arg Lys Leu Arg Gln Lys Gln Leu Gln Gln Gln Phe Arg Glu Arg Met
            260                 265                 270

Glu Lys Gln Gln Val Arg Val Ser Thr Pro Ser Ala Glu Lys Ser Glu
        275                 280                 285

Ala Ala Pro Pro Ala Pro Pro Val Thr His Ser Thr Pro Val Thr Val
    290                 295                 300

Ser Glu Pro Leu Leu Glu Lys Asp Phe Leu Ala Gly Val Thr Gln Glu
305                 310                 315                 320

Leu Ile Lys Thr Leu Glu Asp Asn Ser Glu Lys Trp Ala Val Thr Pro
                325                 330                 335

Asp Ala Gly Asp Gly Val Val Lys Pro Ser Ser Arg Ala Asp Pro Ala
            340                 345                 350

Gln Thr Ser Asp Thr Leu Ala Leu Asn Asn Gln Met Val Thr Gln Asn
        355                 360                 365

Arg Thr Pro His Ser Val Cys His Gln Lys Pro Gln Ala Lys Ser Gly
    370                 375                 380

Ser Trp Asp Leu Gln Thr Tyr Ser Ala Asp Gln Arg Thr Thr Gly Asn
385                 390                 395                 400

Trp Glu Ser His Arg Lys Ser Gln Asp Met Lys Lys Arg Lys Tyr Asp
                405                 410                 415

Pro Ser


<210> SEQ ID NO 36
<211> LENGTH: 2673
<212> TYPE: DNA
<213> ORGANISM: Artificial Sequence
<220> FEATURE:
```

<223> OTHER INFORMATION: RAD51 sequence

<400> SEQUENCE: 36

```
cccattctcc tctgcgcggc ctccatctaa gatctcttcc ccttgtccat agcctagatc     60
gagctccctg tgtgcaccgc gcgctgcccg aggcgcaggt caaccagaat caagatgtct    120
gggactgagg aagcaattct tggaggacgt gacagccatc ctgctgctgg cggcggctca    180
gtgttatgct ttggacagtg ccagtacaca gcagaagagt accaggccat ccagaaggcc    240
ctgaggcaga ggctgggccc agaatacata agtagccgca tggctggcgg aggccagaag    300
gtgtgctaca ttgagggtca tcgggtaatt aatctggcca atgagatgtt tggttacaat    360
ggctgggcac actccatcac gcagcagaat gtggattttg ttgacctcaa caatggcaag    420
ttctacgtgg gagtctgtgc atttgtgagg gtccagctga aggatggttc atatcatgaa    480
gatgttggtt atggtgttag tgagggcctc aagtccaagg ctttatcttt ggagaaggca    540
aggaaggagg cggtgacaga cgggctgaag cgagccctca ggagttttgg gaatgcactt    600
ggaaactgta ttctggacaa agactacctg agatcactaa ataagcttcc acgccagttg    660
cctcttgaag tggatttaac taaagcgaag agacaagatc ttgaaccgtc tgtggaggag    720
gcaagataca acagctgccg accgaacatg gccctgggac acccacagct gcagcaggtg    780
acctcccctt ccagacccag ccatgctgtg ataccggcgg accaggactg cagctcccga    840
agcctgagct catccgccgt ggagagcgag gccacgcacc agcggaagct ccggcagaag    900
cagctgcagc agcagttccg ggagcggatg gagaagcagc aggttcgagt ctccacgccg    960
tcagctgaga agagtgaggc agcgcctccg gcccctcctg tgacgcacag cactcctgta   1020
actgtctcag aaccactcct ggagaaagac ttccttgcag gagtgactca agaattaatc   1080
aagactcttg aagacaactc tgaaaagtgg gctgtgactc ccgatgcagg ggatggtgtg   1140
gtcaagccct cgtctagagc agacccagcc cagacctctg acacattagc cttgaacaac   1200
cagatggtga cccagaacag gactccacac agcgtttgcc accagaaacc acaagcaaaa   1260
tctggatctt gggacctcca aacttatagc gctgaccaac gcacaacagg aaactgggaa   1320
tctcatagga agagccagga catgaagaaa aggaaatatg atccatctta actgaggctc   1380
aggccacata attggactct gtcacaaagg gactttggaa aactactttt tggtcatgaa   1440
attgttcatc gctgctggag aatgaacgtc attgcgattt atcttgcttc attctgaacc   1500
ttatcaagag gatctgactg agagcccact gcagttagag ctgagcactt ttgaaaagct   1560
tgtccatcac tctagtaggg agaggctctg gacagatgaa taccttttct tcggcttgtg   1620
aggcttccca ctatttatta ctgaactatt atgttaatga agatggacat tttaggaatc   1680
accaatggct ccttgccctc aagcaatata ggccagactt ggtcctaagc acctgcctca   1740
gcaattgtct acattcagtt gttttgcata acgtctgcct tctttccttt acggtccatg   1800
cctttaatgt tgcccacatt aagcactgtg gatcacgaca ggaaaaaggt tggagcagtg   1860
cttttcacta ctttgtatca atccaggcta caatcttcat ttaatataaa taatttatgg   1920
atttatgaca ttacaatcct gcattgtttc aagactgaca ttttttccta aggaaggaaa   1980
taatcatcta agaccacgaa aaaaggctgt tttttgtttt tttttttttt tttttttttg   2040
agacggggtc tggctgtgtt gccctgactg gagttcagtg gtgcaaacac agctctctcc   2100
acaacctctt gggcccaagt gatactccca cctctgcctt acaaaataca gggattactg   2160
gtgtgagcca ctgtgtctgg ccagaaaagg catttttgag aaagcaaatc gtataccta    2220
ttaacaaaat agaatatata tatattgctt atctgaaatg cttgaaacca gaattgtttt   2280
```

```
gcattttttg aatatttgta tacacataat gagaccttgg ggatgggacc caagtctgaa    2340

cgtggaattc acctgtgttt cgtgtatatg cctcatacac ataattttgt gcatgaaaca    2400

gagtttttgt ataagaagat acactgcagc tgaagagggc tgggtttttt tttctcttag    2460

ggtcgctgca taaactgttg tatgcctggt gctttgcgac ttgtcacacg aggtcacgtg    2520

tggaattttc cacttctggc atcacgtcag tgctcagaaa ttttctgatc tcagagcatt    2580

tcaattaggg atgctcaaac gcaactgttt ctacttcccc atttcaggtg tgagatgtaa    2640

cccaccttga ccataaattg gcttttcata gtg                                 2673
```

COMPOSITIONS OF COMBINATIONS OF NON-COVALENT DNA BINDING AGENTS AND ANTI-CANCER AND/OR ANTI-INFLAMMATORY AGENTS AND THEIR USE IN DISEASE TREATMENT

This application is a 371 application of PCT application No. PCT/US2013/028358, filed Feb. 28, 2013, which claims the priority of U.S. Ser. No. 61/621,149, filed Apr. 6, 2012, the contents of all of which are hereby incorporated by reference in their entirety into the present application.

Throughout this application various publications are referenced. The disclosures of these publications in their entireties are hereby incorporated by reference into this application in order to more fully describe the state of the art to which this invention pertains.

FIELD OF THE INVENTION

The invention relates to non-covalent DNA binding agents, alone or in combination with anti-cancer agents and/or anti-inflammatory agents that can be used to treat cancer and inflammation.

BACKGROUND OF THE INVENTION

Cancers are caused by multiple genetic changes that drive tumorigenesis. Over the past several years, overexpressed oncogenic targets such as receptor tyrosine kinases (RTKs) have been targeted for treatment of cancers. Cancers can also arise from the loss of tumor suppressor gene functions such as through the loss of p53, BRCA1, BRCA2, PTEN and other tumor suppressor genes. Currently no therapeutic approaches have been designed to target cancers that are due to the loss of tumor suppressor gene functions.

The concept of synthetic lethality was introduced, recently, into the field of cancer therapeutics. Initial research in the field of synthetic lethality indicated that two genes are synthetic lethal if mutation of either gene alone is compatible with viability but a mutation of both genes results in cell death. There have been recent examples of treatment of cancers that have a BRCA1 gene deficiency by administration of a DNA crosslinking agent, such as a platinum drug, in combination with an inhibitor of an overexpressed gene, such as PARP, to produce a synthetic lethal outcome in such BRCA1 deficient tumor cells (A. Ashworth: A synthetic lethal therapeutic approach: Poly(ADP) Ribose Polymerase Inhibitors for the Treatment of Cancers Deficient in DNA Double-Strand Break Repair. J Clinical Oncology 26:3785-3790, 2008; Rehman, F. L., Lord, C. J. and Ashworth, A. Synthetic lethal approaches to breast cancer therapy. Nat Rev Clin Oncol 7: 718-724, 2010; O'Shaughnessy, J., Osborne, C., Pippen, J. E., Yoffe, M, Patt, D., Rocha, C., Koo, I. C., Sherman, B. M. and Bradley, C. Iniparib plus chemotherapy in metastatic triple-negative breast cancer. N Engl J Med 364: 205-214, 2011.

Currently, labor intensive bioinformatic analysis and small molecule or RNAi screens are needed to identify synthetic lethal relationships between well-established therapeutic targets and/or lesser-known components of cancer cells' signaling networks.

At present, the only clinical application of synthetic lethality is the use of DNA crosslinking platinum drugs such as carboplatin, together with an antimetabolite such as gemcitabine, in combination with poly (ADP-ribose) polymerase (PARP) inhibitor, such as iniparib in patients with triple-negative breast cancer that have BRCA1 and/or BRCA2 mutations (O'Shaughnessy et al., N Engl J Med 364: 205-214, 2011). Preclinical studies were required to establish synthetic lethal relationships among the combination of a DNA crosslinking agent (platinum), and antimetabolites (gemcitabine) and the inhibition of the DNA repair enzyme PARP, together with the genetic inactivation of tumor suppressor genes BRCA1 or BRCA2.

A clear advantage of cancer treatments based on synthetic lethality is that they have minimal toxicity, because only cells with the impairments that comprise the synthetic lethal relationship (e.g., a mutated gene and a therapeutically inhibited enzyme) should be affected. Those cells should almost exclusively be cancer cells. Treatments based on synthetic lethality offers the advantage of overcoming the problem of targets that, either due to underlying biology or the targets' actual physical make up, are "undruggable" with small molecule and biologic drugs. As much as 75% of the identified molecular targets for cancer may be "undruggable".

A key obstacle to appropriate treatment of cancers and other inflammatory diseases is the resistance or refractory responses to available therapies. For example, it is well known that tumor cells develop mutations in various genes and/or their expressed proteins. Such mutations allow the tumor cells to become refractory to currently available anticancer agents and thus the patients do not have therapeutic options. The novel invention described in this application shows the benefit of using non-covalent DNA binding agents that show synthetic lethality in tumors that carry mutations, particularly in DNA repair or tumor suppressor genes, that result in a "loss of function" in the cell's ability to either repair itself or go into apoptosis or programmed cell death. Since such mutations in DNA repair or tumor suppressor genes also render the tumor cells refractory to available treatments, the novel combinations of one or more non-covalent DNA binding agents with one or more anti-cancer or anti-inflammatory agents, represents a novel and unique way to treat tumor cells that have "loss of function" in tumor suppression and/or DNA repair functions.

Furthermore, in view of the fact that a) it is difficult to identify and/or predict synthetic lethal relationships, and b) the importance of cancer treatments based on synthetic lethality, there is a real and immediate need for methods of disease treatment based on combinations of agents that can leverage synthetic lethality and to develop such novel combinations in a rapid time frame, so that it does not involve time consuming identification of synthetic lethal relationships amongst genes. Moreover, such novel compositions of agents should result in treatment methods that are non-toxic. This application describes unique and novel compositions of combinations or one or more non-covalent binding DNA agents with one or more available anticancer agents, including but not limited to, those agents that have become refractory due to mutations in such cells and provide novel methods of therapies for treatment of highly unmet clinical need in cancer and inflammatory diseases, while leveraging, the concept of synthetic lethality.

SUMMARY OF THE INVENTION

The invention relates to novel compositions and methods of disease treatment comprising using one or more non-covalent DNA binding agents to create synthetic lethal combinations in cells that have "loss of function" in tumor suppressor and/or DNA repair pathways. The invention provides for the use of one or more non-covalent DNA binding agents as a monotherapy, that is, they function in the absence of other active agents, to, e.g., create synthetic lethality in tumors that exhibit loss of tumor suppressor gene function, thereby treating disease. In one embodiment of the invention, one or more non-covalent DNA binding agents may be used in combination with one or more anti-cancer agents and/or anti-inflammatory agents to, e.g., create synthetic lethality in tumors that exhibit loss of tumor suppressor gene function, so as to treat disease.

The invention also relates to novel compositions and methods of disease treatment comprising using one or more non-covalent DNA binding agents to treat a subject with at least one of a DNA repair deficiency, dysregulated apoptosis, a replication deficiency, loss of function of a tumor suppressor gene, deficiencies in DNA recombination, a ubiquitin disorder, cell cycle dysregulation and/or dysregulated translesion synthesis. In a further embodiment, one or more non-covalent DNA binding agents may be used with one or more anti-cancer agents in novel compositions and methods of disease.

The invention provides for novel compositions and methods of treating a subject with at least one of a gene deficiency, a protein deficiency, a DNA repair deficiency, dysregulated apoptosis, a recombination deficiency, a replication deficiency, a cell proliferation disorder, dysregulated transcription, loss of function of a tumor suppressor gene, a ubiquitin disorder, cell cycle dysregulation and/or dysregulation of translesion synthesis, comprising administering to the subject a therapeutically effective amount of one or more non-covalent DNA binding agents, as the only active agents, or in combination with one or more anti-cancer and/or anti-inflammatory active agents.

In one embodiment, the DNA repair deficiency is at least one of: DNA mismatch repair (MMR) deficiency, base excision repair (BER) deficiency, nucleotide excision repair (NER) deficiency, recombinational repair deficiency, homologous recombination repair (HRR) deficiency, non-homologous end joining (NHEJ) deficiency, a deficiency in the repair of double stranded breaks, and a deficiency in the repair of chromosomal damage.

The invention also provides for novel compositions and methods of treating a subject with cancer or inflammation, comprising: identifying a subject in need of treatment; administering to the subject a therapeutically effective amount of one or more non-covalent DNA binding agents, as the only active agents, or in combination with one or more anti-cancer and/or anti-inflammatory active agents; wherein following the administration, there is inhibition of inflammation or growth of a cancer cell.

In one embodiment the identification step comprises determining whether the patient has a mutation in at least one of a gene selected from the group consisting of: PTEN, p53, BRCA1, BRCA2, MLH1, PMS1, PMS2, MSH2, MSH6, REVS, XRCC1, XRCC2, XRCC3, RAD51, RAD52, REV, ATM, ATR, and the MRE1/RPA1/RAD51 complex.

The invention also provides for novel compositions and methods of treating a subject with cancer, comprising administering to the subject a therapeutically effective amount of one or more non-covalent DNA binding agents, as the only agent agents, or in combination with one or more anti-cancer active agents, wherein following the administration, there is inhibition of growth of a cancer cell.

In one embodiment, the subject has a loss of function of at least one tumor suppressor gene.

In another embodiment, at least one tumor suppressor gene and/or the gene pathway is selected from the group consisting of: PTEN, p53, BRCA1, BRCA2, MLH1, PMS1, PMS2, MSH2, MSH6, REV3, XRCC1, XRCC2, XRCC3, RAD51, RAD52, REV, ATM, ATR, K-Ras, BRAF and the MRE1/RPA1/RAD51 complex.

In another embodiment, the subject has a DNA mismatch repair gene or pathway deficiency.

In another embodiment, the subject does not have a DNA mismatch repair gene or gene pathway deficiency i.e. the subject has no loss of function in DNA mismatch repair.

In another embodiment, the cancer is mutant K-ras positive or has mutations in the K-Ras pathway.

In another embodiment the cancer is has wild-type K-ras and no mutations in the K-Ras signaling pathway.

In another embodiment, the identification step comprises determining the response of a patient to a therapy for treating cancer.

In another embodiment, the identification step is reported to the subject and/or a health care professional.

In another embodiment, the non-covalent DNA binding agent binds to the minor groove of DNA.

In another embodiment, the non-covalent DNA binding agent binds to a "G-C rich" region of the minor groove.

In another embodiment, the subject has a mutation in at least one of a gene or gene pathway selected from the group consisting of: PTEN, p53, BRCA1, BRCA2, MLH1, PMS1, PMS2, MSH2, MSH6, REV3, XRCC1, XRCC2, XRCC3, RAD51, RAD52, REV, ATM, ATR, K-Ras, BRAF and the MRE1/RPA1/RAD51 complex.

In another embodiment the patient cannot be treated by other therapies i.e. the tumor is refractory or resistant to available therapies.

In another embodiment, the cancer is selected from the group consisting of: breast cancer, colorectal cancer, leukemia, non-small cell lung cancer, ovarian cancer, renal cancer, melanoma, prostate cancer and CNS-cancers. The cancer may be a primary cancer or a metastatic cancer.

In another embodiment, the cancer is triple negative breast cancer.

In another embodiment, the cancer is MMR-deficient colorectal cancer.

In another embodiment, the cancer is glioblastoma.

In another embodiment, the novel composition comprises the non-covalent DNA binding agent or the pharmaceutically acceptable salt or prodrug thereof.

In another embodiment, the subject is a mammal.

In another embodiment, the subject is a human.

In another embodiment, the therapeutically effective amount of one or more non-covalent DNA binding agent is in the range of 0.001 mg to 1000 mg per subject.

In another embodiment, the administration step comprises administering one or more non-covalent DNA binding agent to the subject in accordance with a daily treatment regimen.

In another embodiment the administration step comprises administering one or more non-covalent DNA binding agent as a pharmaceutical formulation.

In another embodiment, the pharmaceutical formulation is a bioequivalent formulation of one or more non-covalent DNA binding agent.

In another embodiment, the pharmaceutical formulation is a pharmaceutically equivalent formulation.

In another embodiment, the pharmaceutical formulation is a therapeutically equivalent formulation.

The invention also provides for a novel, composition of packaged pharmaceutical comprising one or more non-covalent DNA binding agents or pharmaceutically acceptable salt or prodrug thereof, which, upon administration to a subject, inhibits the growth of a cancer cell.

The invention also provides for a novel composition of packaged pharmaceutical comprising: one or more non-covalent DNA binding agents or pharmaceutically acceptable salt or prodrug thereof; and associated instructions for using the non-covalent DNA binding agent(s) to treat cancer.

In one embodiment, one or more of the non-covalent DNA binding agent is present as a pharmaceutical composition comprising a therapeutically effective salt or prodrug thereof and a pharmaceutically acceptable carrier.

In another embodiment, the packaged pharmaceutical further comprises in the instructions a step of identifying a subject in need of such pharmaceutical.

In another embodiment, the packaged pharmaceutical further comprises in the instructions a step of identifying one or more non-covalent. DNA binding agent and one or more anticancer agent as capable of inhibiting the growth of a cancer cell.

In another embodiment, the invention provides for a novel composition of packaged pharmaceutical for administration to a subject comprising: one or more non-covalent DNA binding agents, as the only active agents, or in combination with one or more anti-cancer and/or anti-inflammatory active agents; a test for determining if the subject has a mutation in at least one of a gene; associated instructions for performing the test; and associated instructions for using the non-covalent DNA binding agent to treat cancer and/or inhibit inflammation.

In one embodiment, the gene or gene pathway is selected from the group consisting of: PTEN, p53, BRCA1, BRCA2, MLH1, PMS1, PMS2, MSH2, MSH6, REV3, XRCC1, XRCC2, XRCC3, RAD51, RAD52, REV, ATM, ATR, K-Ras, BRAF and the MRE1/RPA1/RAD51 complex.

The invention provides for novel compositions and methods of inhibiting the growth of a cancer cell comprising administering to the subject a non-covalent DNA binding agent.

In one embodiment, the cancer cell comprises a mutation in at least one of a gene or gene pathway selected from the group consisting of: PTEN, p53, BRCA1, BRCA2, MLH1, PMS1, PMS2, MSH2, MSH6, REV3, XRCC1, XRCC2, XRCC3, RAD51, RAD52, REV, ATM, ATR, K-Ras, BRAF and the MRE1/RPA1/RAD51 complex.

In another embodiment, the non-covalent DNA binding agent binds to the minor groove.

In another embodiment, the non-covalent DNA binding agent binds to a GC rich region of the minor groove.

In another embodiment the subject has a mutation in at least one of a gene or gene pathway selected from the group consisting of: PTEN, p53, BRCA1, BRCA2, MLH1, PMS1, PMS2, MSH2, MSH6, REV3, XRCC1, XRCC2, XRCC3, RAD51, RAD52, REV, ATM, ATR, K-Ras, BRAF and the MRE1/RPA1/RAD51 complex.

Methods are provided for the synthesis of poly(ethylene glycol) ("PEG") conjugates of non-covalent DNA binding agents of the invention, which conjugates retain unusually high biological potency. Also provides are novel poly(ethylene glycol) ("PEG") conjugates of non-covalent DNA binding agents of the invention and compositions thereof. Preparation of the pegylated conjugates according to the methods of the present invention reduces or avoids steric inhibition of receptor-ligand interactions that may result from the attachment of PEG to a polypeptide of small molecule of interest. The conjugates of the present invention retain a high level of biological potency compared to those produced by traditional PEG coupling methods that are not targeted to avoid receptor-binding domains of cytokines. The biological potency of the PEG conjugates of non-covalent DNA binding agents of the invention may be higher than that of unconjugated non-covalent DNA binding agents of the invention. The conjugates of the present invention may have an extended half-life in vivo compared to the corresponding unconjugated agents of the invention. The present invention also provides kits comprising such conjugates and/or compositions, and methods of use of such conjugates and compositions in a variety of diagnostic, prophylactic and therapeutic applications.

BRIEF DESCRIPTION OF THE DRAWINGS

FIG. 9 presents the results of a comparison of the activity of non-covalent DNA binding agents in U20S cells wherein MMR, p53 and REV functions have been inhibited using RNAi methods (A) NSC 718813; (B) NSC 723734; (C) NSC 726260.

FIG. 11 presents the results of a comparison of the activity of non-covalent DNA binding agents in isogenic MMR-deficient HCTI 16 cells wherein p53 and REV functions have been inhibited using RNAi methods (A) NSC 718813; (B) NSC 723734; (C) NSC 726260; (D) camptothecin.

FIG. 12 presents a comparison of the activity of non-covalent DNA binding agents in p53, mlh1 and rev deficient U20S cells.

FIG. 13 presents the amino acid sequence (A) (SEQ ID NO:1) and the nucleic acid sequence (B) (SEQ ID NO:2) of TP53.

FIG. 14 presents the amino acid sequence (A) (SEQ ID NO:3) and the nucleic acid sequence (B) (SEQ ID NO:4) of MLH1.

FIG. 15 presents the amino acid sequence (A) (SEQ ID NO:5) and the nucleic acid sequence (B) (SEQ ID NO:6) of MSH2.

FIG. 16 presents the amino acid sequence (A) (SEQ ID NO:7) and the nucleic acid sequence (B) (SEQ ID NO:8) of BRCA1.

FIG. 17 presents the amino acid sequence (A) (SEQ ID NO:9) and the nucleic acid sequence (B) SEQ ID NO:10) of REV3L.

FIG. 18 presents the amino acid sequence (A) (SEQ ID NO:11) and the nucleic acid sequence (B) (SEQ ID NO:12) of PARP1.

FIG. 19 presents the amino acid sequence (A) (SEQ ID NO:13) and the nucleic acid sequence (B) (SEQ ID NO:14) of RAD51.

FIG. 20 presents the amino acid sequence (A) (SEQ ID NO:15) and the nucleic acid sequence (B) (SEQ ID NO:16) of MRE11A.

FIG. 21 presents the amino acid sequence (A) (SEQ ID NO:17) and the nucleic acid sequence (B) (SEQ ID NO:18) of ATM.

FIG. 22 presents the amino acid sequence (A) (SEQ ID NO:19) and the nucleic acid sequence (B) (SEQ ID NO:20) of ATR.

FIG. 23 presents the amino acid sequence (A) (SEQ ID NO:21) and the nucleic acid sequence (B) (SEQ ID NO:22) of PTEN.

FIG. 24 presents the amino acid sequence (A) (SEQ ID NO:23) and the nucleic acid sequence (B) (SEQ ID NO:24) of ERCC1.

FIG. 25 presents the amino acid sequence (A) (SEQ ID NO:25) and the nucleic acid sequence (B) (SEQ ID NO:26) of BRCA2.

FIG. 26 presents the amino acid sequence (A) (SEQ ID NO:27) and the nucleic acid sequence (B) (SEQ ID NO:28) of XRCC1.

FIG. 27 presents the amino acid sequence (A) (SEQ ID NO:29) and the nucleic acid sequence (B) (SEQ ID NO:30) of KRAS.

FIG. 28 presents the amino acid sequence (A) (SEQ ID NO:31) and the nucleic acid sequence (B) (SEQ ID NO:32) of BRAF.

FIG. 29 presents the amino acid sequence (A) (SEQ ID NO:33) and the nucleic acid sequence (B) (SEQ ID NO:34) of RAD50.

FIG. 30 presents the amino acid sequence (A) (SEQ ID NO:35) and the nucleic acid sequence (B) (SEQ ID NO:36) of RAD51.

FIG. 46A shows NSC 718813 with Paclitaxel in 172Tag. FIG. 46B shows NSC 718813 with Camptothecin in 172Tag. FIG. 46C shows the effect of NSC 718813 with Doxorubicin in MMR deficient cells (172Tag). FIG. 46D shows the combination effect of NSC 718813 with Trichostatin in MMR deficient cell line (172Tag).

FIG. 47 shows line graphs of 172Tag. FIG. 47A shows the effect of NSC 718813 with Mitomycin C in MMR deficient cell line (172Tag). FIG. 47B shows the combination with NSC 718813 and Actinomycin D in MMR deficient cells (172Tag).

FIG. 48A shows the effect of NSC 718813 with Camptothecin in MMR proficient cells (HeLa). FIG. 48B shows the effect of NSC 718813 with Cyclohexamide in MMR proficient cells (HeLa). FIG. 48C shows the effect of NSC 718813 with Mitomycin C in MMR proficient cells (HeLa). FIG. 48D shows the effect of NSC 718813 with Vinblastine in MMR deficient cells (HEK293T).

FIG. 49A shows the combination effect of NSC 718813 with Mitomycin C in MMR deficient cells (HEK293T). FIG. 49B shows the combination effect of NSC 718813 with Paclitaxel in MMR deficient cells (HEK293T). FIG. 49C shows the combination effect of NSC 718813 with Vincristine in MMR deficient cells (HEK293T). FIG. 49D shows the combination effect of NSC 718813 with Actinomycin in MMR deficient cells (HEK293T).

FIG. 50A shows NSC 718813 with Doxorubicin in MCF7. FIG. 50B shows NSC 718813 with Paclitaxel in MCF7.

FIG. 51A shows the combination effect in CEM cells NSC 718813 with Vinblastin. FIG. 51B shows cyclohexamide. FIG. 51C shows Trichostatin. FIG. 51D shows Mitomycin C.

FIG. 52A shows NSC 718813 with Vinblastin in SW403. FIG. 52B shows NSC 718813 with camptothecin in SW403. FIG. 52C shows NSC 718813 with Trichostatin in SW403. FIG. 52D shows NSC 718813 with cyclohexamide in SW403.

FIG. 53A shows NSC 718813 with Mitomycin in SW403. FIG. 53B shows NSC 718813 with Doxorubicin in SW403. FIG. 53C shows NSC 718813 with Paclitaxel in SW403. FIG. 53D shows NSC 718813 with actinomycin in SW403.

FIG. 54A shows NSC 718813 with olaparib in SW403. FIG. 54B shows NSC 718813 with Oxaliplatin in SW403. FIG. 54C shows NSC 718813 with Gefitinib in SW403. FIG. 54D shows NSC 718813 with 5FU in SW403.

FIG. 55A shows NSC 718813 with Vinblastin in MDA 231. FIG. 55B shows NSC 718813 with Cyclohexamide in MDA-MB-231. FIG. 55C shows NSC 718813 with Trichostatin in MDA-MB-231. FIG. 55D shows NSC 718813 with Mitomycin in MDA-MB-231.

FIG. 56A shows NSC 718813 with Paclitaxel in MDA-MB-231. FIG. 56B shows NSC 718813 with Vincristin in MDA-MB-231. FIG. 56C shows NSC 718813 with Doxorubicin in MDA-MB-231. FIG. 56D shows NSC 718813 with 6TG in MDA-MB-231.

FIG. 57A shows NSC 718813 in Olaparib in MDA 231. FIG. 57B shows NSC 718813 with Oxaliplatin in MDA-MB-231. FIG. 57C shows NSC 718813 with Gefitinib in MDA-MB-231.

FIG. 58A shows NSC 718813 with Vinblastin in MDA-MB-468. FIG. 58B shows NSC 718813 with Camptothecin in MDA-MB-468. FIG. 58C shows NSC 718813 with Trichostatin in MDA-MB-468. FIG. 58D shows NSC 718813 with Cyclohexamide in MDA-MB-468.

FIG. 59A shows NSC 718813 with Mitomycin in MDA-MB-231. FIG. 59B shows NSC 718813 with Doxorubicin in MDA-MB-468. FIG. 59C shows NSC 718813 with Paclitaxel in MDA-MB-468. FIG. 59D shows NSC 718813 with Olaparib in MDA-MB-468.

FIG. 60A shows NSC 718813 with Gefitinib in MDA-MB-468. FIG. 60B shows NSC 718813 with Oxaliplatin in MDA-MB-468. FIG. 60C shows NSC 718813 with Erlonitib in MDA-MB-468.

FIG. 61A shows NSC 718813 with Olaparib in U2OS. FIG. 61B shows NSC 718813 with Erlonitib in U2OS. FIG. 61C shows NSC 718813 with Gefitinib in U2OS. FIG. 61D shows NSC 718813 with Oxaliplatin in U2OS. FIG. 61E shows NSC 718813 with 5FU in U2OS.

FIG. 62A shows NSC 718813 with Olaparib in SW620. FIG. 62B shows effects of NSC 718813 with Oxaliplatin. FIG. 62C shows NSC 718813 with Gefitinib in SW620. FIG. 62D shows combination SW620 (NSC 718813 with 5FU).

FIG. 68 shows line graphs of PBDs that show more potent growth inhibition in K-ras mutant colorectal cancer cells that are DNA mismatch repair (MMR) deficient.

FIG. 73 shows a table and line graphs of comparison of activity of IndUS PBDs in Isogenic U2OS with RNAi knockdowns of MMR, p53 and REV3 functions.

FIG. 74 shows bar graphs of IndUS PBDs showing synthetic lethality as monotherapy in U2OS cells using RNAi knockdown of DNA mismatch repair (MMR), apoptosis (p53) and homologous recombination/translesional synthesis (REV3) genes.

FIG. 75 is a table showing novel PBDs showing synthetic lethality in tumor cells that have loss of DNA mismatch repair (MMR) and/or apoptosis (p53).

FIG. 76 shows line graphs showing lead IndUS PBD compounds having excellent PK with long half-life in rats.

FIG. 83 shows line graphs of quantitative analysis of in vivo SW620 colon tumor xenograft data showing that NSC723734 is synergistic with cisplatin at combination doses achieving >50% efficacy.

FIG. 84 shows line graphs of quantitative analysis of in vivo effects of NSC723734 and cisplatin results in significant dose-reduction index (DRI) supporting the mutual synergism in SW620 colon tumor xenograft mouse model.

FIG. 85 shows a table of novel IndUS anticancer PBDs that are significantly different compared to previously described DNA minor groove binders.

DETAILED DESCRIPTION OF THE INVENTION

I. Definitions

Figure 1:
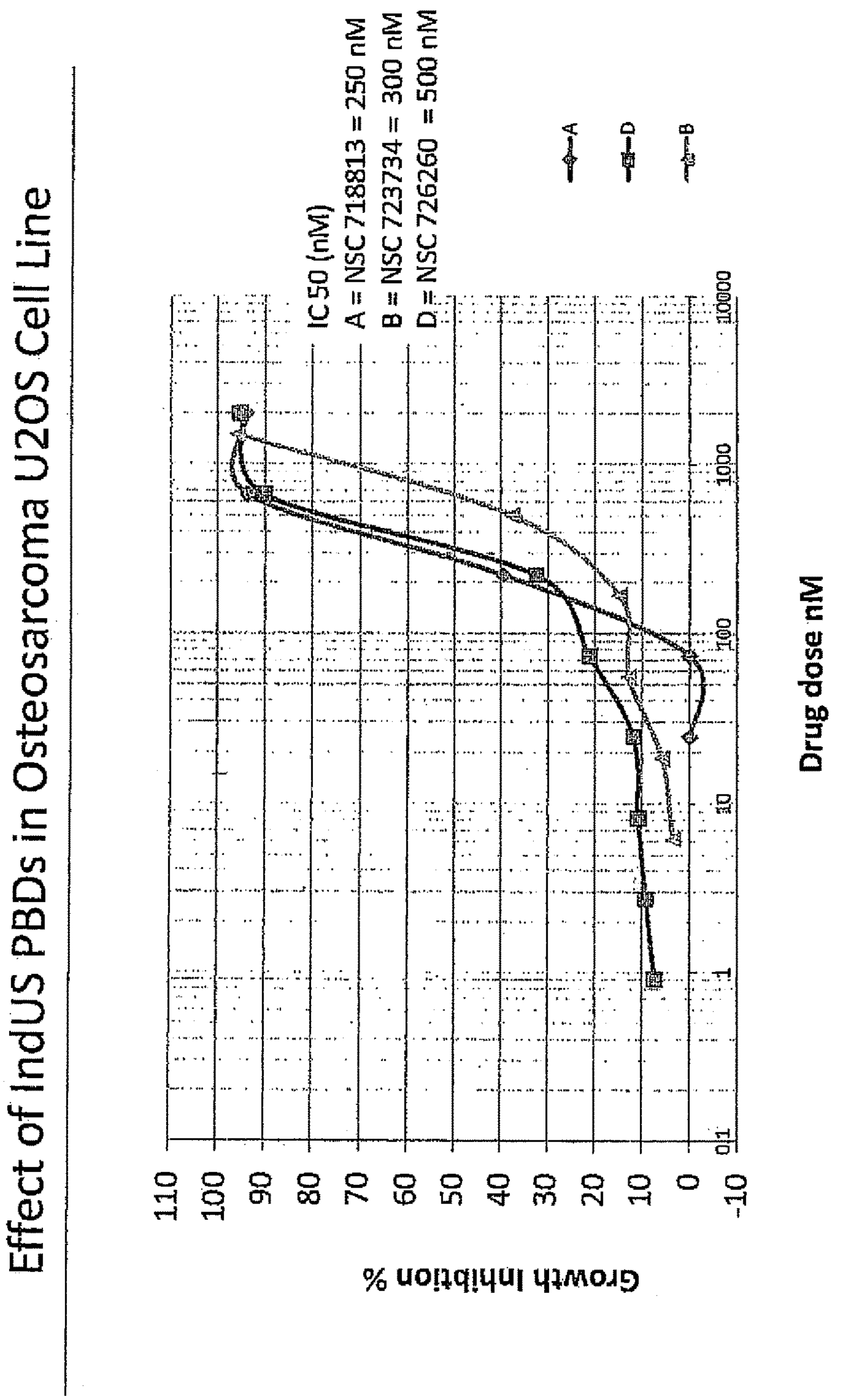
FIG. 1 presents the effects of non-covalent DNA binding agents in osteosarcoma U20S cells.
Figure 2:
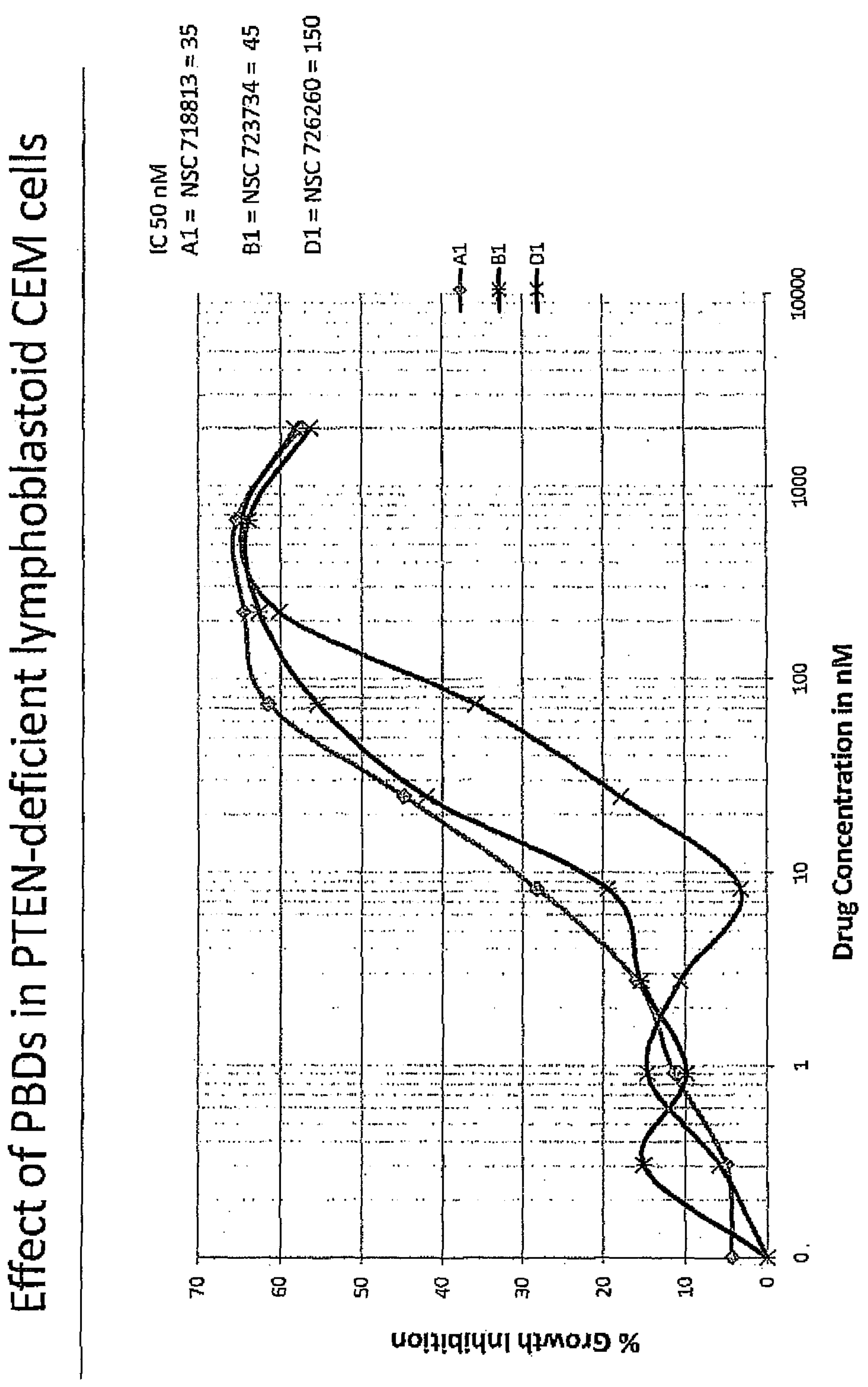
FIG. 2 presents the effects of non-covalent DNA binding agents in PTEN-deficient lymphoblastoid CEM cells.
Figure 3:
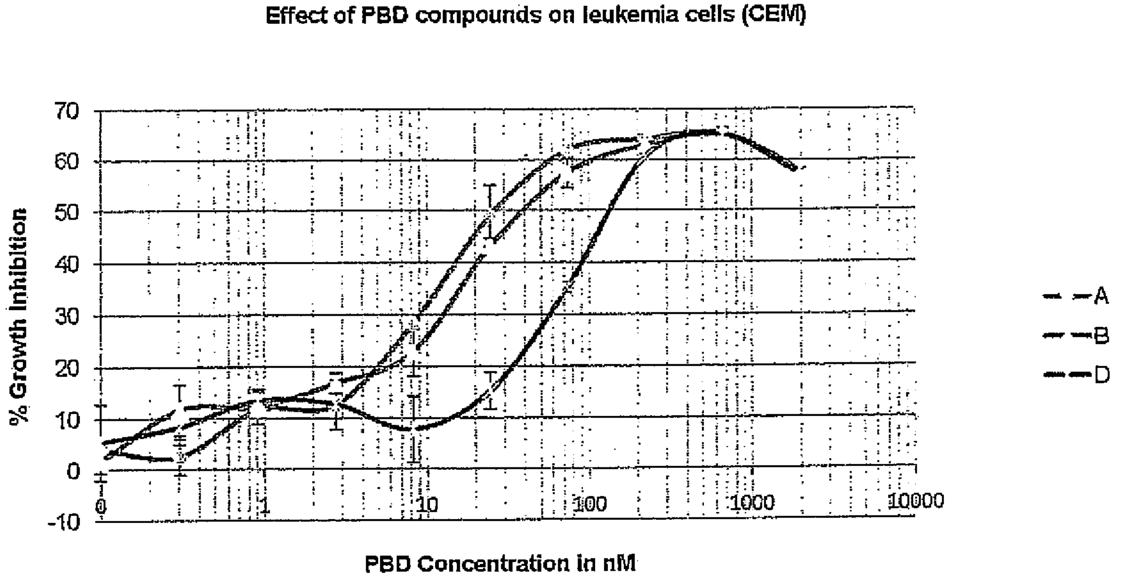
FIG. 3 presents the effects of non-covalent DNA binding agents in leukemia (CEM) cells with PTEN (homologous recombination deficiency).
Figure 4:
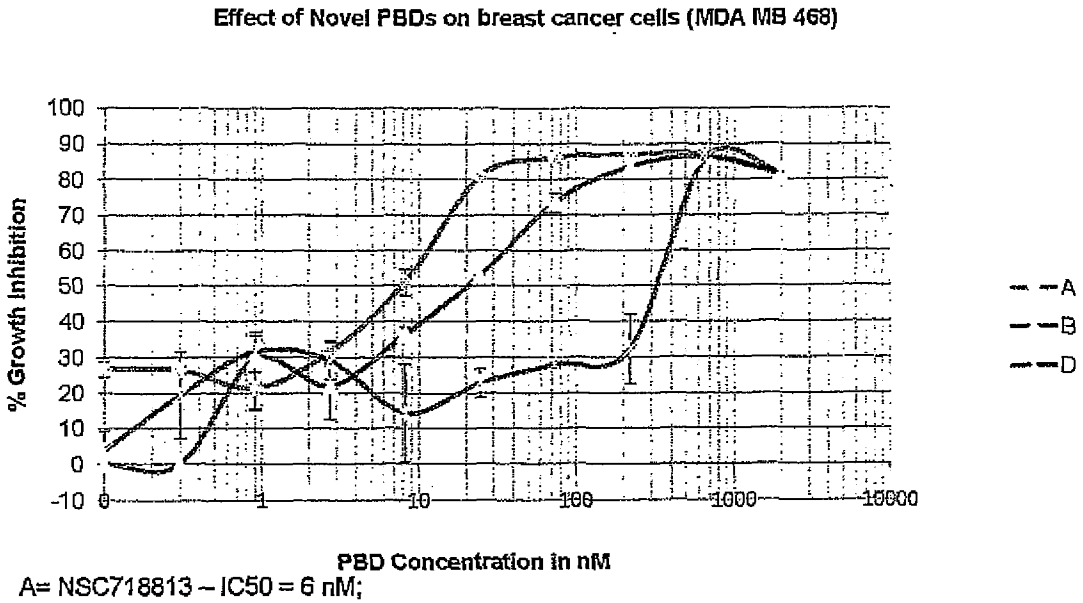
FIG. 4 presents the effects of non-covalent DNA binding agents in genetically resistant breast cancer cells (MDA-MB-468) cells with deficiencies in PTEN and epigenetic DNA mismatch repair mutations.
Figure 5:
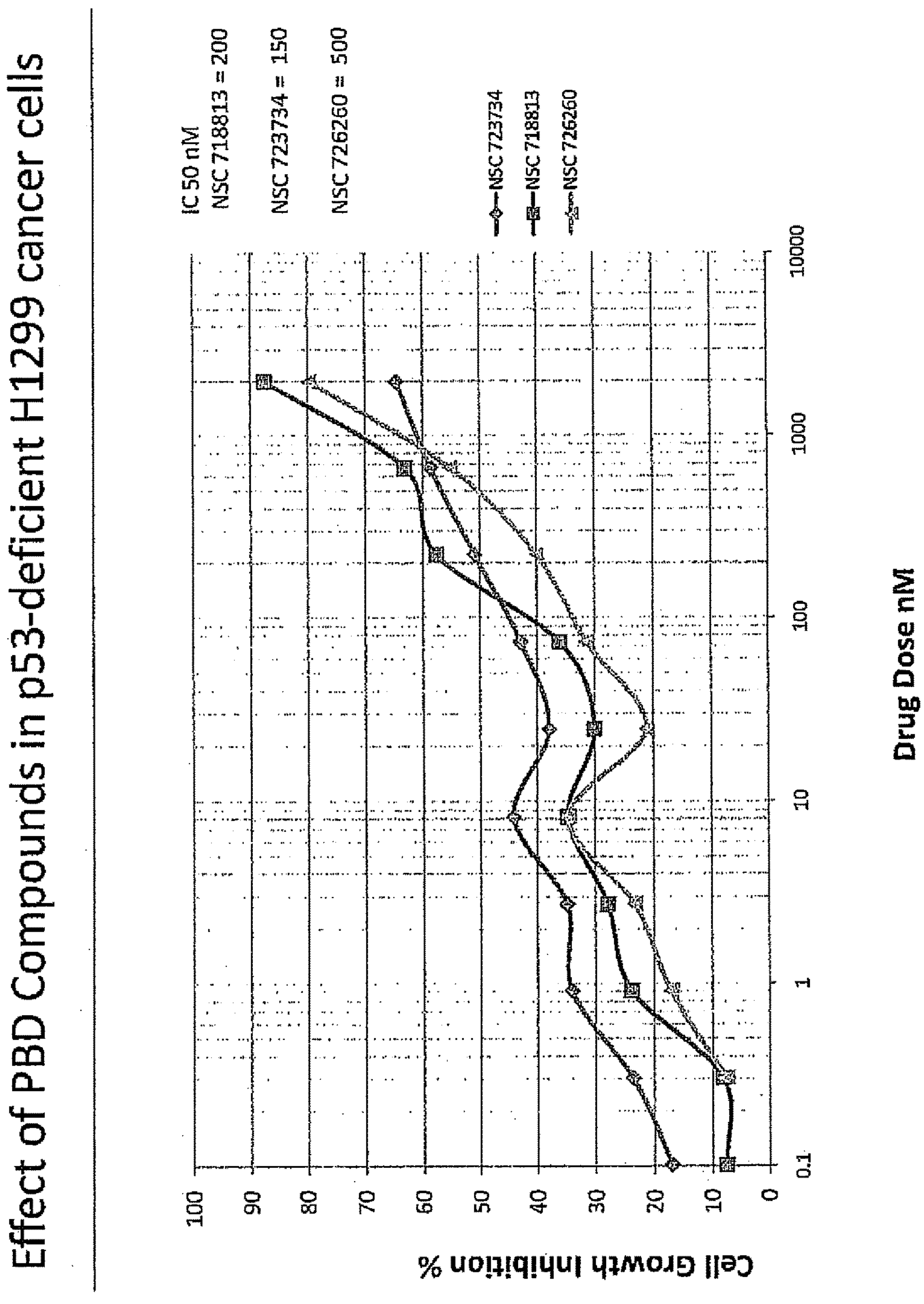
FIG. 5 presents the effects of non-covalent DNA binding agents in p53-deficient H1299 cells.
Figure 6A:
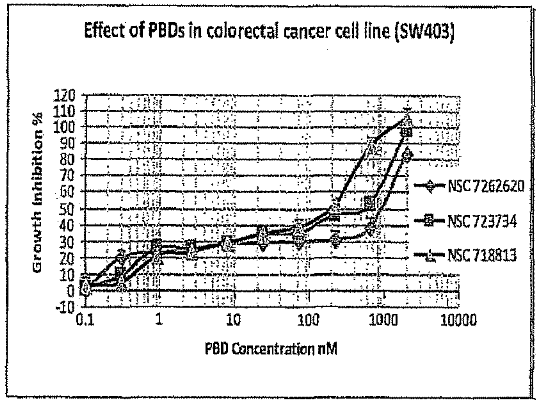
FIG. 6 presents the effects of non-covalent DNA binding agents in colorectals cells with (A) normal (SW403) or (B) mutated (SW480) kras.
Figure 6B:
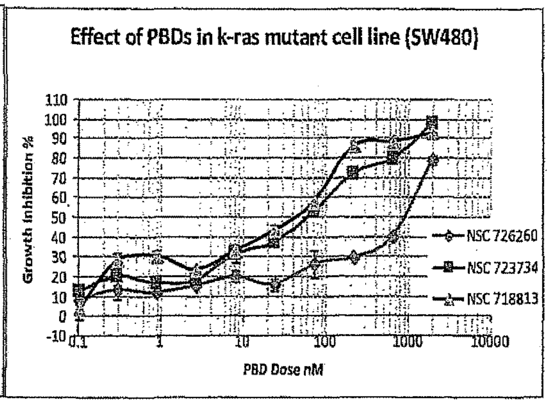
Figure 7A:
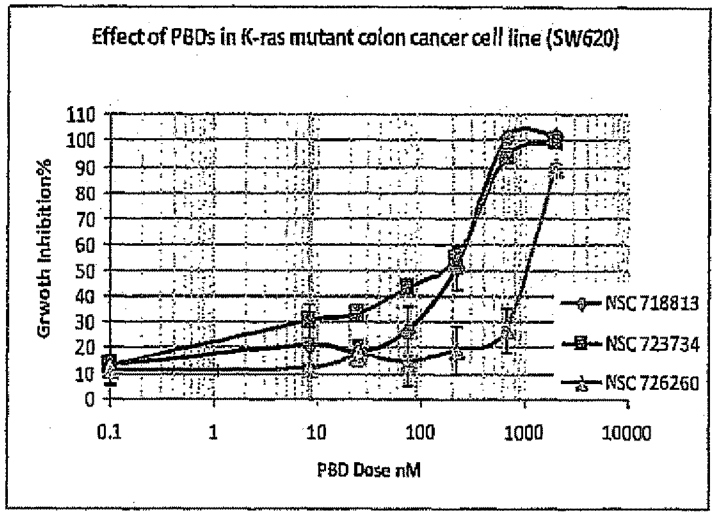
FIG. 7 presents the effects of non-covalent DNA binding agents in colorectal cancer cells with (A) mutated kras or (B) mutated kras and having a mismatch repair (MMR) deficiency.
Figure 7B:
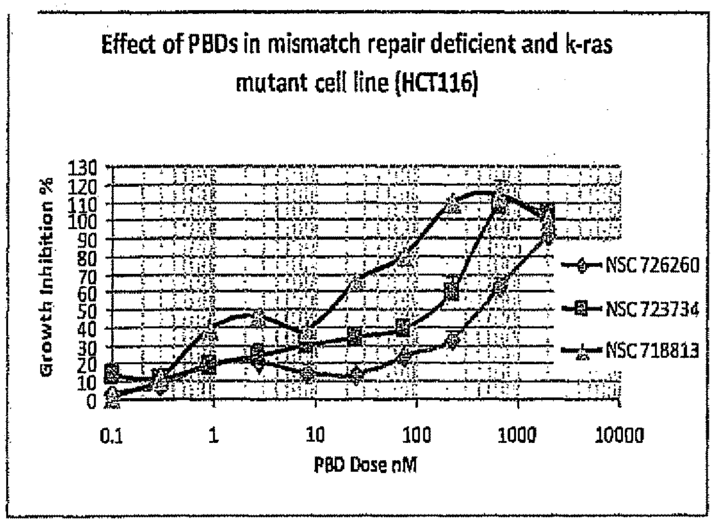
Figure 8A:
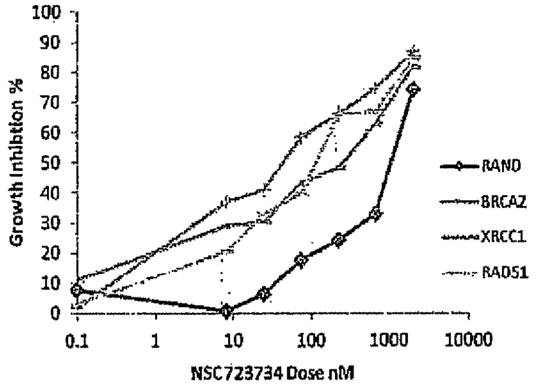
FIG. 8 shows that non-covalent DNA binding agents ((A) 723734 and (B) 726260), are synthetic lethal with homologous recombination repair deficiencies.
Figure 8B:
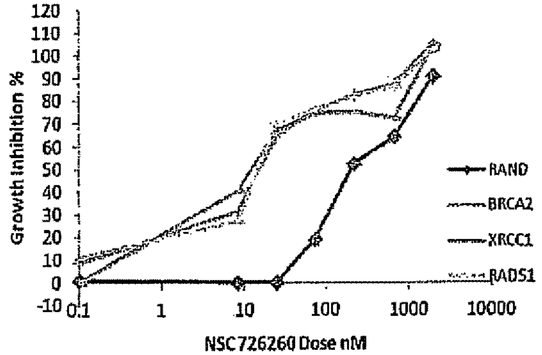
Figures 10A, 10B:
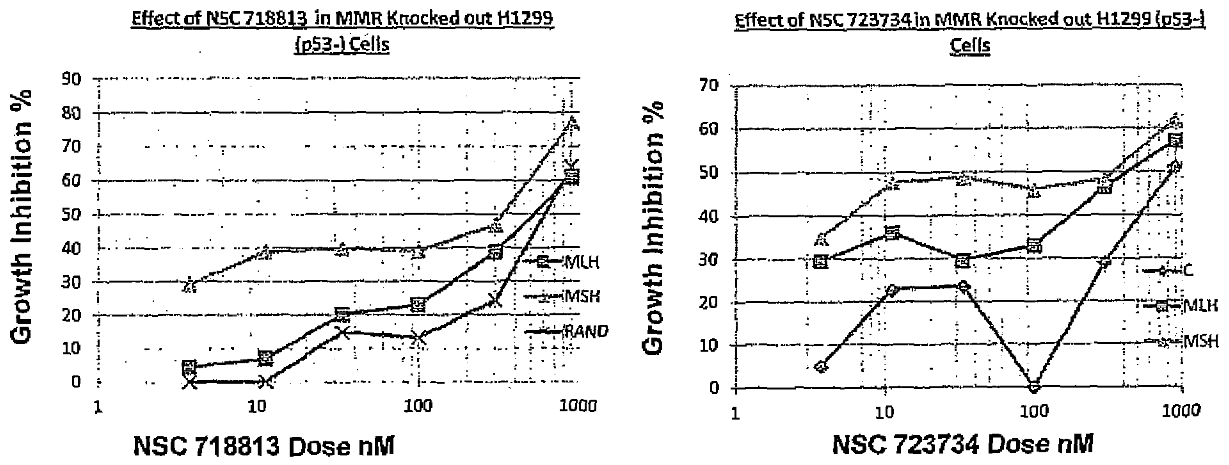
FIG. 10 presents the results of a comparison of the activity of non-covalent DNA binding agents in isogenic p53-deficient HI299 cells wherein MMR functions have been inhibited using RNAi methods (A) NSC 718813; (B) NSC 723734.
Figure 31:
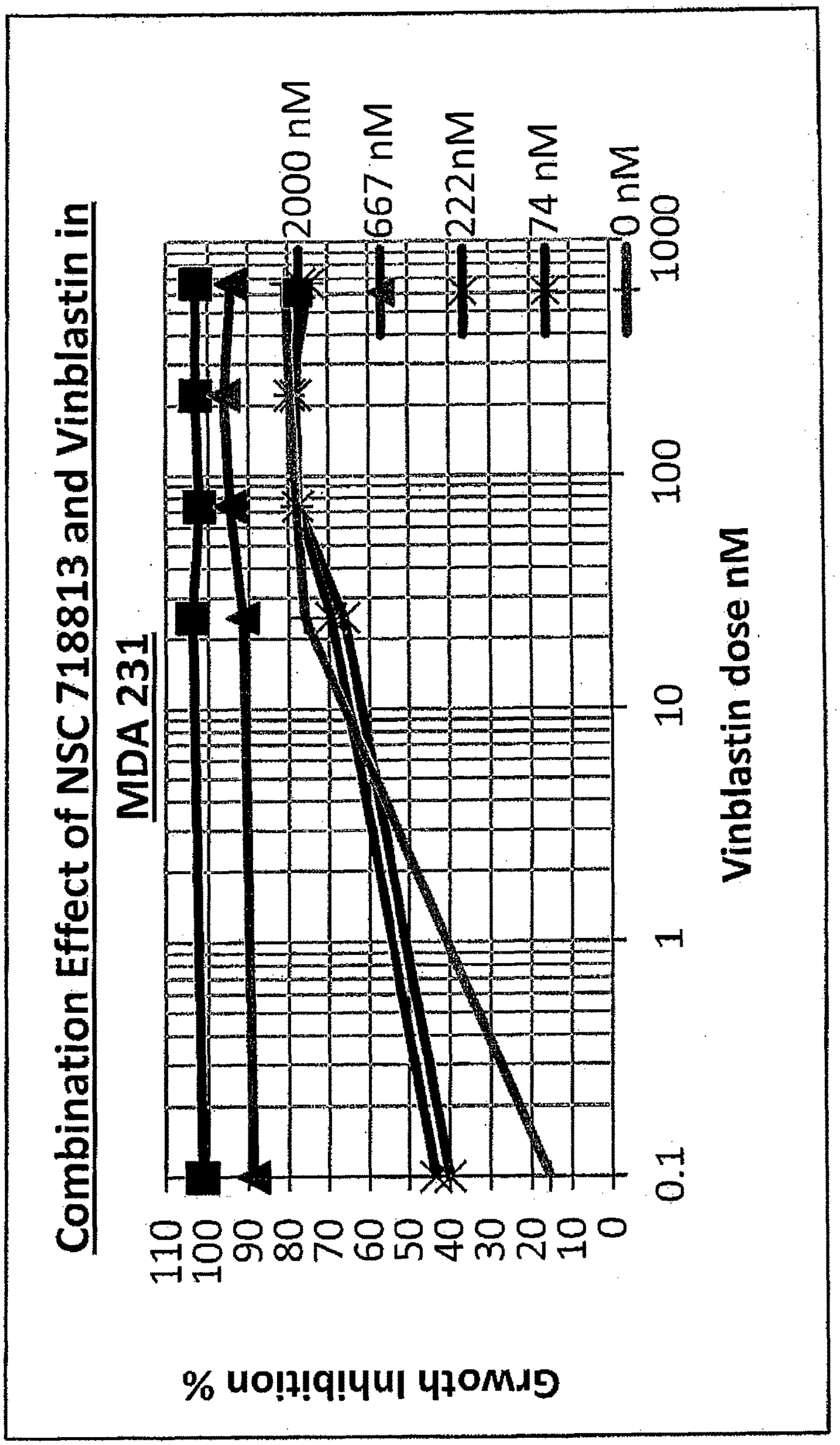
FIG. 31 shows a line graph of the combination effect of NSC 718813 and Vinblastin in MDA-MB-231.
Figure 32:
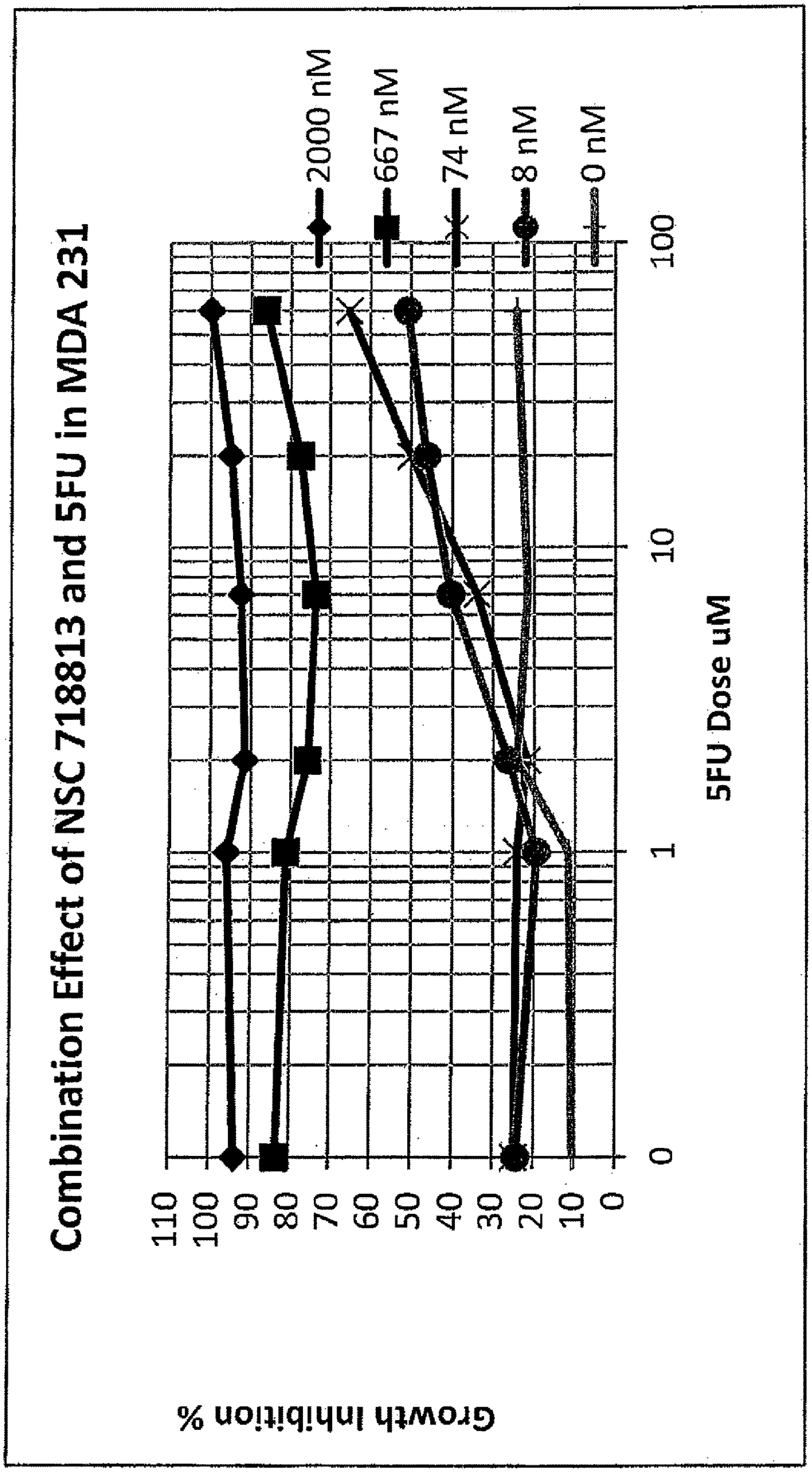
FIG. 32 shows a line graph of the combination effect of NSC 718813 and 5-fluorouracil (5-FU) in MDA-MB-231.
Figure 33:
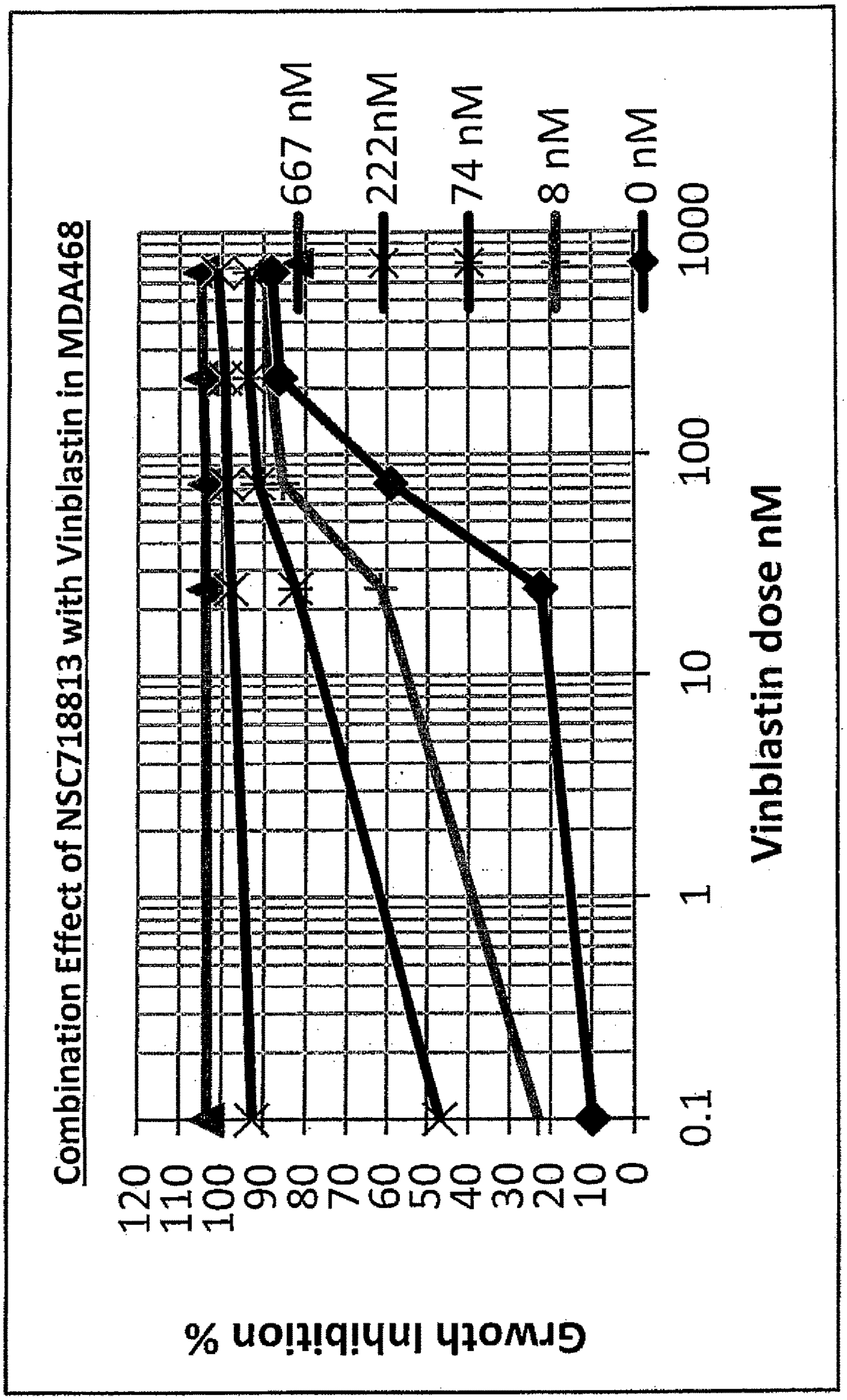
FIG. 33 shows a line graph of the combination effect of NSC718813 with Vinblastin in MDA-MB-468.
Figure 34:
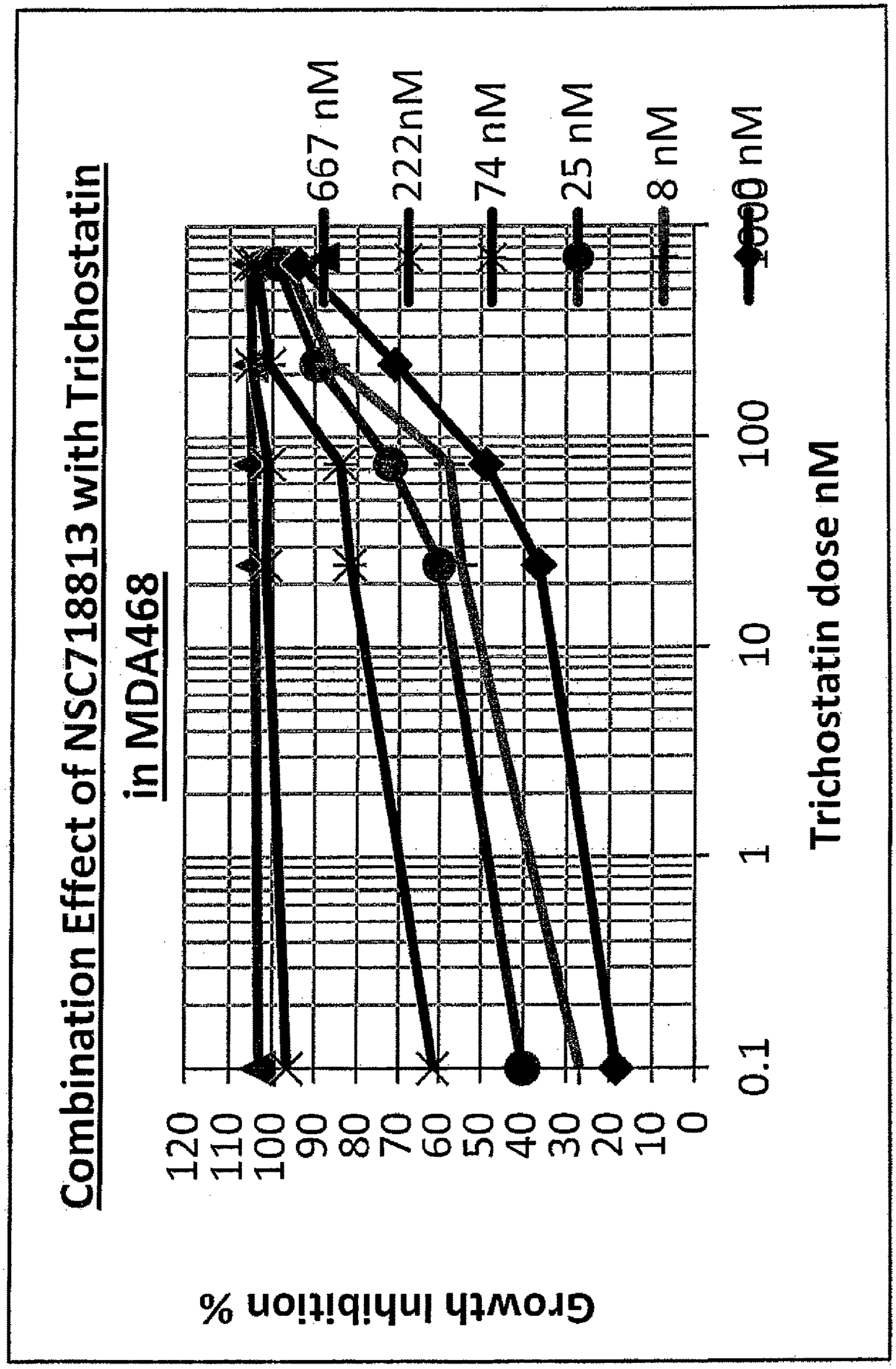
FIG. 34 shows a line graph of the combination effect of NSC718813 with Trichostatin in MDA-MB-468.
Figure 35:
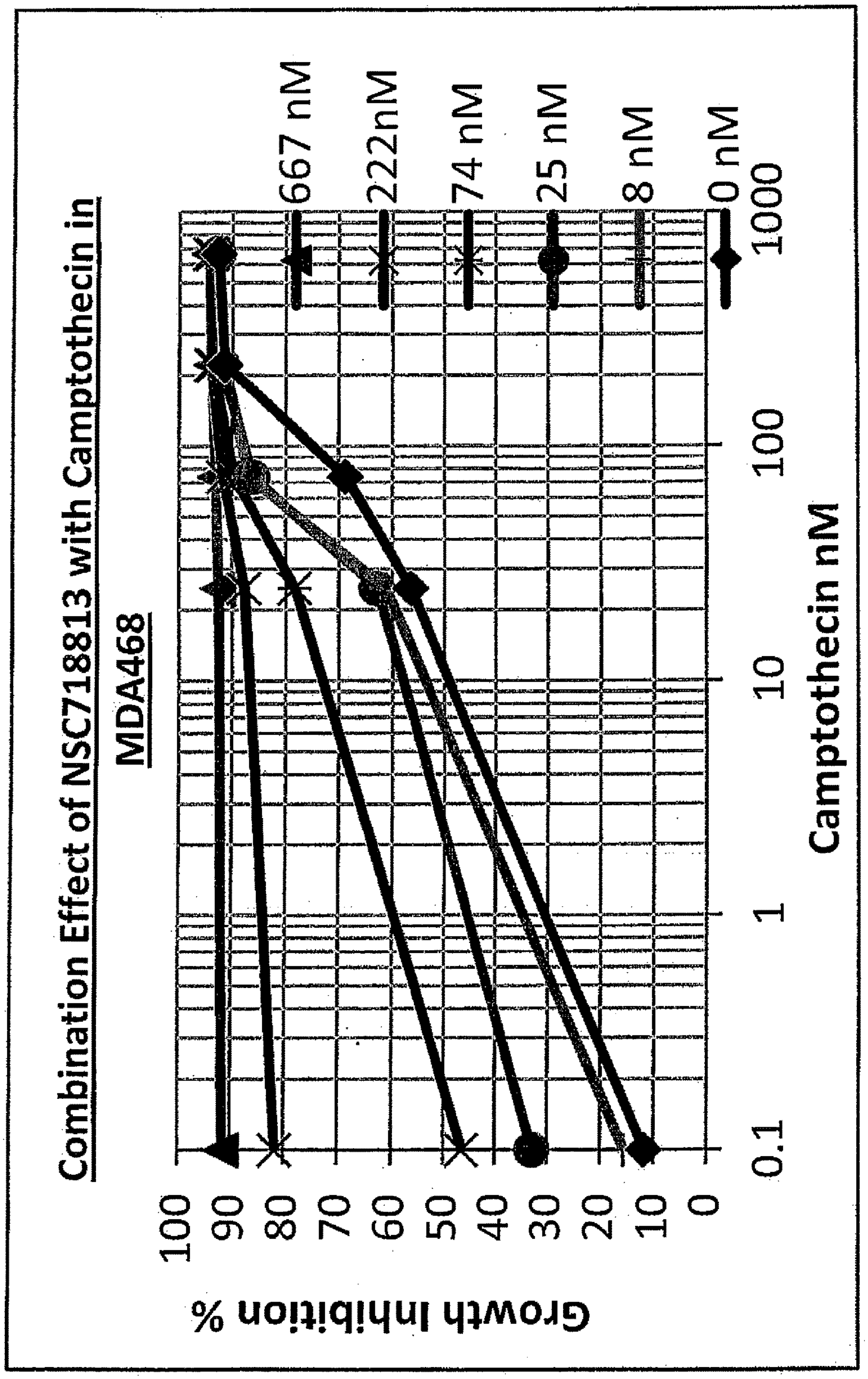
FIG. 35 shows a line graph of the combination effect of NSC718813 with Camptothecin in MDA-MB-468.
Figure 36:
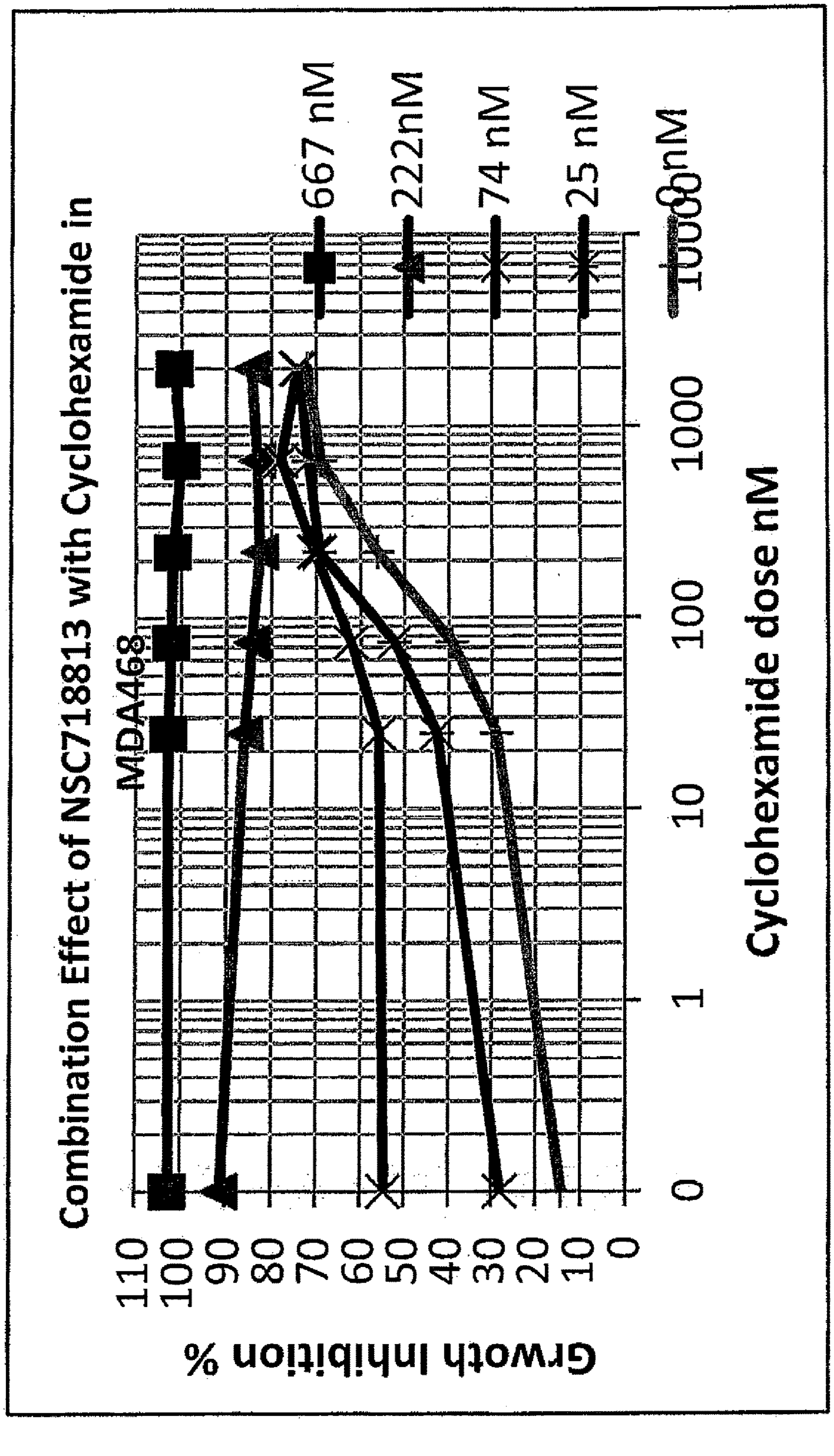
FIG. 36 shows a line graph of the combination effect of NSC718813 with Cyclohexamide in MDA-MB-468.
Figure 37:
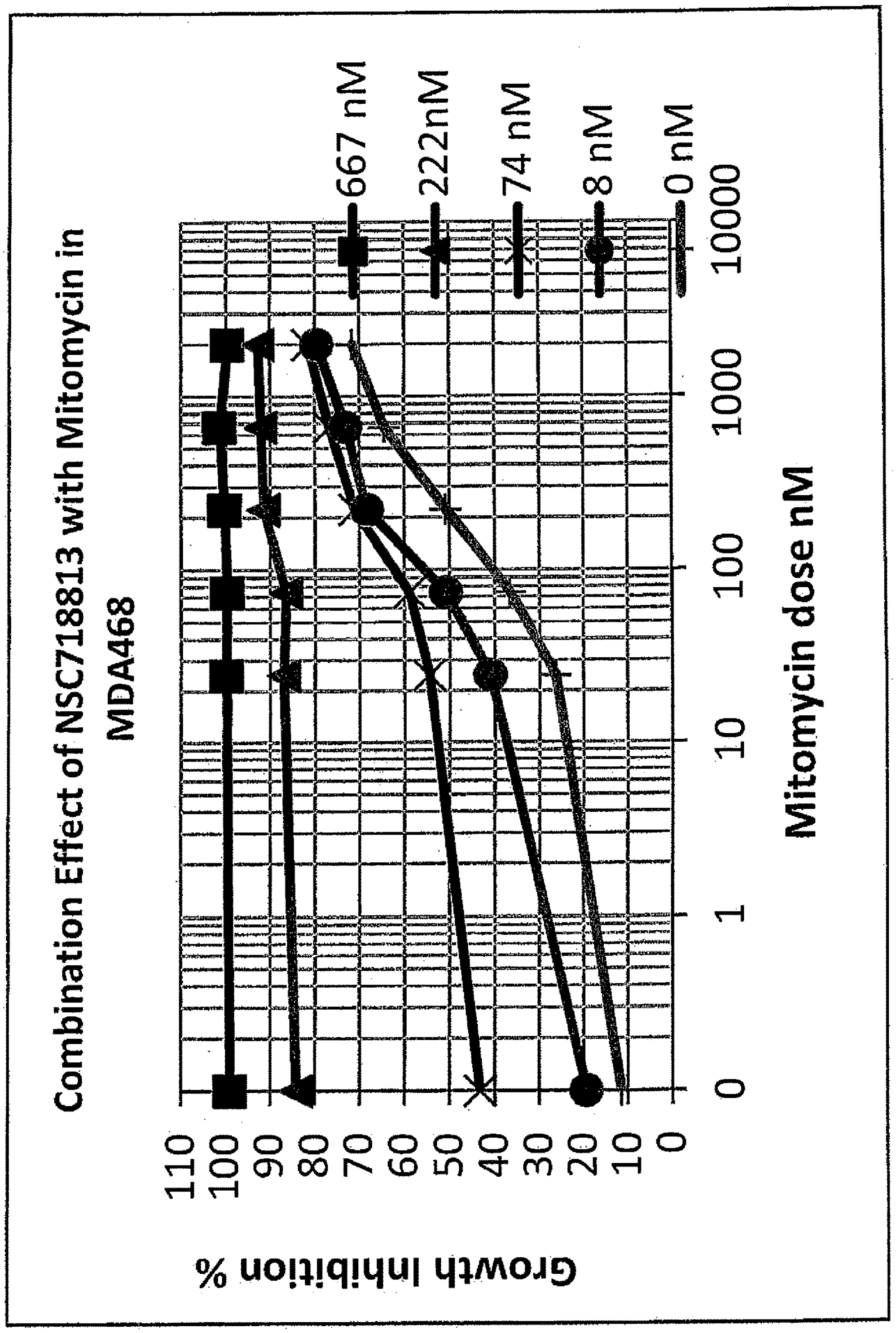
FIG. 37 shows a line graph of the combination effect of NSC718813 with Mitomycin in MDA-MB-468.
Figure 38:
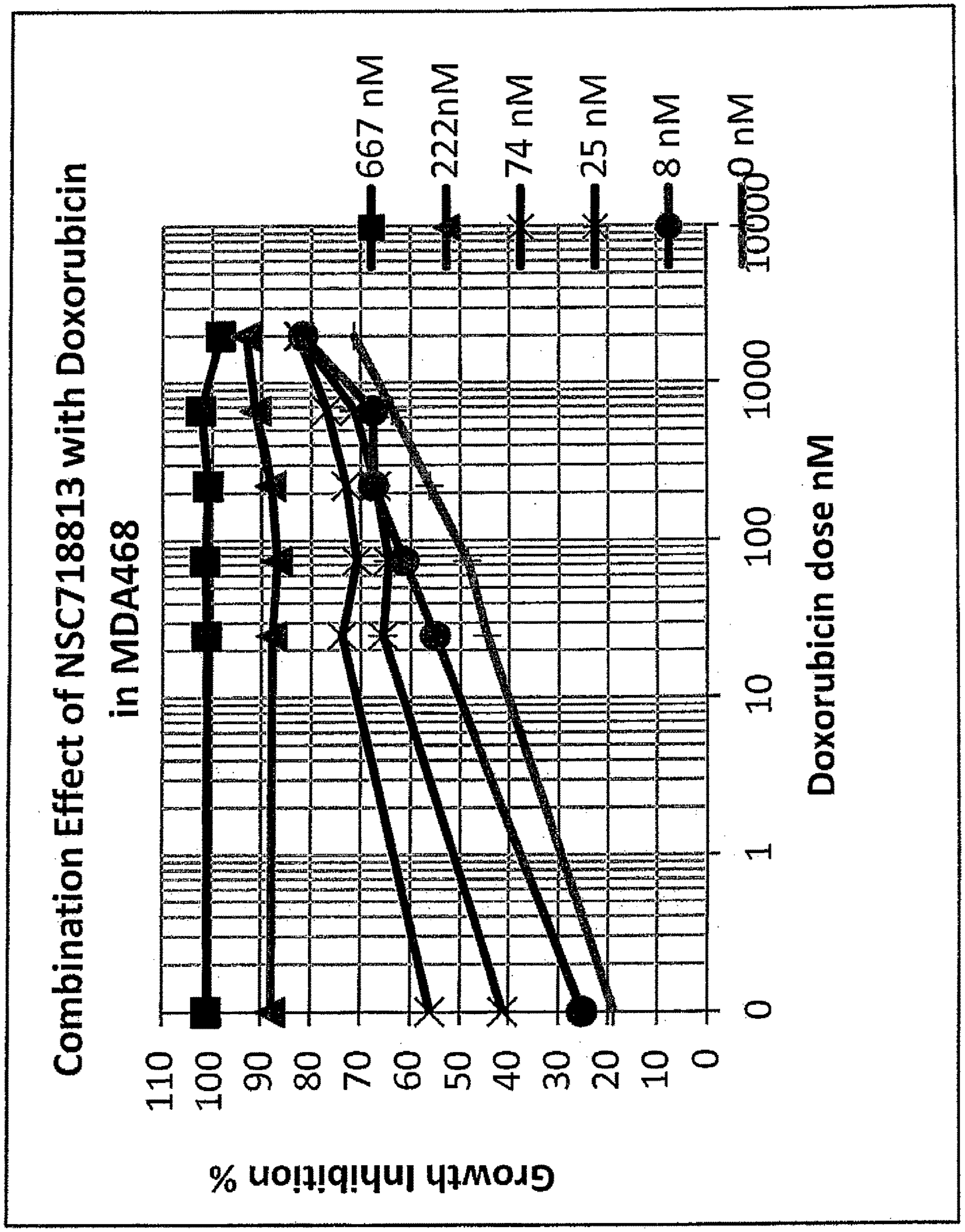
FIG. 38 shows a line graph of the combination effect of NSC718813 with Doxorubicin in MDA-MB-468.
Figure 39:
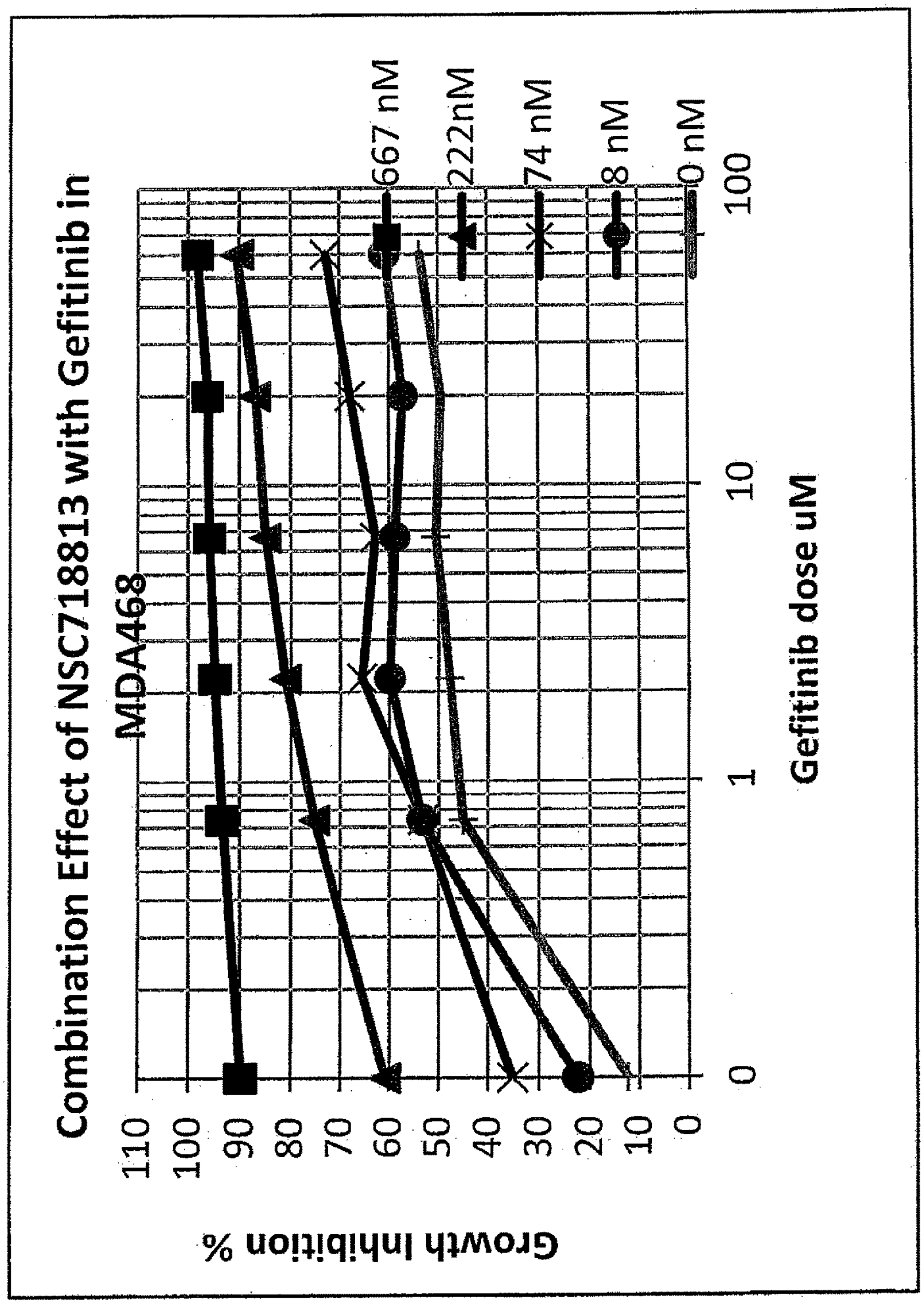
FIG. 39 shows a line graph of the combination effect of NSC718813 with Gefitinib in MDA-MB-468.
Figure 40:
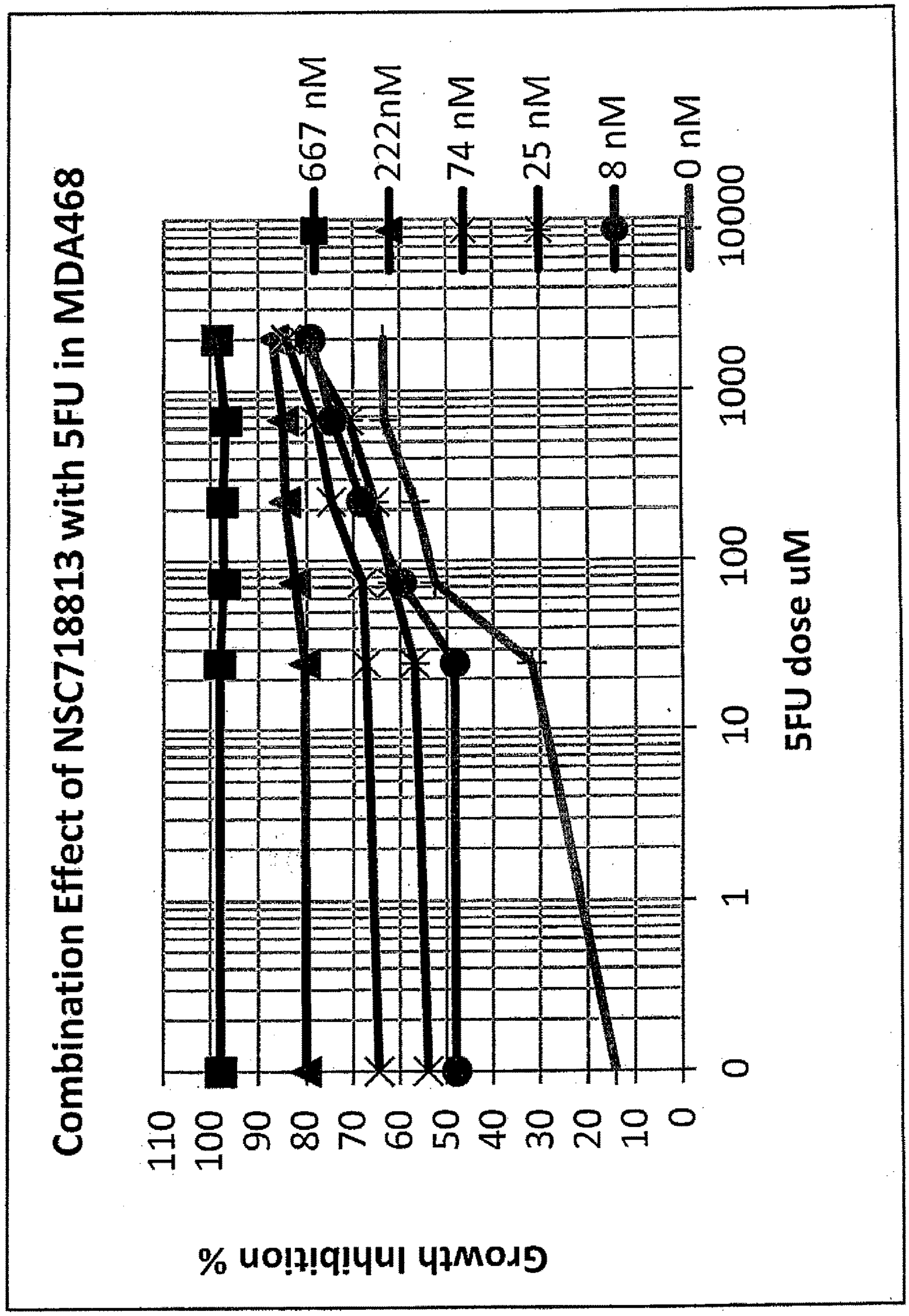
FIG. 40 shows a line graph of the combination effect of NSC718813 with 5FU in MDA-MB-468.
Figure 41:
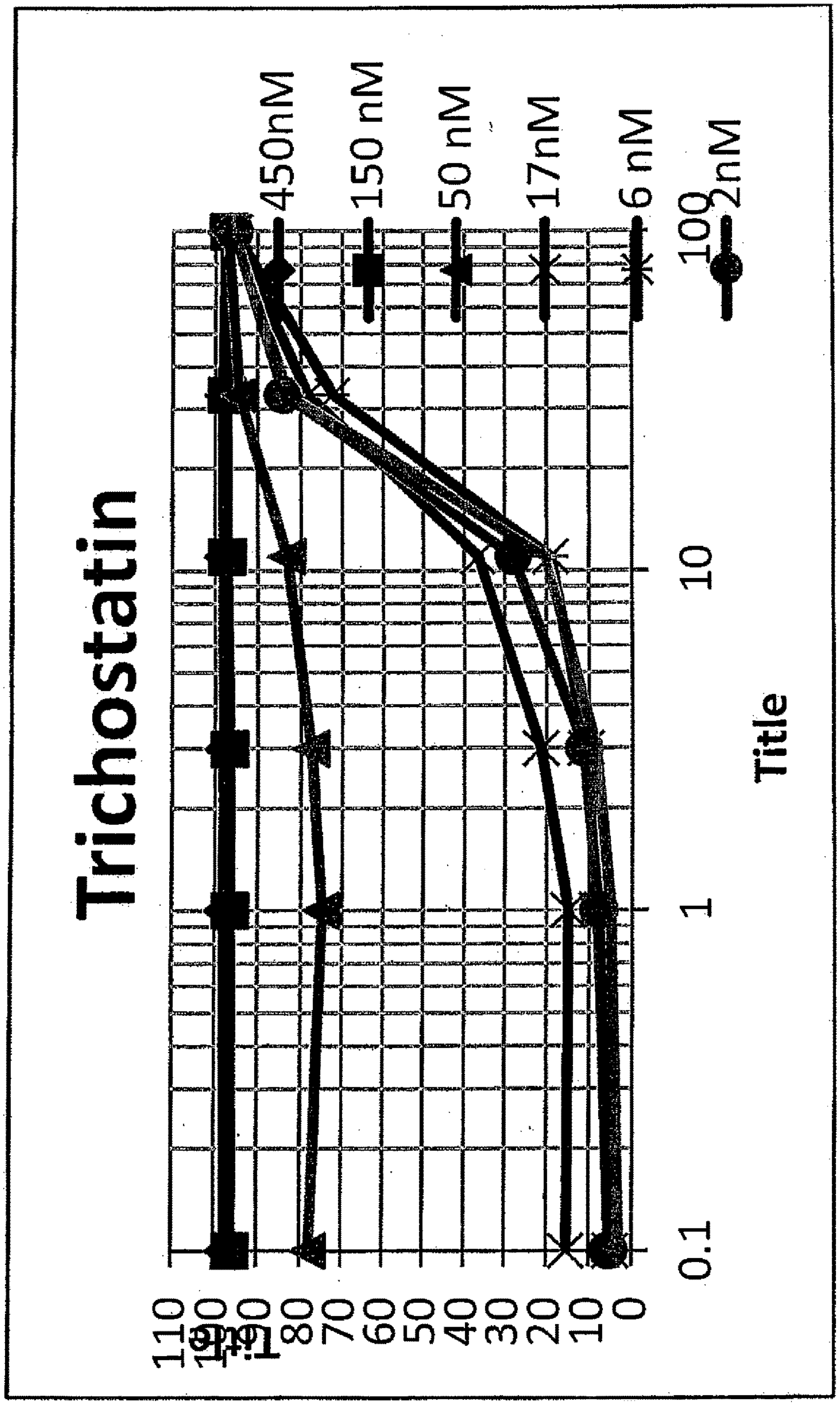
FIG. 41 shows a line graph of Trichostatin in CEM cells.
Figure 42:
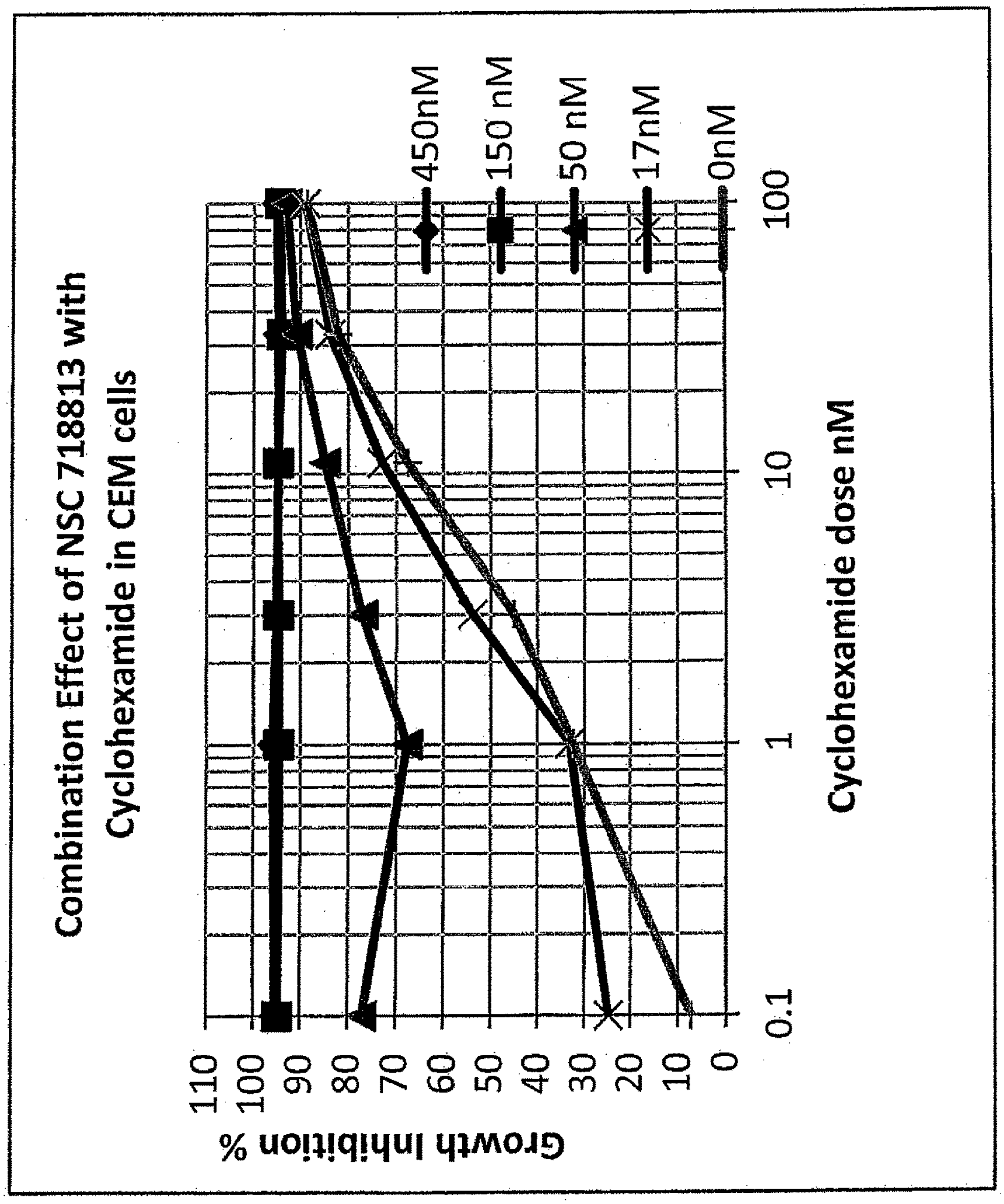
FIG. 42 shows a line graph of the combination effect of NSC 718813 with Cyclohexamide in CEM cells.
Figure 43:
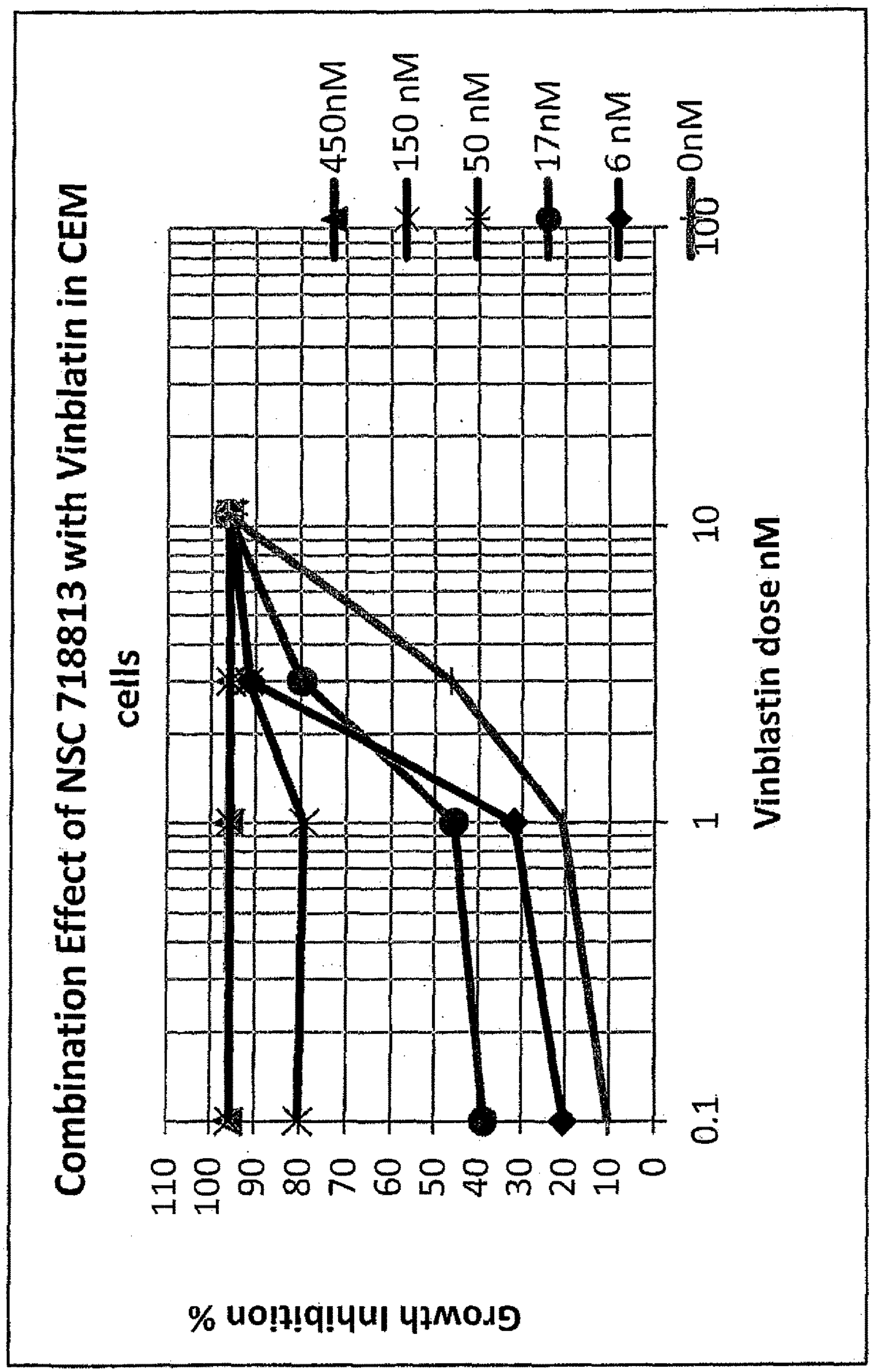
FIG. 43 shows a line graph of the combination effect of NSC 718813 with Vinblastin in CEM cells.
Figure 44:
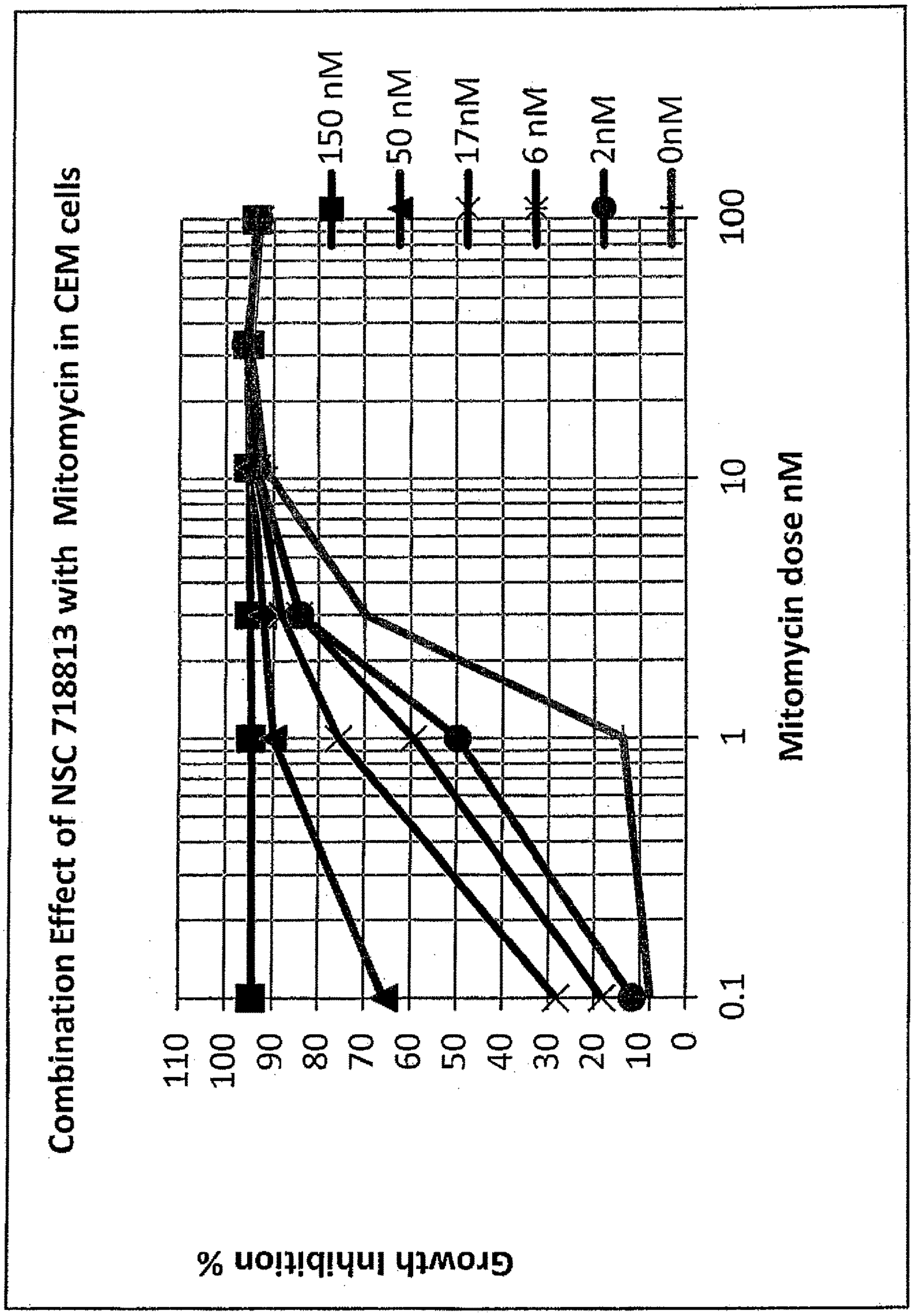
FIG. 44 shows a line graph of the combination effect of NSC 718813 with Mitomycin in CEM cells.
Figure 45:
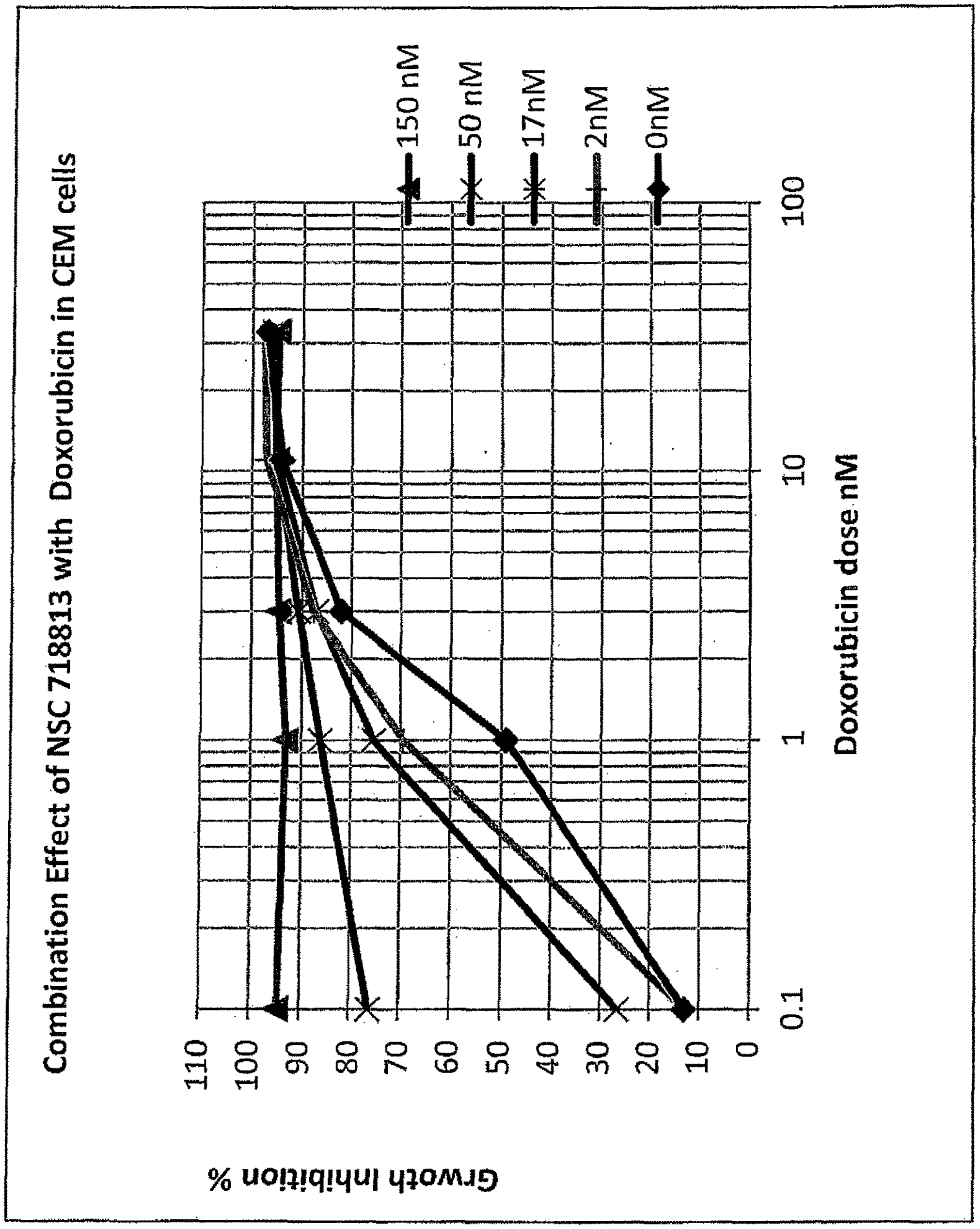
FIG. 45 shows a line graph of the combination effect of NSC 718813 with Doxorubicin in CEM cells.
Figure 46:
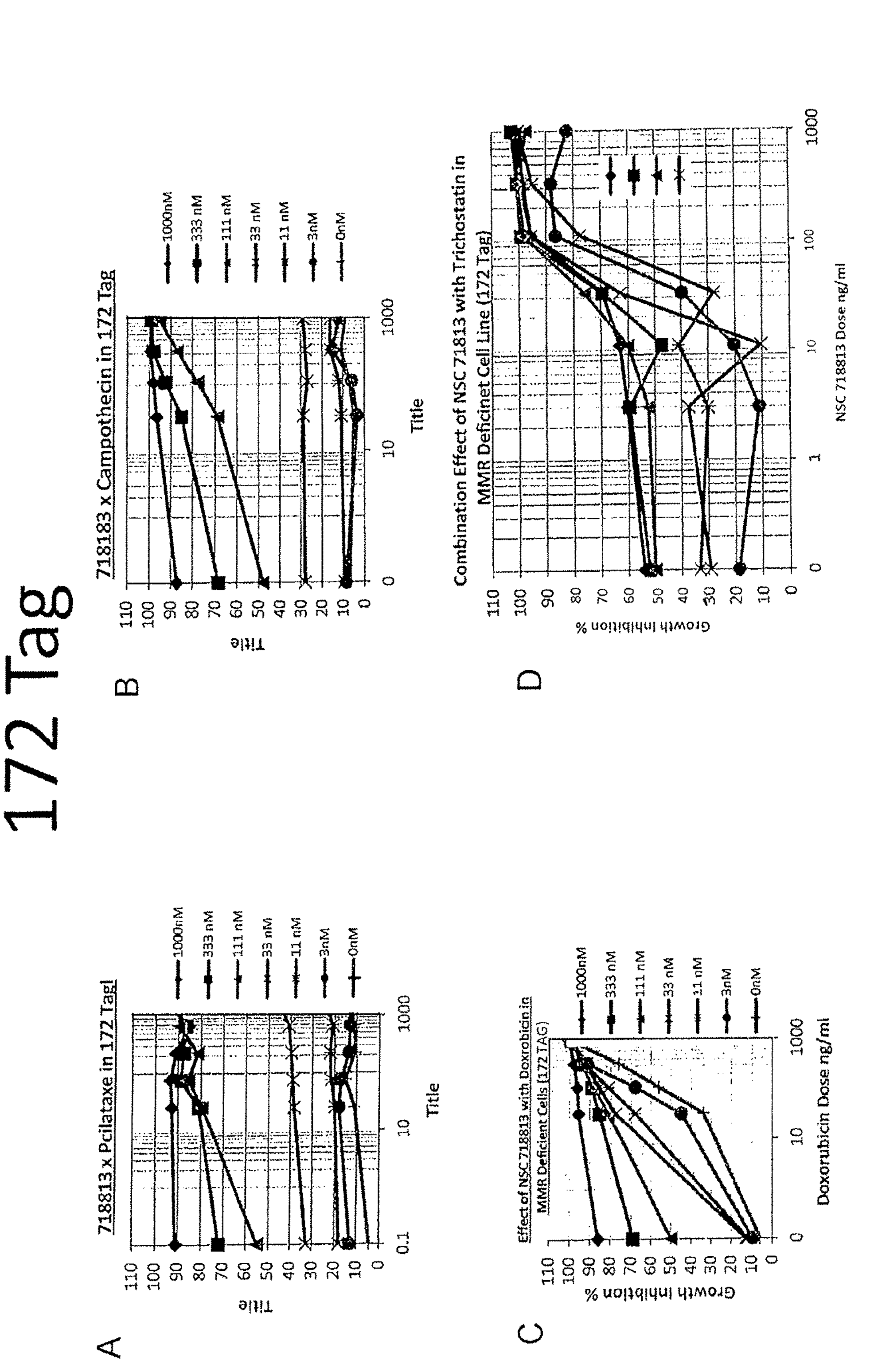
FIG. 46 shows line graphs of 172Tag.
Figure 48:
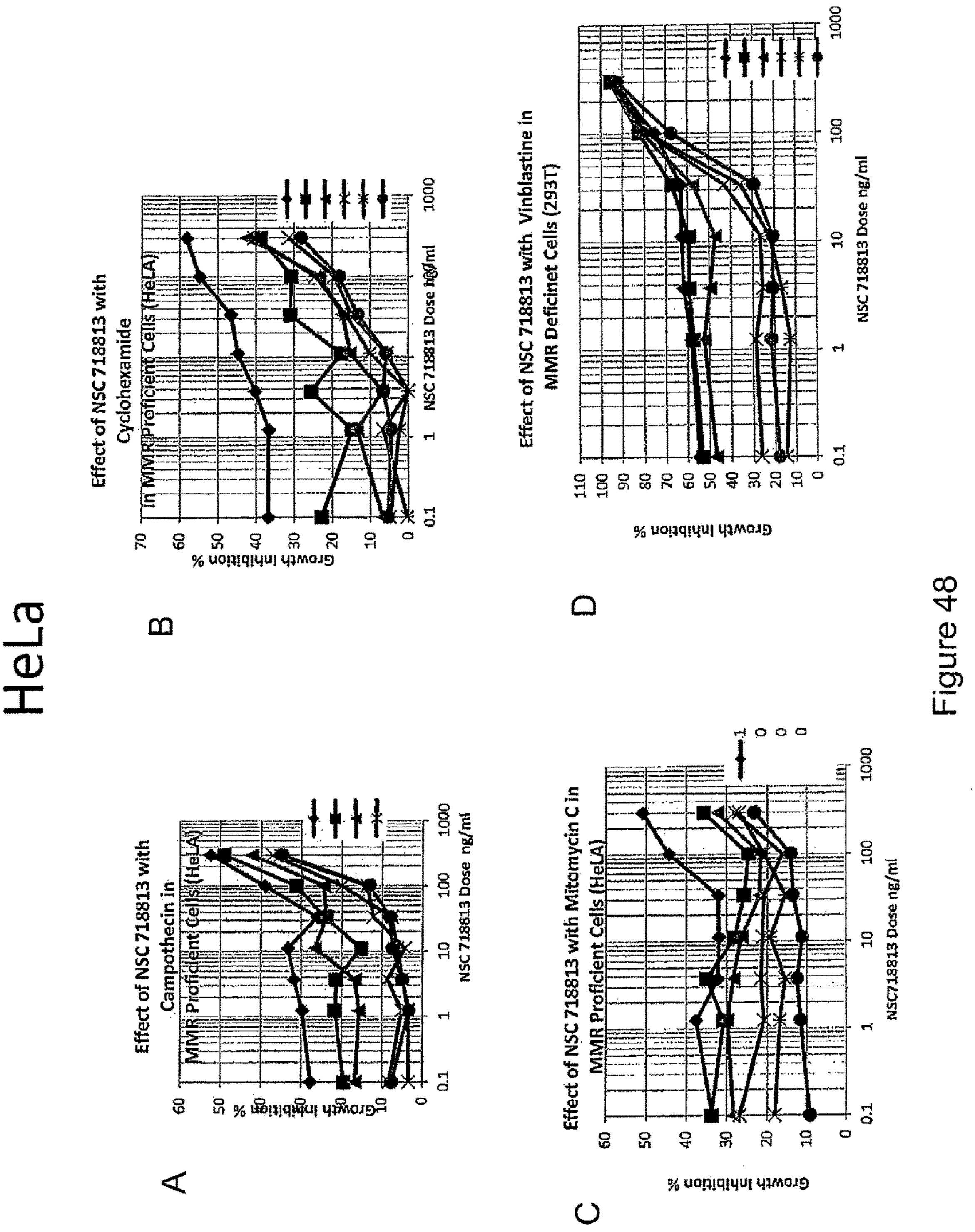
FIG. 48 shows line graphs of HeLa.
Figure 49:
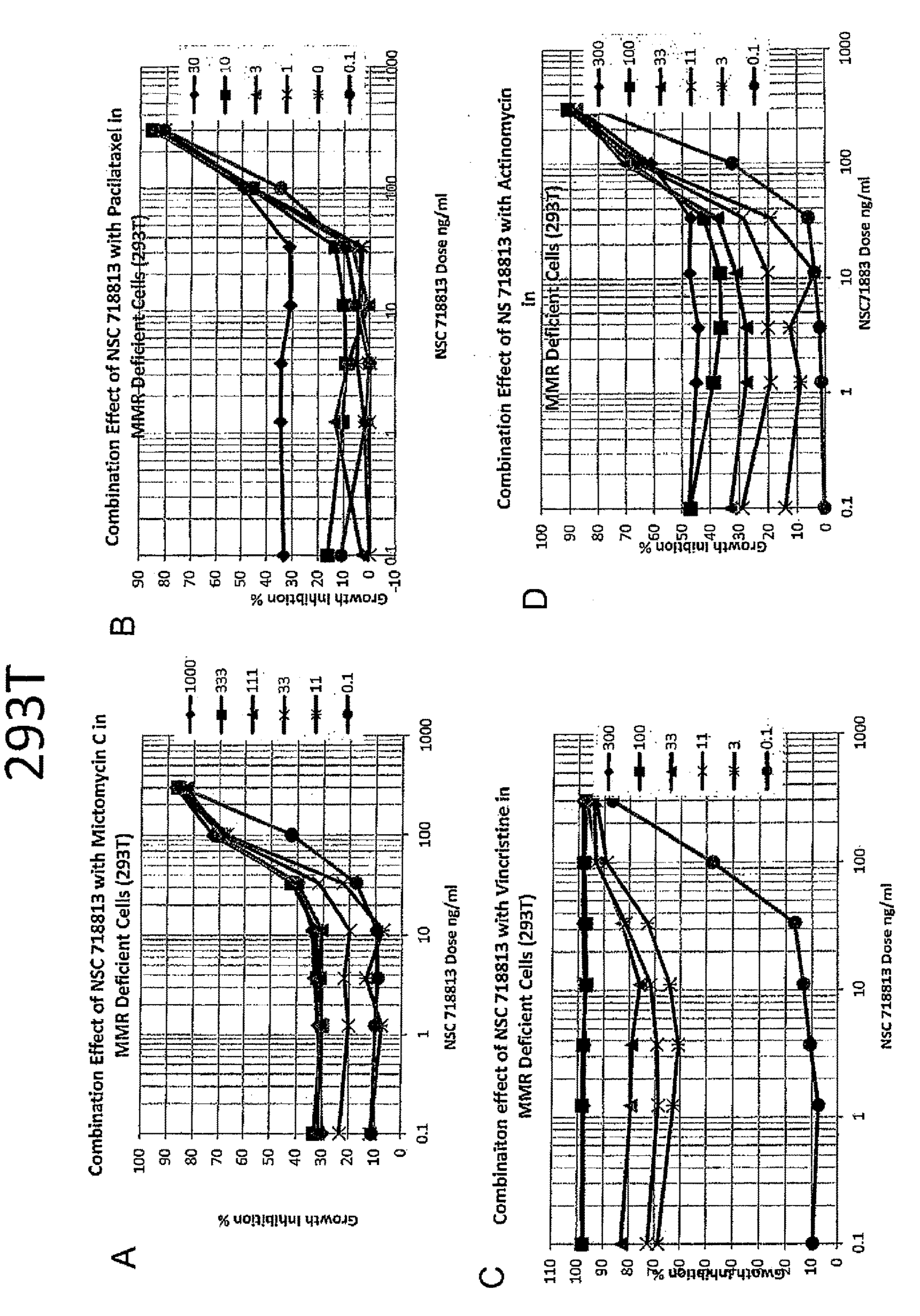
FIG. 49 shows line graphs of 293T.
Figure 50:
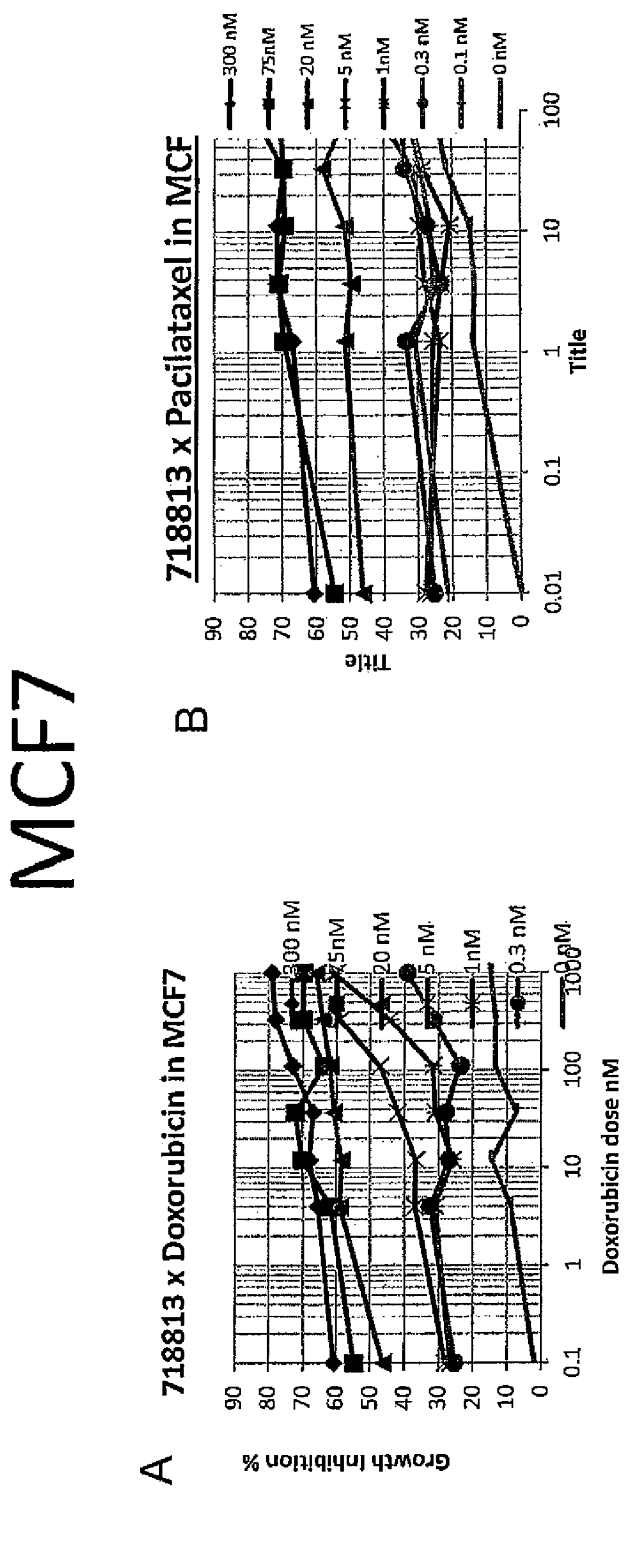
FIG. 50 shows line graphs of MCF7.
Figure 51:
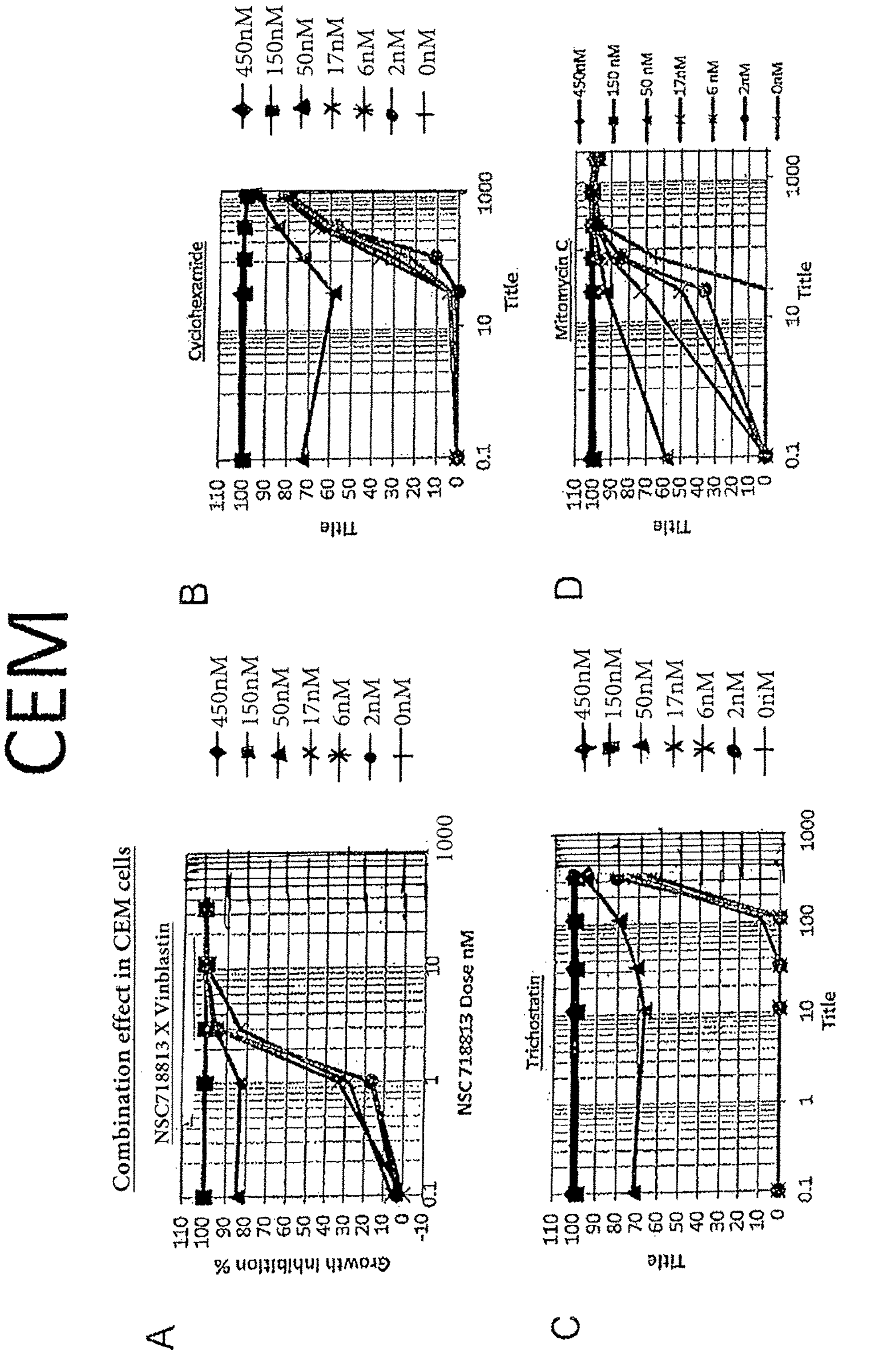
FIG. 51 shows line graphs of CEM.
Figure 52:
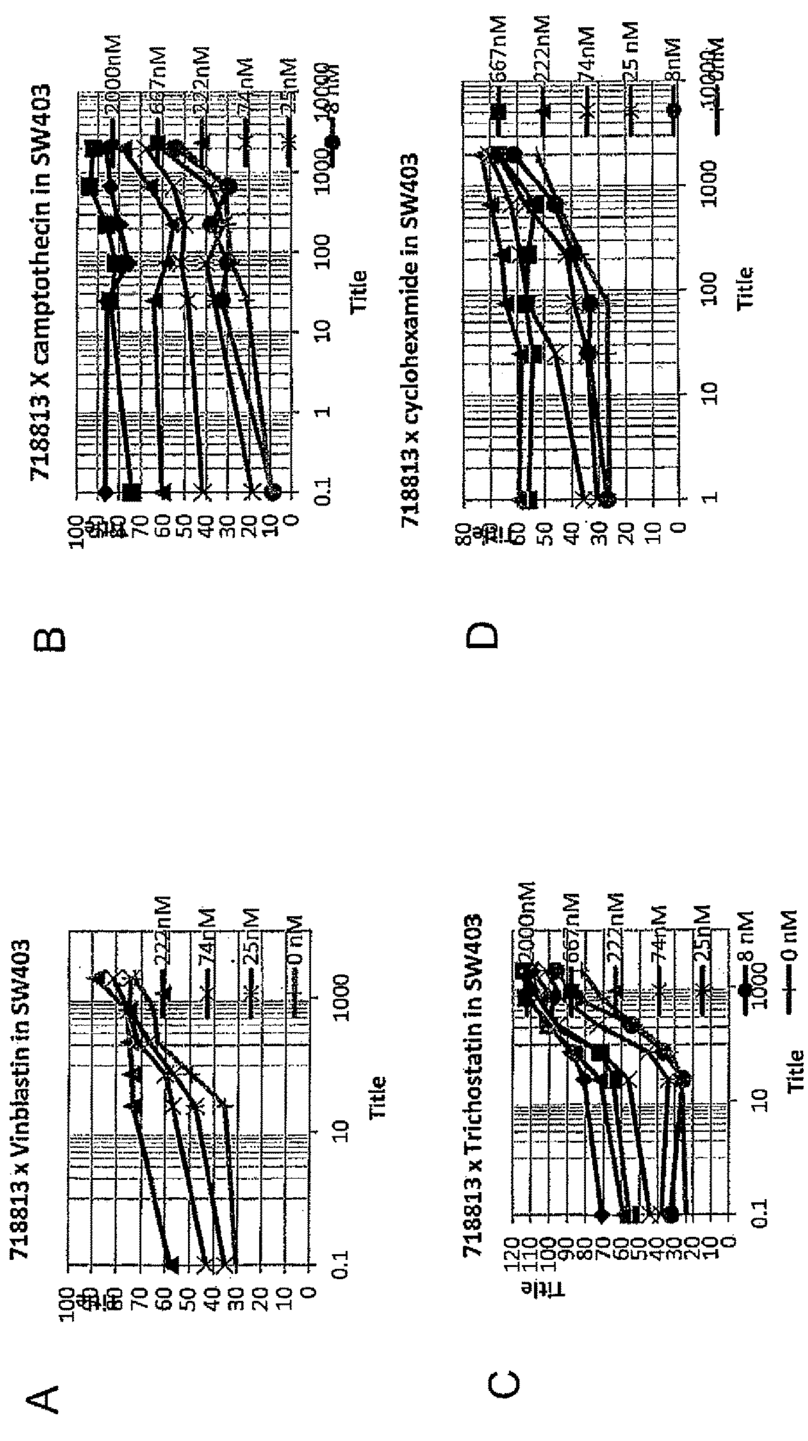
FIG. 52 shows line graphs of SW403.
Figure 53:
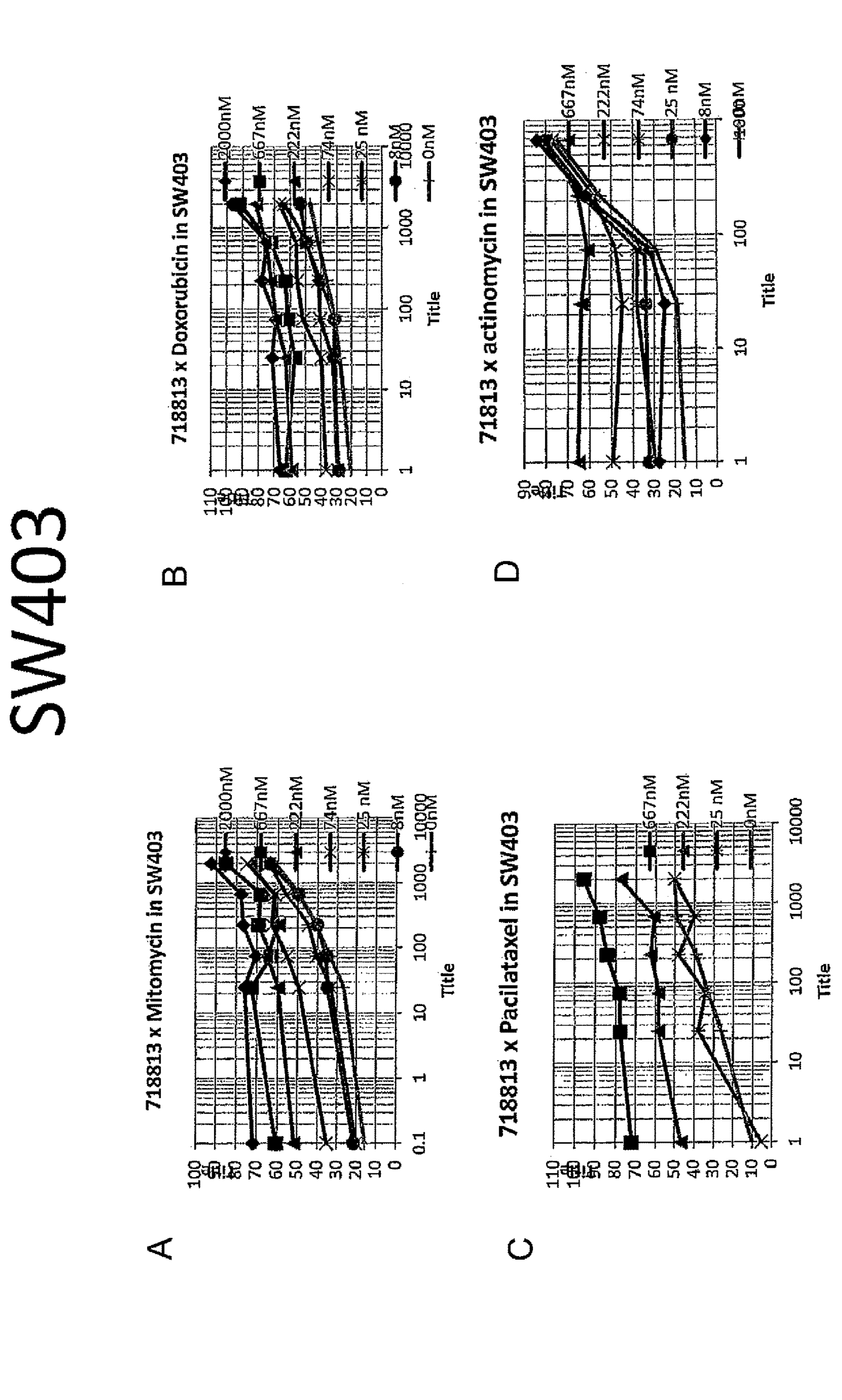
FIG. 53 shows line graphs of SW403.
Figure 54:
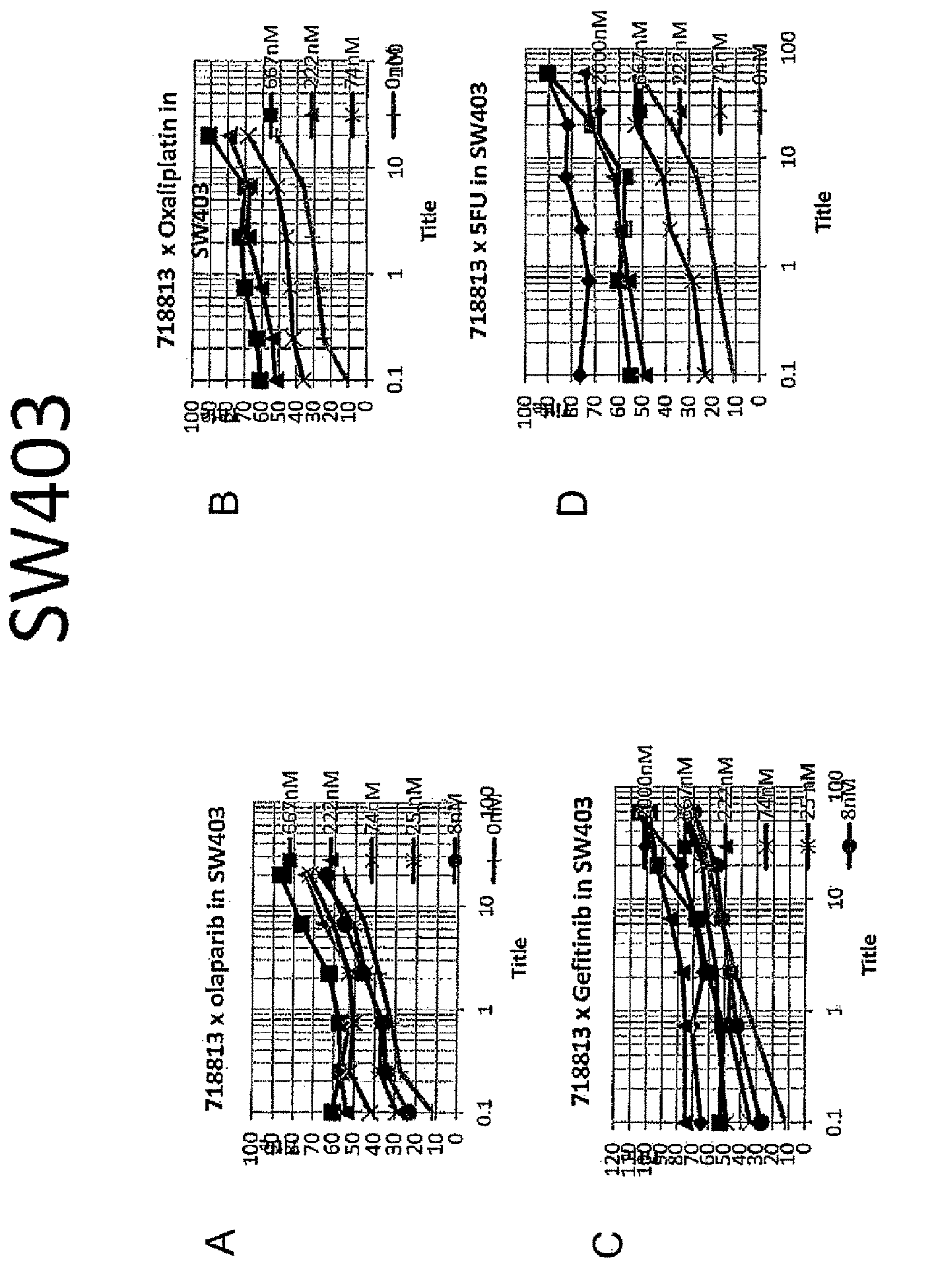
FIG. 54 shows line graphs of SW403.
Figure 55:
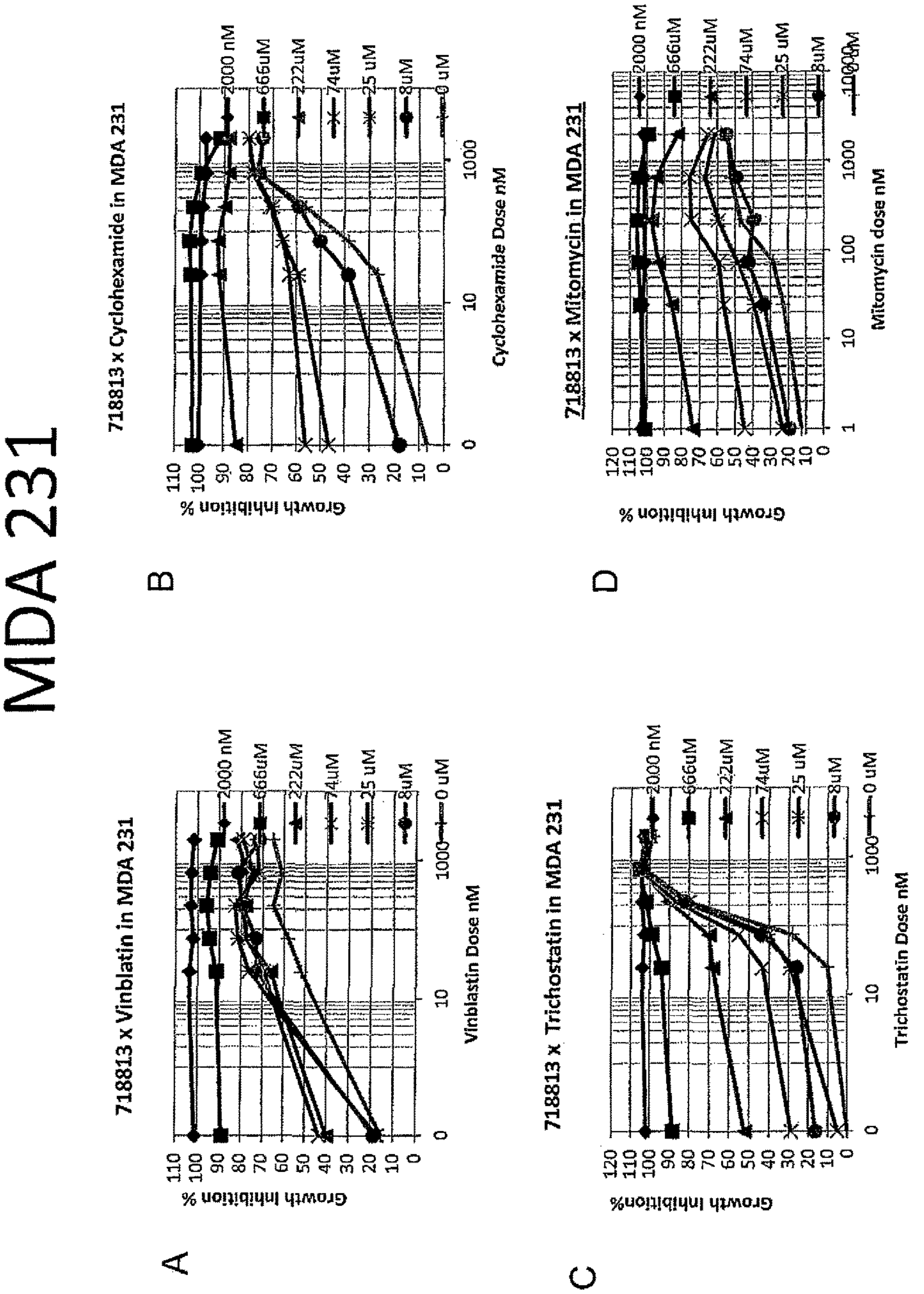
FIG. 55 shows line graphs of MDA 231.
Figure 56:
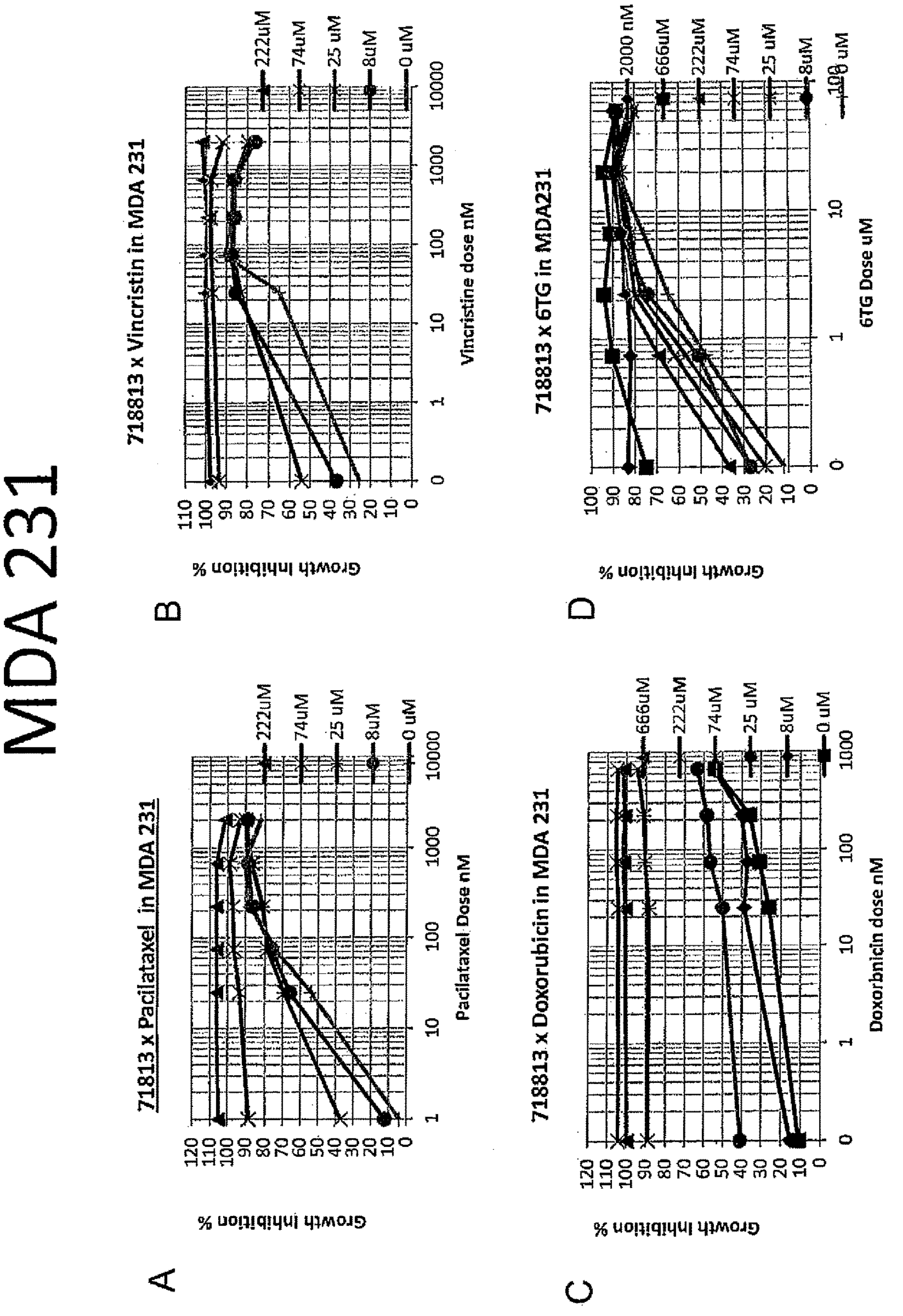
FIG. 56 shows line graphs of MDA-MB-231.
Figure 57:
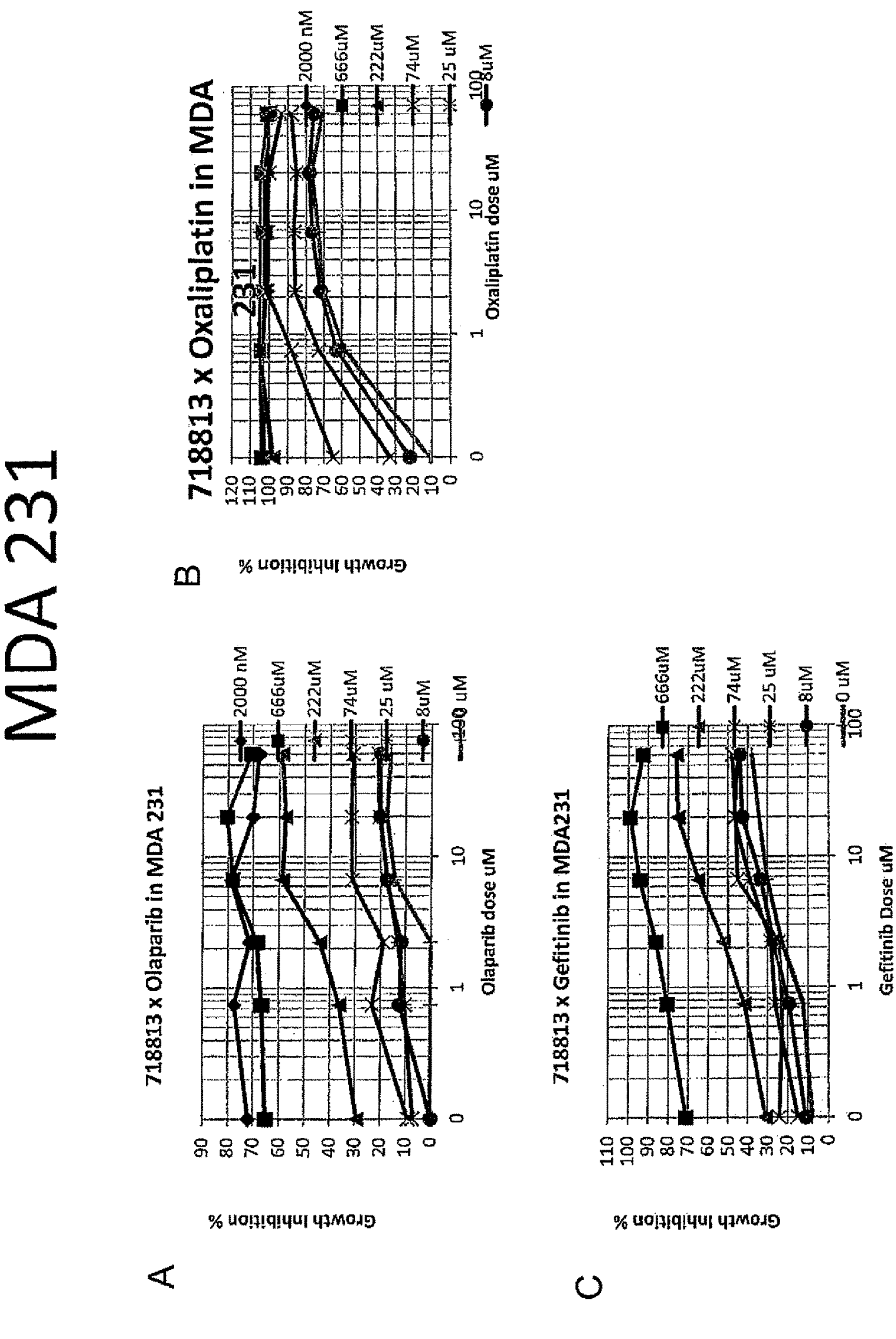
FIG. 57 shows line graphs of MDA-MB-231.
Figure 58:
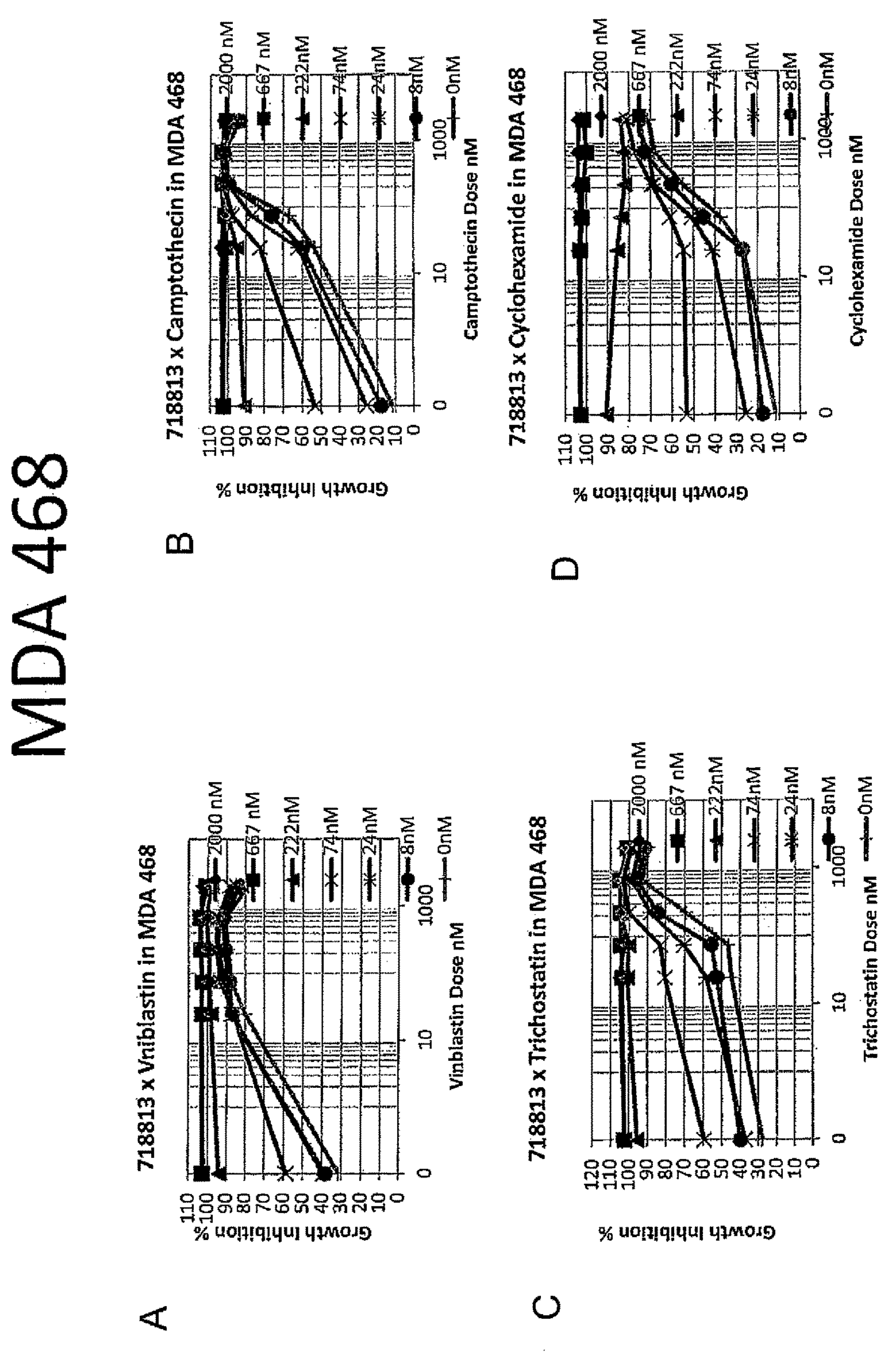
FIG. 58 shows line graphs of MDA-MB-468.
Figure 59:
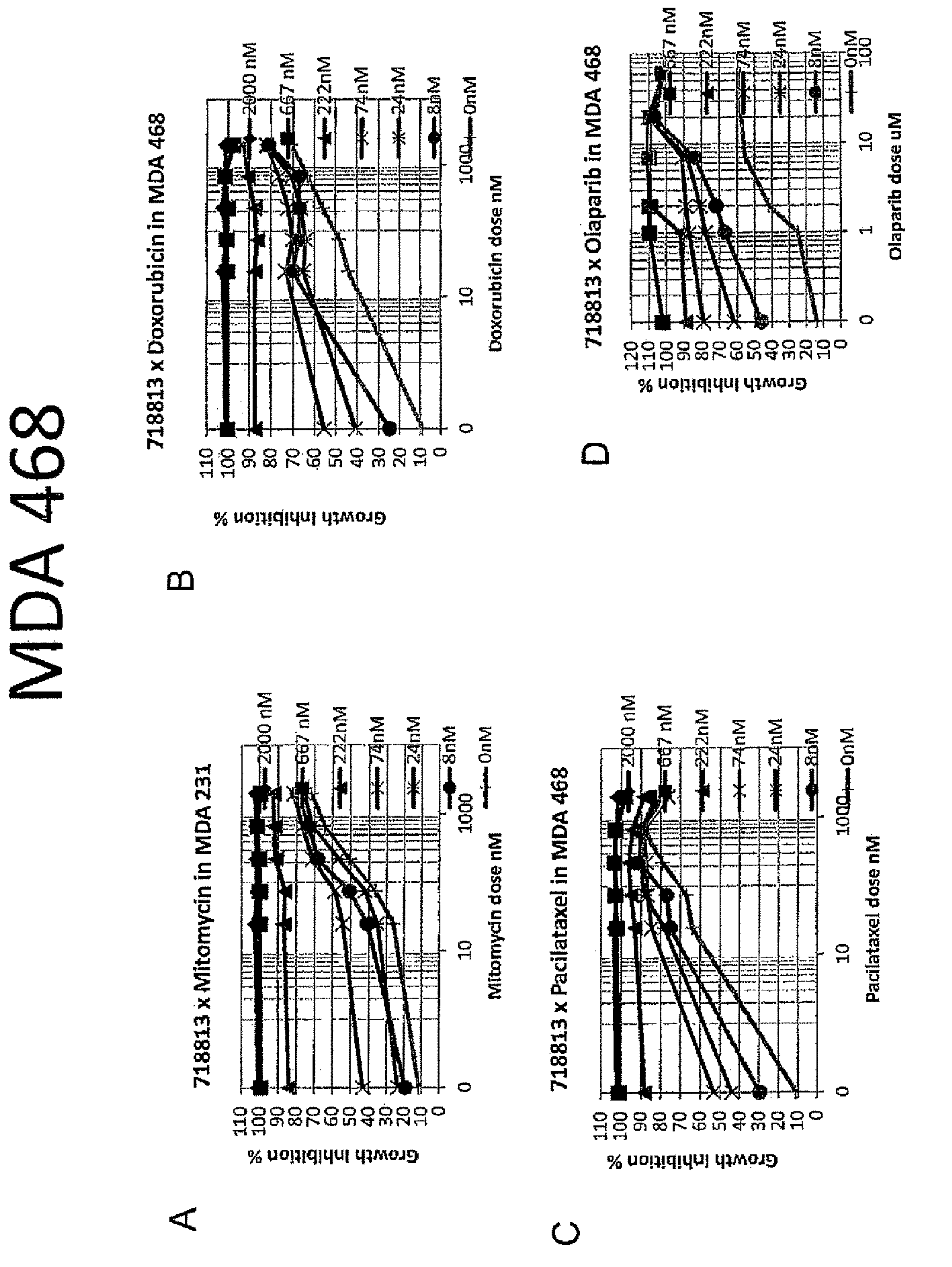
FIG. 59 shows line graphs of MDA-MB-468.
Figure 60:
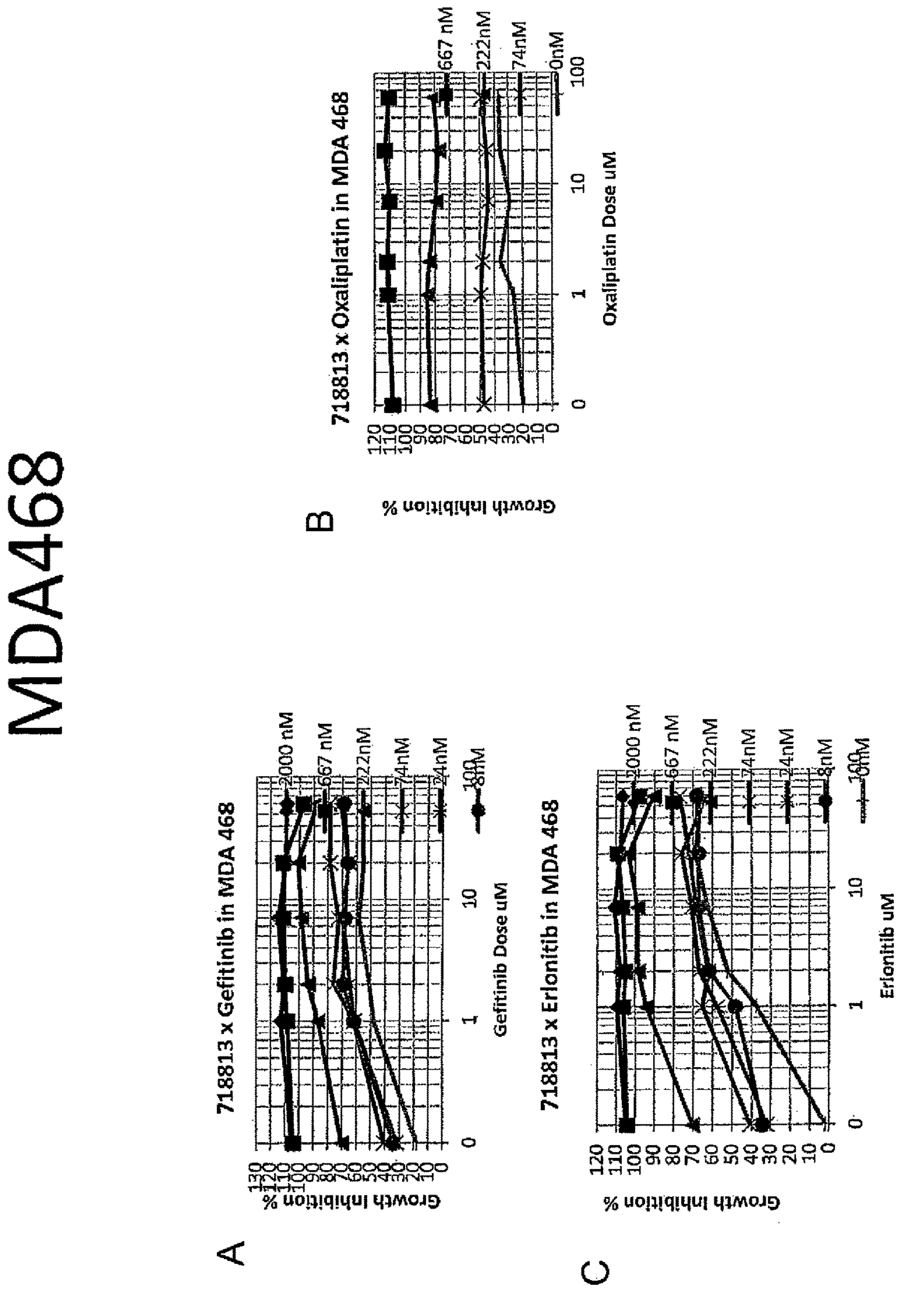
FIG. 60 shows line graphs of MDA-MB-468-468.
Figure 61:
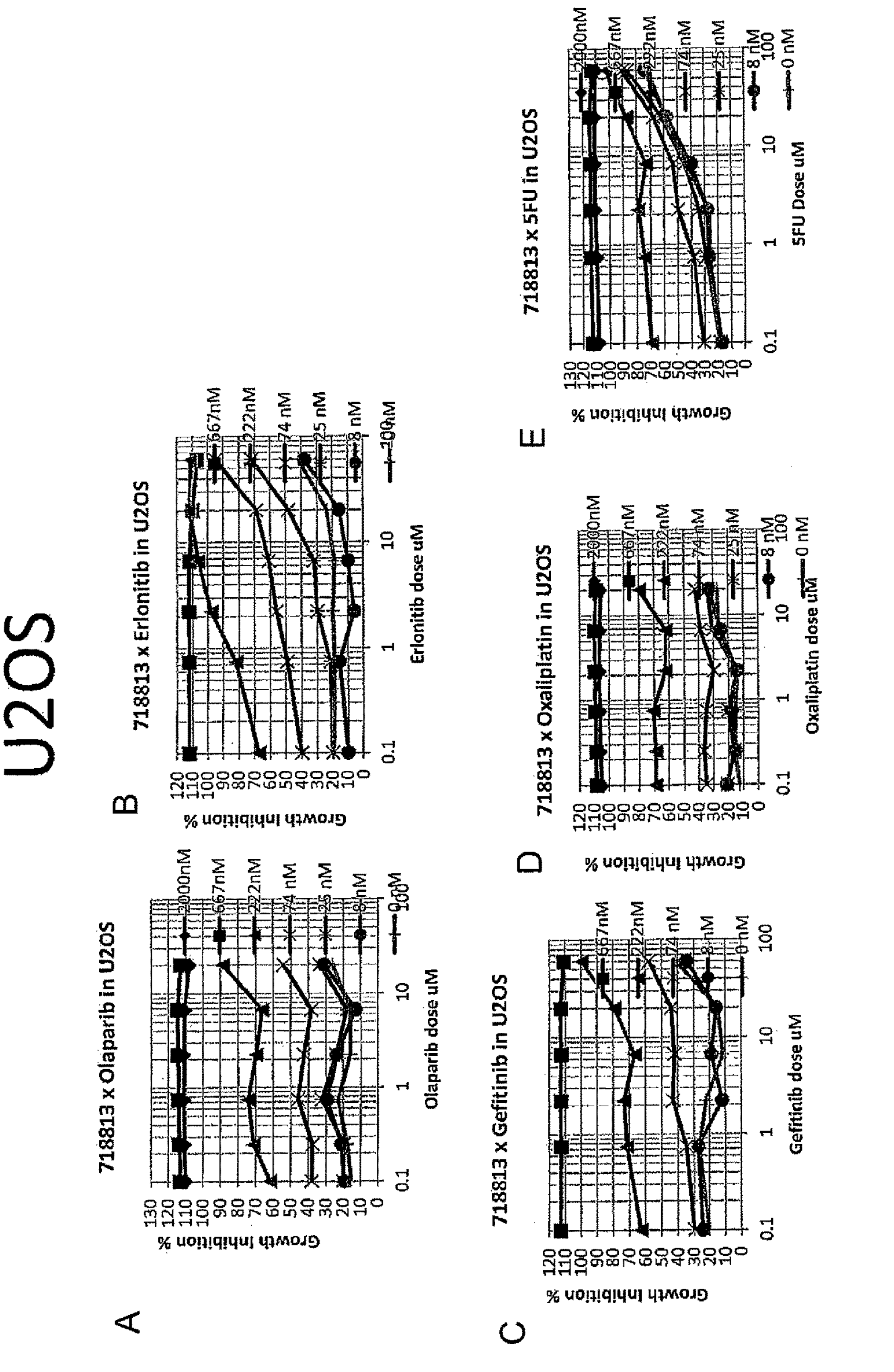
FIG. 61 shows line graphs of U2OS.
Figure 62:
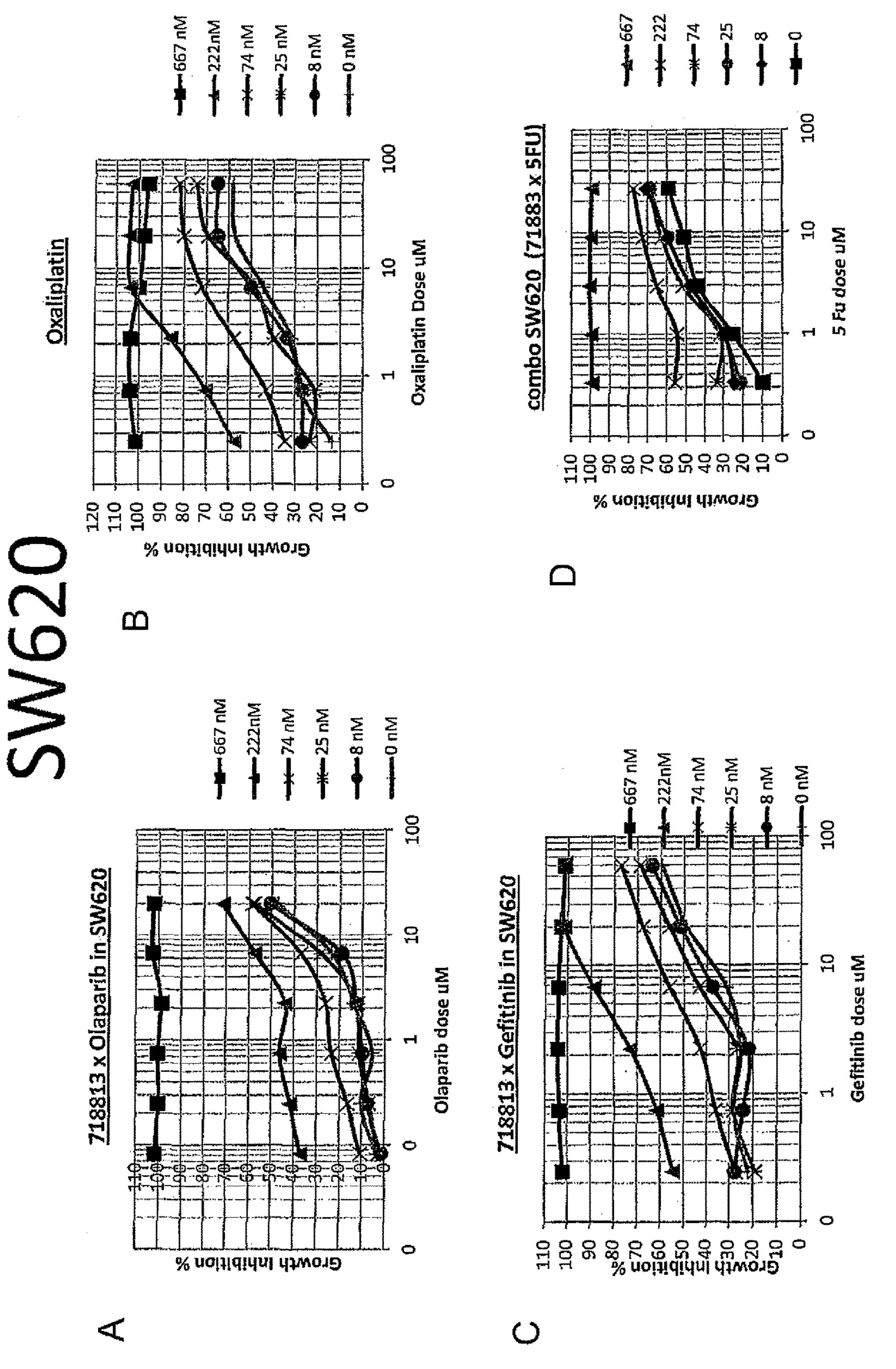
FIG. 62 shows line graphs of SW620.
Figure 63:
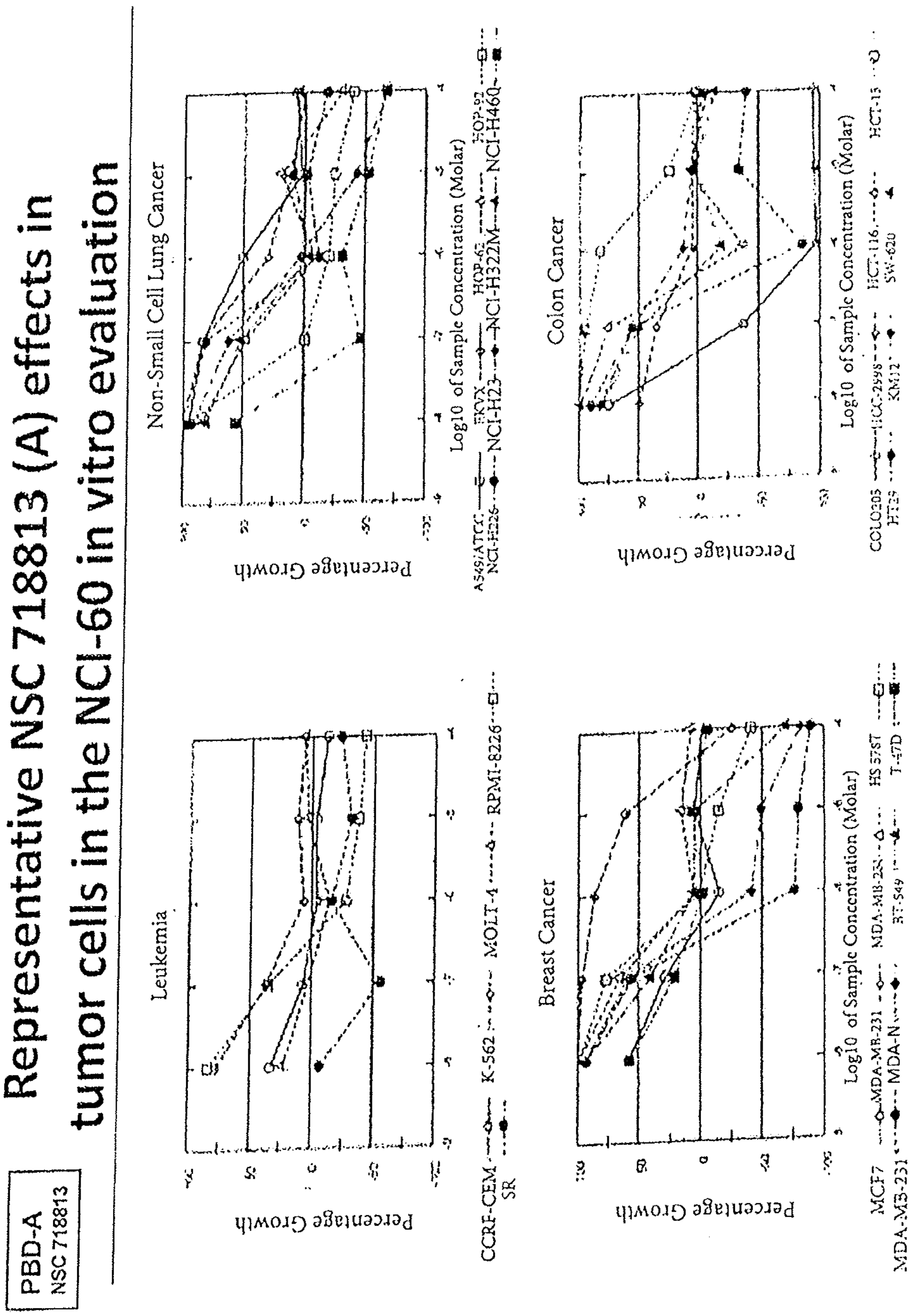
FIG. 63 shows line graphs of representative NSC 718813 (A) effects in tumor cells in the NCI-60 in vitro evaluation.
Figure 64:
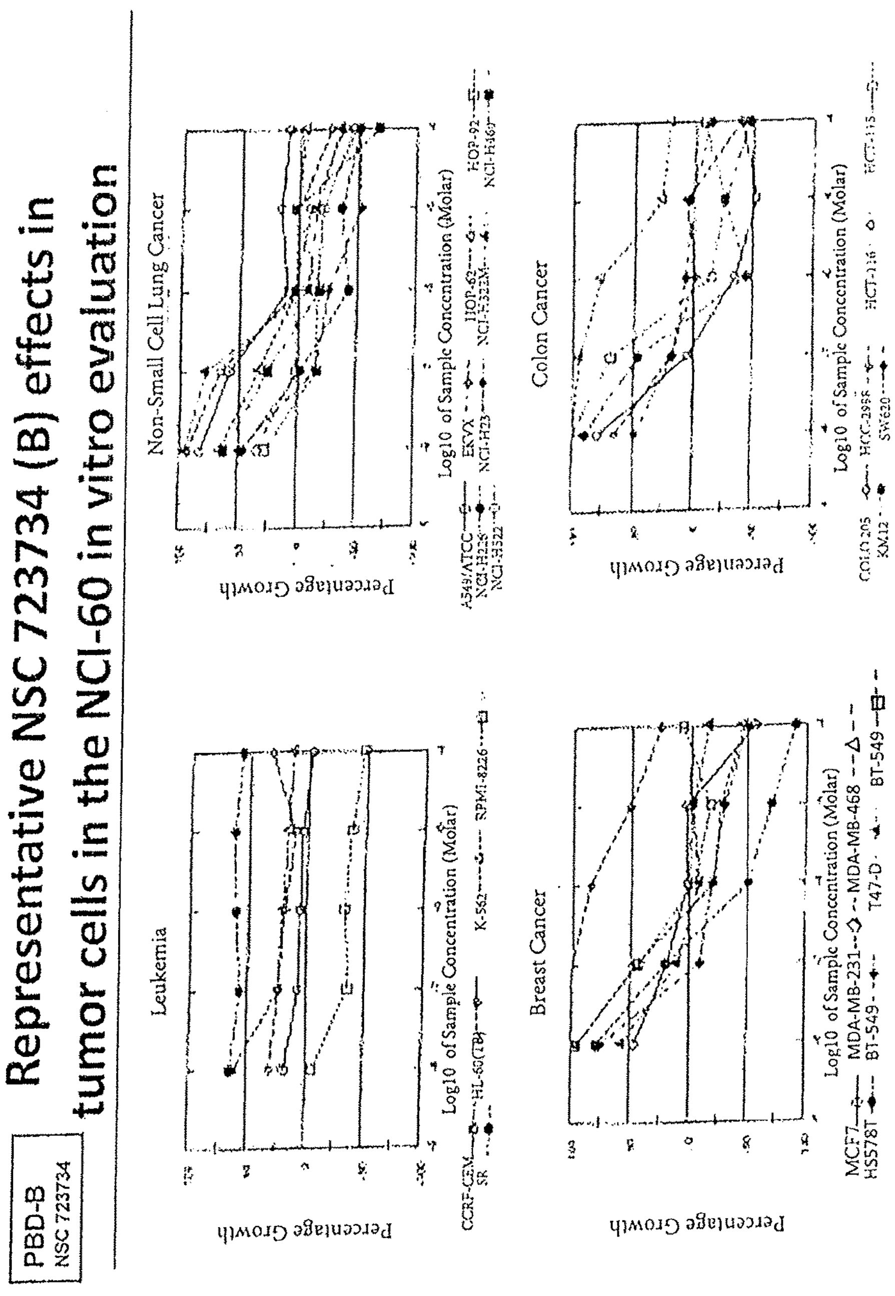
FIG. 64 shows line graphs of representative NSC 723734 (B) effects in tumor cells in the NCI-60 in vitro evaluation.
Figure 65:
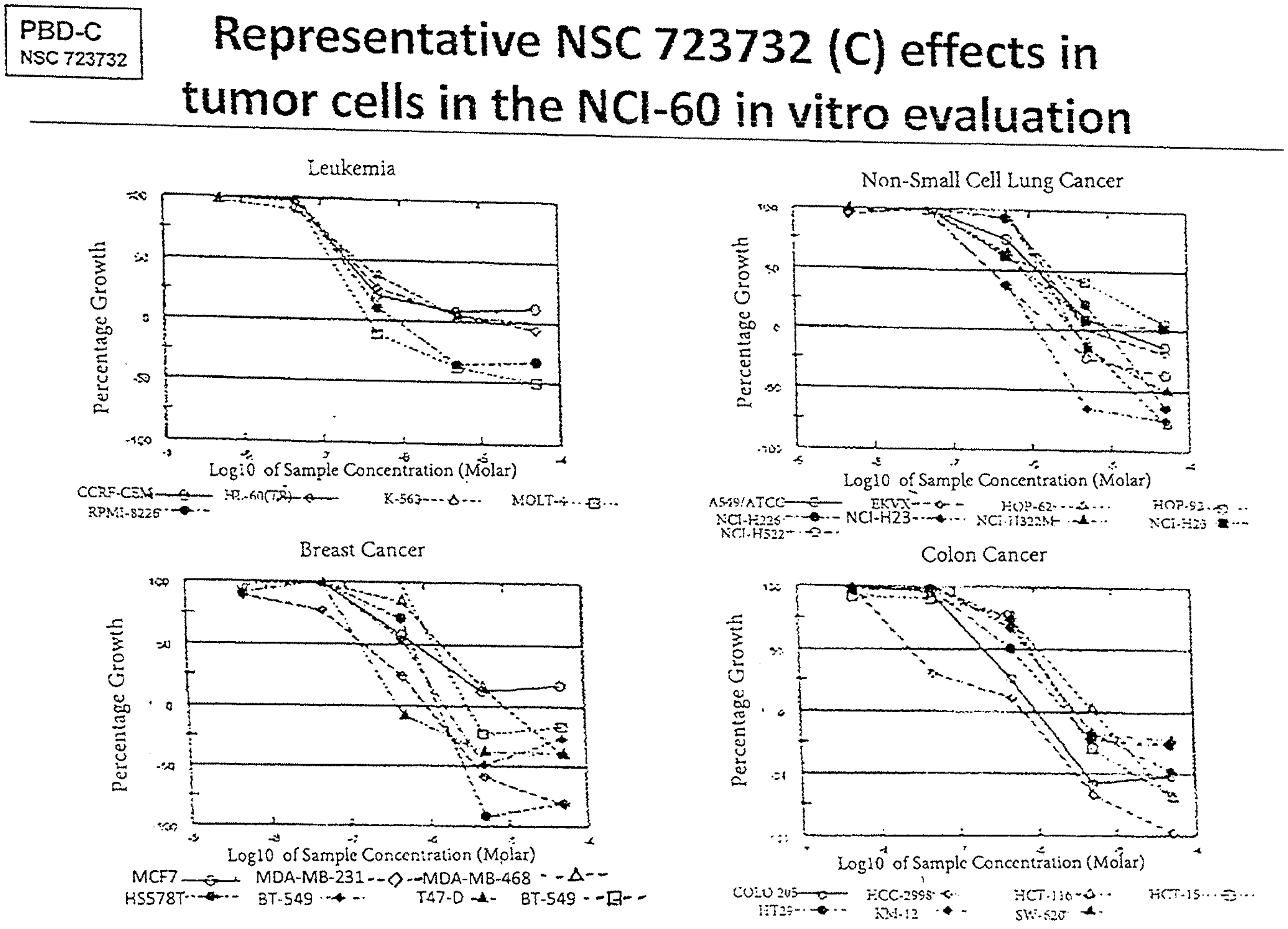
FIG. 65 shows line graphs of representative NSC 723732 (C) effects in tumor cells in the NCI-60 in vitro evaluation.
Figure 66:
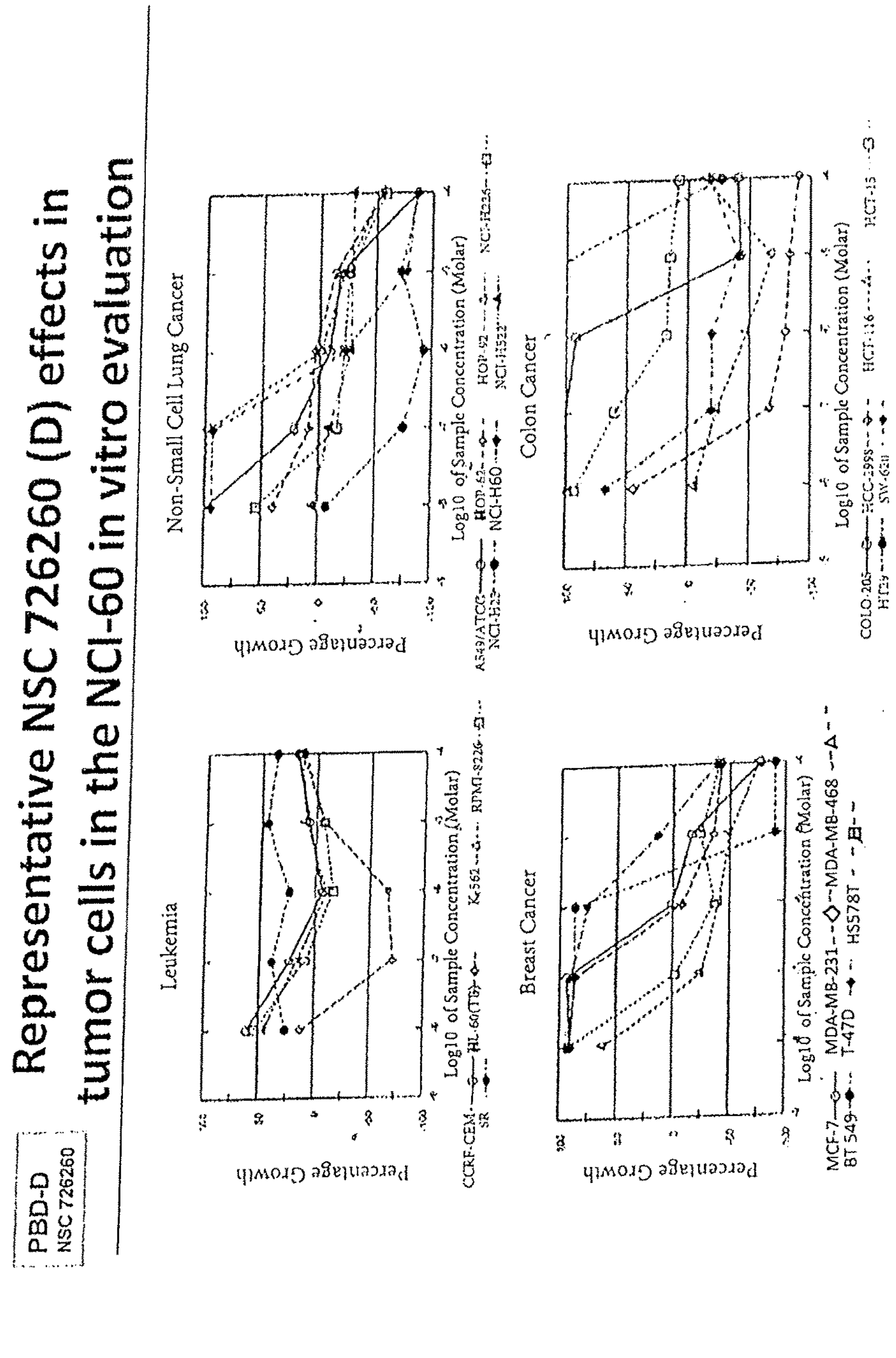
FIG. 66 shows line graphs of representative NSC 726260 (D) effects in tumor cells in the NCI-60 in vitro evaluation.
Figure 67:
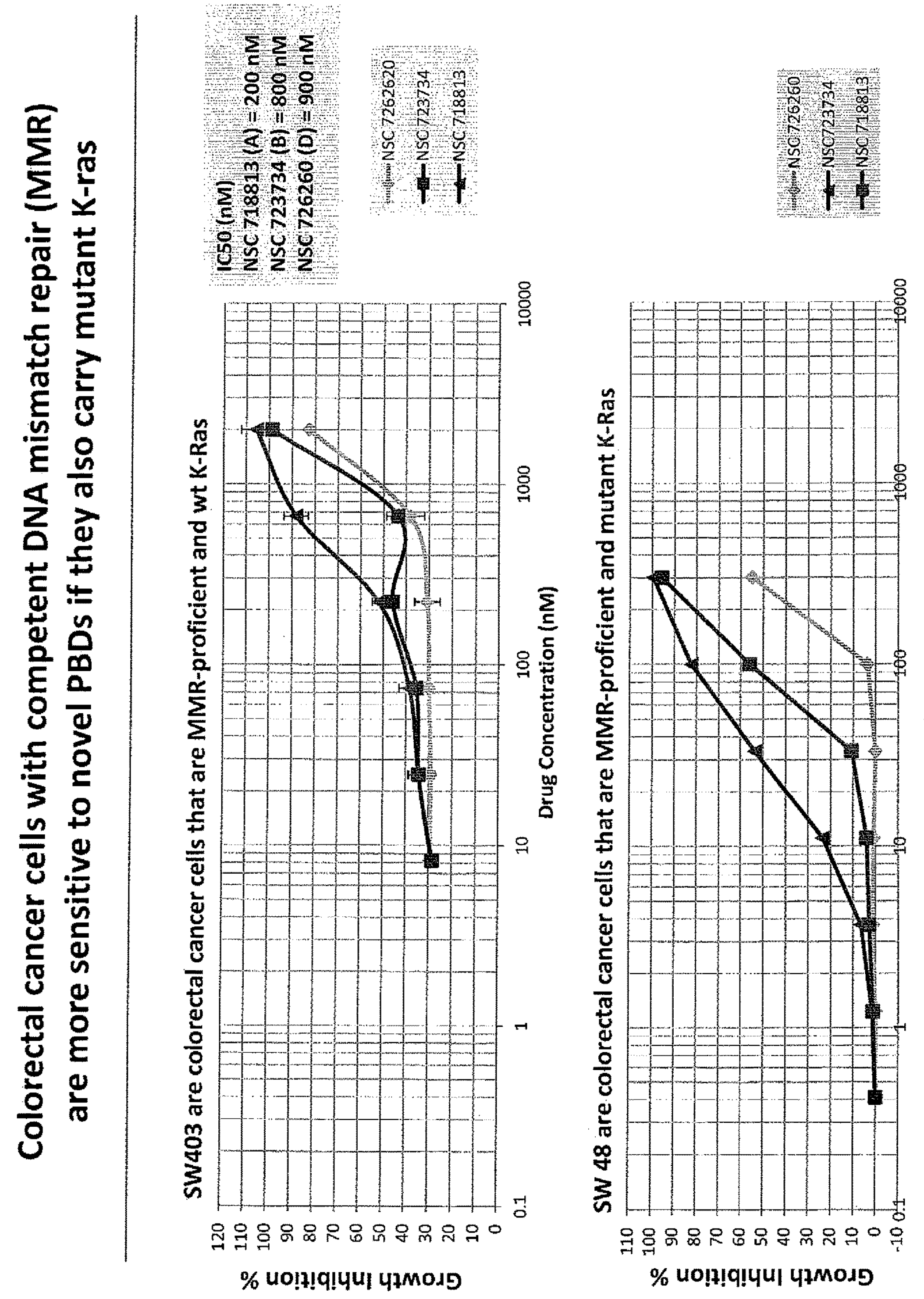
FIG. 67 shows line graphs of colorectal cancer cells with competent DNA mismatch repair (MMR) are more sensitive to novel PBDs if they also carry mutant K-ras.
Figure 69:
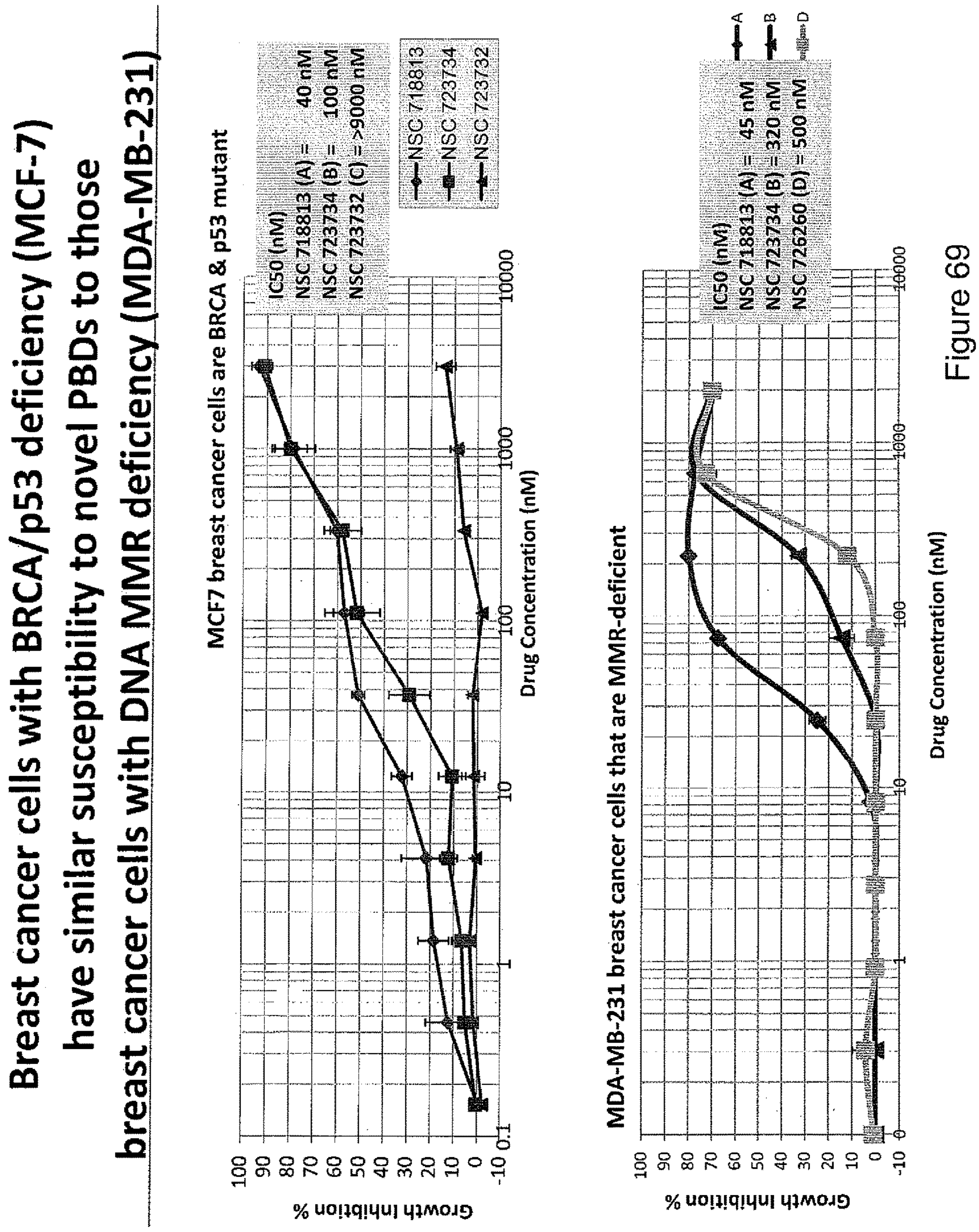
FIG. 69 shows line graphs of breast cancer cells with BRCA/p53 deficiency (MCF-7) that have similar susceptibility to novel PBDs to those breast cancer cells with DNA MMR deficiency (MDA-MB-231).
Figure 70:
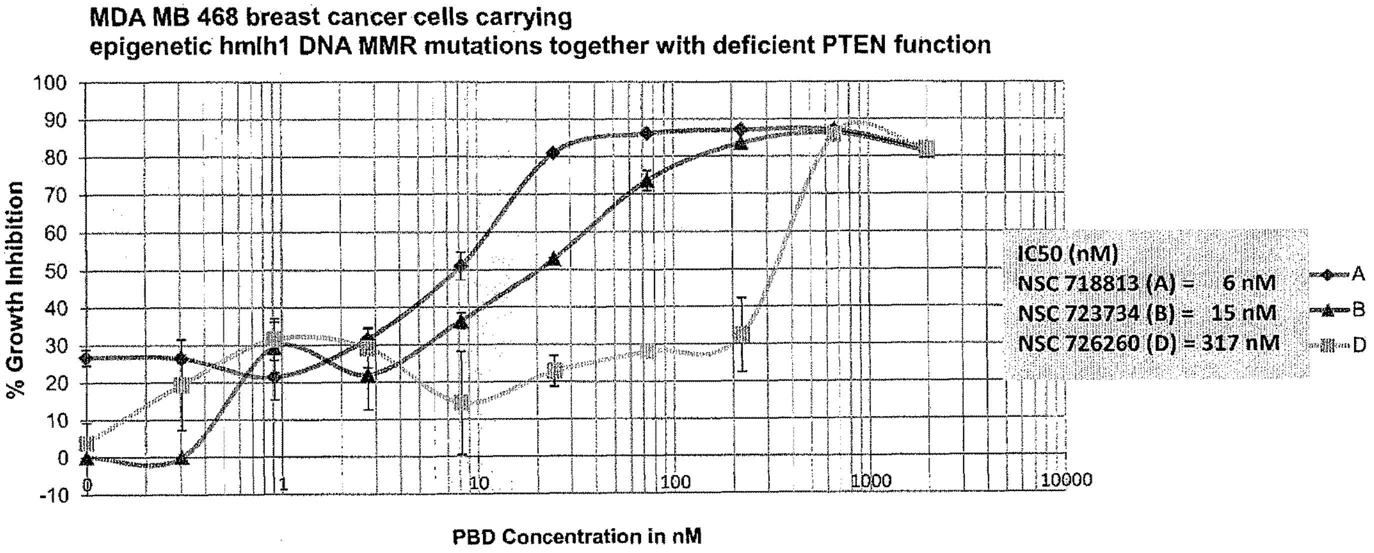
FIG. 70 shows a line graph of breast cancer cells (MDA-MB-468) with loss of function in PTEN and mlh1 hypermethylation (deficient DNA mismatch repair) that are more susceptible to novel IndUS PBDs.
Figure 71:
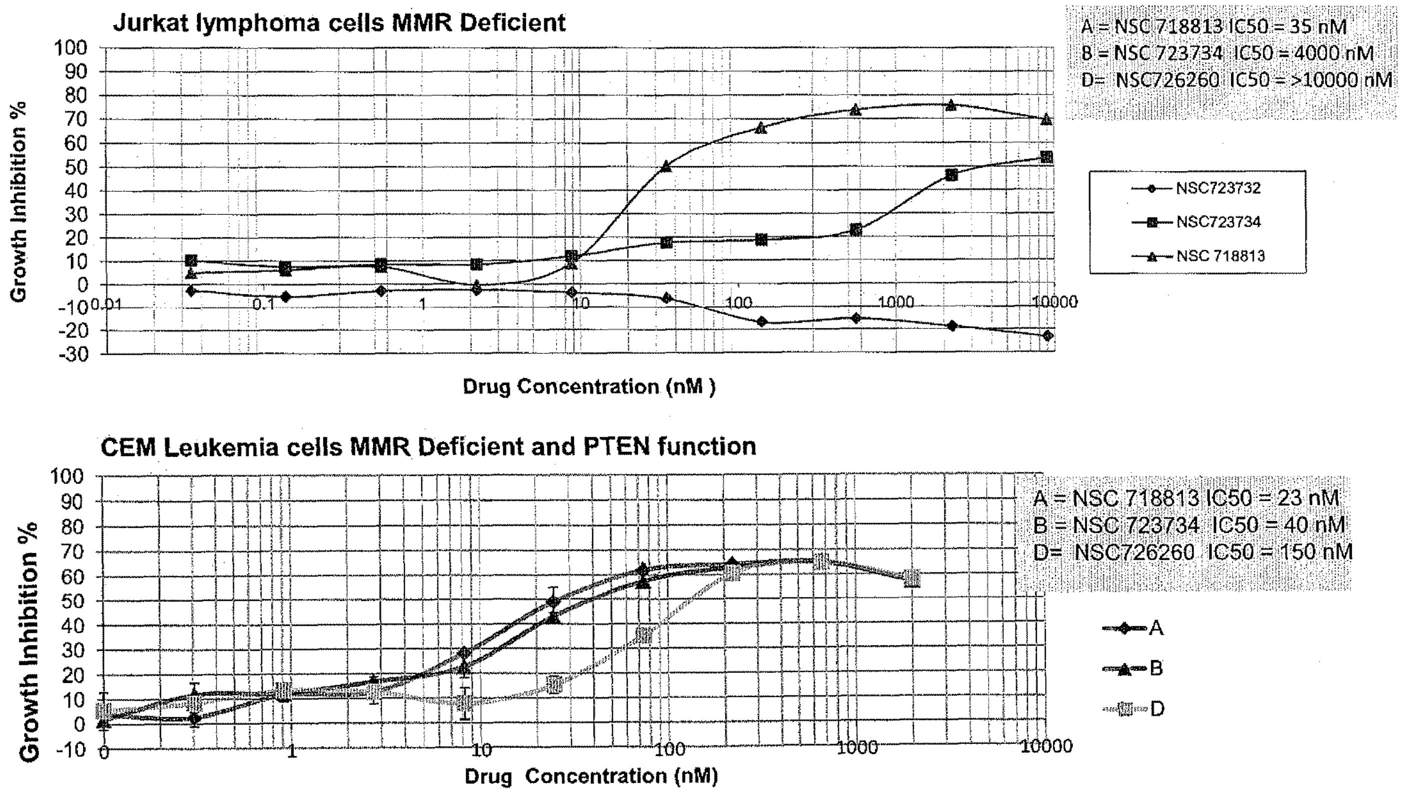
FIG. 71 shows line graphs of novel IndUS PBDs that are very potent in leukemia cells (CEM) that have loss of function in DNA MMR and PTEN compared to that in MSH2 deficient Jurkat lymphoma cells.
Figure 72:
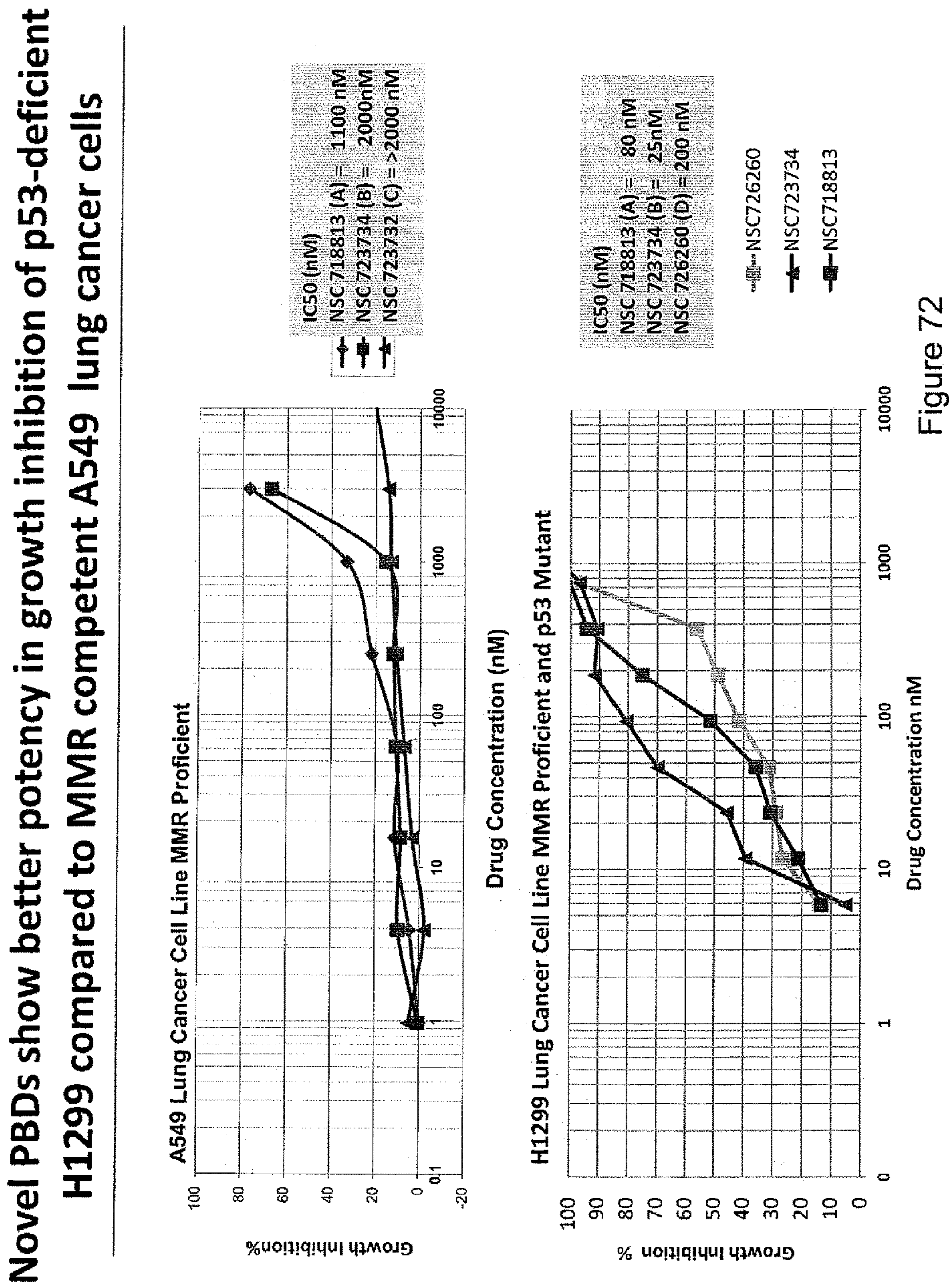
FIG. 72 shows line graphs of novel PBDs that show better potency in growth inhibition of p53-deficient H1299 compared to MMR competent A549 lung cancer cells.
Figure 77:
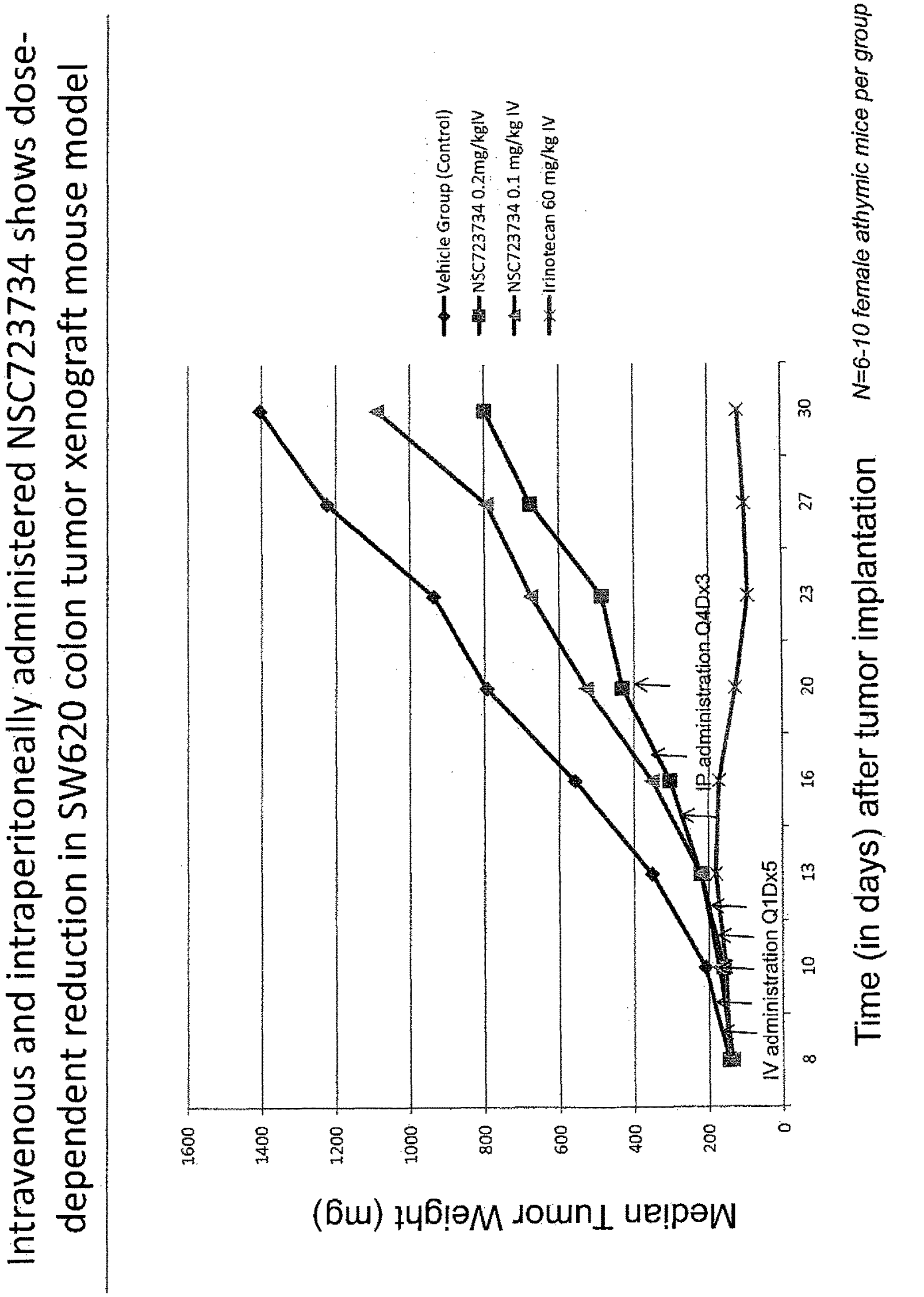
FIG. 77 shows a line graph of intravenous and intraperitoneally administered NSC723734 showing dose-dependent reduction in SW620 colon tumor xenograft.
Figure 78:
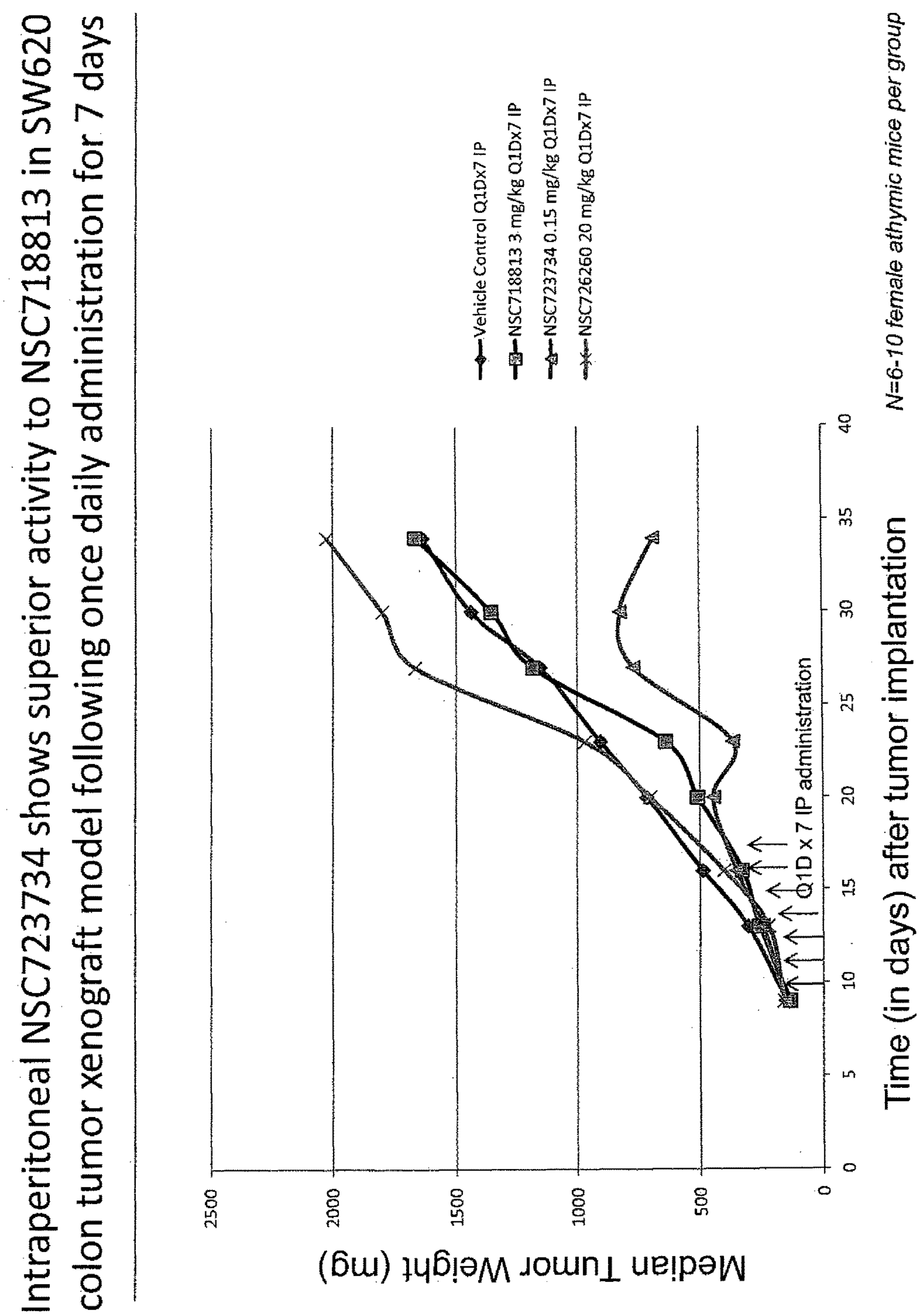
FIG. 78 shows a line graph of intraperitoneal NSC723734 showing superior activity to NSC718813 in SW620 colon tumor xenograft model following once daily administration for 7 days.
Figure 79:
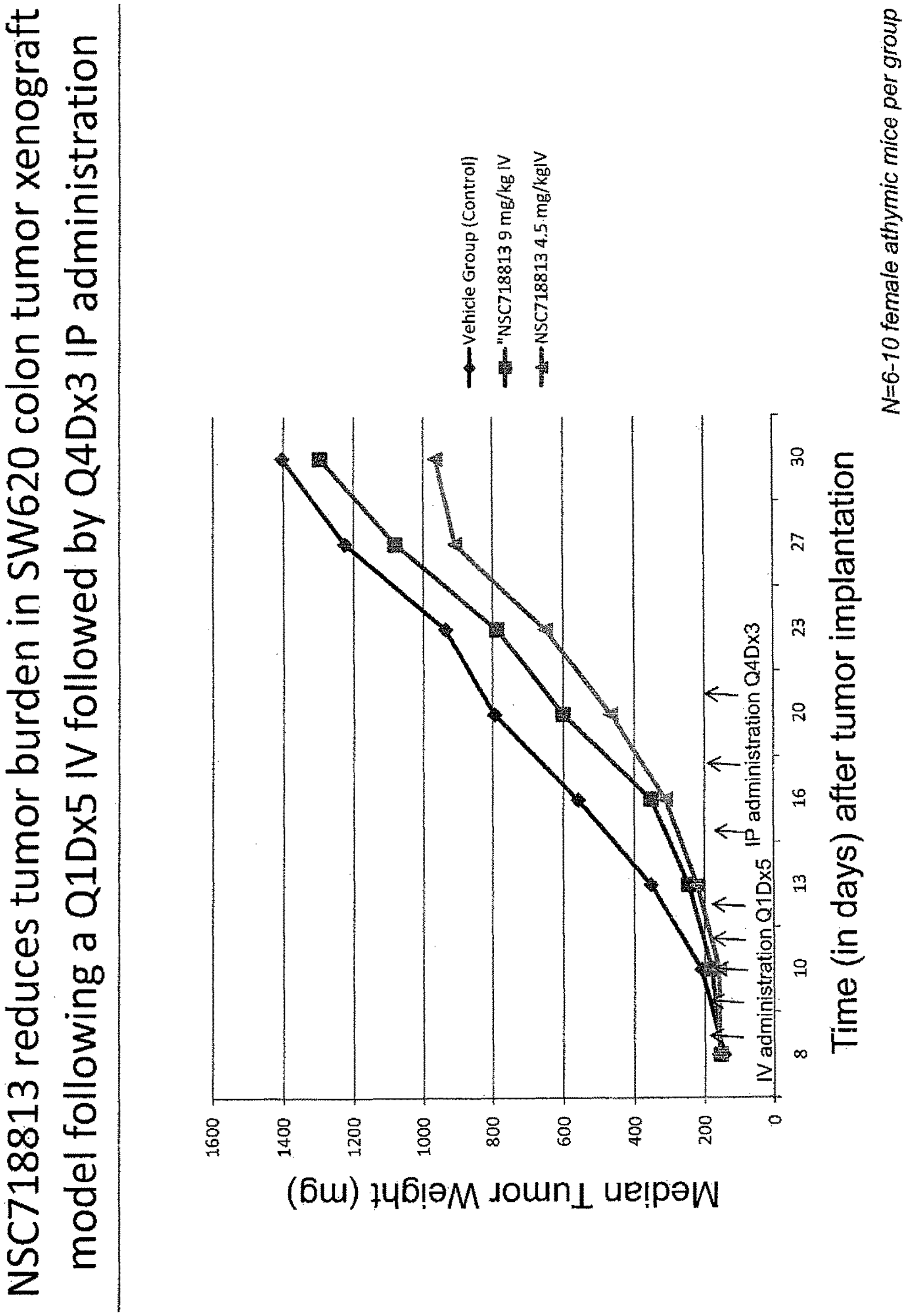
FIG. 79 shows a line graph of NSC718813 that reduces tumor burden in SW620 colon tumor xenograft model following a Q1 Dx5 IV followed by Q4Dx3 IP administration.
Figure 80:
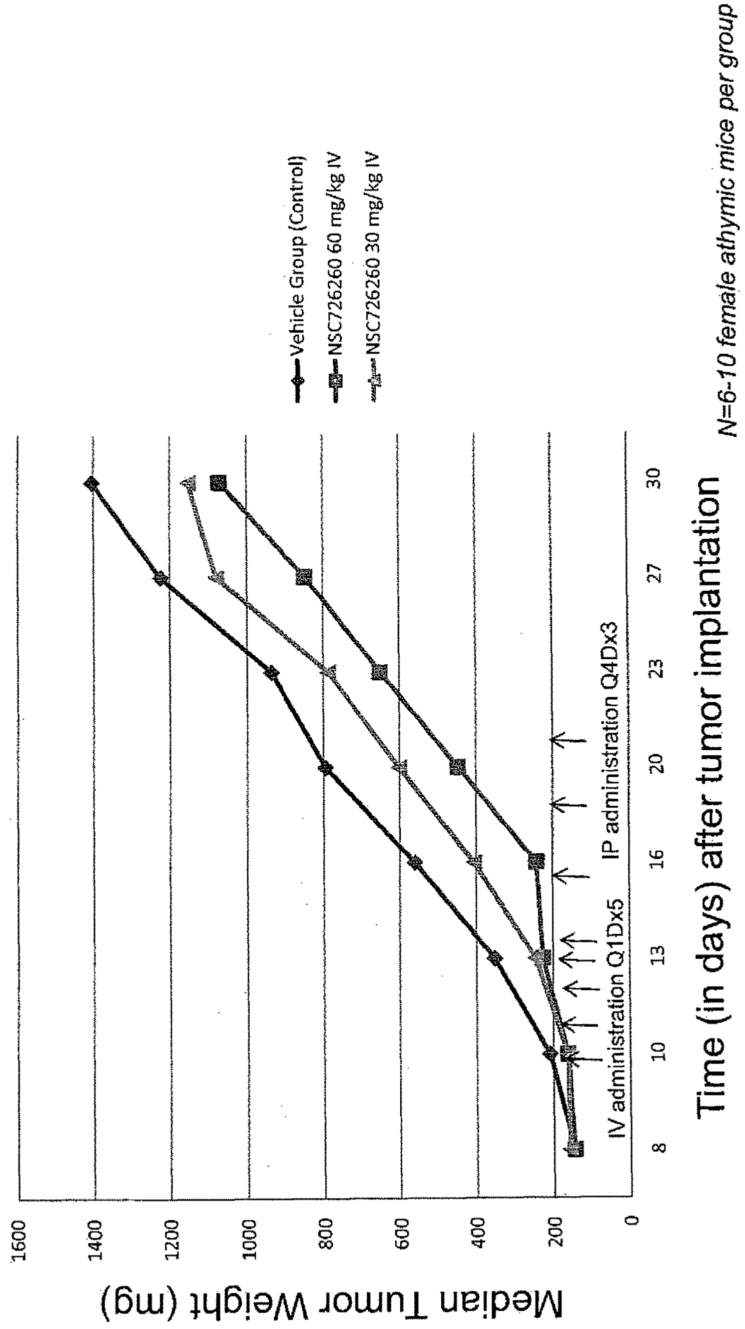
FIG. 80 shows a line graph of NSC726260 showing limited pharmacological activity in SW620 colon tumor xenograft model following combined IV and IP administration.
Figure 81:
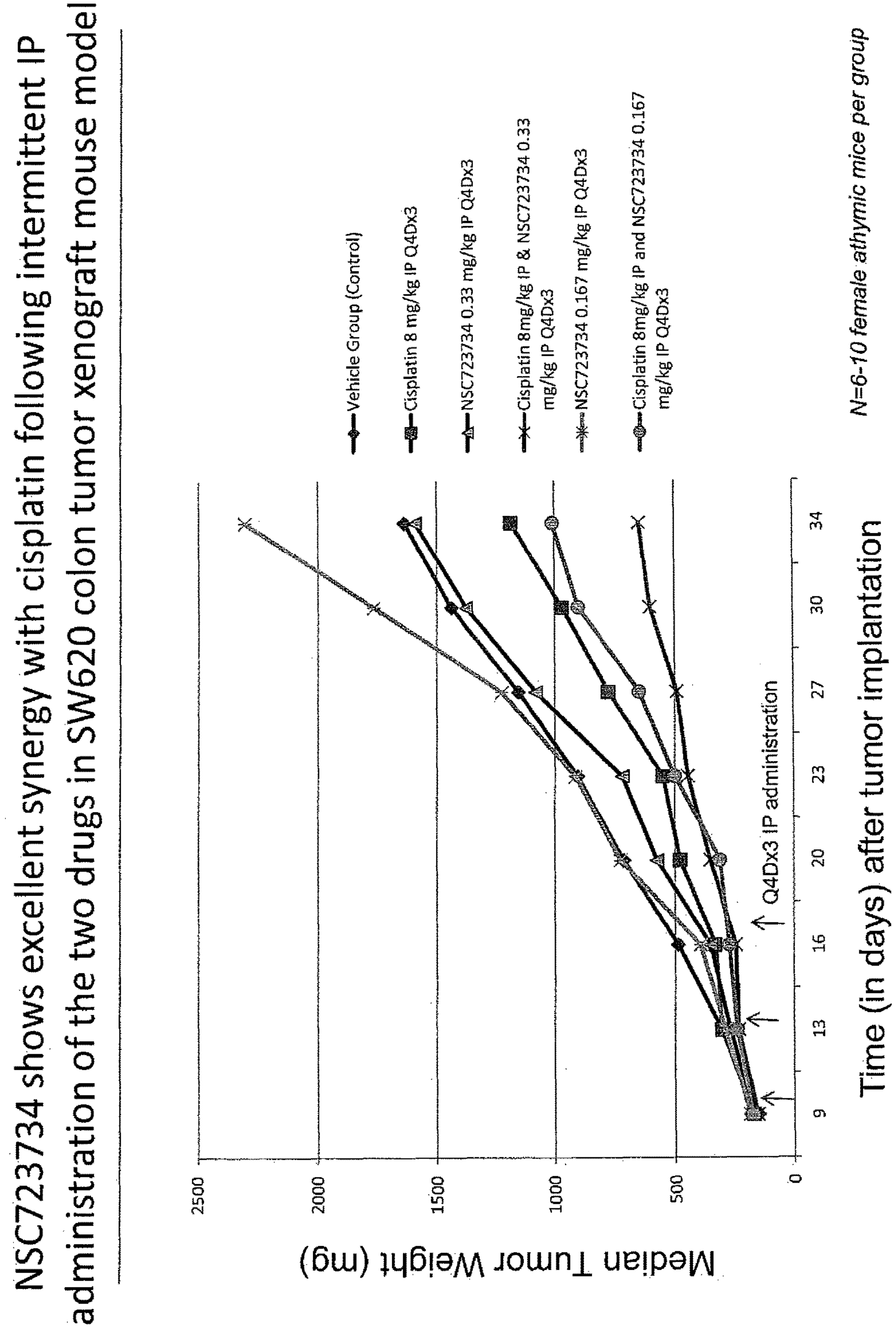
FIG. 81 shows a line graph of NSC723734 showing excellent synergy with cisplatin following intermittent IP administration of the two drugs in SW620 colon tumor xenograft mouse model.
Figure 82:
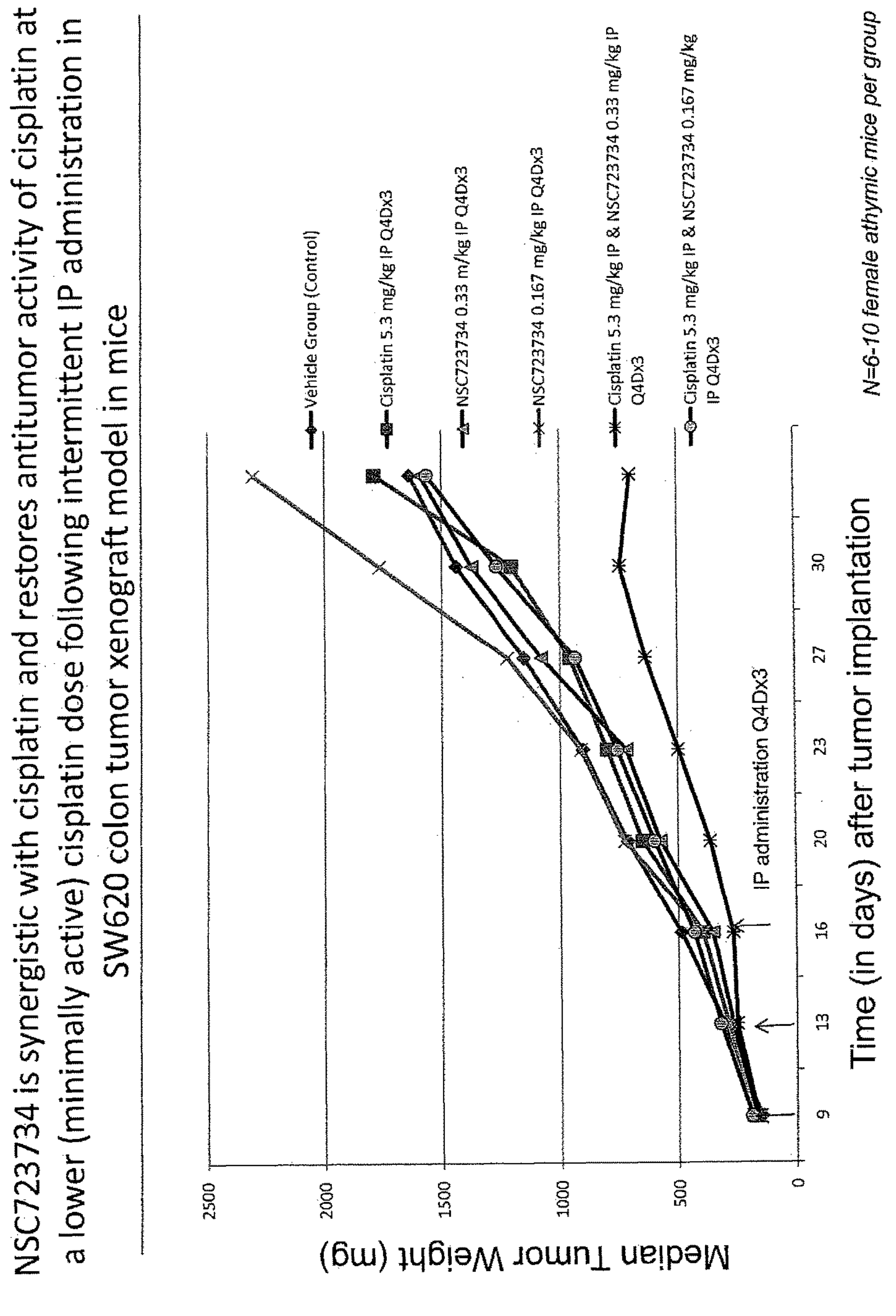
FIG. 82 shows a line graph of NSC723734 that is synergistic with cisplatin and restores antitumor activity of cisplatin at a lower (minimally active) cisplatin dose following intermittent IP administration in SW620 colon tumor xenograft model in mice.

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, "at least one" is intended to mean "one or more" of the listed elements.

Singular word forms are intended to include plural word forms and are likewise used herein interchangeably where appropriate and fall within each meaning, unless expressly stated otherwise.

Except where noted otherwise, capitalized and non-capitalized forms of all terms fall within each meaning.

Unless otherwise indicated, it is to be understood that all numbers expressing quantities, ratios, and numerical properties of ingredients, reaction conditions, and so forth used in the specification and claims are contemplated to be able to be modified in all instances by the term “about”.

All parts, percentages, ratios, etc. herein are by weight unless indicated otherwise.

As used herein, a “non-covalent DNA binding agent” means an agent that reacts with one or more different positions in a DNA molecule, wherein binding can result in the formation of crosslinkages, either in the same strand (intrastrand crosslink) or in the opposite strands of the DNA (interstrand crosslink). Non-covalent DNA binding agents can also cause interactions between DNA and proteins that are recruited by the DNA. For example, DNA replication is blocked by non-covalent DNA binding agents of the invention that modulate interactions between DNA and genes or proteins which subsequently cause replication arrest, cell cycle arrest and/or cell death if the crosslink is not repaired.

A non-covalent DNA binding agent reacts with DNA via non-covalent interactions, for example, hydrogen bonds, Coulombic interactions, ionic bonds, van der Waals forces, and/or hydrophobic interactions. Non-covalent DNA binding agents of the invention include, but are not limited to, the agents presented herein below. The invention provides for a non-covalent DNA binding agent that binds to the minor groove of DNA. A DNA molecule has two types of grooves, the major groove which has the nitrogen and oxygen atoms of the nucleotide base pairs pointing inward toward the helical axis, and the minor groove, wherein the nitrogen and oxygen atoms of the nucleotides point outwards. The major groove is 22 Å wide and the minor groove is 12 Å wide. The majority of currently available DNA damaging chemotherapeutic agents target the major groove of the DNA.

Most of the currently studied DNA minor groove binding agents target “AT rich” regions of DNA. The current invention provides novel non-covalently linked, DNA minor groove binding agents that target “G-C” rich” regions of the DNA. As used herein, “GC rich region” means between 25% and 80% of the human genome and regions of hundreds of kilobases, often referred to as the isochores, that have relatively homogenous base compositions (Fullerton, S. M., Carvalho, A. B. and Clark, A. G. Local rates of recombination are positively correlated with GC content in human genome. Mol Biol Evol 18(6): 1139-1142, 2001). “GC rich regions” are preferably between 35% and 75% GC, and more preferably between 45% and 75% GC and most preferably, between 60% and 70% GC. There is evidence that the longest eukaryotic exons and the longest prokaryotic genes are the most “GC-rich” Furthermore, the expected length for random reading frames is a function of the sequence GC content, i.e. the higher the GC content, the higher the probability for longer reading frames. On the other hand, the most GC-rich introns are the shorter ones and GC content has a greater effect on the reduction of intron length (Oliver, J. L. and Marin, A. A relationship between GC content and Coding-sequence length. J Mol Evol 43: 216-223, 1996).

As used herein, “DNA repair deficiency” refers to a decrease in the ability of a cell to repair DNA as compared to a wild type or control cell. A “DNA repair deficiency” can be genetic and/or epigenetic in nature (Loeb, L. A., Loeb, K. R. and Anderson, J. P. Multiple mutations and cancer. Proc Nat Acad Sci 100(3): 776-781, 2003; Jones, P. A. and Baylin, S. B. The fundamental role of epigenetic events in cancer. Nat Rev Genetics 3: 415-428, 2002). For instance, DNA repair deficiencies can result in “microsatellite instability”, a key feature of several cancers that are collectively referred to as Lynch tumors (Hewish, M., Lord, C. J., Martin, S. A., Cunningham, D. and Ashworth, A. Mismatch repair deficient colorectal cancer in the era of personalized treatment. Nat Rev Clin Oncol 7: 197-208, 2010). Further, a well defined subtype of colorectal cancer (CRC) is characterized by a deficiency in the mismatch repair (MMR) pathway. MMR deficiency not only contributes to the pathogenesis of a large proportion (~70%) of colorectal cancer, but also determines the response of that subtype of colorectal cancer to many of the drugs that are frequently used to treat colorectal cancer.

A DNA repair deficiency can be determined by methods known in the art including but not limited to assays for microsatellite instability, for example by using a microsatellite instability test distributed by Roche (Cat. No. 12 041 901 00).

Assays for DNA mismatch repair tumors include but are not limited to those presented in Marcus et al., 1999 Am J Surg Pathol Oct: 23(10): 1248-55.

Although there are typical clinical and pathological features associated with MMR-deficiency phenotype in Lynch syndrome cancers, approximately 40% of the Lynch syndrome cases cannot be reliably diagnosed by morphological characteristics alone. A strong relationship exists between sporadic MMR deficiency colorectal cancer (dMMR CRC) and the CpG island methylator phenotype (CIMP) subtype of CRC. CIMP is characterized by regional hypermethylation of CpG islands in the DNA and thus results in the loss of functional MLH1 expression (Hewish et al., Nat Rev Clin Oncol 7: 197-208, 2010). The relationship of CpG island methylation to microsatellite instability can be used to describe the clinical and pathological features of CRC. Hypermethylation (epigenetic) changes of p16 and MLH1 can be determined by methylation-specific polymerase chain reaction (PCR). Methylation of MINT 1, 2, 12 and 31 loci can be assessed by bisulfite PCR. Microsatellite instability and K-ras and p53 status of patient cancer tissues can be assessed by microsatellite PCR, restriction enzyme-mediated PCR and/or immunohistochemistry (IHC) (Hawkins, N., Norrie, M, Cheong, K., Mokany, E., Ku, S-L., Meagher, A., O'Connor, T. and Ward, R. CpG island methylation in sporadic colorectal cancers and its relationship to microsatellite instability. Gastroenterology 122(5): 1376-1387, 2002).

As used herein, a “decrease” in the ability of a cell to repair DNA means that the cell repairs damaged DNA, either due to genetic or epigenetic mutations, such that the repaired DNA is less than 100% error free (for example, 99%, 90%, 85%, 80%, 75%, 70%, 65%, 60%, 55%, 50%, 45%, 40, 35%, 30%, 25%, 20%, 15%, 10%, 5% or less). A cell that has a DNA repair deficiency also refers to a cell that cannot perform any DNA repair.

As used herein, a “decrease” in the ability of a cell to repair DNA means that the cell repairs damaged DNA at a rate that is less than the rate at which a wild type or control cell repairs DNA.

As used herein, “less than” as it refers to the rate of repair of DNA damage, means that the rate of repair of DNA damage is 5-fold, 10-fold, 20-fold, 30-fold, 40-fold, 50-fold, 100-fold, or more, lower than the rate of repair of DNA damage in a wild type or control cell. As used herein, “less than” as it refers to the rate of repair of DNA damage also means that the rate of repair of DNA damage in a cell is 90%, 80%, 70%, 60%, 50%, 40%, 30%, 25%, 20%, 15%, 10%, 5% or less, lower than the rate of repair of DNA damage in a control or wild type cell.

As used herein, a "DNA repair deficiency" includes but is not limited to: base excision repair deficiency, a deficiency in the repair of double stranded breaks and a deficiency in the repair of chromosomal damage. DNA repair deficiencies can result from genetic changes such as mutated DNA mismatch repair genes like MSH2, Furthermore, DNA repair deficiencies can also include epigenetic changes such as hypermethylation of genes involved in DNA mismatch repair, recombination, replication and/or apoptosis. (Helleday, T., Petermann, E., Lundin, C., Hodgson, B and Sharma, R. A. DNA repair pathways as targets for cancer therapy. Nat Rev. Cancer 8: 193-204, 2008).

As used herein, "apoptosis" or "programmed cell death" refers to a mechanism whereby a cell undergoes death or destruction, for example, to control cell number and proliferation or in response to DNA damage. Many cancer cells do not undergo apoptosis and certain cancers involve an alteration in the apoptotic pathway.

As used herein, "dysregulated apoptosis" refers to a decrease in the ability of a cell to undergo apoptosis or a decrease in the number of cells that undergo apoptosis as compared to a wild type or control cell, for example apoptosis in response to DNA damage. For example, mutations in the p53 gene are a feature of 50% of all reported cancer cases. In the other 50% of cancer cases, the p53 gene is not itself mutated, but the p53-directed apoptosis pathway is partially inactivated (Check, C. F., Verma, C. S., Baselga, J. and Lane, D. P. Translating p53 into the clinic. Nat Rev Clin Oncol 8: 25-37, 2011). P53 protein is a transcription factor that controls the cellular response to stress signals through the induction of cell-cycle arrest, apoptosis and senescence. Apoptosis is detected by any one of the following assays including but not limited to DNA laddering, COMET assays and/or TUNEL staining.

As used herein, a "decrease" in the ability of a cell to undergo apoptosis means that within a population of cells, less than 100% (for example, 99%, 90%, 85%, 80%, 75%, 70%, 65%, 60%, 55%, 50%, 45%, 40, 35%, 30%, 25%, 20%, 15%, 10%, 5% or less) of the cells undergo apoptosis, as compared to a wild type or control population of cells, for example, wherein 100% of the cells undergo apoptosis A cell that has dysregulated apoptosis also refers to a cell that does not undergo apoptosis As used herein, "dysregulated apoptosis" also means that a cell or population of cells undergoes apoptosis at a rate that is less than that of a wild type or control cell or a population thereof.

As used herein, "less than" as it refers to the rate of apoptosis, means 5-fold, 10-fold, 20-fold, 30-fold, 40-fold, 50-fold, 100-fold or more, less than the rate at which a wild type or control cell or a population thereof, undergoes apoptosis. As used herein, "less than" as it refers to the rate of apoptosis also means that the rate of apoptosis is 90%, 80%, 70%, 60%, 50%, 40%, 30%, 25%, 20%, 15%, 10%, 5% or less, than the rate of apoptosis of a control or wild type cell or a population thereof.

As used herein, a "recombination deficiency" refers to an abnormality in homologous recombination repair in a cell, as compared to a wild type or control cell. While DNA repair is essential for cells to maintain genomic stability, there is increasing evidence that defects in homologous recombination repair (HRR) underlie hereditary and sporadic tumorigenesis (Evers, B. Helleday, T. and Jonkers, J. Targeting homologous recombination repair defects in cancer. Trends Pharmacol Sci 31: 372-380, 2010). Deficiencies in HRR may determine the sensitivity of tumors to many currently available DNA-damaging anti-cancer agents. Furthermore, HRR-deficient tumors are also more susceptible to synthetic lethal interactions. More importantly, HRR-deficient tumors may also have an increased dependence on cell-cycle checkpoints, which could be exploited.

As used herein, a "replication deficiency" refers to an abnormality in DNA replication in a cell, as compared to a wild type or control cell.

A "replication deficiency" includes replication of damaged DNA as determined by, for example, a BrdU assay wherein the thymidine analog, 5-Bromo-2-deoxyuridine (BrdU), is added to the cell growth medium just prior to fixing and the cells are stained with an antibody to BrdU, which detects the thymidine analog in DNA.

A "replication deficiency" also includes replication of DNA prior to cell division.

As used herein, a "cell proliferation disorder" refers to an increase in the number of divisions that a cell undergoes as compared to a wild type or control cell.

A "cell proliferation disorder" also refers to an increase in the rate of cellular division as compared to a wild type or control cell.

A "cell proliferation disorder" also refers to an increase in the frequency of cell division as compared to a wild type or control cell.

A "cell proliferation disorder" also refers to unregulated cell division, for example, the inability of a cell to respond to signals that cause a wild type or control cell to stop dividing or start dividing.

A "cell proliferation disorder" also refers to the inability of a cell to enter senescence.

As used herein, "senescence" refers to a state wherein diploid cells lose the ability to divide.

A "cell proliferation disorder is detected by methods known in the art including but not limited to alamar blue assay, as described herein below.

As used herein, "dysregulated transcription" means transcription of damaged DNA as determined by, for example, real-time reverse transcription polymerase chain reaction (PCR), in vitro transcription methods well known in the art, S1 nuclease assays.

As used herein, a "tumor suppressor gene" includes but is not limited to p53, RB1, WT1, NF1, NF2, APC, TSC1, TSC2, DPC4, DCC, BRCA1, BRCA2, PTEN, STK11, MSH2, MLH1, CDH1, VHL, CDKN2A, PTCH and MEN1.

As used herein, "mutation" refers to a genetic or epigenetic change in phenotype or gene expression.

A "mutation" refers to a change in the genetic sequence, for example a substitution (transition or transversion), a deletion, an insertion (including a duplication) and a translocation.

A "mutation" also refers to a chromosomal rearrangement or a chromosomal translocation.

A "mutation" also refers to an epigenetic mutation or a heritable change in phenotype and or gene expression that occurs via a mechanism that does not require a change in the genetic sequence.

An epigenetic mutation can occur by a variety of mechanisms including but not limited to post-translational modification of amino acids encoding a histone protein, thereby resulting in chromatin remodelling, DNA methylation (hypermethylation or hypomethylation), production of alternate splice forms of RNA and formation of double stranded RNA.

A "mutation" according to the invention can result in a gain in function, a loss of function, an increase or decrease in expression, an increase or decrease in the rate of expression, expression of a defective mRNA and/or expression or translation of a defective protein.

A "function" as used herein includes but is not limited to DNA repair, apoptosis, recombination, replication, cell proliferation, transcription, ubiquitination, cell cycle regulation and translesion synthesis.

"Loss of function" refers to the inability of any cell to perform any of these functions due to any reasons including, but not limited to, mutations, gene silencing and post-translational modifications, that result in a reduction of these functions.

"Gain of function" refers to the increased activity of any cell to perform any of these functions due to any reasons including but not limited to, mutations, gene amplification, overexpression of gene product or proteins and post-translational modifications resulting in amplified activity of such functions.

As used herein, "dysregulation of translesion synthesis" means a decrease in the ability of a cell to undergo translesion synthesis as compared to a wild type or control cell.

As used herein, "translesion synthesis" refers to a DNA damage tolerance process that allows the DNA replication machinery to replicate past DNA lesions such as thymine dimers or AP sites. Translesion synthesis involves replacing the DNA polymerases that mediate DNA synthesis in the absence of DNA damage with specialized, translesion polymerase (i.e. DNA polymerase IV or V). In addition to replication functions, translesion synthesis is also involved in the homologous recombination repair pathways.

As used herein, "decrease" as it refers to translesion synthesis means that the level of translesion synthesis is 5-fold, 10-fold, 20-fold, 30-fold, 40-fold, 50-fold, 100-fold, or more, less than the level of translesion synthesis as compared to a wild type or control cell. As used herein, "decrease" as it refers to translesion synthesis also means that the level of translesion synthesis is 90%, 80%, 70%, 60%, 50%, 40%, 30%, 25%, 20%, 15%, 10%, 5% or less lower than the level of translesion synthesis in a control or wild type cell.

A "decrease" in translesion synthesis also refers to a decrease in the rate of translesion synthesis as compared to a wild type or control cell.

As used herein, "decrease" as it refers to the rate of translesion synthesis, means 5-fold, 10-fold, 20-fold, 30-fold, 40-fold, 50-fold, 100-fold or more, less than the rate of translesion synthesis in a wild type or control cell. As used herein, "decrease" as it refers to the rate of translesion synthesis also means that the rate is 90%, 80%, 70%, 60%, 50%, 40%, 30%, 25%, 20%, 15%, 10%, 5% or less, than the rate of translesion synthesis in a control or wild type cell.

As used herein, a "control cell" or "wild type cell" means a cell that is derived from a subject that does not have at least one of a DNA repair deficiency, dysregulated apoptosis, a recombination deficiency, a replication deficiency, a cell proliferation disorder, dysregulated transcription, loss of function of a tumor suppressor gene, a ubiquitin disorder, cell cycle dysregulation and dysregulation of translesion synthesis.

A "control cell" or "wild type cell" also means a cell that is derived from a subject that does not have cancer or an inflammatory disease, and/or does not exhibit any detectable symptoms associated with the disease.

In certain embodiments, a "control cell" means a cell from a subject that has at least one of a DNA repair deficiency, an apoptosis deficiency, a recombination deficiency, a replication deficiency, a cell proliferation disorder, dysregulated transcription, loss of function of a tumor suppressor gene, a ubiquitin disorder, cell cycle dysregulation and dysregulation of translesion synthesis, prior to administration of a DNA binding agent of the invention.

In certain embodiments, a "control cell" means a cell from a subject that has been diagnosed with cancer, prior to administration of a non-covalent DNA binding agent of the invention.

In certain embodiments, a "control cell" means a cell from a subject that has been diagnosed with an inflammatory disease, prior to administration of a non-covalent DNA binding agent of the invention.

In certain embodiments, "patient" or "subject" refers to a mammal that is diagnosed with a disease, e.g., a cancer (including but not limited to cancer of the lung, breast, colon, prostate, kidney, pancreas, ovary, and lymphatic organs; melanomas) an inflammatory disease (including but not limited to autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease) or an infection (including but not limited to bacterial infections, parasitic infections or viral infections. The term "patient" or "subject" includes human and other mammalian subjects that receive either prophylactic or therapeutic treatment.

As used herein, "mammal" refers to any mammal including but not limited to human, mouse, rat, sheep, monkey, dog, cat, goat, rabbit, hamster, horse, cow or pig.

A "non-human mammal", as used herein, refers to any mammal that is not a human.

As used herein, "control subject" means a subject that does not have a disease, and/or does not exhibit any detectable symptoms associated with that disease, for example cancer or an inflammatory disease.

A "control subject" also means a subject that has a disease, prior to administration of a non-covalent DNA binding agent of the invention.

A "control subject" also means a subject that does not have at least one of a DNA repair deficiency, dysregulated apoptosis, a recombination deficiency, a replication deficiency, a cell proliferation disorder, dysregulated transcription, loss of function of a tumor suppressor gene, a ubiquitin disorder, cell cycle dysregulation and dysregulation of translesion synthesis.

A "control subject" also means a subject that has at least one of a DNA repair deficiency, dysregulated apoptosis, a recombination deficiency, a replication deficiency, a cell proliferation disorder, dysregulated transcription, loss of function of a tumor suppressor gene, a ubiquitin disorder, cell cycle dysregulation and dysregulation of translesion synthesis, prior to administration of a non-covalent DNA binding agent of the invention.

A "control subject" also means a subject that does not have a mutation in at least one of a gene or gene pathway selected from the group consisting of: PTEN, p53, BRCA1, BRCA2, MLH1, PMS1, PMS2, MSH2, MSH6, REV3, XRCC1, XRCC2, XRCC3, RAD51, RAD52, REV, ATM, ATR, K-Ras, BRAF and the MRE1/RPA1/RAD51 complex.

A "control subject" also means a subject has a mutation in at least one of a gene or gene pathway selected from the group consisting of: PTEN, p53, BRCA1, BRCA2, MLH1, PMS1, PMS2, MSH2, MSH6, REV3, XRCC1, XRCC2, XRCC3, RAD51, RAD52, REV, ATM, ATR, K-Ras, BRAF and the MRE1/RPA1/RAD51 complex, prior to administration or a non-covalent DNA binding agent of the invention.

"Treatment", or "treating" as used herein, is defined as the application or administration of one or more non-covalent DNA binding agent and one or more anticancer or anti-inflammatory agent of the invention, for example, one or more non-covalent DNA minor groove binding agent of the invention, to a subject or patient, or application or administration of one or more non-covalent DNA binding agent and one or more anticancer or anti-inflammatory agent of the invention to an isolated tissue or cell line from a subject or patient, who has a disease, e.g., cancer or an inflammatory disease, with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective amount" or "effective dosage" or "therapeutic dosage" is defined as an amount sufficient to achieve or at least partially achieve the desired effect. The terms "therapeutically effective dose" and "therapeutically effective amount" are defined as an amount sufficient to cure or at least partially arrest the disease and its complications in a patient already suffering from the disease.

As used herein, "treating" a disease refers to preventing the onset of disease and/or reducing, delaying, or eliminating disease symptoms, such as an increase in the rate of growth or number of cancer cells. By "treating" is meant restoring the patient or subject to the basal state as defined herein, and/or to prevent a disease in a subject at risk thereof. Alternatively, "treating" means arresting or otherwise ameliorating symptoms of a disease.

"Treatment," as used herein, includes any drug, drug product, method, procedure, lifestyle change, or other adjustment introduced in an attempt to effect a change in a particular aspect of a subject's health (i.e., directed to a particular disease, disorder, or condition).

As used herein, "inhibition" as it refers to growth of a cancer cell means a decrease in the rate of growth, or a decrease in the amount of growth.

For example, an inhibition of growth of a cancer cell means that the rate of growth of a cancer cell that has been treated with a non-covalent DNA binding agent of the invention is 5-fold, 10-fold, 20-fold, 30-fold, 40-fold, 50-fold, 100-fold, or more, less than that of a cancer cell that has not been treated with a non-covalent DNA binding agent of the invention. As used herein, "inhibition" as it refers to the rate of growth of a cancer cell that has been treated with a non-covalent DNA binding agent of the invention also means that the rate is 90%, 80%, 70%, 60%, 50%, 40%, 30%, 25%, 20%, 15%, 10%, 5% or less, lower than the rate of growth of a cancer cell that has not been treated with a non-covalent DNA binding agent of the invention.

An inhibition of growth of a cancer cell also means that the number or growth of cancer cells that have been treated with a non-covalent DNA binding agent of the invention is 5-fold, 10-fold, 20-fold, 30-fold, 40-fold, 50-fold, 100-fold, or more, less than the number or growth of cancer cells that have not been treated with a non-covalent DNA binding agent of the invention. As used herein, "inhibition" as it refers to the rate of growth of a cancer cell also means that the number or growth of cancer cells that have been treated with a non-covalent DNA binding agent of the invention is 90%, 80%, 70%, 60%, 50%, 40%, 30%, 25%, 20%, 15%, 10%, 5% or less, lower than the growth or number of cancer cells that have not been treated with a non-covalent DNA binding agent of the invention.

As used herein, "K-ras positive" means activating mutations including but not limited to, in the RAS oncogene (KRAS, HRAS and NRAS), PI3K, BRAF, MEK, ERK and MAPK pathways, that are frequent in human cancers. For example, KRAS mutations occur in 60% of pancreatic cancers, 32% of cancers of the large intestine and 17% of lung cancers (Karnoub, A. E. and Weinberg, R. A. Ras oncogenes: split personalities. Nat Rev Mol Cell Biol 9: 517-531, 2008). RAS family members signal through numerous effector molecules with diverse functions such as RAF/MAPK, PI3K and RAL proteins (Bommi-Reddy, A. and Kaelin, W. G. Slaying RAS with a synthetic lethal weapon. Cell Res 20: 119-121, 2010).

As used herein, "K-ras negative tumors" means tumors presenting with wild type K-ras. Similarly, "BRAF negative tumors" refers to tumors presenting with wild-type BRAF.

As used herein, a cancer that is "genetically resistant" means those cancers that have developed genetic and/or epigenetic mutations in oncogenes as well as tumor suppressor and DNA repair genes; thereby leading to the genesis of various cancers. Furthermore, those tumors that have loss of tumor suppressor gene function, resulting in dysregulation of DNA repair, recombination, replication, cell cycle regulation and/or apoptosis pathways, are also considered "genetically resistant".

More specifically, "genetically-resistant" cancers are defined to include all those cancers that either have "functional loss of tumor suppressor genes", and subtypes of cancers that are resistant to currently available anti-cancer agents. For example, such subtypes of "genetically resistant" cancers include, but are not limited to, metastatic colorectal cancer (mCRC) and other Lynch syndrome tumors, such as endometrial and bladder cancers, that have deficiencies in DNA mismatch repair pathways (dMMR tumors); p53-deficient and/or p53-pathway-deficient tumors; BRCA1 and/or BRCA2-mutated (i.e. homologous recombination repair deficient (dHRR)) tumors such as triple-negative breast cancer and basal-like breast cancer; and PTEN-deficient mCRC subtypes.

Furthermore, "genetically resistant" cancers are also defined to include 'gain of function' cancers with KRAS-mutator phenotype, such as mCRC and pancreatic cancers.

As used herein, "determining the response to a therapy for cancer" means comparing a parameter that is indicative of a response to treatment, for example tumor size, rate or growth or number of cancer cells, in a subject before receiving a particular therapy for cancer and after receiving a particular therapy for cancer. "Determining the response to a therapy for cancer" also means comparing a parameter that is indicative of a response to treatment, for example tumor size, rate of growth or number of cancer cells, in a subject that has received a therapy for cancer as compared to a subject that has not received a therapy for cancer. "Determining the response to a therapy for cancer" also means comparing a parameter that is indicative of a response to treatment, for example tumor size, rate of growth or number of cancer cells, in a subject that has received a therapy for cancer as compared to a control subject that has not been diagnosed with cancer and is not in need of cancer treatment.

As used herein, "cannot be treated" means that following receipt of a therapy for cancer there is no change in a parameter that is indicative of a response to treatment, for example tumor size, rate or growth or number of cancer cells, in a subject, as compared to the parameter before receiving the therapy for cancer. "Cannot be treated" also means that following receipt of a particular therapy for cancer, there is no change in a parameter that is indicative of a response to treatment, for example tumor size, rate of growth or number of cancer cells, in a subject that has received a therapy for cancer as compared to a subject that has not received a therapy for cancer. "Cannot be treated" also means that an individual cannot receive a therapy for cancer, for example due to an adverse reaction to the therapy or because they are receiving another treatment that makes it medically unadvisable, for example, due to a negative drug interaction.

"Gene," as used herein, means a segment of DNA that contains information for the regulated biosynthesis of an RNA product, including promoters, exons, introns, and other noncoding or untranslated regions that control gene expression.

The invention contemplates novel compositions and methods of treating a subject who has either failed to respond to prior therapy or has been diagnosed with mutations that would render the treatment regimens ineffective based on existing knowledge among those skilled in treatment of cancers. Both cases would result in "refractory" tumors. Such 'refractory' tumors would be candidates to receive treatment comprising administering to the subject, a therapeutically effective amount of one or more non-covalent DNA binding agent and one or more available anticancer or anti-inflammatory agents of the invention, for example, one or more DNA minor groove binding agent, either alone or in combination with one or more anti-cancer agents.

As used herein, prior treatment or therapy as it applies to cancer treatment includes but is not limited to surgery, radiotherapy (for example, gamma-radiation, neutron beam radiotherapy, electron beam radiotherapy, proton therapy, brachytherapy, and systemic radioactive isotopes), endocrine therapy, biologic response modifiers (for example, interferons, interleukins, antibodies, aptamers, siRNAs, oligonucleotides, enzyme, ion channel and receptor inhibitors or activators), hyperthermia and cryotherapy, agents to attenuate any adverse effects (e.g., antiemetics), and other approved chemotherapeutic drugs, including, but not limited to, alkylating drugs (e.g., mechlorethamine, chlorambucil, Cyclophosphamide, Melphalan, Ifosfamide), antimetabolites (e.g., Methotrexate), purine antagonists and pyrimidine antagonists (e.g., 6-Mercaptopurine, 5-Fluorouracil, Cytarabile, Gemcitabine), spindle poisons (e.g., Vinblastine, Vincristine, Vinorelbine, Paclitaxel), podophyllotoxins (e.g., Etoposide, Irinotecan, Topotecan), antibiotics (Doxorubicin, Bleomycin, Mitomycin), nitrosoureas (e.g., Carmustine, Lomustine), inorganic ions (e.g., Cisplatin, Carboplatin), enzymes (e.g., Asparaginase), and hormones (e.g., Tamoxifen, Leuprolide, Flutamide, and Megestrol).

A method of "administration" useful according to the invention includes but is not limited to intravenous, subcutaneous, intramuscular, intraperitoneal, intracranial and spinal injection, ingestion via the oral route, inhalation, trans-epithelial diffusion (such as via a drug-impregnated, adhesive patch), by the use of an implantable, time-release drug delivery device, which may comprise a reservoir of exogenously-produced agent or may, instead, comprise cells that produce and secrete the therapeutic agent or topical application or administration directly to a blood vessel, including artery, vein or capillary, intravenous drip or injection. Additional methods of administration are provided herein below in the section entitled "Dosage and Administration."

A "therapeutically effective amount" of a non-covalent DNA binding agent, according to the invention is in the range of 0.001 mg-1000 mg per subject. In another embodiment, a "therapeutically effective amount" of a non-covalent DNA binding agent according to the invention is in the range of 0.01 mg to 100 mg per subject. In another embodiment, a "therapeutically effective amount" of a non-covalent DNA binding agent according to the invention is in the range of 0.1 mg to 10 mg per subject.

As used herein, "basal state" refers to an individual who does not have a disease, e.g., cancer or an inflammatory disorder.

A subject who "does not have a disease" has no detectable symptoms of the disease.

As used herein, "diagnosing" or "identifying a patient or subject having" refers to a process of determining if an individual is afflicted with a disease or ailment, for example cancer as defined herein. Methods well known and accepted in the art are used to diagnose any of the cancers recited herein.

"Cancer" refers to any one of cancer, tumor growth, cancer of the colon, breast, bone, brain and others (e.g., osteosarcoma, neuroblastoma, colon adenocarcinoma), chronic myelogenous leukemia (CML), acute myeloid leukemia (AML), acute promyelocytic leukemia (APL), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancers (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

An "inflammatory disorder" includes any one or more of the following: autoimmune diseases or disorders: diabetes mellitus, arthritis (including rheumatoid arthritis, juvenile rheumatoid arthritis, osteoarthritis, psoriatic arthritis), multiple sclerosis, myasthenia gravis; systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens Johnson syndrome, idiopathic sprue, lichen planus, Graves ophthalmopathy, sarcoidosis, primary biliary cirrhosis, uveitis posterior, and interstitial lung fibrosis.

"Inflammatory disorder" also includes any one of rheumatoid spondylitis; post ischemic perfusion injury; inflammatory bowel disease; chronic inflammatory pulmonary disease, eczema, asthma, ischemia/reperfusion injury, acute respiratory distress syndrome, infectious arthritis, progressive chronic arthritis, deforming arthritis, traumatic arthritis, gouty arthritis, Reiter's syndrome, acute synovitis and spondylitis, glomerulonephritis, hemolytic anemia, aplastic anemia, neutropenia, host versus graft disease, allograft rejection, chronic thyroiditis, Graves' disease, primary binary cirrhosis, contact dermatitis, skin sunburns, chronic renal insufficiency, Guillain-Barre syndrome, uveitis, otitis media, periodontal disease, pulmonary interstitial fibrosis, bronchitis, rhinitis, sinusitis, pneumoconiosis, pulmonary insufficiency syndrome, pulmonary emphysema, pulmonary fibrosis, silicosis, or chronic inflammatory pulmonary disease.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, "bioequivalence" or "bioequivalent", refers to non-covalent DNA binding agents or drug products of the agents of the invention, which are pharmaceutically equivalent, and their bioavailabilities (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which the non-covalent DNA binding agent becomes available from such formulations at the site of action when administered at the same molar dose under similar conditions, e.g., the rate at which a non-covalent DNA binding agent can leave such a formulation and the rate at which it can be absorbed and/or become available at the site of action to affect cancer. In other words, there is a high degree of similarity in the bioavailabilities of two non-covalent DNA binding agent pharmaceutical products (of the same galenic form) from the same molar dose, that are unlikely to produce clinically relevant differences in therapeutic effects, or adverse reactions, or both. The terms "bioequivalence", as well as "pharmaceutical equivalence" and "therapeutic equivalence" are also used herein as defined and/or used by (a) the FDA, (b) the Code of Federal Regulations ("C.F.R."), Title 21, (c) Health Canada, (d) European Medicines Agency (EMEA), and/or (e) the Japanese Ministry of Health and Welfare.

Thus, it should be understood that the present invention contemplates novel compositions of one or more non-covalent DNA binding agent formulations, as the only active agents, or in combination with one or more anti-cancer or anti-inflammatory active agents or drug products that may be bioequivalent to other non-covalent DNA binding agent and anti-cancer or anti-inflammatory formulations or drug products of the present invention. By way of example, a first non-covalent DNA binding agent formulation or drug product is bioequivalent to a second non-covalent DNA binding agent formulation or drug product, in accordance with the present invention, when the measurement of at least one pharmacokinetic parameter(s), such as a Cmax, Tmax, AUC, etc., of the first non-covalent DNA binding agent formulation or drug product varies by no more than about ±25%, when compared to the measurement of the same pharmacokinetic parameter for the second non-covalent DNA binding agent formulation or drug product.

As used herein, "bioavailability" or "bioavailable", means generally the rate and extent of absorption of a non-covalent DNA binding agent into the systemic circulation and, more specifically, the rate or measurements intended to reflect the rate and extent to which a non-covalent DNA binding agent becomes available at the site of action or is absorbed from a drug product and becomes available at the site of action. In other words, and by way of example, the extent and rate of absorption of a non-covalent DNA binding agent from a formulation of the present invention as reflected by a time-concentration curve of the non-covalent DNA binding agent in systemic circulation.

With respect to absolute bioavailability, absolute bioavailability compares the bioavailability (estimated as area under the curve, or AUC) of the active drug in systemic circulation following non-intravenous administration (i.e., after oral, rectal, transdermal, subcutaneous administration), with the bioavailability of the same drug following intravenous administration. It is the fraction of the drug absorbed through non-intravenous administration compared with the corresponding intravenous administration of the same drug. The comparison must be dose normalized if different doses are used; consequently, each AUC is corrected by dividing the corresponding dose administered.

As used herein, the terms "pharmaceutical equivalence" or "pharmaceutically equivalent", refer to non-covalent DNA binding agent formulations or drug products of these agents that contain the same amount of non-covalent DNA binding agent, in the same dosage forms, but not necessarily containing the same inactive ingredients, for the same route of administration and meeting the same or comparable compendial or other applicable standards of identity, strength, quality, and purity, including potency and, where applicable, content uniformity and for stability. Thus, it should be understood that the present invention contemplates non-covalent DNA binding agent formulations or drug products that may be pharmaceutically equivalent to other non-covalent DNA binding agent formulations or drug products used in accordance with the present invention.

As used herein, the terms "therapeutic equivalence or therapeutically equivalent", mean those non-covalent DNA binding agent formulations or drug products which (a) will produce the same clinical effect and safety profile when utilizing a non-covalent DNA binding agent drug product to treat a disease, for example cancer, in accordance with the present invention and (b) are pharmaceutical equivalents, e.g., they contain the non-covalent DNA binding agent in the same dosage form, they have the same route of administration; and they have the same non-covalent DNA binding agent strength. In other words, therapeutic equivalence means that a chemical equivalent of a non-covalent DNA binding agent formulation of the present invention (i.e., containing the same amount of the non-covalent DNA binding agent in the same dosage form when administered to the same individuals in the same dosage regimen) will provide essentially the same efficacy and toxicity.

"Biological sample," as used herein, refers to a material containing, for example, a nucleic acid or other biological or chemical material of interest. Biological samples containing DNA include hair, skin, cheek swab, and biological fluids such as blood, serum, plasma, sputum, lymphatic fluid, semen, vaginal mucus, feces, urine, spinal fluid, and the like. Isolation of DNA from such samples is well known to those skilled in the art.

"Drug" or "drug substance," as used herein, refers to an active ingredient, such as a chemical entity or biological entity, or combinations of chemical entities and/or biological entities, suitable to be administered to a subject to treat a disease, e.g., cancer or an inflammatory disease. In accordance with the present invention, the drug or drug substance is a non-covalent DNA binding agent or a pharmaceutically acceptable salt thereof.

The term "drug product," as used herein, is synonymous with the terms "medicine," "medicament," "therapeutic intervention," or "pharmaceutical product." Most preferably, a drug product is approved by a government agency for use in accordance with the methods of the present invention. A drug product, in accordance with the present invention, contains a non-covalent DNA binding agent.

II. Non-Covalent DNA Binding Agents

The invention provides for novel compositions of one or more non-covalent DNA binding agents, for example one or more non-covalent DNA minor groove binding agents, alone or in combination with one or more available anticancer or anti-inflammatory agent, and their use in treating a disease, for example cancer or an inflammatory disease, according to the methods defined herein.

The invention provides for a library of pyrrolobenzodiazepine dimers (PBDs) (for example as described in U.S. Pat. Nos. 6,362,331, 6,800,622, 6,683,073, 6,884,799 and 7,015,215 the contents of which are incorporated herein by reference in their entirety). Non-covalent DNA binding agents of the invention that are PBDs are non-anthramycin DNA minor groove binding agents that exhibit improved properties, for example, water solubility, and decreased cardiotoxicity and metabolic inactivation as compared to natural anti-cancer antibiotics, for example anthramycin, tomaymycin, sibiromycin and neothramycin. The invention provides for PBDs that demonstrate unique S-phase cell cycle specificity resulting in the stalling of the DNA replication fork.

The invention provides for non-covalent DNA binding agents that are pyrrolobenzodiazepine dimers.

The non-covalent DNA binding agents of the invention are distinct from anti-tumor antibiotics because of the following:

- They are potent minor groove binders of the DNA with specificity for G-C rich sequences;
- These non-covalent DNA binding agents or intercalators are distinct from previously described DNA minor groove binding agents;
- They exhibit excellent pharmacokinetics in rats;
- They exhibit excellent potency in tumor cells that are deficient in DNA mismatch repair genes and/or pathways, such as those involved in the development of Lynch tumors, that have DNA mismatch repair gene deficiencies-either through genetic or epigenetic mutations;
- These non-covalent DNA binding agents have excellent potency in tumors that exhibit 'loss of tumor suppressor gene' function of apoptotic genes such as p53 and PTEN;
- The non-covalent DNA binding agents of the invention show excellent cytotoxic potency in tumor cells that have loss of function in multiple gene targets that regulate DNA repair, replication and/or apoptosis.

Non-covalent DNA binding agents useful according to the invention include but are not limited to the PBDs presented below:

pyrrolo[2,1-c][1,4]benzodiazepine compounds
1)
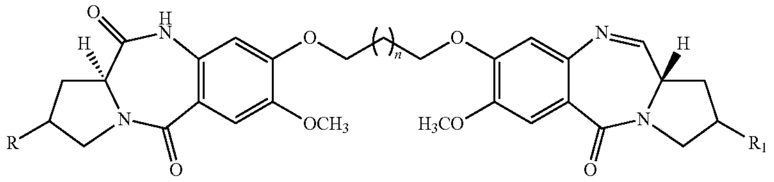
n = 3-5
R = H, OH, OAc
$R_1$ = H
| Linker | NSC No. |
|---|---|
| n = 3 | 718811/1 |
| n = 4 | 718812/1 |
| n = 5 | 718813/1 |
2)
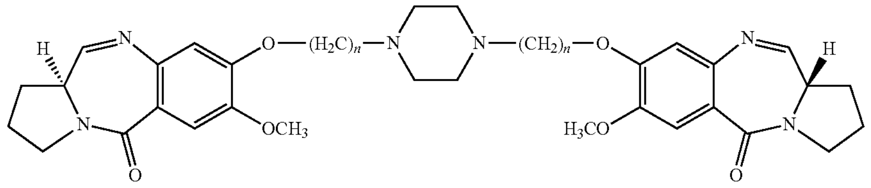
n = 2-10
| Linker | NSC No. |
|---|---|
| n = 2 | 723733/1 |
| n = 3 | 726262/1 |
| n = 4 | 723734/1 |
| n = 5 | 726263/1 |
3)
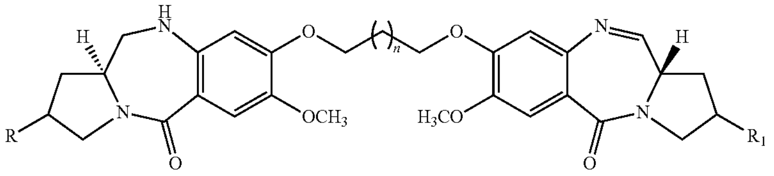
n = 3-5
R and $R_1$ = H and/or OH
| Linker | NSC No. |
|---|---|
| n = 3 | 724005/1 |
| n = 4 | 726528/1 |
pyrrolo[2,1-c][1,4]benzodiazepine hybrids
4)
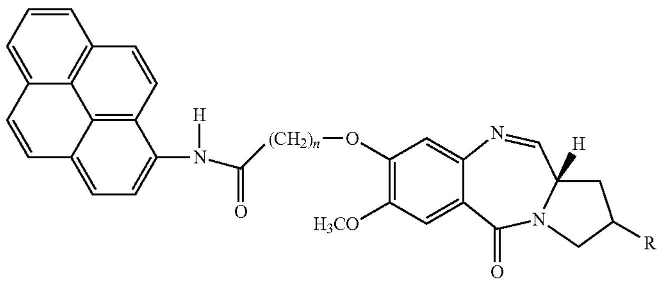
n = 1-4
R = H, OH
| Linker | NSC No. |
|---|---|
| n = 3 | 726260/1 |

-continued

5)

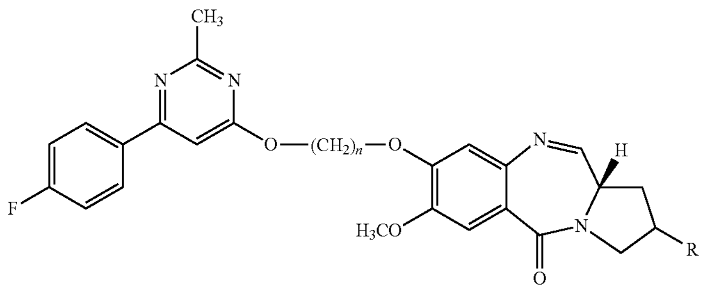

n = 3-5
R = H, OH, OAc

| Linker | NSC No. |
|---|---|
| n = 3 | 724004/1 |
| n = 4 | 723732/1 |
| n = 5 | 727728/1 |

III. Non-Covalent DNA Binding Agents May be Conjugated

PEGylation of Molecules

Non-covalent DNA binding agents of the invention may be joined to a PEG molecule (also referred to herein as pegylated non-covalent DNA binding agents of the invention) in order to enhance its stability and effectiveness.

Poly(ethylene glycol) (PEG) may be a linear or branched polyether terminated with hydroxyl groups and having the general structure:

$$HO—(CH_2CH_2O)_n—CH_2CH_2—OH$$

A useful modification for PEG is monomethoxy PEG (mPEG) having the general structure:

$$CH_3O—(CH_2CH_2O)_n—CH_2CH_2—OH$$

The monofunctionality of mPEG makes it particularly suitable for conjugation with non PEG molecules because it can yield reactive PEGs that do not produce crosslinked products. mPEG can be further modified to have a functional group useful for conjugation with non PEG molecules.

To conjugate a PEG molecule to a non-PEG molecule such as a non-covalent DNA binding agent of the invention, it is necessary to activate the PEG by preparing a derivative of the PEG having a functional group at one or both termini. The functional group can be chosen based on the type of available reactive group on the molecule that will be conjugated to the PEG, In certain embodiments of this invention, it can be desirable to use the succinimidyl ester of the monopropionic acid derivative of PEG, as disclosed in Harris, J. M., et al., U.S. Pat. No. 5,672,662, which is incorporated herein fully by reference, or other succinimide activated PEG-carboxylic acids. In certain other embodiments, it can be desirable to use the p-nitrophenyl carbonate derivative of PEG, as disclosed in Kelly, S. J., et al. (2001) supra; PCT publication WO 00/07629 A2, supra, and in PCT publication WO 01/59078 A2 supra. Additional PEG derivatives include, but are not limited to, aldehyde derivatives of PEGs (Royer, G. P., U.S. Pat. No. 4,002,531; Harris, J. M., et al., U.S. Pat. No. 5,252,714), amine, bromophenyl carbonate, carbonylimidazole, chlorophenyl carbonate, fluorophenyl carbonate, hydrazide, iodoacetamide, maleimide, orthopyridyl disulfide, oxime, phenylglyoxal, thiazolidine-2-thione, thioester, thiol, triazine and vinylsulfone derivatives of PEGs.

In accordance with the practice of the invention, one or several (e.g., 1, 2, 3, 4, 5, 6, 7, 8, 9, and up to 10) strands of one or more PEGs can be coupled to a non-covalent DNA binding agents of the invention. In one embodiment, one or two strands of PEG may be coupled to a non-covalent DNA binding agents of the invention.

In an embodiment of the invention, coupling of PEG to non-covalent DNA binding agents of the invention may be effected by, for example, reductive alkylation (also known as reductive amination) using standard methods (see e.g., Bentley, M. D., et al., U.S. Pat. No. 5,990,237; references 1-69).

In one embodiment, a PEG derivative suitable for conjugation with N-terminal amino acid groups of proteins or polypeptides (e.g. non-covalent DNA binding agents of the invention) is mPEG-propionaldehyde as shown below in a reductive alkylation reaction (see for example U.S. Pat. No. 5,252,714?). In this embodiment, sodium cyanoborohydride may be used as the reducing agent (Cabacungan, J. C., et al., (1982) Anal Biochem 124:272-278; U.S. Pat. No. 5,252,714). In accord with the practice of the invention, $H_2N—R$ can be non-covalent DNA binding agents of the invention.

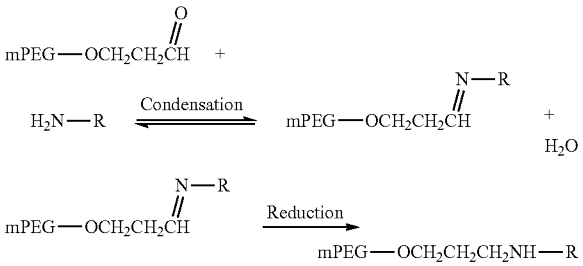

Other PEG derivatives suitable for conjugation with N-terminal amino acid groups include, but are not limited to: PEG-acetaldehyde, PEG carboxylic acids (e.g., PEG propionic acid, PEG butanoic acid).

Reversible conjugation using PEG derivative molecules can be beneficial in some circumstances. Examples of PEG derivatives that can conjugate and release non-PEG molecules include, but are not limited to: PEG-succinimidyl succinate, PEG maleic anhydride, mPEG phenyl ether succinimidyl carbonates and mPEG benzamide succinimidyl carbonates.

Heterobifunctional PEGs are PEGs bearing dissimilar terminal groups. Heterobifunctional PEGs with appropriate functional groups can be used to link two entities where a hydrophilic, flexible, and biocompatible spacer is needed. Heterobifunctional PEGs can be used in a variety of ways including, but not limited to, linking molecules to surfaces (for immunoassays, biosensors or various probe applications, etc), targeting of drugs, liposomes, and viruses to specific tissues, liquid phase peptide synthesis and other applications.

In addition to the linear PEG molecules described above, branched and/or forked PEGs can be used to conjugate non-PEG molecules (e.g. non-covalent DNA binding agents of the invention). Branched PEG molecules have a single functional group at the end of two PEG chains. A branched PEG structure can be more effective than a linear PEG in protecting conjugated agents from proteolysis and in reducing antigenicity and immunogenicity of such conjugates. Forked PEGs have two reactive groups at one end of a single PEG chain. Forked PEG molecules can be used to bring two non PEG molecules in close proximity to each other by attaching the non PEG molecules to the single forked PEG molecule.

Examples of branched and/or forked PEG molecules are shown below.

Branched PEG:

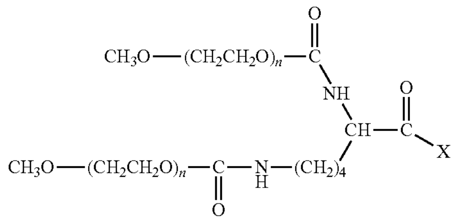

Linear Forked PEG:

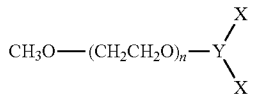

Branched Forked PEG:

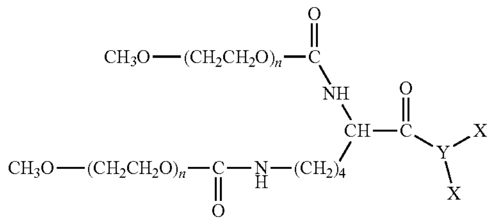

Enhanced Activity of PEGylated Non-Covalent DNA Binding Agents of the Invention

Enhanced receptor binding activity and functional activity (e.g., increased or extended half-life) may be an advantage of the pegylated non-covalent DNA binding agents of the invention. Increased receptor binding activity and increased functional activity can be measured, or employed, in vitro, and increased potency, can be measured either in vitro or in vivo.

III. Anti-Inflammatory Agents

Anti-inflammatory agents useful in the combination therapy of the invention include, but are not limited to, dihydrofolic acid reductase inhibitors e.g., methotrexate; cyclophosphamide; cyclosporine; cyclosporin A; chloroquine; hydroxychloroquine; sulfasalazine (sulphasalazopyrine) gold salts D-penicillamine; leflunomide; azathioprine; anakinra; a Non-Steroidal Anti-Inflammatory Drug (NSAID); TNF blockers e.g., infliximab (REMICADE®) or etanercept; and a biological agent that targets an inflammatory cytokine. In accordance with the practice of the invention, therapeutically effective salts or prodrugs of these agents may also be used.

NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors, meloxicam and tramadol. In accordance with the practice of the invention, therapeutically effective salts or prodrugs of these agents may also be used.

IV. Anti-Cancer Agents

Anti-cancer agents useful in the combination therapy of the invention include, but are not limited to: histone deacetylase inhibitors (HDIs or HDACIs) (such as trichostatin A (7-[4-(dimethylamino)phenyl]-N-hydroxy-4,6-dimethyl-7-oxohepta-2,4-dienamide)); topoisomerase I inhibitors such as camptothecin (S)-4-ethyl-4-hydroxy-1H-pyrano[3',4':6,7]indolizino[1,2-b]quinoline-3,14-(4H,12H)-dione), topotecan (S)-10-[(dimethylamino)methyl]-4-ethyl-4,9-dihydroxy-1H-pyrano[3',4':6,7]indolizino[1,2-b]quinoline-3,14(4H,12H)-dione monohydrochioride) and irinotecan ((S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate); protein synthesis inhibitors such as cyclohexamide(4-[(2R)-2-[(1S,3S,5S)-3,5-Dimethyl-2-oxocyclohexyl]-2-hydroxyethyl]piperidine-2,6-dione); DNA alkylating agents such as mitomycin C ([6-Amino-8a-methoxy-5-methyl-4,7-dioxo-1,1a,2,4,7,8,8a,8b-octahydroazireno[2',3':3,4]pyrrolo[1,2-a]indol-8-yl]methyl carbamate); topoisomerase II inhibitors such as anthracycline antibiotics like doxorubicin ((8S,10S)-10-(4-amino-5-hydroxy-6-methyl-tetrahydro-2H-pyran-2-yloxy)-6,8,11-trihydroxy-8-(2-hydroxyacetyl)-1-methoxy-7,8,9,10-tetrahydrotetracene-5,12-dione) and etoposide (4'-demethyl-epipodophyllotoxin 9-[4,6-O—(R)-ethylidene-beta-D-glucopyranoside], 4'-(dihydrogen phosphate)); anti-metabolite agents (such as 6-thioguanine (6TG) (2-amino-6,7-dihydro-3H-purine-6-thione), and 5-fluorouracil (5-FU) (5-fluoro-1H-pyrimidine-2,4-dione); epidermal growth factor receptor (EGFR) inhibitors (such as gefitinib (N-(3-chloro-4-fluoro-phenyl)-7-methoxy-6-(3-morpholin-4-yl-propoxy)quinazolin-4-amine) and erlonitib (N-(3-ethynyl-phenyl)-6,7-bis(2-methoxyethoxy) quinazolin-4-amine)); RNA synthesis inhibitor such as actinomycin D (2-amino-N,N'-bis[(6S,9R,10S,13R,18aS)-6,13-diisopropyl-2,5,9-trimethyl-1,4,7,11,14-pentaoxohexadecahydro-1H-pyrrolo[2,1-i][1,4,7,10,13]oxatetraazacyclohexadecin-10-yl]-4,6- dimethyl-3-oxo-3H-phenoxazine-1,9-dicarboxamide); anti-mitotic agents like tubulin inhibitors such as paclitaxel ((2α,4α,5β,7β, 10β,13α)-4,10-bis(acetyloxy)-13-{[(2R, 3S)-3-(benzoylamino)-2-hydroxy-3-phenylpropanoyl]oxy}-1,7-dihydroxy-9-oxo-5,20-epoxytax-11-en-2-yl benzoate) (also known as Taxol) and vinca alkaloids like vincristine (methyl(1R,9R,10S,11R,12R,19R)-11-(acetyloxy)-12-ethyl-4-[(13S,15S,17S)-17-ethyl-17-hydroxy-13-(methoxy-carbonyl)-1,11-diazatetracyclo[13.3.1.$0^{4,12}$.$0^{5,10}$]nonadeca-4(12),5,7,9-tetraen-13-yl]-8-formyl-10-hydroxy-5-methoxy-8,16-diazapentacyclo[10.6.1.$0^{1,9}$.$0^{2,7}$.$0^{16,19}$] nonadeca-2,4,6,13-tetraene-10-carboxylate) and vinblastine (dimethyl(2β,3β,4β,5α,12β,19α)-15-[(5S,9S)-5-ethyl-5-hydroxy-9-(methoxycarbonyl)-1,4,5,6,7,8,9,10-octahydro-2H-3,7-methanoazacycloundecino[5,4-b]indol-9-yl]-3-hydroxy-16-methoxy-1-methyl-6,7-didehydroaspidospermidine-3,4-dicarboxylate); DNA synthesis inhibitors like fludarabine ([(2R,3R,4S,5R)-5-(6-amino-2-fluoro-purin-9-yl)-3,4-dihydroxy-oxolan-2-yl] methoxyphosphonic acid) and hydroxyurea; Poly ADP ribose polymerase (PARP) inhibitors (such as olaparib (4-[(3-[(4-cyclopropylcarbonyl)piperazin-4-yl]carbonyl)-4-fluorophenyl]methyl(2H)phthalazin-1-one)); and DNA crosslinking agents such as such as cisplatin ((SP-4-2)-diamminedichloridoplatinum), carboplatin (cis-diammine (cyclobutane-1,1-dicarboxylate-O,O')platinum(II)) and oxaliplatin ([(1R,2R)-cyclohexane-1,2-diamine](ethanedioato-O,O')platinum(II)). In accordance with the practice of the invention, therapeutically effective salts or prodrugs of these anti-cancer agents may be used.

V. Genes

The invention provides for novel compositions and use of one or more non-covalent DNA binding agents, alone (as the only active agent(s)) or in combination with other anticancer or anti-inflammatory active agents, in the treatment of cancer or inflammatory disease in patients with, for example, mutations in genes including but not limited to:

- genes regulating DNA replication, recombination, repair and/or apoptosis such as PTEN, p53, BRCA1 and/or BRCA2, together with the associated BRCA1/rad51/MRE11/replication protein A (RPA) complex;
- genes regulating DNA mismatch repair such as mlh1, MSH2, MSH6, PMS1, PMS2;
- genes regulating translesion synthesis such as REV3 and its associated protein complexes at the replication fork;
- genes regulating cell proliferation such as KRAS and BRAF kinase pathways.
- Genes encoding kinases regulating DNA replication, recombination, repair and/or apoptosis such as ATM, ATR, Chk1 and/or Chk2 kinases;
- genes involved in base excision repair such as XRCC1;
- nucleotide excision repair genes such as ERCC1;
- homologous recombination genes such as RAD51, RAD52, RAD54, BRCA1, BRCA2, XRCC2 and XRCC3;
- genes regulating non-homologous recombination such as KU70, KU80, XRCC4 and DNA ligase4; and
- genes regulating transcription-coupled repair such as CSA, CSB and XPG.

The invention therefore provides for novel compositions and use of one or more non-covalent DNA binding agents alone, as the only active agent(s), or in combination with other anticancer or anti-inflammatory active agents, in the treatment of cancer or inflammatory disease in patients with, for example, a mutation in a gene or gene pathway including but not limited to PTEN, p53, BRCA1, BRCA2, MLH1, PMS1, PMS2, MSH2, MSH6, REV3, KRAS, BRAF, Chk1, Chk2, KU70, KU80, DNA ligase 4, CSA, CSB, XRCC1, XRCC2, XRCC3, XRCC4, RAD51, RAD52, RAD54, REV, ATM, ATR, XPF, Ercc1, XPA, XPB, XPD, XPF, XPG, MSH6/3, PCNA, BARD1, RAD50, NBS1, Mre11, BLM, PMS2, MLH1, MEDI, RFC, polγ/ϵ, RPA, DNA ligase I and the MRE1/RPA1/RAD51 complex.

TABLE 1

| Symbol | Entrez Gene ID | NCBI Reference Sequence |
|---|---|---|
| TP53 | 7157 | NM_000546 |
| MLH1 | 4292 | NM_000249 |
| MSH2 | 4436 | NM_000251 |
| BRCA1 | 672 | NM_007294 |
| REV3L | 5980 | NM_002912 |
| PARP1 | 142 | NM_001618 |
| RAD51 | 5888 | NM_002875 |
| MRE11A | 4361 | NM_005591 |
| ATM | 472 | NM_000051 |
| ATR | 545 | NM_001184 |
| PTEN | 5728 | NM_000314 |
| ERCC1 | 2067 | NM_001983 |
| BRCA2 | 675 | NM_000059 |
| XRCC1 | 7515 | NM_006297 |
| KRAS | 3845 | NM_033360 |
| BRAF | 673 | NM_004333 |
| RAD50 | 10111 | NM_005732 |
| RAD51 | 5393 | NM_134424 |

PTEN

Phosphatase and tensin homolog (PTEN) is a protein that is encoded by the PTEN gene. Mutations of this gene are a step in the development of many cancers. PTEN acts as a tumor suppressor gene through the action of its phosphatase protein product. This phosphatase is involved in the regulation of the cell cycle, preventing cells from growing and dividing too rapidly.

This gene was identified as a tumor suppressor that is mutated in a large number of cancers at high frequency. The protein encoded by this gene is a phosphatidylinositol-3,4,5-trisphosphate 3-phosphatase. It contains a tensin like domain as well as a catalytic domain similar to that of the dual specificity protein tyrosine phosphatases. Unlike most of the protein tyrosine phosphatases, this protein preferentially dephosphorylates phosphoinositide substrates. It negatively regulates intracellular levels of phosphatidylinositol-3,4,5-trisphosphate in cells and functions as a tumor suppressor by negatively regulating the Akt/PKB signaling pathway.

p53 p53 is a tumor suppressor protein that in humans is encoded by the TP53 gene. p53 is important in multicellular organisms, where it regulates the cell cycle and, thus, functions as a tumor suppressor that is involved in preventing cancer. As such, p53 plays a role in conserving stability by preventing genome mutation.

BRCA1

BRCA1 (breast cancer 1) is a human tumor suppressor gene, which produces a protein, called breast cancer type 1 susceptibility protein. BRCA1 is expressed in the cells of breast and other tissue, where it helps repair damaged DNA, or destroy cells if DNA cannot be repaired. If BRCA1 itself is damaged, damaged DNA is not repaired properly and this increases risks for cancers.

The protein encoded by the BRCA1 gene combines with other tumor suppressors, DNA damage sensors, and signal transducers to form a large multi-subunit protein complex known as the BRCA1-associated genome surveillance complex (BASC). The BRCA1 protein associates with RNA polymerase II, and, through the C-terminal domain, also interacts with histone deacetylase complexes. This protein thus plays a role in transcription, DNA repair of double-stranded breaks, ubiquitination, transcriptional regulation as well as other functions.

BRCA2

BRCA2 (Breast Cancer 2 susceptibility protein) is a protein that in humans is encoded by the BRCA2 gene. BRCA2 belongs to the tumor suppressor gene family and the protein encoded by this gene is involved in the repair of chromosomal damage with an important role in the error-free repair of DNA double strand breaks.

DNA Mismatch Repair Genes

DNA mismatch repair is a system for recognizing and repairing erroneous insertion, deletion and mis-incorporation of bases that can arise during DNA replication and recombination, as well as repairing some forms of DNA damage.

Mismatch repair is strand-specific. During DNA synthesis it is common that errors are introduced into the newly synthesized (daughter) strand.

Any mutational event that disrupts the superhelical structure of DNA carries with it the potential to compromise the genetic stability of a cell.

Examples of mismatched bases include a G/T or A/C. Mismatches are commonly due to tautomerization of bases during synthesis. The damage is repaired by recognition of the deformity caused by the mismatch, determination of the template and non-template strand, and excision of the wrongly incorporated base and replacement of the incorrect base with the correct nucleotide. The removal process involves more than just the mismatched nucleotide itself. A few or up to thousands of base pairs of the newly synthesized DNA strand can be removed.

Mismatch repair (MMR) genes are involved in recognition and repair of certain types of DNA damage or replication errors. These genes also function to help preserve the fidelity of the genome through successive cycles of cell division.

The protein products of MMR genes also repair branched DNA structures, prevent recombination of divergent sequences, direct non-MMR proteins in nucleotide excision and other forms of DNA repair, and are involved in regulation of meiotic crossover. Defects in MMR genes lead to Microsatellite Instability (MSI) and cancer.

MLH1

MutL homolog 1, colon cancer, nonpolyposis type 2 (*E. coli*), also known as MLH1, is a human gene located on Chromosome 3. It is a gene commonly associated with hereditary nonpolyposis colorectal cancer.

This gene was identified as a locus frequently mutated in hereditary nonpolyposis colon cancer (HNPCC). It is a human homolog of the *E. coli* DNA mismatch repair gene mutL, consistent with the characteristic alterations in microsatellite sequences (RER+ phenotype) found in HNPCC. Alternatively spliced transcript variants encoding different isoforms have been described, but their full-length natures have not been determined.

PMS1

PMS1 protein homolog 1 is a protein that in humans is encoded by the PMS1 gene.

The protein encoded by this gene was identified by its homology to a yeast protein involved in DNA mismatch repair. This protein forms heterodimers with MLH1, a DNA mismatch repair protein, and some cases of hereditary nonpolyposis colorectal cancer have been found to have mutations in this gene.

PMS2

Mismatch repair endonuclease PMS2 is an enzyme that in humans is encoded by the PMS2 gene.

This gene is one of the PMS2 gene family members which are found in clusters on chromosome 7. The product of this gene is involved in DNA mismatch repair. The protein forms a heterodimer with MLH1 and this complex interacts with MSH2 bound to mismatched bases. Defects in this gene are associated with hereditary nonpolyposis colorectal cancer, with Turcot syndrome, and are a cause of supratentorial primitive neuroectodermal tumors. Alternatively spliced transcript variants have been observed.

MSH2

MSH2 is a gene commonly associated with Hereditary nonpolyposis colorectal cancer.

MSH2 was identified as a locus frequently mutated in hereditary nonpolyposis colon cancer (HNPCC). When cloned, it was discovered to be a human homolog of the *E. coli* mismatch repair gene mutS, consistent with the characteristic alterations in microsatellite sequences (RER+ phenotype) found in HNPCC. It is also associated with some endometrial cancers.

MSH3

DNA mismatch repair protein Msh3 is a protein that in humans is encoded by the MSH3 gene. MSH3 has been shown to interact with MSH2, PCNA and BRCA1.

MSH6

MSH6 is a gene commonly associated with hereditary nonpolyposis colorectal cancer.

MSH6 has been shown to interact with MSH2, PCNA and BRCA1.

VI. Cells and Cell Lines

Cell lines useful according to the invention include but are not limited to breast cancer cell lines (MMR- or PTEN-deficient or BRCA1 mutant), e.g., MDA-MB-231, MCF-7, MDA-MB-468; colon cancer cell lines (MMR-deficient; KRAS-mutant cells) e.g., HCT-116, SW-620, SW-480, SW48, SW-403, Colo205; lymphoblastoid cell lines (MSH2- or PTEN-deficient cells) e.g., CEM and Jurkat; ovarian and uterine cancer cell lines (DNA MMR-deficient cells) e.g., HeLa, SKOV-3; osteosarcoma cells (MMR-competent) e.g., U2OS; and lung cancer cells (MMR-competent or MMR-deficient) e.g., A549 and H1299.

Cell lines derived from patients with any of the cancers or inflammatory diseases recited herein are also useful according to the methods of the invention.

VII. Diseases

The invention provides for novel compositions and methods for treatment of a subject with a disease comprising administration of a pharmaceutically effective amount of one or more of a non-covalent DNA binding agent, for example, a non-covalent DNA minor groove binding agent, alone, as the only active agent(s) or in combination with one or more anti-cancer and/or anti-inflammatory active agents. For example, the invention provides for treating cancer with one or more non-covalent DNA-minor groove binding agents that result in DNA crosslinking or intercalation, alone, as the only active agent(s) or in combination with one or more anti-cancer active agents. The invention contemplates treating any one of one of cancer, tumor growth, cancer of the colon, breast, bone, brain and others (e.g., osteosarcoma, neuroblastoma, colon adenocarcinoma), chronic myelogenous leukemia (CML), acute myeloid leukemia (AML), acute promyelocytic leukemia (APL), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

In particular, the invention relates to novel compositions of one or more non-covalent DNA binding agents, alone, as the only active agent(s) or in combination with one or more anti-cancer active agents and their use to treat those cancers that are genetically-resistant and have a loss of at least one tumor suppressor gene function. Such cancers include tumors of the brain (such as gliomas and glioblastomas), blood (such as leukemias and lymphomas), bladder, breast, colorectal, endometrial, lung, melanomas, ovarian, prostate, renal and testicular cancers.

In one embodiment the invention provides for treating MMR-deficient colorectal cancer using a novel composition of one or more non-covalent DNA binding agents, alone, as the only active agent(s) or in combination with one or more anti-cancer active agents of the invention. One of the most studied genotypic subtypes of colorectal cancer is that characterized by a deficient mismatch repair (dMMR) pathway, usually found in combination with microsatellite instability (see Hewish et al., Nature Reviews 7: 197-208, 2010). MMR-deficient colorectal cancer can occur as a result of inherited or sporadic abnormalities in DNA repair pathways. The phenotypic characteristics of this cancer include proximal anatomical location, mucinous features and lymphocytic infiltration.

Preclinical and clinical studies have demonstrated that MMR-deficient colorectal cancer shows resistance to 5-fluorouracil. Heterogeneity exists within MMR-deficient colorectal cancer subtype, possibly due to secondary mutations from MMR-deficiency-associated mutator phenotype.

In another embodiment, the invention provides for treating 'triple negative' and 'basal-like' breast cancers with novel compositions of one or more non-covalent DNA binding agents, alone, as the only active agents, or in combination with one or more anti-cancer active agents of the invention. Triple-negative breast cancer is the subgroup of breast cancer that does not express clinically significant levels of the estrogen receptor (ER), progesterone receptor (PR) and HER2/neu (HER2) (Carey, L., Winer, E, Viale, G, Cameron, D. and Gianni, L. Triple-negative breast cancer: disease entity or title of convenience. Nature Reviews 7: 683-692, 2010).

BRCA1 protein expression levels are significantly lower in tumors of high histological grade that lack hormone receptors (triple negative and basal-like breast tumors). Further, basal-like breast cancers also have significant TP53 (P53) gene mutations and BRCA1 pathway dysfunction. BRCA1-pathway related cancers likely have DNA repair defects. These BRCA1 pathway dysfunction tumors show sensitivity to DNA crosslinking agents, for example platinum, in combination with antimetabolite drugs, such as gemcitabine, and poly ADP-ribose polymerase (PARP) inhibitors, such as olaparib and iniparib.

In another embodiment, the invention provides for treating human glioblastomas with novel compositions of one or more non-covalent DNA binding agents, alone, as the only active agent(s) or in combination with one or more anti-cancer active agents of the invention. One of the key markers for glioblastomas is the methylation status of MGMT. The MGMT methylation status predicts the sensitivity of human glioblastomas to alkylating agents, e.g., temozolomide.

The invention also contemplates treating any one of the inflammatory disease recited herein with novel compositions of one or more non-covalent DNA binding agents, alone, as the only active agent(s) or in combination with one or more anti-inflammatory active agents of the invention.

The invention also contemplates treating a subject having an infection (e.g. bacterial infection, viral infection, yeast infection, or parasitic infection) with therapeutically effective amount of one or more of a PBD such as NSC718813, NSC723734, NSC 723732 and NSC726260 so as to treat the subject with the infection.

The invention also contemplates treating a subject suffering from an infection (e.g. bacterial infection, viral infection, yeast infection, or parasitic infection) by administering to the subject a therapeutically effective amount of one or more of the following PBD's:

(5)

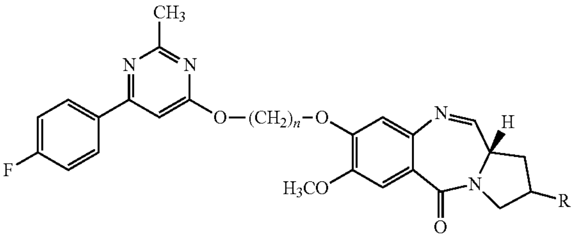

n = 3-5
R = H, OH, OAc wherein R is H, OH, or OAc and n is 3 to 5;

(4)

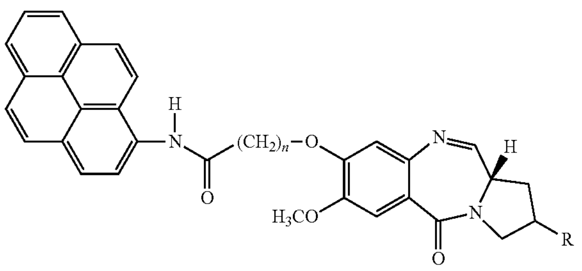

n = 1-4
R = H, OH wherein R is H, OH, and n is 1 to 4;

VIII. Dosages and Modes of Administration

In general, non-covalent DNA binding agents of the invention may be administered in therapeutically effective amounts via any of the usual and acceptable modes known in the art, either as one or more non-covalent DNA binding agents like the PBDs alone or in combination with one or more additional therapeutic agents, e.g., anti-cancer agents and/or anti-inflammatory agents. A therapeutically effective amount may vary widely depending on the disease, the severity of the disease, the age and relative health of the subject, the potency of the compound used and other factors. In general, satisfactory results are indicated to be obtained systemically at daily dosages of from about 0.001 mg to 1000 mg per subject. An indicated daily intravenous dosage in the larger mammal, e.g. humans, is in the range from about 0.0001 mg to about 100 mg per subject, conveniently (3)

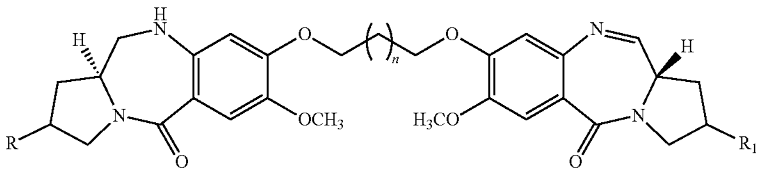

n = 3-5
R and $R_1$ = H and/or OH wherein R and $R_1$ are independently H or —OH, and n is an integer from 3 to 5;

(2)

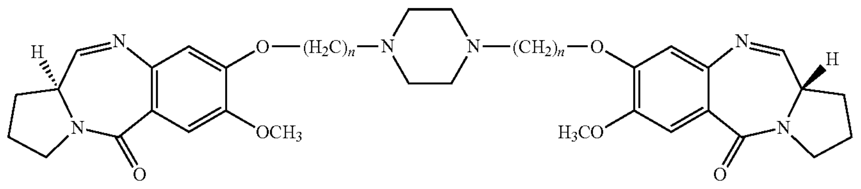

n = 2-10 wherein n is 2 to 10; or (1)

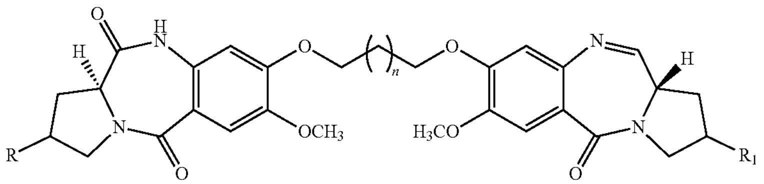

n = 3-5
R = H, OH, OAc
$R_1$ = H wherein R is H, OH, OAc, and $R_1$ is H, and n is 3 to 5.

administered, e.g. in divided doses up to 1-2 times a day or in retard form. Suitable unit dosage forms for intravenous administration comprise from about 0.001 mg to about 10 mg/ml active ingredient.

In certain embodiments, a therapeutic amount or intravenous dose of one or more of a non-covalent DNA binding agent of the present invention may range from about 0.001 mg to about 100 mg per subject, alternatively from about 0.01 mg to about 10 mg per subject. In general, treatment regimens according to the present invention comprise administration to a patient in need of such treatment from about 0.001 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of one or more of a non-covalent DNA binding agent, either alone or in combination with one or more additional therapeutic agents, e.g., a chemotherapeutic agent, may be administered, if necessary. Subsequently, the dosage or frequency of administration, or both, may be altered, for example reduced, as a function of the symptoms, to a level at which the improved condition is retained and when the symptoms have been alleviated to the desired level, treatment should cease. The subject may, however, require intermittent treatment on a long-term basis upon any recurrence of disease symptoms.

It will be understood, however, that the total daily usage of one or more non-covalent DNA binding agents alone or in combination with one or more anti-cancer and/or anti-inflammatory agents of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In general, the anti-inflammatory agents of the invention may be administered in therapeutically effective amounts via any of the acceptable modes known in the art. Depending on the anti-inflammatory agent, an effective amount can be in a range of about 0.01 to about 5000 mg/day. This range can be modified to an amount of about 0.1 to 10 mg/day, about 10 to 50 mg/day, about 50 to 100 mg/day, about 100 to 150 mg/day, about 150 to 200 mg/day, about 200 to 250 mg/day, about 250 to 300 mg/day, about 300 to 350 mg/day, about 350 to 400 mg/day, about 400 to 450 mg/day, about 450 to 500 mg/day, about 500 to 550 mg/day, about 550 to 600 mg/day, about 600 to 650 mg/day, about 650 to 700 mg/day, about 700 to 750 mg/day, about 750 to 800 mg/day, about 800 to 850 mg/day, about 850 to 900 mg/day, about 900 to 950 mg/day, about 950 to 1000 mg/day, about 1000 to 1100 mg/day, about 1100 to 1200 mg/day, about 1200 to 1300 mg/day, about 1300 to 1400 mg/day, about 1400 to 1500 mg/day, about 1500 to 1600 mg/day, about 1600 to 1700 mg/day, about 1700 to 1800 mg/day, about 1800 to 1900 mg/day, about 1900 to 2000 mg/day, about 2000 to 2500 mg/day, about 2500 to 3000 mg/day, about 3000 to 3500 mg/day, about 3500 to 4000 mg/day, about 4000 to 4500 mg/day or about 4500 to 5000 mg/day. It would be clear to one skilled in the art that dosage will vary depending on the particular anti-inflammatory agent being used Specific examples of appropriate dosages, depending on the anti-inflammatory agent, are described below.

In another embodiment, an effective amount of an anti-inflammatory agent can be in a range of about 0.1 mg/week to 40 mg/week; 0.1 mg/week to 5 mg/week; 5 mg/week to 10 mg/week; 10 mg/week to 30 mg/week; 30 mg/week to 35 mg/week; 0.1 mg/week to 100 mg/week; or 30 mg/week to 50 mg/week. In another embodiment, an anti-inflammatory agent can be administered in an amount of about 50 mg/week or 25 mg twice weekly. It would be clear to one skilled in the art that dosage range will vary depending on the particular anti-inflammatory agent being used, for example see below.

Methotrexate is an antimetabolite molecule that interferes with DNA synthesis, repair and cellular replication. Methotrexate is an inhibitor of dihydrofolic acid reductase i.e. it is a folic acid antagonist. Methotrexate may be administered in an amount about 0.1 to 40 mg per week with a dosage ranging from about 5 to 30 mg per week. Methotrexate may be administered to a subject in various increments: about 0.1 to 5 mg/week, about 5 to 10 mg/week, about 10 to 15 mg/week, about 15 to 20 mg/week, about 20 to 25 mg/week, about 25 to 30 mg/week, about 30 to 35 mg/week, or about 35 to 40 mg/week. In one embodiment, an effective amount of methotrexate, may be about 10 to 30 mg/week.

Cyclophosphamide, an alkylating agent, may be administered in dosages ranging about 0.1 to 10 mg/kg body weight per day.

Cyclosporine (e.g. NEORAL®) also known as Cyclosporin A, may be administered in dosages ranging from about 1 to 10 mg/kg body weight per day. Dosages ranging about 2.5 to 4 mg per body weight per day may be used.

Chloroquine or hydroxychloroquine (e.g. PLAQUENIL®), may be administered in dosages ranging about 100 to 1000 mg daily. Preferred dosages range about 200-600 mg administered daily.

Sulfasalazine (e.g., AZULFIDINE EN-Tabs®) may be administered in amounts ranging about 50 to 5000 mg per day, with a dosage of about 2000 to 3000 mg per day for adults. Dosages for children may be about 5 to 100 mg/kg of body weight, up to 2 grams per day.

Injectable gold salts may be prescribed in dosages about 5 to 100 mg doses every two to four weeks. Orally administered gold salts may be prescribed in doses ranging about 1 to 10 mg per day.

D-penicillamine or penicillamine (CUPRIMINE®) may be administered in dosages about 50 to 2000 mg per day, with dosages about 125 mg per day up to 1500 mg per day.

Azathioprine may be administered in dosages of about 10 to 250 mg per day. For example, a dosage range of about 25 to 200 mg per day is acceptable.

Anakinra (e.g. KINERET®) is an interleukin-1 receptor antagonist. A possible dosage range for anakinra is about 10 to 250 mg per day. In one example, the dosage may be about 100 mg per day.

Infliximab (REMICADE®) is a chimeric monoclonal antibody that binds tumor necrosis factor alpha (TNFα) and inhibits the activity of TNFα. Infliximab may be administered in dosages about 1 to 20 mg/kg body weight every four to eight weeks. Dosages of about 3 to 10 mg/kg body weight may be administered every four to eight weeks depending on the subject.

Etanercept (e.g. ENBREL®) is a dimeric fusion protein that binds the tumor necrosis factor (TNF) and blocks its interactions with TNF receptors. In one example, the dosage range of etanercept may be about 10 to 100 mg per week for adults. In another example, the dosage may be about 50 mg per week. Dosages for juvenile subjects may range from about 0.1 to 50 mg/kg body weight per week with a maximum of about 50 mg per week. For adult patients, etanercept may be administered e.g., injected, in 25 mg doses twice weekly e.g., 72-96 hours apart in time.

Leflunomide (ARAVA®) may be administered at dosages from about 1 and 100 mg per day. In one embodiment, the dosage range is from about 10 to 20 mg per day.

It is contemplated that global administration of a therapeutic composition to a subject is not needed in order to achieve a highly localized effect. Localized administration of a therapeutic composition according to the invention is preferably by injection, catheter or by means of a drip device, drug pump or drug-saturated solid matrix from which the composition can diffuse implanted at the target site. When a tissue that is the target of treatment according to the invention is on a surface of an organism, topical administration of a pharmaceutical composition is possible. For example, antibiotics are commonly applied directly to surface wounds as an alternative to oral or intravenous administration, which methods necessitate a much higher absolute dosage in order to counter the effect of systemic dilution, resulting both in possible side-effects in otherwise unaffected tissues and in increased cost.

Systemic administration of a therapeutic composition according to the invention may be performed by methods of whole-body drug delivery well known in the art. These include, but are not limited to, intravenous drip or injection, subcutaneous, intramuscular, intraperitoneal, intracranial and spinal injection, ingestion via the oral route, inhalation, trans-epithelial diffusion (such as via a drug-impregnated, adhesive patch) or by the use of an implantable, time-release drug delivery device. Note that injection may be performed by conventional means.

Systemic administration is advantageous when a pharmaceutical composition must be delivered to a target tissue that is widely-dispersed, inaccessible to direct contact or, while accessible to topical or other localized application, is resident in an environment (such as the digestive tract) wherein the native activity of the nucleic acid or other agent might be compromised, e.g. by digestive enzymes or extremes of pH.

A novel therapeutic composition for use in the invention can be given in a single- or multiple doses. A multiple dose schedule is one in which a primary course of administration can include 1-10 or more separate doses, followed by other doses given at subsequent time intervals required to maintain and or reinforce the level of the therapeutic agent. Such intervals are dependent on the continued need of the recipient for the therapeutic agent, and/or the half-life of a therapeutic agent. The efficacy of administration may be assayed by monitoring the reduction in the levels of a symptom indicative or associated with the disease which it is designed to inhibit. The assays can be performed as described herein or according to methods known to one skilled in the art.

A therapeutically effective regimen may be sufficient to arrest or otherwise ameliorate symptoms of a disease. An effective dosage regimen requires providing the regulatory drug over a period of time to achieve noticeable therapeutic effects wherein symptoms are reduced to a clinically acceptable standard or ameliorated. The symptoms are specific for the disease in question. For example, when the disease is associated with tumor formation, the claimed invention is successful when tumor growth is arrested, or tumor mass is decreased by at least 50% and preferably 75%.

IX. Pharmaceutical Compositions

In another aspect, the invention provides for novel pharmaceutical compositions comprising one or more non-covalent DNA binding agents, alone or in combination with other anticancer or anti-inflammatory agents, or a pharmaceutically acceptable ester, salt, or prodrug thereof, together with a pharmaceutically acceptable carrier. This invention provides for a pharmaceutical composition comprising one or more non-covalent DNA binding agent, alone, as the only active agent(s) or in combination with one or more therapeutic active agents, e.g., a chemotherapeutic agent.

Non-covalent DNA binding agents of the invention can be administered as pharmaceutical compositions by any conventional route, in particular parenterally such as intravenously or by subcutaneous or intramuscular injections; enterally, e.g., orally, e.g., in the form of tablets or capsules, topically, e.g., in the form of lotions, gels, ointments or creams, or in a nasal or suppository form for localized delivery. Pharmaceutical compositions comprising a non-covalent DNA binding agent of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

One or more non-covalent DNA binding agents of the invention can be administered in therapeutically effective amounts, alone, as the only active agent(s) or in combination with one or more therapeutic active agents (pharmaceutical combinations), resulting in novel compositions. For example, synergistic effects can occur with other anti-proliferative, anti-cancer, immunomodulatory or anti-inflammatory substances. Where the compounds of the invention are administered in conjunction with other therapies, dosages of the co-administered compounds will of course vary depending on the type of co-drug employed, on the specific drug employed, on the condition being treated and so forth.

The present invention encompasses pharmaceutically acceptable topical formulations of inventive compounds. The term "pharmaceutically acceptable topical formulation," as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination with the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend on several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et ah, Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, IU. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide. fatty acid esters (e.g., isopropyl myristate, methyl laurate, glycerol monooleate, and propylene glycol monooleate) and N-methyl pyrrolidine.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof, Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the descriptions of novel compositions and methods of treatment of the present invention, disorders are treated or prevented in a subject, such as a human or other animal, by administering to the subject a therapeutically effective amount of one or more non-covalent DNA binding agent, alone, as the only active agent(s) or in combination with one or more other active agents, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

The invention also provides for novel compositions of pharmaceutical combinations, e.g. a kit, comprising an agent which is a compound of the invention as disclosed herein, in free form, or in pharmaceutically acceptable salt form. The kit can comprise instructions for its administration to a subject suffering from or susceptible to a disease or disorder.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The non-covalent DNA binding agent compounds (e.g., including those delineated herein), or pharmaceutical salts thereof may be formulated into pharmaceutical compositions for administration to animals or humans. These pharmaceutical compositions, which comprise an amount of the non-covalent DNA binding agent compounds effective to treat or prevent a non-covalent DNA cross-link mediated condition and a pharmaceutically acceptable carrier, are another embodiment of the present invention.

This invention also encompasses novel pharmaceutical compositions containing, and methods of treating disorders through administering, pharmaceutically acceptable prodrugs of one or more non-covalent DNA binding agents of the invention alone, as the only active agent(s) or in combination with other available active agents. For example, non-covalent DNA binding agents of the invention having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the invention. The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Combinations of substituents and variables envisioned by this invention are only those that result in the formation of stable compounds. The term "stable", as used herein, refers to compounds which possess stability sufficient to allow manufacture and which maintain the integrity of the compound for a sufficient period of time to be useful for the purposes detailed herein (e.g., therapeutic or prophylactic administration to a subject).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments of the invention the compound is at least 85% pure, more preferably at least 90% pure, more preferably at least 95% pure, and most preferably at least 99% pure.

X. Kits or Pharmaceutical Systems

The novel Compositions described in this application may be assembled into kits or pharmaceutical systems for use in disease treatment, e.g., cancer treatment or treatment of an inflammatory disease. Kits or pharmaceutical systems according to this aspect of the invention comprise a carrier means, such as a box, carton, tube or the like, having in close confinement therein one or more container means, such as vials, tubes, ampules, bottles and the like. The kits or pharmaceutical systems of the invention may also comprise associated instructions for using one or more non-covalent DNA binding agents of the invention, alone, as the only active agent(s) or in combination with other active agents. The non-covalent DNA binding agents of the kits or pharmaceutical systems of the invention may have any one of the functional properties described for the non-covalent DNA binding agents of the methods of the invention.

In certain embodiments, the kits of the invention include a test for determining if a subject has a mutation in a particular gene of interest.

XI. Uses

The methods of the invention can be used to treat a subject with a disease, e.g., cancer and/or inflammatory disease.

XII. Animal Models

The invention provides for animal models for various diseases, including but not limited to cancer.

Additional animal models known in the art are also useful according to the invention, such as those models for inflammatory disorders such as rheumatoid arthritis, psorias, Crohn's disease and ulcerative colitis.

A. Rheumatoid Arthritis:

Animal models for Rheumatoid arthritis include but are not limited to collagen induced arthritis in mouse and rat, collagen antibody induced arthritis in mouse, spontaneous rheumatoid arthritis in K/B×N mice, arthritis induced by adoptive transfer of serum from K/B×N mice and spontaneous arthritis in TNFα transgenic mice.

Multiple Sclerosis:

Animal models for Multiple Sclerosis include but are not limited to experimental autoimmune encephalopathy in mouse and rat induced by injection of myelin oligodendrocyte glycoprotein and experimental autoimmune encephalopathy in mouse and rat induced by injection of proteolipid protein.

C. Inflammatory Bowel Disease (Crohn's Disease):

Animal models for Crohn's Disease include but are not limited to Dextran sodium sulfate induced colitis in mouse and rat and colitis induced by adoptive transfer of CD4+ CD45RBhigh cells into SCID mice D. Inflammatory Bowel Disease (Ulcerative Colitis):

An animal model for ulcerative colitis includes but is not limited to trinitrobenzene sulfonic acid induced colitis in mouse and rat.

E. Type I Diabetes: Spontaneous Type I Diabetes

An animal model for Type I Diabetes includes but is not limited to BB/Wor rat or NOD mice.

F. Graft Versus Host Disease

An animal model for graft versus host disease includes but is not limited to transfer of allogenic donor lymphocytes and stem cells into irradiated host mice and transfer of allogenic donor lymphocytes and stem cells into immune competent host mice.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Having now generally described the invention, the same will be more readily understood through reference to the following Examples which are provided by way of illustration, and are not intended to be limiting of the present invention, unless specified.

The following examples are put forth for illustrative purposes only and are not intended to limit the scope of what the inventors regard as their invention.

Example 1

Potency of Non-Covalent DNA Binding Agents in MMR-Proficient Tumor Cells-Pharmacological Profile Three novel non-covalent DNA binding agents of the invention, NSC 718813, NSC 723734 and NSC 726260, are tested in five different EGFR-resistant, K-Ras mutant cancer cell lines. These cell lines represent colorectal (SW480, SW620 and HCT116) and breast cancer (MDA-MB-231 and MDA-MA-468). The growth inhibitory effects of novel non-covalent DNA binding agents of the invention in EGFR-resistant, mutant K-ras cancer cells are compared to those observed in tumor cells that either do not express EGFR (U2OS) and/or carry the wild-type KRAS gene, and/or have normal EGFR expression or wild-type K-ras (SW403). The tumor cell lineage and their respective mutations in EGF receptor and/or its signaling cascade genes are shown in Table 2.

In Vitro Cancer Screening Methods

The in vitro assays to evaluate the anticancer potential of non-covalent DNA binding agents were measured by using one or more of the assays described below.

Sulforhodamine B (SRB) Uptake Assay:

The human tumor cell lines of the cancer screening panel are grown in RPMI 1640 medium containing 5% fetal bovine serum and 2 mM L-glutamine. For a typical screening experiment, cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% $CO_2$, 95% air and 100% relative humidity for 24 h prior to addition of experimental drugs.

After 24 h, two plates of each cell line are fixed in situ with TCA, to represent a measurement of the cell population for each cell line at the time of drug addition (Tz). Experimental drugs are solubilized in dimethyl sulfoxide at 400-fold the desired final maximum test concentration, and stored frozen prior to use. At the time of drug addition, an aliquot of frozen concentrate is thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions are added to the appropriate microtiter wells already containing 100 μl of medium, resulting in the required final drug concentrations.

Following drug addition, the plates are incubated for an additional 48 h at 37° C., 5% $CO_2$, 95% air, and 100% relative humidity. For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of drug at the five concentration levels (Ti)], the percentage growth is calculated at each of the drug concentration levels. Percentage growth inhibition is calculated as:

$[(Ti-Tz)/(C-Tz)]\times 100$ for concentrations for which $Ti>/=Tz$ $[(Ti-Tz)/Tz]\times 100$ for concentrations for which $Ti<Tz$.

Three dose response parameters are calculated for each experimental agent.

Growth inhibition of 50% ($GI_{50}$) is calculated from $[(Ti-Tz)/(C-Tz)]\times 100=50$, which is the drug concentration resulting in a 50% reduction in the net protein increase (as measured by SRB staining) in control cells during the drug incubation.

The drug concentration resulting in total growth inhibition (TGI) is calculated from Ti Tz.

The $LC_{50}$ (concentration of drug resulting in a 50% reduction in the measured protein at the end of the drug treatment as compared to that at the beginning) indicating a net loss of cells following treatment is calculated from $[(Ti-Tz)/Tz]\times 100=-50$.

Values are calculated for each of these three parameters if the level of activity is reached. However, if the effect is not reached or is exceeded, the value for that parameter is expressed as, greater or less than the maximum or minimum concentration tested.

Alamar Blue Cell Survival Assay in Human Tumor Cells:

Tumor cells are plated in 96 well plates at a density of 8,000 to 10,000 cells per well in 100 uL volume and grown overnight. On the second day, the cells are supplemented with medium containing an appropriate dilution of the compounds to be tested. The cells are treated with the test compounds for two more days and the growth medium was replaced with fresh medium containing 3% Alamar Blue, incubated for 2-3 hours and plates are read in a SpectraMax Gemini XS fluorescence plate reader (Molecular Devices).

Alamar Blue Cell Survival Assay in Yeast Cells:

The cells are diluted 100-fold in yeast complete medium. 100 μL of diluted cells are seeded in 96 well plates with or without a non-covalent DNA binding compound and incubated for 24 hours at 30° C. The following day, an equal volume of yeast complete medium containing 1% alamar blue is added and incubated at 30° C. for two hours. Fluorescence intensity is measured in a fluorescent reader to calculate the inhibition effect of non-covalent DNA binding agents in mutant and wild type yeast cells.

Half-Maximal Trypan Blue Exclusion Cytotoxic Concentration (CC50) Assay:

In this assay non-specific cytotoxicity of various test compounds is determined based upon trypan blue exclusion. For the trypan blue dye exclusion assay, the cells are seeded at 10*5 cells per well in a 24-well plate and incubated overnight. The medium is replaced with fresh medium containing serial dilutions of a test compound which is diluted in DMSO. DMSO alone is used as a control. The maximum amount of DMSO in each well does not exceed more than 10%. The cells are incubated with compound for 48 hours and the supernatant which may contain dead cells is collected. The attached cells are trypsinized and transferred to the supernatant. The number of cells which do not incorporate trypan blue dye are calculated as viable cell number by hemocytometer. From the dose-response curve, the 50% CC50 is determined.

siRNA Inhibition of MMR, p53, and REV Functions siRNA specific for different genes is purchased from Dharmacon (Thermo. Fisher Scientific Dharmacon Products, Lafayette, Colo. 80026) and the protocol recommended by the supplier is utilized. Confluent cells are trypsinized and 5000 cells are seeded in a well in the presence or absence of siRNA in 100 μL medium. The cells are incubated with siRNA for two days. A non-covalent DNA binding agent of the invention is added in a 10 μL volume and incubated for another 48 hours. After treatment with the agent, the medium is replaced with 1% alamar blue containing medium to measure fluorescence after two hours. The difference in fluorescence intensity shows the growth inhibition.

Methods for Combination Experiments

Tumor cells are plated in 96 well plates at a density of 8,000 to 10,000 cells per well in 100 uL volume and grown overnight. On the second day, the cells are supplemented with medium containing an appropriate dilution of the compounds to be tested as follows: In each well 100 uL of medium is added to all the wells. 50 uL of 3× concentration of novel non-covalent DNA binding agents are added to the top row (row A). After mixing 50 uL is added to next row (row B) and 1/3 dilution is continued up to row F (six rows) leaving seventh and eighth rows. 50 uL 3× concentration of other compounds in the combination are added to seven wells (A to G) in the left column 1 and diluted (1/3 dilution) from left to right until column 6. This is repeated other half of the plate from 7 to 12. The cells are incubated with combination of compounds for two more days and the growth medium was replaced with fresh medium containing 3% Alamar Blue, incubated for 2-3 hours and plates are read in a SpectraMax Gemini XS fluorescence plate reader (Molecular Devices). Mean of two wells is taken for calculation of combination effect.

Results:

Novel non-covalent DNA binding agents have $IC_{50}$ values ranging from 8 nM to 1075 nM in tumor cells that have wild type K-RAS gene. In tumor cells harboring mutations in genes in EGFR pathways, both K-RAS and K-RAS/BRAF with or without PTEN deficiency, the $IC_{50}$ values for novel non-covalent DNA binding agents of the invention are similar or better than those observed in tumor cells with the wild type K-RAS, U2OS.

The colon cancer cell line HCT 116, which has double mutations in K-RAS and in the DNA mismatch repair gene MLH, is more susceptible to non-covalent DNA binding agents of the invention than the colon cancer cells which have a K-RAS mutation only. The tumor cells which are deficient in PTEN are more sensitive to novel non-covalent DNA binding agents of the invention then are other mutated tumor cell lines. Among the three compounds tested NSC 718813 and NSC 723734 have similar potency (<100 nM), while NSC 726260 is comparatively less potent, with $IC_{50}$ values around 1 uM. These cellular potency estimates for novel non-covalent DNA binding agents of the invention, in tumor cells that have K-RAS mutations and/or PTEN or mismatch repair gene deficiencies, provides a novel approach to treating genetically-resistant cancers with such genetic mutations.

The results are presented in FIG. 1—U2OS, 2-Col205, 3-HeLa, 4-lymphoblastoid 4-CEM cells, 5-leukemia cells (CEM), 6-Jurkat Cells, 7-MDA-MB-468, 8-2E-H1299 cancer cells, 9A-SW403, 9B-SW403, 10A-SW620 and 10B-HCT116, and Table 2.

Novel Non-Covalent DNA Binding Agents of the Inventions are Effective in K-RAS Mutant Colon Cancer Cells:

TABLE 2

| Cell Line | Type of Cancer | Mutation (Gain of function) | Deficiency (Loss of function) | IC50 nM NSC 718813 | IC50 nM NSC 723734 | IC50 nM NSC 726260 |
|---|---|---|---|---|---|---|
| U2OS | Osteosacroma | WT | Lack of EGFR | 202 + 27.3 | 178 + 40.9 | 397 + 51.6 |
| SW403 | Colon | WT (EGFR Over Expression) | — | 210 + 35.4 | 550 + 141.4 | 1025 + 106.1 |
| SW620 | Colon | KRAS | — | 236 ± 37.2 | 175 ± 25.0 | 1050 ± 50.0 |
| SW480 | Colon | KRAS | — | 48 + 17.7 | 575 + 35.4 | 1075 + 35.0 |
| HCT116 | Colon | KRAS | MLH1 | 17 + 2.5 | 160 + 42.4 | 550 + 167.5 |
| MDA231 | Breast | KRAS & BRAF (ERK+) | — | 54 + 2.3 | 394 + 17.0 | 501 + 29.0 |
| MDA-MB-468 | Breast | ERK+ (EGFR over expression) | PTEN | 8 ± 1.2 | 22 ± 0.7 | 364 + 54.8 |
| CEM | Leukemia | — | PTEN | 51 ± 0.6 | 49 ± 0.8 | 161 ± 0.4 |
| Jurkat | Leukemia | — | PTEN | 17 ± 0.2 | 45 ± 4.0 | 114 ± 26.7 |

WT: Wild Type tumor cell line

Example 2

Non-Covalent DNA Binding Agents Cause Double Strand Breaks

As evidenced by the sensitivity of yeast RAD52 mutants to the cytotoxicity of novel DNA binding agents, these agents cause double stranded breaks.

Yeast cells that carry mutations in different genes involved in homologous recombination (rad 50, rad51, rad52, and rad57) and nucleotide excision/double strand repair (rad1) are grown to stationary culture overnight. Results are shown in Table 3.

TABLE 3

| | IC50 uM | | | |
|---|---|---|---|---|
| Yeast | PBD-A | PBD-B | PBD-C | PBD-D |
| mutation | 718813 | 723734 | 723732 | 726260 |
| rad1 | 11 | 15 | R | 15 |
| rad50 | 90 | 17 | R | 20 |
| rad51 | 7 | 28 | 100 | 4.5 |
| rad52 | 90 | 50 | 105 | 15 |
| rad57 | ND | ND | ND | 0.3 |
| Wild type yeast | R | R | R | 45 |

R = Resistant
(No killing up to 250 uM)

Example 3

Half-Life of Non-Covalent DNA Binding Agents in Rats

Determination of Pharmacokinetics of Novel Non-Covalent DNA Binding Agents in Rats:

Intravenous and oral pharmacokinetic studies are conducted on the novel non-covalent DNA binding agents, NSC 718813, NSC 723734 and NSC 726260, in male Sprague-Dawley rats. The studies are conducted in a parallel design with two groups of four male rats each for intravenous and oral administration of the test agents. The protocols for the studies are approved by the appropriate institutional animal care and use committee.

Groups of rats designated to receive oral doses of the novel non-covalent DNA binding agents of the invention molecules receive an oral dose of 20 mg/kg in a formulation vehicle comprised of N,N-dimethylacetamide (DMA), polyethylene glycol 400 (PEG400), ethanol, Cremophor EL and water (10:10:10:5:65 v/v). The dose volume for the oral doses of the test compounds is 8 mL/kg. Groups of rats are randomized to receive intravenous doses of agents. These rats receive a single intravenous bolus dose of 3 mg/kg of the test compound in a vehicle comprised of DMA:PEG400:ethanol:Cremophor EL:0.9% sodium chloride (saline) (10:10:10:5:65 v/v). The dose volume for intravenous doses of test agents is 1 mL/kg.

Predose blood samples are obtained from all rats from both, oral and intravenous dosing groups. For the intravenously dosed rats, blood samples (100 uL each) are obtained at 0.083, 0.25. 0.5, 1.0, 2.0, 4.0, 8.0, 12.0 and 24.0 hours post-dose. For the oral dose groups, the sampling times are identical to the intravenous dose group, except that the 0.083 hour sample is not collected. Following the collection of the blood samples, an equal volume of water is added to the blood sample to hemolyze the blood sample and the samples are stored frozen at −70° C. until bioanalysis.

Plasma samples are analyzed for the concentration of the test non-covalent DNA binding agents of the invention using an HPLC method with mass spectrometric (MS/MS) detection, following a liquid:liquid extraction of the plasma samples using a dichloromethane:ethyl acetate (20:80) mixture. To a 100 μL aliquot of sample, 50 μL of an internal standard (NSC 723732) is added. After mixing the internal standard wen, 2.5 mL of the extracting solvent (dichloromethane:ethyl acetate 20:80 v/v) is added. The mixture is vortexed for one minute and the samples are centrifuged at 3000 rpm for 3 minutes. Approximately 2 mL of the supernatant is taken from the centrifuged tubes and the sample is dried under a nitrogen stream at 50° C. The residue is reconstituted with 100 μL of the mobile phase and 20 μL is injected into the HPLC system for analysis. The mobile phase is comprised of milli-Q water:acetonitrile:formic acid (20:80:0.05) adjusted to pH 7.5 with ammonia.

Liquid Chromatography Mass Spectrometric (LC/MS/MS) Conditions:

The analysis of the test agent concentration is conducted by an HPLC method using a Shimadzu Prominence HPLC system and the eluent is analyzed using an API 4000 LC-MS/MS system (Applied Biosystems). The samples are analyzed on a HyPurity Advance, 50×4.6 mm, 5 u, Thermoelectron column. An injection volume of 20 μL is used for the analytical sample and the flow rate of the mobile phase is 0.6 mL/minute. Mass spectrometric analysis is conducted on the eluent using the API 4000 LC-MS/MS system and the mass parameters are analyzed for MRM transitions using NSC 723732 as the internal standard, in a positive ionization mode at a temperature of 400 C.

Pharmacokinetics of Novel Non-Covalent DNA Binding Agents, NSC 718813, NSC 723734 and NSC 726260 Following Intravenous and Oral Administration in Male Sprague-Dawley Rats:

The pharmacokinetics of NSC 718813, NSC723734 and NSC726260 are evaluated in the rat following intravenous and oral administration to evaluate the metabolic stability and clearance profile of these novel agents. Furthermore, the formulation properties of these agents are evaluated to assess their aqueous solubility and ability to administer formulations of these non-covalent DNA binding agents in vehicles similar to those used for various chemotherapeutic agents. Non-covalent DNA binding compounds have somewhat limited aqueous solubility, and require the addition of non-aqueous solvents such as polyethylene glycol 400, Cremophor and dimethylacetamide to allow intravenous administration of these agents in rats.

Pharmacokinetics of NSC 718813

NSC 718813 achieves excellent exposure in the blood following intravenous administration of a dose of 3 mg/kg. Concentrations well above its in vitro GI50 and/or TGI are achieved in rat blood for at least 4 hours following intravenous administration (see Table 4 and FIG. 11 below).

TABLE 4

Pharmacokinetic parameters (mean ± SD) of NSC 718813/1 in male Sprague Dawley rats following oral solution and intravenous bolus administration

| Route | $T_{max}$[a] (h) | $C_{max}$ (ng/mL) | $AUC_{0\text{-}t}$ (ng · h/mL) | $AUC_{0\text{-}inf}$ (ng · h/mL) | $T_{1/2}$[b] (h) | $CL_{blood}$ (mL/min/kg) | $Vd_{ss}$ (L/kg) | F (%)[c] |
|---|---|---|---|---|---|---|---|---|
| IV-bolus (N = 4) | 0.08 (0.08-0.13) | 5723 ± 1005 | 2376 ± 304 | 2424 ± 309 | 2.2 ± 0.4 | 20.0 ± 2.9 | 1.5 ± 0.4 | |
| Oral (N = 5) | 0.5 (0.25-2.0) | 112 ± 32 | 303 ± 129 | 345 ± 142 | 1.8 ± 0.6 | NA[d] | NA | 2.0 |

[a]median (range);

[b]harmonic mean;

[c]$F = (AUC_{0\text{-}inf})_{oral} \times dose_{iv}/(AUC_{0\text{-}inf})_{iv} \times dose_{oral}$, mean oral dose: 20.50 mg/kg; mean intravenous dose: 2.90 mg/kg;

[d]not applicable

These novel non-covalent DNA binding agents of the invention are designed to address the metabolic instability and rapid clearance of the naturally occurring antitumor antibiotics like anthramycin and neothramycin. As shown in Table 4, the systemic clearance of NSC 718813 is estimated to be approximately 20 mL/min/kg, which is significantly lower than the hepatic blood flow in the rat—showing that NSC 718813 has a low to moderate clearance following intravenous administration. NSC-718813 has better metabolic stability than its naturally occurring antitumor antibiotic analogs. NSC 718813 at an oral dose of 20 mg/kg has low, but measurable blood levels for up to 8 hours post-dose (see FIG. 11) and has an estimated oral bioavailability of 2%. The poor oral bioavailability of NSC 718813 coupled with its low systemic clearance, suggests absorption-limited oral bioavailability, either due to poor absorption across the gut wall and/or luminal or gastrointestinal mucosal pre-systemic elimination.

The pharmacokinetic profile and estimated parameters following intravenous and oral administration for NSC723734 are shown in FIG. 12 and Table 5, below.

Following intravenous administration, NSC723734 shows a low clearance (11 mL/min/kg) which is about 20% of normal liver blood flow in rat (55 mL/min/kg). The compound is well distributed with a mean volume of distribution (3 L/kg) that is about 4 times the total body water. The compound is eliminated with a mean (harmonic) elimination $T_{1/2}$ of 6.3 h. The mean intravenous $C_{max}$ is 4053 ng/mL and the mean overall intravenous exposure ($AUC_{0\text{-}inf}$) is 4405 ng·h/mL. After oral dosing, NSC723734 shows a median $T_{max}$ of 0.25 h, indicating that the compound undergoes rapid absorption. The mean oral $C_{max}$ is 91 ng/mL, and the mean overall exposure ($AUC_{0\text{-}inf}$) is 216 ng·h/mL. The oral absolute bioavailability of NSC723734 in rats is estimated to be approximately 1%. Because the overall blood clearance of the compound in the rat is low, it is unlikely that the low bioavailability of the compound results from a significant first-pass effect. It is possible that low solubility or membrane permeability may determine the oral bioavailability.

Pharmacokinetics of NSC 726260

The pharmacokinetic profile and estimated parameters following intravenous and oral administration for NSC726260 are shown in FIG. 13 and Table 6, below.

TABLE 5

Pharmacokinetic parameters (mean ± SD) of NSC 723734 in male Sprague Dawley rats (N = 4) following oral solution and intravenous bolus administration

| Route | $T_{max}$[a] (h) | $C_{max}$ (ng/mL) | $AUC_{0\text{-}t}$ (ng · h/mL) | $AUC_{0\text{-}inf}$ (ng · h/mL) | $T_{1/2}$[b] (h) | $CL_{blood}$ (mL/min/kg) | $Vd_{ss}$ (L/kg) | F (%)[c] |
|---|---|---|---|---|---|---|---|---|
| IV-bolus | 0.083 (0.083-0.083) | 4053 ± 472 | 4246 ± 311 | 4405 ± 330 | 6.3 ± 0.3 | 11.4 ± 0.5 | 3.2 ± 0.3 | NA[d] |
| Oral | 0.25 (0.25-0.25) | 90.5 ± 56 | 196 ± 93 | 216 ± 84 | 2.3 ± 0.7 | NA | NA | 0.7 |

[a]median (range);

[b]harmonic mean;

[c]$F = (AUC_{0\text{-}inf})_{oral} \times dose_{iv}/(AUC_{0\text{-}inf})_{iv} \times dose_{oral}$, mean oral dose: 20.34 mg/kg; mean intravenous dose: 3.00 mg/kg;

[d]not applicable

TABLE 6

Pharmacokinetic parameters (mean ± SD) of NSC726260 in male Sprague-Dawley rats (N = 4) following oral solution and intravenous bolus administration

| Route | $T_{max}$[a] (h) | $C_{max}$ (ng/mL) | $AUC_{0-t}$ (ng · h/mL) | $AUC_{0-inf}$ (ng · h/mL) | $T_{1/2}$[b] (h) | $CL_{blood}$ (mL/min/kg) | $Vd_{ss}$ (L/kg) | F (%)[c] |
|---|---|---|---|---|---|---|---|---|
| IV-bolus | 0.083 (0.083-0.083) | 5587 ± 1195 | 5058 ± 874 | 5112 ± 871 | 4.8 ± 0.5 | 10.4 ± 2.0 | 1.9 ± 0.7 | NA[d] |
| Oral | 4.0 (4.0-4.0) | 438 ± 146 | 2474 ± 844 | 2536 ± 896 | 4.6 ± 1.7 | NA | NA | 7.9 |

[a]median (range);
[b]harmonic mean;
[c]$F = (AUC_{0-inf})_{oral} \times dose_{iv}/(AUC_{0-inf})_{iv} \times dose_{oral}$, mean oral dose: 19.55 mg/kg; mean intravenous dose: 3.12 mg/kg;
[d]not applicable Following intravenous administration, NSC726260 shows a low clearance (10.4 mL/min/kg) which is about 20% of normal liver blood flow in rat (55 mL/min/kg). The compound is well distributed with a mean volume of distribution (1.9 L/kg) that is about 3 times the total body water. The compound is eliminated with a mean (harmonic) elimination $T_{1/2}$ of 4.8 h. The mean intravenous $C_{max}$ is 5587 ng/mL and the mean overall intravenous exposure ($AUC_{0-inf}$) is 5112 ng·h/mL. After oral dosing, NSC 726260 shows a median $T_{max}$ of 4.0 h, indicating that the compound undergoes sustained absorption. The mean oral $C_{max}$ is 438 ng/mL, and the mean overall exposure ($AUC_{0-inf}$) is 2536 ng·h/mL.

The oral absolute bioavailability of NSC726260 in rats is estimated to be approximately 8%. Because the overall blood clearance of the compound in the rat is low, it is unlikely that the low bioavailability of the compound results from a significant first-pass effect. It is possible that low solubility or membrane permeability may determine the oral bioavailability.

Example 4 siRNA Inhibition of MMR, p53, and REV Functions siRNA specific for different genes is purchased from Dharmacon (Thermo Fisher Scientific Dharmacon Products, Lafayette, Colo. 80026) and the protocol recommended by the supplier is utilized. Confluent cells are trypsinized and 5000 cells are seeded in a well in the presence or absence of siRNA in 100 μL medium. The cells are incubated with siRNA for two days. A non-covalent DNA binding agent of the invention is added in a 10 μL volume and incubated for another 48 hours. After treatment with the agent, the medium is replaced with 1% alamar blue containing medium to measure fluorescence after two hours. The difference in fluorescence intensity shows the growth inhibition. The results are presented in FIGS. 14-18 (SEQ ID NO:3-12, respectively) and Table 7.

TABLE 7

| | | | IC50 (uM) | | | | | | | |
|---|---|---|---|---|---|---|---|---|---|---|
| | | | si RNA knock out | | | | Fold improvement in IC50 | | | |
| Cell line | Compound | Control | p53 | rev | mlh1 | msh2 | p53 | rev | mlh1 | msh2 |
| U2OS | NSC 718813 | 0.30 | 0.03 | 0.06 | 0.1 | | 10 | 5 | 3.0 | |
| Wild type | NSC 723734 | 0.07 | 0.06 | 0.001 | 0.015 | | 1.2 | >70 | 3.5 | |
| | NSC 726260 | 0.4 | 0.35 | 0.003 | 0.003 | | 1.1 | 135 | 135 | |
| | Doxorubicin | 0.7 | >1 uM | >2 uM | >3 uM | | 0.7 | 0.35 | 0.23 | |
| H1299 (p53−) | NSC 718813 | 0.6 | — | — | 0.5 | 0.35 | | | 1.3 | 1.9 |
| | NSC 723734 | 0.9 | — | — | 0.45 | 0.35 | | | 2.0 | 2.6 |
| HCT116 (mlh−) | NSC 718813 | 0.1 | 0.04 | 0.07 | — | — | 12.5 | 7.1 | | |
| | NSC 723734 | 0.3 | 0.18 | 0.18 | — | — | 2.2 | 2.2 | | |
| | NSC 726260 | 0.75 | 0.2 | 0.15 | — | — | 3.8 | 5.0 | | |
| | Camptothecin | 0.25 | 0.2 | 0.15 | — | — | 1.3 | 1.7 | | |

What is claimed is:

1. A composition for treating a cancer or an inflammatory disorder comprising a combination of agents in a pharmaceutically acceptable carrier, wherein said agents comprise:
   (i) a non-covalent DNA-binding pyrrolobenzodiazepine dimer (PBD); and
   (ii) topoisomerase II inhibitor, wherein the PBD is selected from the group consisting of NSC718813, NSC723734, NSC723732 and NSC726260, wherein the topoisomerase II inhibitor is selected from the group consisting of an anthracycline antibiotics, doxorubicin, etoposide and cisplatin, and wherein the combination provides a synergistic effect for treating a cancer or an inflammatory disorder.

2. A kit for treating a cancer or an inflammatory disorder comprising a combination of agents in a pharmaceutically acceptable carrier, wherein said agents comprise:
   (i) a non-covalent DNA: binding pyrrolobenzodiazepine dimer (PBD); and
   (ii) topoisomerase II inhibitor, wherein the PBD is selected from the group consisting of NSC718813, NSC723734, NSC723732 and NSC726260, wherein the topoisomerase II inhibitor is selected from the group consisting of an anthracycline antibiotics, doxorubicin, etoposide and cisplatin, and wherein the combination provides a synergistic effect for treating a cancer or an inflammatory disorder.

3. The kit of claim 2, wherein the pharmaceutically acceptable carrier is selected from the group consisting of alumina, aluminum stearate, lecithin, albumin, glycine, sorbic acid, potassium sorbate, partial glyceride mixtures of saturated vegetable fatty acids, phosphate buffered saline solution, water, emulsions, salts or electrolytes, colloidal silica, magnesium trisilicate, polyvinyl pyrrolidone, cellulose-based substances, polyethylene glycol, sucrose, glucose, maltose, and lipids.

4. The kit of claim 2, additionally comprising an instruction for use of said agents.

5. The kit of claim 4, wherein the instruction comprises instructions for administration of said agents to a subject suffering from cancer.

6. The kit of claim 4, wherein said cancer is selected from the group consisting of: lung cancer, breast cancer, osteosarcoma, neuroblastoma, colon adenocarcinoma, chronic myelogenous leukemia (CML), acute myeloid leukemia (AML), acute promyelocytic leukemia (APL), sarcoma, myxoma, rhabdomyoma, fibroma, lipoma, teratoma; bronchogenic carcinoma, alveolar carcinoma, bronchial adenoma, sarcoma, lymphoma, chondromatous hamartoma, mesothelioma, esophageal cancer, stomach cancer, pancreatic cancer, small bowel cancer, large bowel cancer; kidney cancer, bladder cancer, urethra cancer, prostate cancer, testis cancer; hepatoma, cholangiocarcinoma, hepatoblastoma, angiosarcoma, hepatocellular adenoma, hemangioma, osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma, giant cell tumors, cancer of the skull, meninges cancer, brain cancer, spinal cord cancer, uterus cancer, cervical cancer, cancer of the ovaries, vulva cancer, vagina cancer, Hodgkin's disease, non-Hodgkin's lymphoma, malignant melanoma, basal cell carcinoma, squamous cell carcinoma, Karposi's sarcoma, moles dysplastic nevi, lipoma, angioma and dermatofibroma.

7. The composition of claim 1, wherein the pharmaceutically acceptable carrier is selected from the group consisting of alumina, aluminum stearate, lecithin, albumin, glycine, sorbic acid, potassium sorbate, partial glyceride mixtures of saturated vegetable fatty acids, phosphate buffered saline solution, water, emulsions, salts or electrolytes, colloidal silica, magnesium trisilicate, polyvinyl pyrrolidone, cellulose-based substances, polyethylene glycol, sucrose, glucose, maltose, and lipids.

8. The composition of claim 1, wherein said cancer is selected from the group consisting of: lung cancer, breast cancer, osteosarcoma, neuroblastoma, colon adenocarcinoma, chronic myelogenous leukemia (CML), acute myeloid leukemia (AML), acute promyelocytic leukemia (APL), sarcoma, myxoma, rhabdomyoma, fibroma, lipoma, teratoma; bronchogenic carcinoma, alveolar carcinoma, bronchial adenoma, sarcoma, lymphoma, chondromatous hamartoma, mesothelioma, esophageal cancer, stomach cancer, pancreatic cancer, small bowel cancer, large bowel cancer; kidney cancer, bladder cancer, urethra cancer, prostate cancer, testis cancer; hepatoma, cholangiocarcinoma, hepatoblastoma, angiosarcoma, hepatocellular adenoma, hemangioma, osteogenic sarcoma, fibrosarcoma, malignant fibrous histiocytoma, chondrosarcoma, Ewing's sarcoma, malignant lymphoma, multiple myeloma, malignant giant cell tumor chordoma, osteochronfroma, benign chondroma, chondroblastoma, chondromyxofibroma, osteoid osteoma, giant cell tumors, cancer of the skull, meninges cancer, brain cancer, spinal cord cancer, uterus cancer, cervical cancer, cancer of the ovaries, vulva cancer, vagina cancer, Hodgkin's disease, non-Hodgkin's lymphoma, malignant melanoma, basal cell carcinoma, squamous cell carcinoma, Karposi's sarcoma, moles dysplastic nevi, lipoma, angioma and dermatofibroma.

9. The composition of claim 1, wherein the combination of said agents resulting in inhibition of cancer or inflammatory disorder despite a previous resistance or refractory response to an anti-cancer therapy.

* * * * *